United States Patent
Gorek et al.

(10) Patent No.: US 11,413,037 B2
(45) Date of Patent: *Aug. 16, 2022

(54) NEEDLE RECEPTACLE FOR INCREASED OPERATING ROOM EFFICIENCY

(71) Applicant: SHARP FLUIDICS, LLC, Hayward, CA (US)

(72) Inventors: Josef E. Gorek, Ross, CA (US); Kenneth B. Trauner, San Francisco, CA (US); Douglas G. Rimer, Los Altos Hills, CA (US)

(73) Assignee: SHARP FLUIDICS, LLC, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/301,108

(22) Filed: Mar. 25, 2021

(65) Prior Publication Data
US 2021/0267591 A1    Sep. 2, 2021

Related U.S. Application Data

(63) Continuation of application No. 16/782,825, filed on Feb. 5, 2020, now Pat. No. 10,987,100, which is a
(Continued)

(51) Int. Cl.
*A61B 17/06* (2006.01)
*A45F 5/00* (2006.01)
(Continued)

(52) U.S. Cl.
CPC .......... *A61B 17/06061* (2013.01); *A44C 5/00* (2013.01); *A45C 11/00* (2013.01);
(Continued)

(58) Field of Classification Search
CPC ........ A61B 17/06161; A61B 17/06061; A61B 17/06114; A61B 2017/06142;
(Continued)

(56) References Cited

U.S. PATENT DOCUMENTS 3,301,393 A    1/1967 Regan, Jr.
3,861,521 A    1/1975 Burtz
(Continued)

FOREIGN PATENT DOCUMENTS

CA    1215658    12/1986
CN    201441484 U    4/2010
(Continued)

OTHER PUBLICATIONS

International Search Report and Written Opinion for International Application No. PCT/US2015/027659 (dated Oct. 2, 2015).
(Continued)

*Primary Examiner* — Justin M Larson
(74) *Attorney, Agent, or Firm* — FisherBroyles LLP; John Shimmick

(57) ABSTRACT

Systems, devices and methods to improve safety and efficiency in an operating room comprise providing a suture package that holds new suture needles and needle receptacles for storing used needles. The devices can be safely worn for the surgeon to self-dispense new suture needles in the near surgical field and to secure the used needles into a needle trap or a needle retainer located on his extremity, on his operative instruments or on the surgical drapes. The device may provide automated and/or simplified needle counting both during use and after removal from the surgical field. The device may be configured for ergonomic and efficient use so as to minimize the actions and motions of the surgeon to dispense and secure the needle.

20 Claims, 221 Drawing Sheets

Related U.S. Application Data continuation of application No. 16/566,704, filed on Sep. 10, 2019, now Pat. No. 10,603,033, which is a continuation of application No. 16/167,369, filed on Oct. 22, 2018, now Pat. No. 10,478,177, which is a continuation of application No. 15/895,896, filed on Feb. 13, 2018, now Pat. No. 10,485,534, which is a continuation of application No. PCT/US2016/059599, filed on Oct. 28, 2016.

(60) Provisional application No. 62/248,029, filed on Oct. 29, 2015.

(51) Int. Cl.

| | | |
|---|---|---|
| *A44C 5/00* | (2006.01) | |
| *A61B 17/32* | (2006.01) | |
| *A45C 11/00* | (2006.01) | |
| *A61B 50/36* | (2016.01) | |
| *A61B 46/00* | (2016.01) | |
| *A61B 42/10* | (2016.01) | |
| *A61B 50/20* | (2016.01) | |
| *A61B 17/04* | (2006.01) | |
| *A61B 17/3201* | (2006.01) | |
| *A61B 17/30* | (2006.01) | |
| *A61B 17/00* | (2006.01) | |
| *A61B 90/00* | (2016.01) | |
| *A61B 34/20* | (2016.01) | |
| *A61B 90/98* | (2016.01) | |

(52) U.S. Cl.
CPC ............ *A45F 5/00* (2013.01); *A61B 17/0467* (2013.01); *A61B 17/0491* (2013.01); *A61B 17/06004* (2013.01); *A61B 17/06066* (2013.01); *A61B 17/06114* (2013.01); *A61B 17/06133* (2013.01); *A61B 17/06161* (2013.01); *A61B 17/32* (2013.01); *A61B 42/10* (2016.02); *A61B 46/00* (2016.02); *A61B 50/20* (2016.02); *A61B 50/362* (2016.02); *A45C 2011/007* (2013.01); *A45F 2005/008* (2013.01); *A61B 17/0469* (2013.01); *A61B 17/3201* (2013.01); *A61B 34/20* (2016.02); *A61B 90/98* (2016.02); *A61B 2017/00442* (2013.01); *A61B 2017/00862* (2013.01); *A61B 2017/00889* (2013.01); *A61B 2017/00907* (2013.01); *A61B 2017/06142* (2013.01); *A61B 2017/305* (2013.01); *A61B 2034/2055* (2016.02); *A61B 2050/21* (2016.02); *A61B 2090/0807* (2016.02); *A61B 2090/0808* (2016.02)

(58) Field of Classification Search
CPC .. A61B 2017/06147; A61B 2019/4821; A61B 19/0288; A61B 50/3001; A61B 2050/3002; B65D 85/24
See application file for complete search history.

(56) References Cited

U.S. PATENT DOCUMENTS

| | | |
|---|---|---|
| 3,933,286 A | 1/1976 | Karkas |
| 3,944,069 A | 3/1976 | Eldridge, Jr. |
| 4,008,802 A | 2/1977 | Freitag |
| 4,013,109 A | 3/1977 | Sandel |
| 4,243,140 A | 1/1981 | Thrun |
| 4,260,056 A | 4/1981 | Horvath |
| 4,321,999 A | 3/1982 | Higgins |
| 4,418,821 A | 12/1983 | Sandel |
| 4,466,539 A | 8/1984 | Frauenhoffer |
| 4,586,614 A | 5/1986 | Ger |
| 4,591,048 A | 5/1986 | Eldridge, Jr. |
| 4,596,329 A | 6/1986 | Eldridge, Jr. |
| 4,637,513 A | 1/1987 | Eldrige, Jr. |
| 4,736,844 A | 4/1988 | Scott |
| 4,809,850 A | 3/1989 | Laible |
| 4,938,354 A | 7/1990 | Hernandez |
| 4,969,893 A | 11/1990 | Swor |
| 5,005,590 A | 4/1991 | Eldridge, Jr. |
| 5,024,326 A | 6/1991 | Sandel |
| 5,036,866 A | 8/1991 | Eldrige, Jr. |
| 5,181,609 A | 1/1993 | Spielmann |
| 5,193,678 A | 3/1993 | Janocik |
| 5,316,142 A | 5/1994 | Jain |
| 5,344,005 A | 9/1994 | Kettner |
| 5,350,060 A | 9/1994 | Alpern |
| 5,353,974 A | 10/1994 | Maurizio |
| 5,361,902 A | 11/1994 | Abidin |
| 5,454,185 A | 10/1995 | Love |
| 5,538,132 A | 7/1996 | Propp |
| 5,566,822 A | 10/1996 | Scanlon |
| 5,615,766 A | 4/1997 | Gemma, Jr. |
| 5,617,952 A | 4/1997 | Kranendonk |
| 5,658,277 A | 8/1997 | Marshall |
| D382,995 S | 9/1997 | Hale |
| 5,665,810 A | 9/1997 | Patchett |
| 5,706,942 A | 1/1998 | Vila |
| 5,749,376 A | 5/1998 | Wilk |
| 5,787,820 A | 8/1998 | Dittoe |
| 5,788,062 A | 8/1998 | Cerwin |
| 5,799,788 A | 9/1998 | Webb |
| 6,159,224 A | 12/2000 | Yoon |
| 6,234,327 B1 | 5/2001 | Reed |
| 6,257,888 B1 | 7/2001 | Barham |
| 6,308,875 B1 | 10/2001 | Almo |
| 6,558,399 B1 | 5/2003 | Isbell |
| 6,663,582 B2 | 12/2003 | Ballard |
| 6,827,212 B2 | 12/2004 | Reaux |
| 6,854,598 B2 | 2/2005 | Koseki |
| 6,938,755 B2 | 9/2005 | Braginsky |
| 6,986,780 B2 | 1/2006 | Rudnick |
| 7,036,661 B2 | 5/2006 | Anthony |
| 7,208,004 B2 | 4/2007 | Murdoch |
| 7,402,164 B2 | 7/2008 | Watson, Jr. |
| 7,497,330 B2 | 3/2009 | Anthony |
| 7,513,363 B2 | 4/2009 | Brown |
| 7,763,038 B2 | 7/2010 | O'Brien |
| 7,770,365 B2 | 8/2010 | Enriquez, III |
| 7,815,046 B2 | 10/2010 | Sansoucy |
| 7,976,555 B2 | 7/2011 | Meade |
| 8,096,414 B2 | 1/2012 | Finnestad |
| 8,113,349 B2 | 2/2012 | Sansoucy |
| 8,118,163 B2 | 2/2012 | Alcouloumre |
| 8,418,851 B2 | 4/2013 | Culligan |
| 8,506,158 B2 | 8/2013 | Keung |
| 8,517,233 B2 | 8/2013 | Podda-Heubach |
| 8,568,391 B2 | 10/2013 | Kerns |
| 8,573,391 B2 | 11/2013 | Cerwin |
| 8,702,586 B2 | 4/2014 | Thierfelder |
| 8,727,189 B2 | 5/2014 | Zieman |
| 8,752,700 B1 | 6/2014 | Hoftman |
| 8,777,006 B2 | 7/2014 | Jatana |
| 8,800,766 B2 | 8/2014 | Sandel |
| 8,863,951 B2 | 10/2014 | Erickson |
| 8,869,978 B2 | 10/2014 | Margueritte |
| 9,307,982 B2 | 4/2016 | Gorek |
| 9,320,516 B2 | 4/2016 | Gorek |
| 9,433,408 B2 | 9/2016 | Gorek |
| 9,451,949 B2 | 9/2016 | Gorek |
| 9,572,568 B2 | 2/2017 | Gorek |
| 9,826,975 B2 | 11/2017 | Gorek |
| 9,936,948 B2 | 4/2018 | Gorek |
| 10,478,177 B2 | 11/2019 | Gorek |
| 10,485,534 B2 | 11/2019 | Gorek et al. |
| 10,603,033 B2 | 3/2020 | Gorek |
| 10,813,635 B2 | 10/2020 | Gorek |
| 10,987,100 B2 | 4/2021 | Gorek |
| 11,259,797 B2 * | 3/2022 | Gorek .............. A61B 17/06061 |
| 2001/0028860 A1 | 10/2001 | Fang |

(56) References Cited

U.S. PATENT DOCUMENTS

| | | |
|---|---|---|
| 2002/0029989 A1 | 3/2002 | Anthony |
| 2002/0088728 A1 | 7/2002 | Sugama |
| 2003/0155259 A1 | 8/2003 | Koseki |
| 2004/0020795 A1 | 2/2004 | Braginsky |
| 2004/0040873 A1 | 3/2004 | Koseki |
| 2004/0059269 A1 | 3/2004 | Ballard |
| 2004/0129591 A1 | 7/2004 | Koseki |
| 2004/0138004 A1 | 7/2004 | Grace |
| 2004/0222175 A1 | 11/2004 | Keating |
| 2005/0082188 A1 | 4/2005 | Reaux |
| 2005/0101990 A1 | 5/2005 | Aragon |
| 2007/0039845 A1 | 2/2007 | Kaforey |
| 2007/0055294 A1 | 3/2007 | Giap |
| 2007/0100266 A1 | 5/2007 | Hargrave |
| 2007/0135824 A1 | 6/2007 | O'Brien |
| 2008/0039767 A1 | 2/2008 | Nordt |
| 2008/0091221 A1 | 4/2008 | Brubaker |
| 2008/0208093 A1 | 8/2008 | Hassler |
| 2009/0005795 A1 | 1/2009 | Giap |
| 2009/0114667 A1 | 5/2009 | Sansoucy |
| 2009/0205996 A1 | 8/2009 | Celis |
| 2009/0266729 A1 | 10/2009 | Alcouloumre |
| 2009/0317002 A1 | 12/2009 | Dein |
| 2010/0084293 A1 | 4/2010 | Erickson |
| 2010/0095427 A1 | 4/2010 | Romiti |
| 2010/0187134 A1 | 7/2010 | Margueritte |
| 2010/0243688 A1 | 9/2010 | Gutierrez |
| 2010/0248601 A1 | 9/2010 | McGrogan |
| 2010/0258601 A1 | 10/2010 | Thrope |
| 2011/0046667 A1 | 2/2011 | Culligan |
| 2011/0106142 A1 | 5/2011 | Van Furth |
| 2011/0163137 A1 | 7/2011 | Podda-Heubach |
| 2012/0210678 A1 | 8/2012 | Alcouloumre |
| 2012/0259239 A1 | 10/2012 | Chenaux |
| 2013/0146626 A1 | 6/2013 | Garnett |
| 2013/0269713 A1 | 10/2013 | Bui |
| 2014/0039527 A1 | 2/2014 | Rui |
| 2014/0110290 A1 | 4/2014 | Choudhury |
| 2014/0299739 A1 | 10/2014 | Bradow |
| 2015/0108021 A1 | 4/2015 | Erickson |
| 2015/0305735 A1 | 10/2015 | Gorek |
| 2015/0313673 A1 | 11/2015 | Erickson |
| 2015/0320416 A1 | 11/2015 | Gorek |
| 2015/0320418 A1 | 11/2015 | Gorek |
| 2015/0320419 A1 | 11/2015 | Gorek |
| 2018/0055511 A1 | 3/2018 | Gorek |
| 2018/0185025 A1 | 7/2018 | Gorek |
| 2019/0053800 A1 | 2/2019 | Gorek |
| 2020/0345350 A1 | 11/2020 | Gorek |
| 2020/0405299 A1 | 12/2020 | Trauner |

FOREIGN PATENT DOCUMENTS

| | | |
|---|---|---|
| CN | 201453312 U | 5/2010 |
| EP | 0498460 A1 | 8/1992 |
| EP | 2586397 | 5/2013 |
| GB | 2502141 | 11/2013 |
| JP | 2003126097 | 5/2003 |
| JP | 2003126097 A | 5/2003 |
| JP | 2013099395 | 5/2013 |
| JP | 2013099395 A | 5/2013 |
| WO | 0202017 | 1/2002 |
| WO | 2005102180 | 11/2005 |
| WO | 2009019021 | 2/2009 |
| WO | 2015164830 A1 | 10/2015 |
| WO | 2017075548 A1 | 5/2017 |

OTHER PUBLICATIONS

International Search Report and Written Opinion for International Application No. PCT/US2016/059599 (dated Mar. 17, 2017).

* cited by examiner

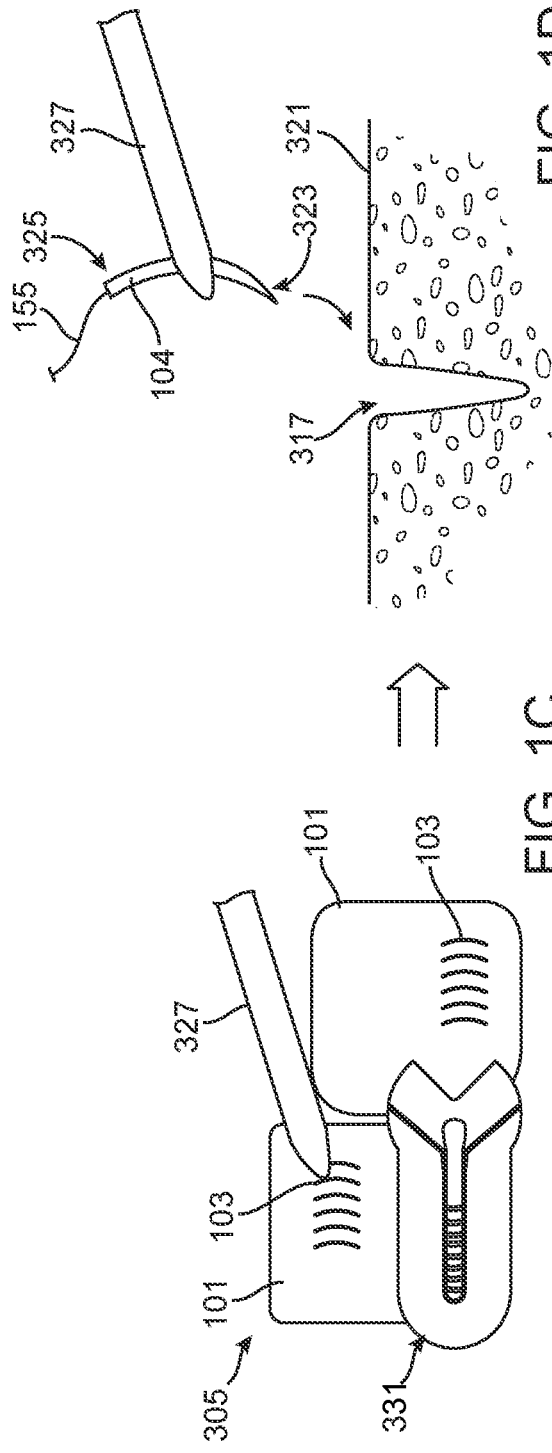

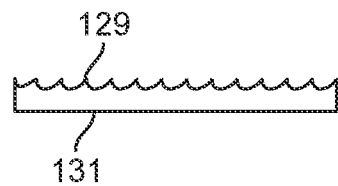
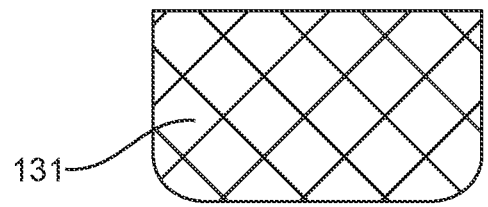
FIG. 23  FIG. 24
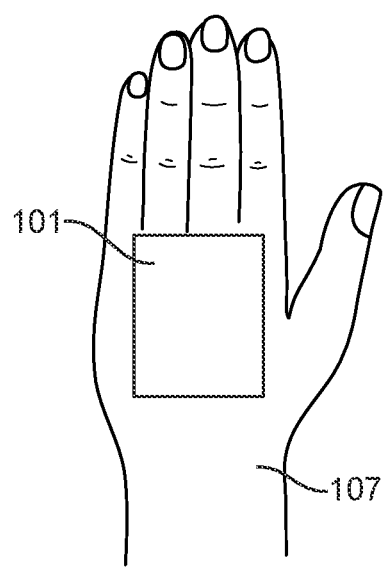
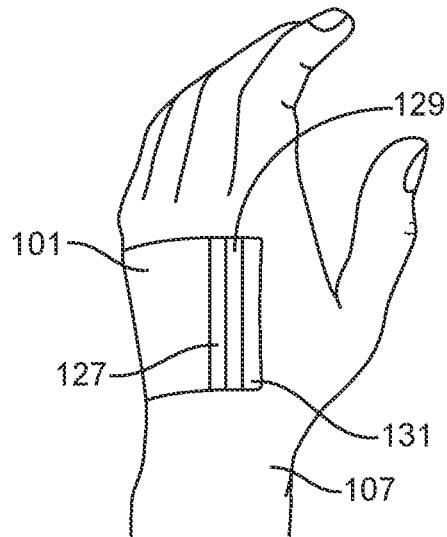
FIG. 25  FIG. 26

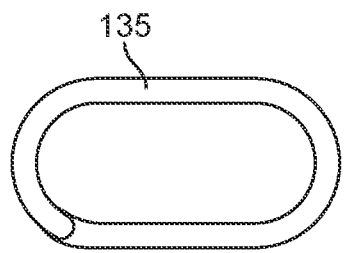 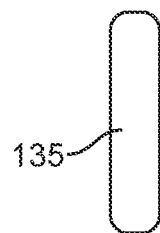
FIG. 29  FIG. 30
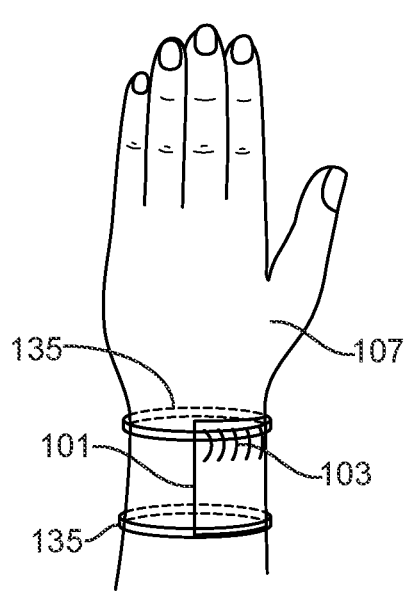 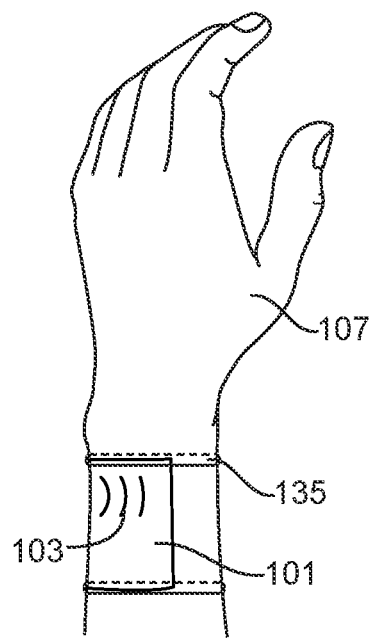
FIG. 31  FIG. 32
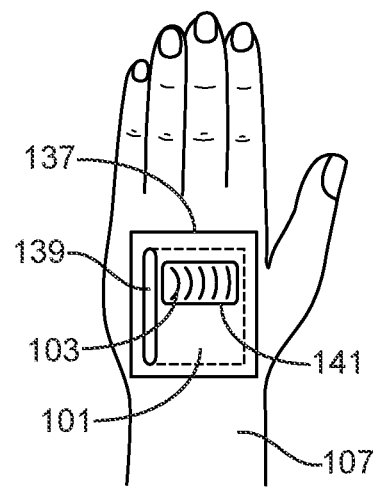 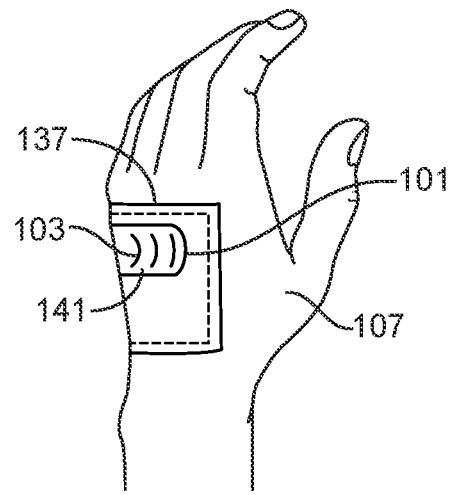
FIG. 33  FIG. 34

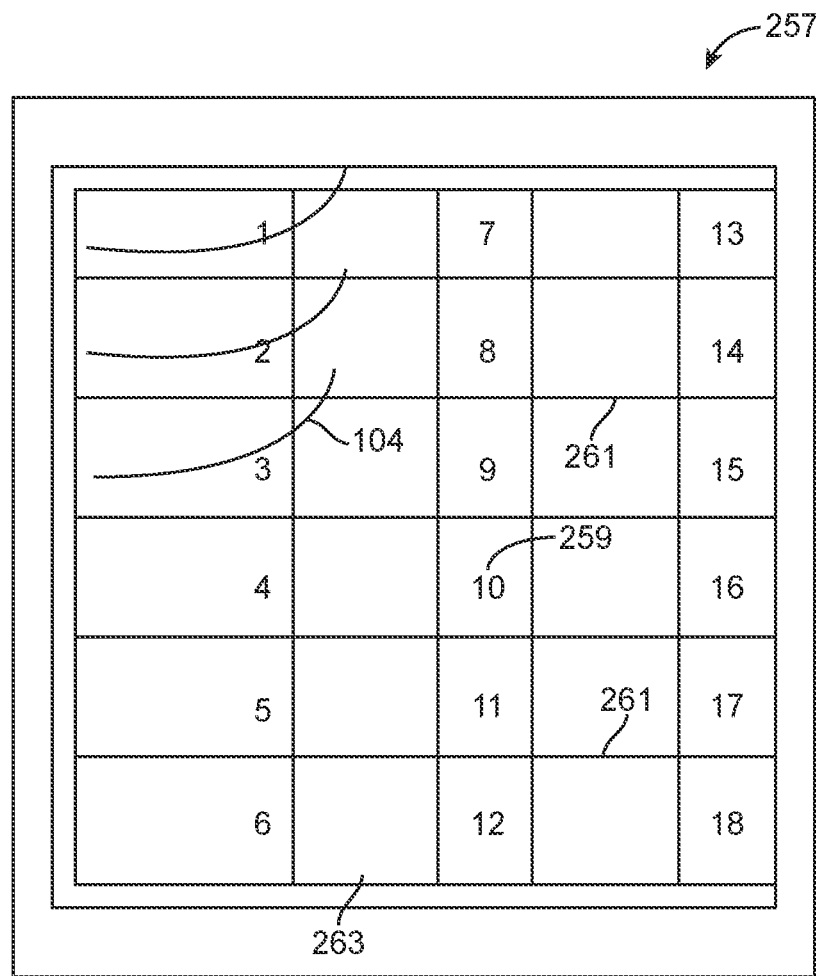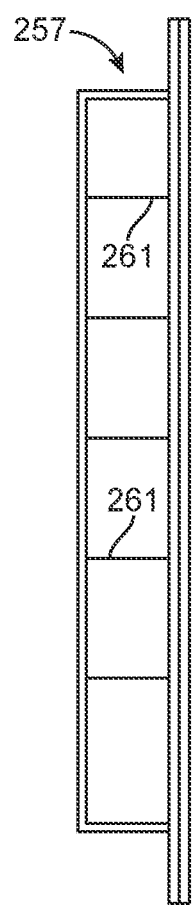
FIG. 111  FIG. 112
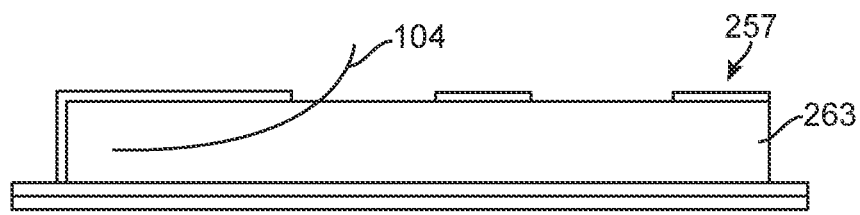
FIG. 113

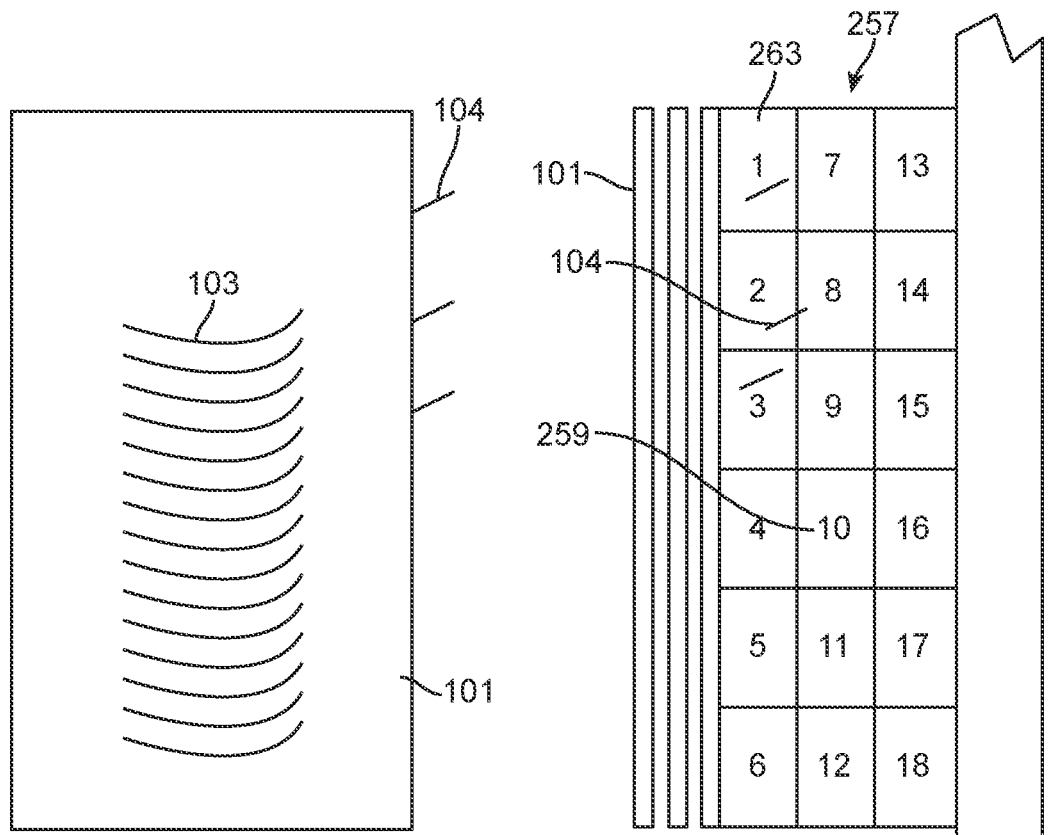
FIG. 114
FIG. 115
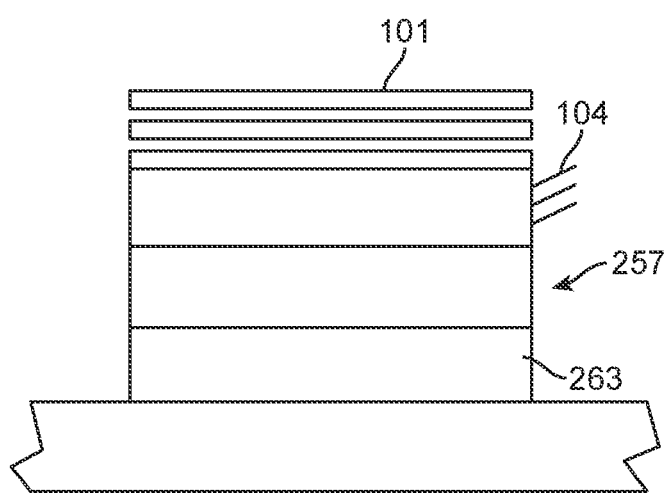
FIG. 116

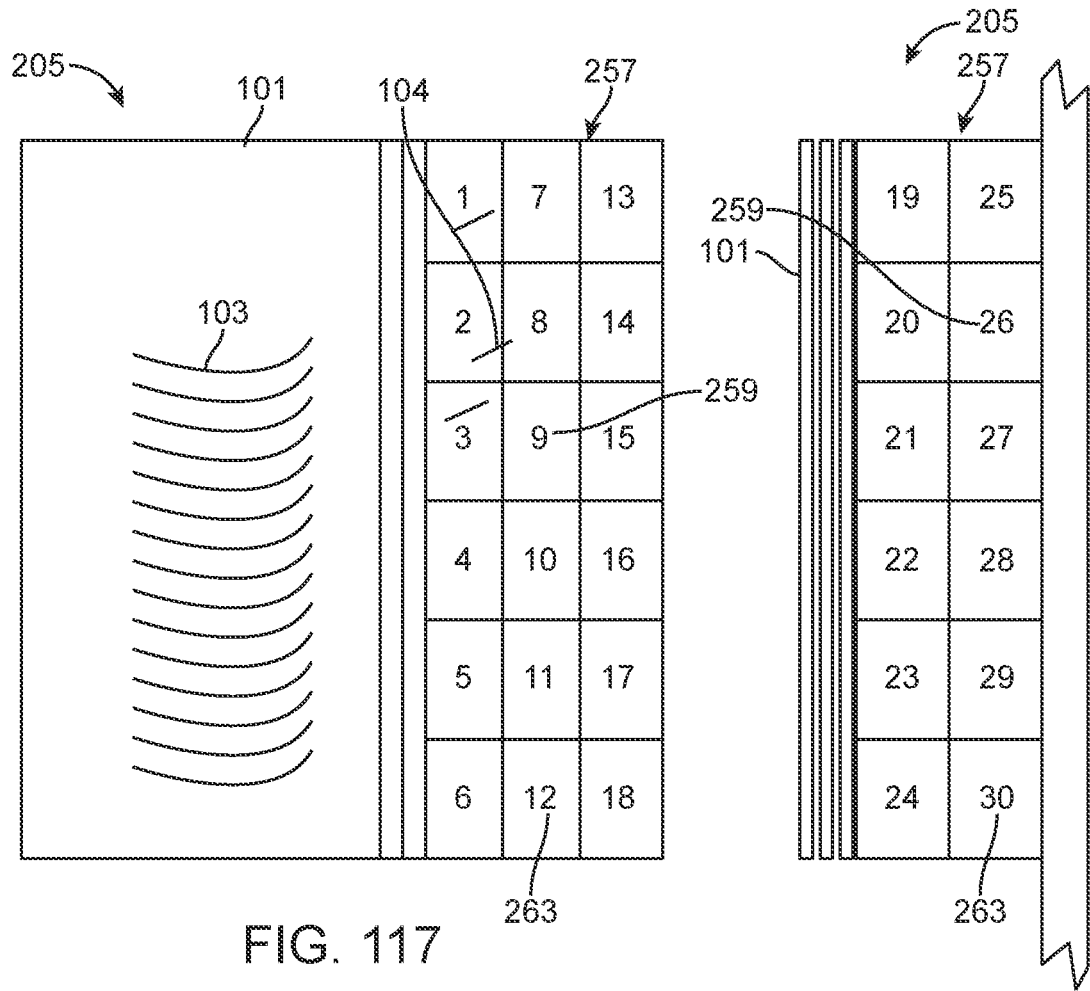
FIG. 117
FIG. 118
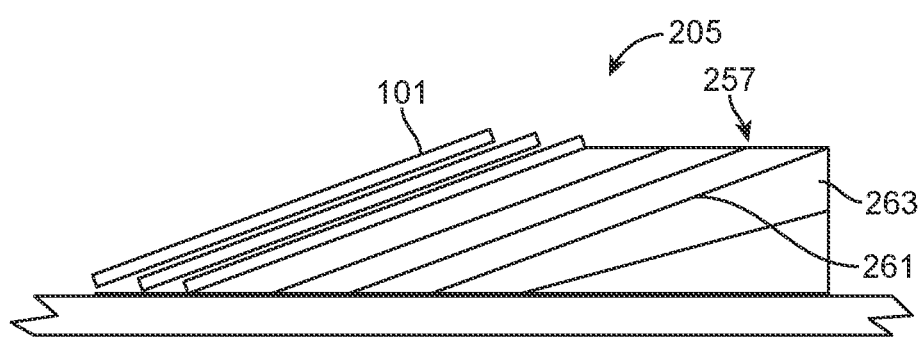
FIG. 119

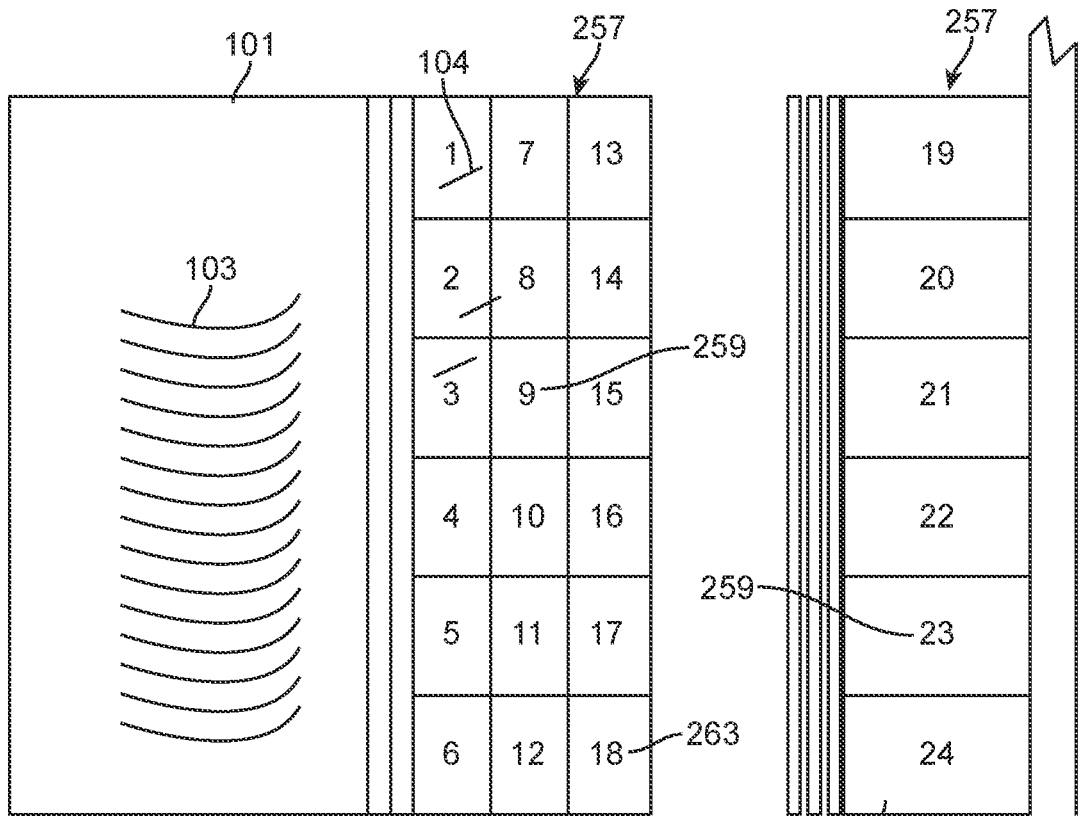
FIG. 120
FIG. 121
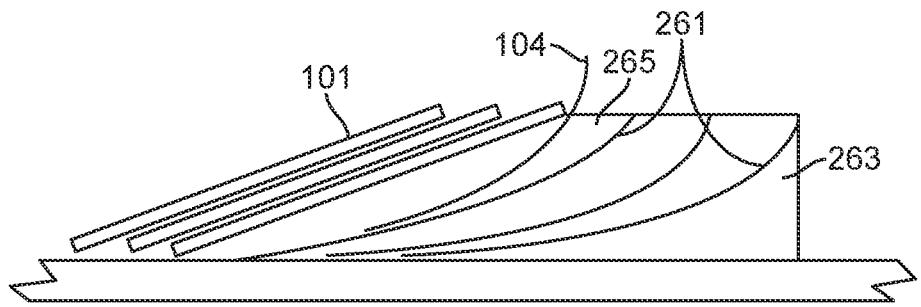
FIG. 122

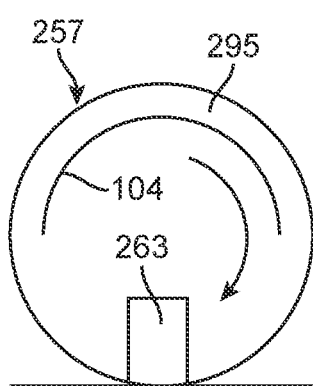
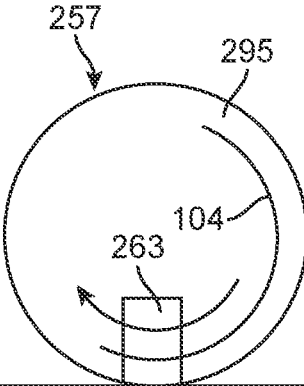
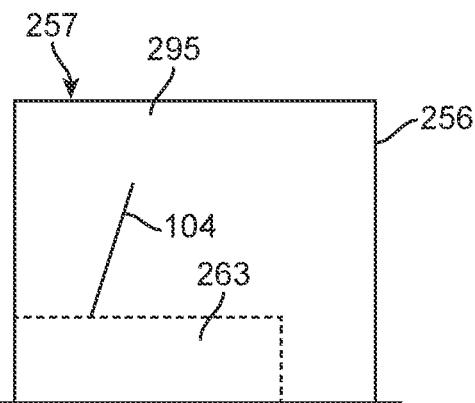
FIG. 223　　FIG. 224　　FIG. 225
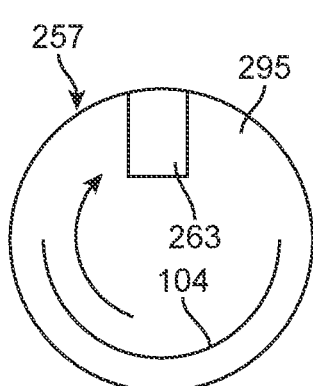
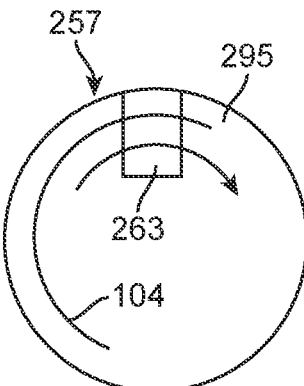
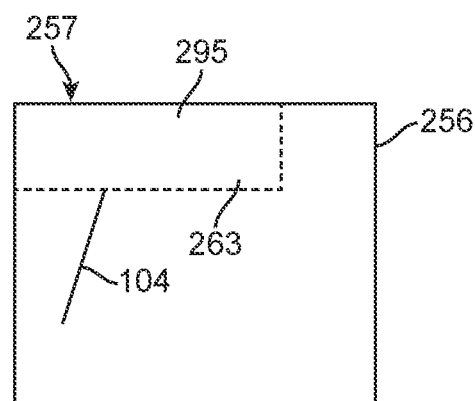
FIG. 226　　FIG. 227　　FIG. 228

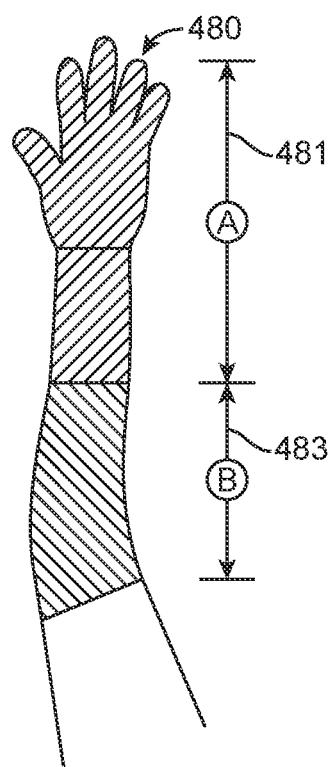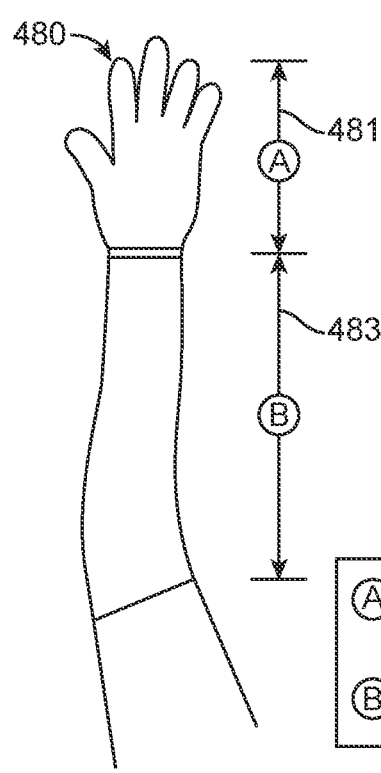
FIG. 286  FIG. 287
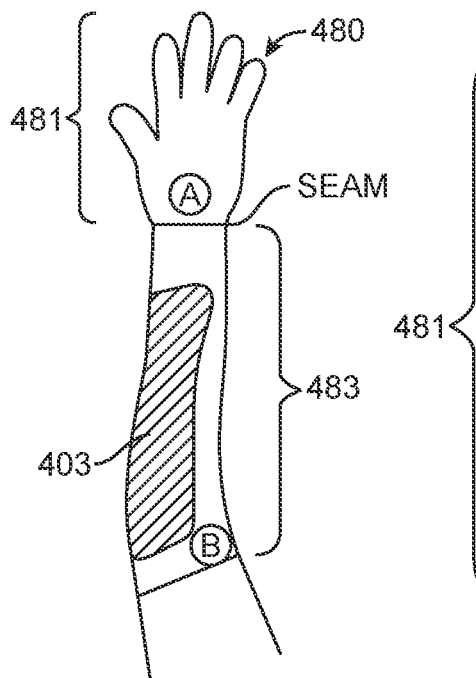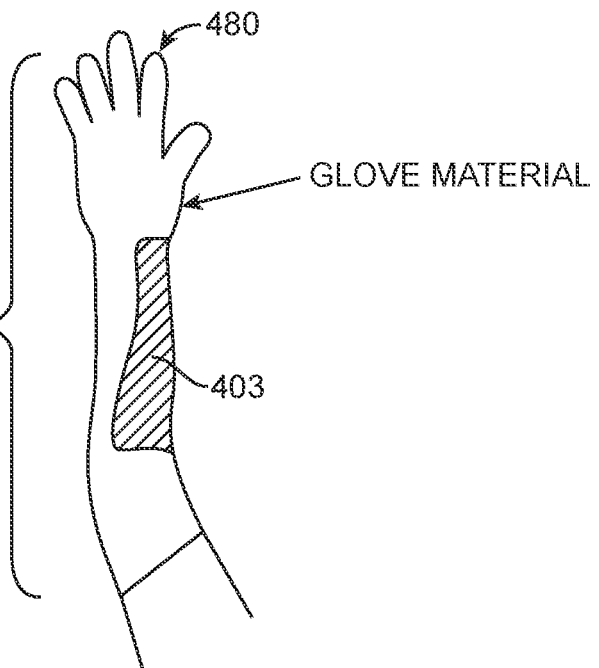
FIG. 288  FIG. 289

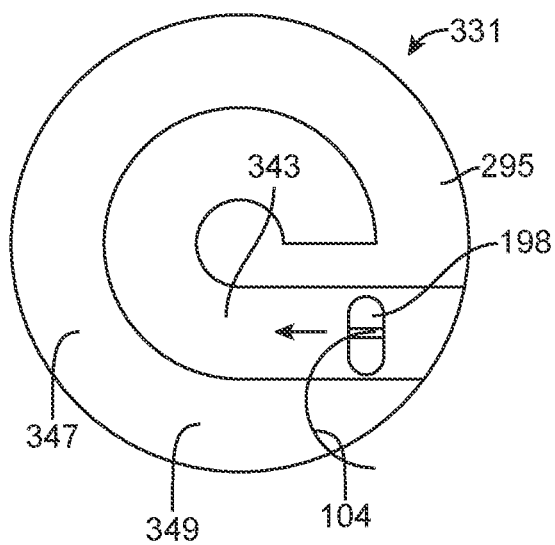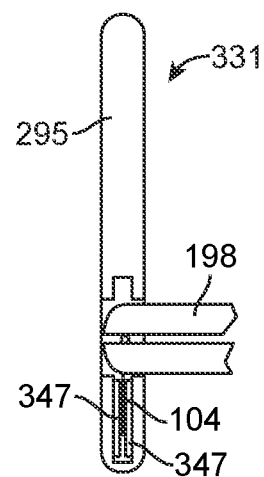
FIG. 299　　　　　　　FIG. 300
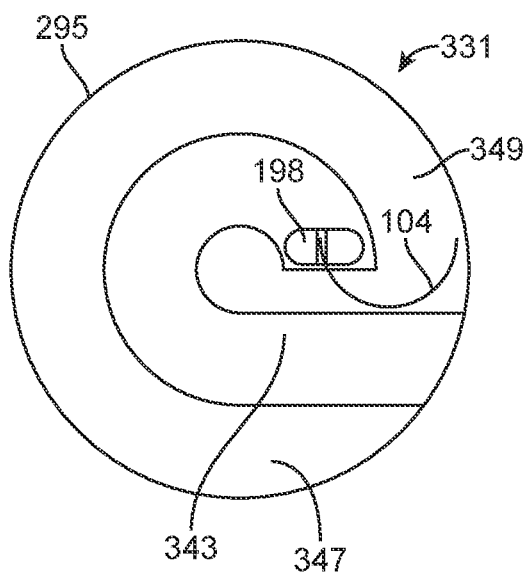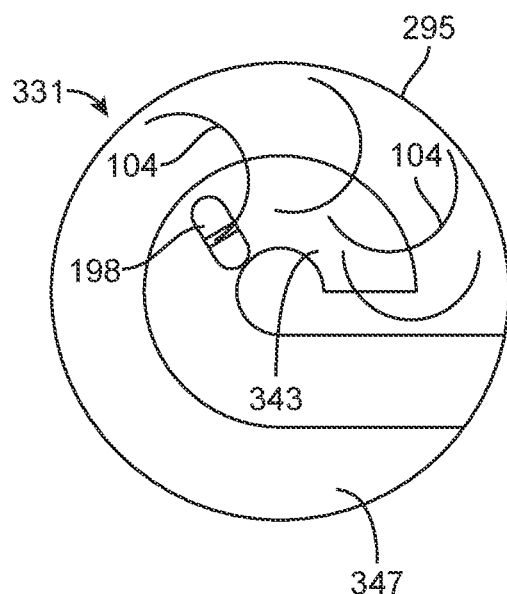
FIG. 301　　　　　　　FIG. 302

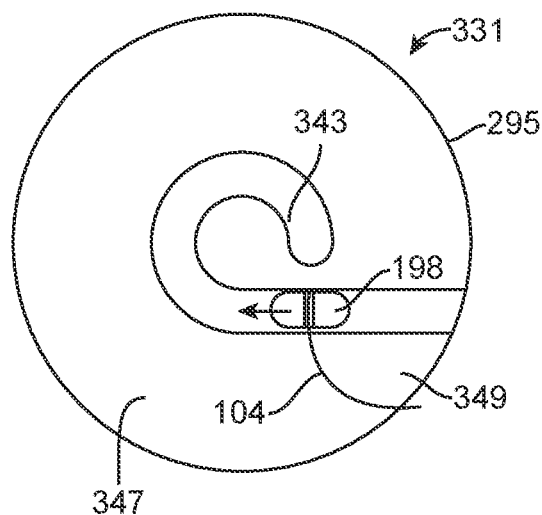
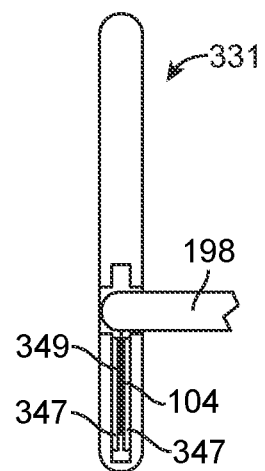
FIG. 303   FIG. 304
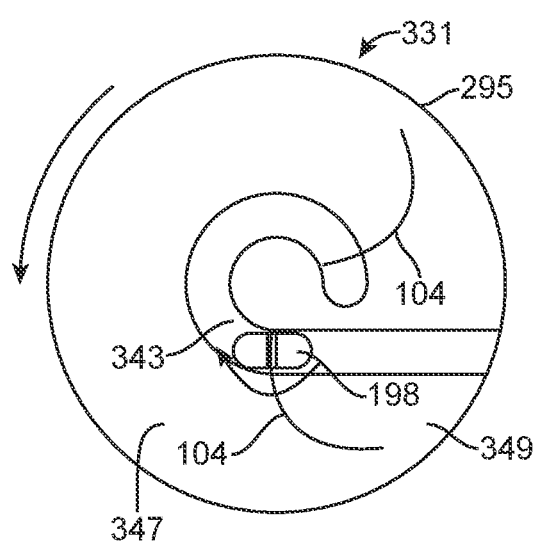
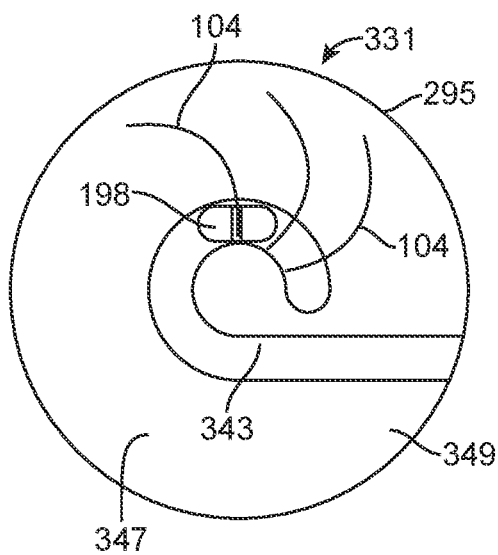
FIG. 305   FIG. 306

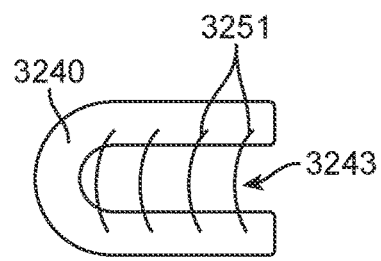
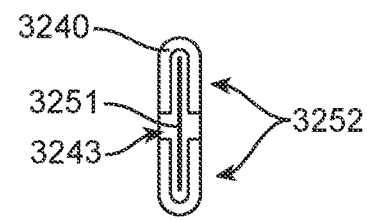
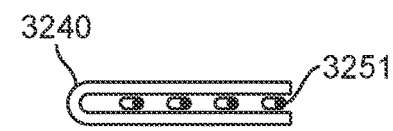
FIG. 325A  FIG. 325B  FIG. 325C
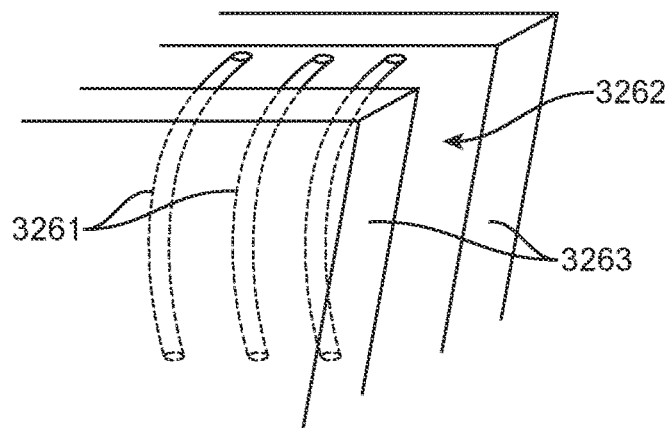
FIG. 326A
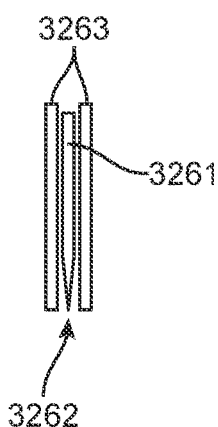
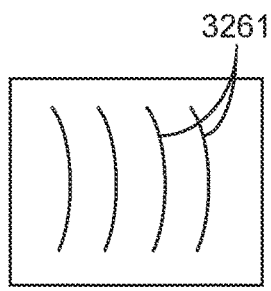
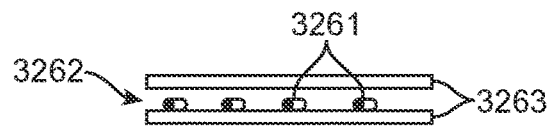
FIG. 326B  FIG. 326C  FIG. 326D

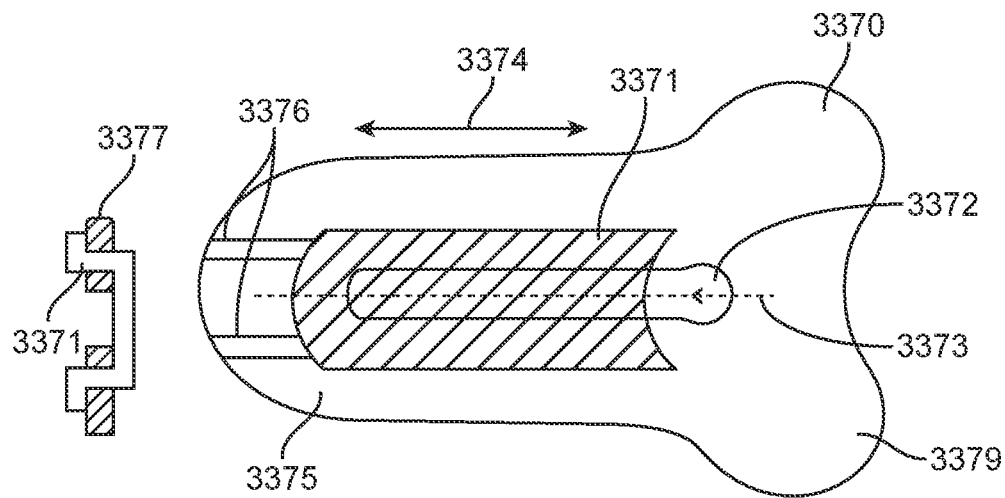
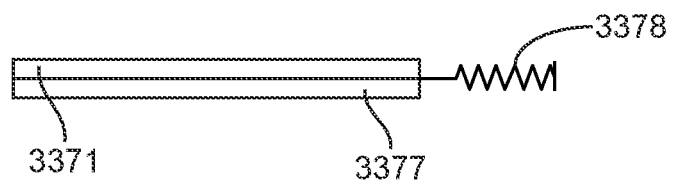
FIG. 337B  FIG. 337A
FIG. 337C
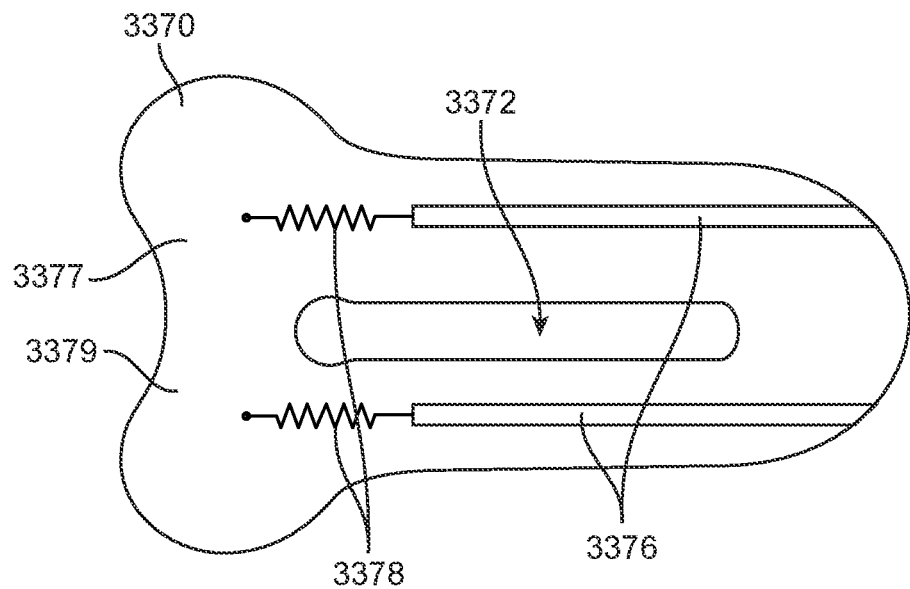
FIG. 337D

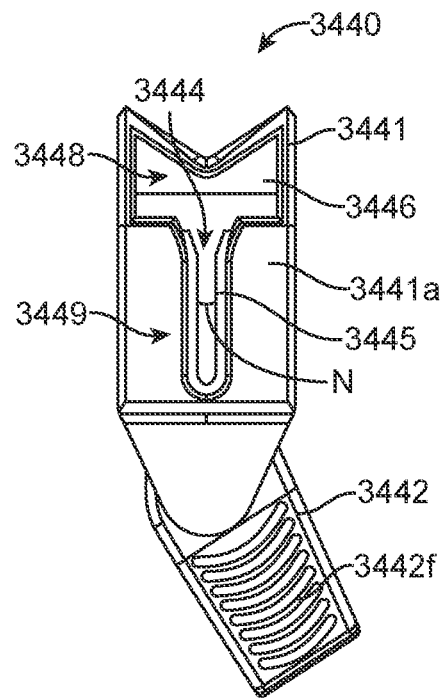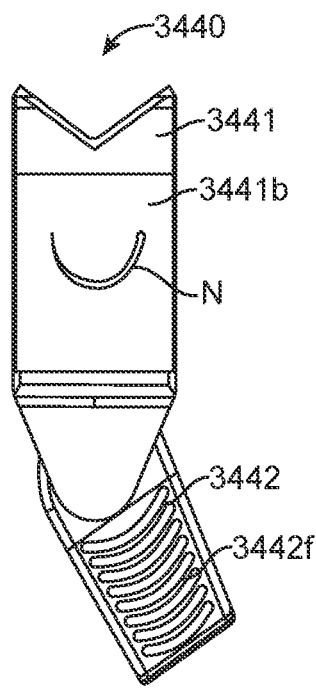
FIG. 344A  FIG. 344B
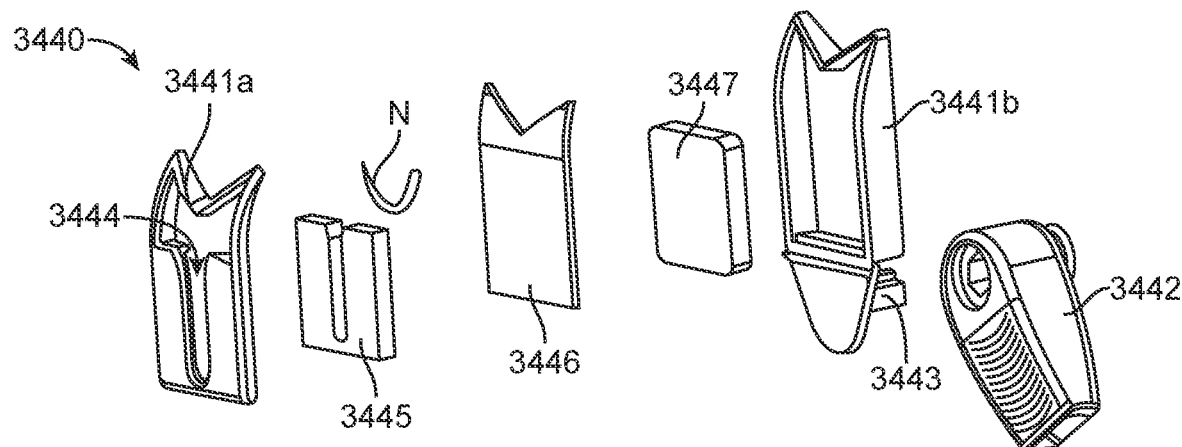
FIG. 344C

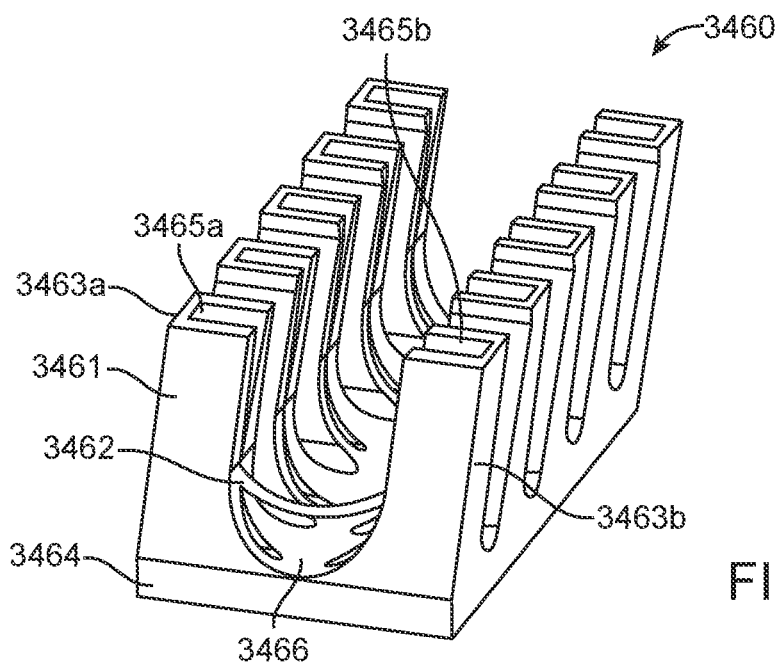
FIG. 346
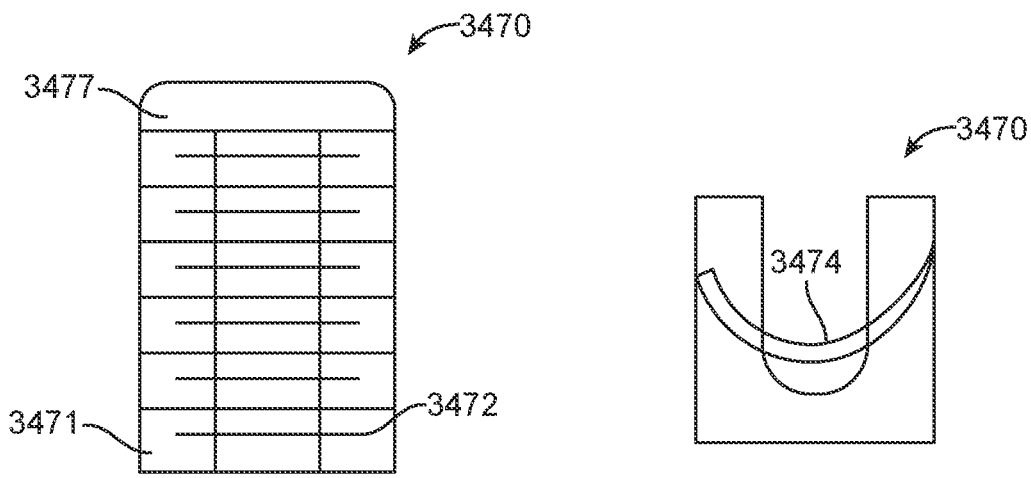
FIG. 347A
FIG. 347C
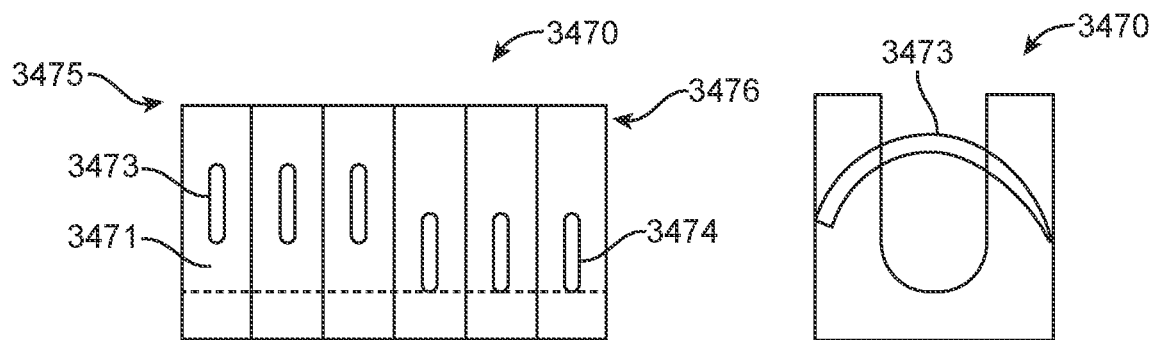
FIG. 347B
FIG. 347D

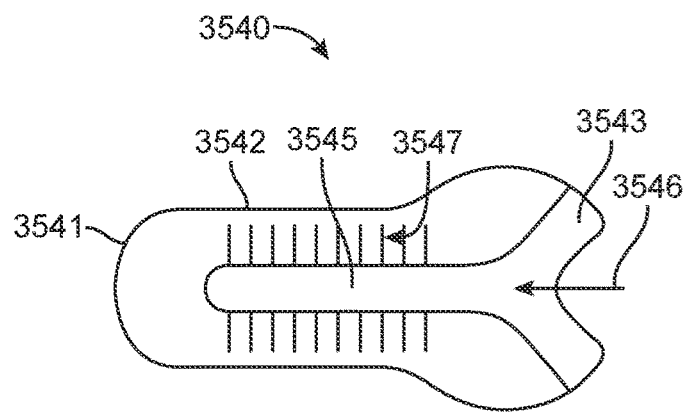
FIG. 354A
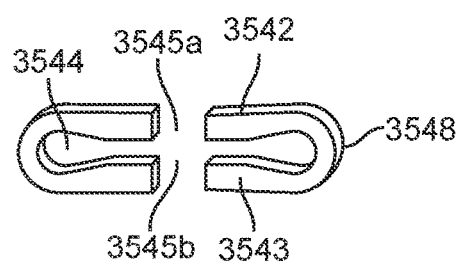
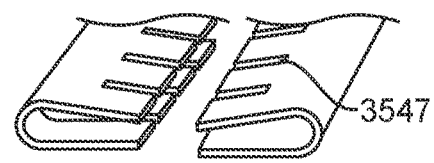
FIG. 354B
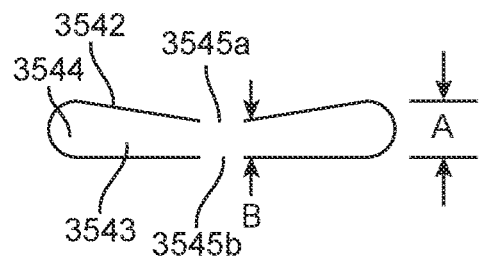
FIG. 354C
FIG. 354D
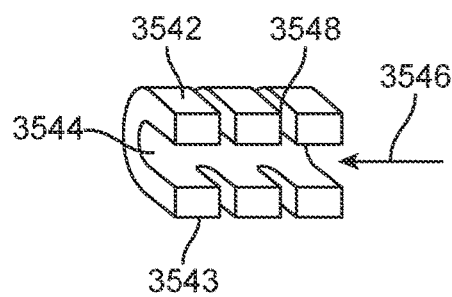
FIG. 354E
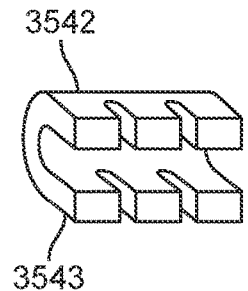
FIG. 354F
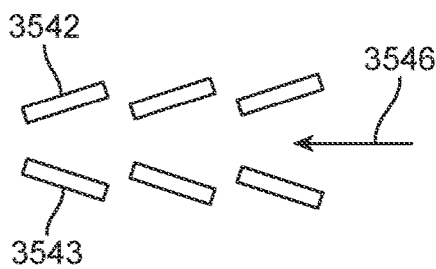
FIG. 354G

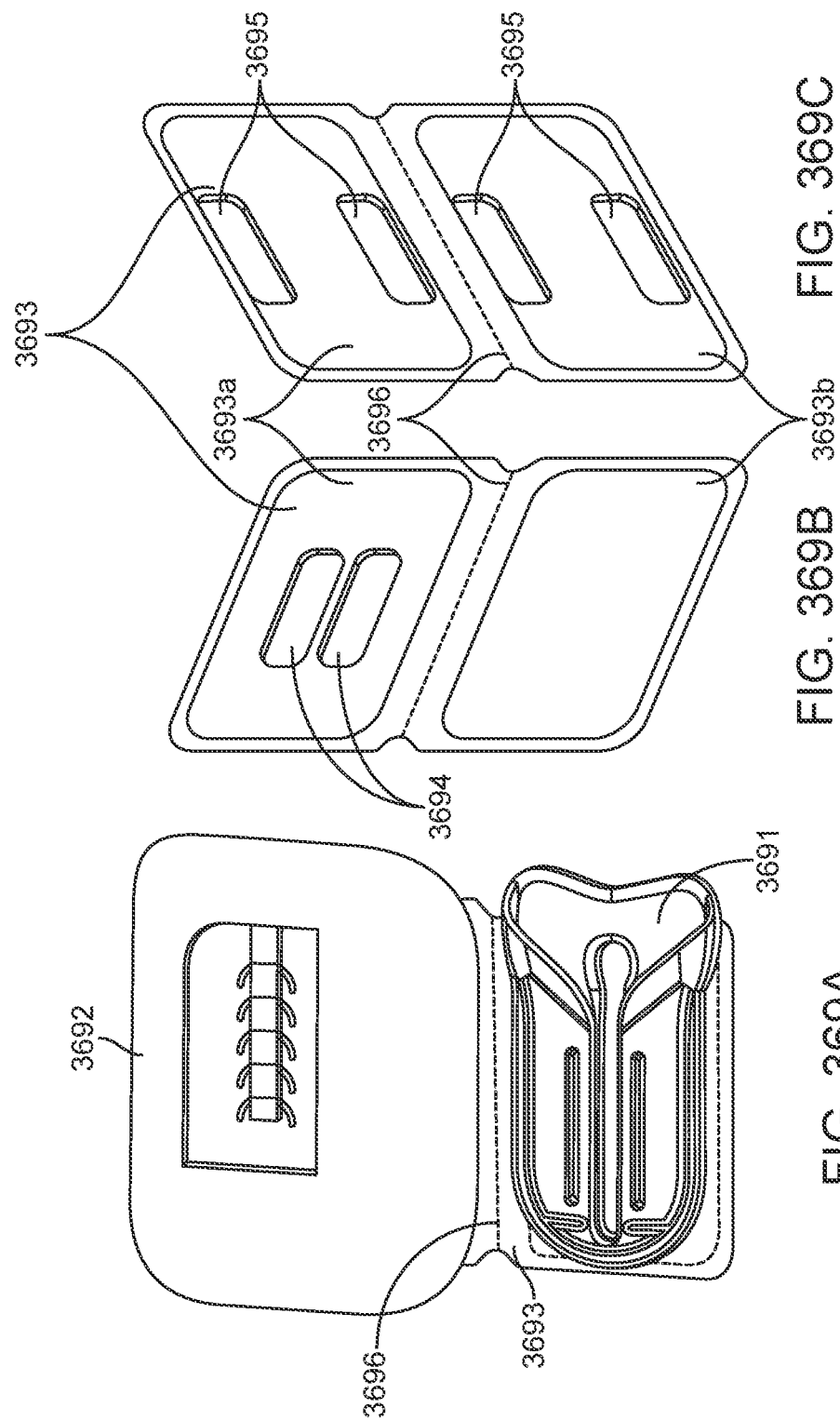

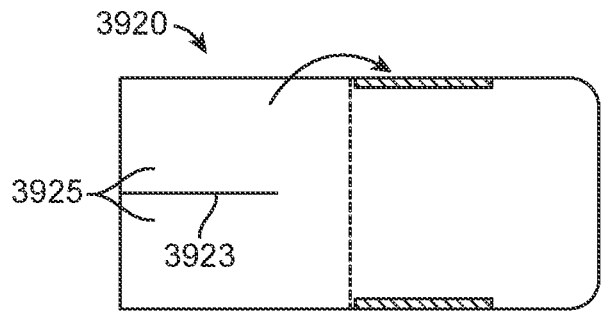
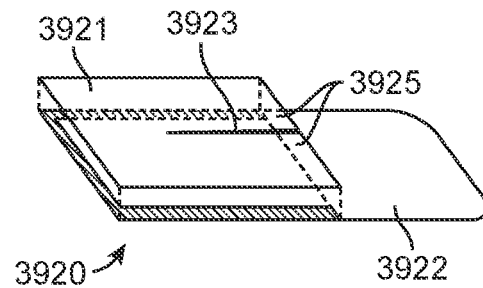
FIG. 392A1            FIG. 392A2
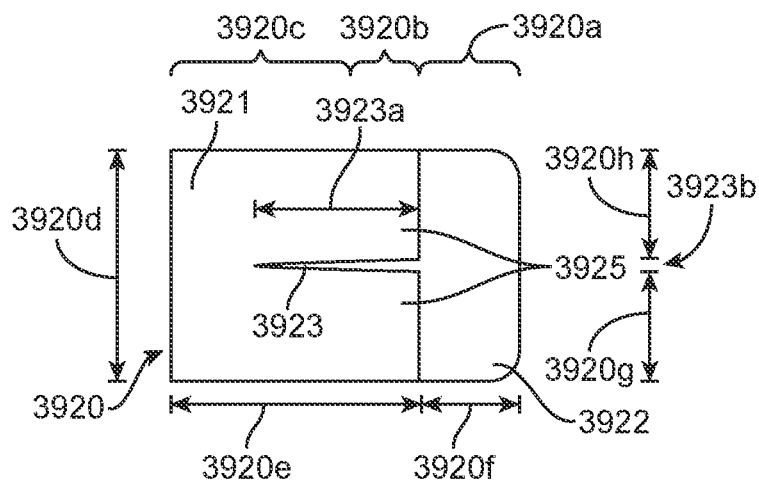
FIG. 392A3
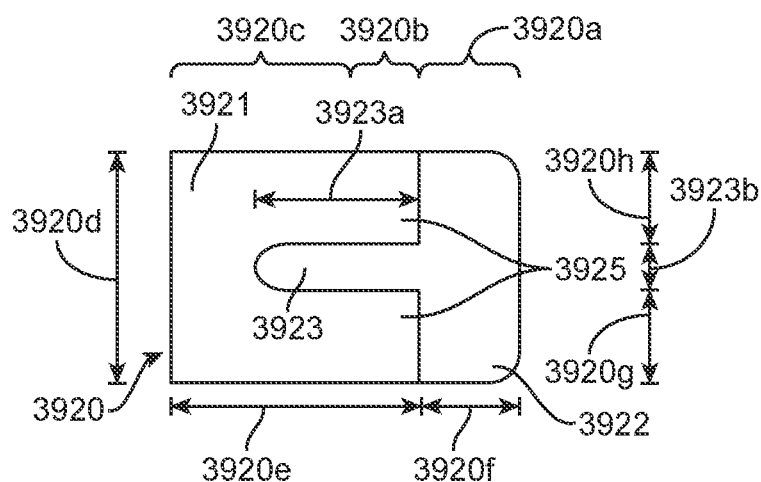
FIG. 392A4

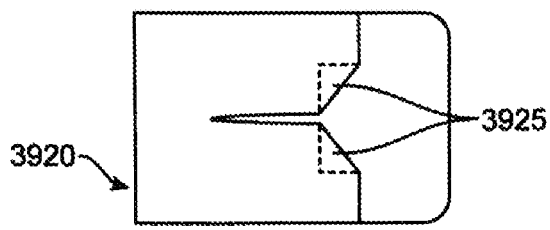
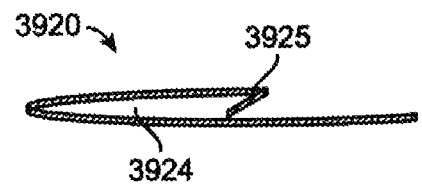
FIG. 392A5     FIG. 392A6
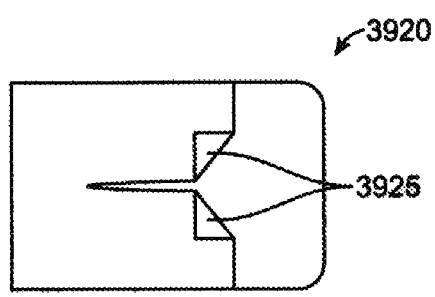
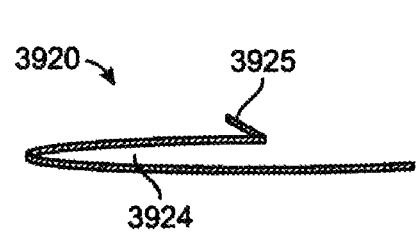
FIG. 392A7     FIG. 392A8
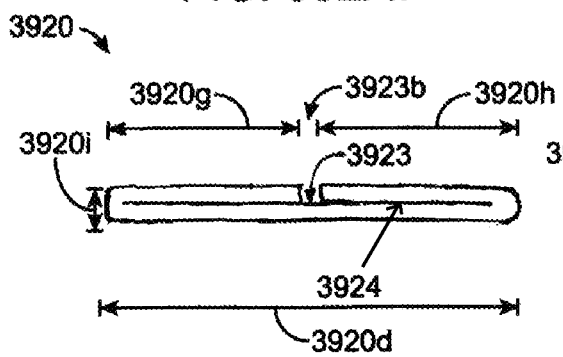
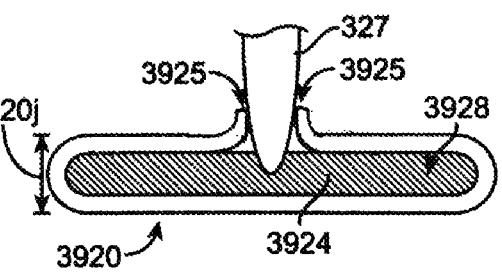
FIG. 392A9     FIG. 392A10
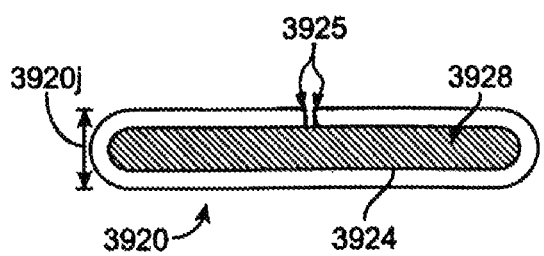
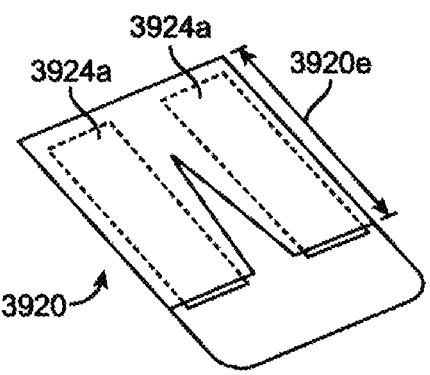
FIG. 392A11     FIG. 392A12

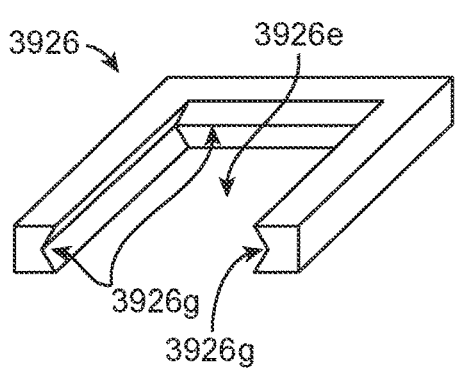
FIG. 392B1
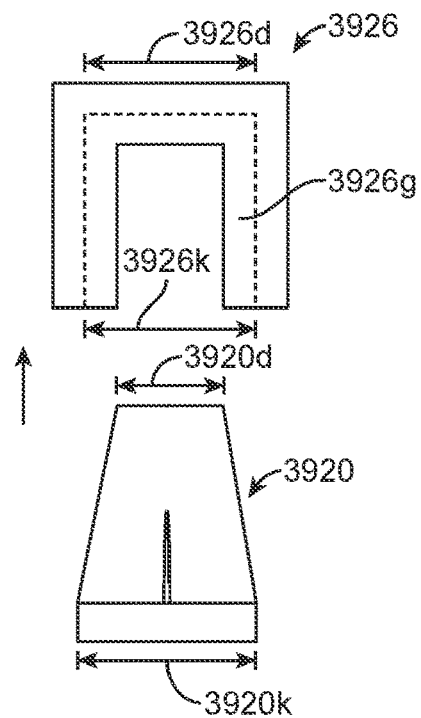
FIG. 392B2
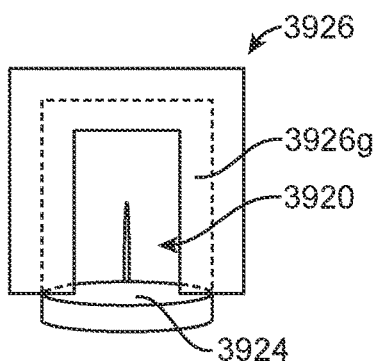
FIG. 392B3
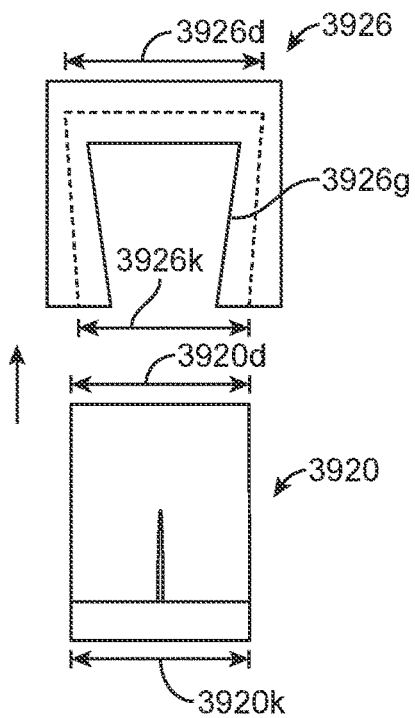
FIG. 392B4
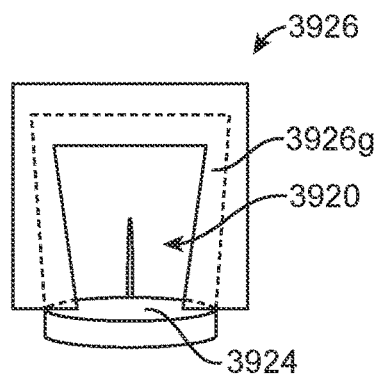
FIG. 392B5

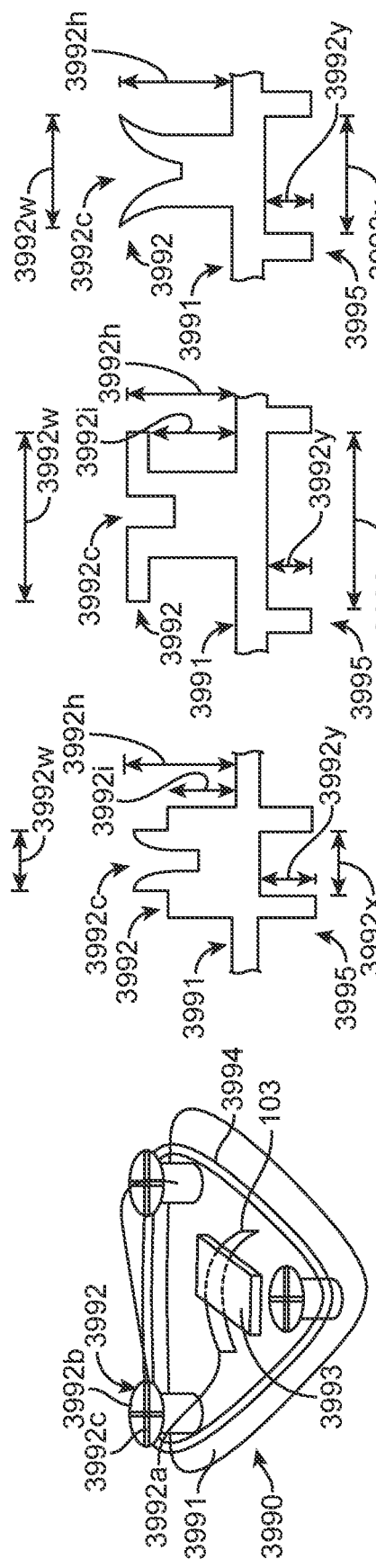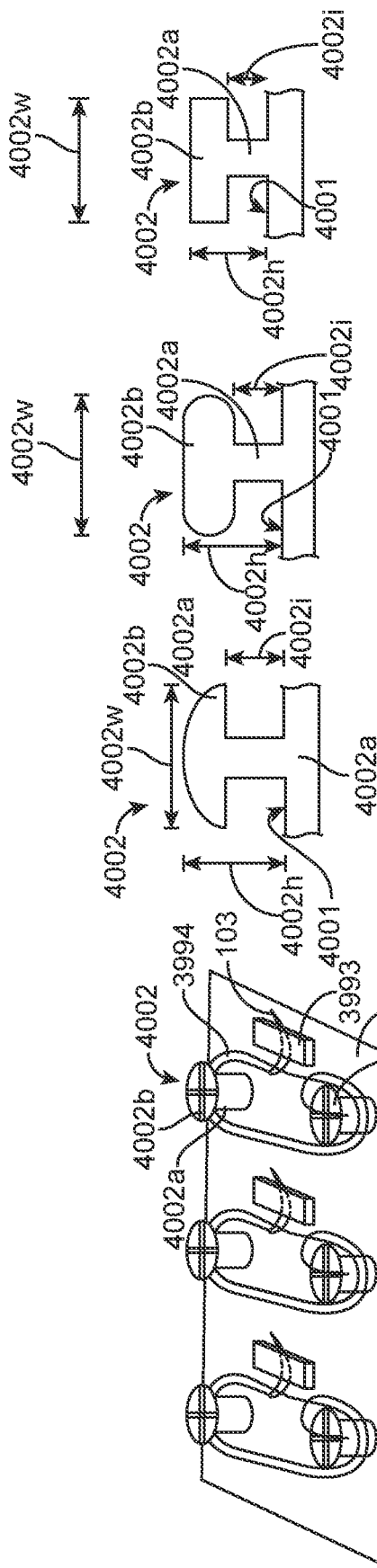

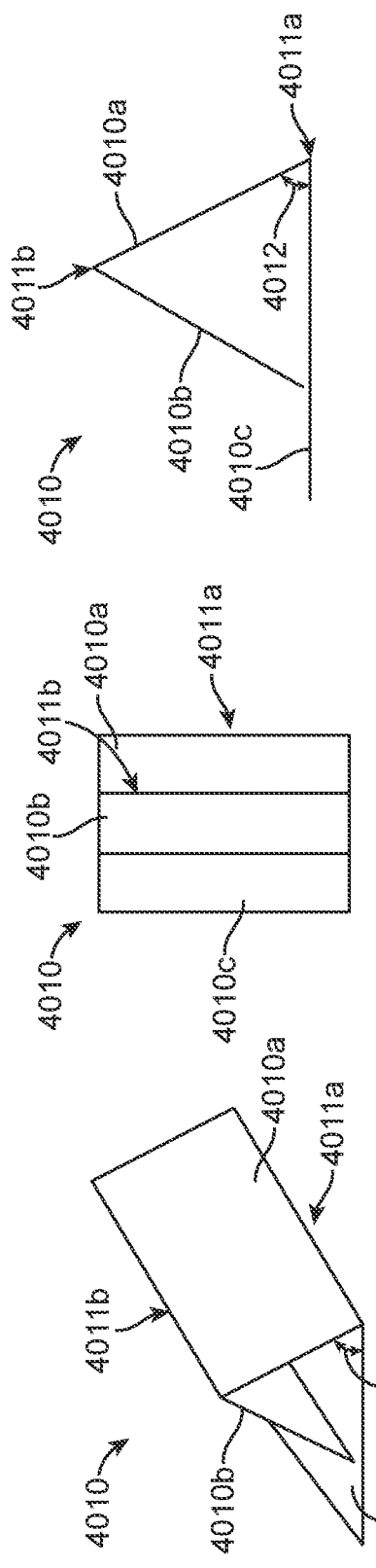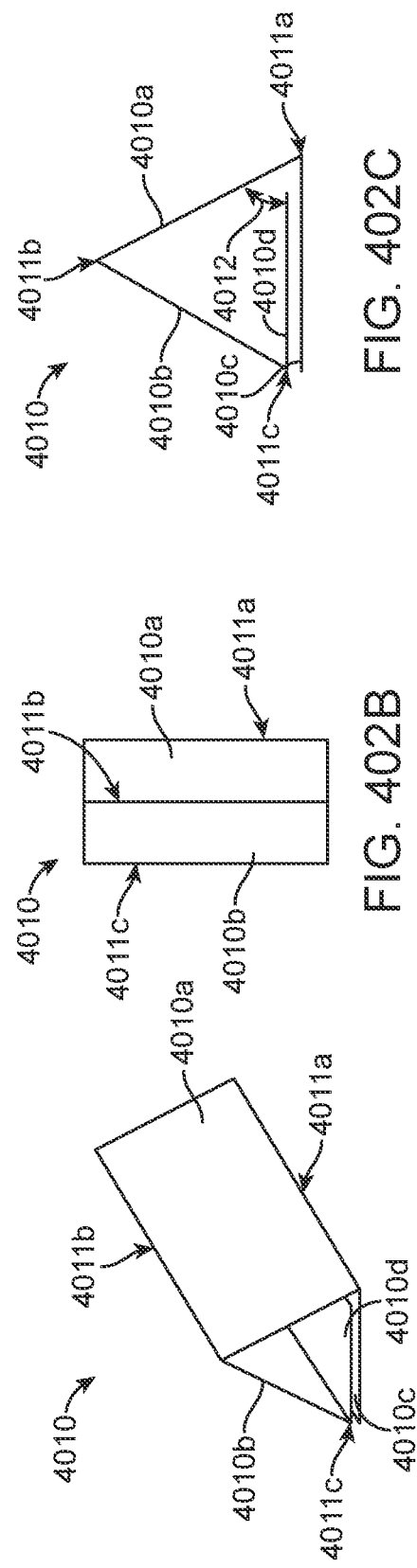

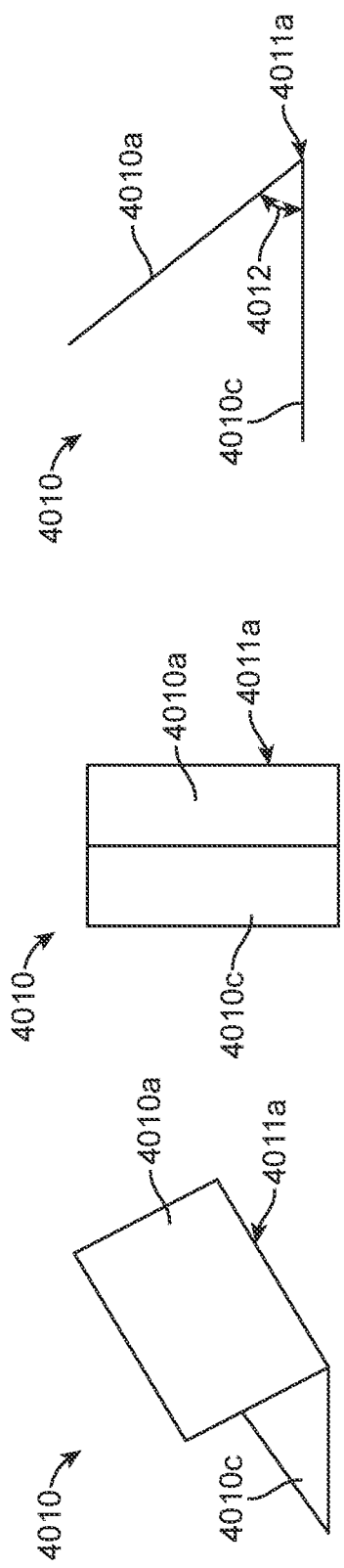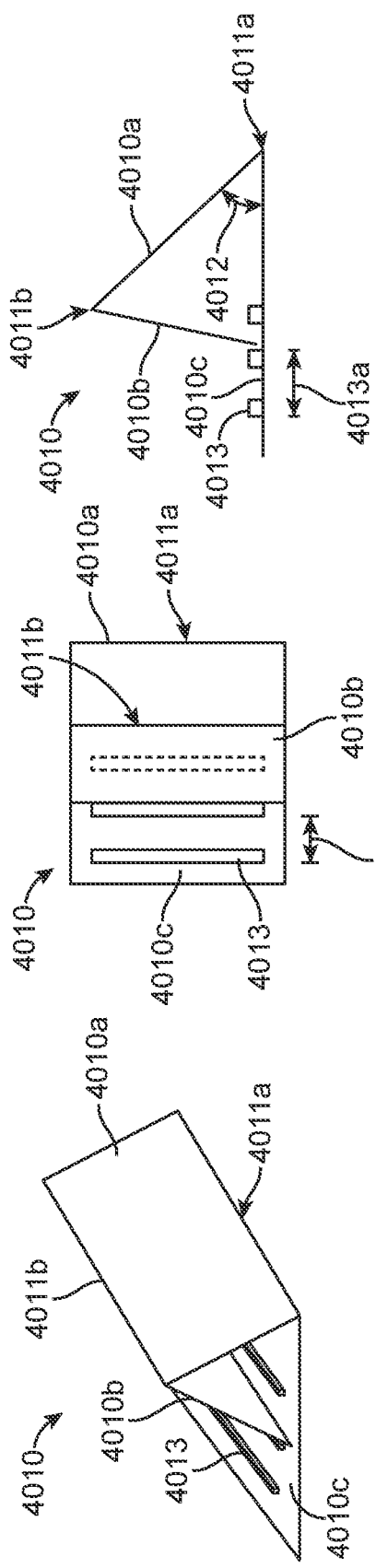

NEEDLE RECEPTACLE FOR INCREASED OPERATING ROOM EFFICIENCY

RELATED APPLICATIONS

This application is a continuation of U.S. patent application Ser. No. 16/782,825, filed Feb. 5, 2020, now U.S. Pat. No. 10,987,100, issued Apr. 27, 2021, which is a continuation of U.S. patent application Ser. No. 16/566,704, filed Sep. 10, 2019, now U.S. Pat. No. 10,603,033, issued Mar. 31, 2020, which is a continuation of U.S. patent application Ser. No. 16/167,369, filed Oct. 22, 2018, now U.S. Pat. No. 10,478,177, issued Nov. 19, 2019, which is a continuation of U.S. patent application Ser. No. 15/895,896, filed Feb. 13, 2018, now U.S. Pat. No. 10,485,534, issued Nov. 26, 2019, which is a continuation of International Patent Application No. PCT/US2016/059599, filed Oct. 28, 2016, published as WIPO Publication No. WO 2017/075548 on May 4, 2017, which claims the benefit under 35 U.S.C. § 119(e) of U.S. Provisional Application No. 62/248,029, filed Oct. 29, 2015, the entire disclosures of which are incorporated herein by this reference.

The subject matter of the present application is related to U.S. application Ser. No. 14/697,050, filed on Apr. 27, 2015, now U.S. Pat. No. 9,451,949, issued Sep. 27, 2016, and International Application No. PCT/US2015/027659, filed Apr. 24, 2015, published as WIPO Publication No. WO 2015/164830 on Oct. 29, 2015, the entire contents of which are incorporated herein by this reference.

BACKGROUND

The use of an operating room can present expensive medical service costs. It is estimated that operating room time can cost between about $30 to $100 per minute. An operating room must be sterilized before each operation and the medical staff must also prepare for the operation. Because each employee is usually paid for their time in the operating room, the operating room use costs can be very high. By increasing the efficiency of the employees within the operating room, the time for each procedure can be reduced and the cost of the surgery can also be reduced. Further, it is important to account for surgical objects such as needles and sponges during a surgical procedure. If a needle becomes lost during the surgery, steps need to be taken to ensure patient safety and that the needle has not been accidently left in the patient. Accounting for needles during a surgical procedure in an accurate manner can be time-consuming. Therefore, it would be desirable to provide improved ways to keep track of used needles in an operating room. Also, needle puncture through a surgical glove can present risks to operating room personnel.

The process of loading a needle holder is often carried out by those personnel assisting the surgeon in the process of surgery. A scrub technician or surgical assistant can pass the loaded needle holder to the surgeon. Both unused needles not yet having been used and those already used needles can be maintained on an instrument tray such as a Mayo stand, and an accounting of the needles is often made by the surgical assistant and circulating nurse during the course of surgery.

At the time of surgical incision wound closure, or other tissue repair, during which multiple armed sutures are to be utilized, the surgical assistant can be fully focused on the needs of the surgeon. The assistant passes the loaded needle holder to the surgeon's hand for use.

Used needles may be dispensed and accounted for in a less than optimal and safe manner. As a substitute for having the loaded needle driver passed to the surgeon, the surgeon may awkwardly load the armed suture himself. This often requires the surgeon turning to the instrument tray (e.g., Mayo stand), locating the suture package, and grasping and orienting the package such that the needle can be effectively and properly loaded onto the needle holder, which takes additional time and movement than would be ideal and undesirably directs the surgeons attention away from the patient.

In prior neutral zone approach, objects and instruments that are passed between a scrub tech and a surgeon must be placed in a neutral zone area. The process may require a scrub tech to place the object into the neutral zone and the surgeon cannot pick up the object until the scrub tech's hands are removed from the neutral zone. Similarly when the surgeon no longer needs a surgical object, it is placed in the neutral zone and the surgeon's hand removed. This system is less than ideal because the surgeon and scrub tech must often be very careful and clearly communicate and look at the neutral zone, away from the site of the operation, when any objects are passed. This can be particularly difficult when trying to perform actions quickly which can easily happen in an operating room procedure, for example when attempting to save a patient's life.

In many currently used suture handling methods and systems, the surgeon can be handed a needle driver with an armed suture needle. The surgeon may drive the needle through the flesh of the patient and then hands the needle driver with used needle to the scrub tech. The scrub tech then moves the used needle away from the surgical field and removes the used needle. The scrub tech then places a new armed needle in the needle driver and then hands the surgeon the needle driver. The described process is repeated, and results in more movement than would be ideal.

In addition to being highly inefficient, such systems can also have poor micro-ergonomics.

In light of the above, improved methods and apparatus are needed to improve operating rooms. Ideally such methods and apparatus would provide improved efficiency, outcomes, needle handling, counting, and safety.

SUMMARY

The present invention relates to systems and methods for increasing operating room efficiency. Although specific reference is made to dispensing and securing needles, the embodiments described herein are well suited for use with many types of objects used in an operating room, such as sharp objects.

Systems and methods for improving operating room efficiency as described herein improve the manner in which surgeons' access and dispose of objects used in surgery such as sutures and needles. The methods and apparatus disclosed herein can improve safety by decreasing the number of needle passes between the surgeon and assistant, and by placing needles in a receptacle prior to being passed from the surgeon to the assistant.

Many embodiments relate to the dispensing and loading of surgical needles that can be facilitated and made more efficient and ergonomic by associating the needles, sutures and the packaging onto the surgeon's forearm, wrist, and/or hand. Furthermore and in many embodiments, the invention relates to the association of used needle temporary storage device as associated with the surgeon's forearm, wrist, and/or hand. The association of the surgeon's forearm wrist and/or hand can be accomplished in many ways, such as with mounting onto the surgeon's forearm wrist or hand, mounting to a surgical instrument such as forceps, or with a support extending into a near surgical field of the surgeon, and combinations thereof. Packaging and devices as described herein facilitate the safe and efficient dispensing of armed sutures in the proper orientation from the surgeon's forearm, wrist, and/or hand for use by the surgeon. Alternatively or in combination, the sutures can be dispensed from a support coupled to a surgical instrument such as forceps and the dispensed needles subsequently placed in the receptacle. The methods and apparatus disclosed herein allow the physician to self-load the needle into the needle driver, self-place the dispensed needle into a used needle receptacle, and optionally install the suture in the patient, which have the benefits of decreasing reliance on assistants, improving operating room efficiency and the safety of needle handling. In many embodiments, one or more needles can be secured in the receptacle prior to passing the needle to an assistant, which increases safety by placing the needle in the receptacle prior to passing to the assistant. A plurality of needles can be surgeon dispensed and surgeon placed in the container, such that the safety and efficiency can be increased by decreasing the number of passes between the surgeon and assistant.

In many embodiments, an "armed" suture comprises a suture that has a surgical needle attached. Furthermore, packages of armed sutures often contain more than one such suture and needle. The package may contain not only one, but also perhaps five and possibly more such as 8 or more sutures and needles. In the course of surgery, many such armed sutures can often be used, each needing to be "loaded" onto the needle holder or "needle driver". The surgeon can hold the needle driver in his dominant hand and a tissue forceps in the non-dominant hand in order to manipulate and hold tissues to be sutured. Thus the surgeon can use both hands when suturing to self-dispense and self-secure the dispensed needles.

By associating the suture packaging and the enclosed armed sutures onto the surgeon's forearm, wrist or hand, the surgeon can more efficiently access armed sutures for loading onto the needle driver. Furthermore, the surgeon's forearm, wrist or hand can also provide a location for attachment of a used needle temporary or permanent storage device. In many embodiments, by associating the suture package to the volar or dorsal-radial region of the surgeon's non-dominant forearm, wrist, or hand, the mechanics of grasping the needle with the needle holder can be facilitated. Such an approach allows the surgeon to instantly reorient the suture pack and into a more appropriate position such that grasping the needles with the needle holder is facilitated. Associating the package with the surgeon's non-dominant extremity can allow the surgeon to, without significant body motion or without needing to grasp the package with his non dominant hand, reposition the needle package and needles in space such that they are readily accessible to be grasped with the needle driver.

In many embodiments a forearm-mounted system comprises a needle trap that can include an integrated suture pack mount that can be easily attachable to and detachable from a needle puncture resistant barrier worn on a forearm. The puncture resistant barrier provides a stable surface for dispensing of new sutures/needles from a standard suture pack and securement of contaminated needles after the stitch is completed. A benefit of the integration of the suture pack mount with the needle trap is that this configuration can enable real time proximity reconciliation within the near surgical field of used and unused needles. Integration of the suture pack mount with the needle trap within the near surgical field enables the surgeon to maintain focus on the incision closure process without having to divert visual attention to locate the needle securement container and deposit the used needles.

In many embodiments, the puncture resistant barrier provides protection to at least the volar surface of a forearm from inadvertent needle sticks and may also provide additional protection to the dorsal surface of a forearm. The puncture resistant barrier can also provide additional mounting surfaces for tool holders, running-suture spools, or other procedure specific materials that are optimally located in the near surgical field. The puncture resistant barrier can provide protection from sharps and can be comfortable, anatomically conformal, lightweight, unobtrusive, and quickly attachable to the surgeon's forearm with one hand.

The present disclosure provides multiple concepts, technologies and devices by which currently available armed sutures and the packages from which they are dispensed can be associated with the surgeon's forearm, wrist or hand for easier and more efficient loading by the surgeon, reducing the need for assistance from the scrub technician. Furthermore, disclosed herein are newly designed suture packages or modifications to currently available packages, which can incorporate concepts and technologies that allow for easy and efficient attachment of single or multiple suture packages to the support platform on the surgeon's forearm, wrist or hand or other support. The embodiments disclosed herein are well suited for use when the surgeon is gowned and gloved. The needle storage devices for dispensed used needles can also be associated with the surgeon's forearm, wrist or hand, as well as protective barriers and mechanisms that decrease the likelihood of needle stick to the surgeon.

The methods and apparatus disclosed herein allow a person who is closing an incision or wound with suture needles to reconcile needles dispensed from a suture pack with needles secured in a needle receptacle, in order to ensure that all needles used in a surgical procedure are accounted for. In many instances, the surgeon closing the incision can dispense suture needles from a suture pack in the near surgical field and place needles removed from the suture pack into a secure container within the near surgical field, and count the needles removed from the suture pack and the needles placed in the needle receptacle while the suture pack and needle receptacle remain in the near surgical field in order to reconcile the needles in the near surgical field. The reconciled needles secured in the receptacle and any remaining needles in the suture pack can then be passed from the near surgical field to another person outside the near surgical field or to a neutral zone. This needle reconciliation within the near surgical field allows the surgeon and others to act quickly if a needle is not accounted for and to take corrective action, for example by finding the missing needle. In many instances, needle reconciliation within the near surgical field also allows the surgeon to notice the missing needle sooner than reconciliation outside the near surgical field, and can make it easier to find the missing needle because the needle is missing for a shorter time. Needle reconciliation within the near surgical field also allows the surgeon or other person closing an incision or wound to have greater control over the surgical procedure, and also decreases the staffing requirements for surgery and associated costs. Although reference is made to needle reconciliation within the near surgical field outside of the patient, the methods and apparatus disclosed herein are well suited for needle reconciliation within the patient, for example within the patient during laparoscopic and robotic surgery.

Aspects of the present disclosure may provide barriers for placement on a forearm of a user. An exemplary barrier may comprise a curved shell defining a longitudinal axis extending between a proximal end and a distal end, with the curved shell extending with curvature about the longitudinal axis.

In many embodiments, the proximal end of the shell defines a cross-section with a long axis and a short axis, the distal end of the shell defines a cross-section with a long axis and a short axis, and the long axis of the proximal end is rotated about the longitudinal axis relative to the long axis of the distal end.

In many embodiments, the barrier long axis of the distal end is rotated relative to the long axis of the proximal end when placed on a forearm of a user, the proximal end is located toward an elbow of the user, and the distal end is located toward a wrist of the user when placed.

In many embodiments, the barrier comprises a pre-formed self-supporting barrier shaped to define the long axis on the proximal end and the short axis on the distal end as opposing edges of the barrier are urged toward each other.

In many embodiments, the long axis of the proximal end is longer than the long axis of the distal end.

In many embodiments, the proximal end comprises a short axis and the distal end comprises a short axis, and the short axis of the proximal end is longer than the short axis of the distal end. The long axis of the distal end may be shorter than the short axis of the proximal end.

In many embodiments, the barrier may comprise a thermoformed sheet of material having substantially uniform thickness.

In many embodiments, the barrier comprises a preformed self-supporting structure.

In many embodiments, the barrier comprises a dorsal aspect having a dorsal length extending between the proximal end and the distal end, a radial aspect having a radial length extending between the proximal end and the distal end, and a volar aspect having a volar length extending between the proximal end and the distal end. The radial aspect may be disposed between the dorsal aspect and the volar aspect. The radial length may be shorter than the dorsal length and the volar length. The barrier may comprise indicia on the radial aspect for a user to align the barrier with a radial ridge of the forearm of the user.

In many embodiments, the barrier may further comprise a proximal tab having a proximal tab length and a distal tab having a distal tab length, the proximal tab longer than the distal tab. The distal tab length may be within a range from about 25% to about 75% of the proximal tab length. The proximal tab and the distal tab may be preformed to have a curved shape extending around the longitudinal axis in a free standing configuration.

In many embodiments, the barrier is shaped to fit a left forearm of a user or a right forearm of a user.

In many embodiments, the barrier comprises a dorsal taper on a dorsal side between the proximal end and the distal end and a volar taper on a volar side between the proximal end and the distal end. The volar taper may be greater than the dorsal taper.

In many embodiments, the barrier comprises a placed configuration when opposite edges on opposite sides have been drawn toward each other.

In many embodiments, the barrier comprises a placed configuration when opposite edges on opposite sides have been drawn toward each other and wherein dorsal, volar and radial aspects of the barrier define a proximal center at the proximal end and a distal center at a distal end, an intermediate portion of the barrier defines an intermediate center with intermediate dorsal volar and radial aspects, and the center of the intermediate portion is located away from a straight line extending between the proximal center and the distal center. The plurality of intermediate dorsal, radial, and volar portions may define a plurality of intermediate centers. The proximal center, the intermediate center, and the plurality of intermediate centers may define a curved path extending between the proximal center and the distal center. A perpendicular cross-section of the proximal portion through the proximal point may define a plane and an orthogonal axis extending from the proximal center perpendicular to the plane. The distal center may be offset from the orthogonal axis by an amount within a range from about 1 cm to about 4 cm.

The barrier may be in a variety of dimensions. The barrier may comprise a thickness within a range from about 0.4 mm to about 5 mm. The may comprise a longitudinal length within a range from about 6 inches to about 11 inches. The barrier may comprise a ratio of the distance across the proximal end to the distance across the distal end within a range from about 1.1 to about 1.5.

In many embodiments, the barrier may comprises a preformed shaped barrier. The barrier may comprise a volar edge on a volar side and a dorsal edge on a dorsal side. The volar edge may separate from the dorsal edge when advanced over the forearm for placement. An amount of force to separate the volar edge from the dorsal by about one inch from a free standing configuration may be within a range from about 25 grams to about 400 grams, or from about 50 grams to about 150 grams.

In many embodiments, the barrier comprises a shell and an underlying foam which extends distally beyond the distal border of the shell of the barrier. The foam may curve over a leading distal edge of the shell to pad the interface of the shell when the barrier impinges on the wrist to provide comfort.

In many embodiments, the barrier comprises a shell and an underlying foam which extends distally beyond the distal border of the shell of the barrier to pad the interface of the shell when the barrier impinges on the wrist to provide comfort.

In many embodiments, the barrier may comprise a shell and an underlying foam which curves over a leading distal edge of the shell to pad the interface of the shell when the barrier impinges on the wrist to provide comfort.

In many embodiments, the barrier may comprise a shell and a distal edge of the shell has a curvature with a diameter equal to the thickness of the shell.

In many embodiments, the barrier may comprise a shell and a distal end of the shell curves away from the forearm of a user, such as with a radius of curvature of between 2 mm and 5 mm.

In many embodiments, the barrier comprises a shell having a radial curvature at a distal edge of shell with displacement within a range from about 3 mm to 1.5 cm to distribute a load of the barrier on a wrist of a user.

In many embodiments, the barrier comprises a shell and a foam padding the distal edge of the shell.

In many embodiments, the barrier may comprise a thickened distal edge.

In many embodiments, the barrier may be configured to distribute a load when device abuts the dorsal or radial or volar aspect of the wrist with motion of the wrist.

Aspects of the present invention include barriers for placement on a forearm of a user. An exemplary barrier may comprise a curved shell defining a longitudinal axis extending between a proximal end and a distal end. The curved shell may extend with a curvature about the longitudinal axis. The proximal end of the shell may define a cross-section. The distal end of the shell may define a cross-section. The barrier may comprise a pre-formed shaped barrier. The barrier may comprise a volar edge on a volar side and a dorsal edge on a dorsal side. The volar edge may separate from the dorsal edge when advanced over the forearm for placement. An amount of force to separate the volar edge from the dorsal by about one inch from a free standing configuration may be within a range from about 25 grams to about 400 grams, or from about 50 grams to about 150 grams.

Aspects of the present invention may provide a method comprising providing a barrier as disclosed herein.

Aspects of the present invention may provide needle receptacles. An exemplary needle receptacle may comprise a lower structure that has an entry zone and a secure zone, an upper structure that has a secure zone, a needle slot for receiving one or more suture needles between the lower structure and the upper structure, and an upper needle driver slot that extends through a portion of the upper structure and a lower needle driver slot that extends through portion of the lower structure. A lower protrusion on a bottom side of the lower structure may comprise a height sufficient to provide clearance for the needle driver when a needle grasped away from a tip of the needle driver advances along the needle slot. The lower protrusion may comprise a standout extending along the lower needle driver slot.

Another exemplary needle receptacle may comprise a housing comprising a lower structure and an upper structure. The upper structure may comprise an optically transmissive material and the lower structure may comprise an optically transmissive material in order to view needles within a secure zone of the receptacle with backlight illumination. The upper portion may comprise a transparent material to view the needles, and the lower portion may comprise a translucent material to pass backlight illumination light to the needles. The needle receptacle may further comprise a slot through the upper structure in order to view needles within a secure zone of the receptacle. The upper structure may have a longitudinal slot to receive a needle driver. The secure zone may comprise an elongate needle slot to receive a plurality of needles. The elongate needle slot may extend between the upper structure and the lower structure. The needles in the needle slot can be viewed through the top structure with backlight illumination through the lower structure.

Another exemplary needle receptacle may comprise a lower structure that has an entry zone and a secure zone, an upper structure that has a secure zone, and a needle slot for receiving one or more suture needles between the lower structure and the upper structure. A plurality of protrusions may extend along the needle slot with a periodicity in order to provide tactile feedback to a user to indicate a positon of the needle along the needle slot.

Another exemplary needle receptacle may comprise a lower structure that has an entry zone and a secure zone, an upper structure that has a secure zone and a needle driver slot extending along the secure zone, and a needle slot for receiving one or more suture needles between the lower structure and the upper structure. A plurality of protrusions may extend along the needle driver slot to provide tactile feedback to a user as to the depth of the needle driver along the needle driver slot. The plurality of protrusions may comprise one or more of teeth, inclined teeth, ratchet teeth or circular cutouts. The plurality of protrusions may comprise one or more of teeth, inclined teeth, ratchet teeth or circular cutouts, flaps, bristles, or filaments. The plurality of protrusions may be arranged with periodicity to provide an indication of depth of the needle driver along the needle driver slot.

Another exemplary needle receptacle may comprise a lower structure that has an entry zone and a secure zone, an upper structure that has a secure zone, and a needle slot for receiving one or more suture needles between the lower structure and the upper structure. A plurality of asymmetric protrusions may extend along the needle slot in order to inhibit removal of the needle along the needle slot. Each of the plurality of asymmetric protrusions may comprise a base extending to a peak. The base may comprise a distal edge toward an entrance of the slot and a proximal edge toward a stop on a proximal end of the slot. The peak may be located closer to the proximal edge than the distal edge. The plurality of asymmetric protrusions may comprise one or more of bristles or fibers inclined proximally toward a stop in order to facilitate movement toward the stop and inhibit movement toward an opening of the slot through which the needle is passed for placement in the secure zone. The entry zone may be at a distal end of the needle receptacle and the secure zone may be at a proximal end of the needle receptacle. The plurality of asymmetric protrusions may comprise one or more of bristles or fibers inclined towards a stop in order to facilitate movement toward the stop and inhibit movement toward an opening of the slot through which the needle is passed for placement in the secure zone.

Another needle receptacle may comprise a structure to receive a needle with resistance or force to remove the needle, wherein an amount of resistance or force to remove the needle is within a range from about 5 grams to 250 grams, within a range from about 15 grams to about 150 grams, within a range from about 25 grams to about 100 grams, or within a range from about 30 grams to about 90 grams. The amount of force to remove the needle may be greater than the amount of force to insert the needle. The needle receptacle may comprise a needle slot, and the amount of force may comprise an amount of force to advance the needle along the needle slot. The needle receptacle may comprise a needle driver slot, and the amount of force may comprise an amount of force to advance the needle driver along the needle driver slot to secure the needle in the needle slot.

Aspects of the present invention may provide a method comprising a step of inserting a needle into a needle receptacle. The needle receptacle may resist insertion of the needle with an amount of force within a range from about 5 grams to 250 grams, within a range from about 15 grams to about 150 grams, within a range from about 25 grams to about 100 grams, or within a range from about 30 grams to about 90 grams. The amount of force to remove the needle may be greater than the amount of force to insert the needle.

Aspects of the present invention may provide needle traps. An exemplary needle trap may comprise a landing zone and a secure zone. The landing zone may be substantially coplanar with the secure zone.

Aspects of the present invention may provide a method comprising steps of moving a needle to a landing zone of a needle receptacle and sliding the needle from the landing zone into a secure zone of the needle receptacle.

Aspects of the present invention may provide a receptacle comprising a slotted structure that allows a tip and a tail of the needle to be substantially enclosed while suspending a mid-portion of the needle in the slot.

Aspects of the present invention may provide a needle receptacle comprising a slot along a secure zone. The slot may be sized smaller than a finger tip having a size of about 10 mm.

Aspects of the present invention may provide a needle receptacle comprising a needle groove having a thickness small enough to inhibit rotational movement of the needle out of the needle groove.

Aspects of the present invention may provide sterile barrier kits. An exemplary sterile barrier kit may comprise a sterile package and a sterile barrier contained within the package. The kit may be configured for one or more of regional anesthesia, spinal anesthesia, emergency room suturing, or intravenous (IV) line placement. The kit may be configured to one or more of regional anesthesia, spinal anesthesia, emergency room suturing, intravenous (IV) line, arterial line, or central line placement.

In the needle receptacles disclosed herein, the receptacle may be sized to a range of needles, and may optionally comprise a smaller slot for smaller needle drivers, in which the slot comprises a width of no more than a diameter of a largest needle for which the trap is designed to store.

A longitudinal slot for the needle driver may comprise a through and through slot, in which the slot extends though both sides of the receptacle.

A longitudinal slot or groove for the needle driver may comprise a lower solid wall, in which the wall is located at a sufficient depth to allow the tip of the needle driver to protrude beyond the needle securement slot plane. The needle driver groove or slot may extend beneath the needle slot by a distance within a range from about 0.1 mm to about 10 mm.

In the needle receptacles disclosed herein, the receptacle may comprise a longitudinal slot bounded by a structure to one or more sides of the slot that creates a varying resistance to translation as the needle is drawn along the slot. Optionally, the varying resistance may be provided with one or more of discrete or asymmetric features that protrude into the needle slot, in order to increase compression of the needle and provide tactile feedback as the needle is drawn along the slot.

The needle receptacle may comprise a secure zone, can be applied to the forearm, and may comprise a width of less than 12 cm and a length of less than 26 cm.

A compressive member may be configured to secure a needle and provide resistance to movement of the needle against an apposed surface. The foam structure may comprise a gap of less than 2 mm between the foam and the apposed surface.

Aspects of the present disclosure may provide a method of inserting a needle into a needle receptacle. The method may comprise steps of placing the needle at an entry zone of the needle receptacle coupled to a forearm and moving the needle along a plane of the forearm to secure the needle within a housing of the needle receptacle.

The barrier may comprise a recess in an outer surface of the barrier. The recess may be configured to receive at least a portion of a needle receptacle therein to couple the needle receptacle to the barrier in a low profile.

The barrier may comprise an integrated needle receptacle such that the needle receptacle is provided on the barrier in a low profile.

The needle receptacle may comprise a needle driver slot cover configured to at least partially cover a longitudinal needle driver slot of the needle receptacle to reduce risk of exposure of needle tips through the needle driver slot. The needle driver slot cover may comprise one or more flexible strips configured to elastically deform when a needle driver tip is translated along the needle driver slot. The needle driver slot cover may comprise a flexible strip disposed over the needle driver slot. The flexible strip may comprise a longitudinal slit positioned over the needle driver slot and extending longitudinally along the needle driver slot. The flexible strip may further comprise a plurality of vertical slits disposed over a length of the needle driver slot and extending orthogonally with respect to the longitudinal slit. The needle driver slot cover may comprise a transparent material. The needle driver slot cover may be slidably coupled to the needle receptacle and configured to slide to expose or cover the needle driver slot when the needle driver tip is translated along the needle driver slot. The needle driver slot cover may be configured to slide along a longitudinal axis of the needle driver slot. The needle driver slot cover may be configured to slide along an axis orthogonal to the longitudinal axis of the needle driver slot.

The needle receptacle may comprise a compressive member mounted laterally along a first longitudinal edge of a needle driver slot. The compressive member may be configured to be displaced by translation of a needle driver tip along the needle driver slot. Upon removal of the needle driver tip from the needle driver slot, exposed ends of a needle may be compressively pushed toward a second longitudinal edge of the needle driver slot opposite the first edge. The compressive member may be configured to provide a compressive force in a direction orthogonal to a longitudinal axis of the needle driver slot.

A housing of the needle receptacle may comprises a light guide. The needle receptacle may be coupled to a light source configured to transmit light to the light guide to provide backlighting.

A housing of the needle receptacle may comprise a light scattering material or surface to provide for non-uniform light transmission therethrough. The light scattering surface may comprise a surface of the lower or upper structure. The light scattering surface may comprise a roughened surface. The light scattering surface may comprise a sandblasted surface.

Aspects of the present disclosure may provide apparatuses for dispensing and securing a swaged needle. An exemplary apparatus may comprise a housing and a swaged needle. The housing may comprise a top portion, a bottom portion, and a side wall. The swaged needle may be coupled to the top portion of the housing. The swaged needle may comprise an attached suture. The attached suture may be wrapped around the side wall. A leading end of the swaged needle may be covered. The housing may comprise a spindle configured to allow rotation of the housing about a central axis of the housing. The apparatus may further comprise a mounting mechanism to mount the apparatus to a barrier. A height of the housing may be in a range from about 0.3 mm to about 15 mm, such as a range from about 1.5 cm to about 8 cm. The apparatus may be configured to couple to another identical apparatus in a stacked configuration. The housing may comprise a lid coupled to the top portion. The swaged needle may be covered by the lid. The top portion of the housing may comprise a slot to receive the leading end of the swaged needle and secure the swaged needle thereto.

Aspects of the present disclosure may provide apparatuses for dispensing and securing a swaged needle. An exemplary apparatus may comprise a housing, a plurality of spindles, and a swaged needle. The housing may comprise a bottom portion and a side wall extending from the bottom portion.

The plurality of spindles may extend from a surface of the bottom portion. The swaged needle may be coupled to the housing. The swaged needle may comprise an attached suture. The attached suture may be wrapped around at least two of the plurality of spindles. The plurality of spindles may be arranged on the bottom portion in pairs and the suture may be wrapped around a first pair of spindles. The apparatus may further comprise a second swaged needle coupled to the housing. The second swaged needle may comprise an attached second suture. The second suture may be wrapped around a second pair of spindles.

Aspects of the present disclosure may provide needle receptacles for mounting to a surgical tool. An exemplary needle receptacle may comprise a housing, a tool-mounting interface, and a coupling mechanism. The housing may comprise a planar needle slot to receive a needle and secure the needle therein. The tool-mounting interface may be configured to couple to a distal end of the surgical tool. The coupling mechanism may be configured to couple the housing to the tool-mounting interface. The housing may be configured to receive at least 5 needles therein. The tool-mounting interface may comprise an elastomeric cap configured to fit over the distal end of the surgical tool. The housing may comprise a rigid enclosure configured to receive a plurality of needles in a planar array aligned along a length of the rigid enclosure. The housing may comprise a circular array of compartments. Each compartment may be configured to receive a single needle therein. The circular array of compartments may be configured to rotate about a central axis of the housing to allow access to each compartment.

A needle driver slot may comprise an upper groove and a lower groove. The upper groove and the lower groove may comprise rounded edges.

A needle driver slot may comprise an upper groove and a lower groove. A width of the upper groove may be greater than a width of the lower groove.

A needle driver slot may comprise an upper groove and a lower groove. The upper groove and the lower groove may comprise beveled edges.

A needle driver slot may comprise an upper groove and a lower groove. The edges of the upper groove and lower groove may be angled and collinear.

In the needle receptacles disclosed herein, the needle driver slot may comprise an upper groove and a lower groove. The edges of the upper groove and lower groove may correspond to a subsection of a prolonged curving plane.

Aspects of the present disclosure may provide needle handling systems. An exemplary needle handling system may comprise a needle dispensing unit, a needle receptacle, and a barrier mounting base. The needle dispensing unit may comprise a plurality of sterile needles secured therein. The needle receptacle may comprise a planar needle slot configured to receive a plurality of used needles in a planar array. The barrier mounting base may comprise a top side and a bottom side. The top side may be configured to couple to the needle dispensing unit and the needle receptacle. The bottom side may be configured to couple to a barrier. The barrier mounting base may comprise a first portion configured to couple to the needle dispensing unit and a second portion configured to couple to the needle receptacle. The barrier mounting base may further comprise a hinge disposed between the first portion and the second portion to allow the first portion to bend with respect to the second portion.

The needle receptacle may comprise a first compressive member and a second compressive member. The first compressive member may be configured to engage a leading end of a needle. The second compressive member may be configured to engage a trailing end of the needle so as to entrap the needle between the compressive members.

A needle receptacle as in any one of the preceding claims, the needle receptacle comprising one or more clips configured to receive and enclose one or more ends of a needle and apply compressive force to the one or more ends to secure the one or more ends therein.

Aspects of the present disclosure may provide a needle receptacle comprising a housing and a rotatable cover coupled to the housing. The housing may comprise a plurality of compartments. Each compartment may be configured to contain a single needle therein. The rotatable cover may be coupled to the housing. The rotatable cover may comprise a window. The rotatable cover may be configured to rotate about a central axis of the housing to align the window with a single compartment to allow access to the single compartment through the window.

The methods, apparatuses, receptacles, kits, and barriers disclosed herein may further comprise associating a combination of both dispensing unit and used needle repository on the forceps.

In the methods, apparatuses, receptacles, kits, and barriers disclosed herein more than one setup of a suture package and needle receptacle may be ready for use.

The methods, apparatuses, receptacles, kits, and barriers disclosed herein may further comprise a sterile disposable forceps, a needle and suture package in combination with a used needle receptacle.

In the methods, apparatuses, receptacles, kits, and barriers disclosed herein, a sterile disposable forceps, a needle, and suture package in combination with a used needle receptacle may be co-manufactured into a common package.

In the methods, apparatuses, receptacles, kits, and barriers disclosed herein, a balanced surgical forceps may have an attached needle retention device onto the forceps.

In the methods, apparatuses, receptacles, kits, and barriers disclosed herein, a configuration may comprise a back to back relationship of the suture package and needle receptacle on opposing sides.

In the methods, apparatuses, receptacles, kits, and barriers disclosed herein, the suture package and needle receptacle may be attached to the forceps to allow for containment, coverage, securement, of both tip and end (tail) of one or more needles.

In the methods, apparatuses, receptacles, kits, and barriers disclosed herein, a forceps mounted needle receptacle may promote an organized deposition or array of used needles to facilitate counting and reconciliation of needle count.

In the methods, apparatuses, receptacles, kits, and barriers disclosed herein, the needle receptacle may be configured with a size and shape for five needles and may comprise five zones, one for each needle.

The methods, apparatuses, receptacles, kits, and barriers disclosed herein may further comprise five tactile bumps to facilitate localization into individual zones.

The methods, apparatuses, receptacles, kits, and barriers disclosed herein may further comprise 2-20 tactile bumps to facilitate localization into individual zones.

The methods, apparatuses, receptacles, kits, and barriers disclosed herein may further comprise 5-8 tactile bumps to facilitate localization into individual zones.

The methods, apparatuses, receptacles, kits, and barriers disclosed herein may further comprise 3-10 tactile bumps to facilitate localization into individual zones.

The methods, apparatuses, receptacles, kits, and barriers disclosed herein may be further configured for back lighting to enhance needle profile contrast.

The methods, apparatuses, receptacles, kits, and barriers disclosed herein may further comprise five zone specific light sources and may be configured to provide one light source on per needle into the receptacle. Light sources may be located on the needle receptacle.

The methods, apparatuses, receptacles, kits, and barriers disclosed herein may further comprise five light sources or sensors on a trap in a receptacle. The light sources may be coupled with the barrier. The barrier may be configured with five lights sources that light up according to a number of needles in the trap in the receptacle.

The methods, apparatuses, receptacles, kits, and barriers disclosed herein may further comprise a translational slot cover with ratcheted counting mechanism.

Aspects of the present disclosure may provide a needle apparatus which may comprise a pair of opposing needle receptacles. Each needle receptacle may have a front side and a back side and an opening to receive needles on the front side. The back sides may be oriented toward each other and the front sides may be oriented away from each other.

Aspects of the present disclosure may provide a needle apparatus which may comprise a pair of opposing suture packages. Each suture package may have a front side and a back side. The front side may be open to access a plurality of needles therefrom. The back sides may be oriented toward each other and the front sides may be oriented away from each other.

Aspects of the present disclosure may provide a needle apparatus which may comprise a needle receptacle and a suture package. The needle receptacle may have a front side and a back side and having an opening to receive needles on the front side. The suture package may have a front side and a back side. The front side may be open to access a plurality of needles therefrom. The back sides may be oriented toward each other and the front sides may be oriented away from each other.

A needle apparatus as disclosed herein may further comprise an interface to mount the needle apparatus on a surgical instrument. The interface may optionally comprise a slot to receive a proximal end of the instrument.

A needle apparatus as disclosed herein may further comprise an interface to mount the needle apparatus on forceps and the interface may optionally comprise a slot to receive a proximal end of the forceps.

A needle apparatus as disclosed herein may further comprise an interface to mount the needle apparatus on tweezers. The interface may optionally comprise a slot to receive a proximal end of the tweezers. The interface may comprise an adhesive.

A needle apparatus as disclosed herein may have opposing back sides which are rotatable about a common axis.

A needle apparatus as disclosed herein may have opposing back sides which are independently rotatable about a common axis.

A needle apparatus as disclosed herein may further comprise a pair of disposable forceps.

A needle apparatus as disclosed herein may be sterile and contained within a sterile package.

A barrier as disclosed herein may comprise a padding layer and a mechanical barrier layer. One or more magnets may be coupled to a surface of the mechanical barrier layer facing the padding layer such that the one or more magnets are disposed between the padding layer and the mechanical barrier layer.

A barrier as disclosed herein may comprise a mechanical barrier layer comprising a polymer material.

A barrier as disclosed herein may barrier comprise a polymer material with a thickness in range from about 0.5 mm to about 5 mm.

Aspects of the present disclosure may provide methods for handling suture needles. In an exemplary method, a suture needle may be grasped with a needle driver to dispense the suture needle from a suture package mounted on a support. The dispensed suture needle may be placed into a needle receptacle mounted on the support. A tip of the dispensed suture needle may be oriented away from a surgeon during the grasping step and the placing step.

The dispensed suture needle may travel a variety of distances. The dispensed suture needle may travel less than two feet from the grasping step to the placing step. The suture needle may travel a round trip distance of less than four feet from the grasping step to the placing step. The suture needle may travel no more than two feet from the suture pack to a wound and no more than two feet from the wound to the needle receptacle.

In many embodiments, the dispensed suture needle remains within a near surgical field during the steps of grasping and placing. The near surgical field may be bounded by a length extending from a front side of a torso of a surgeon to an incision, a width extending between forearms of the surgeon in a neutral rotation position, and a height extending vertically from a height of the incision to shoulders of the surgeon.

In many embodiments, the suture package and the needle receptacle are arranged for the surgeon to dispense a plurality of needles from the suture package and place the plurality of needles in the needle receptacle without an external rotation of an arm of a surgeon with respect to an anatomical neutral plane of the arm.

In many embodiments, the suture package and the needle receptacle are arranged for the surgeon to dispense a plurality of needles from the suture package and place the plurality of needles in the needle receptacle without an external rotation of an arm of a surgeon beyond a coronal plane of the surgeon.

In many embodiments, the suture package and the needle receptacle are arranged for the surgeon to dispense a plurality of needles from the suture package and place the plurality of needles in the needle receptacle without an external rotation of an arm of a surgeon beyond a plane perpendicular to the coronal plane of the surgeon at the surgeon's shoulder.

In many embodiments, the suture package and the needle receptacle are arranged for the surgeon to dispense a plurality of needles from the suture package and place the plurality of needles in the needle receptacle without an external rotation of an arm of a surgeon beyond a sagittal plane that bisects the coronal plane at the surgeon's shoulder.

In many embodiments, the suture package and the needle receptacle are arranged for the surgeon to dispense a plurality of needles from the suture package and place the plurality of needles in the needle receptacle without an external rotation of an arm of a surgeon beyond a mid-sagittal plane of the surgeon.

In many embodiments, the near surgical field comprises a space disposed within one or more of about 2 feet of the incision, 1.5 feet of the incision or about 1 foot of the incision.

In many embodiments, the suture package and the needle receptacle are attached to the support.

In many embodiments, the method further comprises repeating the steps of grasping and placing until a plurality of suture needles has been dispensed from the suture package and placed into the needle receptacle.

In many embodiments, the dispensed suture needle is attached to a suture, and the method further comprises installing the suture into a patient with the dispensed suture needle and the needle driver. The steps of grasping, installing, and placing may be repeated until a plurality of sutures have been installed in the patient.

In many embodiments, the suture pack and the needle receptacle are arranged for a surgeon to perform the steps of grasping and placing with one hand.

In many embodiments, the support comprises a movable support controlled by a surgeon.

In many embodiments, the needle receptacle comprises a structure located to place into a stable configuration one or more reels of suture coupled to a swaged on needle in order to dispense suture of the swaged needle from the one or more reels stably supported on the needle receptacle.

In many embodiments, the suture pack comprises a structure located to place into a stable configuration one or more reels of suture each coupled to a swaged on needle in order to dispense the one or more reels of suture and needle from the structure stably supported on the suture pack.

In many embodiments, the suture pack comprises a structure located to place into a stable configuration one or more reels of suture coupled to a swaged on needle in order to dispense suture of the swaged needle from the one or more reels stably supported on the suture pack.

In many embodiments, a suture attached to the dispensed suture needle is cut with one hand.

In many embodiments, the support comprises a barrier supported by a surgeon. The barrier may be coupled to a limb of the surgeon. The barrier may be releasably coupled to a limb of the surgeon. The suture package may be selected among a plurality of suture packages supported on a tray, and the suture package may be placed on the barrier. The needle receptacle may be selected among a plurality of needle receptacles supported on a tray, and the needle receptacle may be placed on the barrier.

In many embodiments, the suture package, the needle receptacle, and the support are sterile. One or more of the support or the barrier is configured for placement on a back portion of a hand of a surgeon with one or more structures extending from the barrier.

In many embodiments, the suture package and the needle receptacle comprise a self-contained package capable of being passed together from a surgeon to an assistant and vice versa with a plurality of innocuous needles supported with the suture package and the needle receptacle. The suture package may be attached to the needle receptacle. The suture package may be flexibly attached to the needle receptacle with a hinged support member. A combination of the suture package and needle receptacle may be attached to a support on an extremity of the surgeon. A combination of the suture package and needle receptacle may attach conformably to the support on an extremity of the surgeon.

The suture pack may comprise a planar suture package, and the needle receptacle may lie at an oblique angle of less than 45 degrees relative to the planar suture package. The suture package and the needle receptacle may each in contact with the support so as to decrease a profile of the needle receptacle. The suture package may be assembled together on the support.

The suture package and the trap may at least partially overlap in order to decrease size on barrier. The suture package and the trap may at least partially overlap in order to decrease a footprint of the suture package and the trap on barrier. The package and the needle receptacle trap may overlap in a proximal to distal direction. The suture package and the needle receptacle may overlap in a medial to lateral direction. The suture package and the needle receptacle may comprise an attachment mechanism. The suture package may comprise a standard commercially available needle package.

A needle receptacle attachment mechanism may allow attachment of the suture package to one or more of a lateral border or a distal border of the needle receptacle.

The step of coupling the barrier to a limb of the surgeon may comprise placing the barrier over a volar portion of a forearm of the surgeon.

The needle receptacle may be placed over a volar forearm of the surgeon. The needle receptacle may comprise a planar structure placed over the volar forearm. The needle receptacle may comprise a planar structure placed over the volar forearm and optionally the planar structure may be placed over a medial portion of the volar forearm. The needle receptacle may be arranged over the volar forearm to allow easy insertion of a used needle when a hand holding needle holder is slightly supinated. The needle may be placed in the receptacle with rotation of an arm holding a needle driver with shoulder joint rotation in order to align and place the used needle into an opening of the needle receptacle.

The needle receptacle may be arranged over the volar forearm to allow easy insertion of a used needle when a hand holding needle holder is slightly pronated. The needle may be placed in the receptacle with rotation of an arm holding a needle driver with shoulder joint rotation in order to align and place the used needle into an opening of the needle receptacle.

The needle receptacle may comprise a longitudinal length, a transverse width, and a height. The length may be greater than the width and the height. The width may be greater than the height. The length may be within a range from about 4 cm to about 15 cm, the width may be within a range from about 3 cm to about 6 cm, and the height may be within a range from about 0.5 cm to about 2 cm.

The step of coupling the barrier to the limb of the surgeon may comprise steps of providing legs that extend from sides of the barrier and engaging the legs on the limb of the surgeon to stabilize the barrier on the forearm of the surgeon. The step of engaging the legs on the limb of the surgeon may comprise a step of engaging one or more of a distal portion or a proximal portion of a forearm of the surgeon. The legs may comprise at least a plurality of legs for stable placement on one or more the first portion or the second portion. The legs may comprise slap bracelets. The legs may comprise a first leg and a second leg. The method may further comprise a step of securing a first coupling mechanism on the first leg to a second coupling mechanism on the second leg to secure the barrier to the limb of the surgeon.

The method may further comprise a step of coupling the suture package to the barrier. The method may further comprise a step of coupling the needle receptacle to the barrier. One or more of the support or the barrier may comprise a barrier layer configured to protect the limb of the surgeon from contact with the suture needles.

The support may comprise a surgical tool held by a surgeon. The surgeon may perform the steps of grasping and placing with one hand, while holding the surgical tool with the other hand.

A plurality of suture packages may be mounted on the support.

The step of placing the dispensed suture needle into the needle receptacle may comprise a step of rendering innocuous both ends of the dispensed suture needle within the needle receptacle.

The step of placing the dispensed suture needle into the needle receptacle may comprise a step of compressing a component of the needle receptacle against a tip of the dispensed suture needle.

The step of placing the dispensed suture needle into the needle receptacle may comprise a step of placing the dispensed suture needle in contact with a foam material in the needle receptacle.

The step of placing the dispensed suture needle into the needle receptacle may comprise placing a tip of the dispensed suture needle into a tapered structure that guides the dispensed suture needle into the needle receptacle.

The method may further comprise a step of actuating a lever coupled to a door of the needle receptacle to open the door. The method may further comprise a step of inserting the dispensed suture needle through the door in the needle receptacle. The method may further comprise a step of actuating the lever to close the door.

The method may further comprise a step of rotating the support so that the suture package faces the needle drive before grasping the suture needle with the needle driver.

The method may further comprise a step of rotating the support so that the needle receptacle faces the needle driver before placing the dispensed suture needle into the needle receptacle with the needle driver.

The needle receptacle may comprise a plurality of channels separated by dividers. The step of placing the dispensed suture needle into the needle receptacle may comprise a step of placing the dispensed suture needle into one of the plurality of channels. A plurality of suture needles may be dispensed from the suture package. The step of placing the suture needle into the needle receptacle may comprise placing each of the plurality of dispensed suture needles into a different one of the plurality of channels. The dividers may surround one or more of a proximal end or a distal end of the dispensed suture needle.

The needle receptacle may comprise a transparent structure.

The support may be coupled to a proximal portion of surgical forceps.

One or more of the suture package or the needle receptacle may be coupled to a proximal portion of surgical forceps.

The suture package and the needle receptacle may be arranged for a surgeon to count a plurality of undispensed needles and a plurality of dispensed needles within a near surgical field.

The suture package and the needle receptacle may be arranged for a surgeon to maintain a needle inventory within a near surgical field.

The suture package and the needle receptacle may be arranged for a surgeon to reconcile a needle inventory within a near surgical field.

The step of placing the dispensed suture needle into a needle receptacle mounted on the support may further comprise a step of securing the needle to the needle receptacle.

Aspects of the present disclosure provide apparatuses for handling suture needles. The apparatus may comprise a suture package, a needle receptacle, and a support. The suture package may be configured to dispense a plurality of suture needles. The needle receptacle may be configured to store a plurality of dispensed suture needles. The support may be configured to support one or more of the suture package or the needle receptacle.

In many embodiments, the needle receptacle is arranged to place the suture needle in the receptacle with a tip of the suture needle oriented away from the surgeon.

In many embodiments, the needle receptacle is arranged to place the suture needle in the receptacle with a tip of the suture needle oriented away from a direction of translation of the suture needle into the needle receptacle.

In many embodiments, the suture needle comprises a curved suture needle and the needle receptacle is arranged to place the suture needle in the receptacle with each end of the suture needle oriented away from the surgeon.

In many embodiments, the needle receptacle comprises a structure to receive the suture package and stably support the suture package.

In many embodiments, the suture package and the needle receptacle are arranged for the surgeon to dispense a plurality of needles from the suture package and place the plurality of needles in the needle receptacle without an external rotation of an arm of a surgeon with respect to an anatomical neutral plane of the arm.

In many embodiments, the suture package and the needle receptacle are arranged for the surgeon to dispense a plurality of needles from the suture package and place the plurality of needles in the needle receptacle without an external rotation of an arm of a surgeon outside a near surgical field of the surgeon.

In many embodiments, the needle receptacle comprises a structure located to place into a stable configuration one or more reels of suture coupled to a swaged on needle in order to dispense suture of the swaged needle from the one or more reels stably supported on the needle receptacle.

In many embodiments, the needle receptacle comprises a structure located to place into a stable configuration one or more reels of suture each coupled to a swaged on needle in order to dispense suture of the swaged needle from the one or more reels stably supported by a common base mounted to one of the group selected from: the a barrier on an arm of a surgeon, a drape over the patient, and a support.

In many embodiments, the apparatus further comprises a cutter arranged with the support in order to cut a suture of the suture needle with one hand.

In many embodiments, the apparatus further comprises a sterile tray having a plurality of suture packages supported thereon.

In many embodiments, the suture package, the needle receptacle and the support are sterile.

In many embodiments, one or more of the support or the platform is configured for placement on a back portion of a hand of a surgeon with one or more structures extending from the platform.

In many embodiments, the support is configured to attach to the suture package and to the needle receptacle in order to stably support the suture package and the needle receptacle on the support and in order to inhibit sliding or falling of the suture package and the needle receptacle from the support when the support is inverted or inclined and wherein the support is configured to release the suture package and the needle receptacle.

In many embodiments, the suture pack and the needle receptacle are arranged for a surgeon to perform the steps of grasping and placing with one hand.

In many embodiments, the support comprises a movable support configured to be controlled by a surgeon.

In many embodiments, the support comprises a platform configured to be supported by a surgeon.

In many embodiments, the support comprises a platform configured to be supported by one of the group selected from: a surgeon, a drape, and, a mount coupled to the surgical table, and a stable mount. The platform may comprise a coupling configured to couple the platform to a limb of the surgeon. The coupling may comprise one or more legs that extend from sides of the platform. The legs may be configured to engage the limb of the surgeon. The coupling may comprise slap bracelets. One or more of the support or the platform may comprise a barrier configured to protect the surgeon from contact with one or more ends of a dispensed suture needle.

In many embodiments, the support comprises a platform coupled to an adjustable support structure to place the platform within a near surgical field.

In many embodiments, the support comprises a platform is within a near surgical field and coupled to one of the group consisting of: an adjustable support structure, a stable mount, and a drape.

In many embodiments, the support is configured to couple to surgical forceps configured to engage tissue with pinching motion. The support may be configured to couple to a proximal end of the surgical forceps. The surgical forceps may comprise one or more of Adson forceps or Bonney forceps. The apparatus may weigh less than 45 grams. The apparatus may further comprise a coupling to couple the suture package and the needle receptacle to a proximal portion of the surgical tool. The apparatus may further comprise a suture package holder configured to support one or more suture packages. The suture package holder may be coupled to a proximal portion of the surgical tool. The needle receptacle and the suture package may be supported on opposite sides of the surgical tool. The suture package holder and the needle receptacle may be supported on a same side of the surgical tool. The coupling may comprise a tool attachment pocket and the proximal portion of the surgical tool may be placed in the tool attachment pocket. The tool attachment pocket may be coupled to the surgical tool with an adhesive layer. The apparatus may comprise two suture packages coupled to the proximal portion of the surgical tool. The needle receptacle may be sandwiched between the two suture packages.

In many embodiments, the apparatus further comprises a tool holder mounted on the support for holding a needle driver.

In many embodiments, the apparatus further comprises a tool holder mounted on the support for holding scissors.

In many embodiments, the needle receptacle is configured to contain both ends of a dispensed suture needle placed into the needle receptacle.

In many embodiments, the needle receptacle comprises a mechanism that compresses a component of the needle receptacle against a tip of a dispensed suture needle placed into the needle receptacle.

In many embodiments, the needle receptacle comprises a tapered structure that guides a tip of a dispensed suture needle into the needle receptacle.

In many embodiments, the needle receptacle comprises a tapered structure that guides a portion of a dispensed suture needle into the needle receptacle.

In many embodiments, the portion of the dispensed suture needle is a tip of the needle.

In many embodiments, the needle receptacle comprises a foam material shaped to contact a tip of a dispensed suture needle placed into the needle receptacle.

In many embodiments, the needle receptacle comprises a door coupled to a lever for opening and closing the door.

In many embodiments, the needle receptacle weighs less than 45 grams.

In many embodiments, the needle receptacle comprises a plurality of channels for storing the plurality of dispensed suture needles. The needle receptacle may further comprise a power source, a first conductor electrically coupled to the power source, and a first visual indicator electrically coupled between the power source and a second conductor. The first visual indicator may indicate the presence of a first dispensed suture needle in a first channel of the plurality of channels when the first dispensed suture needle is placed in contact with both the first conductor and the second conductor. The power source may comprise a battery. The first visual indicator may comprise a first light. The needle receptacle may further comprises a second visual indicator electrically coupled between the power source and a third conductor. The second visual indicator may indicate the presence of a second used needle in a second channel of the plurality of channels when the second used needle is placed in contact with both the second conductor and the third conductor. The second visual indicator may comprise a second light. The needle receptacle may further comprise numerical markings for the plurality of channels.

In many embodiments, the needle receptacle is configured to render innocuous both ends of the suture needle when placed in the receptacle. The needle receptacle may comprise a structure to view the needle with both ends rendered innocuous.

In many embodiments, the needle receptacle is configured to receive the suture needle and to stabilize the surgical needle within the needle receptacle on a needle receptacle support. The needle receptacle support may comprise one or more of a magnet, an adhesive, or a deflectable material to stabilize the suture needle.

In many embodiments, the needle receptacle is configured to receive the suture needle with sliding movement and corresponding resistance to the sliding movement in order to stabilize the surgical needle within the needle receptacle.

In many embodiments, the needle receptacle comprises a transparent cover to view a plurality of suture needles rendered innocuous therein. The needle receptacle may comprise an opening to place the plurality of suture needles within the suture needle receptacle.

In many embodiments, the needle receptacle comprises a structured array to arrange a plurality of needles along the array for counting.

Aspects of the present disclosure may provide methods for securing of a suture needle by a surgeon. A suture needle may be inserted into an opening of a needle receptacle with a needle driver. The suture needle may be rotated inside the needle receptacle to insert an end of the needle into a material. The suture needle may be released from the needle driver. With the inserting step, the needle may be translated away from a leading end. With the rotating step, a trailing end of the needle may be inserted into the deformable structure. The material may comprise one or more of a deformable material, an adhesive material or an elastic material. The material may comprise one or more of a foam, elastic membrane, or an adhesive.

Aspects of the present disclosure provide methods for securing of a suture needle by a surgeon. A suture needle may be inserted into an opening of a needle receptacle with a needle driver. The suture needle may be secured inside the needle receptacle. The suture needle may be released from the needle driver. The needle receptacle may be configured to store a plurality of suture needles.

In many embodiments, the needle receptacle is located within a near surgical field.

In many embodiments, the needle receptacle comprises an entry zone and a secure zone. The inserting step may comprise placing the suture needle on the entry zone of the needle receptacle. The securing step may comprise sliding the suture needle from the entry zone into a needle slot in the secure zone.

In many embodiments, the needle receptacle is coupled to a second needle receptacle. The method may further comprise steps of placing a second suture needle on a second entry zone of the second needle receptacle, and sliding the second suture needle from the second entry zone into a second secure zone of the second needle receptacle.

In many embodiments, the secure zone comprises a needle driver slot and the inserting step comprises moving a distal portion of the needle driver along the needle driver slot to place the suture needle in the secure zone.

In many embodiments, the secure zone comprises a compressive member that compresses against at least a portion of the suture needle during the securing step.

In many embodiments, the secure zone comprises a compressive member that applies a force against at least a portion of the suture needle during the securing step.

In many embodiments, secure zone comprises a plurality of protrusions that extend into the needle slot. The securing step may comprise moving the suture needle against a plurality of protrusions in the secure zone.

In many embodiments, the method may further comprise steps of detecting the suture needle placed into the needle receptacle, determining a number of suture needles disposed within the needle receptacle, and displaying the number of the sutures needles disposed within the needle receptacle on a visual display. The needle receptacle may comprise a first conductor and a second conductor that are electrically coupled to a power source. The suture needle may be disposed within the needle receptacle is in contact with both the first conductor and the second conductor. The detecting step may comprise measuring an electrical current through the first conductor and the second conductor.

In many embodiments, securing step may comprises a step of rotating a first suture needle within the needle receptacle so that an end of the suture needle is pressed into a first surface of a first structure mounted to the needle receptacle. The first structure may comprise one or more of a deformable material, an adhesive material or elastic structure, the first structure comprising one or more of a foam, elastic membrane, or an adhesive. The needle receptacle may comprise an offset zone between the opening and the first structure. During the insertion step, the first suture needle may be moved through the offset zone before performing the rotating step. The method may further comprise steps of inserting a second suture needle through the opening of the needle receptacle with the needle driver and rotating the second suture needle within the needle receptacle so that an end of the second suture needle is pressed into a second surface of the first structure mounted to the needle receptacle. The first suture needle may be rotated in a clockwise direction about a longitudinal axis of the needle driver. The second suture needle may be rotated in a counterclockwise direction about the longitudinal axis of the needle driver. The first structure may comprise one or more of a foam or an adhesive or a deformable material.

In many embodiments, the method further comprises steps of viewing the suture needle through a wall of the needle receptacle, wherein the wall is transparent, and counting suture needles disposed within the needle receptacle. The needle receptacle may be mounted on a proximal portion of a surgical tool.

Aspects of the present disclosure provide needle receptacles. An exemplary needle receptacle may comprise a lower structure, an upper structure, a needle slot, and a needle driver slot. The lower structure may have an entry zone and a secure zone. The upper structure may have a secure zone. The needle slot may be for receiving one or more suture needles between the lower structure and the upper structure. The needle driver slot may extend through a portion of the upper structure.

In many embodiments, the needle driver slot is perpendicular to the needle slot.

In many embodiments, a long axis of the needle driver slot is perpendicular to a long axis of the needle slot.

In many embodiments, the needle driver slot extends through a portion of the lower structure.

In many embodiments, the needle receptacle further comprises a compressible member that is adjacent to the needle slot.

In many embodiments, the needle receptacle further comprises a plurality of protrusions that are adjacent to the needle slot.

In many embodiments, the needle receptacle further comprises comprising a needle counting mechanism configured to detect a number of suture needles disposed in the secure zone of the needle receptacle.

In many embodiments, the needle receptacle further comprises a power source, a first conductor electrically coupled to the power source, a second conductor electrically coupled to control circuitry, and a visual display electrically coupled to the control circuitry. The visual display may indicate the number of suture needles disposed in the secure zone when the suture needles are placed in contact with both the first conductive element and the second conductive element.

In many embodiments, the needle receptacle is coupled to a second needle receptacle through a coupling in direct contact with both the needle receptacle and the second needle receptacle. The coupling may comprise a tool slot adapted to fit over a proximal end of a surgical tool.

In many embodiments, the needle receptacle further comprises a camera for obtaining a photographic image of the suture needle in the secure zone. The needle receptacle may further comprise a transmitter for transmitting the photographic image of the suture needle to a receiver.

In many embodiments, the needle receptacle may further comprise a camera for obtaining a photographic image for the presence of the suture needle in the secure zone. The needle receptacle may further comprise a transmitter for transmitting the photographic image for the presence of the suture needle to a receiver.

Another exemplary needle receptacle may comprise a housing having an opening and an interior volume and a first elongated member coupled to an interior surface of the housing. The first elongated member may have a needle insertion surface that extends inward from the interior surface of the housing.

In many embodiments, the first member comprises one or more of a deformable material, an adhesive material, or elastic structure. The deformable material may comprise one or more of a foam, elastic membrane, or an adhesive. The interior volume may be substantially cylindrical. The first deformable member may extend from the interior surface substantially radially inward into the interior volume.

In many embodiments, the needle receptacle may further comprise a second elongated member coupled to the interior surface of the housing. The first member and the second deformable member may be on opposite sides of the interior surface of the housing. The second member may comprise one or more of a deformable material, an adhesive material, or elastic structure. The first member may comprise one or more of a foam, elastic membrane, or an adhesive.

In many embodiments, the opening comprises an elongated slot that is longer than a length of the needle.

In many embodiments, the housing is transparent.

Aspects of the present disclosure provide apparatuses for protecting a limb of a surgeon from contact with a needle. An exemplary apparatus may comprise a barrier having a curved cross section and a coupling to couple the barrier to the limb of the surgeon. The barrier may be configured to support one or more of a suture package or a needle receptacle.

In many embodiments, the apparatus further comprises a barrier mount. The barrier mounting base may be configured to support one or more of a suture package or a needle receptacle. The barrier may be configured to support the barrier mount.

In many embodiments, the barrier comprises a sterile barrier and the coupling comprises a sterile coupling.

In many embodiments, the barrier comprises an extension sized to extend over a dorsal side of a hand of a surgeon. The extension may comprise a stiffness to support one or more of a suture package or a needle receptacle.

In many embodiments, the barrier comprises an extension sized to extend over a dorsum of a hand of a surgeon. The extension may comprise a deflection to allow movement of the hand to a dorsal radial side of the surgeon.

In many embodiments, the barrier comprises an extension sized to extend over a hand of a surgeon.

In many embodiments, the coupling comprises one or more of a first leg or a second leg.

In many embodiments, the coupling comprises a first leg and a second leg. The first leg may extend outward from a distal portion of the barrier in a first direction. The second leg may extend outward from the distal portion of the barrier in a second direction that is opposite to the first direction.

In many embodiments, the coupling comprises a plurality of proximal legs.

In many embodiments, the coupling comprises one or more slap bracelets.

In many embodiments, the coupling comprises a strap configured to wrap around a portion of a forearm of the surgeon. The strap may be coupled to opposite edges of the barrier.

In many embodiments, the coupling comprises a thumb loop disposed on a distal portion of the barrier. The thumb loop may be configured to couple to a thumb of the surgeon. The thumb loop may be made of a flexible material. The thumb loop may be formed in the barrier.

In many embodiments, the barrier may comprise a malleable material configured to deform to curve around the limb. The barrier may comprise a plurality of grooves extending in a parallel to a length of the limb. The barrier may comprise an inner foam layer configured to be compressed against the limb. The barrier may be configured to support a needle receptacle on a volar portion of the barrier. The barrier may be configured to support a suture package with one or more of a volar or a radial portion of the barrier. The dorsal portion of the barrier may comprise a tool holder.

In many embodiments, the barrier comprises the curved cross section in a free standing configuration.

In many embodiments, the barrier comprises a curved thermoformed barrier material.

Aspects of the present disclosure may provide a method comprising the steps of providing a needle receptacle comprising a housing having a needle slot and a needle driver slot wherein the needle driver slot intersects a side portion of the needle slot, grasping an end portion of a suture needle with a needle driver, moving the suture needle along the needle slot by sliding the needle driver along the needle slot, and releasing the suture needle within the needle slot.

In many embodiments, the needle driver moves through the needle driver slot in a straight path or a spiral path.

In many embodiments, the needle driver moves through the needle driver slot in a circular path.

In many embodiments, the method further comprises steps of providing a compressive member adjacent to the needle slot and compressing the compressive member against the needle.

In many embodiments, the method further comprises steps of applying a rotational torque about a center axis to the needle driver.

In many embodiments, the method further comprises steps of viewing the end portion of the needle within the needle driver slot and determining a number of the needles within the needle receptacle based upon the viewing step.

In many embodiments, the method further comprises steps of detecting the suture needle placed into the needle slot, determining a number of the needles within the needle receptacle, and displaying the number of the needles within the needle receptacle on a visual display.

In many embodiments, the method further comprises steps of providing a barrier and coupling the needle receptacle to the barrier.

In many embodiments, the barrier is adapted to be placed on a limb of a surgeon.

In many embodiments, the coupling of the needle receptacle to the barrier is via a magnetic coupling or a hook and loop coupling.

In many embodiments, the method further comprises steps of providing one or more straps that extend from the barrier. The straps may be adapted to secure the barrier to a limb of a surgeon.

Aspects of the present invention may provide needle receptacles. An exemplary needle receptacle may comprise a housing, a needle slot, a first needle driver slot, and a second needle driver slot. The housing may have a cross section having a width and a thickness. The needle slot may be for storing used suture needles within the cross section of the housing. The first needle driver slot may extend through the thickness of the housing. The first needle driver slot may intersect a side portion of the needle slot. The needle driver slot may extend through a portion of the upper structure.

In many embodiments, the needle driver slot is substantially perpendicular to the needle slot.

In many embodiments, the needle driver slot has a circular portion or a spiral portion.

In many embodiments, the needle receptacle further a compressible member that is adjacent to the needle slot.

In many embodiments, the needle receptacle further comprises a needle counting mechanism for detecting a number of needles in the needle receptacle. The needle receptacle may further comprise a power source and a visual display electrically coupled to needle counting circuitry. The visual display may indicate a number of needles in the needle receptacle.

In many embodiments, the needle receptacle further comprises a barrier, and the needle receptacle is attached to the barrier. The needle receptacle may further comprise a suture pack holder for holding suture packs attached to the barrier. The needle receptacle may further comprise one or more straps that extend from side of the barrier adapted to secure the barrier to a limb of a surgeon.

Aspects of the present disclosure may provide an apparatus for handling suture needles, the apparatus comprising a support configured to receive a suture package and a needle receptacle.

Aspects of the present disclosure may provide an apparatus for handling suture needles, the apparatus comprising a platform to attach a suture package and a used needle holder.

Aspects of the present disclosure may provide an apparatus for handling suture needles, the apparatus comprising a platform to attach a suture package and a used needle receptacle.

Aspects of the present disclosure may provide an apparatus for receiving a plurality of contaminated surgical suture needles, each needle having a tip, a trailing end and a needle body extending between the tip and the trailing end. The apparatus may comprise a housing having a top and a bottom, at least one opening between the top and the bottom configured and dimensioned to receive a contaminated surgical needle inserted therethrough, a window, and an innocuous zone within the housing to hold the plurality of contaminated surgical needles in an arrangement for counting through the window with each tip and trailing end.

Aspects of the present disclosure may provide an apparatus for receiving a contaminated surgical suture needle, the needle having a tip, a trailing end and a needle body extending between the tip and the trailing end. The apparatus may comprise a housing having a top and a bottom, at least one opening between the top and the bottom configured and dimensioned to receive a contaminated surgical needle inserted therethrough, and a secure zone within the housing to hold the contaminated surgical needle in an orientation with the needle tip secured.

In many embodiments, the orientation comprises a predetermined orientation.

In many embodiments, the at least one opening is configured and dimensioned to receive the contaminated surgical needle in a lateral orientation.

In many embodiments, wherein the at least one opening is configured and dimensioned to receive the contaminated surgical needle in a transverse orientation.

In many embodiments, the surgical needle is a curved needle and at least a portion of the curved needle body enters the opening before the tip or the trailing end thereof.

In many embodiments, the apparatus further comprises a first side connected to and extending between the top and the bottom, a second side connected to and extending between the top and the bottom, a first end, and a second end. The at least one opening may be disposed in the first end.

In many embodiments, the top and bottom are circular in shape.

In many embodiments, the secure zone is configured and dimensioned to receive a plurality of contaminated surgical needles.

In many embodiments, at least a portion of the top is sufficiently transparent to permit visualization of contaminated needles disposed in the secure zone.

In many embodiments, the apparatus includes a window permitting inspection and counting of a plurality of contaminated surgical needles contained therein. The plurality of contaminated surgical needles may comprise at least five surgical needles.

In many embodiments, the housing top includes a slot configured and dimensioned to receive a tip of a needle driver, facilitating insertion of the contaminated surgical needle into the housing under control of the needle driver.

In some embodiments, the slot is offset to view a trailing end of the needle.

In some embodiments, the slot is linear.

In some embodiments, the slot is curved.

In some embodiments, the slot is straight and is oriented along the center of the top.

In some embodiments, the slot is straight and is oriented off the longitudinal axis of the top.

In some embodiments, the apparatus comprises a plurality of slots.

In some embodiments, the slot is configured and dimensioned to orient the needle driver into a specific orientation relative to the slot.

In many embodiments, the secure zone includes needle retention features to hold a plurality of contaminated surgical needles in a predetermined orientation.

In many embodiments, the apparatus further comprises needle retention features to hold the contaminated surgical needle between the top and bottom. The needle retention features may comprise foam disposed between the top and bottom, such as urethane foam.

In some embodiments, the needle retention features comprise loop and hook fasteners disposed between the top and bottom.

In some embodiments, the needle retention features comprise a plurality of protrusions extending from one or both of the top and bottom. The plurality of protrusions may comprise dimples, protuberances, or filaments. The plurality of protrusions may be angled away from the at least one opening to permit the needle to pass into the secure zone and to resist movement of the needle toward the at least one opening. The needle retention features may comprise flaps disposed between the top and bottom.

In some embodiments, the needle retention features comprise gel disposed between the top and bottom.

In some embodiments, the needle retention features comprise hemispherical nubs disposed between the top and bottom.

In some embodiments, the needle retention features comprise angled bristles disposed between the top and bottom.

In many embodiments, the apparatus further includes a sterile mounting member attached to the housing for mounting the apparatus in the near surgical field.

In many embodiments, the top and bottom are injection molded.

In many embodiments, the top and bottom snap fit together.

In many embodiments, the top and bottom are welded together, such as ultrasonically welded together.

In many embodiments, the top and bottom are adhesively connected.

In many embodiments, the top surface is comprised of clear polycarbonate.

In many embodiments, the top and bottom are comprised of polycarbonate.

In many embodiments, the apparatus further comprises a slot through the top surface.

In many embodiments, the top and bottom are flexible.

In many embodiments, the top and bottom are rigid.

In many embodiments, one or both of the top and bottom define an entry zone, a transition zone, and a secure zone. The entry zone may define a landing zone which is wider than the entry zone to facilitate movement of the needle toward the entry zone. The entry zone may include at least one structure to urge a needle driver holding a contaminate needle toward a slot in the top surface. The structure may include a V-shaped entry edge of the entry zone.

In many embodiments, the apparatus may further comprise a sterile package containing the apparatus.

In many embodiments, the apparatus may further include a sterile mounting member attached to the housing for mounting the apparatus in the near surgical field. The mounting apparatus may comprises a barrier configured and dimensioned to be mounted to a forearm of a surgeon. The barrier may be configured and dimensioned to support a sterile package of surgical needles and sutures.

In many embodiments, the innocuous zone within the housing is configured to hold the plurality of contaminated surgical needles in an arrangement for counting through the window with either of each tip and trailing end beneath the window.

Aspects of the present disclosure may provide an apparatus comprising one or more of a sterile surgical gown, a sterile glove, or a sterile cover configured with a barrier to inhibit needle sticks and a surface configured to stably support one or more of a suture pack or a needle receptacle over one or more of a hand, a radial forearm or a volar forearm.

Aspects of the present disclosure may provide an apparatus comprising one or more of a sterile surgical gown, a sterile glove, or a sterile cover configured with a barrier to inhibit needle sticks and a surface configured to stably support one or more of a suture pack or a needle receptacle over one or more of a hand, a radial forearm, a volar forearm, a dorsal forearm, a ulnar forearm, and wrist.

Aspects of the present disclosure may provide an apparatus comprising one or more of a sterile cover or a sterile drape configured with a barrier to inhibit needle sticks and a surface configured to stably support one or more of a suture pack or a needle receptacle in a near surgical field.

Aspects of the present disclosure may provide a surgical suturing kit comprising a sterile enclosure that may contain a sterile package of sterile sutures and a sterile apparatus for receiving at least one contaminated surgical suture needle.

Aspects of the present disclosure may provide a surgical suturing kit comprising a sterile enclosure that may contain a sterile package of sterile sutures and a sterile apparatus for receiving at least one contaminated surgical suture needle. The needle may have a tip, a trailing end, and a needle body extending between the tip and the trailing end. The sterile apparatus may comprise a sterile housing having a top and a bottom, at least one opening between the top and the bottom configured and dimensioned to receive a contaminated surgical needle inserted therethrough, and a secure zone within the housing to hold the contaminated surgical needle in a predetermined orientation with the needle tip secured.

The surgical kit may further comprise a barrier configured and dimensioned to support the package of sterile sutures and the apparatus for receiving the at least one contaminated surgical suture needle.

The barrier layer may be configured and dimensioned to be mounted to a forearm of a surgeon.

Aspects of the present disclosure may provide a method comprising a step of placing a needle in a used needle holder.

Aspects of the present disclosure may provide an apparatus comprising a used needle holder.

Aspects of the present disclosure may provide an apparatus comprising means for securing a used needle.

Aspects of the present disclosure may provide an apparatus for handling sutures, comprising a sterile housing, a suture dispensing portion disposed within the housing, the suture dispensing portion configured to support one or more sterile suture needles, and a needle receptacle portion disposed within the housing, the needle receptacle portion configured to secure a plurality of dispensed suture needles.

Aspects of the present disclosure may provide an apparatus comprising needle receptacle means for stabilizing and rendering innocuous a dispensed needle.

Aspects of the present disclosure may provide an apparatus comprising needle receptacle means for stabilizing and rendering innocuous a dispensed needle and barrier means for supporting the needle receptacle means in order to place dispensed needles in the needle receptacle means.

Aspects of the present disclosure may provide an apparatus comprising needle receptacle means for stabilizing and rendering innocuous a dispensed needle and a barrier means for supporting the needle receptacle means in order to place dispensed needles in the needle receptacle means.

Aspects of the present disclosure may provide an apparatus for use in a sterile operating room. The apparatus may comprise a dispensed needle receptacle, a suture package, and a barrier to support one or more of the dispensed needle receptacle or the suture package and inhibit needle penetration through the barrier. The dispensed needle receptacle, the suture package, and the barrier may be arranged within a near surgical field of a surgeon.

The apparatus may comprise a barrier mounting base to support one or more of the dispensed needle receptacle or the suture package and inhibit needle penetration through the barrier. The barrier may be to support the barrier mounting base.

Aspects of the present disclosure may an apparatus for use in a sterile operating room comprising a dispensed needle receptacle comprising five or more dispensed surgical needles. The dispensed surgical needles may be stabilized and innocuous within the needle receptacle. The needle receptacle may comprise one or more of an opening, a window, or a transparent material for counting the stabilized innocuous dispensed needles. The needles may be arranged for counting within the receptacle.

Aspects of the present disclosure may provide a method of securing dispensed needles, comprising a step of receiving a dispensed needle receptacle comprising five or more dispensed surgical needles from a neutral zone. The dispensed surgical needles may be stabilized and innocuous within the needle receptacle. The needle receptacle may comprise one or more of an opening, a window, or a transparent material for counting the stabilized innocuous dispensed needles. The needles may be arranged for counting within the receptacle.

Aspects of the present disclosure may provide a method of securing dispensed needles comprising a step of receiving a dispensed needle receptacle comprising five or more dispensed suture needles from a neutral zone. The dispensed surgical needles may be stabilized and innocuous within the needle receptacle. The needle receptacle may comprise one or more of an opening, a window, or a transparent material for counting the stabilized innocuous dispensed needles. The needles may be arranged for counting within the receptacle.

Aspects of the present disclosure may provide a method of securing dispensed needles comprising a step of receiving a dispensed needle receptacle comprising five or more dispensed suture needles from a near surgical field. The dispensed surgical needles may be stabilized and innocuous within the needle receptacle. The needle receptacle may comprise one or more of an opening, a window, or a transparent material for counting the stabilized innocuous dispensed needles. The needles may be arranged for counting within the receptacle.

Aspects of the present disclosure may provide a method of securing dispensed needles comprising steps of inserting a suture needle into an opening of a needle receptacle with a needle driver and releasing the dispensed needle from the needle driver. The needle receptacle may be configured to store a plurality of five or more dispensed needles. The dispensed needle may be stabilized, innocuous, and arranged with four or more stabilized innocuous dispensed needles for counting in the container though one or more of a channel, an opening, a window, or a transparent material.

Aspects of the present disclosure may provide an apparatus for handling needles. The apparatus may comprise a suture package configured to dispense a plurality of needles, a needle receptacle configured to store a plurality of dispensed needles, and a support configured to support one or more of the suture package or the needle receptacle.

Aspects of the present disclosure may provide a method for handling suture needles. The method may comprise steps of grasping a needle with a needle driver to dispense the needle from a suture package mounted on a support and placing the dispensed needle into a needle receptacle mounted on the support.

The apparatuses or method disclosed herein may comprise a barrier comprising a weight of no more than about 6 ounces (170 grams) and a needle receptacle comprising a capacity of at least about 5 needles, an overall thickness of no more than about 0.5 inches (12.5 mm), a length of no more than about 5" (127 mm), and a width of no more than about 2.5" (63.5 mm) to receive and store the at least about 8 needles in a linear array.

The apparatuses or method disclosed herein may comprise a barrier comprising a weight of no more than about 6 ounces (170 grams) and a needle receptacle comprising a capacity of at least about 5 needles, an overall thickness of no more than about 0.5 inches (12.5 mm), a length of no more than about 5" (127 mm), and a width of no more than about 2.5" (63.5 mm) to receive and store the at least about 5 needles in a linear array or an arcuate array.

The apparatuses or method disclosed herein may comprise a barrier comprising a weight of no more than about 6 ounces (170 grams) and a needle receptacle comprising a capacity of at least about 8 needles, an overall thickness of no more than about 0.5 inches (12.5 mm), a length of no more than about 5" (127 mm), and a width of no more than about 4" (101.6 mm) to receive and store the at least about 8 needles in an arcuate array.

The apparatuses or method disclosed herein may comprise a barrier comprising a weight of no more than about 6 ounces (170 grams) and a needle receptacle comprising a capacity of at least about 8 needles, an overall thickness of no more than about 0.5 inches (12.5 mm), a length of no more than about 5" (127 mm), and a width of no more than about 4" (101.6 mm) to receive and store the at least about 8 needles in a linear array.

In the apparatuses, methods, and needle receptacle disclosed herein, the needle receptacle may comprise a channel having an elongate cross section sized to receive a plurality of suture needles in an ordered array and a slot extending into the channel to receive a needle driver and advance a suture needle of the plurality along the channel for placement among the plurality of needles of the ordered array.

The apparatuses, methods, and needle receptacle disclosed herein may further comprise one or more of a sterile surgical gown, a sterile glove, or a sterile cover configured with a barrier to inhibit needle sticks and a surface configured to stably support one or more of a suture pack or a needle receptacle over one or more of a hand, a radial forearm or a volar forearm.

In the apparatuses, methods, and needle receptacle disclosed herein, one or more of a sterile cover or a sterile drape may be configured with a barrier to inhibit needle sticks and a surface configured to stably support one or more of a suture pack or a needle receptacle.

The apparatuses, methods, and needle receptacle disclosed herein may enable passing of a plurality of suture needles into and out of a near surgical field, thereby eliminating passing of individual suture needles between a surgeon and a surgical assistant.

The apparatuses, methods, and needle receptacle disclosed herein may enable passing of a plurality of secured into and out of a near surgical field, thereby eliminating passing of individual suture needles between a surgeon and a surgical assistant.

The apparatuses, methods, and needle receptacle disclosed herein may enable passing of a plurality of innocuous needles into and out of a near surgical field, thereby eliminating passing of individual suture needles between a surgeon and a surgical assistant.

The apparatuses, methods, and needle receptacle disclosed herein may enable passing of a plurality of used needles into and out of a near surgical field, thereby eliminating passing of individual suture needles between a surgeon and a surgical assistant.

The apparatuses, methods, and needle receptacle disclosed herein may comprise a step of dispensing of a suture needle by a surgeon from a near surgical field.

The apparatuses, methods, and needle receptacle disclosed herein may comprise a means for mounting one or more suture needle packages within a near surgical field.

The apparatuses, methods, and needle receptacle disclosed herein may comprise a needle resistant barrier mounted on a surgeon's arm. The needle resistant barrier may be configured to provide a mounting surface for one or more suture needle packages.

In the apparatuses, methods, and needle receptacle disclosed herein, a needle resistant barrier may comprise a light weight material and may be configured to conform to one or more of a surgeons arm, wrist, or hand.

In the apparatuses, methods, and needle receptacle disclosed herein, a needle resistant barrier may comprise a thin, puncture-resistant material integrated with a flexible web.

In the apparatuses, methods, and needle receptacle disclosed herein, a needle resistant barrier may be configured to adjust in order to accommodate a range of forearm sizes.

In the apparatuses, methods, and needle receptacle disclosed herein, a needle resistant barrier may comprise a plurality of bi-stable springs connected by a flexible web.

In the apparatuses, methods, and needle receptacle disclosed herein, a needle resistant barrier may comprise a malleable metal material having one or more grooves to control bending of the malleable metal material.

In the apparatuses, methods, and needle receptacle disclosed herein, a needle resistant barrier may comprise a plastic material having one or more hinges.

In the apparatuses, methods, and needle receptacle disclosed herein, a needle resistant barrier may be configured to be donned and doffed quickly with one hand.

In the apparatuses, methods, and needle receptacle disclosed herein, a needle resistant barrier may comprise a plurality of stacked bi-stable springs to adjust a compressive force.

In the apparatuses, methods, and needle receptacle disclosed herein, a needle resistant barrier may be configured to provide a modular mounting surface on a dorsal side of one or more of a forearm or a wrist. The modular mounting surface may be configured to support one or more surgical tools or materials.

In the apparatuses, methods, and needle receptacle disclosed herein, a suture needle package may be configured to mount on one or more of a surgeon's arm, wrist, or a back of a hand.

In the apparatuses, methods, and needle receptacle disclosed herein, a suture needle package may be configured to mount on the needle receptacle.

In the apparatuses, methods, and needle receptacle disclosed herein, a needle resistant barrier may be configured to provide protection to a volar side of one or more of a forearm or a wrist.

In the apparatuses, methods, and needle receptacle disclosed herein, the needle receptacle may be configured to couple to a surgical drape.

In the apparatuses, methods, and needle receptacle disclosed herein, the needle receptacle may be configured to couple to a needle resistant barrier mounted on a surgeon's forearm.

In the apparatuses, methods, and needle receptacle disclosed herein, the needle receptacle may be configured to attach and detach from a needle resistant barrier with one hand.

In the apparatuses, methods, and needle receptacle disclosed herein, the needle receptacle may be configured to attach to a surgical tool In the apparatuses, methods, and needle receptacle disclosed herein, the needle receptacle may be configured to attach to a surgical tool, and the needle receptacle may be configured to accommodate a variety of handle widths and thicknesses of a surgical tool.

In the apparatuses, methods, and needle receptacle disclosed herein, the needle receptacle may be configured to couple to a needle resistant barrier integrated into a surgical apparel.

In the apparatuses, methods, and needle receptacle disclosed herein, the needle receptacle may be configured to couple to a needle resistant barrier integrated into a surgical gown, a gown sleeve, or an extended glove.

In the apparatuses, methods, and needle receptacle disclosed herein, the needle receptacle may be configured to provide protection from both leading and trailing ends of a plurality of used suture needles by one or more of encapsulating or covering.

In the apparatuses, methods, and needle receptacle disclosed herein, the needle receptacle may be configured to inhibit one or more of unintentional removal or dislodgment.

In the apparatuses, methods, and needle receptacle disclosed herein, the needle receptacle may be configured to facilitate needle insertion into the needle receptacle by allowing needles to be inserted with minimal hand-eye precision.

In the apparatuses, methods, and needle receptacle disclosed herein, the needle receptacle may be configured to facilitate needle insertion into the needle receptacle by allowing needles to be inserted with gross motor movement.

In the apparatuses, methods, and needle receptacle disclosed herein, the needle receptacle may be configured to facilitate needle insertion into the needle receptacle by allowing needles to be inserted with only articulation or rotation of the shoulder and elbow joints.

In the apparatuses, methods, and needle receptacle disclosed herein, the needle receptacle may comprise means for counting needles during and after the procedure.

In the apparatuses, methods, and needle receptacle disclosed herein, the needle receptacle may comprise means for reconciling needles during or after the procedure.

In the methods disclosed herein, a first set of needles from a first suture pack may be reconciled before a second suture pack enters the near surgical field.

In the apparatuses, methods, and needle receptacle disclosed herein, the needle receptacle is low-profile and lightweight.

In the apparatuses, methods, and needle receptacle disclosed herein the needle receptacle may be configured to receive needles held in needle drivers in various positions.

In the apparatuses, methods, and needle receptacle disclosed herein the needle receptacle may be is configured to inhibit magnetizing the needle driver.

In the apparatuses, methods, and needle receptacle disclosed herein the needle receptacle may be is configured to receive at least about 5 needles.

The apparatuses, methods, and needle receptacle disclosed herein may further comprise a step of cutting of a suture by a surgeon using a cutter disposed in a near surgical field.

In the apparatuses, methods, and needle receptacle disclosed herein, a cutter may be mounted on a surgeon's finger.

In the apparatuses, methods, and needle receptacle disclosed herein, a cutter may be mounted on a needle resistant barrier.

In the apparatuses, methods, and needle receptacle disclosed herein, a cutter may comprise retractable scissors on a cable with take up spool.

In the apparatuses, methods, and needle receptacle disclosed herein, a cutter may comprise an integrated and recessed blade.

In the apparatuses, methods, and needle receptacle disclosed herein, a cutter may be mounted on a surgical tool.

In the apparatuses, methods, and needle receptacle disclosed herein, a cutter may comprise may be integrated with a needle receptacle.

In the apparatuses, methods, and needle receptacle disclosed herein, a cutter may comprise may be configured to prevent unintentional damage to a surgeon's glove.

In the apparatuses, methods, and needle receptacle disclosed herein, the needle receptacle may be arranged over the volar forearm to allow easy insertion of a used needle when a hand holding needle holder is slightly pronated. The needle may be placed in the receptacle with rotation of an arm holding a needle driver with shoulder joint rotation in order to align and place the used needle into an opening of the needle receptacle. The needle may comprise a curved needle having a tip and a tail, and the length may be defined as a straight-line distance between the tip and the tail.

In many embodiments of the barrier, curved shell conforms to the shape of a volar surface of the forearm.

In many embodiments of the barrier, the curvature of the curved shell extending with curvature about the longitudinal axis conforms to a shape of a volar surface of the forearm.

In many embodiments of the barrier, the pre-formed shaped barrier conforms to the shape of a volar surface of the forearm.

In many embodiments of the barrier, the pre-formed shaped barrier is straight along the dorsal edge.

In many embodiments of the barrier, the curved shell is straight along the dorsal edge.

Aspects of the present disclosure may provide needle receptacles. An exemplary needle receptacle may comprise a lower structure and an upper structure above the lower structure to define a needle slot between the upper structure and the lower structure. The needle slot may comprise a secure zone to secure needles. The upper structure may comprise a first edge and a second edge arranged to define a deformable needle driver slit that extends through a portion of the upper structure, wherein the slit deforms to receive a needle driver.

Another exemplary needle receptacle may comprise a housing having a cross section having a width and a thickness, a needle slot for storing used suture needles within the cross section of the housing, and a deformable needle driver slot that extends through a portion of the upper structure.

Another exemplary needle receptacle may be for receiving a surgical suture needle, the needle having a tip, a trailing end and a needle body extending between the tip and the trailing end. The needle receptacle may comprise a housing, at least one opening, a secure zone, and a deformable driver needle slit. The housing may have a top and a bottom. The at least one opening between the top and the bottom may be configured and dimensioned to receive a surgical needle therethough. The secure zone within the housing may be configured to hold the surgical needle in an orientation with the needle tip secured. The secure zone may be in communication with the opening. The deformable needle driver slit may extend through the top of the housing and within the secure zone.

In many embodiments, the first edge separates from the first edge to receive the needle driver.

In many embodiments, the deformable needle driver slit includes a first edge and a second edge opposite the first edge.

In many embodiments, the first edge and the second edge contact each other in a non-deformed free standing state without a needle driver extending therebetween.

In many embodiments, the first edge and the second edge are spaced apart from each other in a non-deformed state, with a gap being defined between the first edge and the second edge.

In some embodiments, the gap is less than 1 mm.

In some embodiments, the gap is less than 2 mm.

In some embodiments, the gap is less than 0.5 mm.

In some embodiments, the upper structure comprises a stiff portion and a deformable portion, with the deformable portion being proximate to and including the needle driver slit.

In some embodiments, the upper structure is deformable.

In some embodiments, the lower structure is deformable.

In some embodiments, the upper structure and lower structure are both deformable.

In some embodiments, the lower structure comprises a landing zone, and the upper and lower structures define an entry zone and a second zone, the entry zone located between the landing zone and the secure zone and wherein separation of the slit increases proximate a needle driver when the needle driver advances along the slit.

In many embodiments of the apparatuses, methods, and needle receptacles disclosed herein, a portion of a needle body is visible through the needle driver slot.

In many embodiments of the apparatuses, methods, and needle receptacles disclosed herein, a mid-body portion a needle body is visible through the needle driver slot.

In many embodiments of the apparatuses, methods, and needle receptacles disclosed herein, a portion of a needle body is visible through the needle driver slot in the upper structure.

In many embodiments of the apparatuses, methods, and needle receptacles disclosed herein, a mid-body portion a needle body is visible through the needle driver slot visible through the needle driver slot in the upper structure.

In many embodiments of the apparatuses, methods, and needle receptacles disclosed herein, a portion of a needle body is visible through the needle driver slot in the lower structure.

In many embodiments of the apparatuses, methods, and needle receptacles disclosed herein, a mid-body portion a needle body is visible through the needle driver slot visible through the needle driver slot in the lower structure.

In many embodiments of the apparatuses, methods, and needle receptacles disclosed herein, a portion of a needle body is visible through both the needle driver slot in the lower structure and the needle driver slot in the upper structure.

In many embodiments of the apparatuses, methods, and needle receptacles disclosed herein, a mid-body portion a needle body is visible through the needle driver slot visible through both the needle driver slot in the lower structure and the needle driver slot in the upper structure.

In many embodiments of the apparatuses, methods, and needle receptacles disclosed herein, the lower structure provides for non-uniform light transmission therethrough.

In many embodiments of the apparatuses, methods, and needle receptacles disclosed herein, the lower structure comprises a translucent material.

In many embodiments of the apparatuses, methods, and needle receptacles disclosed herein, the lower structure comprises a light scattering material selected from the group consisting of a translucent material, a diffuse material, a rough material, and light scattering particles.

In many embodiments of the apparatuses, methods, and needle receptacles disclosed herein, the lower structure is semi opaque.

In many embodiments of the apparatuses, methods, and needle receptacles disclosed herein, the lower structure is opaque.

In many embodiments, the apparatuses, methods, and needle receptacles disclosed herein may be configured to non-uniformly transmit light.

In many embodiments, the apparatuses, methods, and needle receptacles disclosed herein may be configured to non-uniformly transmit backlight illumination.

In many embodiments, the apparatuses, methods, and needle receptacles disclosed herein may be configured to diffuse light from backlight illumination in order to provide more uniform backlight illumination of suture needles.

In many embodiments of the apparatuses, methods, and needle receptacles disclosed herein, the lower structure is dyed.

In many embodiments of the apparatuses, methods, and needle receptacles disclosed herein, the lower structure is colored.

In many embodiments of the apparatuses, methods, and needle receptacles disclosed herein, the lower structure provides includes a roughened surface for non-uniform light transmission therethrough.

In many embodiments, the apparatuses, methods, and needle receptacles disclosed herein may further comprise a flap extending into or along the needle driver slot from an edge of the needle driver slot.

In many embodiments, the apparatuses, methods, and needle receptacles disclosed herein may further comprise flaps extending into or along the needle driver slot from an edge of the needle driver slot.

In many embodiments of the apparatuses, methods, and needle receptacles disclosed herein, the flaps are deformable.

In many embodiments of the apparatuses, methods, and needle receptacles disclosed herein, the needle driver slot includes a first edge and a second edge opposite the first edge, and the flaps extend from one of the first and second edges.

In many embodiments of the apparatuses, methods, and needle receptacles disclosed herein, the needle driver slot includes a first edge and a second edge opposite the first edge, and the flaps extend from both the first edge and the second edge.

In many embodiments, the apparatuses, methods, and needle receptacles disclosed herein may further comprise flaps extending into the needle driver slit from an edge of the needle driver slot.

In many embodiments of the apparatuses, methods, and needle receptacles disclosed herein, the flaps are deformable.

In many embodiments of the apparatuses, methods, and needle receptacles disclosed herein, the needle driver slit includes a first edge and a second edge opposite the first edge and wherein the flaps extend from one of the first and second edges.

In many embodiments of the apparatuses, methods, and needle receptacles disclosed herein, the needle driver slit includes a first edge and a second edge opposite the first edge, and wherein the flaps extend from both the first edge and the second edge.

In many embodiments, the apparatuses, methods, and needle receptacles disclosed herein may further comprise flaps extending into the needle driver slit from an edge of the needle driver slit.

In many embodiments, the apparatuses, methods, and needle receptacles disclosed herein may further comprise protrusions that extend into the needle driver slot from an edge of the needle driver slot.

In many embodiments of the apparatuses, methods, and needle receptacles disclosed herein, the needle driver slot includes a first edge and a second edge opposite the first edge, and wherein the protrusions extend from one of the first and second edges.

In many embodiments of the apparatuses, methods, and needle receptacles disclosed herein, the needle driver slot includes a first edge and a second edge opposite the first edge, and wherein the protrusions extend from both the first edge and the second edge.

In many embodiments, the apparatuses, methods, and needle receptacles disclosed herein may further comprise that extend into the needle driver slit from an edge of the needle driver slot.

In many embodiments of the apparatuses, methods, and needle receptacles disclosed herein, the needle driver slit includes a first edge and a second edge opposite the first edge, and wherein the protrusion extend from one of the first and second edges.

In many embodiments of the apparatuses, methods, and needle receptacles disclosed herein, the needle driver slit includes a first edge and a second edge opposite the first edge, and wherein the protrusions extend from both the first edge and the second edge.

In many embodiments, the apparatuses, methods, and needle receptacles disclosed herein may further comprise protrusions that extend into the needle driver slot from an edge of the needle driver slit.

In many embodiments of the apparatuses, methods, and needle receptacles disclosed herein, the resistance of the needle driver along the needle driver slot is less than the resistance of the needle along the needle slot when the needle is advanced along the slot with a needle driver.

In many embodiments of the apparatuses, methods, and needle receptacles disclosed herein, the resistance of the needle receptacle against the needle driver is less than the resistance of the needle receptacle against the needle.

In many embodiments of the apparatuses, methods, and needle receptacles disclosed herein, the force imparted by the needle driver slot against movement of the needle driver is less than the force imparted by the needle slot against movement of the needle.

In many embodiments of the apparatuses, methods, and needle receptacles disclosed herein, the force imparted by the needle receptacle against movement of the needle driver is less than the force imparted by the needle receptacle against movement of the needle.

In many embodiments of the apparatuses, methods, and needle receptacles disclosed herein, the friction force between the needle driver slot or slit and the needle driver is less than the friction force between needle slot and the needle.

In many embodiments of the apparatuses, methods, and needle receptacles disclosed herein, the friction force between the needle receptacle and the needle driver is less than the friction force between the needle receptacle and the needle.

In many embodiments of the apparatuses, methods, and needle receptacles disclosed herein, a width of the needle driver slot varies along the length of the needle driver slot.

In many embodiments of the apparatuses, methods, and needle receptacles disclosed herein, the needle driver slot includes a first edge and a second edge that is opposite the first edge, the first edge and the second edge being separated by a width, and wherein the width varies along the length of the needle driver slot.

In many embodiments of the apparatuses, methods, and needle receptacles disclosed herein, the needle driver slot includes a first edge and a second edge that is proximate the first edge, the first edge and the second edge being separated by a width, and wherein the width varies along the length of the needle driver slot.

In many embodiments of the apparatuses, methods, and needle receptacles disclosed herein, the needle driver slot has a first end and a second end along a length of the needle driver slot and a width of the needle driver slot at the first end is greater than a width of the needle driver slot at the second end.

In many embodiments of the apparatuses, methods, and needle receptacles disclosed herein, the first end is closed and the second end is open for receiving a needle driver therethough.

In many embodiments of the apparatuses, methods, and needle receptacles disclosed herein, the needle driver slot has a first end and a second end along a length of the needle driver slot and a width of the needle driver slot at the second end is greater than a width of the needle driver slot at the first end.

In many embodiments of the apparatuses, methods, and needle receptacles disclosed herein, the first end of the needle driver slot is closed and the second end of the needle driver slot is open for receiving a needle driver therethrough.

In many embodiments of the apparatuses, methods, and needle receptacles disclosed herein, the first end of the needle driver slot is proximate the secure zone and the second end of the needle driver slot is proximate the transition zone.

In many embodiments of the apparatuses, methods, and needle receptacles disclosed herein, the first end of the needle driver slot is a greater distance from the entry zone than the second end of the needle driver slot.

In many embodiments, the methods, apparatuses, receptacles, kits, and barriers disclosed herein may further comprise 2-20 tactile bumps along the needle driver slot or the needle slot to facilitate localization into a plurality of zones. The tactile bumps may be sized to engage the needle driver moving along the needle driver slot or the needle moving along the needle slot. Each of the plurality of tactile bumps may define a boundary between adjacent zones in order to decrease bunching of a plurality needles when placed.

In many embodiments, the methods, apparatuses, receptacles, kits, and barriers disclosed herein may further comprise 5-8 tactile bumps along the needle driver slot or the needle slot to facilitate localization into individual zones.

In many embodiments, the methods, apparatuses, receptacles, kits, and barriers disclosed herein may further comprise 5 tactile bumps to facilitate localization into individual zones.

In many embodiments, the methods, apparatuses, receptacles, kits, and barriers disclosed herein may further comprise 3-8 tactile bumps to facilitate localization into individual zones.

In many embodiments, the methods, apparatuses, receptacles, kits, and barriers disclosed herein may further comprise 3-6 tactile bumps to facilitate localization into individual zones.

In many embodiments of the methods, apparatuses, receptacles, kits, and barriers disclosed herein, the tactile bumps are pairs of tactile bumps.

In many embodiments of the methods, apparatuses, receptacles, kits, and barriers disclosed herein, the tactile bumps are arranged along a length of the needle receptacle.

In many embodiments of the methods, apparatuses, receptacles, kits, and barriers disclosed herein, the tactile bumps are arranged along a length of the needle driver slot or needle driver slit.

In many embodiments of the methods, apparatuses, receptacles, kits, and barriers disclosed herein, the tactile bumps are arranged along a length of the needle slot.

In many embodiments of the methods, apparatuses, receptacles, kits, and barriers disclosed herein, the tactile bumps are arranged a first distance from each other along the length. The first tactile bump or bumps may be a second distance from an entrance to the needle slot, the second distance being greater than the first distance.

In many embodiments of the methods, apparatuses, receptacles, kits, and barriers disclosed herein, the needle receptacle is configured to be mounted on a barrier mounting base and the barrier mounting base is configured to be mounted on a barrier. The apparatus, method, or needle receptacle may further comprise a suture pack mounted to the barrier mounting base. The apparatus, method, or needle receptacle may further comprise a suture pack mounted to the needle receptacle. The apparatus, method, or needle receptacle may further comprise a suture pack mounted to the needle receptacle and the barrier mounting base.

In many embodiments of the apparatuses, methods, or needle receptacles disclosed herein, the suture pack is mounted to a barrier mounting base and the barrier mounting base is mounted to a barrier.

In many embodiments, the apparatuses, methods, or needle receptacles disclosed herein may further comprises a needle receptacle mounted to the barrier mounting base.

In many embodiments, the apparatuses, methods, or needle receptacles disclosed herein may further comprise a needle receptacle mounted to the suture pack.

In many embodiments, the apparatuses, methods, or needle receptacles disclosed herein may further comprise a needle receptacle mounted to the suture pack and the barrier mounting base.

In many embodiments, adhesion of the needle receptacle to the mounting base is greater than the adhesion of the mounting base to the barrier.

In many embodiments, adhesion of the mounting base to the barrier is sufficiently weak to allow manual removal of the mounting base from the barrier.

In many embodiments, the adhesion of the needle receptacle to the mounting base is sufficiently weak to allow removal of the needle receptacle from the mounting base.

In many embodiments, adhesion of the suture pack to the mounting base is greater than the adhesion of the mounting base to the barrier.

In many embodiments, adhesion of the suture pack to the needle receptacle is greater than the adhesion of the mounting base to the barrier.

Aspects of the present disclosure may provide a method comprising the steps of orienting a needle with respect to a needle receptacle with the tip of the needle directed away from a direction of translation of the needle and moving a needle in the direction of translation to an entry zone of a needle receptacle and into a secure zone of the needle receptacle.

Aspects of the present disclosure may provide a method of inserting a needle into a needle receptacle. The method may comprise the steps of placing the needle at an entry zone of the needle receptacle coupled to a forearm and moving the needle along the needle receptacle in the direction of translation to secure the needle within a housing of the needle receptacle. The needle may be oriented with respect to a needle receptacle with tips of the needle directed away from a direction of translation of the needle into the needle receptacle.

Aspects of the present disclosure may provide a method for securing of a suture needle by a surgeon. The method may comprise the steps of orienting a suture needle with respect to a needle receptacle with tips of the needle directed away from a direction of translation of the needle, inserting the suture needle into an opening of a needle receptacle with a needle driver by moving the needle in the direction of translation, securing the suture needle inside the needle receptacle, and releasing the suture needle from the needle driver.

In many embodiments, the body of the needle leads the needle tip in the direction of translation.

In many embodiments, wherein the needle receptacle inhibits translation of the needle into the needle slot when the needle tip leads the needle body in the direction of translation.

In many embodiments, a translation force to translate the needle within the needle slot is twice a great when translating the needle with the tip leading the body as compared to translating the needle with the body leading the tip.

In many embodiments, a translation force to translate the needle within the needle slot is greater when translating the needle with the tip leading the body as compared to translating the needle with the body leading the tip.

In many embodiments, a translation force to translate the needle within the needle slot is greater when translating the needle with the tip leading the body as compared to translating the needle with the body leading the tip.

In many embodiments, the direction of translation extends between an entry zone of the needle receptacle and a secure zone of a needle receptacle.

In many embodiments, the direction of translation along a longitudinal axis of a needle receptacle.

In many embodiments, the direction of translation is along a length of a needle driver slot.

In many embodiments, the direction of translation is along a length of a needle driver slit.

In many embodiments, the direction of translation is along a length of a user's forearm.

In many embodiments, the direction of translation extends between a wrist and an elbow of a user's arm.

In many embodiments, the direction of translation is parallel to a length of a needle driver slot or slit.

In many embodiments, the direction of translation starts proximate a user's wrist in a direction towards a user's elbow.

In many embodiments, the direction of translation is towards a secure zone.

In many embodiments, the direction of translation is towards a closed end of a needle driver slot or slit.

In many embodiments, the direction of translation is towards a proximal end of a needle driver slot or slit.

In many embodiments, the direction of translation is away from a landing zone.

In many embodiments, the direction of translation is away from a entry zone.

In many embodiments, the direction of translation is away from transition zone.

Aspects of the present disclosure provide needle receptacles. An exemplary needle receptacle may comprise a flexible upper structure, a flexible lower structure, and a needle driver receiving slot. The flexible upper structure and the flexible lower structure may be coupled to each other to define a needle slot to receive needles. The needle driver receiving slot may be formed through the flexible upper structure extending from the perimeter of the upper flexible sheet material.

Another exemplary needle receptacle may comprise a sheet material, a needle slot, and a needle driver. The sheet material may extend between a first end and a second end and may be folded onto itself at a fold to form an upper structure and a lower structure, the upper structure and lower structure having substantially parallel planar surfaces in a narrow profile configuration. The substantially parallel planar surfaces can extend within about ten degrees of each other, and can extend within about five degrees of parallel to each other. The needle slot may be defined between the upper structure and the lower structure. The needle driver receiving slot may be formed though the upper structure and extending from the first end towards the fold.

Another exemplary needle receptacle may comprise a first flexible sheet material forming an upper structure, a second flexible sheet material forming a lower structure, and a slot formed through the first flexible sheet material and extending from the perimeter of the first flexible sheet material. The first flexible sheet material and the second flexible sheet material may be coupled to each other at their respective perimeters.

In many embodiments, the needle receptacle is mounted to a rigid structure.

In many embodiments, the upper structure and lower structure comprise sufficient strength to resist puncture with a sharp tip of a needle with at least 1 pound force applied to the needle tip. The needle may be selected from the group consisting of a tapered suture needle and a cutting suture needle. The force may be selected from the group consisting of at least 2 pounds, at least 3 pounds and at least 4 pounds.

In many embodiments, the upper structure and lower structure comprise sufficient strength to resist puncture with a sharp tip of a needle with at least 0.3 pound force applied to the tip of the needle. The needle may comprise a United States Surgical Corporation GS-21 needle.

In many embodiments, the upper structure and lower structure comprise sufficient strength to resist puncture with a sharp tip of a needle with at least 0.3 pound force applied to the tip of the needle. The needle may comprise a United States Surgical Corporation CV-23 needle.

In many embodiments, the upper structure and lower structure comprise sufficient strength to resist puncture with a sharp tip of a needle with at least 0.3 pound force applied to the tip of the needle. The needle may comprise a United States Surgical Corporation thin bodied half-circle needle.

In many embodiments, the upper structure and lower structure comprise sufficient strength to resist puncture with a sharp tip of a needle with at least 0.3 pound force applied to the tip of the needle, The needle may comprise a United States Surgical Corporation medium bodied half-circle needle.

In many embodiments, the upper structure and lower structure comprise sufficient strength to resist puncture with a sharp tip of a needle with at least 0.5 pound force applied to the tip of the needle. The needle may comprise a United States Surgical Corporation GS-21 needle.

In many embodiments, the upper structure and lower structure comprise sufficient strength to resist puncture with a sharp tip of a needle with at least 0.5 pound force applied to the tip of the needle. The needle may comprise a United States Surgical Corporation CV-23 needle.

In many embodiments, upper structure and lower structure comprise sufficient strength to resist puncture with a sharp tip of a needle with at least 0.5 pound force applied to the tip of the needle. The needle may comprise a United States Surgical Corporation thin bodied half-circle needle.

In many embodiments, the upper structure and lower structure comprise sufficient strength to resist puncture with a sharp tip of a needle with at least 1 pound force applied to the tip of the needle. The needle may comprise a United States Surgical Corporation medium bodied half-circle needle.

In many embodiments, the upper structure and lower structure comprise sufficient strength to resist puncture with a sharp tip of a needle with at least 1 pound force applied to the tip of the needle. The needle may comprise a United States Surgical Corporation GS-21 needle.

In many embodiments, the upper structure and lower structure comprise sufficient strength to resist puncture with a sharp tip of a needle with at least 1 pound force applied to the tip of the needle. The needle may comprise a United States Surgical Corporation CV-23 needle.

In many embodiments, the upper structure and lower structure comprise sufficient strength to resist puncture with a sharp tip of a needle with at least 1 pound force applied to the tip of the needle. The needle may comprise a United States Surgical Corporation thin bodied half-circle needle.

In many embodiments, the upper structure and lower structure comprise sufficient strength to resist puncture with a sharp tip of a needle with at least 1 pound force applied to the tip of the needle. The needle may comprise a United States Surgical Corporation medium bodied half-circle needle.

In many embodiments, the upper structure and lower structure comprise sufficient strength to resist puncture with a sharp tip of a needle with at least 3 pound force applied to the tip of the needle. The needle may comprise a United States Surgical Corporation GS-21 needle.

In many embodiments, the upper structure and lower structure comprise sufficient strength to resist puncture with a sharp tip of a needle with at least 3 pound force applied to the tip of the needle. The needle may comprise a United States Surgical Corporation CV-23 needle.

In many embodiments, the upper structure and lower structure comprise sufficient strength to resist puncture with a sharp tip of a needle with at least 3 pound force applied to the tip of the needle. The needle may comprise a United States Surgical Corporation thin bodied half-circle needle.

In many embodiments, the upper structure and lower structure comprise sufficient strength to resist puncture with a sharp tip of a needle with at least 3 pound force applied to the tip of the needle. The needle may comprise a United States Surgical Corporation medium bodied half-circle needle.

In many embodiments, the upper structure and lower structure are configured to flex together in order to increase a distance of the needle slot between the upper structure and the lower structure from a first distance in a narrow profile configuration for placement inside sterile packaging to a second distance in an expanded profile configuration outside the sterile packaging with the second distance greater than the first distance in order to receive the needles.

In some embodiments, the first structure contacts the second structure in the narrow profile configuration.

In some embodiments, the first structure contacts the second structure in the narrow profile configuration.

In some embodiments, the first structure and the second structure comprise sufficient thickness to hold the needles between the first structure and the second structure.

In some embodiments, the first structure and the second structure comprise sufficient thickness to secure the needles in a secure zone between the first structure and the second structure.

In some embodiments, the upper structure and lower structure are substantially flat in the narrow profile configuration. The upper structure and lower structure may be curved in the expanded profile configuration.

In some embodiments, the needle receptacle comprises a length, a width, and a height, the length being greater than width and the width being greater than the height. The thickness in the narrow profile configuration may be selected from the group consisting of no more than 5 mm, no more than 4 mm, no more than 3 mm, no more than 2 mm, no more than 1 mm, and no more than 0.5 mm. A difference between the first distance and the second distance may be selected from the group consisting of no more than 3 mm, no more than 2 mm, no more than 1 mm, and no more than 0.5 mm.

In some embodiments, the upper structure and the lower structure each comprise a thickness within a range selected from the group consisting of 0.1 mm to 2.5 mm, 0.2 mm to 2 mm, 0.25 mm to 2 mm and 0.5 mm to 1 mm.

In some embodiments, the receptacle comprises a first side and a second side opposite the first side. The upper structure may be connected to the lower structure at a first coupling region along the first side and a second coupling region along the second side. The needle slot may extend between the first coupling region and the second coupling region. A distance between the first coupling region and the second coupling region may define a width of the needle slot.

In some embodiments, first surface is connected to the second coupling surface along a third coupling region defining an end of the needle slot.

In some embodiments, the needle receptacle comprises a first open end and a second open end opposite the second open end with the needle slot extending between the first open end and the second open end. The first structure and the second structure may comprise sufficient stiffness to secure the needles in the needle slot between the first region and the second region.

In some embodiments, the needle receptacle may further comprise a strip of material along a lower surface of the lower structure to adhere the needle receptacle to a support. The strip of material may be oriented along a long axis with a long axis of the needle slot to allow the lower structure to flex with the upper structure when the distance increases from the first distance to the second distance.

Aspects of the present disclosure may provide sterile kits. An exemplary sterile kit may comprise a sterile packing comprising a sterile barrier, a plurality of needles, and a needle receptacle. The plurality of needles may be contained within a needle package. A tip to tip distance of each of the plurality of needles may be less than a width of the needle slot. The plurality of needles and the needle receptacle may be sterile and contained within the sterile barrier of the sterile kit.

In many embodiments, the tip to tip distance of each of the plurality of needles is within a range selected from the group consisting of 75% to 100% of the width of the needle slot, 80% to 99% of the width of the needle slot, and 85% to 98% of the width of the needle slot and 90 to 97% of the width of the needle slot.

In many embodiments, the tip to tip distance of each of the plurality of needles is within a percentage of the width of the needle slot in the expanded configuration, the percentage within range selected from the group consisting of 75% to 100% of the second width of the needle slot, 80% to 99% of the second width of the needle slot, and 85% to 98% of the second width of the needle slot and 90 to 97% of the second width of the needle slot. The needle slot may comprise a length, a width, and a height, the length being greater than the width and the width being greater than the height.

In many embodiments, the upper structure and the lower structure each comprise a needle driver slot to receive a needle driver.

In many embodiments, the upper structure and lower structure are connected to each other at their respective perimeters.

In many embodiments, the upper structure and lower structure are parallel to each other at their respective perimeters.

In many embodiments, the upper structure and lower structure are adhered to each other at their respective perimeters.

In many embodiments, the upper structure forms an upper portion of a secure zone and a transition zone of the needle receptacle.

In many embodiments, the lower structure forms a lower portion of the secure zone and the transition zone of the needle receptacle.

In many embodiments, the lower structure forms a landing zone of the needle receptacle.

In many embodiments, the lower structure that forms the landing zone of the needle receptacle extends from the transition zone away from the secure zone.

In many embodiments, the needle receptacle has a length that extends between a first end and a second end. The entry zone may include the first end and the secure zone may include the second end. The transition zone may be between the first end and the second end.

In many embodiments, the lower structure of the entry zone is a landing zone configured to receive a needle and a needle driver tip.

In many embodiments, the needle driver slot extends from an edge of the upper structure in the transition zone into the secure zone, partitioning the upper structure and the edge into separate first and second portions within the transition zone.

In many embodiments, first and second portions of the upper structure within the transition zone are deformed towards the lower structure, displacing the upper structure from the lower structure and forming an opening in the needle slot therebetween.

In many embodiments, first and second portions of the upper structure within the transition zone are folded towards the lower structure, displacing the upper structure from the lower structure and forming an opening in the needle slot therebetween.

In many embodiments, first and second portions of the upper structure within the transition zone are folded away from the lower structure, displacing the upper structure from the lower structure and forming an opening in the needle slot therebetween.

In many embodiments, the first and second sheet material is flexible.

In many embodiments, the first and second sheet material chosen from the group consisting of: ABS, polycarbonate, polyethylene, polypropylene, thermoformable plastic, and PETG.

In many embodiments, the kit further comprises at least one needle.

In some embodiments, the needle has a length and the needle slot has a width, the length of the needle being substantially similar to, but less than the width of the needle slot.

In some embodiments, the needle has a length and the needle receptacle has a width, the length of the needle being substantially similar to, but less than the width of the needle receptacle.

In some embodiments, the length of the needle and the width of the needle slot are such that the needle deforms the needle slot when the needle is in the needle slot.

In some embodiments, the length of the needle and the width of the needle slot are such that the upper structure and the lower structure of the needle receptacle apply a compressive force on the needle when the needle is in the needle slot.

In some embodiments, the length of the needle and the width of the needle slot are such that the needle deforms the upper structure and the lower structure when the needle is in the needle slot.

In some embodiments, the needle is a curved needle having a tip and a tail, and the length is defined as a straight-line distance between the tip and the tail.

In some embodiments, the length of the needle is the defined as a straight-line distance between the two ends of the needle.

In some embodiments, the lower structure includes a flap that is foldable over the upper structure to close the needle slot.

In some embodiments, the lower structure includes a flap that is foldable over the upper structure to seal the needle slot.

In some embodiments, the flap includes at least a portion of the lower structure extending beyond the transition zone away from the secure zone.

In some embodiments, the flap includes at least a portion of the entry zone of the lower structure.

In some embodiments, the kit further comprises an adhesive on the flap.

In some embodiments, the adhesive on the flap adheres to the upper structure to close the needle slot.

In some embodiments, the adhesive on the flap adheres to the upper structure to seal the needle slot.

In many embodiments, the apparatuses, methods, needle receptacles, and kits disclosed herein may further comprise a stiff structure configured to receive the needle receptacle. The stiff structure may include an open side shaped to receive the needle receptacle. The stiff structure may include a needle driver slot that aligns with a needle driver slot of the needle receptacle when the needle receptacle is within the stiff structure. The stiff structure may be in the shape of a hexahedron. The stiff structure may include an upper structure coupled to a lower structure, with the stiff structure configured to receive and hold the needle receptacle between the upper structure and the lower structure. The stiff structure may include an upper structure coupled to a lower structure, with the upper structure and lower structure configured to exert a clamping force on the needle receptacle to hold the needle receptacle to the stiff structure. The stiff structure may include an upper structure, a lower structure, and a wall structure, with the wall structure coupling the upper structure and the lower structure together. The stiff structure may comprise a receiver configured to receive the needle receptacle.

The stiff structure may include a first stiff member having first and second ends, a second stiff member extending from the first end of the first stiff member, and a third stiff member extending from the second end of the first stiff and in a same plane as the second stiff member. The stiff structure may be configured to receive a needle receptacle of any of the preceding claims between the second and third stiff members.

In some embodiments, the distance between the second and third member at an end proximate the first member is less than a distance between the second and third member at a distal end such that when the needle receptacle is received within the stiff structure. The second and third members may impart a force on the needle receptacle, deforming the needle receptacle and enlarging an entry to the needle slot of the needle receptacle.

In some embodiments, a width of the needle receptacle at an entry zone is greater than a width of the needle receptacle at a secure zone such that when the needle receptacle is received within the stiff structure. The second and third members may impart a force on the needle receptacle, deforming the needle receptacle and enlarging an entry to the needle slot of the needle receptacle.

Aspects of the present disclosure provide needle receptacles. An exemplary needle receptacle may comprise a first sheet of stiff material forming an upper structure, a second sheet of stiff material forming a lower structure, and a slot formed through the second stiff sheet material and extending from the perimeter of the second stiff sheet material. The first sheet stiff material and the second stiff sheet material may be coupled to each other at their respective perimeters.

In many embodiments, the upper structure and lower structure are parallel to each other at their respective perimeters.

In many embodiments, the upper structure and lower structure are adhered to each other at their respective perimeters.

In many embodiments, the upper structure and lower structure are coupled to each other via walls that extend from the perimeter of the lower structure to the perimeter of the upper structure.

In many embodiments, the lateral opening is configured to receive a needle therethrough.

In many embodiments, the upper structure forms an upper portion of a secure zone and a transition zone of the needle receptacle.

In many embodiments, the lower structure forms a lower portion of the secure zone and the transition zone of the needle receptacle.

In many embodiments, the lower structure forms a landing zone of the needle receptacle.

In many embodiments, the lower structure that forms the landing zone of the needle receptacle extends from the transition zone away from the secure zone.

In many embodiments, the needle receptacle has a length that extends between a first end and a second end. The entry zone may include the first end and the secure zone may include the second end. The transition zone may be between the first end and the second end.

In many embodiments, the lower structure of the entry zone is a landing zone configured to receive a needle and a needle driver tip.

In many embodiments, the needle driver slot extends from an edge of the upper structure in the transition zone into the secure zone, partitioning the upper structure and the edge into separate first and second portions within the transition zone.

In many embodiments, first and second portions of the upper structure within the transition zone are deformed towards the lower structure, displacing the upper structure from the lower structure and forming an opening in the needle slot therebetween.

In many embodiments, first and second portions of the upper structure within the transition zone are folded towards the lower structure, displacing the upper structure from the lower structure and forming an opening in the needle slot therebetween.

In many embodiments, the lower structure includes a flap that is foldable over the upper structure to close the needle slot.

In many embodiments, the lower structure includes a flap that is foldable over the upper structure to seal the needle slot.

In many embodiments, the flap includes at least a portion of the lower structure extending beyond the transition zone away from the secure zone.

In many embodiments, the flap includes at least a portion of the entry zone of the lower structure.

In many embodiments, the needle receptacle further comprises an adhesive on the flap.

In many embodiments, the adhesive on the flap adheres to the upper structure to close the needle slot.

In many embodiments, the adhesive on the flap adheres to the upper structure to seal the needle slot.

In many embodiments, the needle receptacle further comprises one or more needle retainers within the needle slot.

In many embodiments, the needle retainers include at least one magnet.

In many embodiments, the at least one magnet is coupled to one or both of the upper structure and the lower structure.

In many embodiments, the at least one magnet is within one or both of the upper structure and the lower structure.

In many embodiments, the needle retainers include at least one adhesive tab.

In many embodiments, the at least one adhesive tab is coupled to one or both of the upper structure and the lower structure.

In many embodiments, the at least one adhesive tab extends into the needle slot from one or both of the upper structure and the lower structure.

In many embodiments, the at least one adhesive tab includes opposite first and second sides, the first side facing an opening in the needle slot and being non-adhesive and the second side facing away from the opening in the needle slot and being adhesive.

In many embodiments, the needle retainer include a compliant material within the needle slot.

In many embodiments, the compliant material includes a first foam structure that extends from the lower structure towards the upper structure and applies a retention force to the upper structure through a needle within the needle slot to retain the needle within the slot.

In many embodiments, the compliant material includes a first foam structure that extends from the upper structure towards the lower structure and applies a retention force to the lower structure through a needle within the needle slot to retain the needle within the needle slot.

In many embodiments, the compliant material includes a first foam structure that extends from the upper structure towards the lower structure and a second foam structure that extends from the lower structure towards the upper structure. A gap may be defined between the first foam structure and the second foam structure. The first foam structure and the second foam structure may exert a force on each other through a needle within the gap to retain the needle within the needle slot.

In many embodiments, the needle retainers include a mechanical divider that allows needles to enter the needle slot and resists needles exiting the needle slot.

In many embodiments, the needle retainers include at least one mechanical divider. The divider may comprise a leading structure, a following structure, and a pivot structure. The pivot structure may couple the leading structure to the following structure. The divider may be configured to permit needles to move into the needle slot, but resist movement of needles out of the needle slot.

In many embodiments, the at least one divider separates one needle from another needle in an ordered array within the needle slot.

In many embodiments, the leading structure and the following structure extend from the pivot structure at a right angle to each other.

In many embodiments, the leading structure and the following structure extend from the pivot structure at an obtuse angle to each other.

In many embodiments, in an initial configuration, the following structure rests against the lower structure of the needle receptacle and the leading structure extends into the needle slot from the pivot structure, the pivot structure being coupled to the lower structure of the needle receptacle.

In many embodiments, the pivot structure includes a spring that holds the following structure against the lower structure of the needle receptacle.

In many embodiments, the spring is a helical spring.

In many embodiments, in a retention configuration, the following structure extends into the needle slot form the pivot structure forming a barrier between a needle within the needle slot and the entry zone of the needle receptacle.

In many embodiments, the needle retainers retain the needles in a planar array within the needle slot.

In many embodiments, the needle retainers retain the needles in such that they do not overlay with each other within the needle slot.

In many embodiments, the needle retainers retain the needles in an array within the needle slot.

In many embodiments, the needle retainers retain the needles in an unstacked configuration within the needle slot.

In many embodiments, the needle retainers retain the needles within the needle slot such that each of the needles is separated for each other of the needles.

In many embodiments, the retaining features are magnetic.

In many embodiments, the one or more clips extending along the length of the needle slot and facing the lateral opening of the needle slot, the one or more clips coupled to the needle receptacle at the lateral opening, such that a needle placed into the needle slot is directed into the one or more clips, and held securely between the upper and lower portions of the clips as the needle is translated away from the lateral opening and towards the closed end.

In many embodiments, each clip comprises an upper portion, a lower portion, and a hinge portion that connects the upper and lower portions, wherein the clip is configured to apply a compressive force against a needle placed between the upper and lower portions.

In many embodiments of the needle receptacle disclosed herein, the upper structure and the lower structure are separated by a first distance at a first end of the secure zone proximate the transition zone and a second distance at a second end of the secure zone distal the transition zone, the first distance being less than the second distance such that the upper and lower structures exert a clamping force on a plurality of needles arranged between the first and the second end within the needle slot.

In many embodiments of the needle receptacle disclosed herein, the needle receptacle further comprises a ratcheting cover, engaged with the needle receptacle and configured to translate longitudinally in a first direction towards the entry zone and resist translation away from the entry zone.

In many embodiments of the needle receptacle disclosed herein, the ratcheting cover covers the needle driver slot as the cover translates towards the entry zone.

In many embodiments of the needle receptacle disclosed herein, the needle receptacle further comprises a needle receiver, the needle receiver comprising an elongated body having an upper surface and shaped to be received within the secure zone of a needle receptacle, and receiving tabs extending from the upper surface of the elongated body.

In many embodiments of the needle receptacle disclosed herein, the receiving tabs are configured to be engaged with a needle.

In many embodiments of the needle receptacle disclosed herein, the needle engages one or more receiving tabs and translates into the secure zone of the needle slot, the needle pulls a portion of the needle receiver into the needle slot.

In many embodiments of the needle receptacle disclosed herein, the needle receptacle further comprises an aperture though the lower structure and within the entry zone or transition zone, the needle receiver configured to pass from underneath the lower structure, though the aperture, and into the needle slot.

In many embodiments of the needle receptacle disclosed herein, the receiving tabs are affixed to the upper surface of the needle receiver.

In many embodiments of the needle receptacle disclosed herein, the receiving tabs are formed by cutting a slit though the needle receiver and plastically deforming the receiving tab formed by the slit in a direction though the upper surface of the needle receiver.

In many embodiments of the needle receptacle disclosed herein, the receiving tabs are formed by cutting a slit though the needle receiver and deflecting the receiving tab formed by the slit in a direction though the upper surface of the needle receiver.

In many embodiments of the needle receptacle disclosed herein, the needle receiver is configured to ratchet into the needle slot.

In many embodiments of the needle receptacle disclosed herein, the needle receiver is configured to permit movement of the needle receiver into the needle driver slot and resist movement of the needle receiver out of the needle slot.

In many embodiments of the needle receptacle disclosed herein, the receiving tabs are configured to hold the needles within the needle slot in a spaced-apart array.

In many embodiments of the needle receptacle disclosed herein, the array is an ordered array.

In many embodiments of the needle receptacle disclosed herein, the array is a planar array.

In many embodiments of the needle receptacle disclosed herein, the needle receptacle further comprises blocking tabs extending from a respective one or both of the upper surface or lower surface towards the other of the upper surface or lower surface and being configured to permit entrance of a needle under load provided by a needle driver but retain the needles within the needle slot when not under load.

In many embodiments of the needle receptacles, apparatuses, barriers, and methods disclosed herein, the stiff portion comprises a rigid portion.

In many embodiments of the needle receptacles, apparatuses, barriers, and methods disclosed herein, the stiff structure comprises a rigid structure.

In many embodiments of the needle receptacles, apparatuses, barriers, and methods disclosed herein, the stiff material comprises a rigid material.

In many embodiments of the needle receptacles, apparatuses, barriers, and methods disclosed herein, the slot comprises a slit.

Aspects of the present disclosure may provide a method comprising providing an apparatus, needle receptacle or barrier as disclosed herein.

Aspects of the present disclosure may provide needle receptacles. An exemplary needle receptacle may comprise a lower structure and an upper structure above the lower structure to define a needle slot between the upper structure and the lower structure. The needle slot may comprise a used needle secure zone to secure used needles and a new needle secure zone to secure new needles. The needle slot may extend from a first end of the needle receptacle at an entry to the needle slot to a second end of the needle receptacle at the new needle secure zone. The upper structure may comprise a first edge and a second edge arranged to define a needle driver slot that extends through the upper structure from the new needle secure zone to the used needle secure zone.

Aspects of the present disclosure provide needle receptacles. An exemplary needle receptacle may comprise an upper structure, a lower structure, and a slot. The upper structure and the lower structure may be coupled to each other at their respective perimeters. The slot may be formed through the upper structure and may extend from the perimeter of the upper structure at a first end to the perimeter of the upper structure at a second end.

In many embodiments, the first end of the upper structure is at an entry to the used needle secure zone and the second end of the upper structure is at an exit to the new needle secure zone.

In many embodiments, new needles are secured in the new needle secure zone and dispensed through the exit to the new needle secure zone.

In many embodiments, used needles are secured in the used needle secure zone and received through the entry to the new needle secure zone.

In many embodiments, the needle receptacle may further comprise a stop between the new needle secure zone and the used needle secure zone. The stop may be configured to resist translation of needles between the new needle secure zone and the used needle secure zone. The stop may extend from the lower structure and into the needle driver slot.

In many embodiments, the lower structure of the entry zone is a landing zone configured to receive a tip of a needle driver.

Aspects of the present disclosure may provide a sterile kit. The sterile kit may comprise a sterile packing comprising a sterile barrier, a suture pack, a needle receptacle of as disclosed herein, and a barrier mounting base. The suture pack and needle receptacle may be coupled to the barrier mounting base. The sterile kit may further comprise a sheet structure. The barrier mounting base may be coupled to the sheet structure.

Aspects of the present disclosure may provide a sterile kit. The sterile kit may comprise a sterile packing comprising a sterile barrier, a suture pack, a needle receptacle as disclosed herein, a barrier mounting base, and a sheet structure. The suture pack, needle receptacle, and the barrier mounting base may be coupled to the sheet structure. The barrier mounting base or the sheet structure may include a living hinge.

The needle receptacles disclosed herein may further comprise needle retention features within the needle slot to hold contaminated surgical needles therein.

In many embodiments, the needle retention features comprise foam disposed between upper and lower surfaces within the needle slot.

In many embodiments, the foam comprises urethane foam.

In many embodiments, the needle retention features comprise loop and hook fasteners disposed between upper and lower surfaces within the needle slot.

In many embodiments, the needle retention features comprise a plurality of protrusions extending from one or both of upper and lower surfaces within the needle slot.

In some embodiments, the plurality of protrusions comprise dimples.

In some embodiments, the plurality of protrusions comprise protuberances.

In some embodiments, the plurality of protrusions comprise filaments.

In some embodiments, the plurality of protrusions are angled away from the at least one opening to permit the needle to pass into the secure zone and to resist movement of the needle toward the at least one opening.

In some embodiments, the needle retention features comprise flaps disposed between upper and lower surfaces within the needle slot.

In many embodiments, the needle retention features comprise gel disposed between upper and lower surfaces within the needle slot.

In many embodiments, the needle retention features comprise hemispherical nubs disposed upper and lower surfaces within the needle slot.

In many embodiments, the needle retention features comprise angled bristles disposed upper and lower surfaces within the needle slot.

In many embodiments of the barrier disclosed herein, the barrier may includes a ferrous metal or magnet to magnetically couple to a needle receptacle.

In many embodiments of the needle receptacles disclosed herein, the needle receptacle includes a ferrous metal or magnet to magnetically couple to a barrier.

In many embodiments of the methods disclosed herein, the support is mounted to a drape over the over a patient.

In many embodiments of the methods disclosed herein, the support is mounted within the near surgical field.

In many embodiments of the methods disclosed herein, the support is mounted to a table within the near surgical field.

In many embodiments of the methods disclosed herein, the support is mounted to a stand within the near surgical field.

In many embodiments of the methods disclosed herein, the support is mounted at a location opposite the surgeon from an incision.

In many embodiments of the methods disclosed herein, the support is mounted proximal the incision of the patient.

In many embodiments of the methods disclosed herein, the support is mounted distal the incision of the patient.

In many embodiments of the methods disclosed herein, the support is mounted superior the incision of the patient.

In many embodiments of the methods disclosed herein, the support is mounted inferior the incision of the patient.

In many embodiments of the barrier mounting base disclosed herein, the barrier mounting base includes a flat surface for coupling one or more of a needle receptacle and a suture pack either directly or indirectly.

In many embodiments of the barrier mounting base disclosed herein, the barrier mounting base includes a concave surface shaped to receive a barrier therein.

In many embodiments of the barrier mounting base disclosed herein, the concave surface is opposite the flat surface.

In many embodiments of the barrier mounting base disclosed herein, the barrier mounting base further comprises torsional stiffeners extending from a surface of the barrier mounting base and is configured to increase the torsional rigidity of the barrier mounting base as compared to the barrier mounting brace without the torsional stiffeners.

In many embodiments of the barrier mounting base disclosed herein, the barrier mounting base further comprises first and second extensions along respective first and second sides of the barrier mounting base and configured to couple with a barrier. A lower surface of the barrier mounting base may contact a curved surface of the barrier at a first location and the first and second extensions may contact the curved surface of the batter at respective second and third locations.

In many embodiments of the support disclosed herein, the support comprises a sheet structure including a first hinge separating a base of the support from a mounting surface of the support.

In many embodiments of the support disclosed herein, the base is configured to couple the support to a surgical drape and the mounting surface is configured to couple to a needle receptacle.

In many embodiments of the support disclosed herein, the base is configured to couple the support to a surgical drape and the mounting surface is configured to couple to a needle receptacle.

In many embodiments of the support disclosed herein, the mounting surface is at an angle with the base of between 30 degrees and 90 degrees.

In many embodiments of the support disclosed herein, the mounting surface is at an angle with the base of between 60 degrees and 75 degrees.

In many embodiments of the support disclosed herein, the mounting surface is at an angle with the base of between 45 degrees and 75 degrees.

In many embodiments of the support disclosed herein, the mounting surface is at an angle with the base of between 45 degrees and 90 degrees.

In many embodiments of the support disclosed herein, the support comprises a sheet structure including a first hinge separating a base of the support from a mounting surface of the support.

In many embodiments of the support disclosed herein, the support comprises a sheet structure including a second hinge separating the mounting surface of the support from a adjustment structure that extends from the hinge and engages with the base.

In many embodiments of the support disclosed herein, the support comprises a plurality of stops that extend from a surface of the base and are engagable by the adjustment structure to adjust an angle of the mounting surface.

In many embodiments of the support disclosed herein, the support further comprises a third hinge between the adjustment structure and a fourth section, the fourth section coupleable to the base.

In many embodiments of the support disclosed herein, the hinge is a living hinge.

In many embodiments of the apparatus disclosed herein, the top and bottom of the spindles may include a coupling the top coupling having a first shape and the bottom coupling being shaped to receive the top coupling.

In many embodiments of the apparatus disclosed herein, the top and bottom of the spindles may include a coupling the top coupling having a first shape and the bottom coupling may be shaped to engage with the first shape of the top coupling.

In many embodiments of the apparatus disclosed herein, the top of the spindle may include an extension and the top of the spindle includes a recess shaped to receive the extension.

Aspects of the present disclosure may provide a needle receptacle comprising a lower structure that has a secure zone, an upper structure that has an entry zone and a secure zone, a needle slot for receiving one or more suture needles between the lower structure and the upper structure, a ramp structure that forms a lower entry zone, and an upper needle driver slot that extends through a portion of the upper structure and a lower needle driver slot that extends through portion of the lower structure and the ramp structure. The ramp structure may include a surface that is angled away from the needle slot and the upper structure. The entry zone of the upper structure may be angled away from the needle slot and the ramp structure. The needle receptacle may further comprise a compliant structure within the needle slot. The compliant structure may apply a holding force against a needle within the needle slot and the secure zone to resist translation of the needle out of the needle slot and the secure zone. The upper structure may apply a holding force against a needle within the needle slot and the secure zone to resist translation of the needle out of the needle slot and the secure zone.

Aspects of the present disclosure may provide needle receptacles. An exemplary needle receptacle may comprise first and second elongated members, a first needle retention slot, and a second needle retention slot. The first and second elongated members may have a first end coupled to a wall, the first and second members being parallel to each other and extending from the wall, the first elongated member having a first surface that faces the second elongated member and the second elongated member has a second surface that faces the first elongated member. The first needle retention slot may be formed in the first surface of the first elongated member and may extend along the length of the first elongated member. The second needle retention slot may be formed in the second surface of the second elongated member and may extend along the length of the second elongated member. The first and second needle retention slots may together form a secure needle zone for securing used suture needles therein.

The first and second elongated members may apply a compressive force to the used suture needles.

A needle driver slot may be formed between the first and second elongated members.

Aspects of the present disclosure may provide needle receptacles. An exemplary needle receptacle may comprise a housing and a cavity. The housing may have an upper portion and a lower portion coupled together by a hinge portion. The upper portion, lower portion, and hinge portion may form a u-shape. The cavity formed between the upper portion and the lower portion may be configured storing a plurality of needles.

In many embodiments of the needle receptacle disclosed herein, the hinge portion is spring-loaded to bias the upper and lower portion of the housing towards one another, such that the needles can be secured within the needle slot by the compressive forces exerted by the upper and lower portions.

In many embodiments of the needle receptacle disclosed herein, each of the upper portion and the lower portion comprises a first arm and a second arm and forming a needle driver slot therebetween.

In many embodiments of the needle receptacle disclosed herein, the lower portion further comprises an extension that extends away from hinge.

In many embodiments of the needle receptacle disclosed herein, the extension forms a landing zone for a needle to be secured in the housing. The needle may be placed in contact with an upper surface of the extension with the needle driver tip aligned with the needle driver slot.

In many embodiments of the needle receptacle disclosed herein, the needle driver slot in the lower portion extends into the extension.

In many embodiments of the needle receptacle disclosed herein, the needle driver slot in the lower portion extends through the extension.

In many embodiments of the needle receptacle disclosed herein, the needle driver slot is closed at an end of the first or second portion proximate the hinge and open at an end of the first or second portion away from the hinge.

In many embodiments of the needle receptacle disclosed herein, the needle receptacle may further comprise blocking tabs extending from a respective one or both of the upper portion or lower portion towards the other of the upper portion or lower portion and being configured to permit entrance of a needle under load provided by a needle driver but retain the needles within the needle slot when not under load.

In many embodiments of the needle receptacle disclosed herein, the needle receptacle may further comprise lateral walls disposed over outer lateral edges of housing.

In many embodiments of the needle receptacle disclosed herein, the lateral walls are integrated with the housing.

In many embodiments of the needle receptacle disclosed herein, the lateral walls are be removably coupled to outer lateral edges of housing.

Aspects of the present disclosure provide needle receptacles. An exemplary needle receptacle may comprise a lower structure having a channel formed in an upper surface thereof, an upper structure formed from a stiff material and a flexible material, a needle slot formed between the upper structure and the lower structure for securing used suture needles therein, and a needle driver slot formed by the upper structure between the stiff material and the flexible material and being above the channel of the lower structure.

In many embodiments, the needle receptacle further comprises a compliant material within the needle slot between the stiff material of the upper structure and the lower structure. The compliant material may comprise foam.

In many embodiments, the needle driver slot formed in the upper structure is parallel to the channel formed in the upper surface of the lower structure.

In many embodiments, the needle driver slot includes a first edge and a second edge opposite the first edge.

In many embodiments, the flexible material includes the first edge of the needle driver slot and the stiff material includes the second edge of the needle driver slot In many embodiments, the first edge separates from the second edge to receive the needle driver.

In many embodiments, the first edge and the second edge contact each other in a non-deformed free standing state without a needle driver extending therebetween.

In many embodiments, the first edge and the second edge are spaced apart from each other in a non-deformed state, a gap being defined between the first edge and the second edge.

In many embodiments, a portion of the lower structure extends beyond an end of the upper structure, forming a landing zone. The needle may be placed in contact with an upper surface of the extension with the needle driver tip aligned with the needle driver slot.

In many embodiments, receiving a needle receptacle comprises receiving five or more dispensed surgical needles from a surgeon, wherein the dispensed surgical needles are stabilized and innocuous within the needle receptacle when received from the surgeon.

In many embodiments, receiving a needle receptacle comprises receiving five or more reconciled dispensed surgical needles from a person who reconciled the surgical needles when the needles were within a near surgical field, and wherein the dispensed surgical needles are stabilized and innocuous within the needle receptacle when received. In many instances, the needles were within the needle receptacle when reconciled and reconciled with surgical needles of a needle pack within the near surgical field.

INCORPORATION BY REFERENCE

All publications, patents, and patent applications mentioned in this specification are herein incorporated by reference to the same extent as if each individual publication, patent, or patent application was specifically and individually indicated to be incorporated by reference.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1C-1F illustrate a method of using a suture handling apparatus in accordance with embodiments.

FIG. 23 illustrates a side view of a lower hook attachment mechanism.

FIG. 24 illustrates a bottom view of a lower hook attachment mechanism.

FIG. 25 illustrates a top view of a multi-layer suture package attached to a glove.

FIG. 26 illustrates a side view of a multi-layer suture package attached to a glove.

FIG. 29 illustrates a front view of an elastic band.

FIG. 30 illustrates a top view of an elastic band.

FIG. 31 illustrates a top view of a suture package held around a wrist portion of a glove with elastic bands.

FIG. 32 illustrates a side view of a suture package held around a wrist portion of a glove with elastic bands.

FIG. 33 illustrates a top view of a glove having a pocket for holding a suture package and a hole for accessing the sutures.

FIG. 34 illustrates a side view of a glove having a pocket for holding a suture package and a hole for accessing the sutures.

FIG. 111 illustrates a top view of an embodiment of a sharps container.

FIGS. 112 and 113 illustrate side views of an embodiment of a sharps container.

FIG. 114 illustrates a top view of an embodiment of suture packs attached to a multi-layer used needle receptacle.

FIGS. 115 and 116 illustrate side views of an embodiment of suture packs attached to a multi-layer used needle receptacle.

FIG. 117 illustrates a top view of an embodiment of suture packs attached to a multi-layer used needle receptacle.

FIGS. 118 and 119 illustrate side views of an embodiment of suture packs attached to a multi-layer used needle receptacle.

FIG. 120 illustrates a top view of an embodiment of suture packs attached to a multi-layer used needle receptacle.

FIGS. 121 and 122 illustrate side views of an embodiment of suture packs attached to a multi-layer used needle receptacle.

FIG. 144 illustrates a side view of an embodiment of a sharps container coupled to a suture pack on a surgical tool.

FIG. 145 illustrates a back view of an embodiment of a sharps container coupled to a suture pack.

FIG. 146 is a block diagram of an integrated suture packet and needle receptacle 308, in accordance with embodiments.

FIGS. 147A-149 illustrate embodiments of cartridge type sharps containers.

FIG. 150 illustrates a cartridge sharps container mounted on a surgical tool held by a hand.

FIGS. 151 and 152 illustrate an embodiment of a sharps container that includes needle locking mechanisms and needle insertion lights.

FIGS. 153 and 154 illustrate an embodiment of a sharps container that includes a locking mechanism.

FIGS. 155 and 156 illustrate an embodiment of a sharps container that includes needle locking mechanisms and needle insertion indicators.

FIGS. 157-159 illustrate embodiments of connection mechanisms for coupling surgical tools to cartridge type sharps containers.

FIGS. 160-166 illustrate embodiments of needle receptacles that include foam covering holes in a receptacle housing.

FIG. 167 illustrates a top view of an embodiment of a needle trap assembly having a suture pack holder coupled via a hinge.

FIG. 168 illustrates a top view of an embodiment of a needle trap assembly having suture pack holders.

Figure 169:
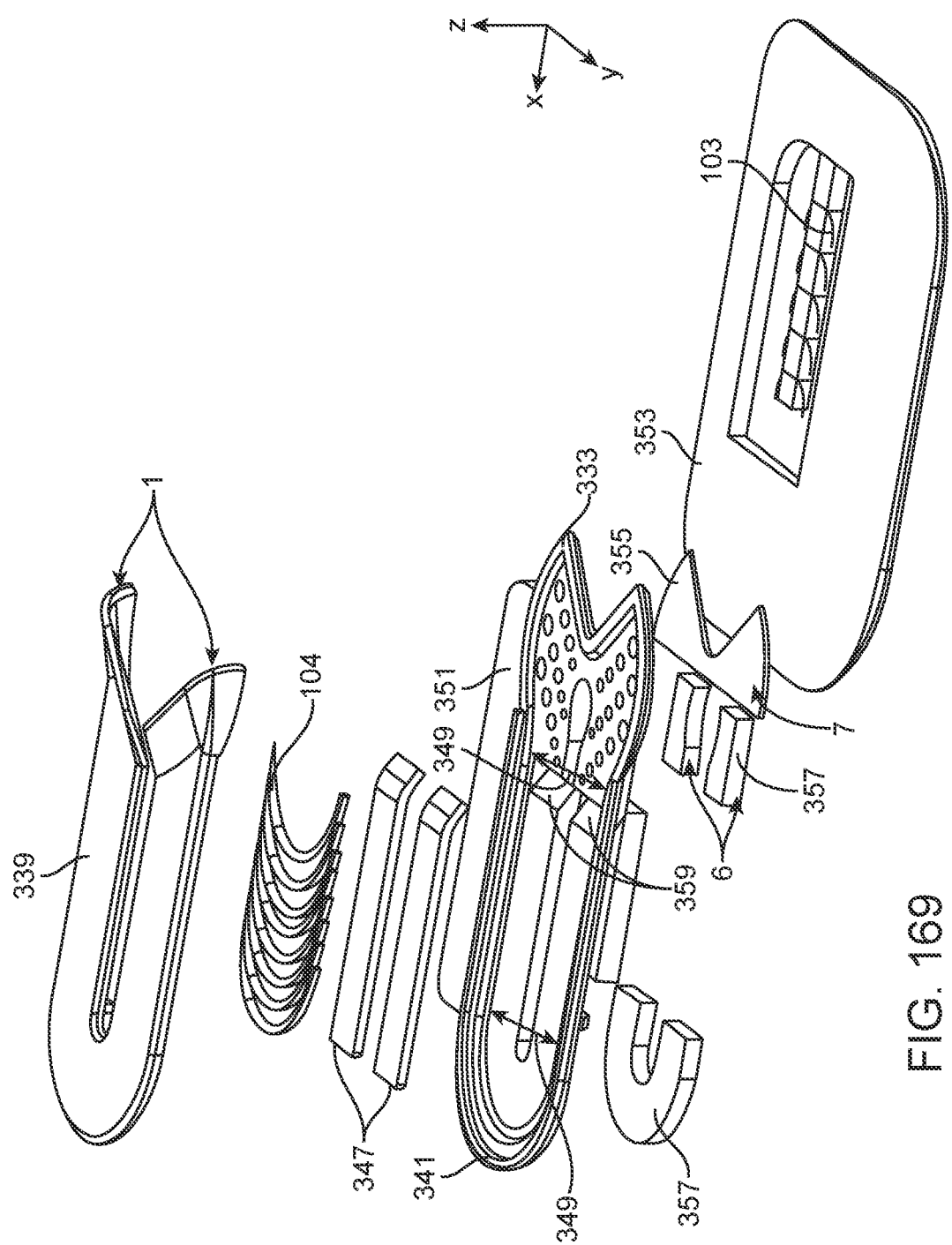

FIG. 169 illustrates an exploded top perspective view of an embodiment of a needle trap assembly having a suture pack holder.

Figure 170:
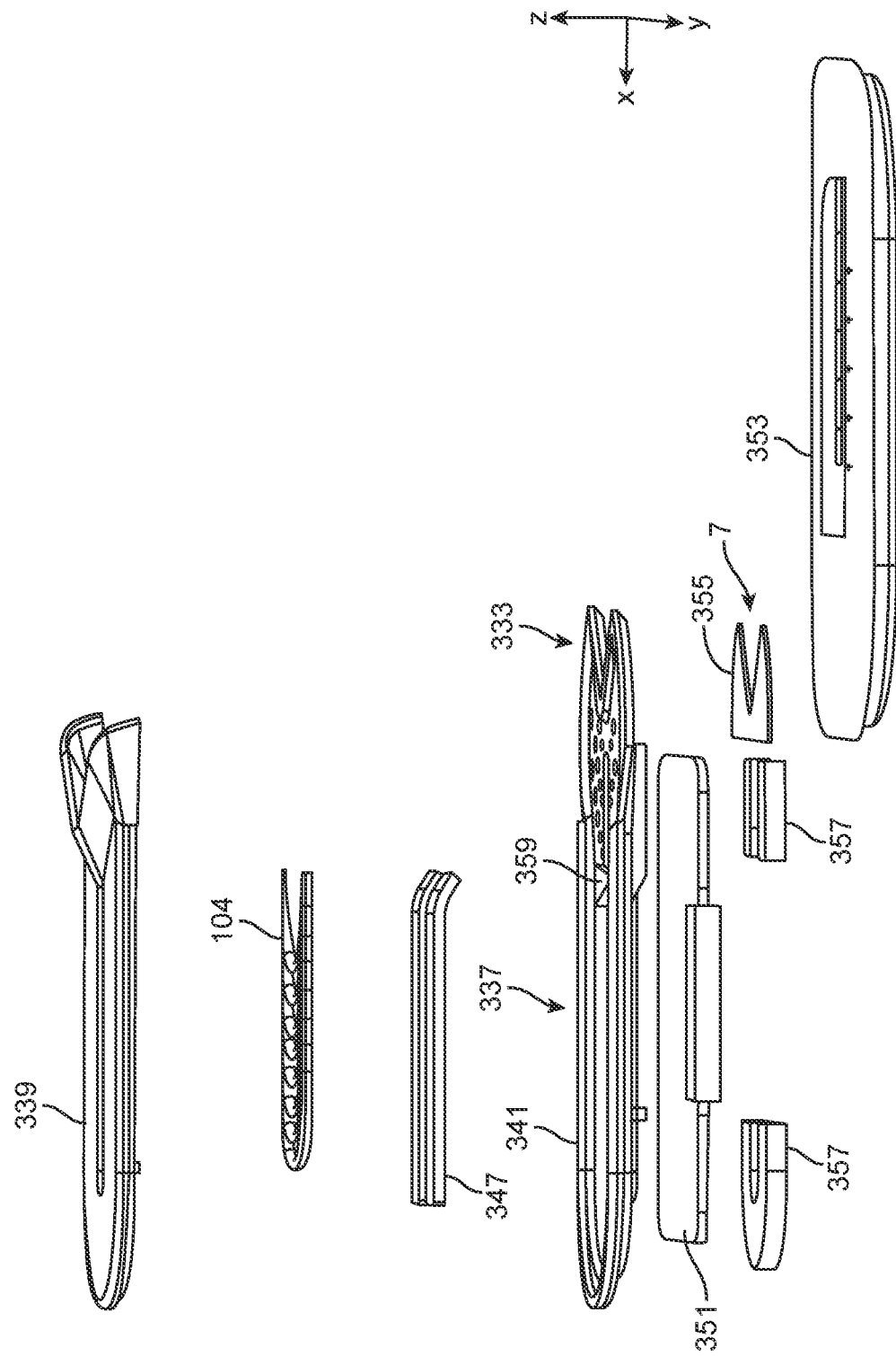

FIG. 170 illustrates an exploded side view of an embodiment of a needle trap assembly having a suture pack holder.

Figure 171:
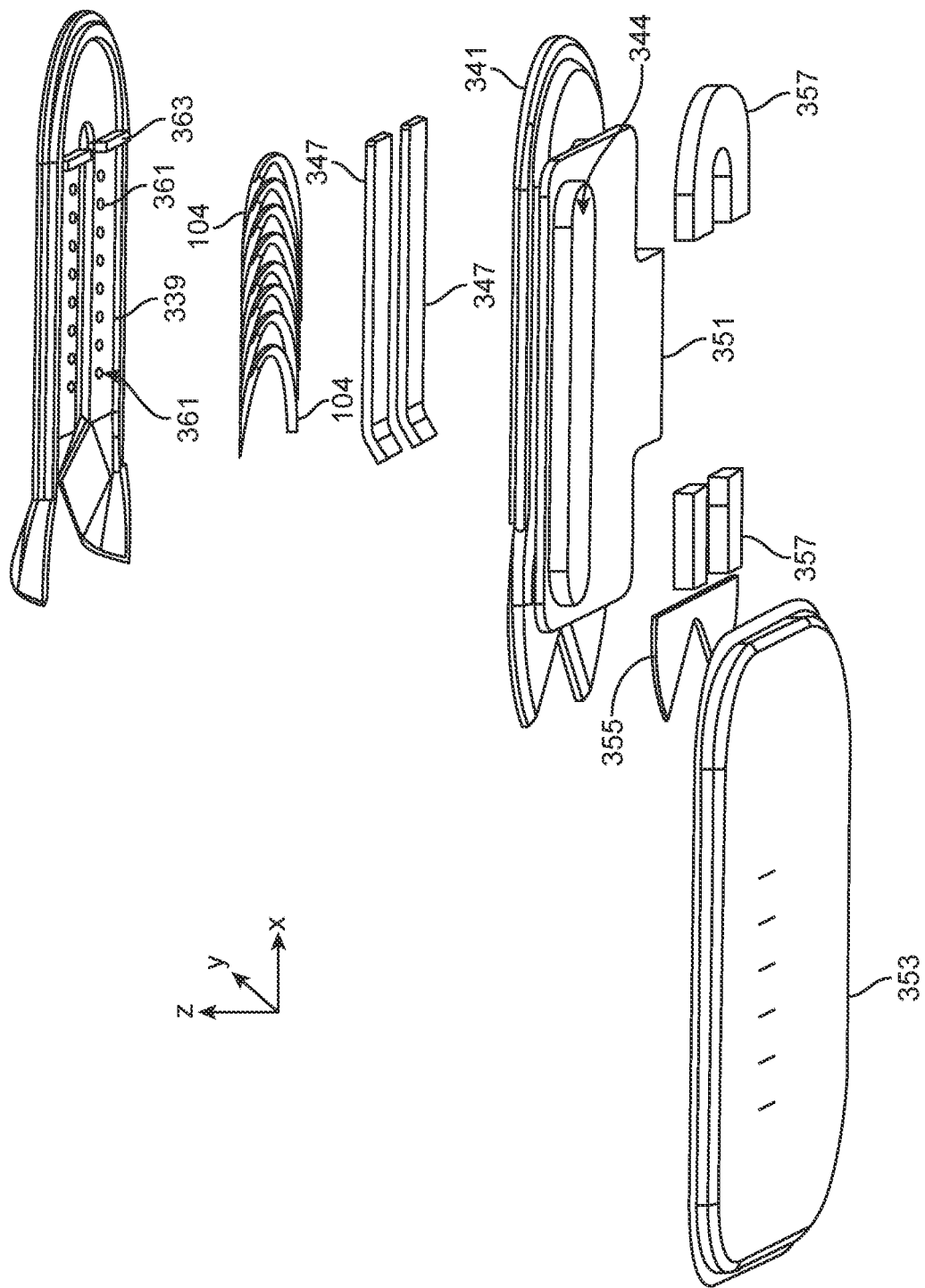

FIG. 171 illustrates an exploded bottom perspective view of an embodiment of a needle trap assembly having a suture pack holder.

Figure 172A:
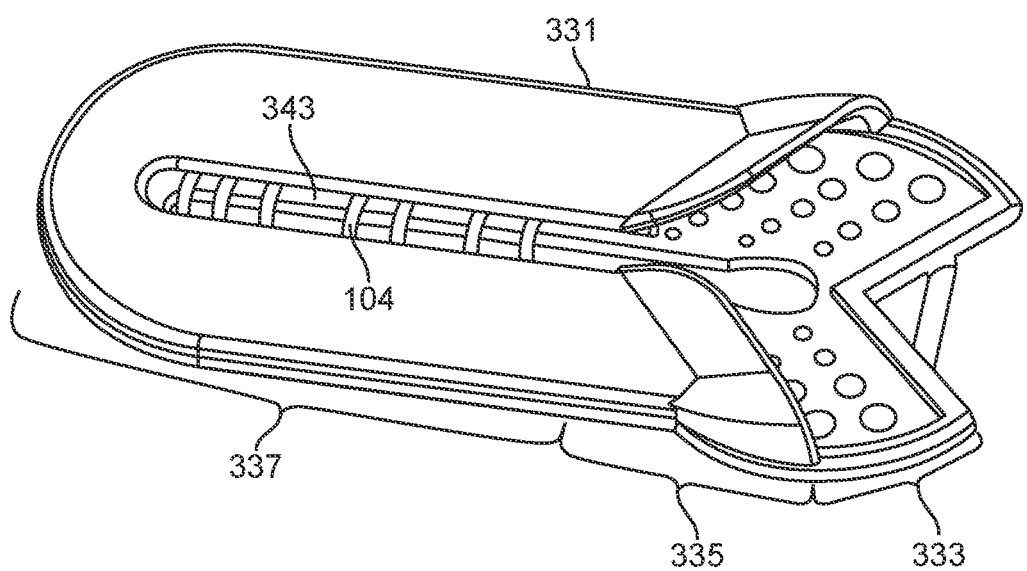

FIG. 172A illustrates a top perspective view of an embodiment of a needle trap.

Figure 172B:
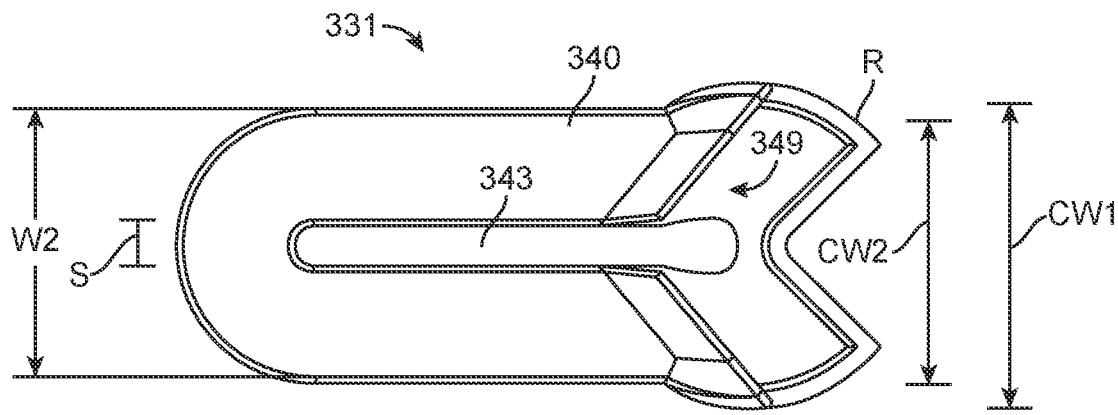
Figure 172C:
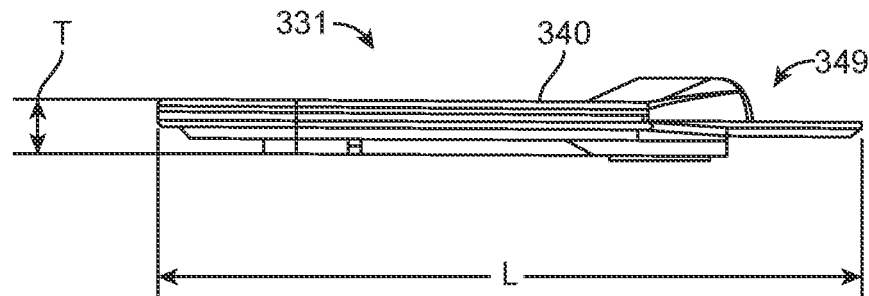
Figure 172D:
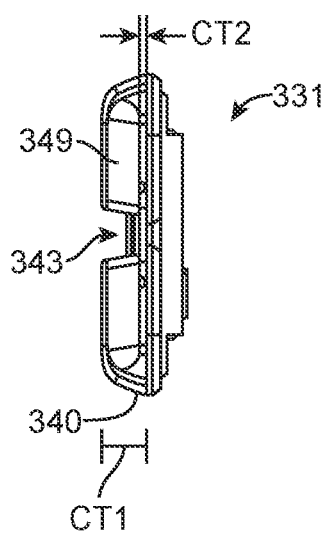

FIGS. 172B-172D show top, side and end views, respectively, of the needle trap of FIG. 172A.

Figure 173:
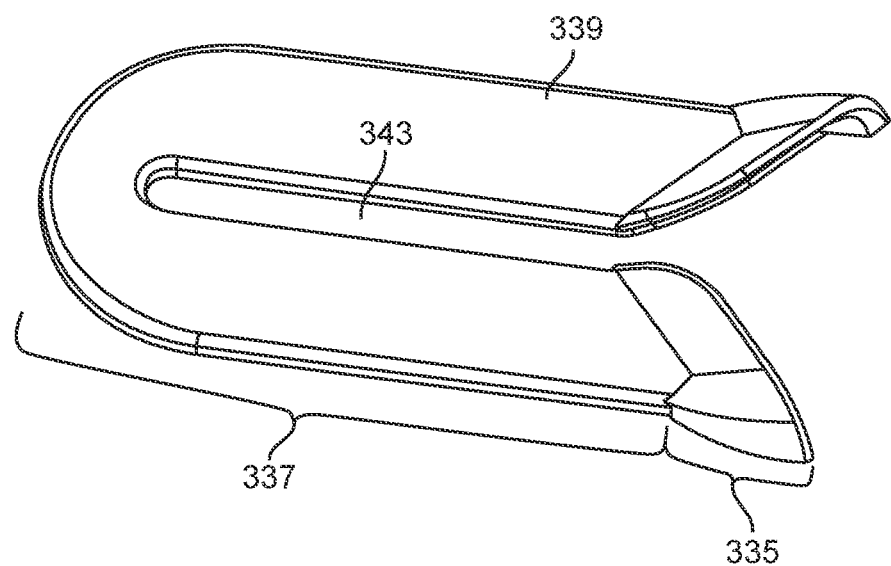

FIG. 173 illustrates a top perspective view of an embodiment of an upper structure component of a needle trap.

Figure 174:
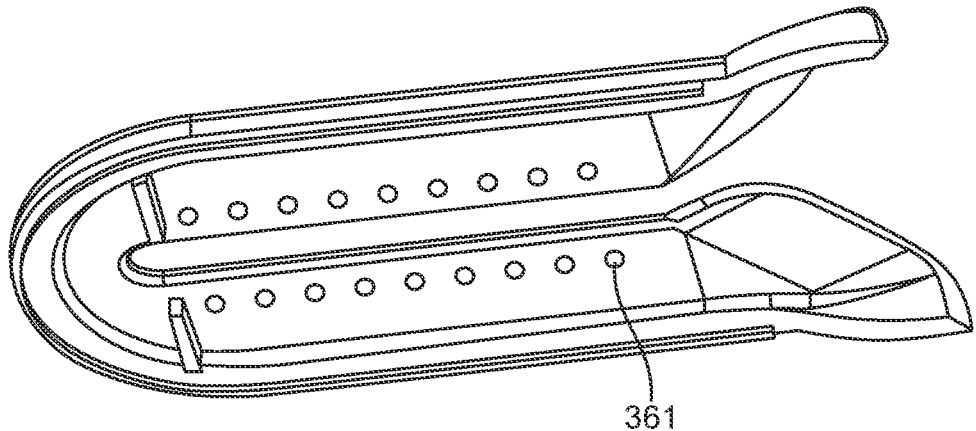

FIG. 174 illustrates a bottom perspective view of an embodiment of an upper structure component of a needle trap.

Figure 175:
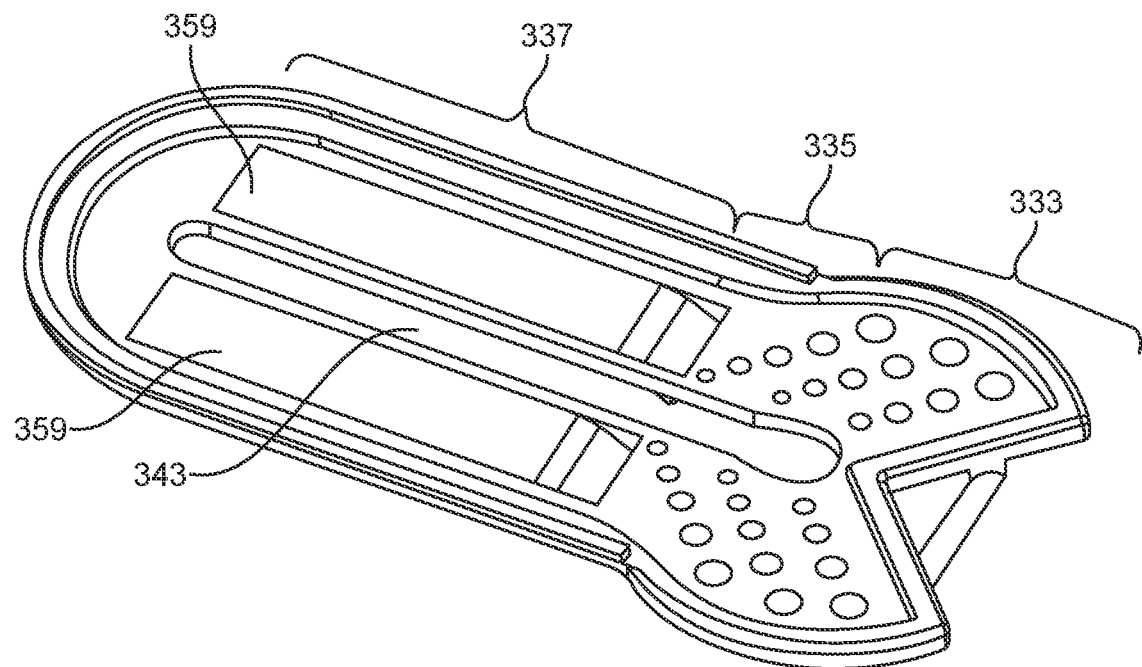
Figure 176:
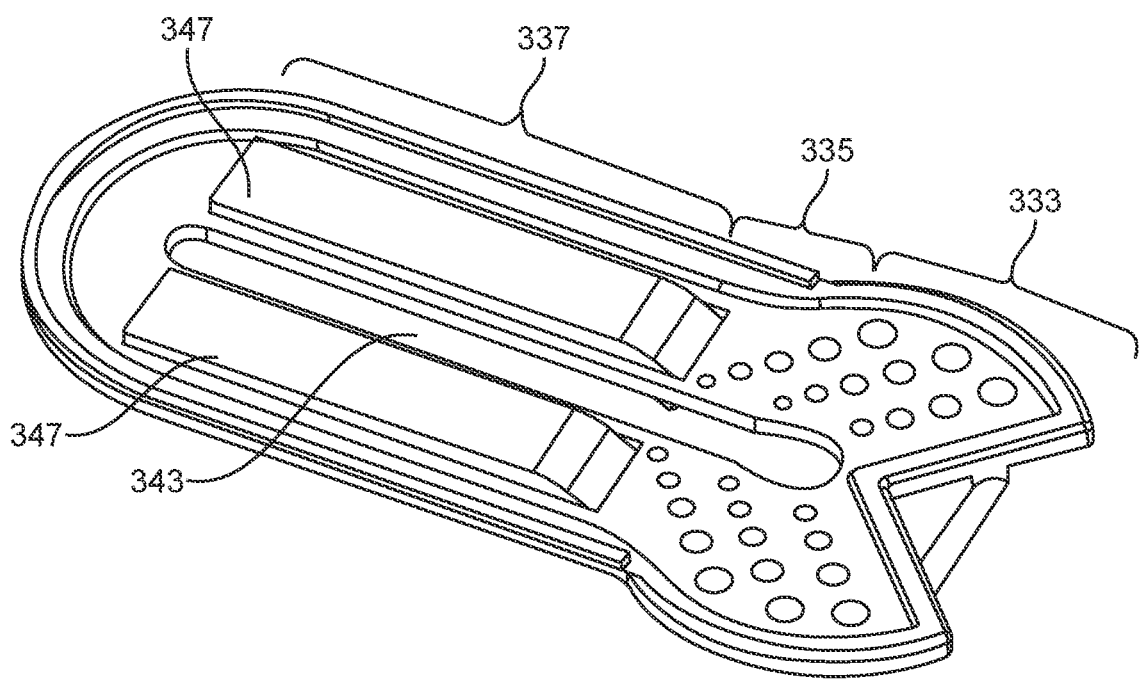

FIGS. 175 and 176 illustrate top perspective views of an embodiment of a lower structure component of a needle trap.

Figure 177:
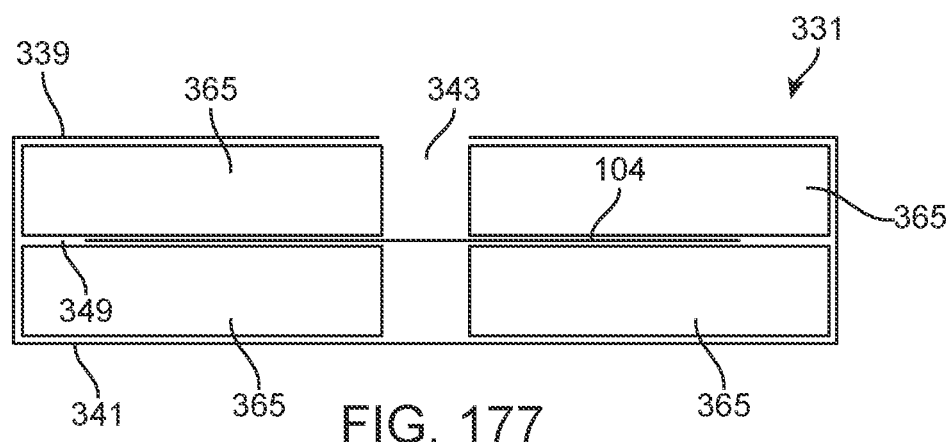

FIG. 177 illustrates a front view of an embodiment of a needle trap.

Figure 178:
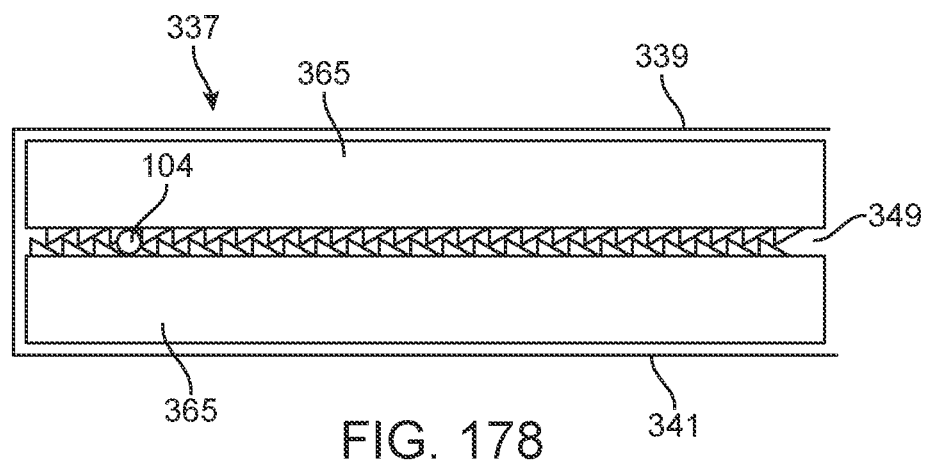

FIG. 178 illustrates a cross section side view of an embodiment of a needle trap.

Figure 179:
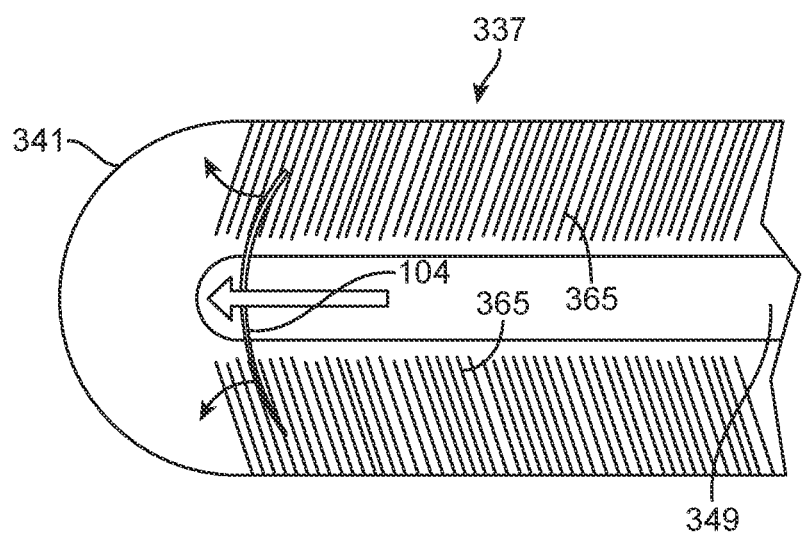

FIG. 179 illustrates a cross section top view of an embodiment of a needle slot.

Figure 180:
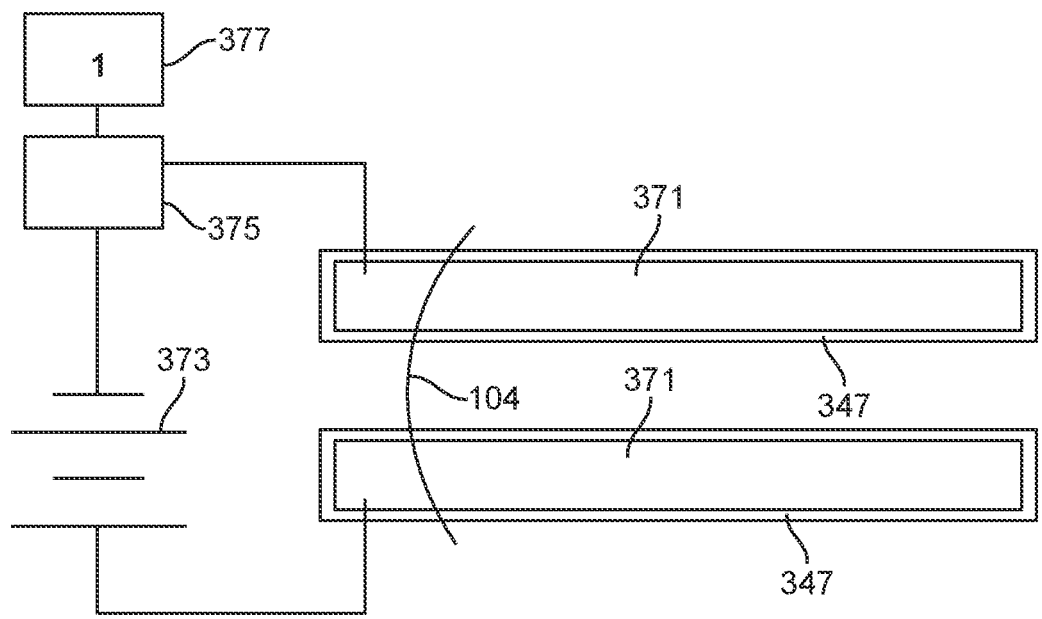
Figure 181:
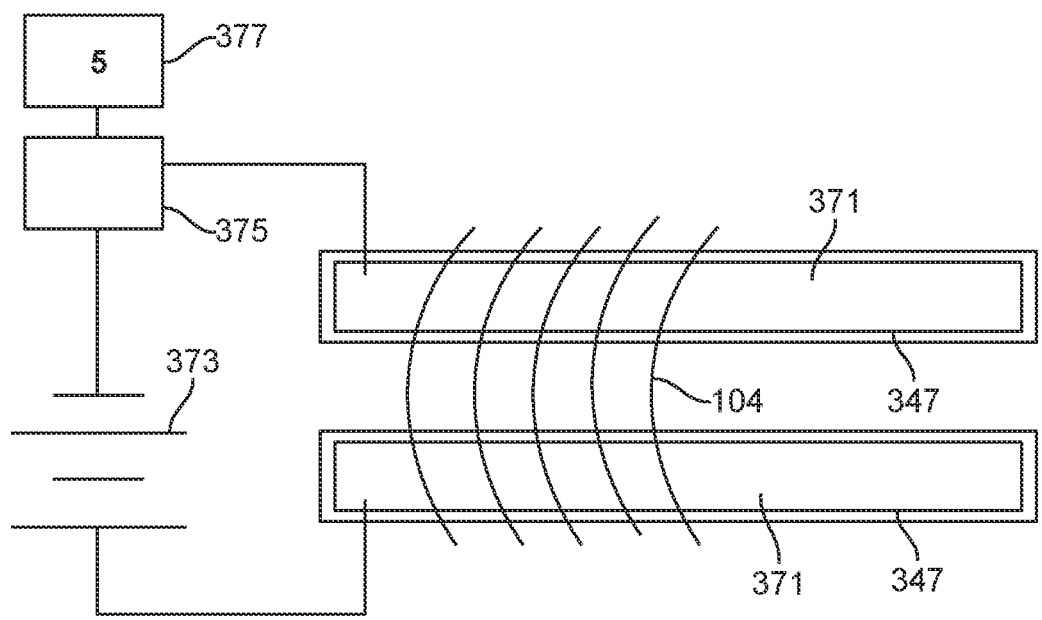

FIGS. 180 and 181 illustrates a block diagram an embodiment of an electrical needle detection system.

Figure 182:
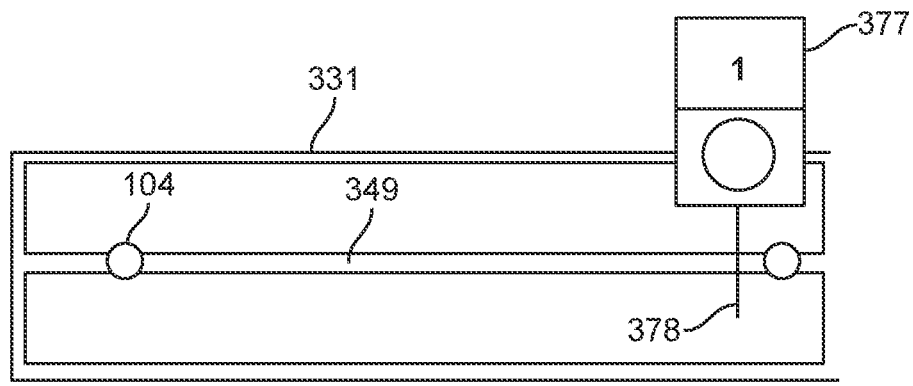
Figure 183:
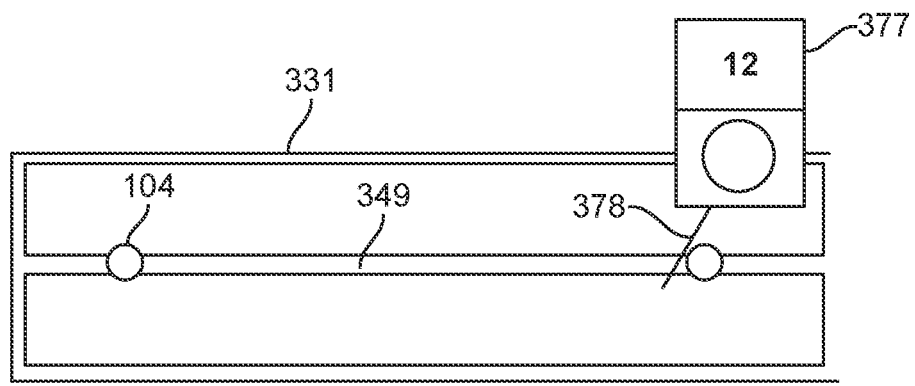
Figure 184:
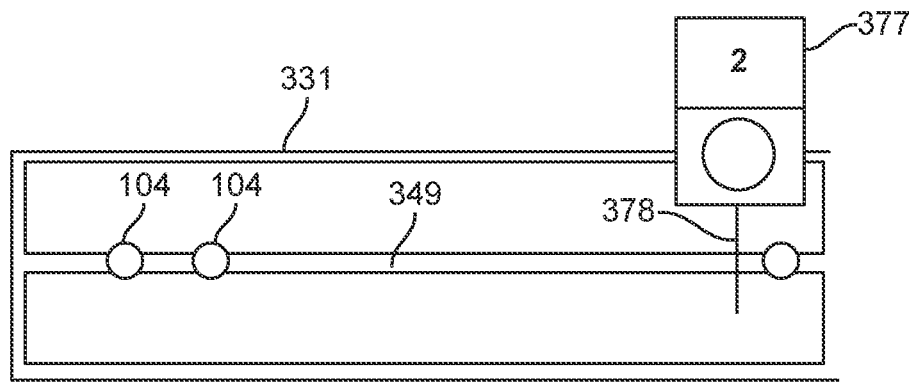

FIGS. 182-184 illustrate an embodiment of a mechanical needle counting system.

Figure 185:
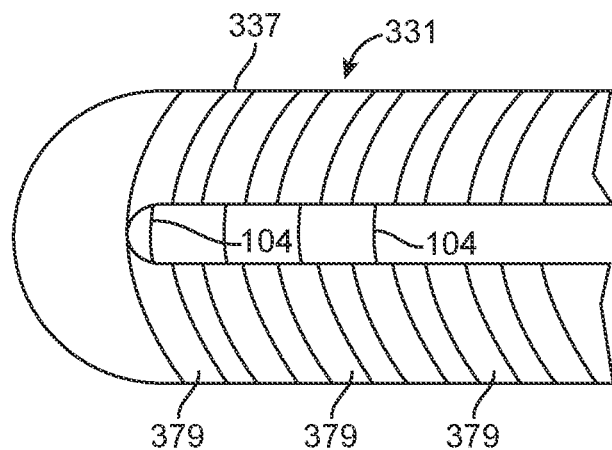

FIG. 185 illustrates an embodiment of a dye based needle counting system.

Figure 186:
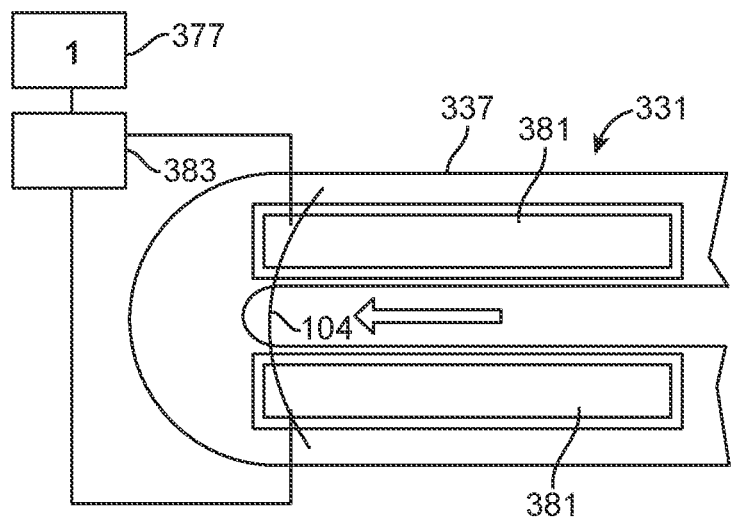

FIG. 186 illustrates an embodiment a scanner based needle counting system.

Figure 187:
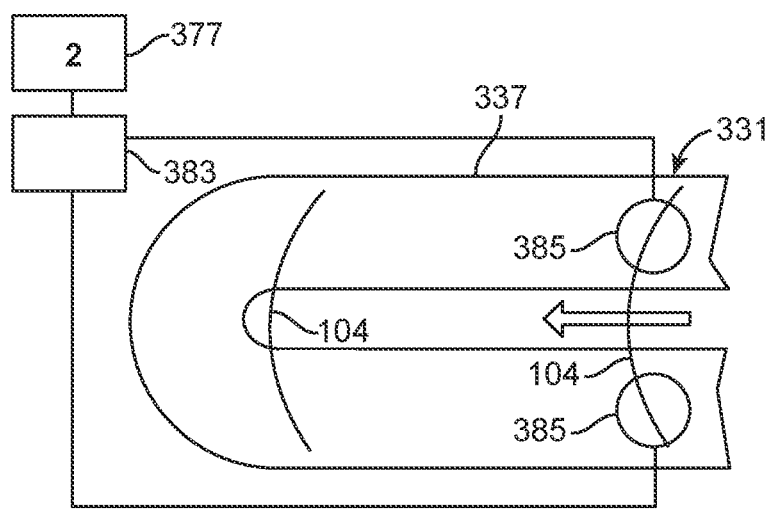

FIG. 187 illustrates an embodiment a camera based needle counting system.

Figure 188:
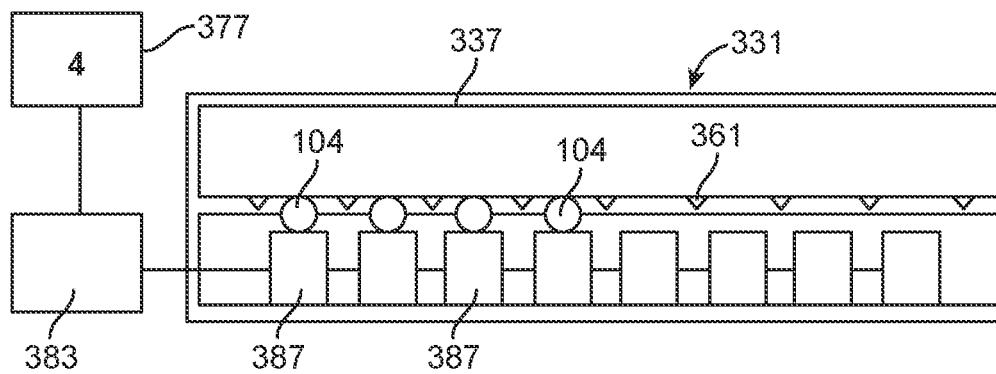

FIG. 188 illustrates an embodiment a pressure based needle counting system.

Figure 189:
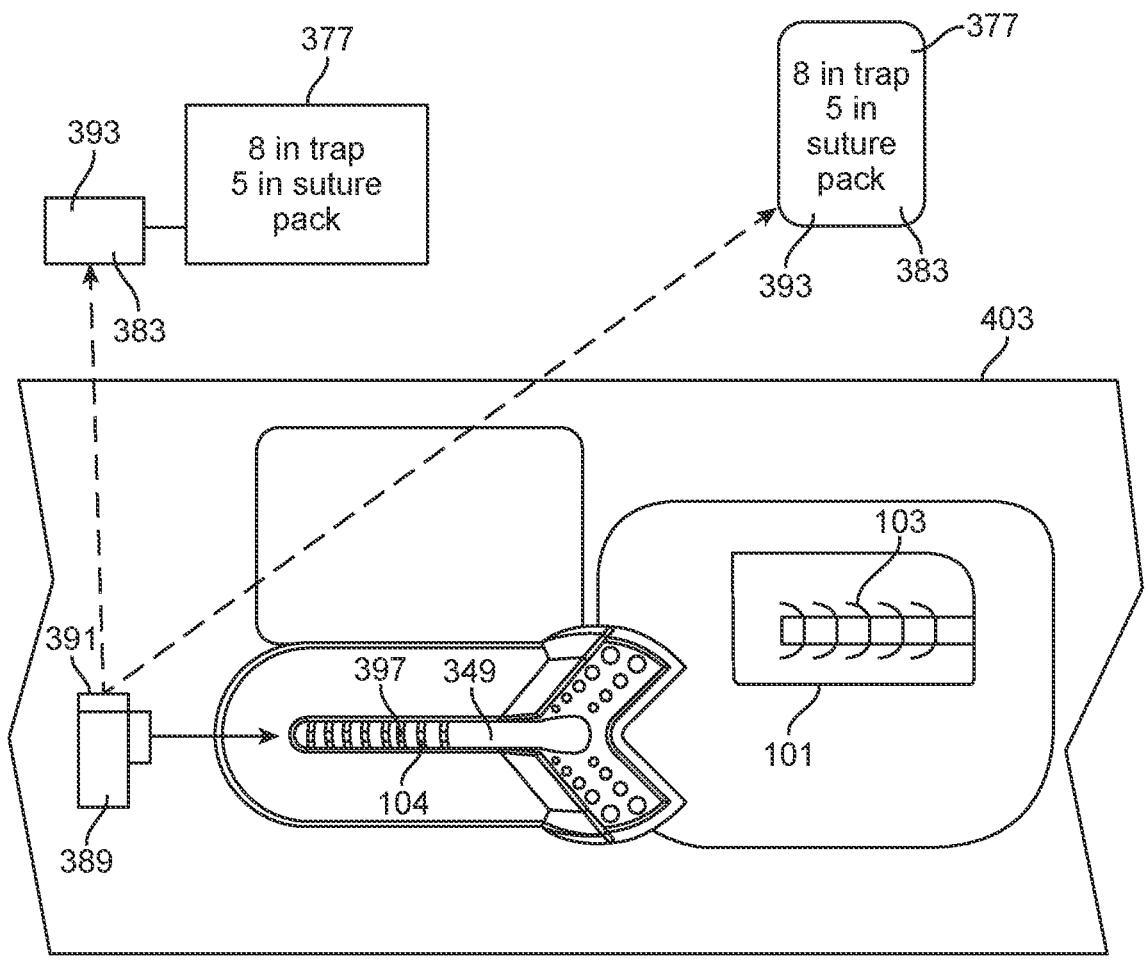

FIG. 189 illustrates an embodiment of a needle counting system with remote monitoring.

Figure 190:
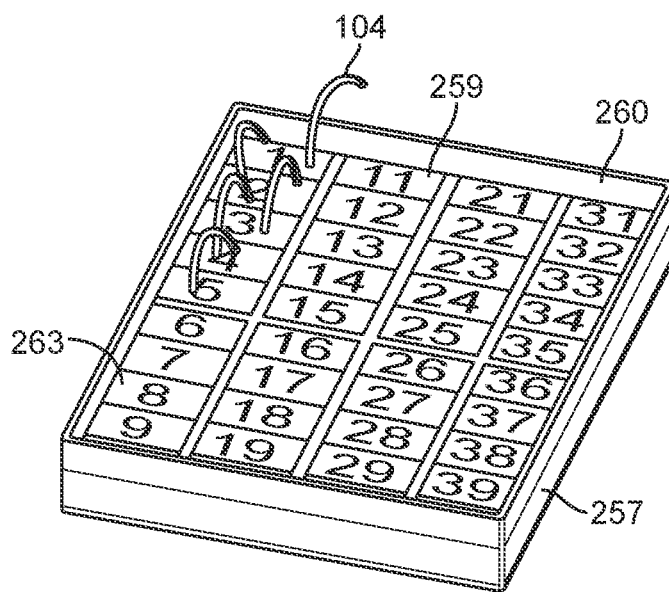

FIG. 190 illustrates an embodiment of a needle retainer.

Figure 191:
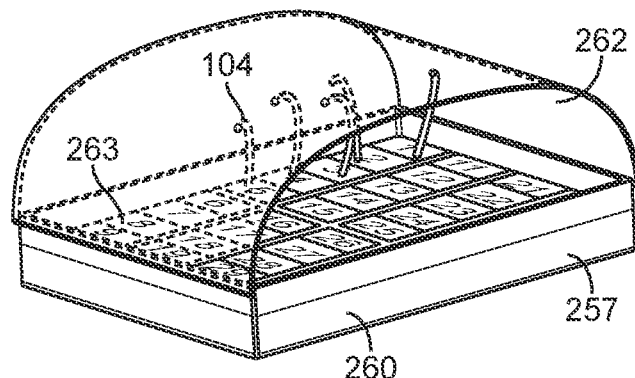

FIG. 191 illustrates an embodiment of a covered needle retainer.

Figure 192:
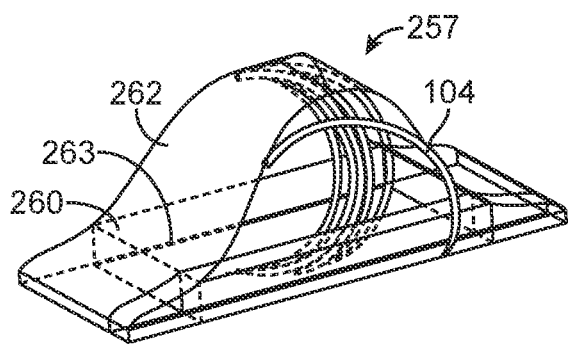

FIG. 192 illustrates an embodiment of a covered needle retainer.

Figure 193:
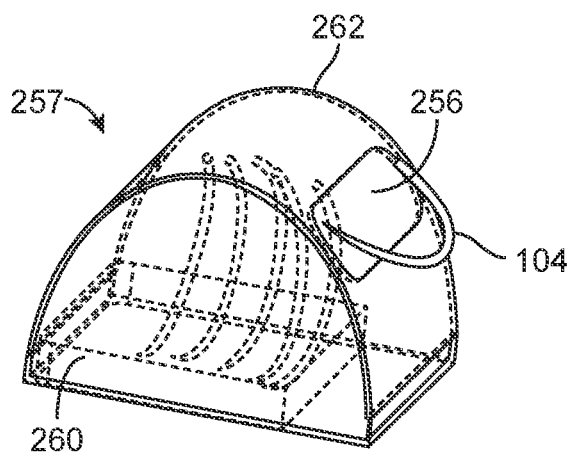
Figure 194:
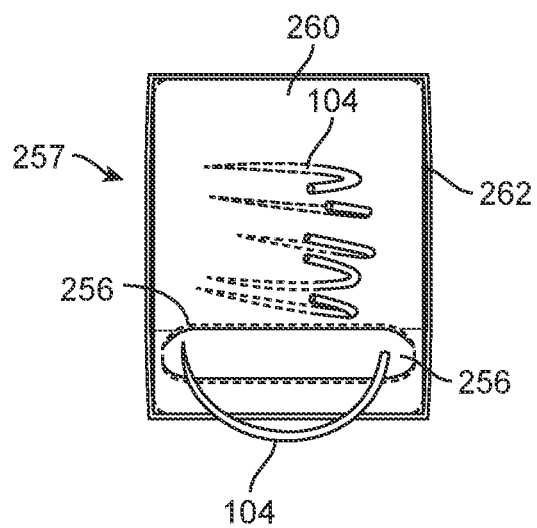

FIGS. 193-194 illustrate an embodiment of a covered needle retainer.

Figure 195:
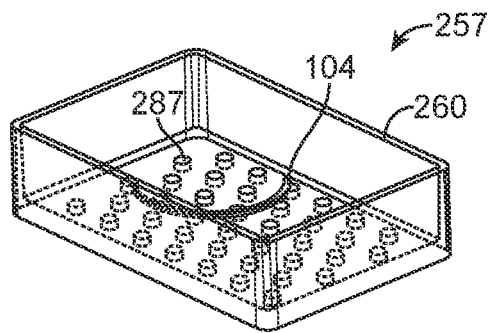

FIG. 195 illustrates an embodiment of a magnetic needle retainer.

Figure 196:
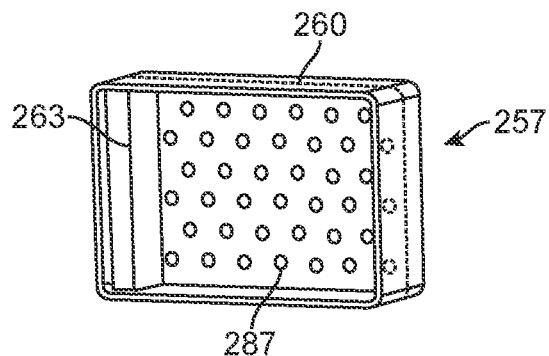
Figure 197:
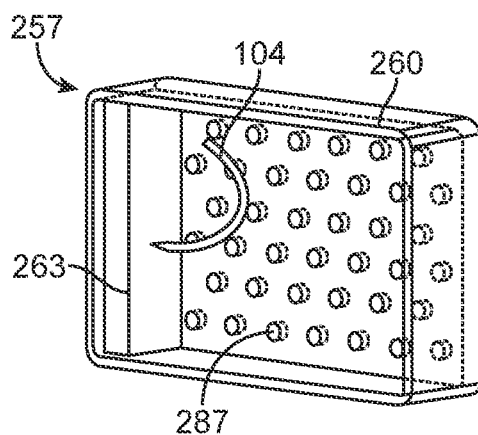

FIGS. 196-197 illustrate an embodiment of a magnetic and foam needle retainer.

Figure 198:
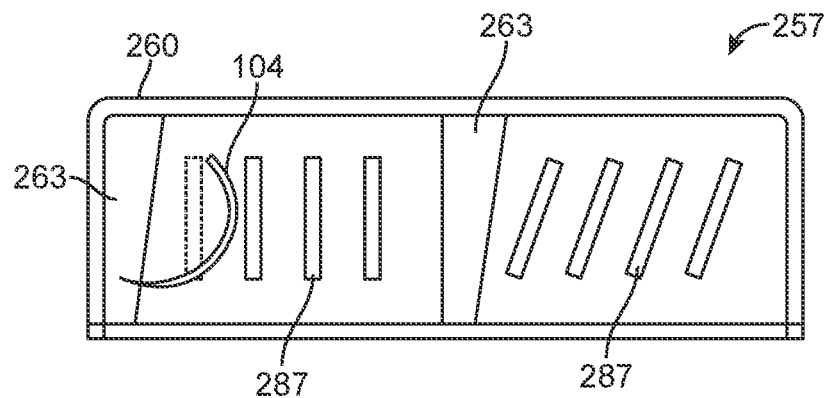

FIG. 198 illustrates an embodiment of a magnetic and foam needle retainer.

Figure 199:
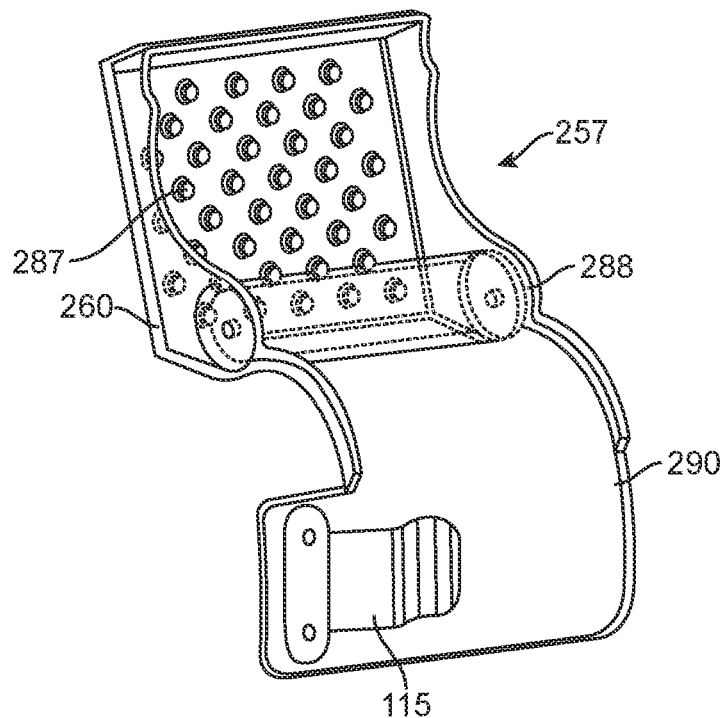

FIG. 199 illustrates an embodiment of a magnetic needle retainer with a cover and suture pack clip.

Figure 200:
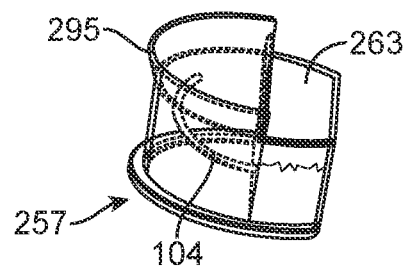
Figure 201:
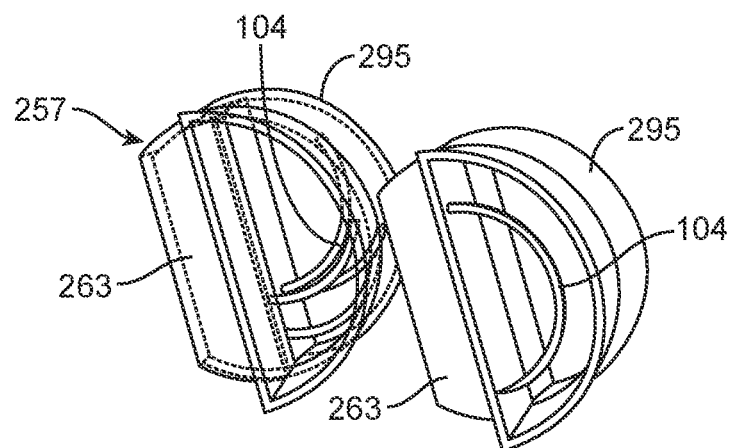

FIGS. 200-201 illustrate an embodiment of an insert and rotate needle retainer.

Figure 202:
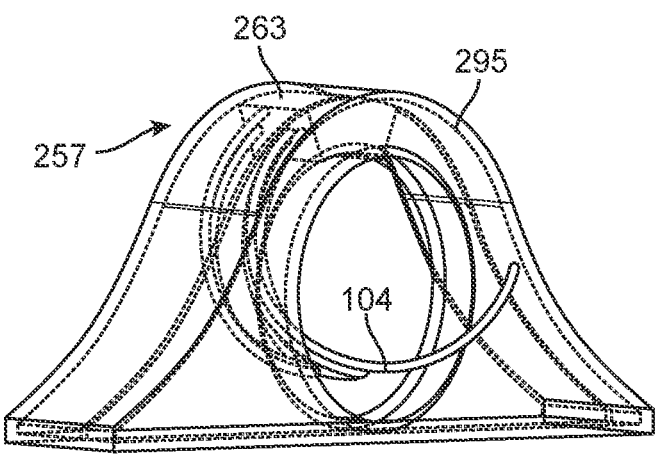

FIG. 202 illustrates an embodiment of an insert and rotate needle retainer.

Figure 203:
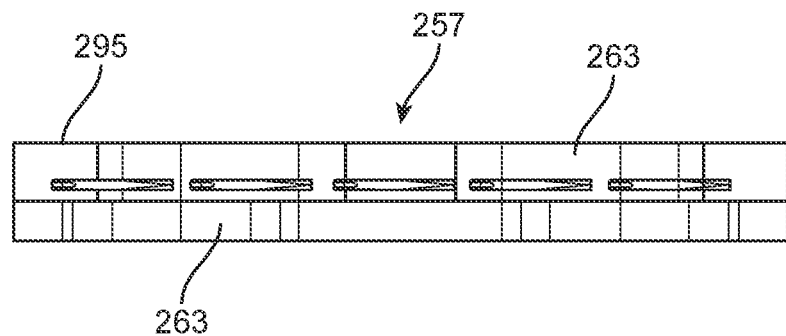
Figure 204:
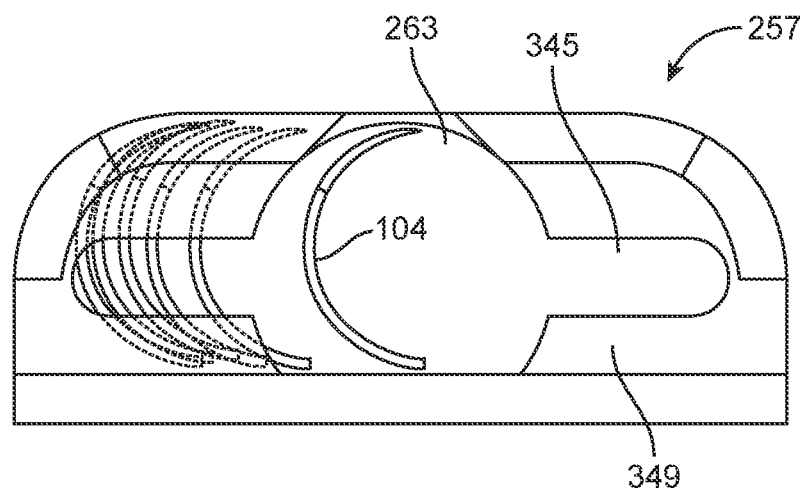

FIGS. 203-204 illustrate an embodiment of a needle trap.

Figure 205:
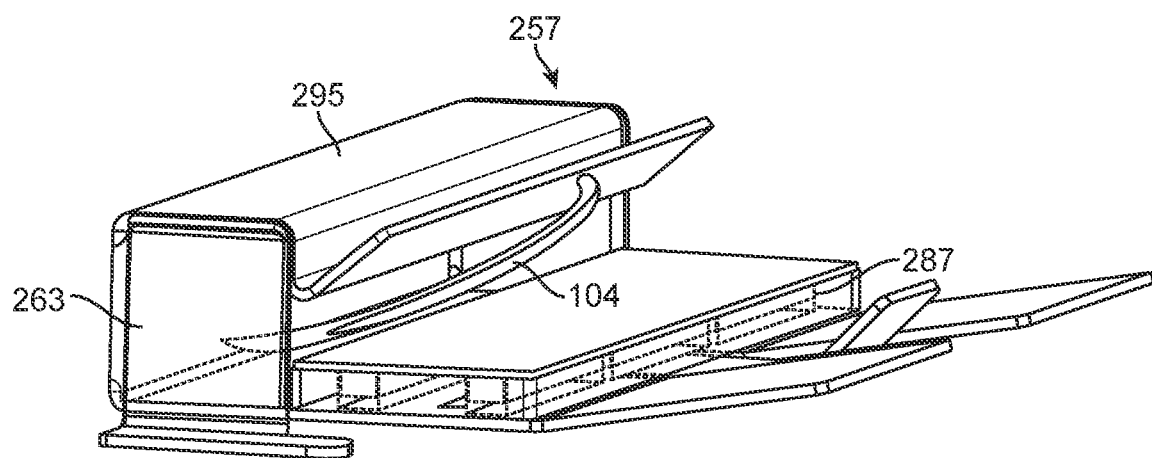

FIG. 205 illustrates an embodiment of a needle retainer.

FIGS. 206-209 illustrate embodiments of needle retaining systems.

FIGS. 210-214 illustrate an embodiment of a modular needle retaining system.

Figure 215:
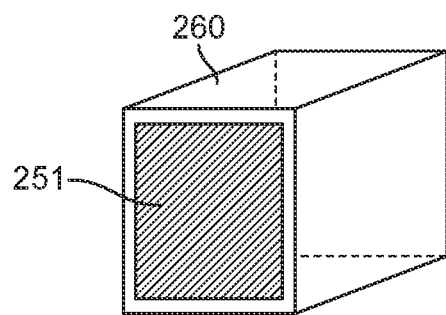
Figure 216:
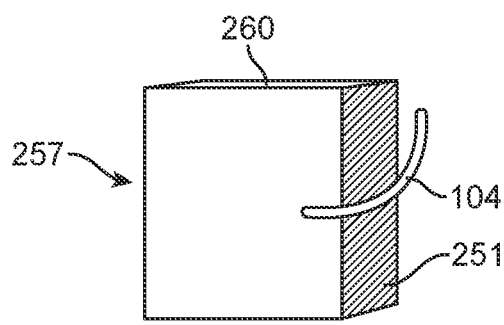
Figure 217:
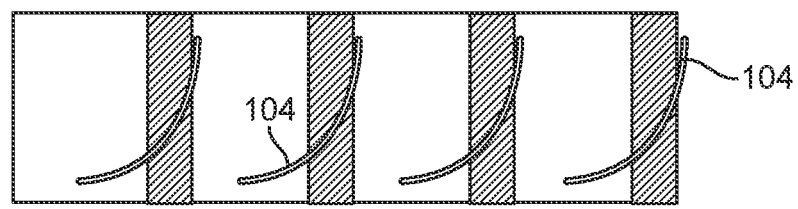

FIGS. 215-217 illustrate an embodiment of a modular needle retaining system.

Figure 218:
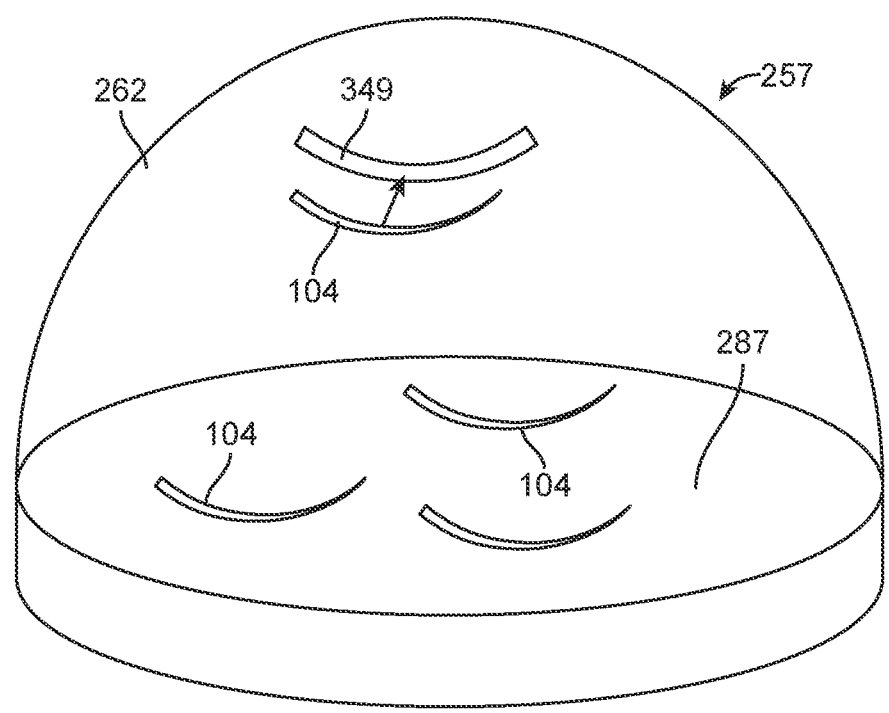
Figure 219:
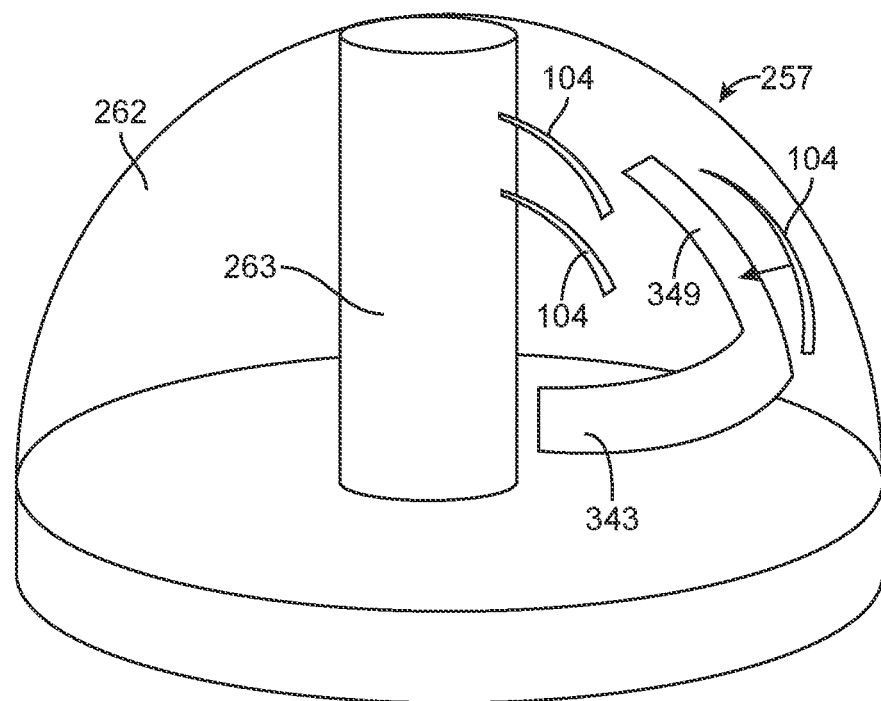

FIGS. 218-219 illustrate embodiments of dome type needle retainers.

Figure 220:
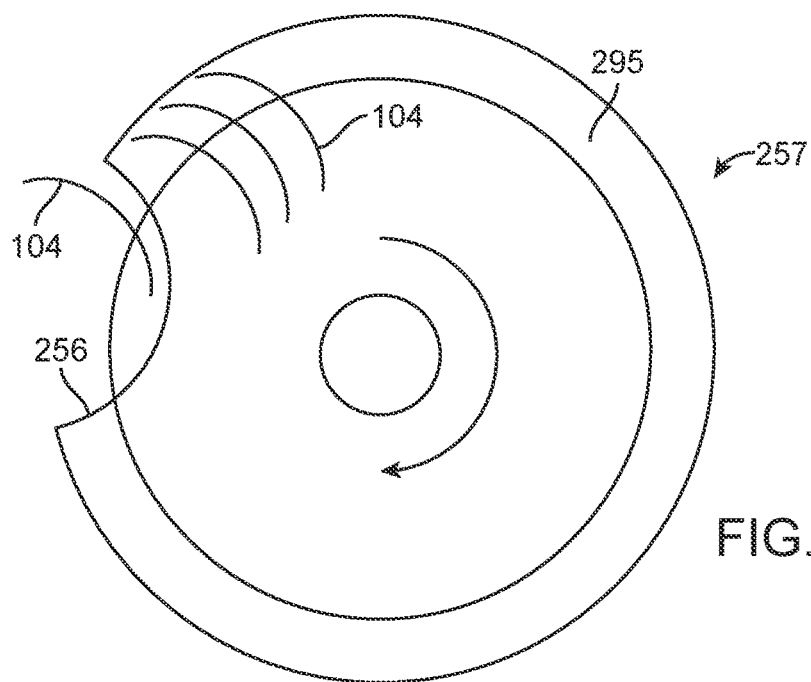

FIG. 220 illustrates an embodiment of a needle retainer system.

Figure 221:
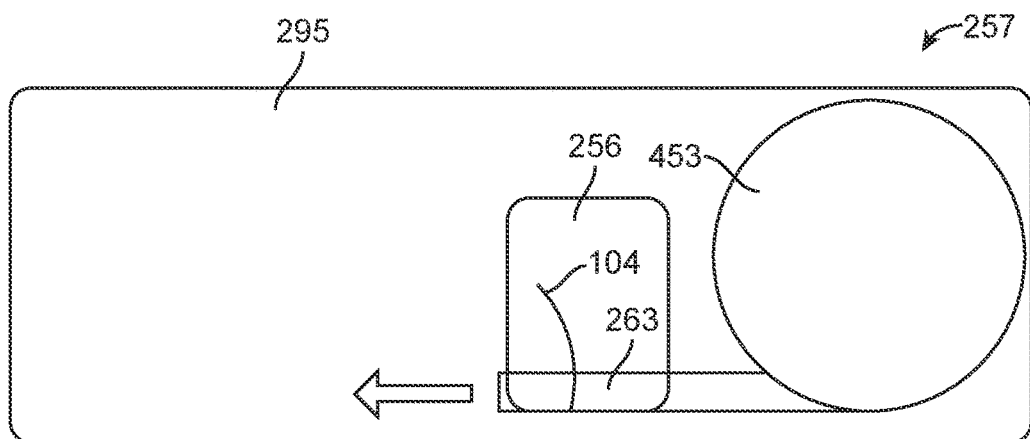
Figure 222:
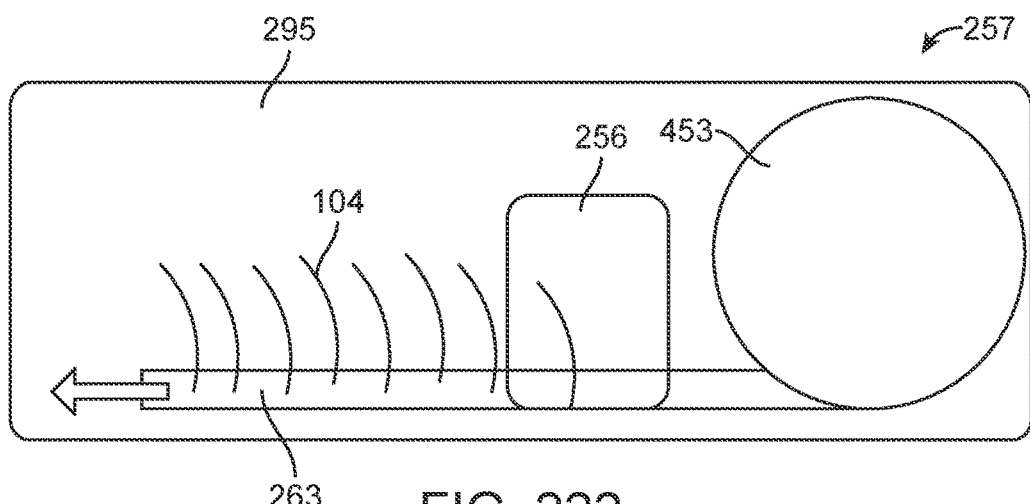

FIGS. 221-222 illustrate an embodiment of a needle retainer system.

FIGS. 223-225 illustrate an embodiment of an insert and rotate needle retainer.

FIGS. 226-228 illustrate an embodiment of an insert and rotate needle retainer.

Figure 229:
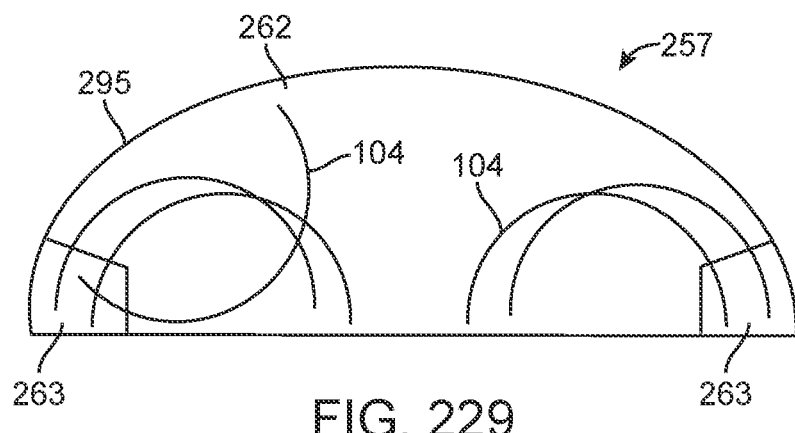
Figure 230:
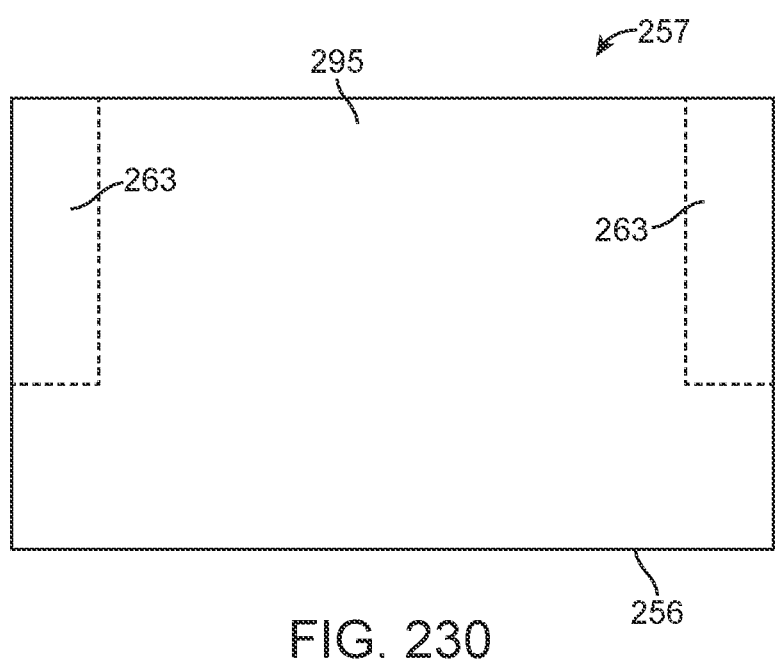

FIGS. 229-230 illustrate an embodiment of an insert and rotate needle retainer.

Figure 231:
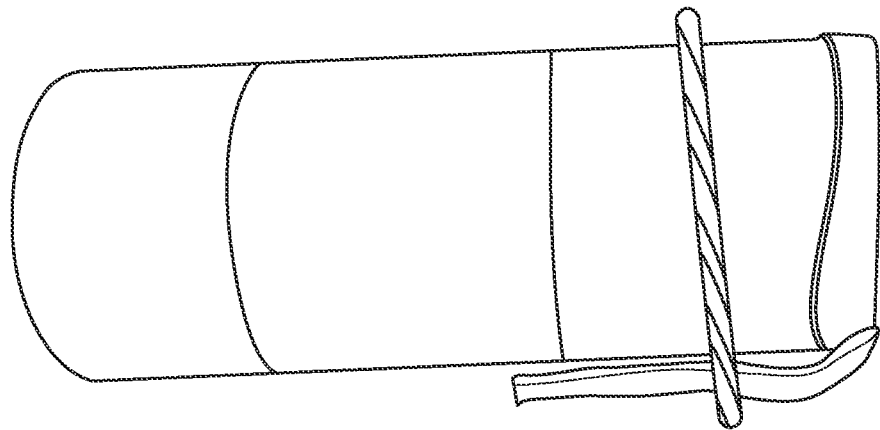
Figure 232:
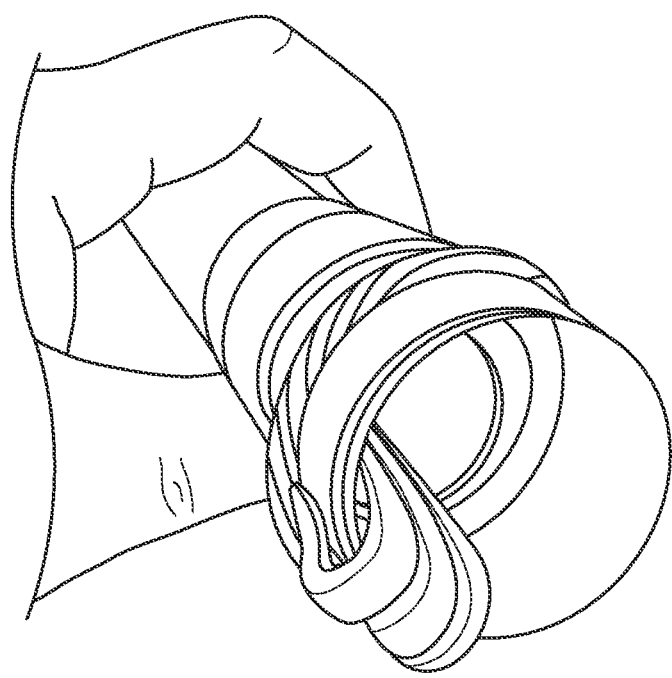

FIGS. 231-232 illustrate an embodiment of an insert and rotate needle retainer.

Figure 233:
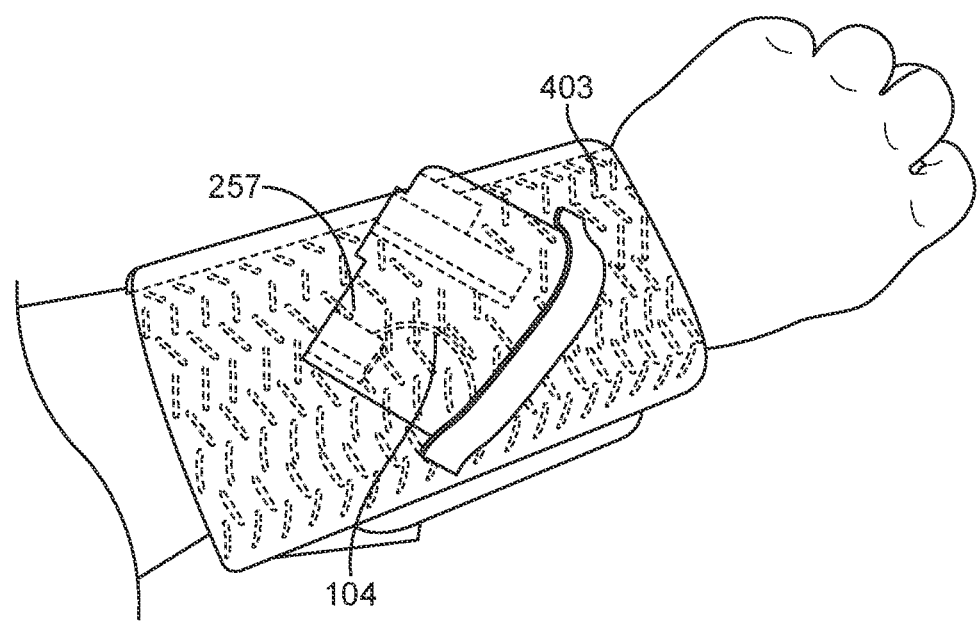
Figure 234:
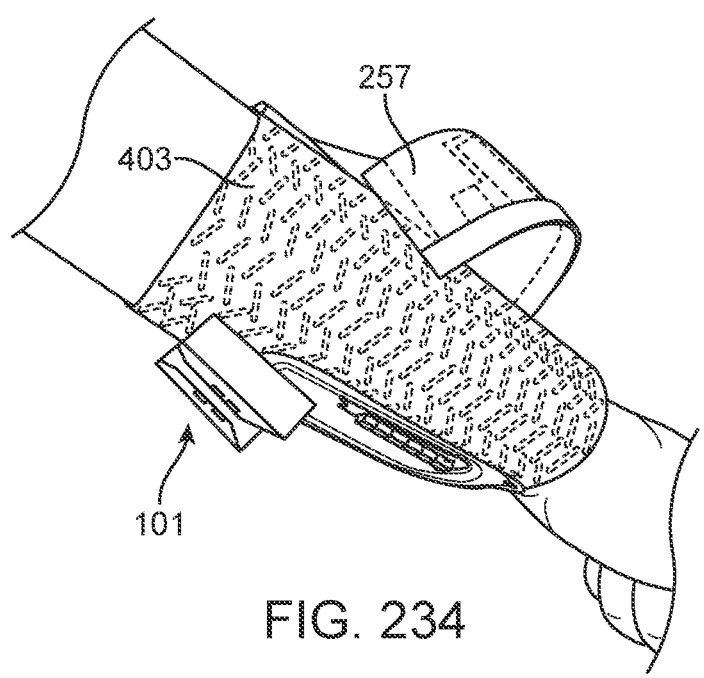

FIGS. 233-234 illustrate an embodiment of an insert and rotate needle retainer mounted on a forearm barrier.

Figure 235:
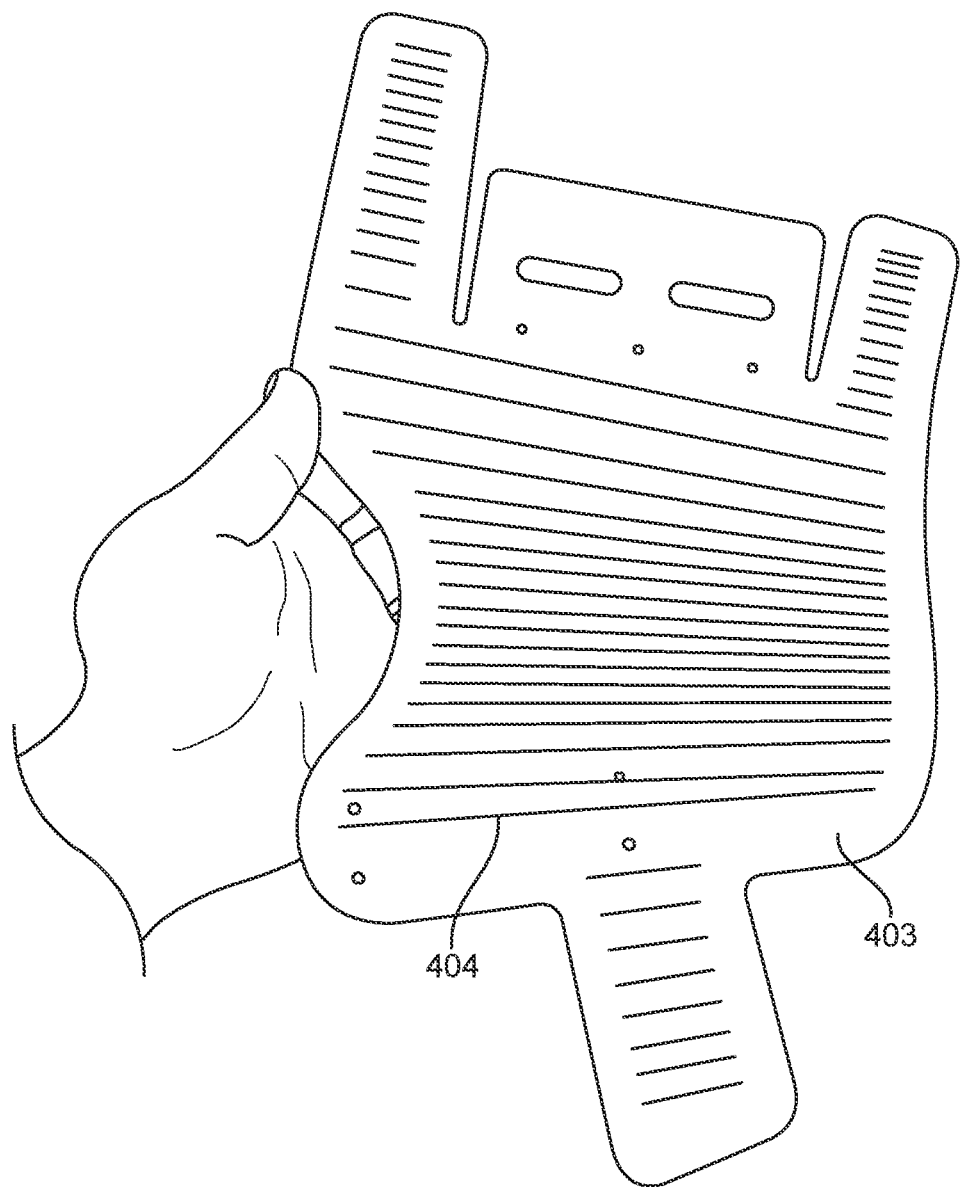

FIG. 235 illustrates a top view of an embodiment of a barrier.

Figure 236:
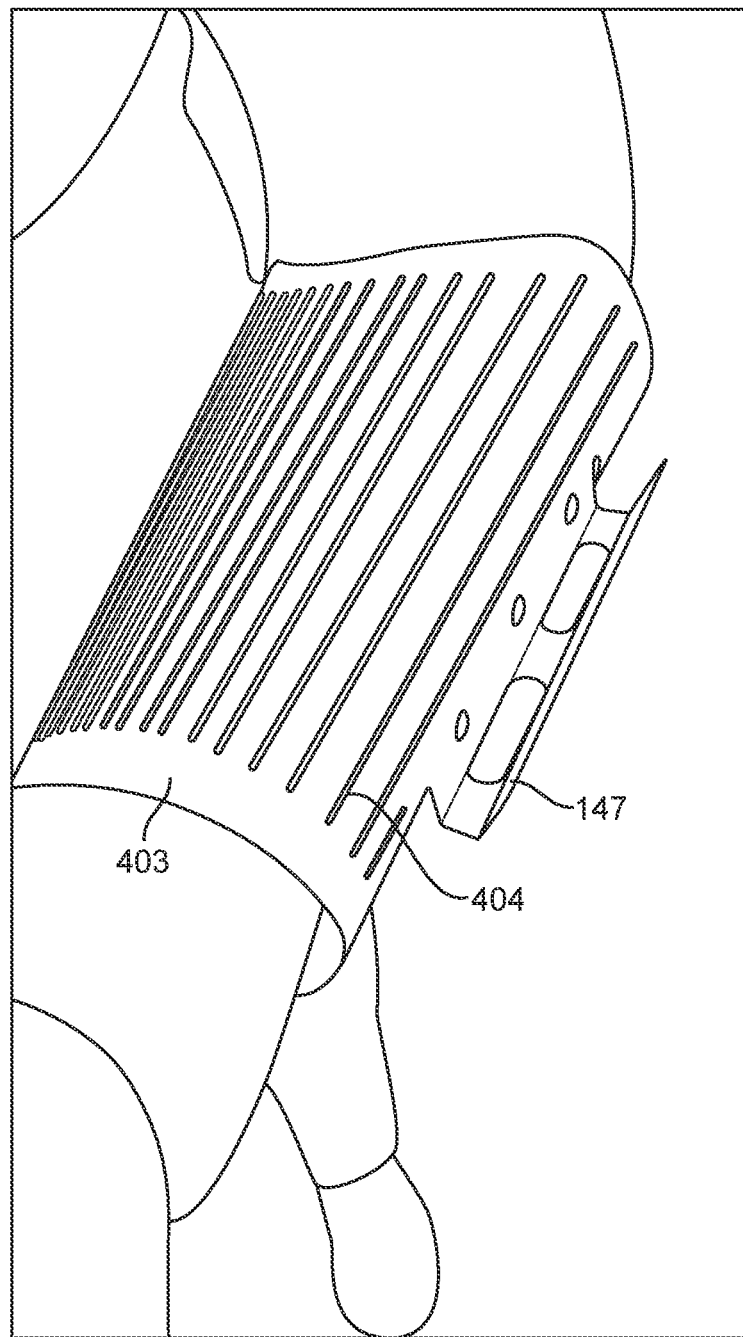

FIG. 236 illustrates a top perspective view of an embodiment of a barrier placed on a forearm.

Figure 237:
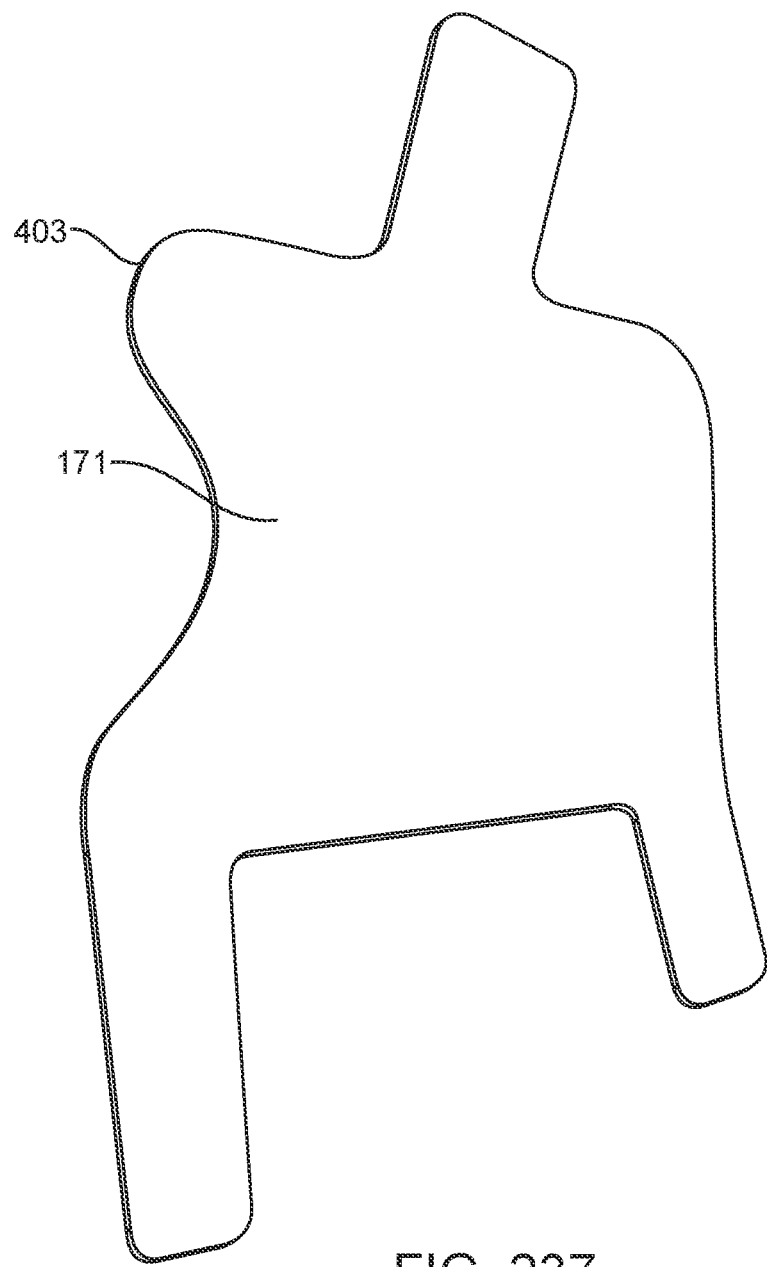

FIG. 237 illustrates a bottom view of an embodiment of a barrier.

Figure 238:
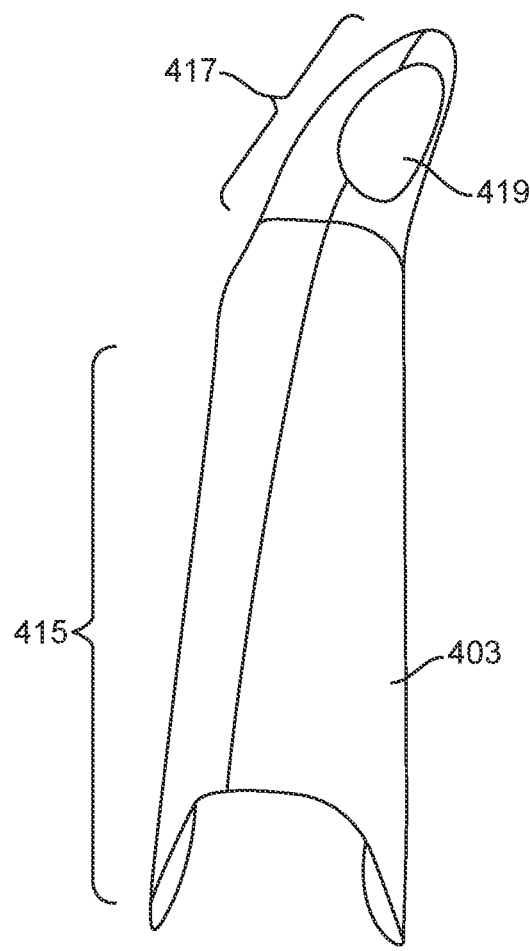

FIG. 238 illustrates a side view of an embodiment of a barrier.

Figure 239:
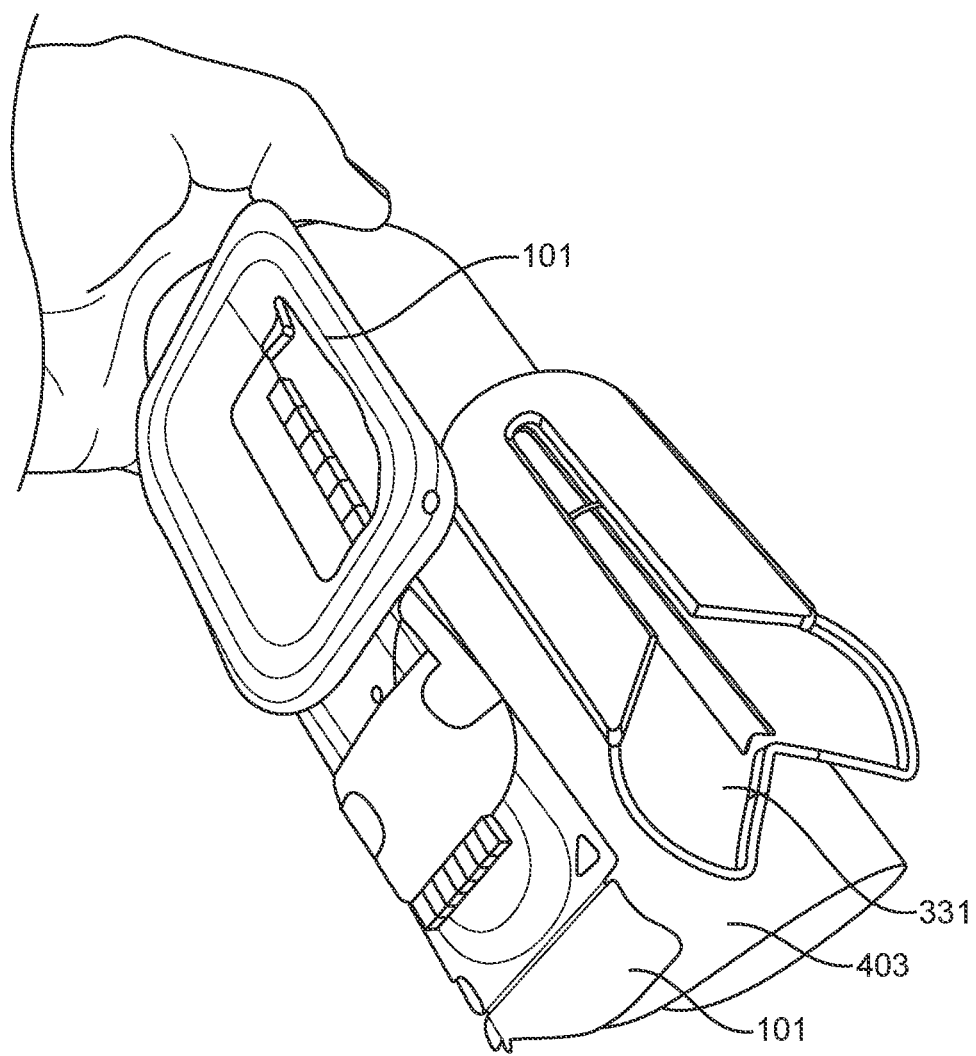
Figure 240:
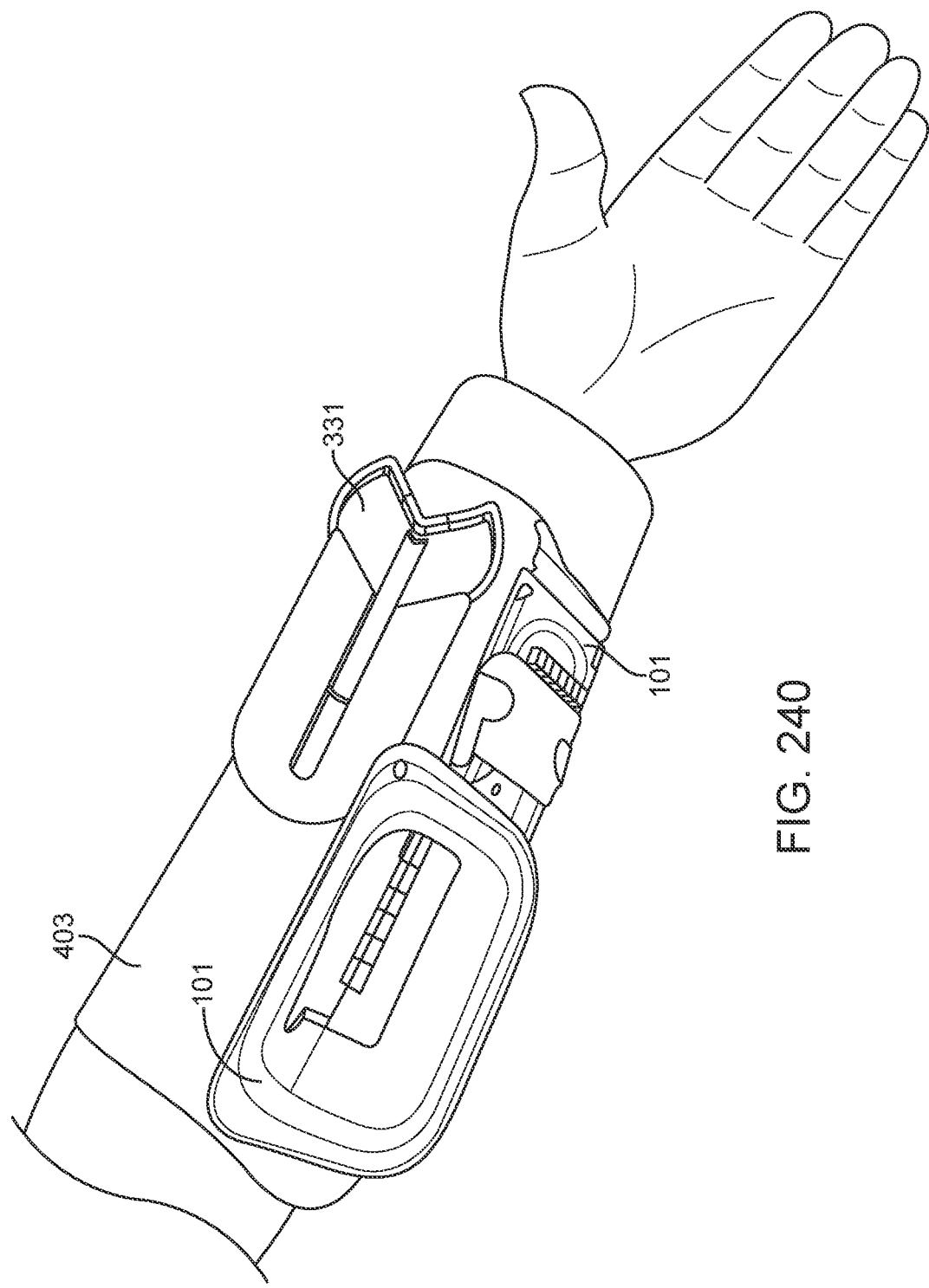
Figure 241:
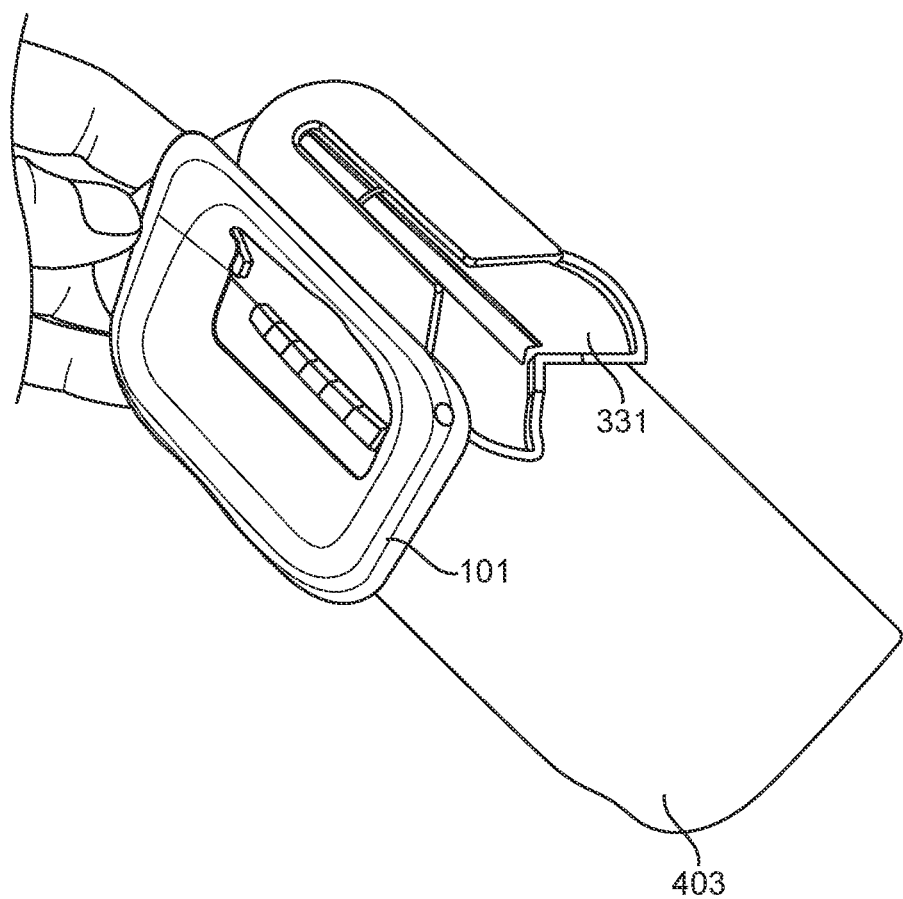

FIGS. 239-241 illustrates top perspective views of an embodiment of a barrier with a needle trap and suture packs mounted on the barrier.

Figure 242:
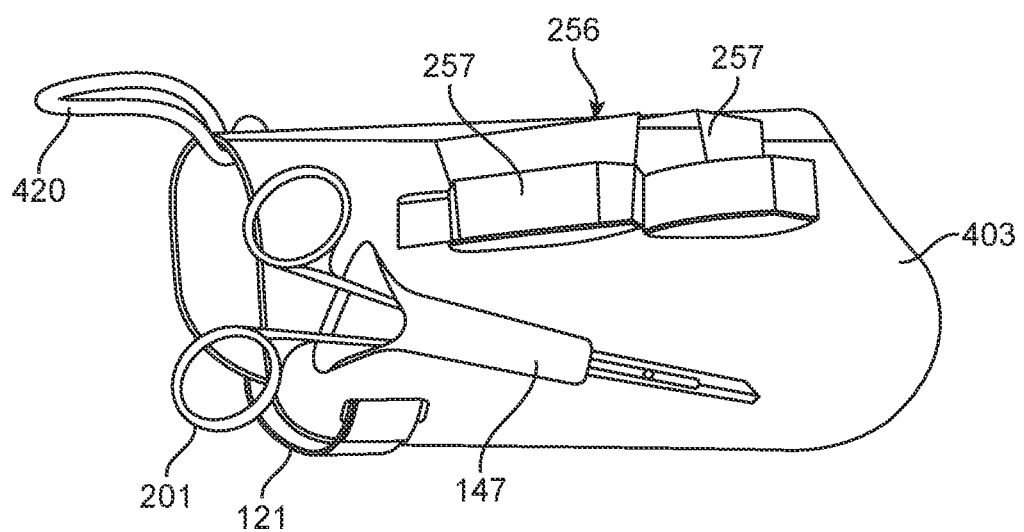
Figure 243:
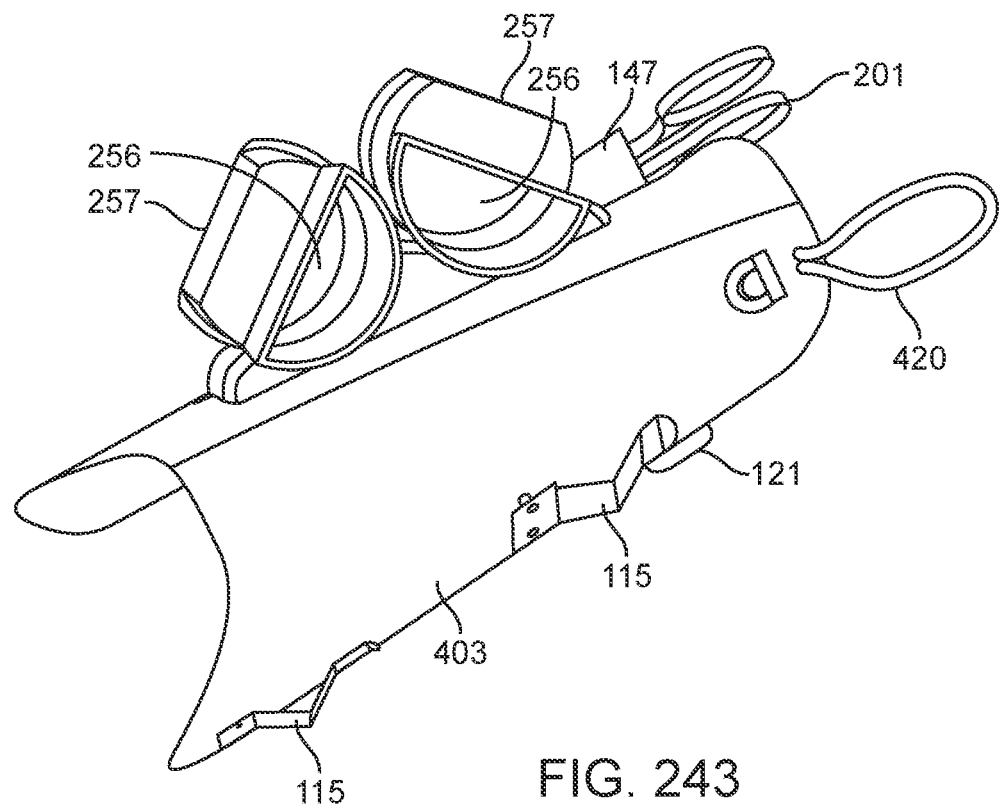
Figure 244:
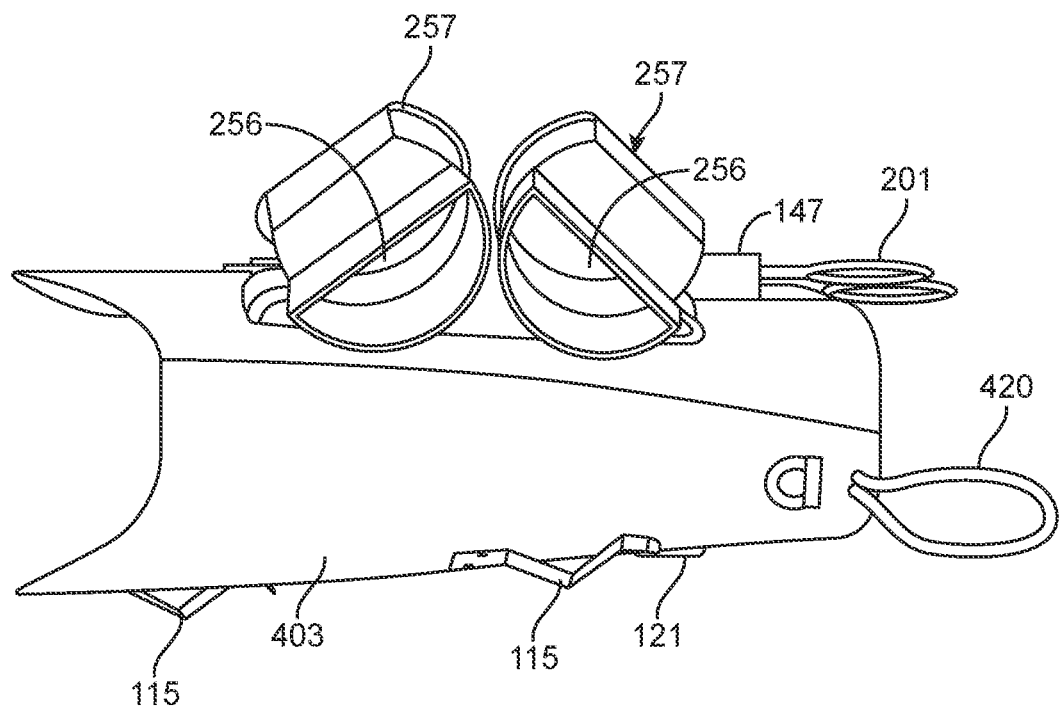

FIGS. 242-244 illustrate top perspective view of an embodiment of a barrier with needle retainers, suture pack clips and a tool holder.

FIGS. 245-248 illustrate perspective views of an embodiment of a needle retaining and suture pack clip assembly coupled to a tool mounting interface.

Figure 249:
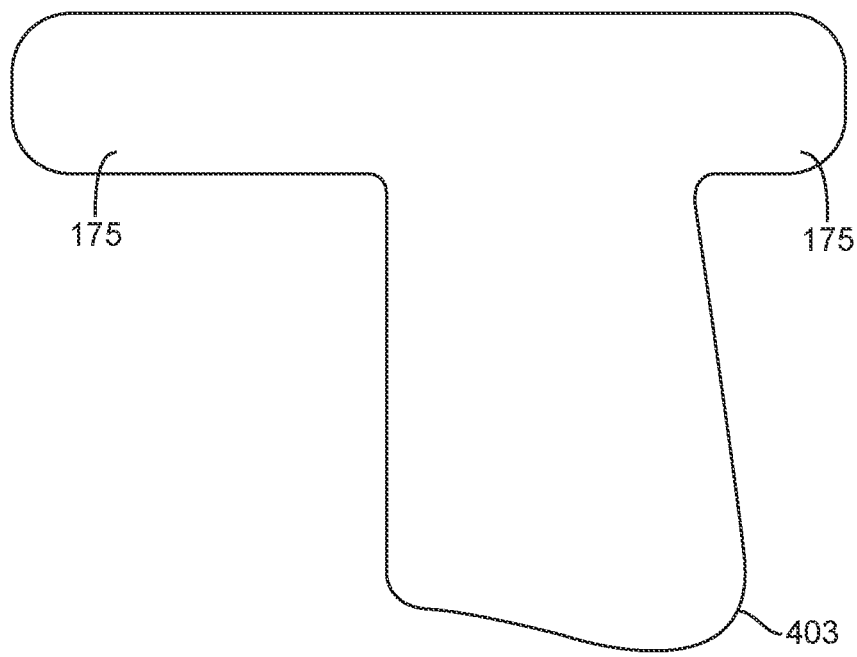

FIG. 249 illustrates a top view of an embodiment of a barrier.

Figure 250:
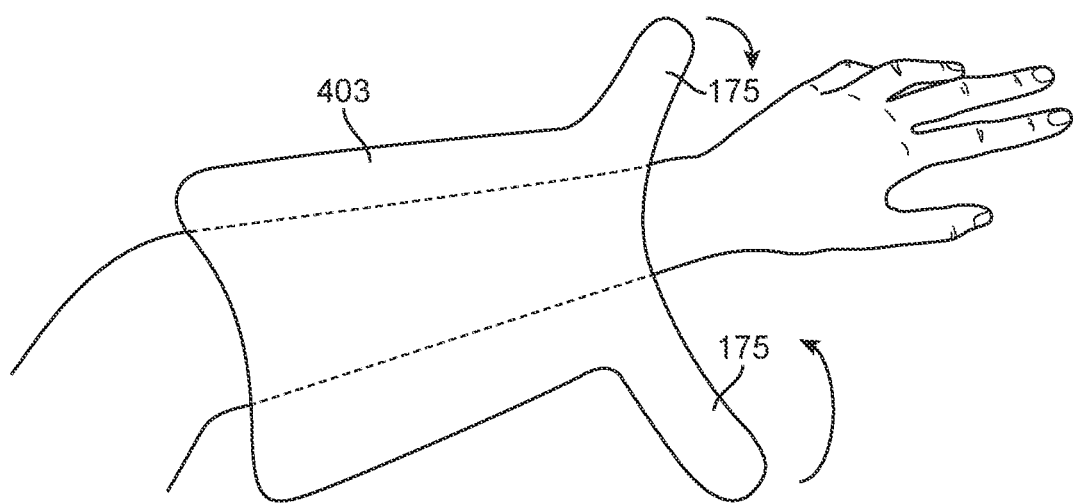
Figure 251:
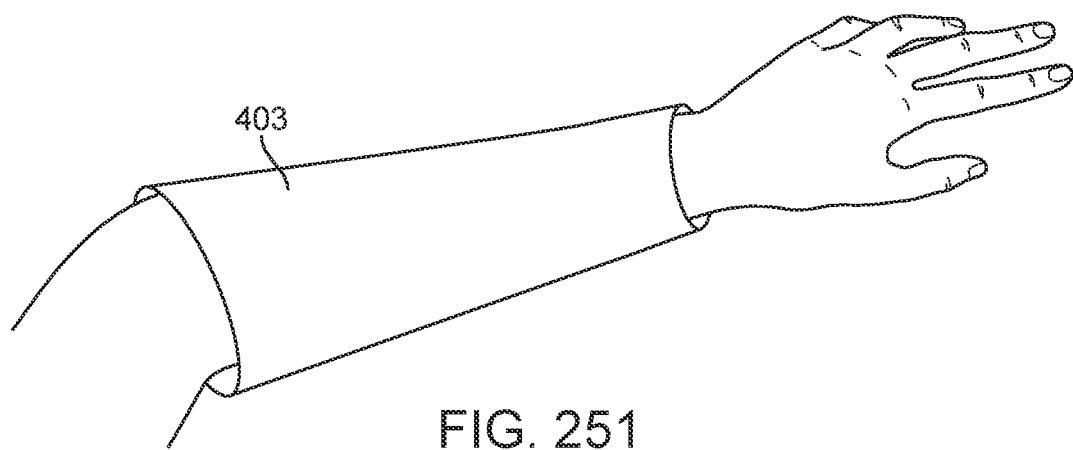
Figure 252:
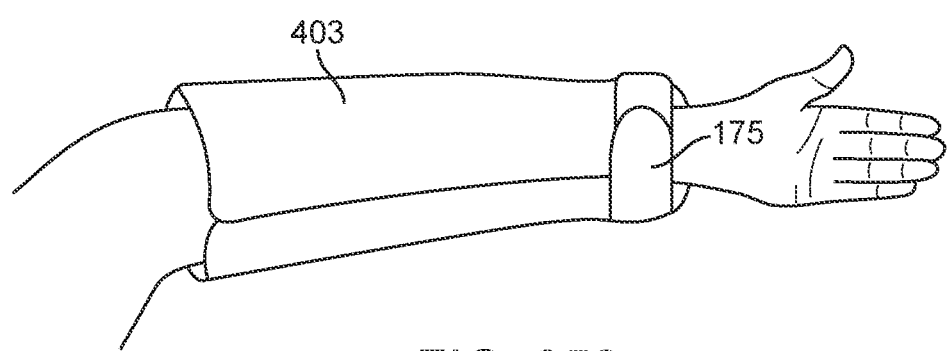

FIGS. 250-252 illustrates an embodiment of method for securing a barrier to a forearm.

Figure 253:
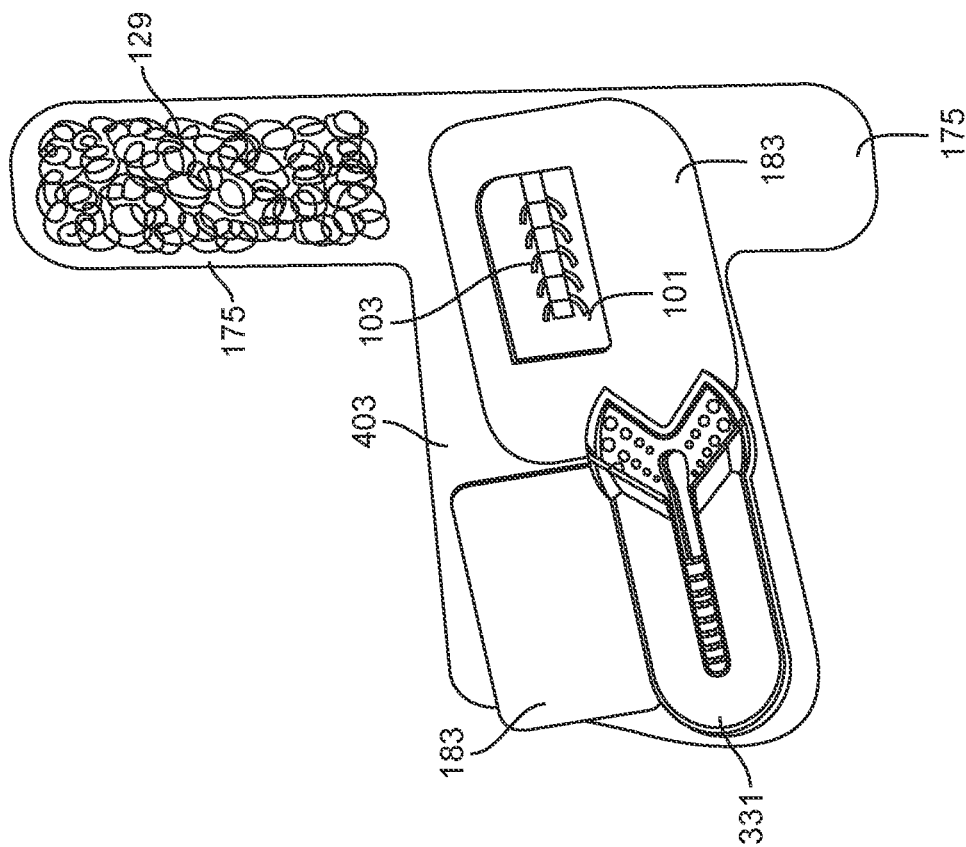

FIG. 253 illustrates a top view of an embodiment of a needle trap and suture pack carriers mounted on a barrier.

Figure 254:
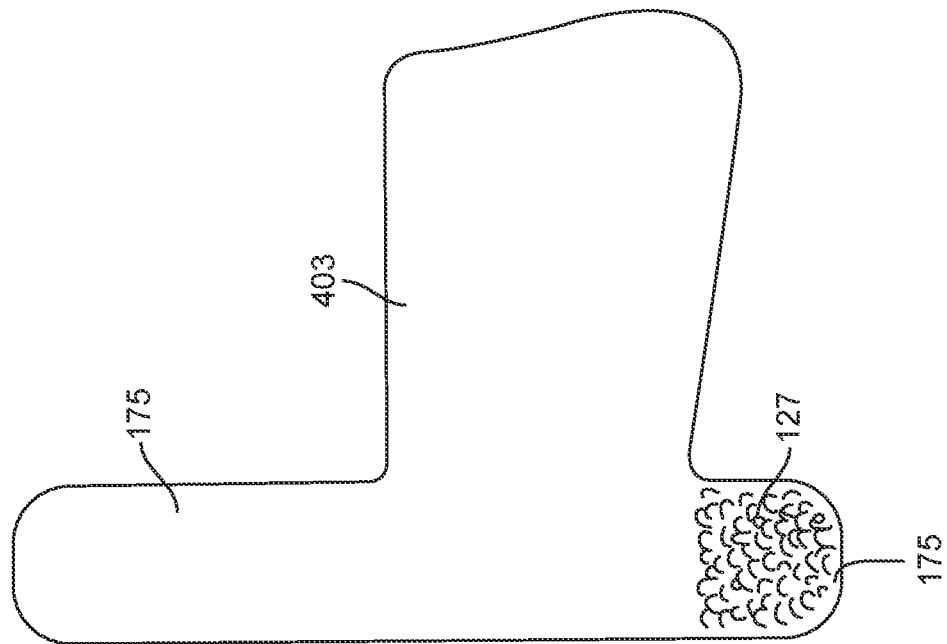

FIG. 254 illustrates a bottom view of an embodiment of a barrier.

Figure 255:
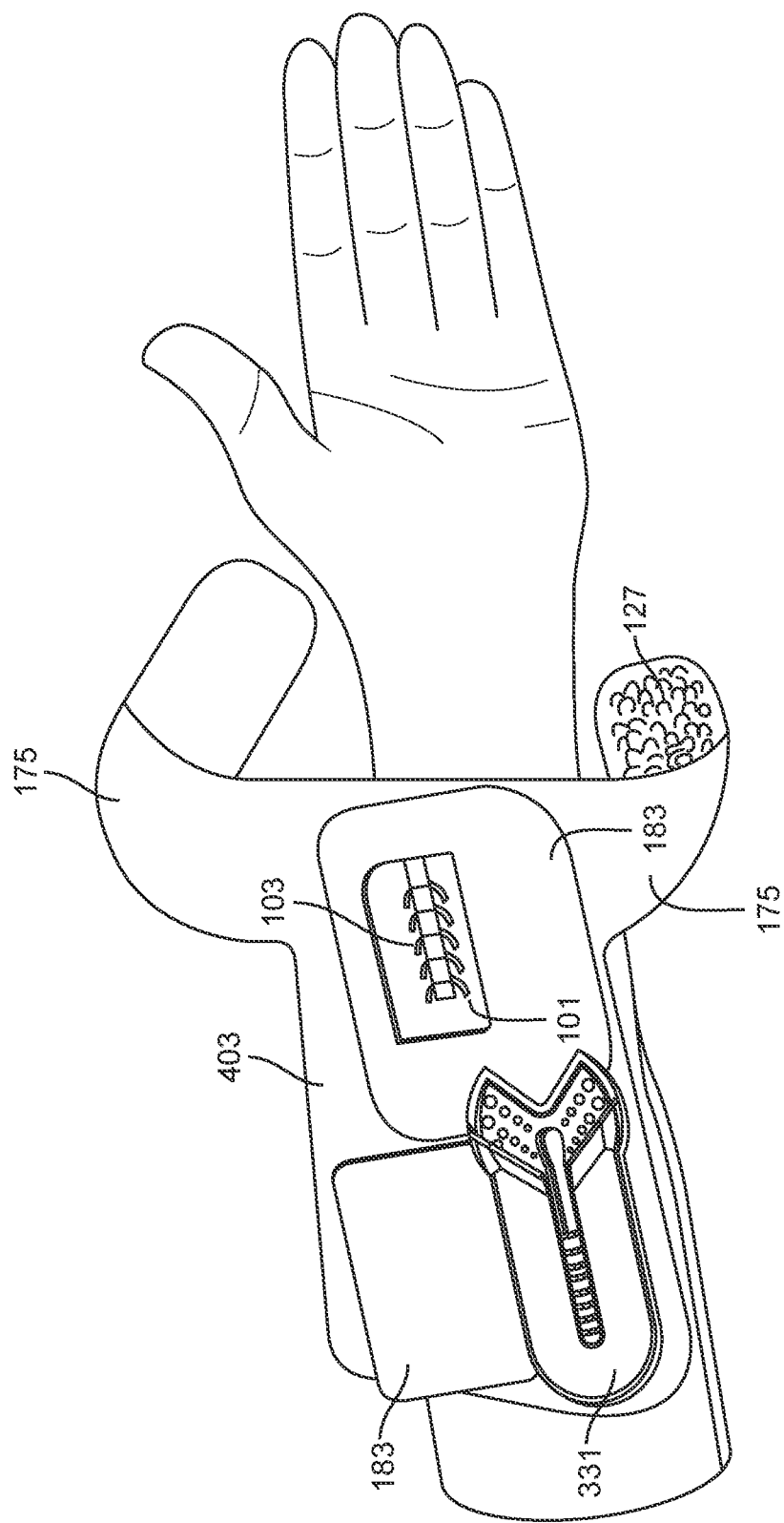
Figure 256:
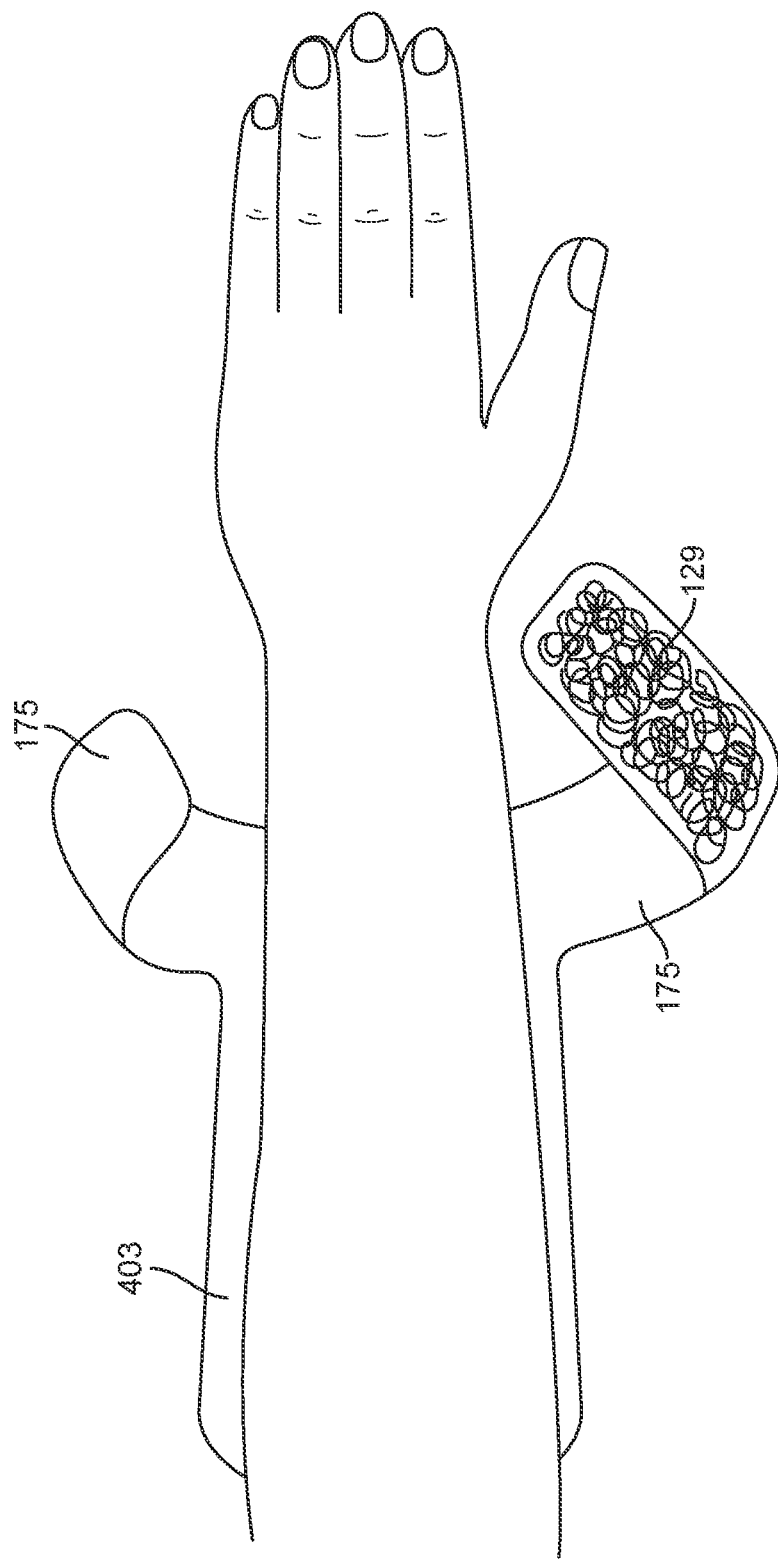

FIGS. 255-256 illustrate an embodiment of a barrier placed on a forearm.

Figure 257:
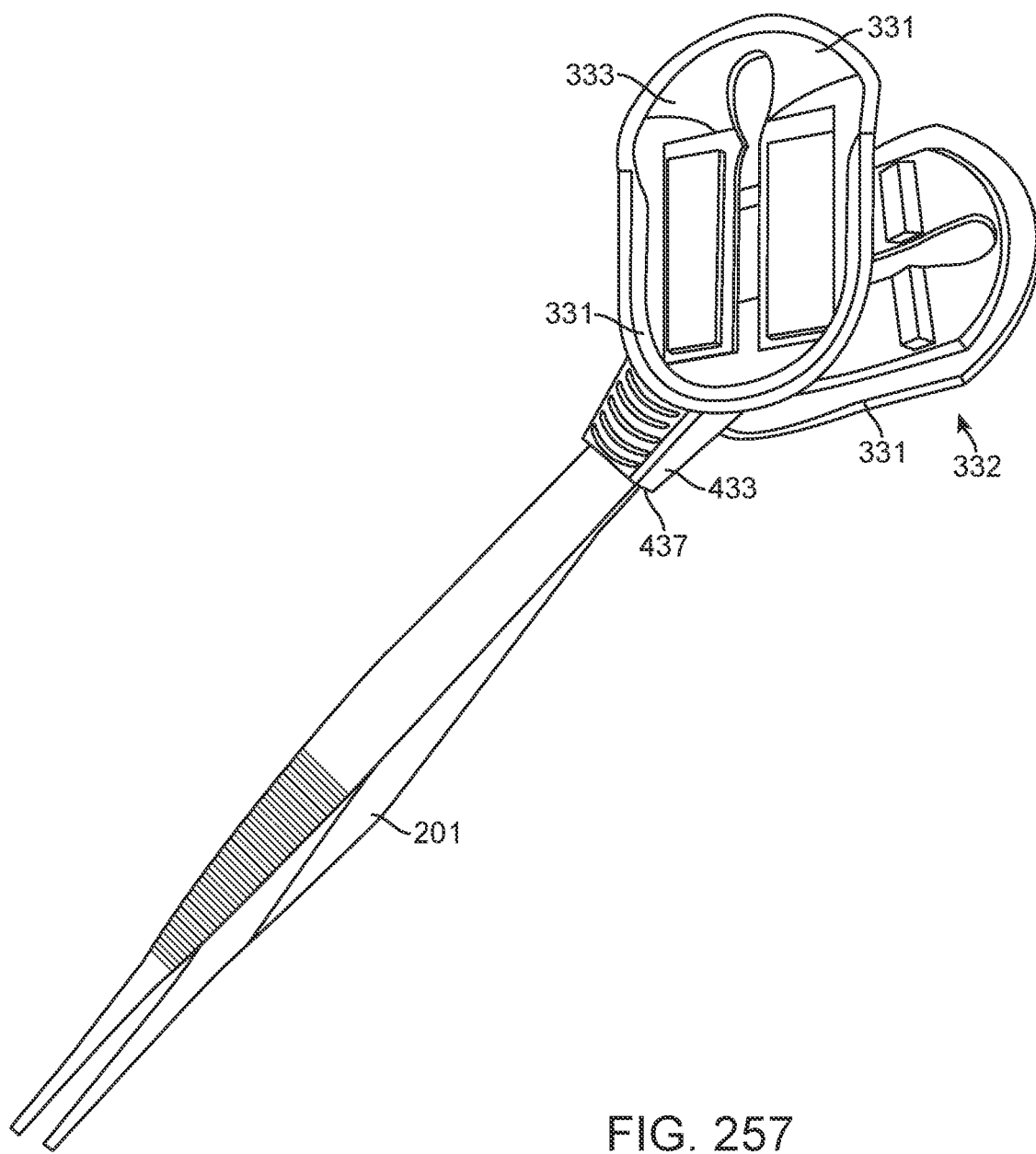

FIG. 257 illustrates a perspective view of an embodiment of a needle trap assembly having a tool mounting interface coupled to a surgical tool.

Figure 258:
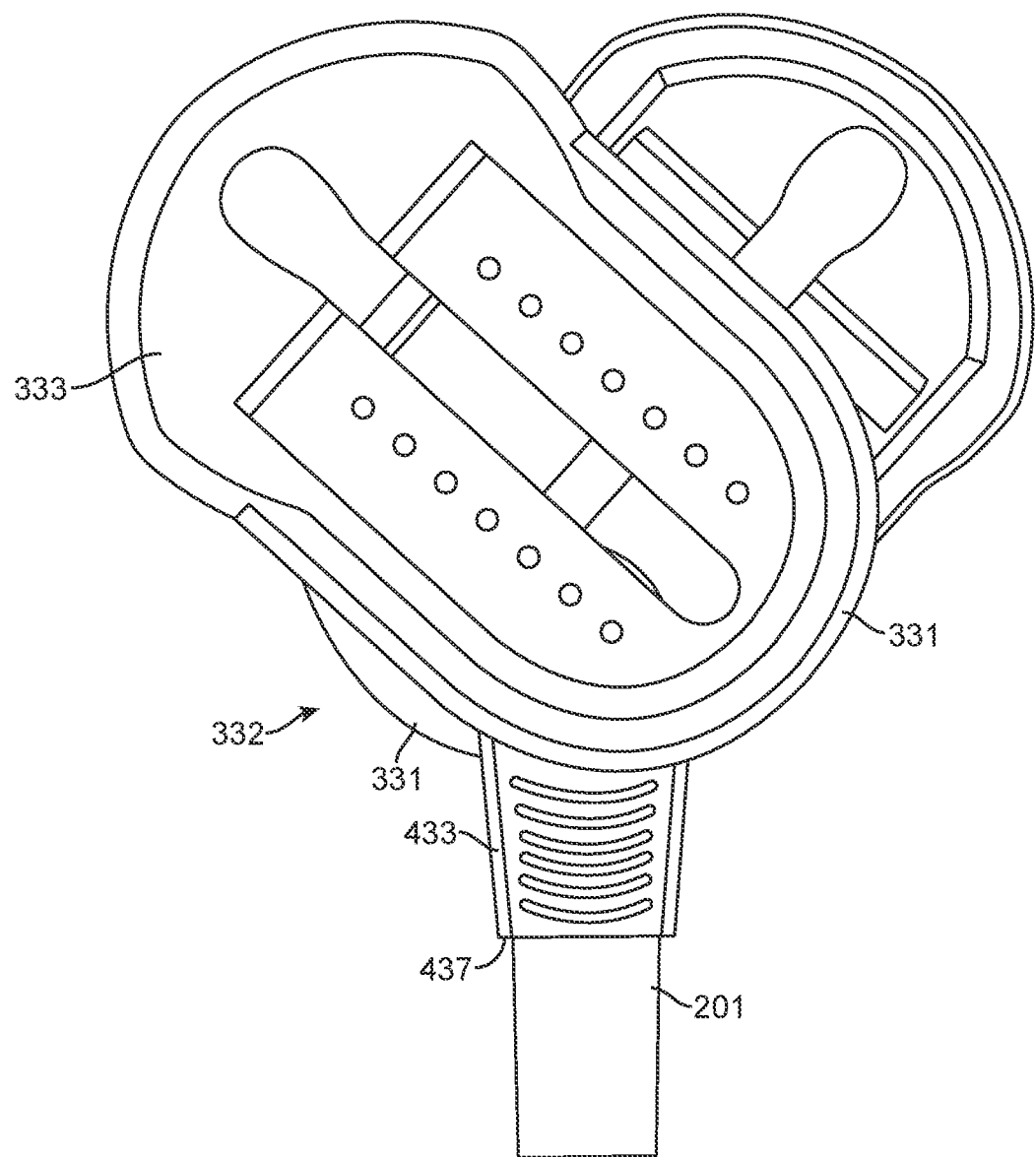

FIG. 258 illustrates a front view of an embodiment of a needle trap assembly having a tool mounting interface coupled to a surgical tool.

Figure 259:
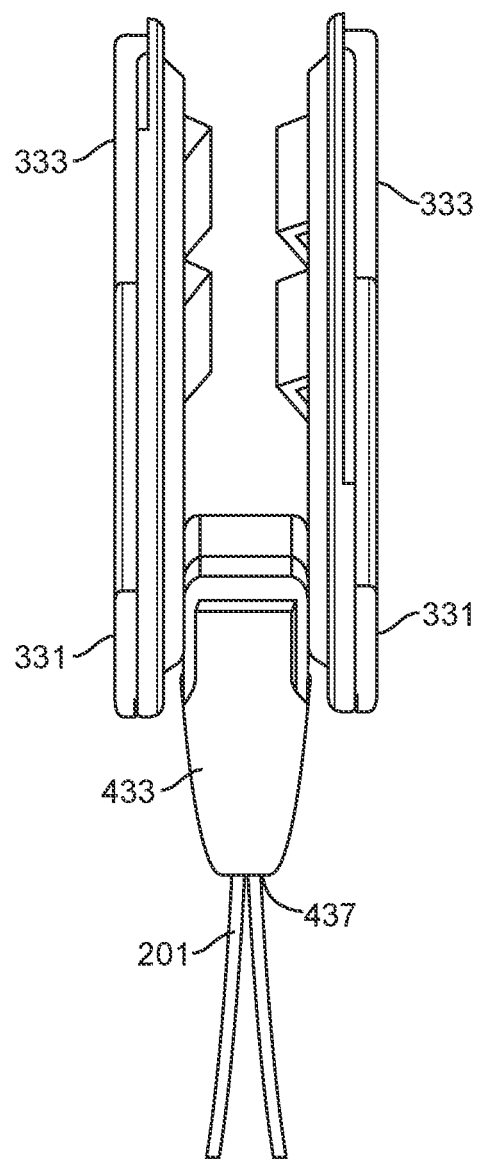

FIG. 259 illustrates a side view of an embodiment of a needle trap assembly having a tool mounting interface coupled to a surgical tool.

Figure 260:
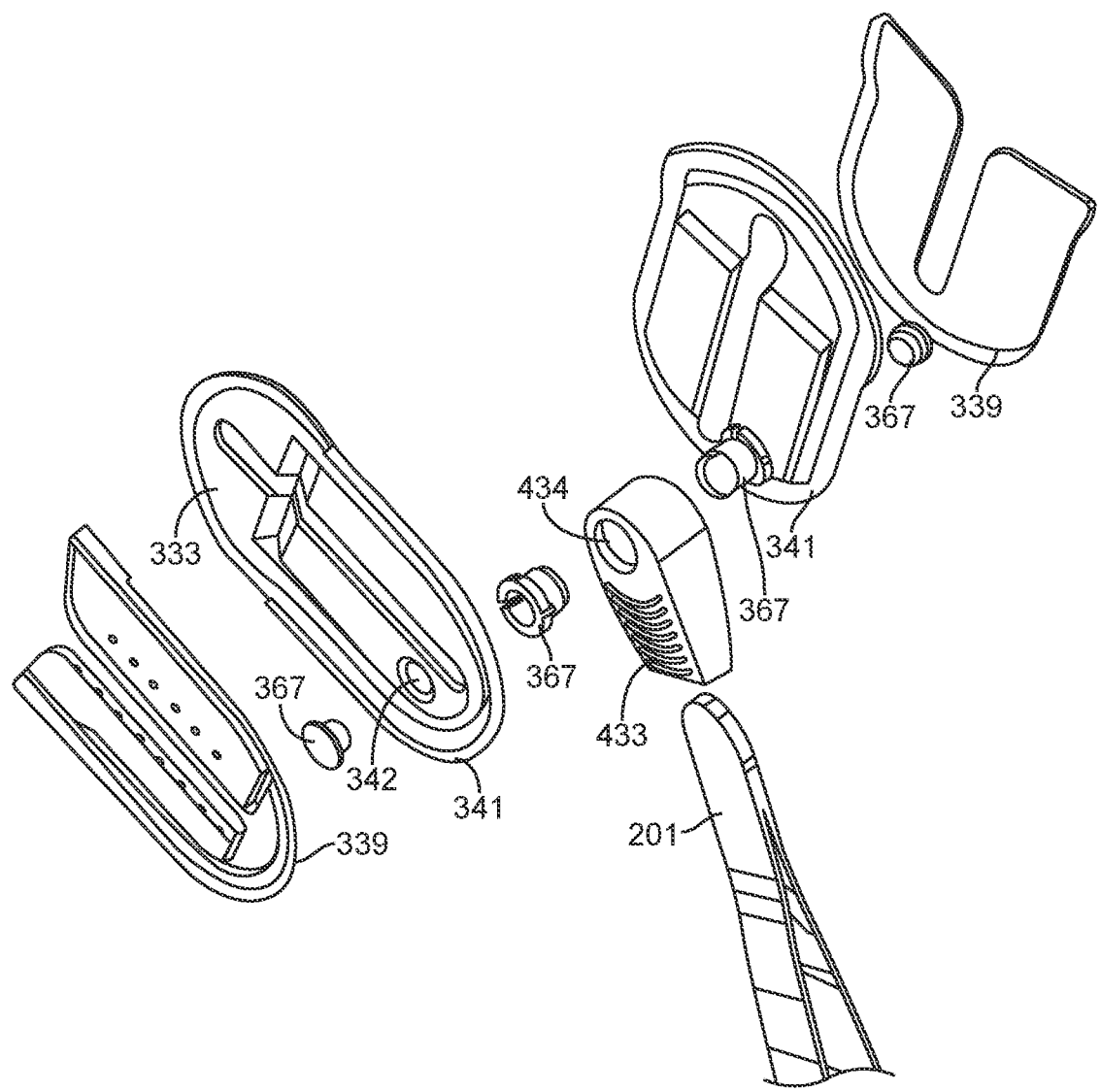

FIG. 260 an exploded perspective view of an embodiment of a needle trap assembly having a tool mounting interface.

Figure 261:
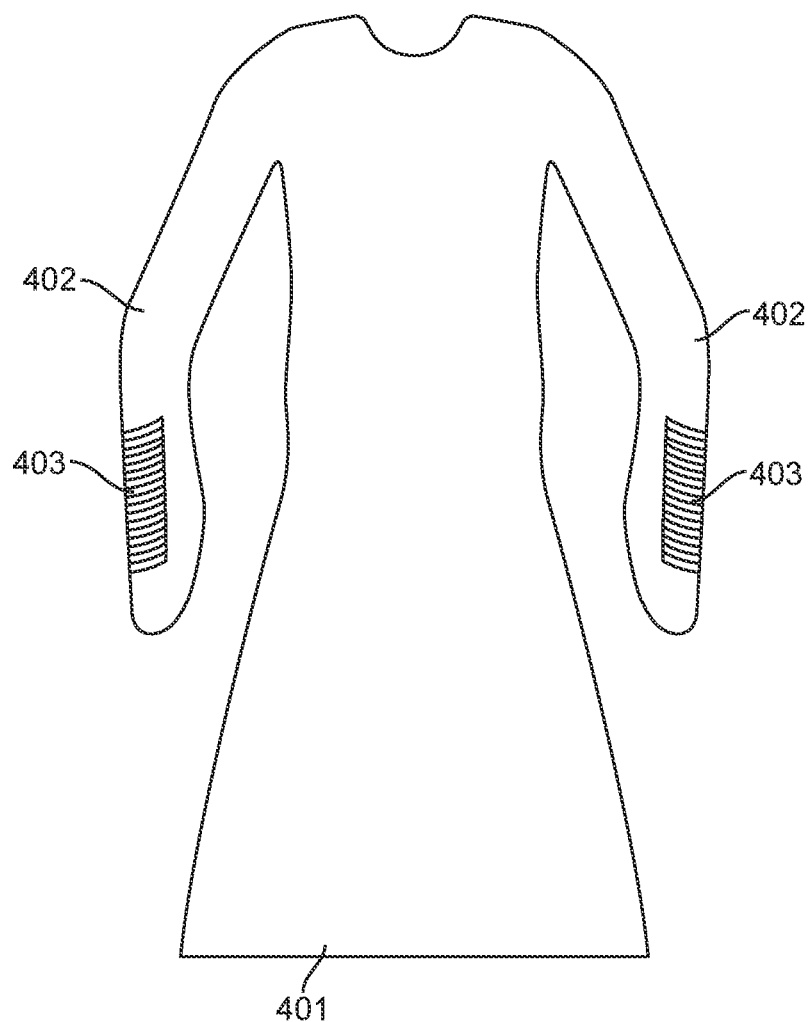

FIG. 261 illustrates a front view of an embodiment of surgical gown having barriers attached to the sleeves.

Figure 262:
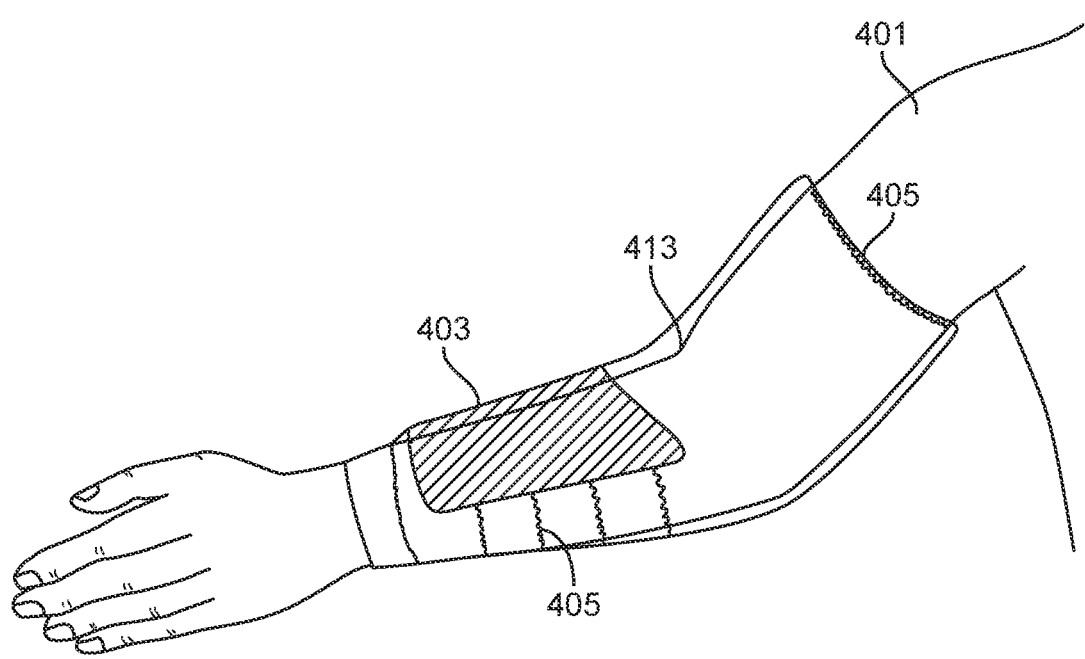

FIG. 262 illustrates a side view of an embodiment of a sleeve having a barrier.

Figure 263:
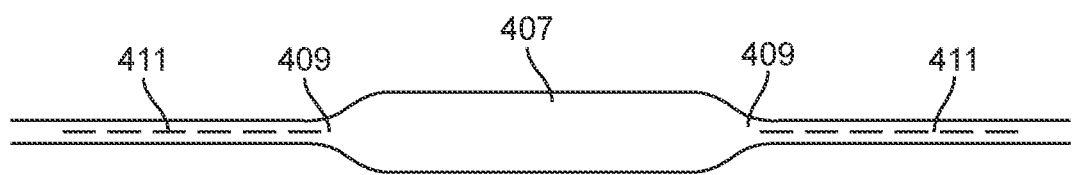
Figure 264:
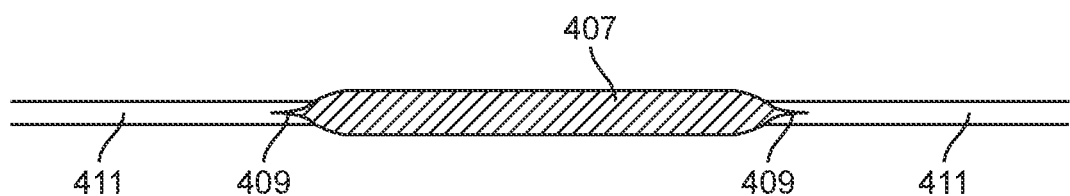
Figure 265:
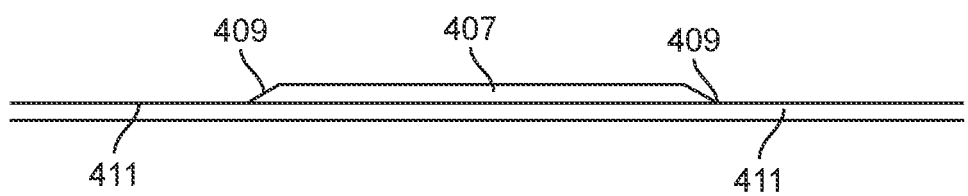

FIGS. 263-265 illustrate cross section views of barriers coupled to surgical gown fabrics.

Figure 266:
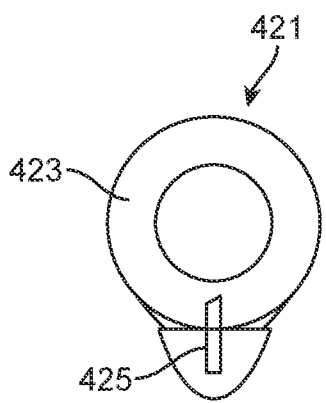
Figure 267:
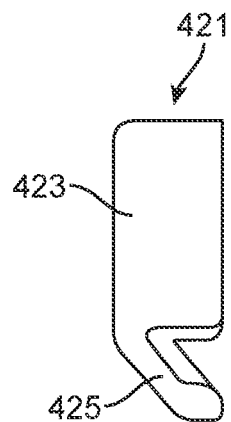

FIGS. 266-267 illustrate an embodiment of a blade ring.

Figure 268:
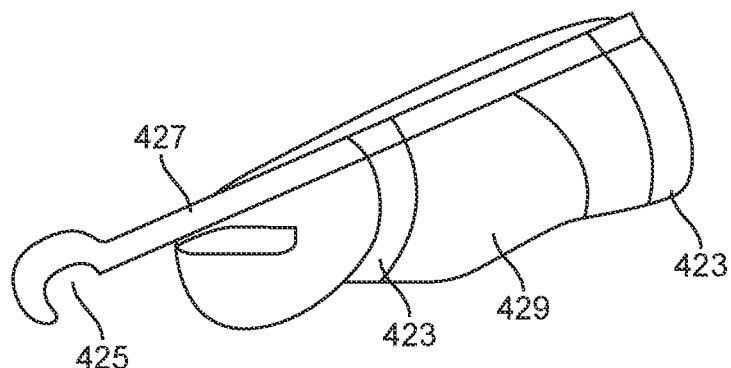

FIG. 268 illustrates an embodiment of a blade ring.

Figure 269:
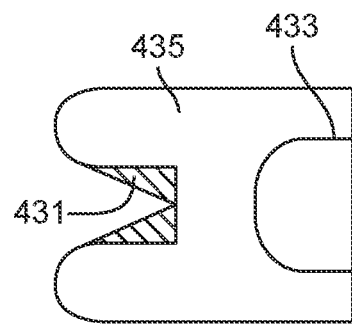
Figures 270, 271:
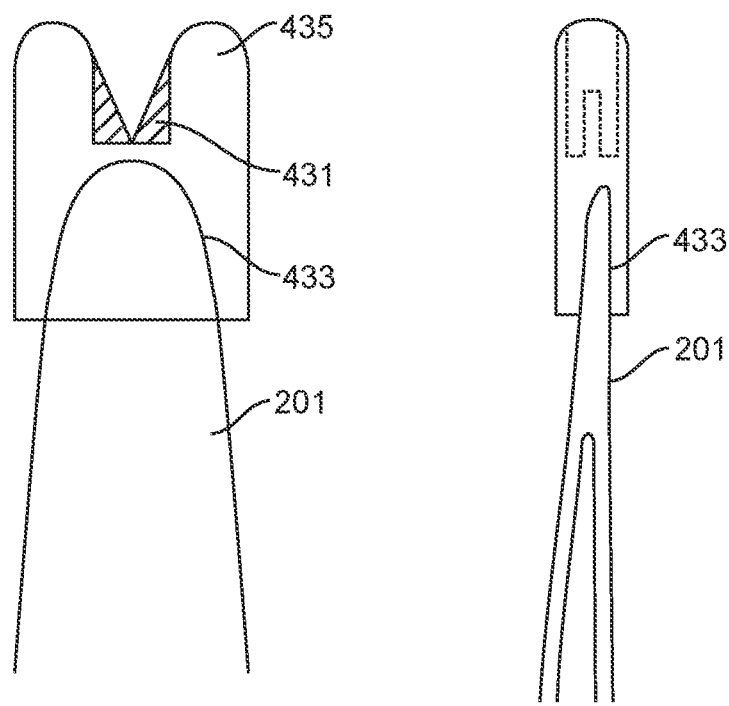

FIGS. 269-271 illustrate an embodiment of a surgical tool cap suture cutter.

Figures 272, 273:
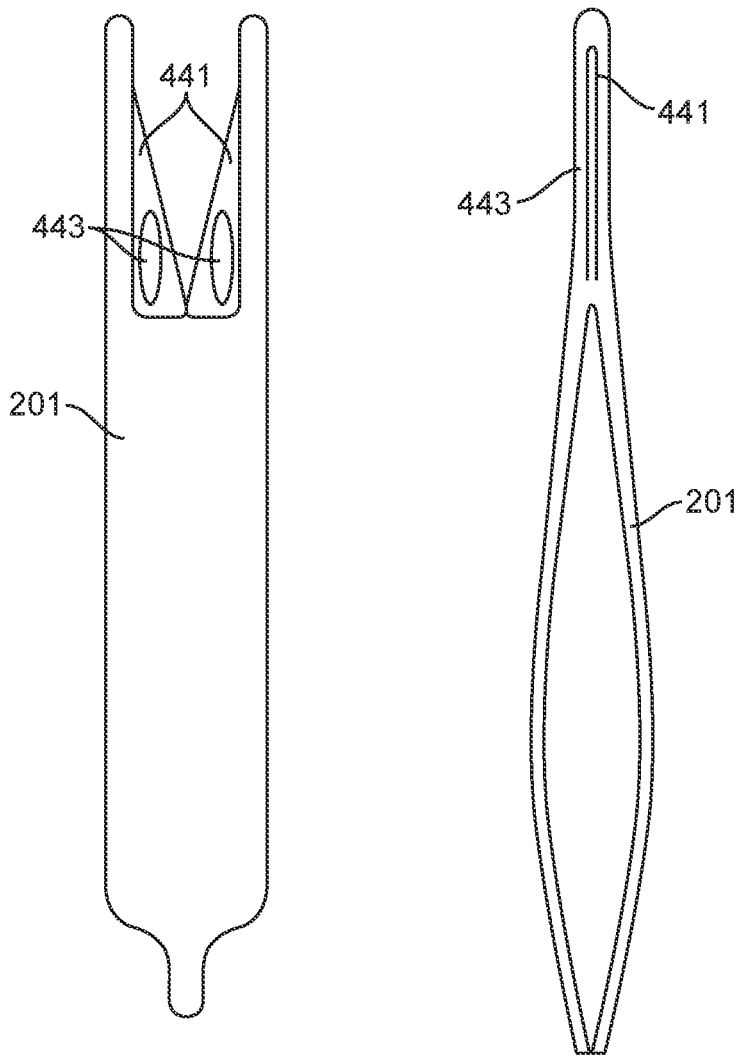

FIGS. 272-273 illustrate an embodiment of a surgical tool having an integrated suture cutter.

Figure 274:
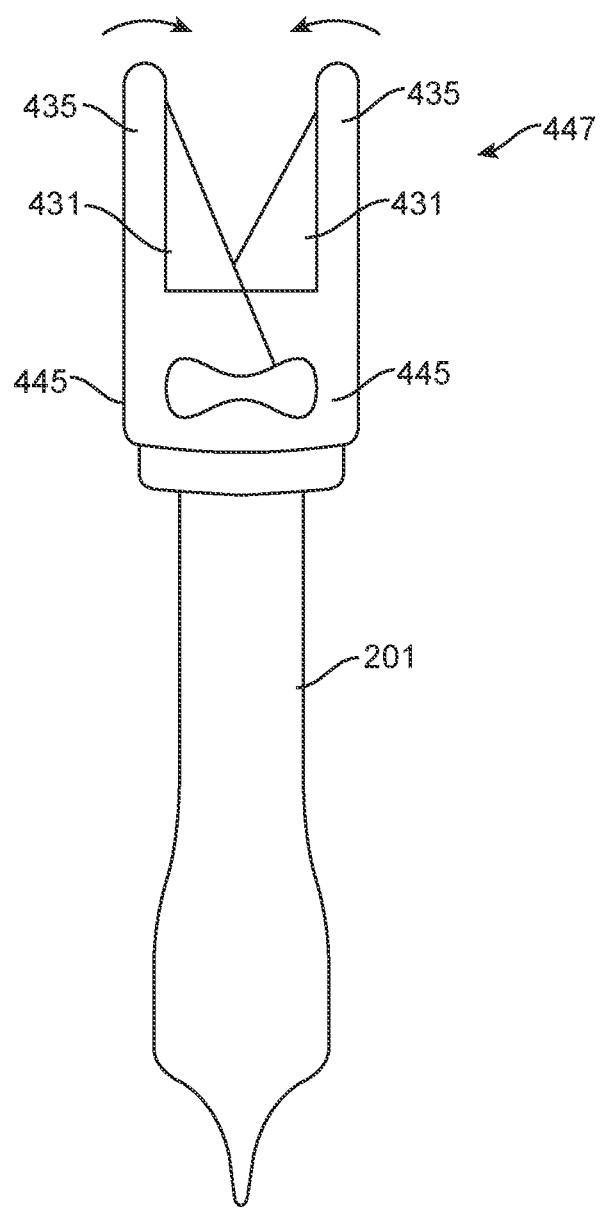

FIG. 274 illustrates an embodiment of a surgical tool mounted scissors.

FIGS. 275-278 illustrate an embodiment of a retractable cable mounted scissors.

Figure 279:
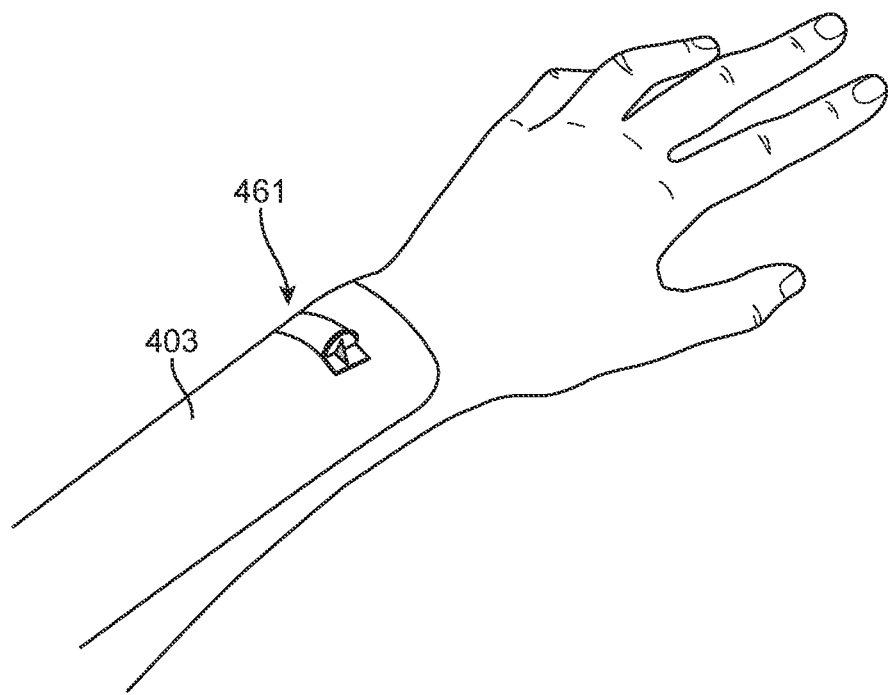
Figure 280:
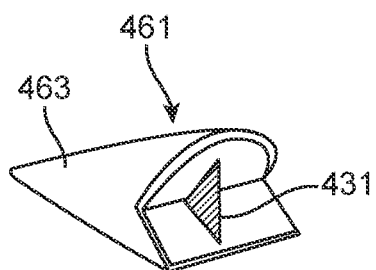

FIGS. 279-280 illustrate an embodiment of a barrier mounted suture cutter.

Figure 281:
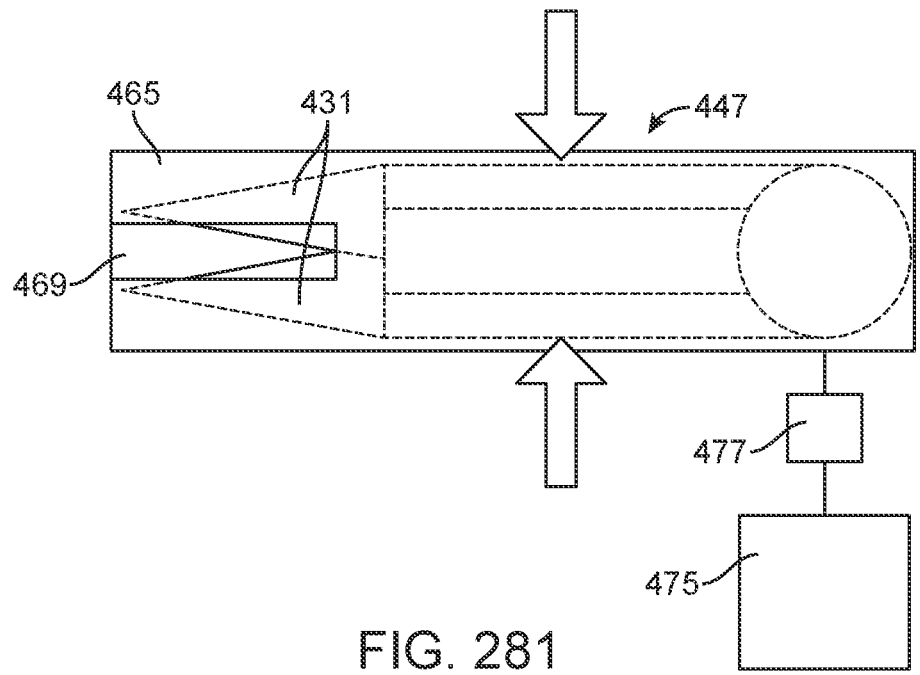

FIG. 281 illustrates an embodiment of a scissors within a safety guard.

FIGS. 282-285 illustrate an embodiment of a suture cutter.

FIGS. 286-289 illustrate different embodiments of surgical gloves.

Figure 290:
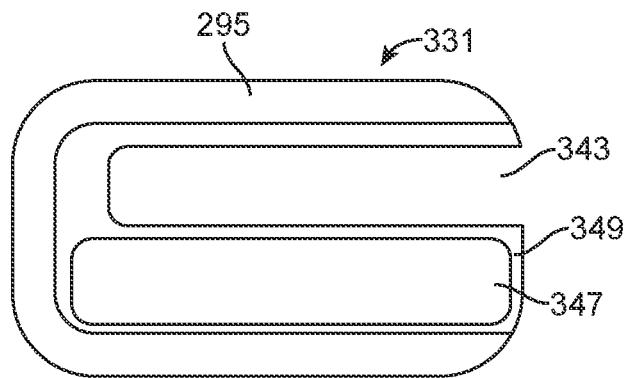

FIG. 290 illustrates a cross sectional side view of an embodiment of a needle trap.

Figure 291:
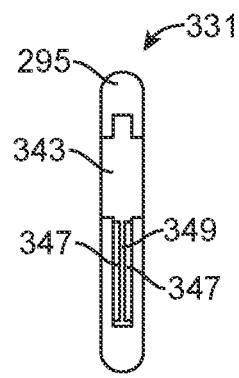

FIG. 291 illustrates a front view of an embodiment of a needle trap.

Figure 292:
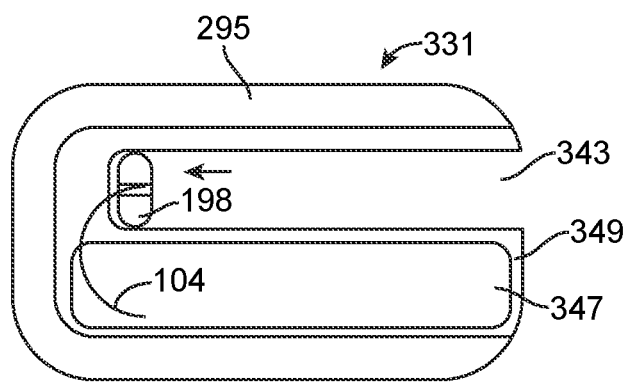

FIG. 292 illustrates a cross sectional side view of an embodiment of a needle trap.

Figure 293:
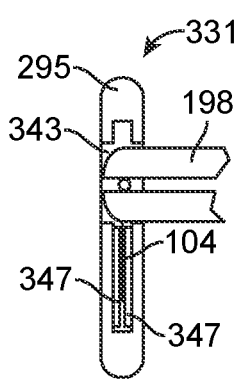

FIG. 293 illustrates a front view of an embodiment of a needle trap.

FIGS. 294-297 illustrate cross sectional side views of embodiments of needle traps.

Figure 298:
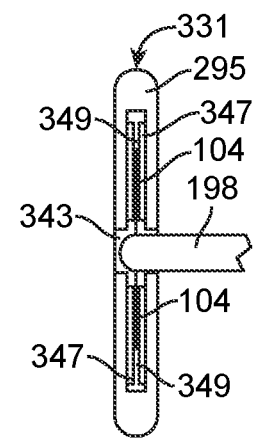

FIG. 298 illustrates a front view of an embodiment of a needle trap.

FIG. 299 illustrates a cross sectional side view of an embodiment of a needle trap.

FIG. 300 illustrates a front view of an embodiment of a needle trap.

FIGS. 301-302 illustrate cross sectional side views of an embodiment of a needle trap.

FIG. 303 illustrates a cross sectional side view of an embodiment of a needle trap.

FIG. 304 illustrates a front view of an embodiment of a needle trap.

FIGS. 305-306 illustrate cross sectional side views of an embodiment of a needle trap.

Figure 307:
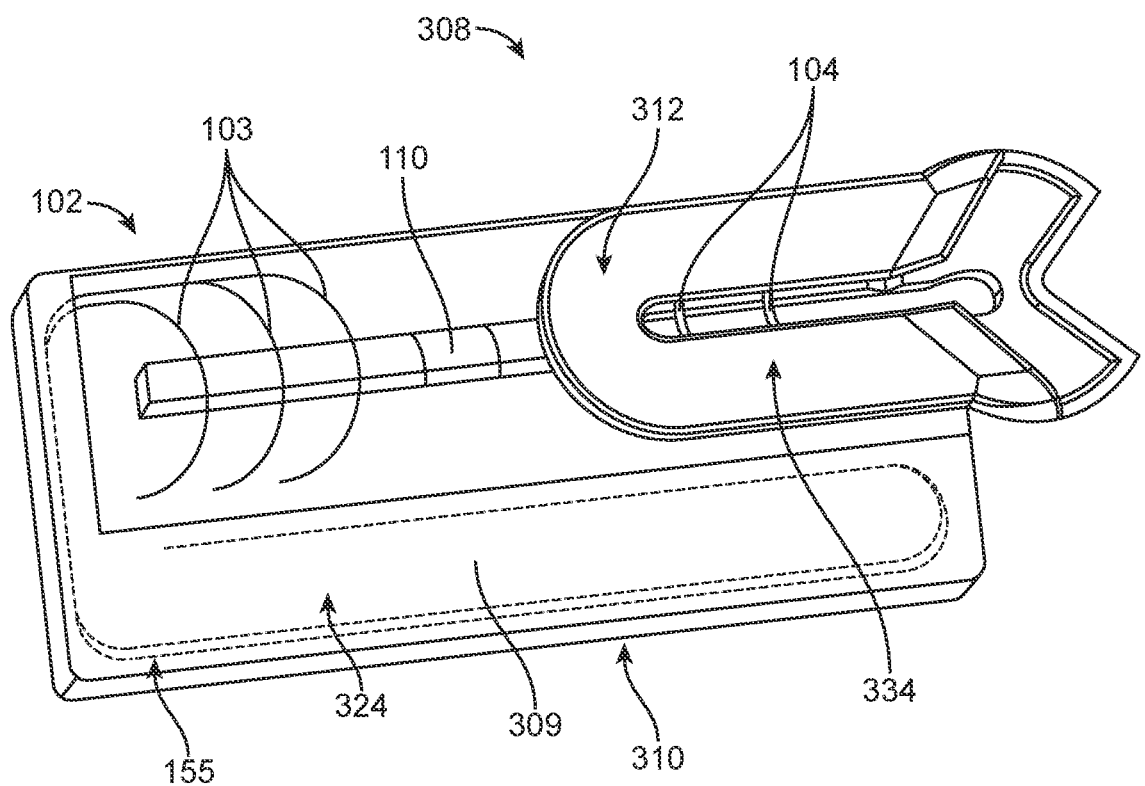

FIG. 307 illustrates an exemplary embodiment of an integrated suture needle dispensing and securing apparatus.

Figure 308:
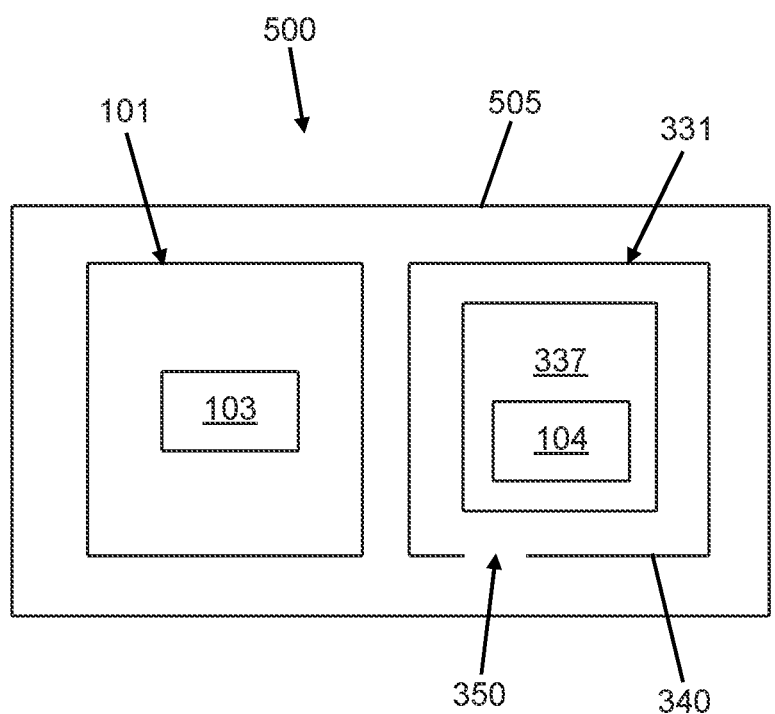

FIG. 308 is a block diagram of a sterile suturing kit in accordance with embodiments.

Figure 309:
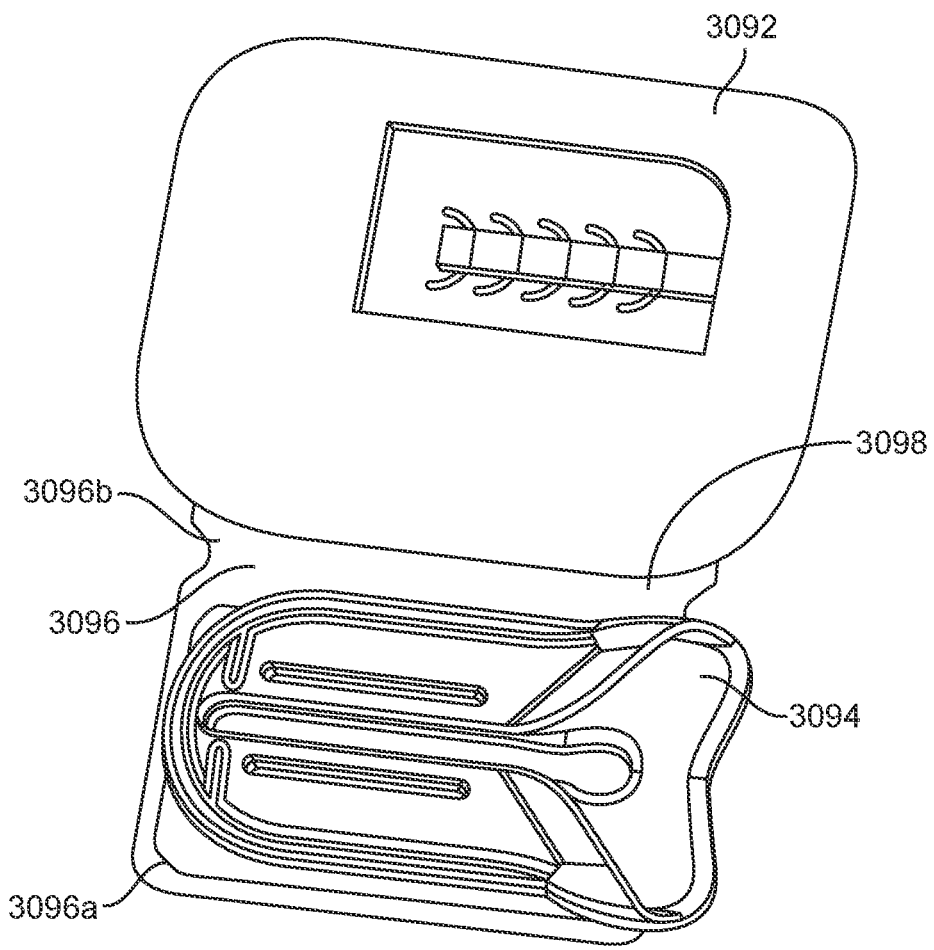

FIG. 309 shows a suture pack and needle receptacle coupled to a barrier mounting base.

Figure 310:
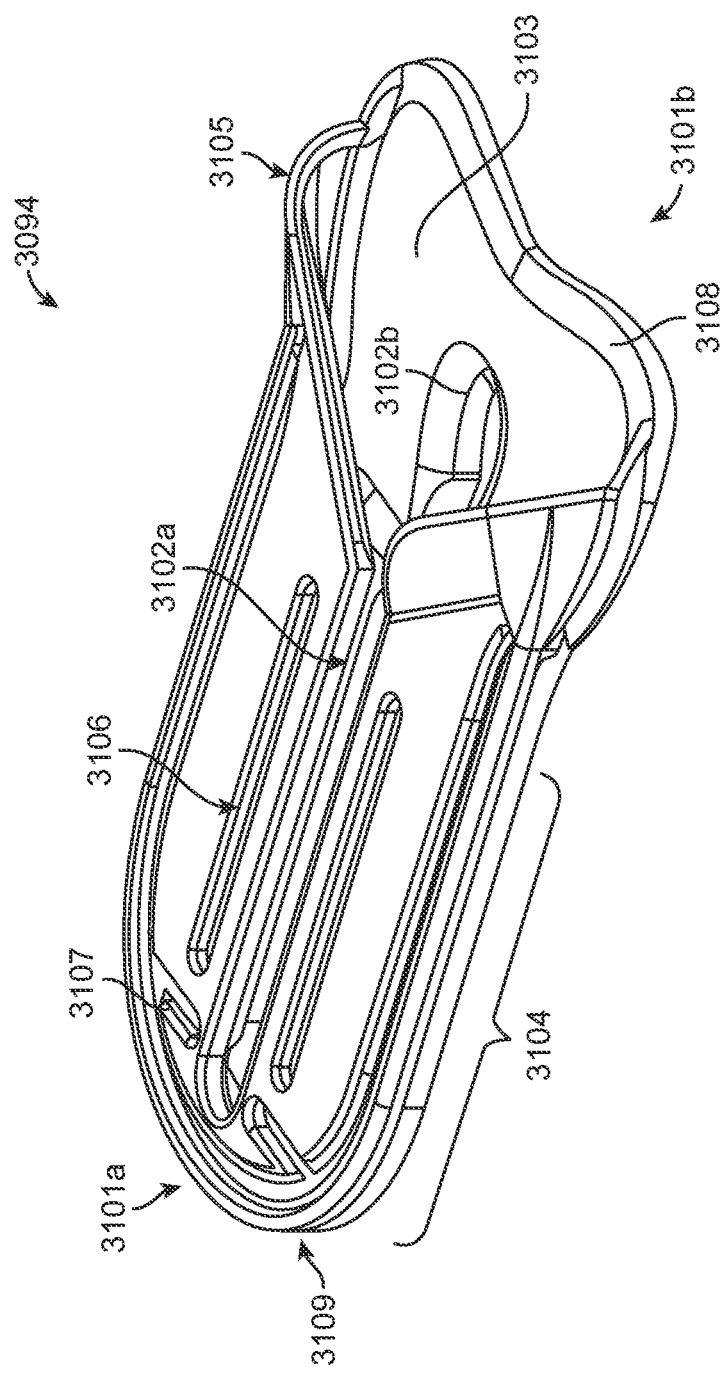

FIG. 310 shows the needle receptacle as in FIG. 309. FIG. 310 shows a top oblique view of the needle receptacle in a fully assembled configuration.

Figure 311:
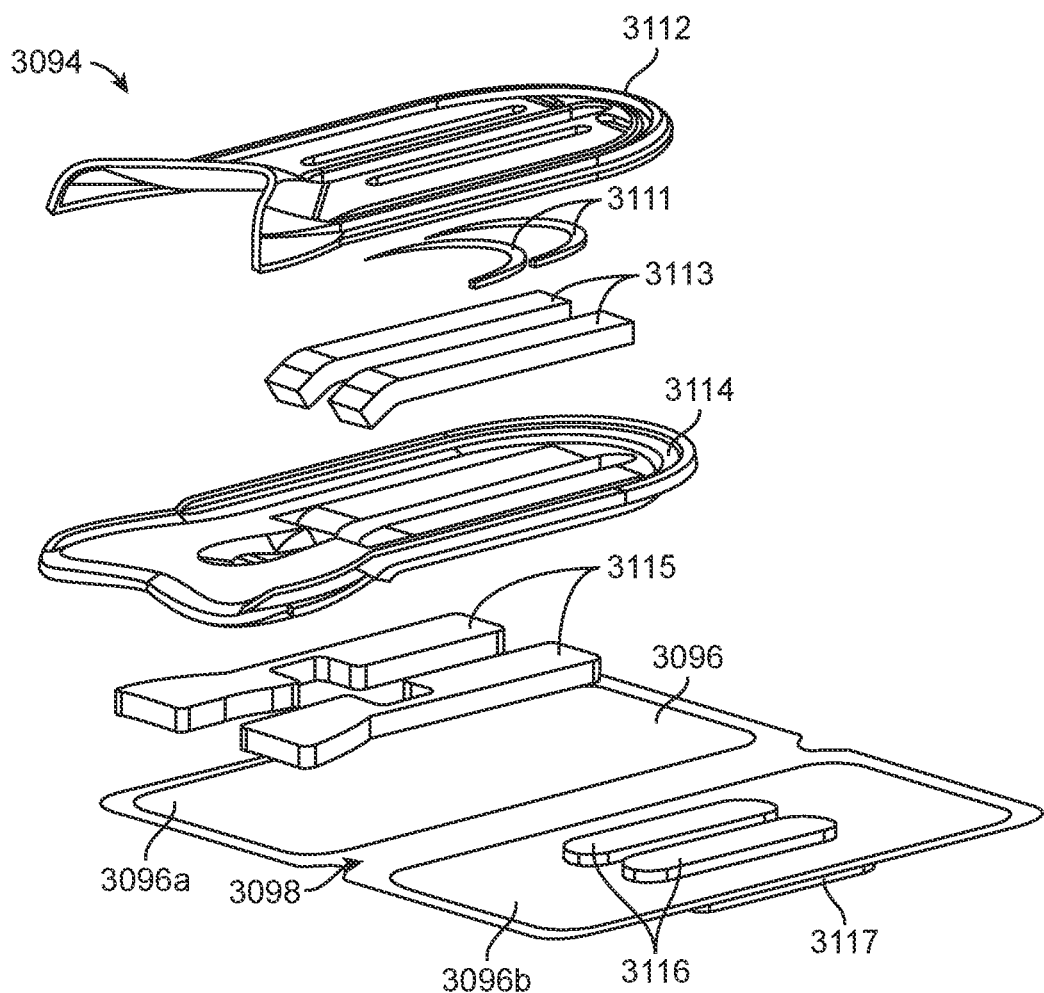

FIG. 311 shows a top exploded view of the needle receptacle with needles coupled to the barrier mounting base.

Figure 312:
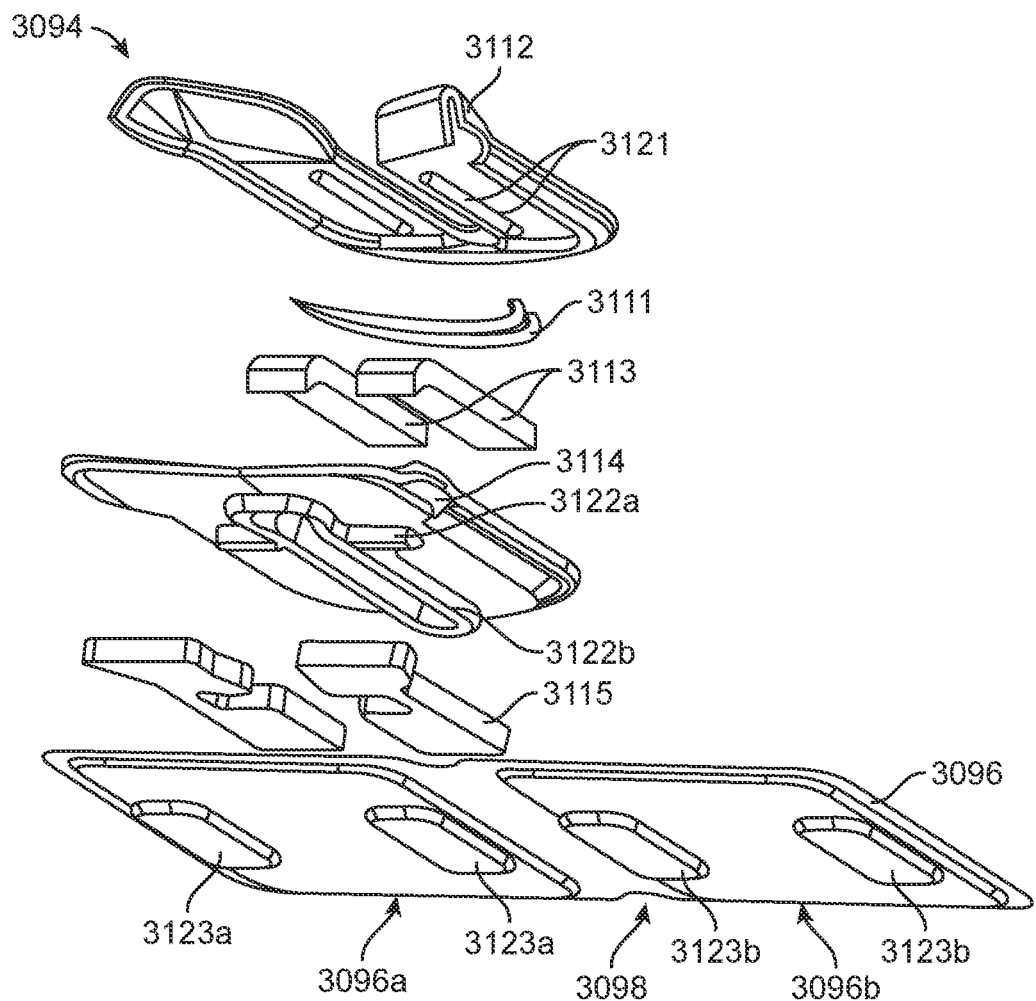

FIG. 312 shows a bottom exploded view of the needle receptacle with needles coupled to the barrier mounting base as in FIGS. 310 and 311.

Figure 313:
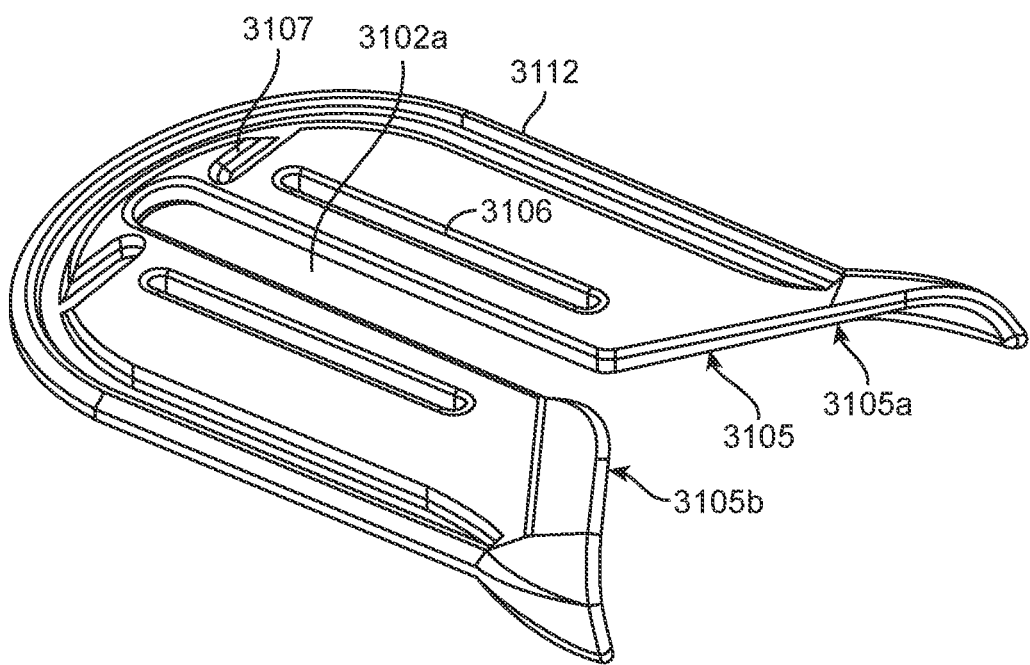

FIG. 313 shows a top oblique view of the top shell of the needle receptacle as in FIG. 312.

Figure 314:
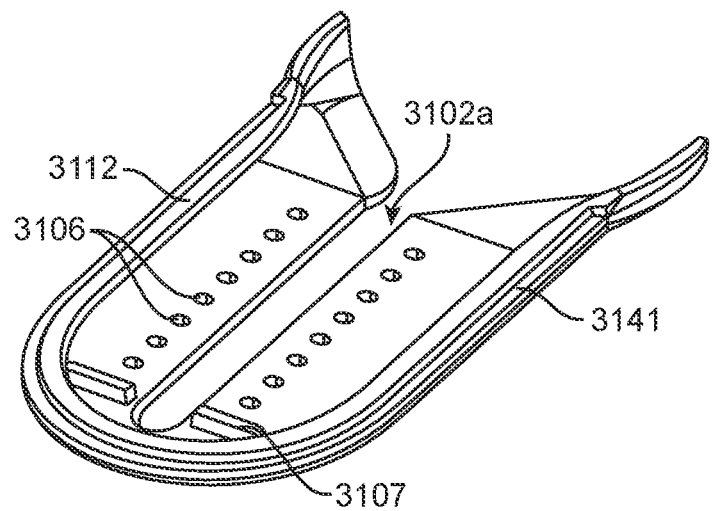

FIG. 314 shows a bottom oblique view of the top shell as in FIG. 313.

Figure 315:
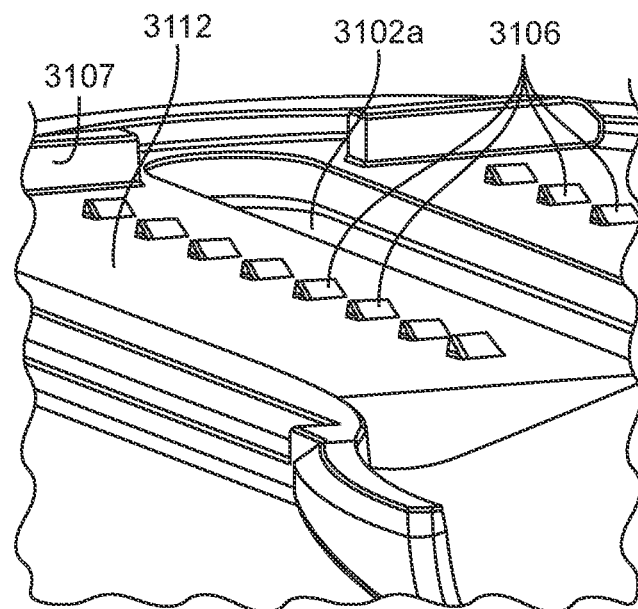

FIG. 315 shows a close-up bottom oblique view of the top shell as in FIG. 314.

Figure 316:
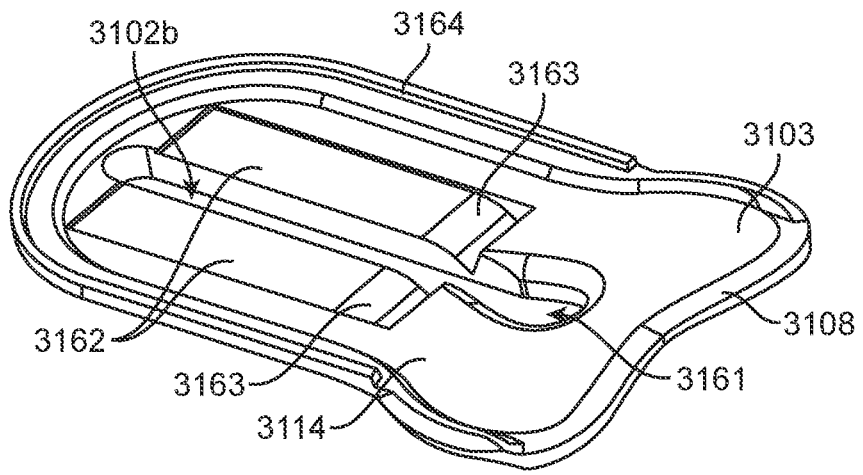

FIG. 316 shows a top oblique view of the bottom shell of the needle receptacle as in FIG. 310.

Figure 317:
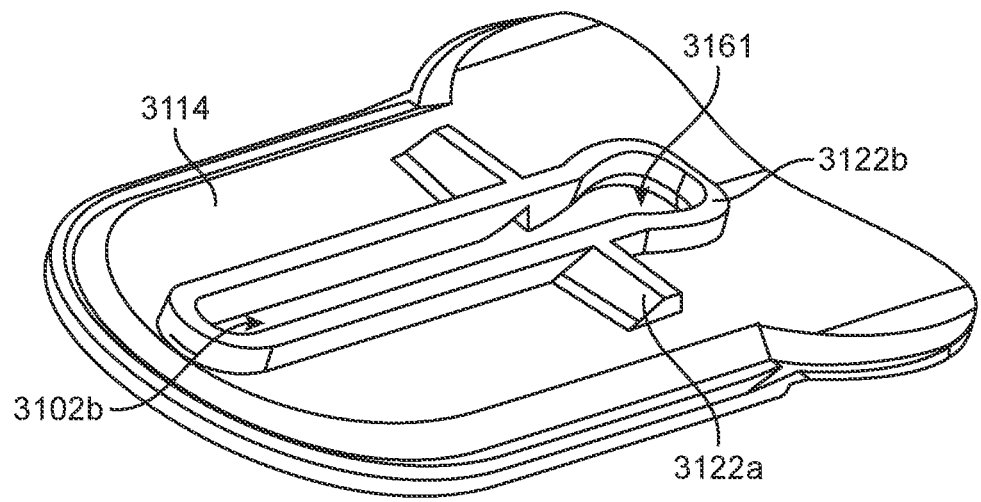

FIG. 317 shows a bottom oblique view of the bottom shell as in FIG. 316. The lower needle driver slot is shown extending along a long axis of the needle receptacle.

Figure 318:
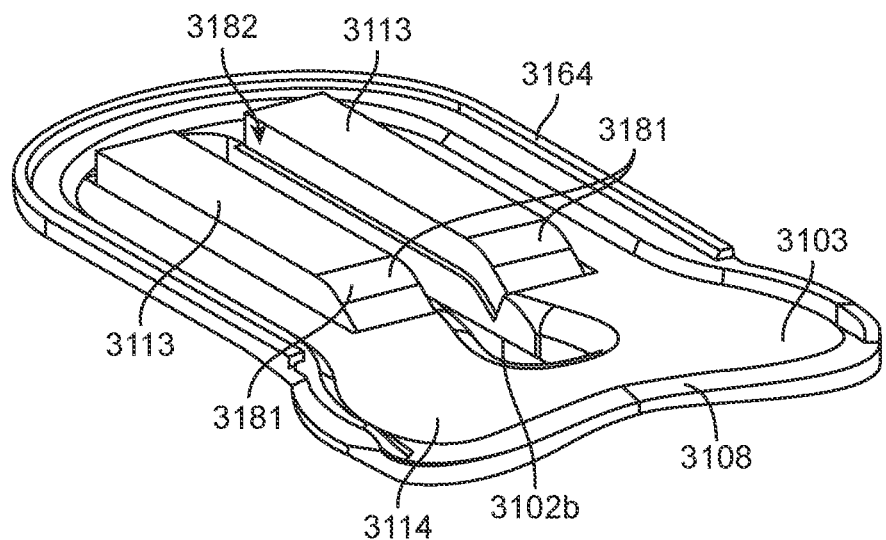

FIG. 318 shows a top oblique view of the bottom shell as in FIG. 317 with compressive members placed thereon.

Figure 319:
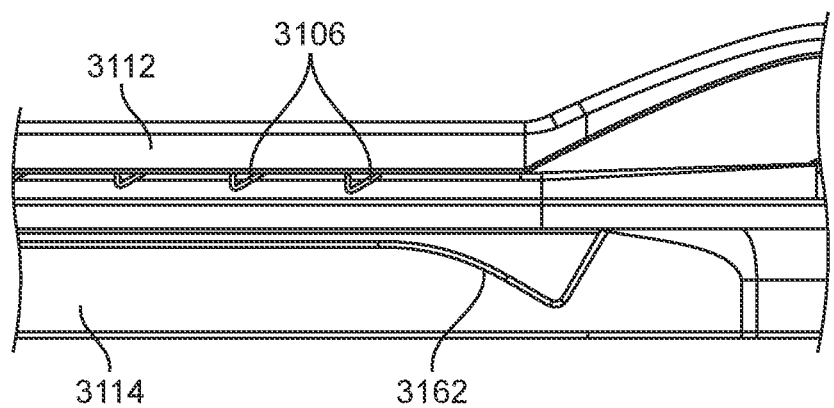

FIG. 319 shows a longitudinal cross-sectional view of the top and bottom shell as in FIG. 310 without the compressive members.

Figure 320:
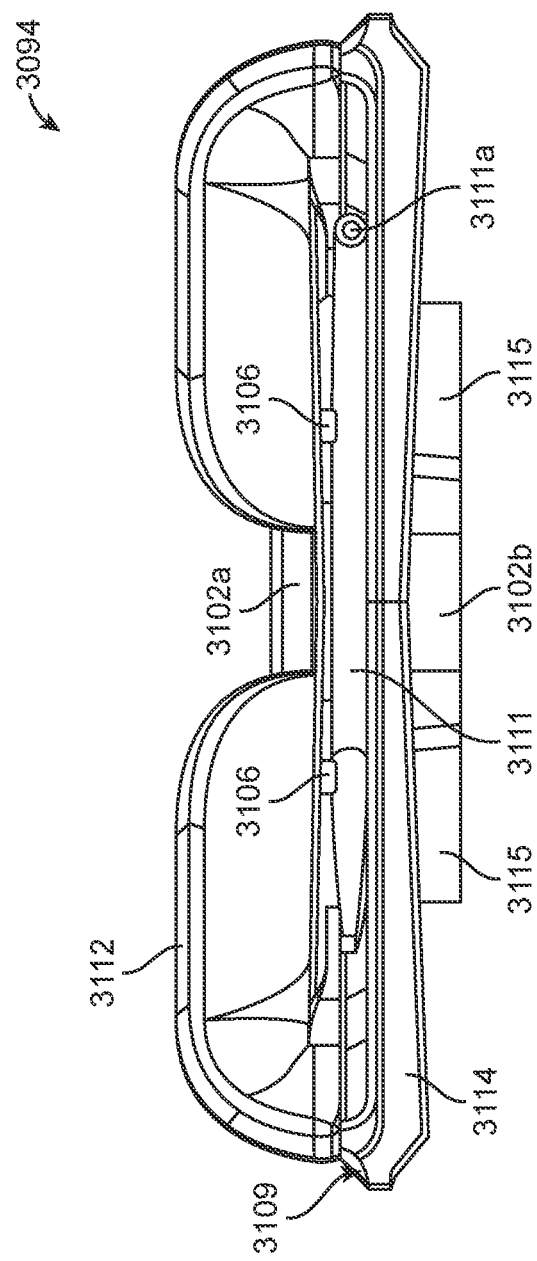

FIG. 320 shows the fully assembled needle receptacle with the needle in a transverse cross-sectional view for the needle receptacle as shown in FIG. 310.

Figure 321:
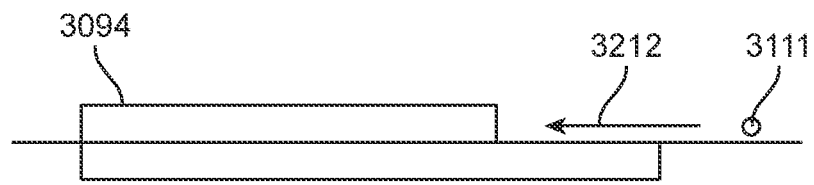

FIG. 321 shows advancement of the needle positioned into the needle receptacle as in FIG. 310.

Figure 322A:
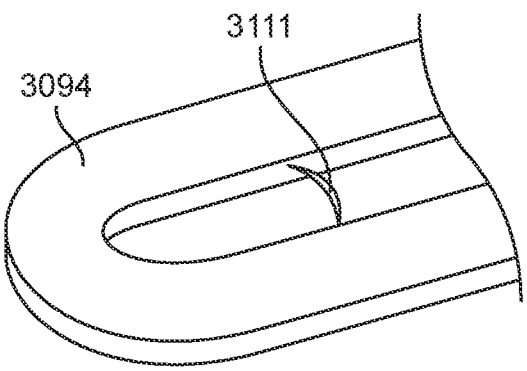
Figure 322B:
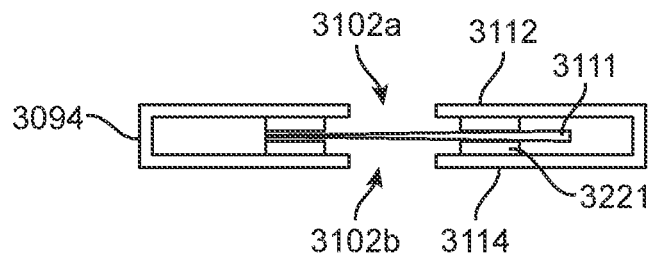

FIGS. 322A and 322B show a needle stabilized in the needle receptacle.

Figure 323:
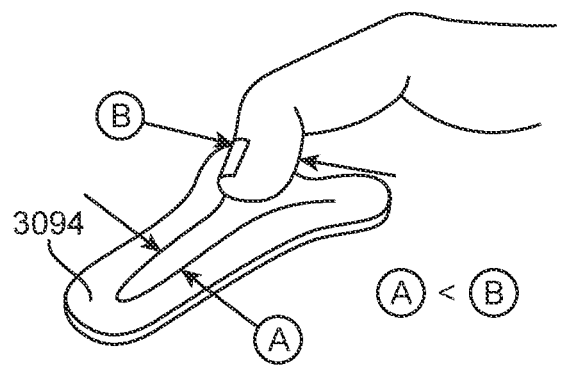

FIG. 323 shows dimensions of the needle receptacle as in FIG. 310. The needle receptacle comprises a cross-sectional dimension of the needle driver slot that is shown with dimension.

Figure 324A:
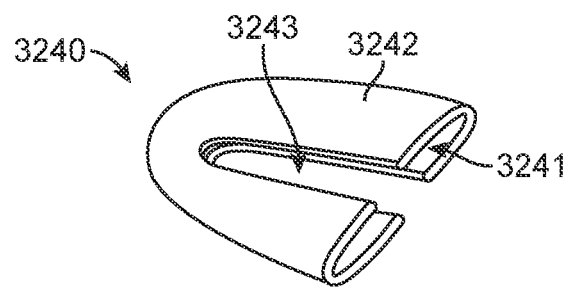
Figure 324B:
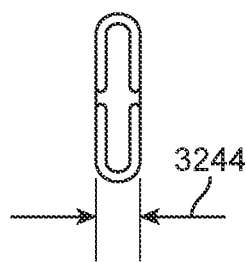

FIGS. 324A and 324B show a needle containment groove defined with a housing similar to FIG. 310.

FIGS. 325A-325C show needles placed in a needle receptacle as in FIG. 324A.

FIGS. 326A-326D show needles placed in a needle receptacle as described herein, for example, with reference to FIGS. 310 and 324.

Figure 327A:
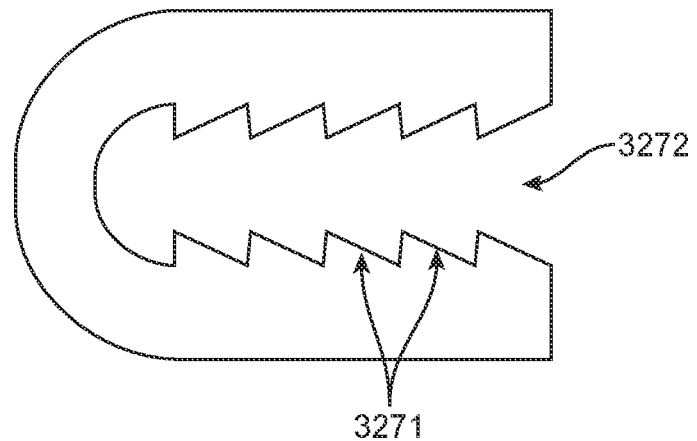

FIG. 327A shows ratcheting along the groove of the needle driver slot for example with reference to FIGS. 310 and 324.

Figure 327B:
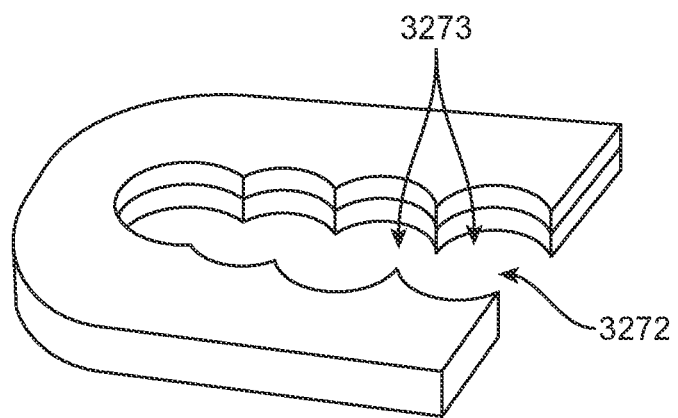

FIG. 327B shows varied apertures along the needle driver slot.

Figure 328:
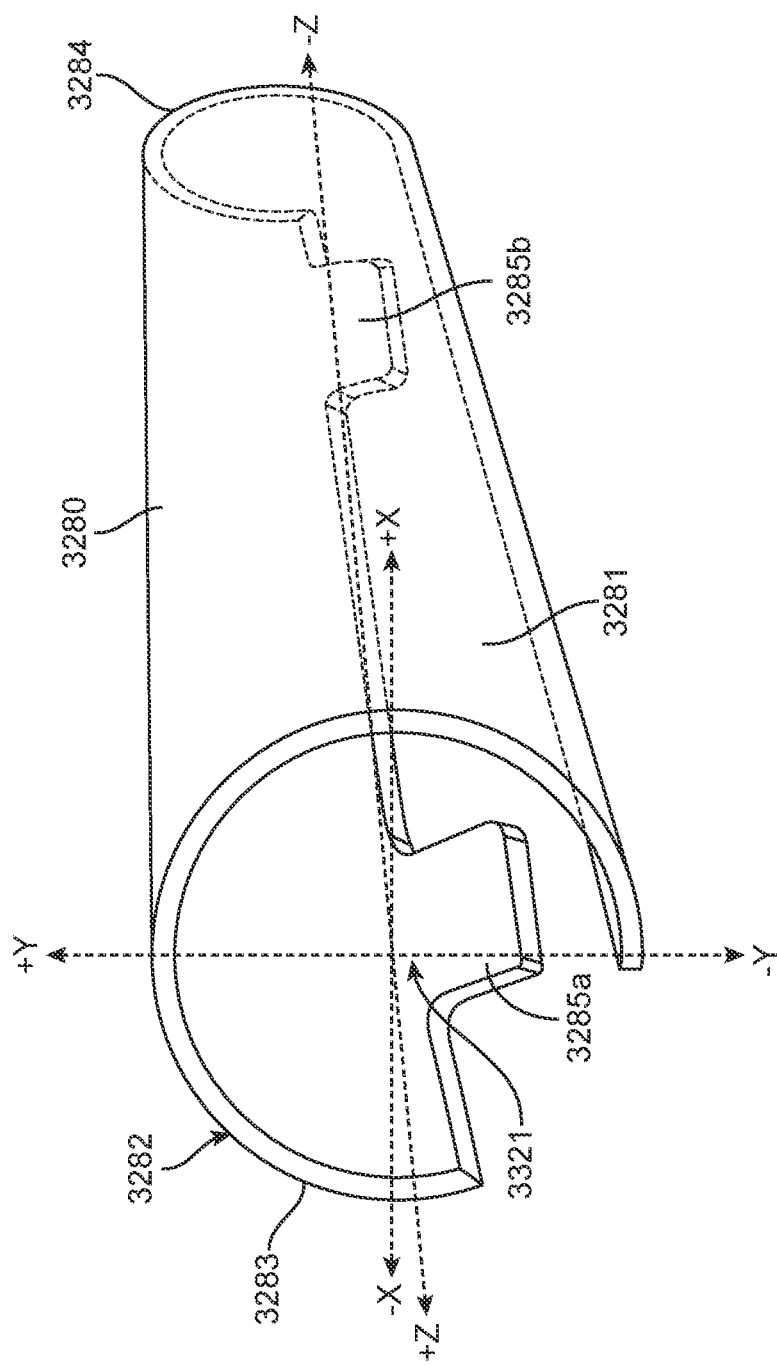

FIG. 328 shows a chiral barrier for placement on the left forearm of the surgeon.

Figure 329:
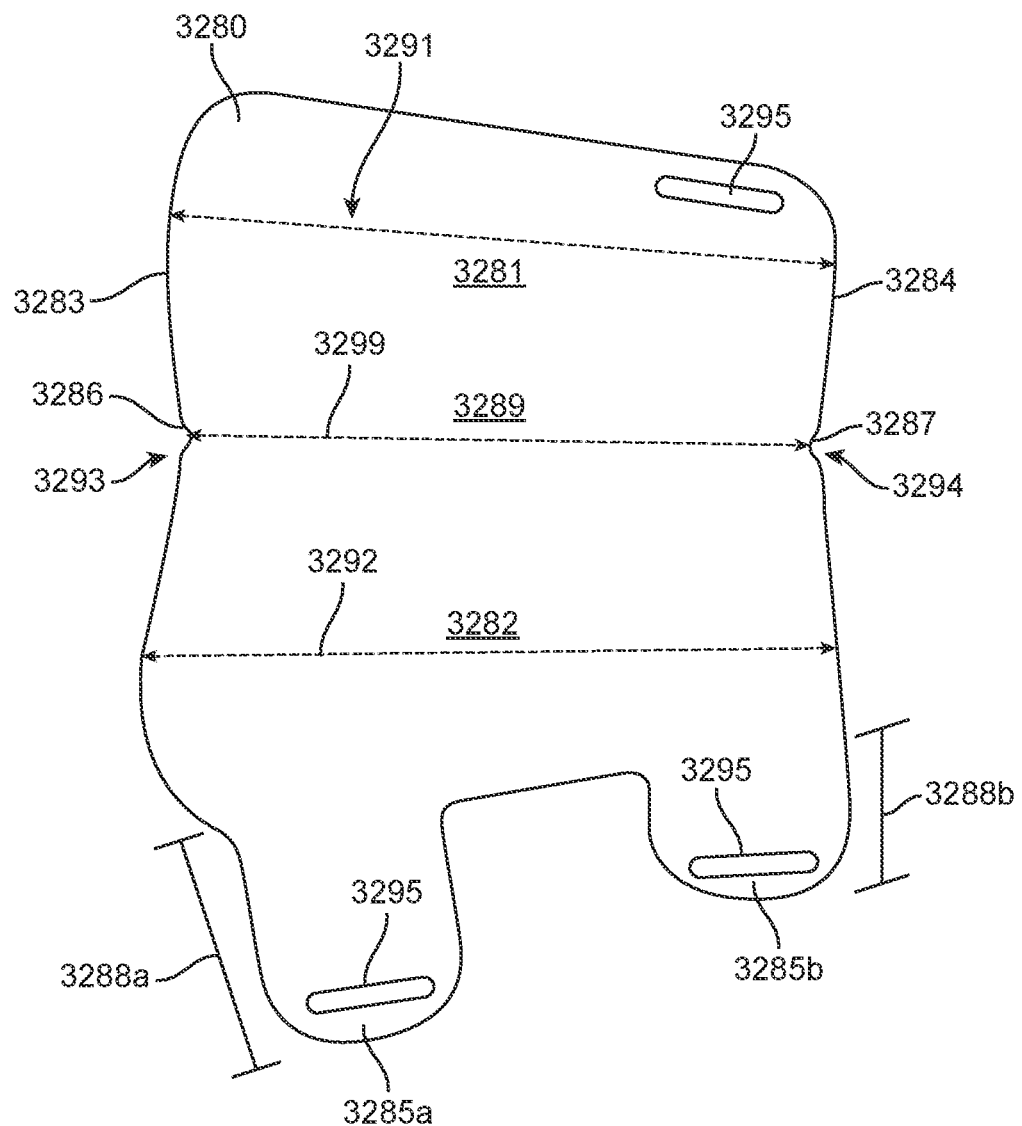

FIG. 329 shows a top plan view of the barrier of FIG. 328 prior to thermal forming.

Figure 330:
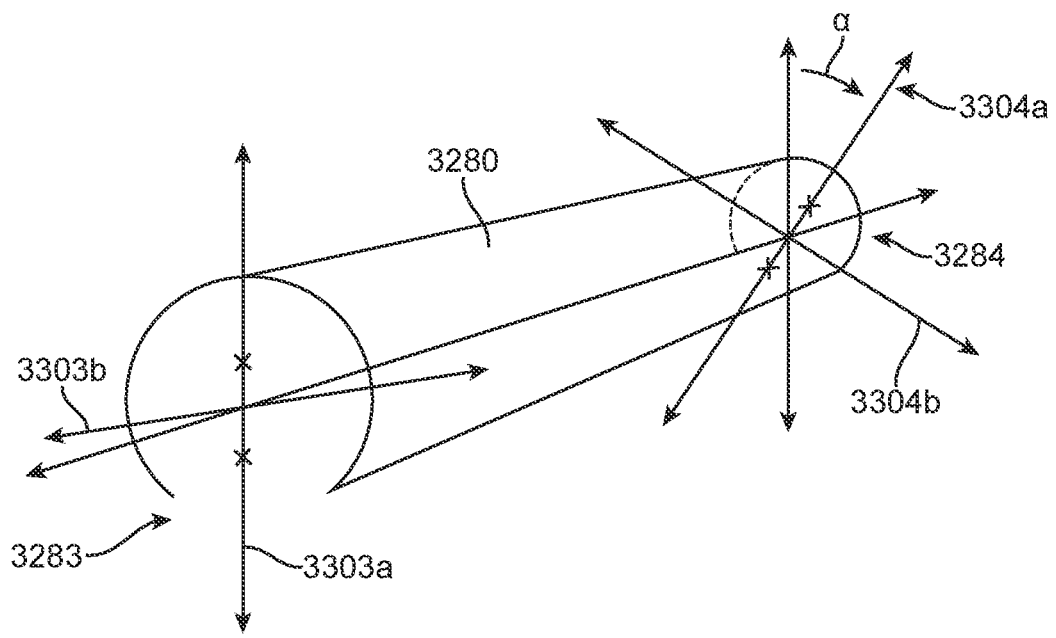

FIG. 330 shows axes of the pre-formed barrier.

Figure 331:
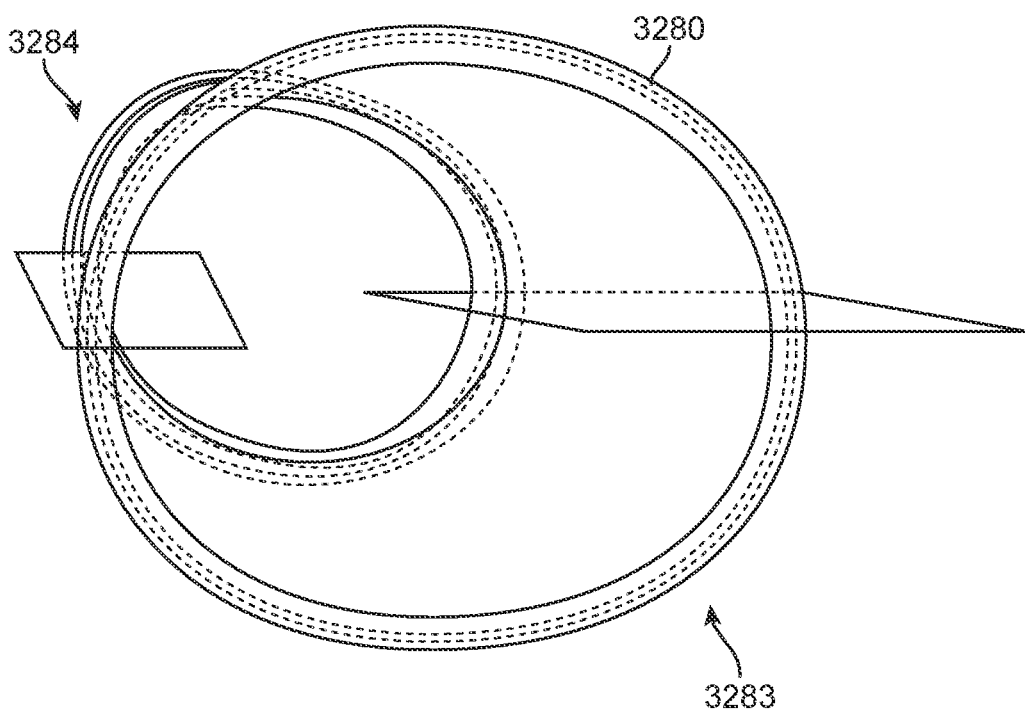

FIG. 331 shows a view from the proximal end of the barrier toward the distal end of the barrier.

Figure 332:
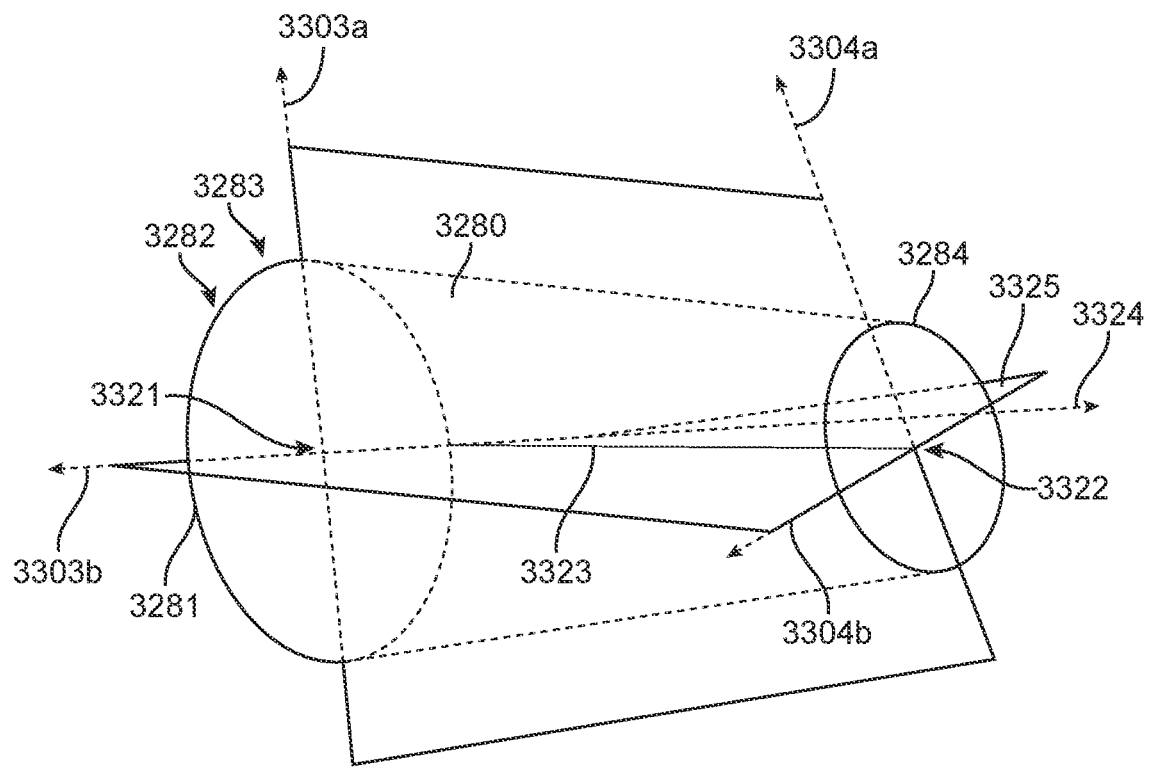

FIG. 332 schematically illustrates structures of chiral barrier.

Figure 333:
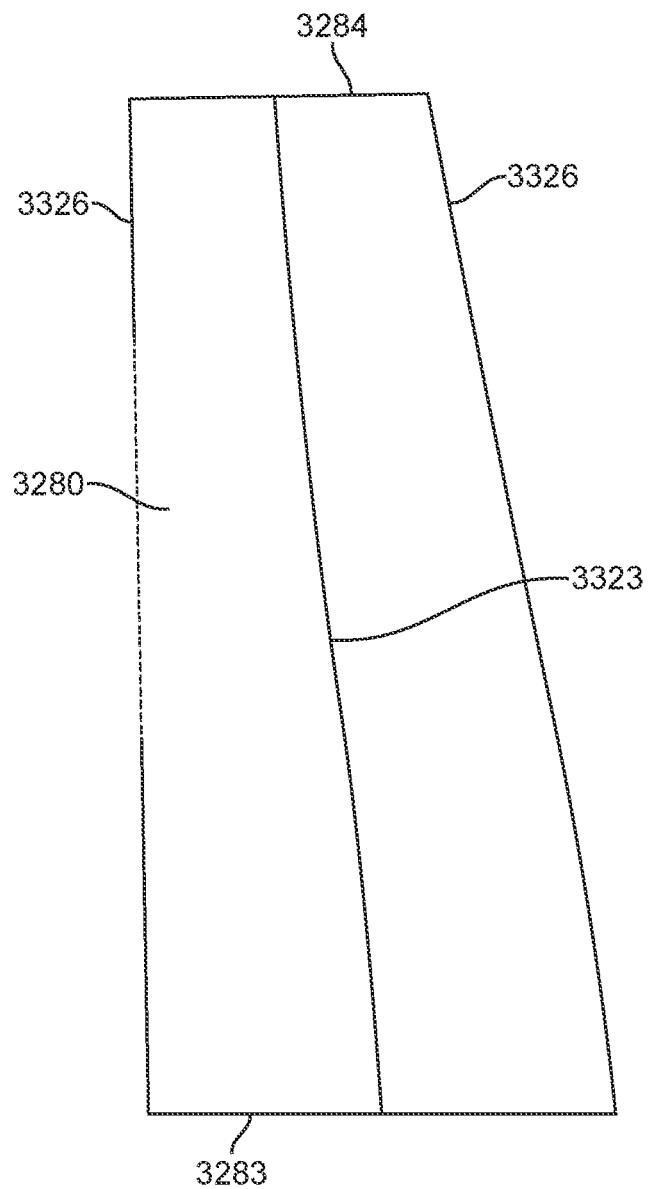

FIG. 333 shows outer surface profiles of the barrier and the curved path of the center of the barrier.

Figure 334:
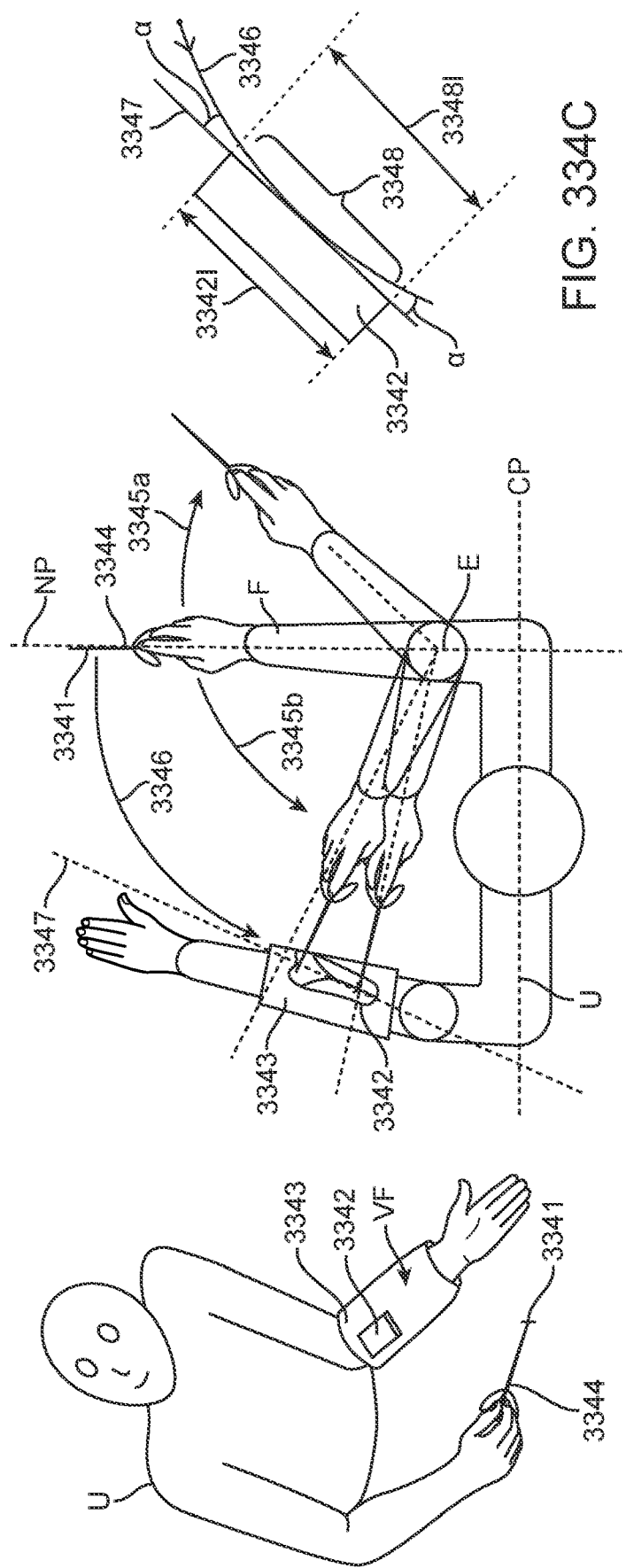

FIGS. 334A-334C illustrate the use of a needle handling system as described herein.

Figure 335:
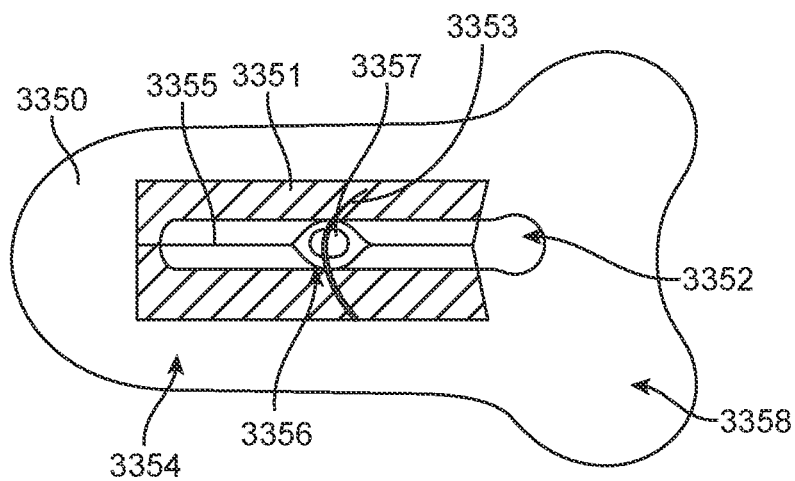

FIG. 335 illustrates an exemplary embodiment of a needle receptacle comprising a cover for the needle driver slot.

Figure 336:
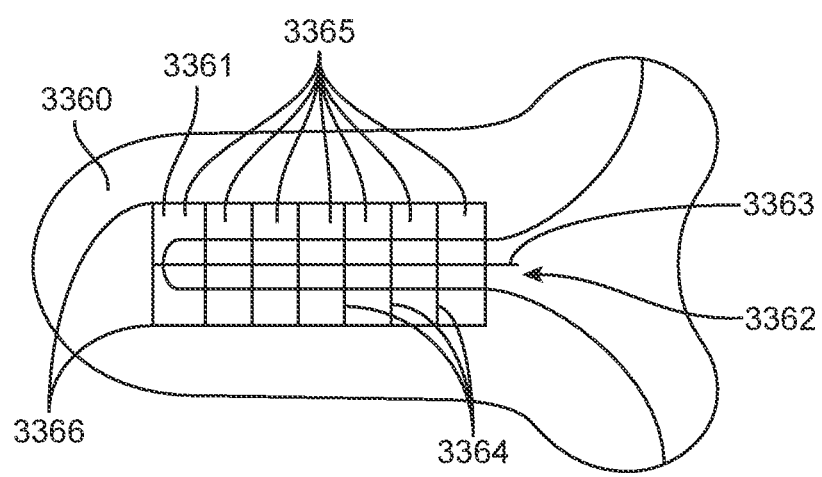

FIG. 336 illustrates another exemplary embodiment of a needle receptacle comprising a cover for the needle driver slot.

FIGS. 337A-337D illustrate another exemplary embodiment of a needle receptacle comprising a cover for the needle driver slot.

Figure 338:
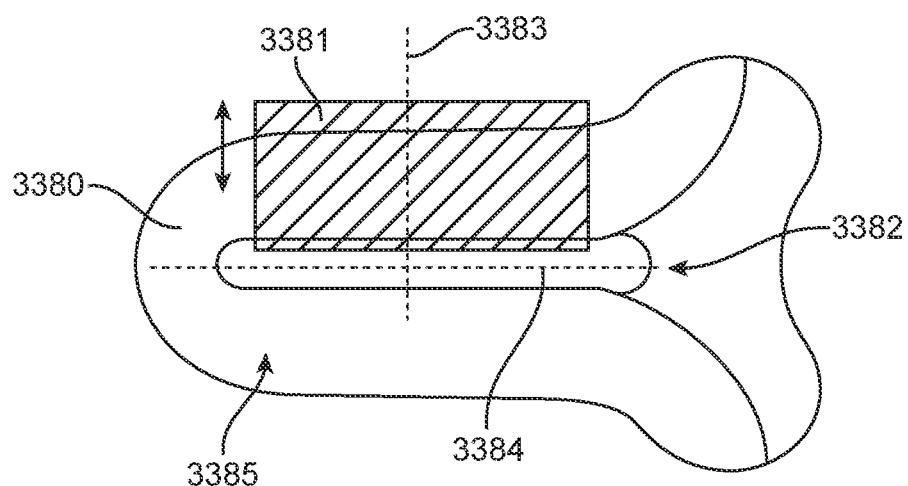

FIG. 338 illustrates an exemplary embodiment of a needle receptacle comprising a compressive cover for the needle driver slot.

Figure 339:
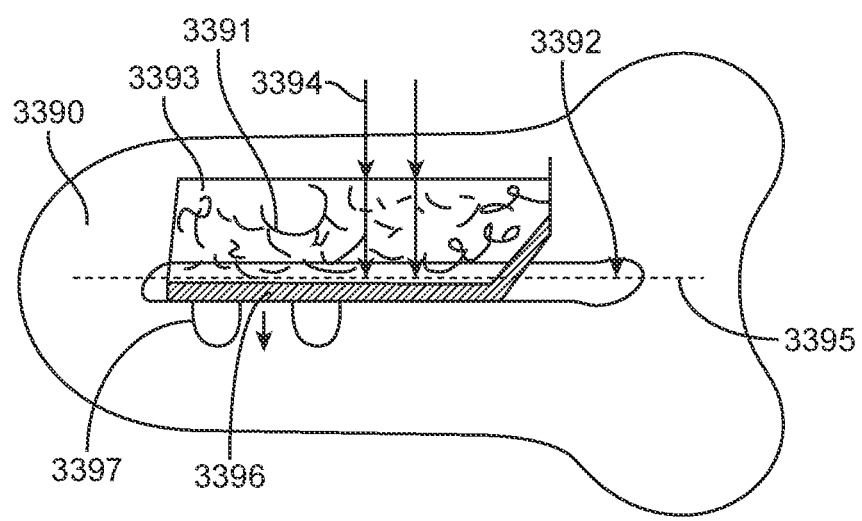

FIG. 339 illustrates another exemplary embodiment of a needle receptacle comprising a compressive cover for the needle driver slot.

Figure 340A:
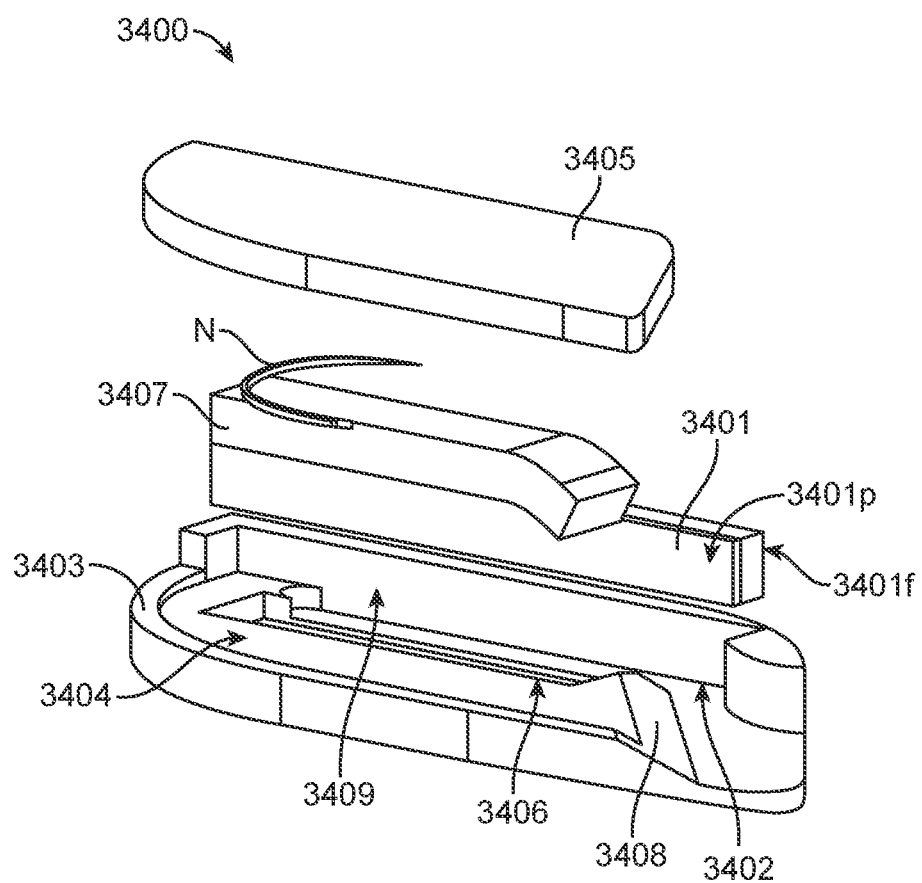
Figure 340B:
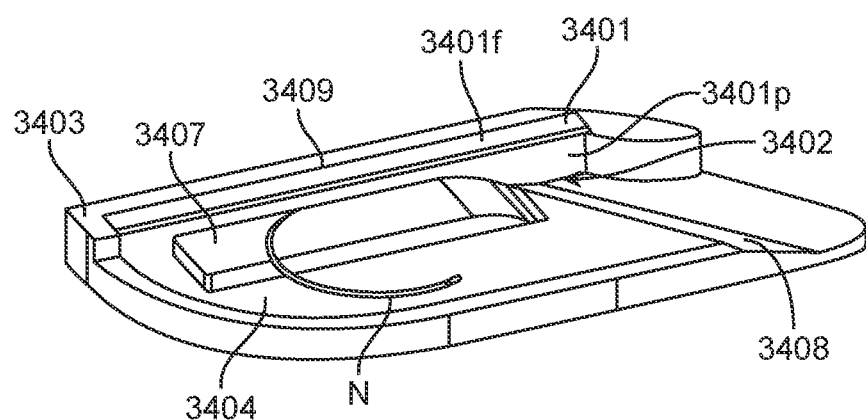
Figure 340C:
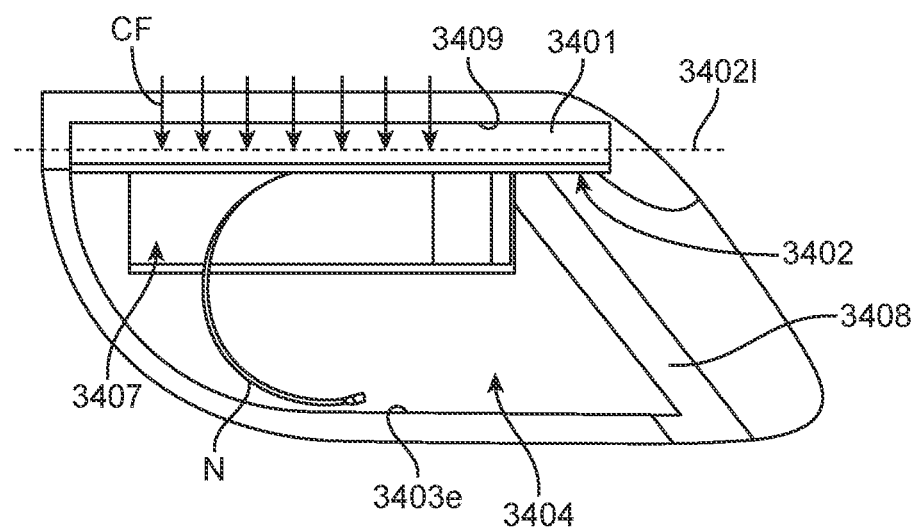

FIGS. 340A-340C illustrate another exemplary embodiment of a needle receptacle comprising a compressive cover for the needle driver slot.

Figure 341A:
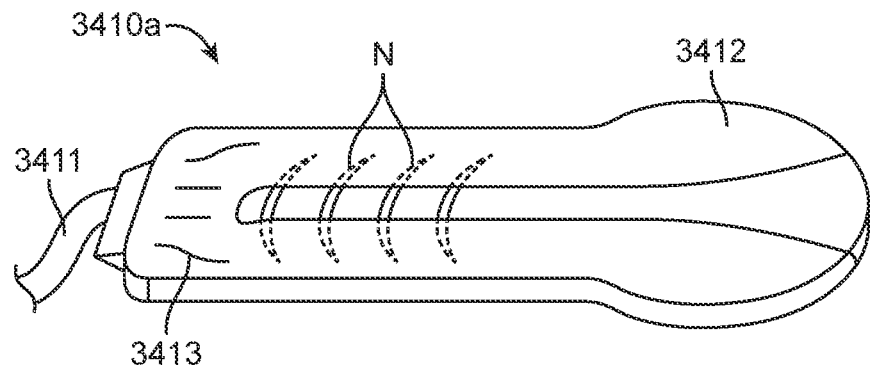
Figure 341B:
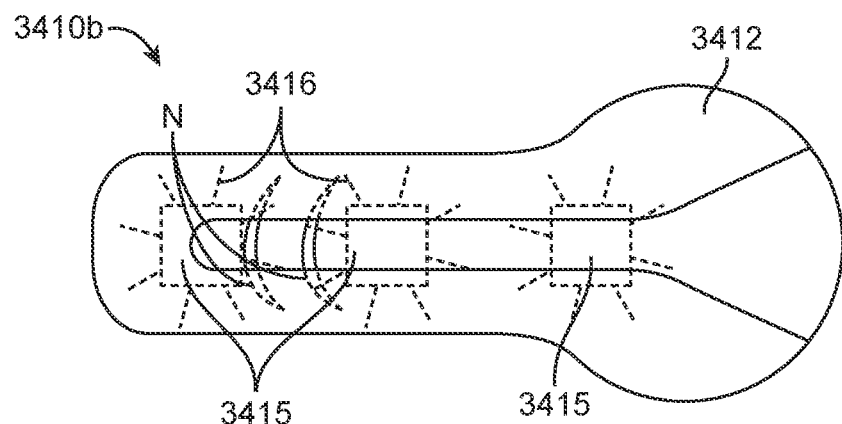
Figure 341C:
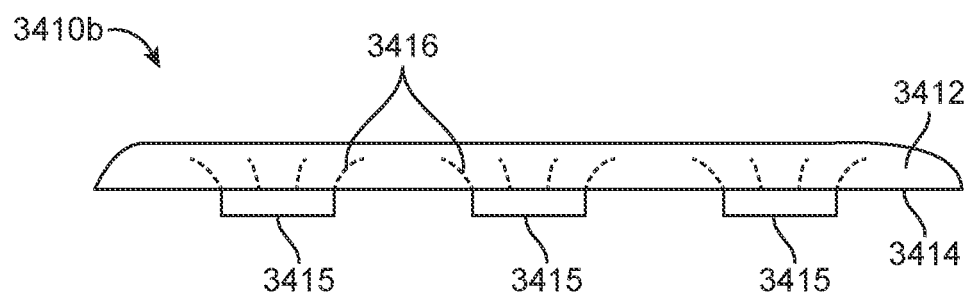

FIGS. 341A-341C illustrate exemplary embodiments of a backlit needle receptacle.

FIGS. 342A-342F schematically illustrate various configurations of a needle driver slot of a needle receptacle.

FIGS. 343A-343G illustrate exemplary embodiments of a swaged needle device for dispensing and securing a swaged needle.

FIGS. 344A-344C illustrate an exemplary embodiment of a tool-mounted needle receptacle.

FIGS. 345A-345D illustrate another exemplary embodiment of a tool-mounted needle receptacle.

FIG. 346 illustrates an exemplary embodiment of a device for securing a plurality of needles, in accordance with many embodiments.

FIGS. 347A-347D illustrate an exemplary embodiment of a device for securing a plurality of needles, in accordance with many embodiments.

Figure 348A:
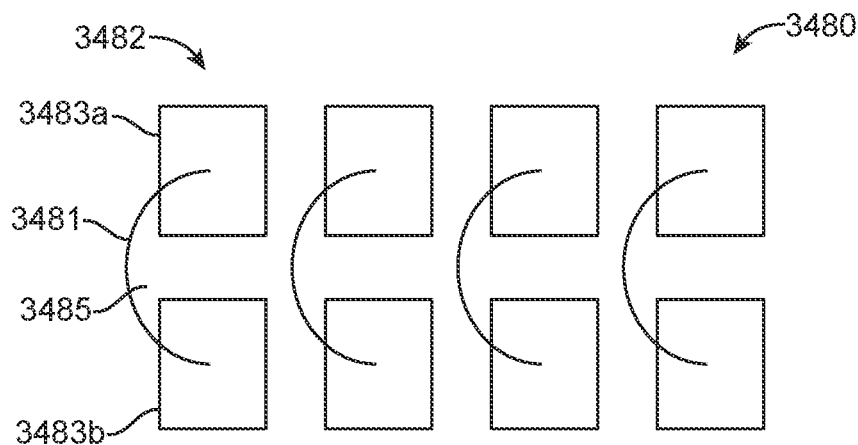
Figure 348B:
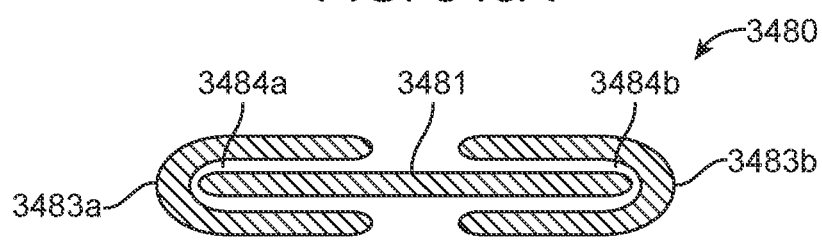

FIGS. 348A-348B illustrate an exemplary embodiment of a device for securing a plurality of needles, in accordance with many embodiments.

Figure 349A:
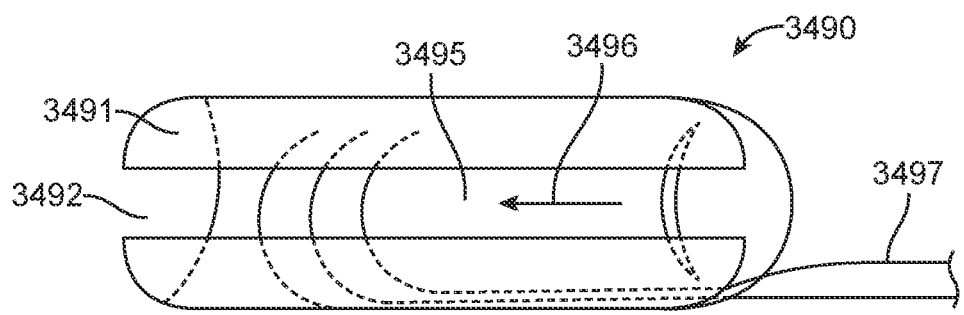
Figure 349B:
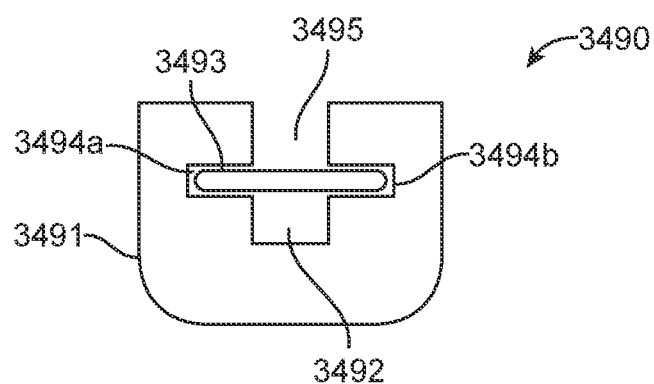

FIGS. 349A-349B illustrate an exemplary embodiment of a device for securing a plurality of needles, in accordance with many embodiments.

Figure 350A:
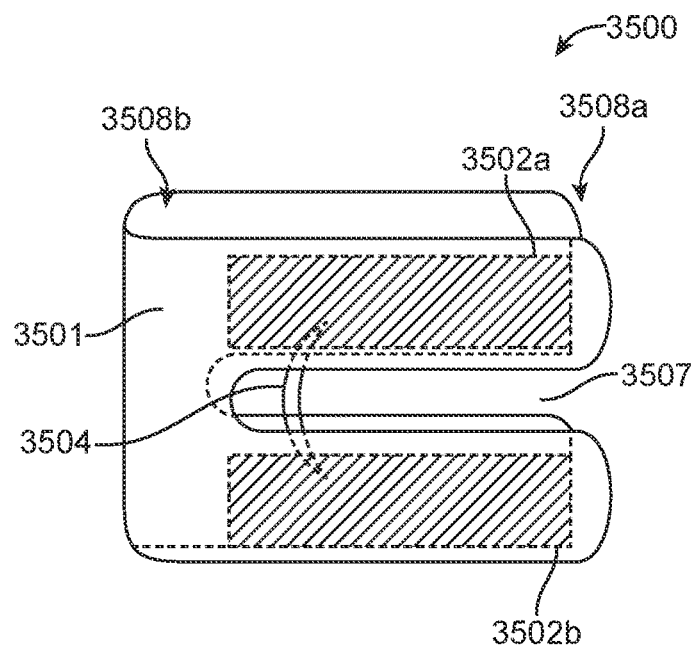
Figure 350B:
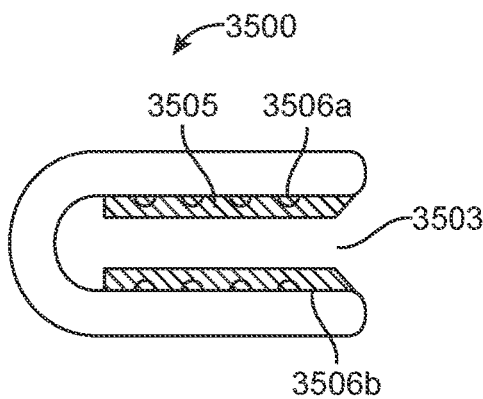

FIGS. 350A-350B illustrate an exemplary embodiment of a device for securing a plurality of needles, in accordance with many embodiments.

Figure 351A:
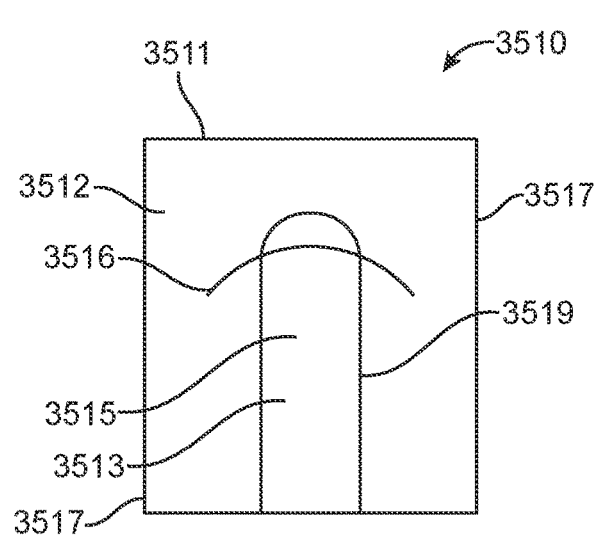
Figure 351B:
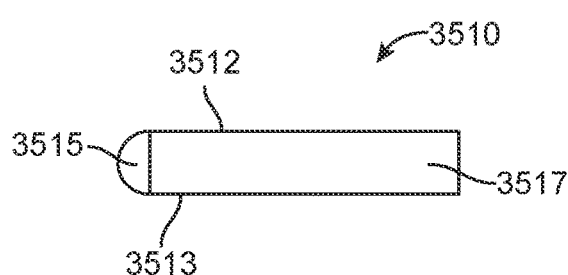
Figure 351C:
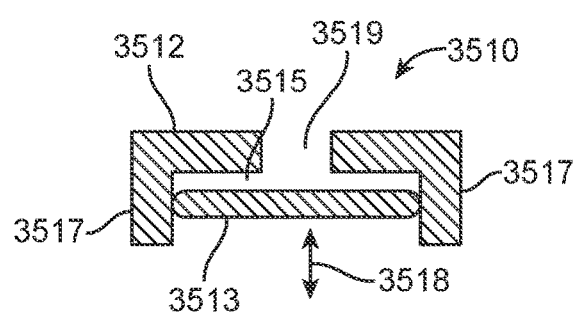

FIGS. 351A-351C illustrate an exemplary embodiment of a device for securing a plurality of needles, in accordance with many embodiments.

Figure 352A:
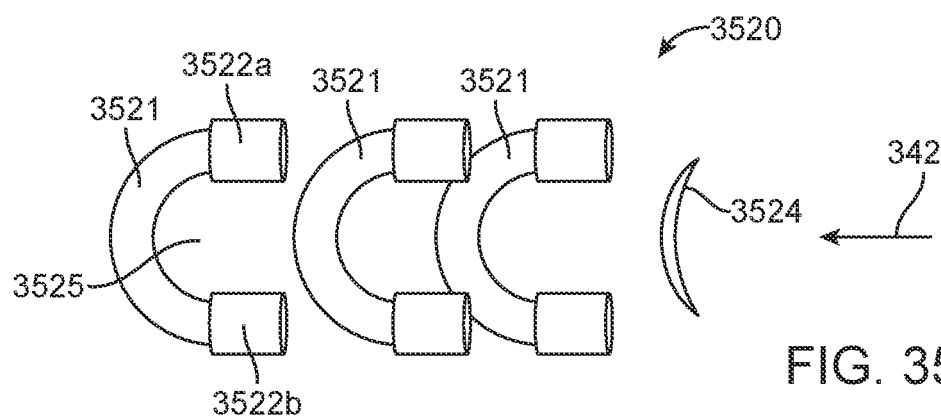
Figure 352B:
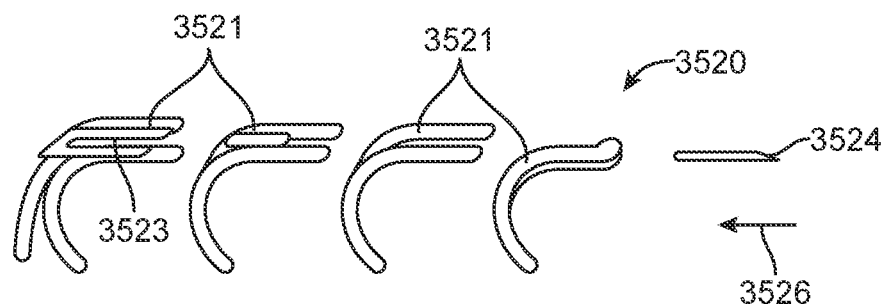
Figure 352C:
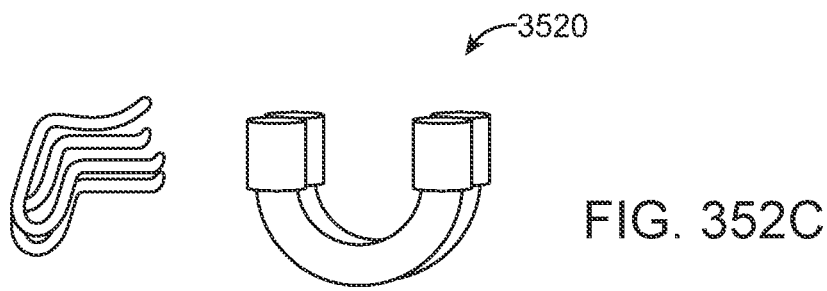

FIGS. 352A-352C illustrate an exemplary embodiment of a device for securing a plurality of needles, in accordance with many embodiments.

Figure 353:
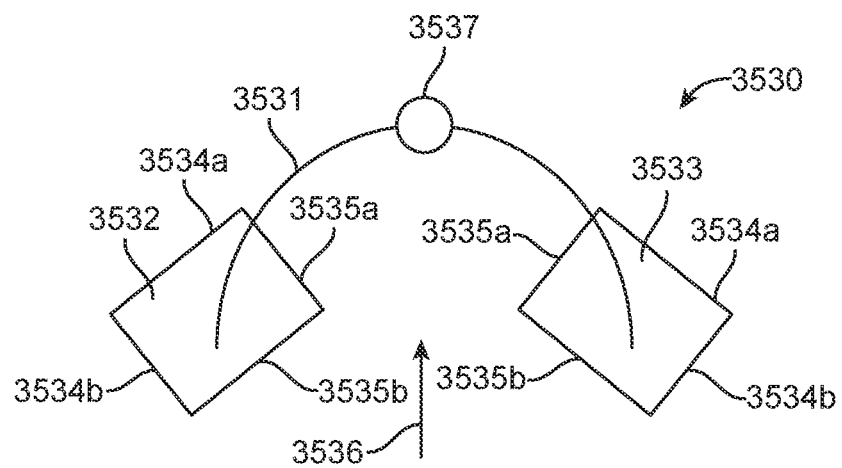

FIG. 353 illustrates an exemplary embodiment of a clip assembly for securing a needle, in accordance with many embodiments.

FIGS. 354A-354G illustrate an exemplary embodiment of a device for securing a plurality of needles, in accordance with many embodiments.

Figure 355A:
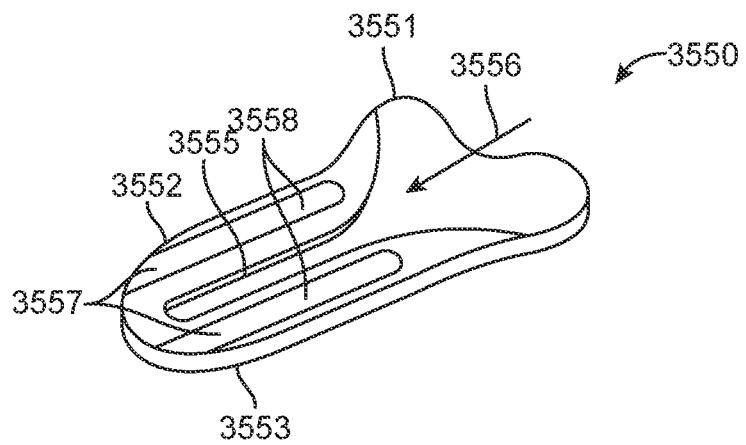
Figure 355B:
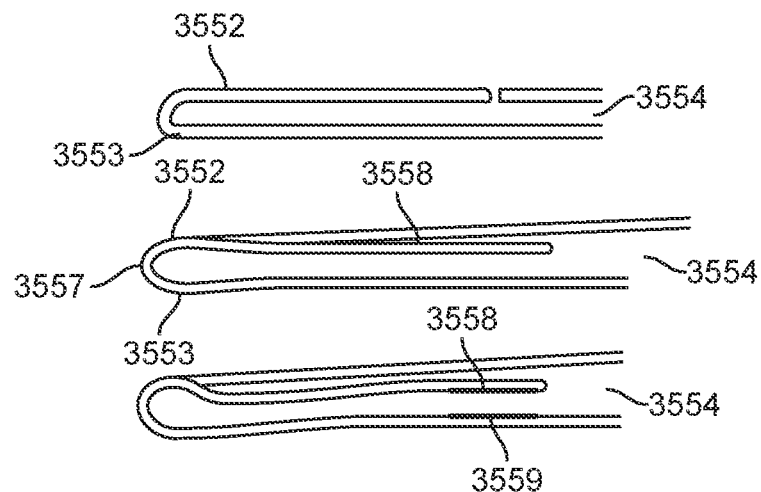

FIGS. 355A-355B illustrate an exemplary embodiment of a device for securing a plurality of needles, in accordance with many embodiments.

Figure 356:
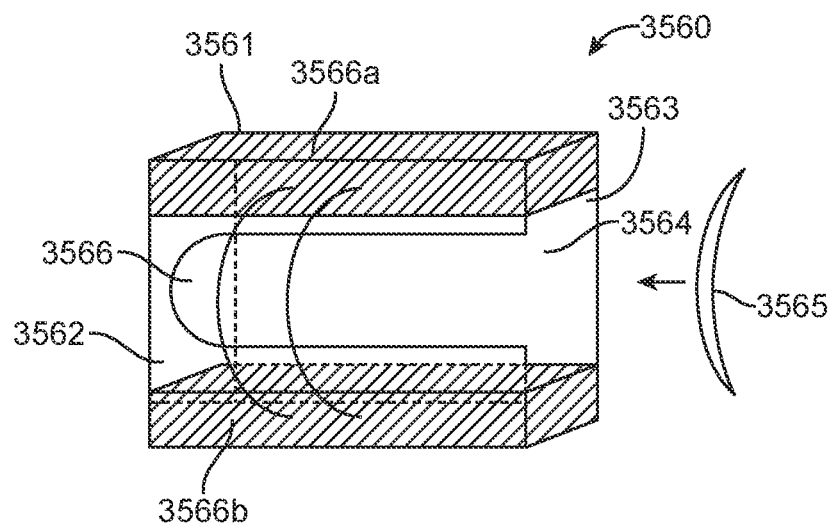

FIG. 356 illustrates an exemplary embodiment of a device for securing a plurality of needles, in accordance with many embodiments.

Figure 357A:
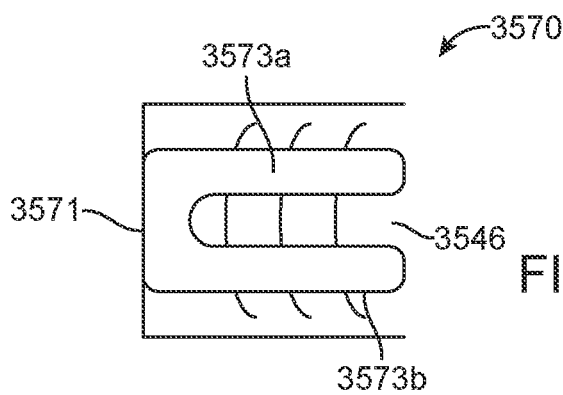
Figure 357B:
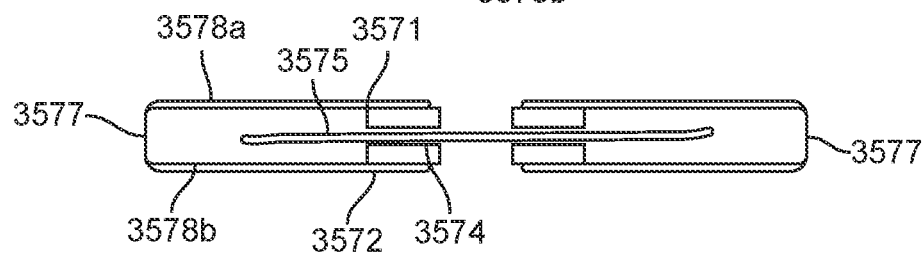
Figure 357C:
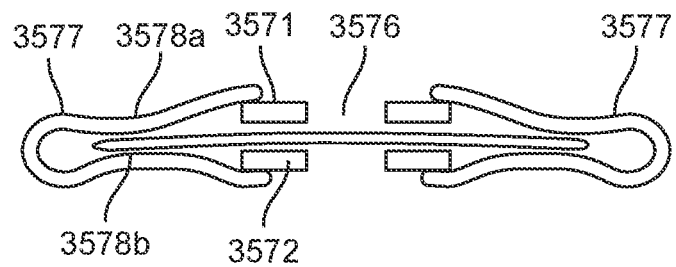

FIGS. 357A-357C illustrate an exemplary embodiment of a device for securing a plurality of needles, in accordance with many embodiments.

Figure 358:
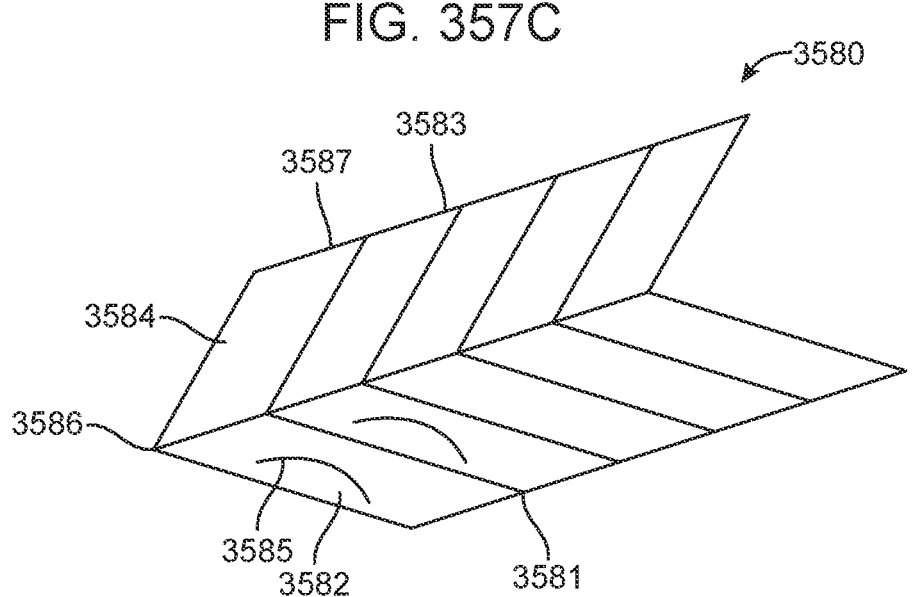

FIG. 358 illustrates an exemplary embodiment of a device for securing a plurality of needles, in accordance with many embodiments.

Figure 359:
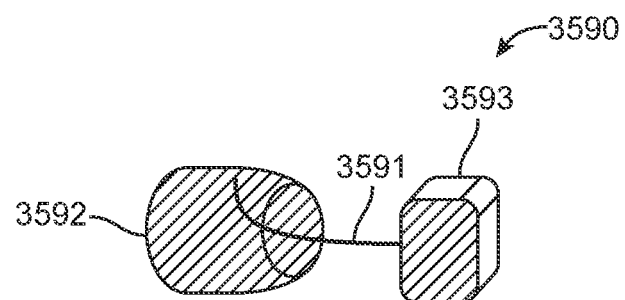

FIG. 359 illustrates an exemplary embodiment of a device for securing a needle, in accordance with many embodiments.

Figure 360A:
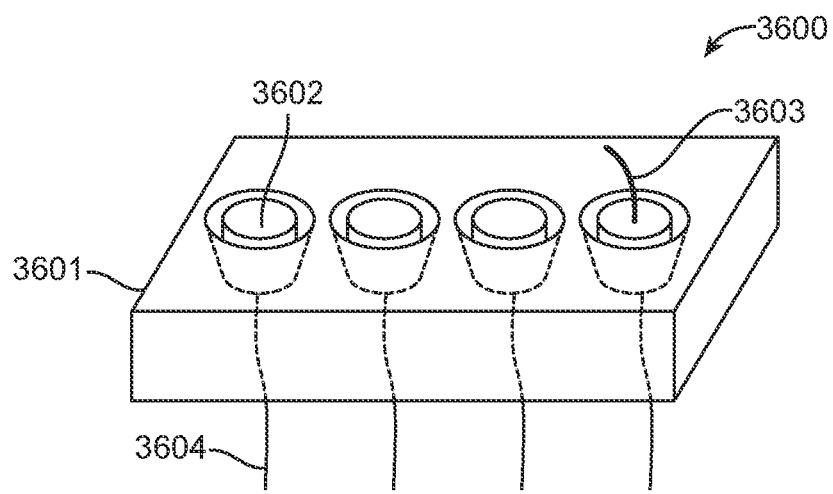
Figure 360B:
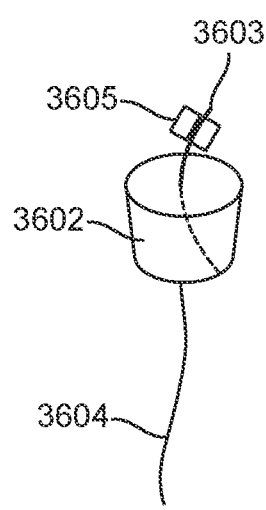
Figure 360C:
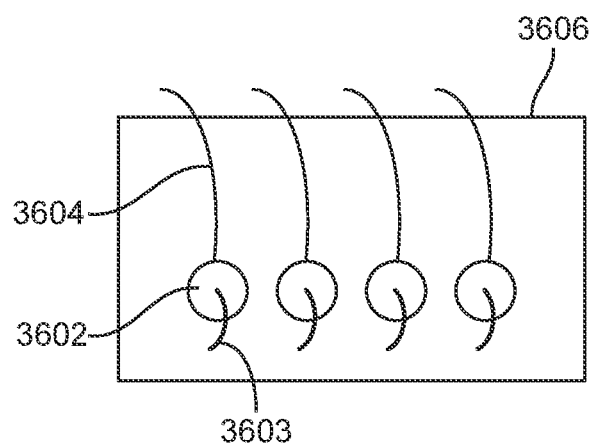

FIGS. 360A-360C illustrate an exemplary embodiment of a device for securing a plurality of needles, in accordance with many embodiments.

Figure 361A:
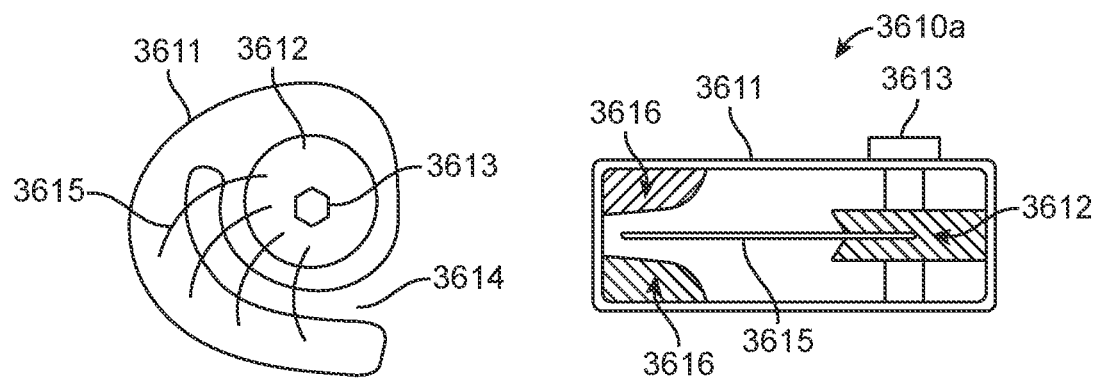

FIG. 361A illustrates an exemplary embodiment of a device for securing a plurality of needles, in accordance with many embodiments.

Figure 361B:
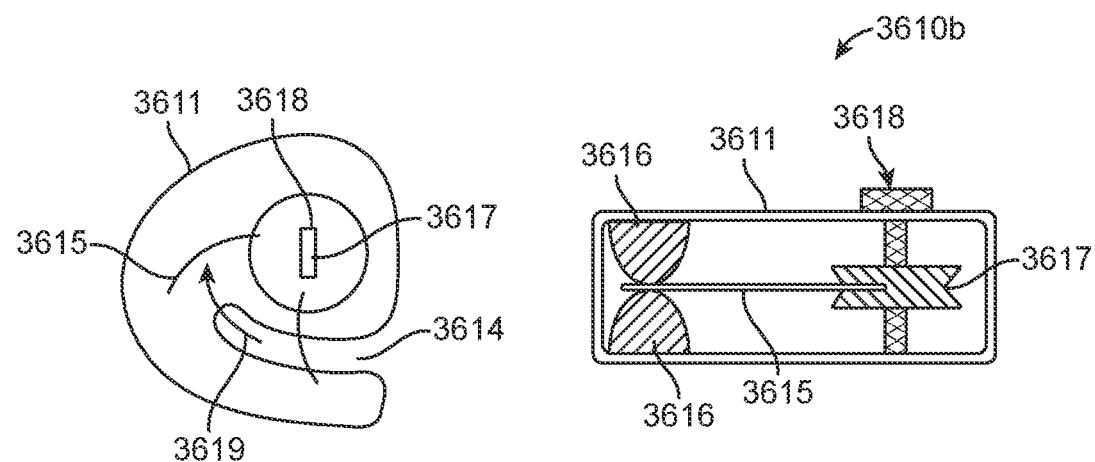

FIG. 361B illustrates an exemplary embodiment of a device for securing a plurality of needles, in accordance with many embodiments.

FIGS. 362A-362D illustrate an embodiment of a needle receptacle with a rotatable cover.

Figure 363:
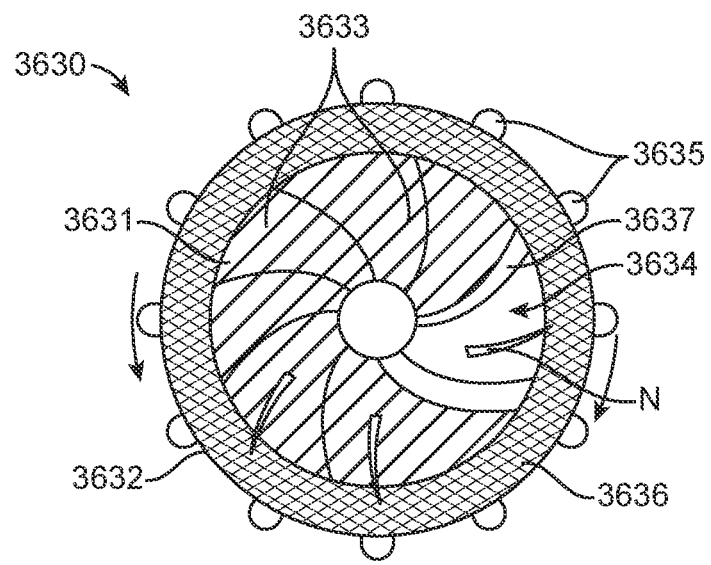

FIG. 363 illustrates another embodiment of a needle receptacle with a rotatable cover.

Figure 364:
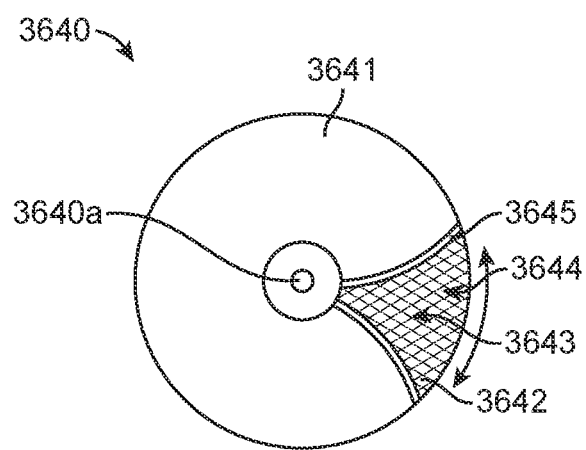
Figure 365A:
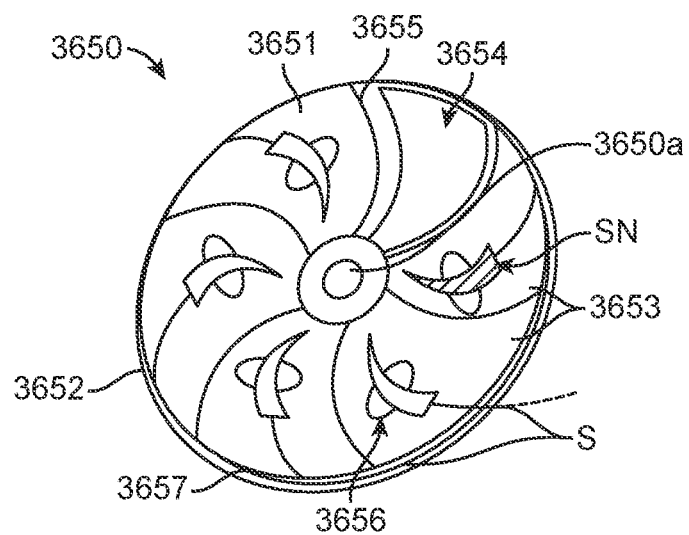
Figure 365B:
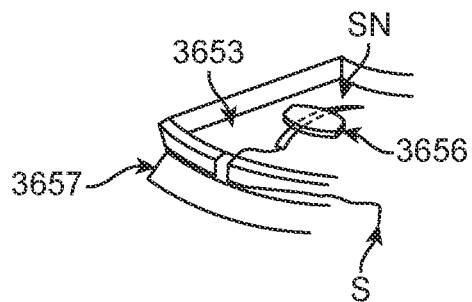
Figure 365C:
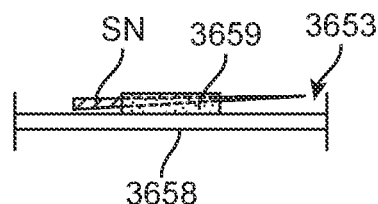
Figure 365D:
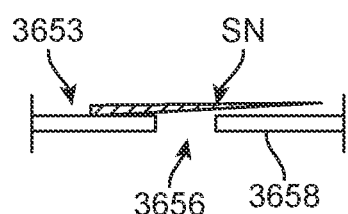

FIG. 364 illustrates another embodiment of a needle receptacle with a rotatable cover.

FIGS. 365A-365D illustrate an exemplary embodiment of a swaged needle device for dispensing and securing a swaged needle, comprising a rotatable cover.

Figure 366A:
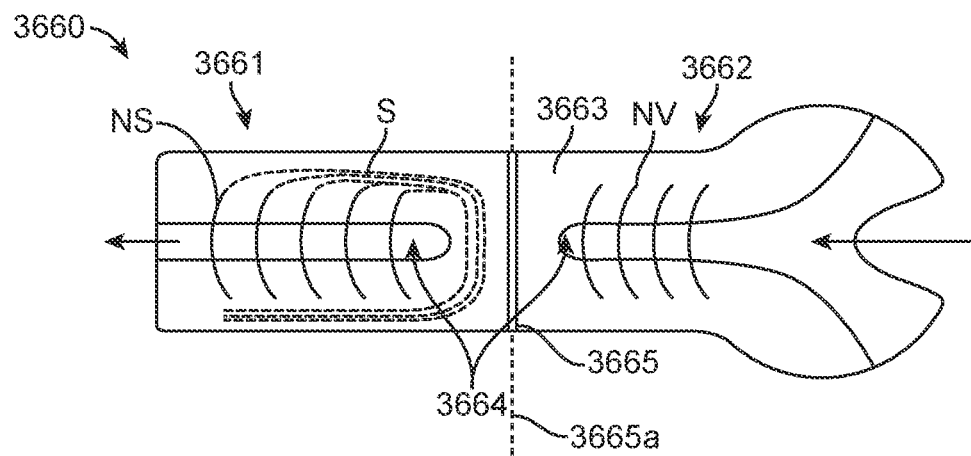
Figure 366B:
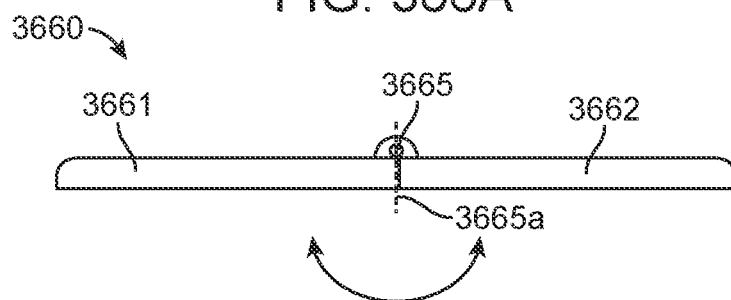
Figure 366C:
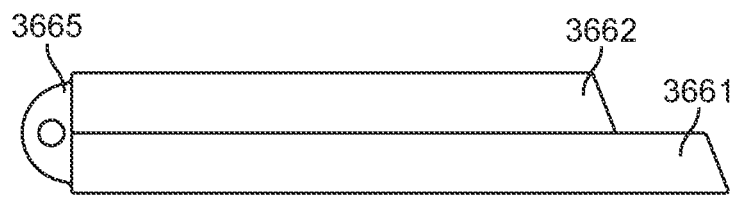

FIGS. 366A-366C illustrate an exemplary embodiment of an integrated suture needle dispensing and securing apparatus.

Figure 367:
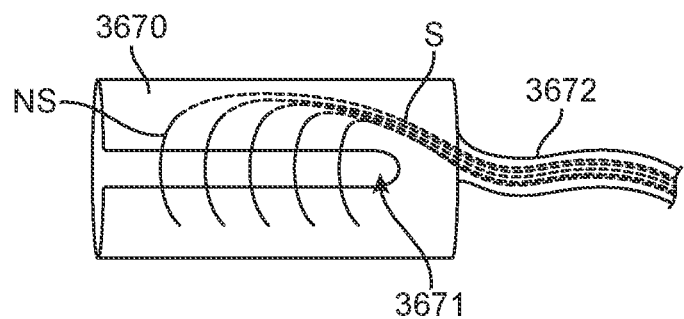

FIG. 367 illustrates an exemplary embodiment of a suture needle dispensing device.

Figure 368A:
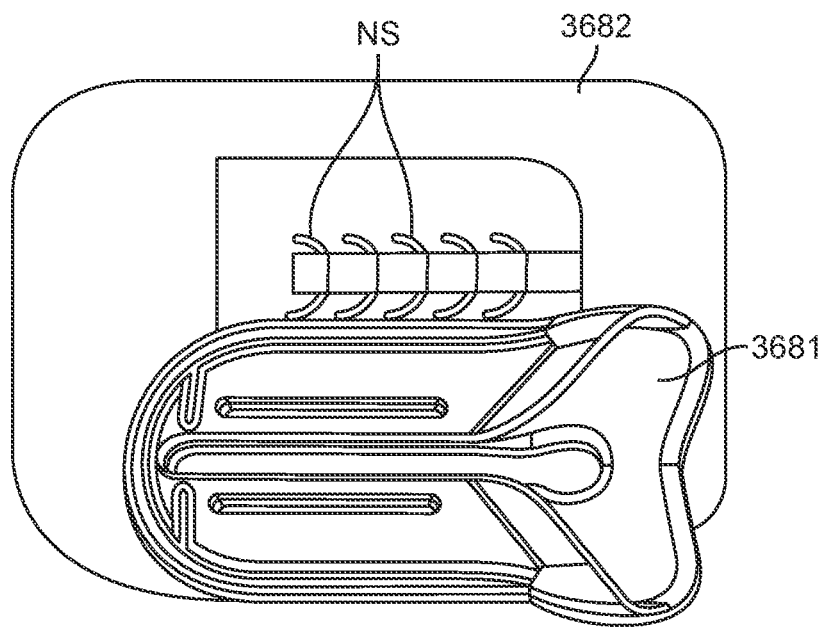
Figure 368B:
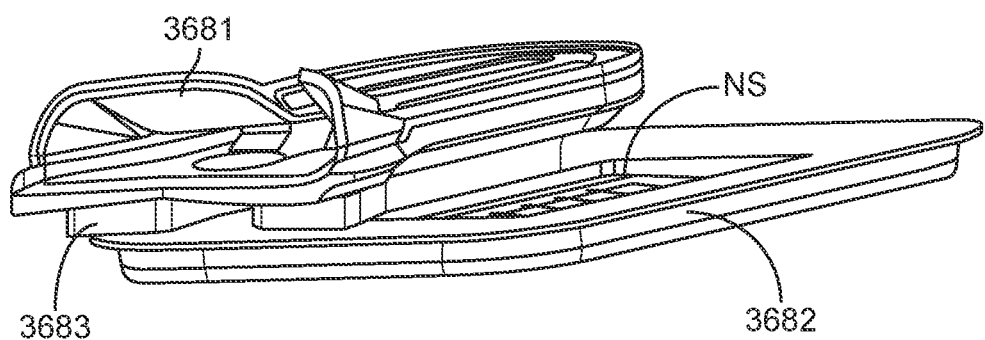

FIGS. 368A-368B illustrate an exemplary configuration for coupling a needle receptacle to a suture package.

FIGS. 369A-369C illustrate another exemplary configuration for coupling a needle receptacle to a needle dispensing unit.

Figures 370A, 370B:
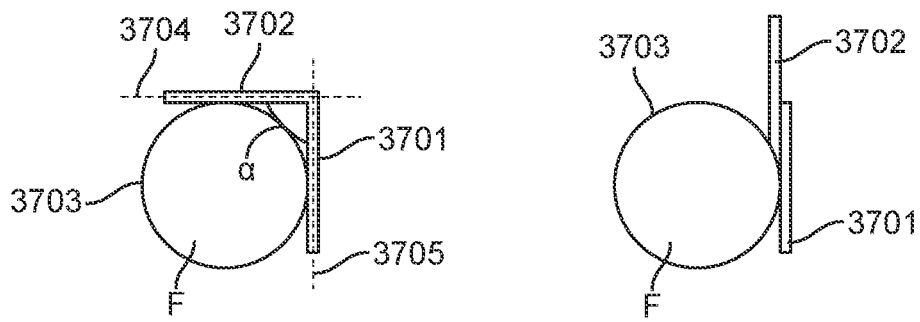

FIG. 370A schematically illustrates an exemplary configuration of a needle dispensing unit and a needle receptacle mounted on a barrier.

FIG. 370B schematically illustrates another exemplary configuration of a needle dispensing unit and a needle receptacle mounted on a barrier.

Figure 371A:
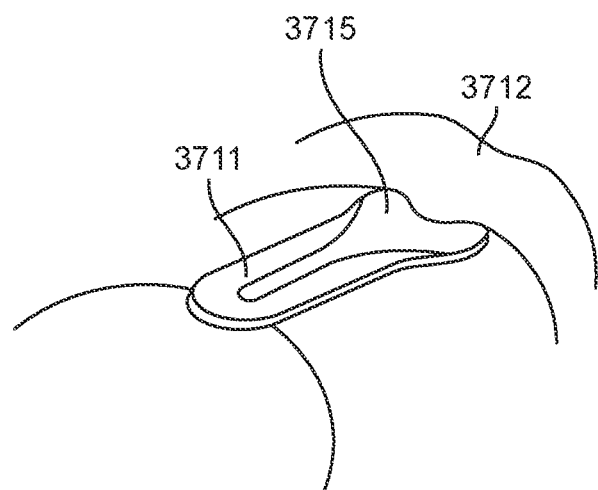
Figure 371B:
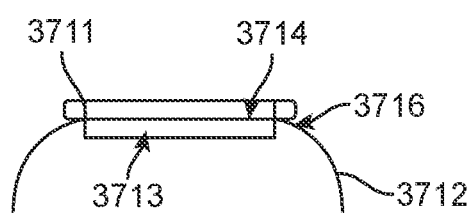

FIGS. 371A-371B illustrate an exemplary configuration of a needle receptacle mounted on a barrier.

Figure 372A:
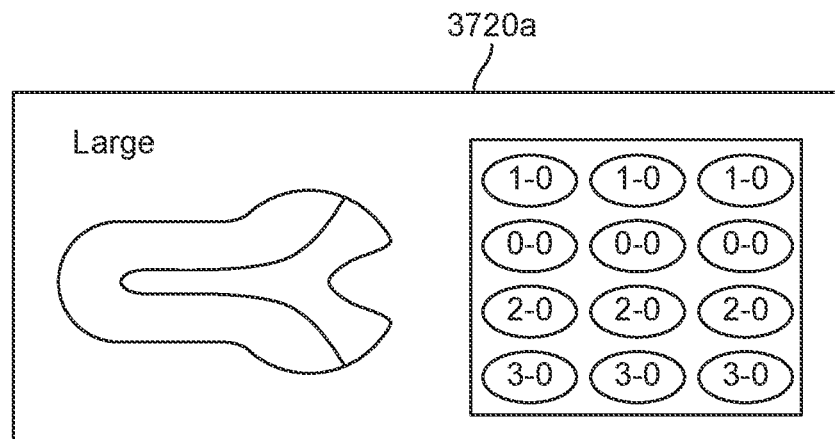
Figure 372B:
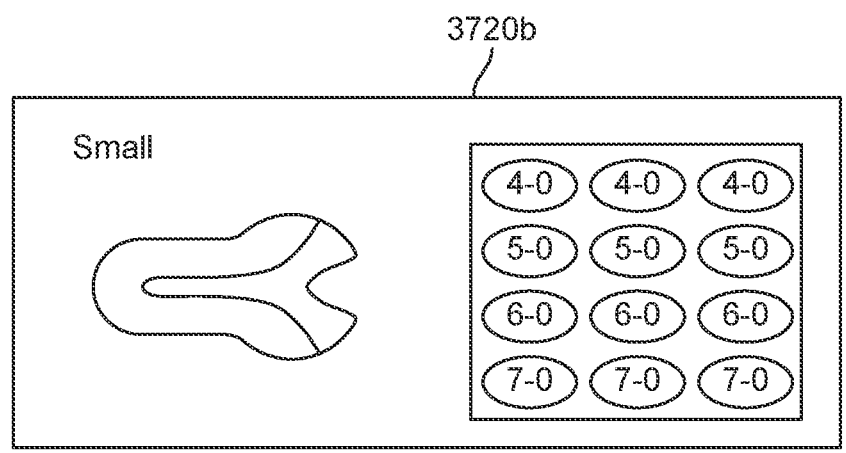

FIGS. 372A-372B illustrate exemplary labels that may be provided for commercially available suture packages to be used with a needle handing system described herein.

Figure 373A:
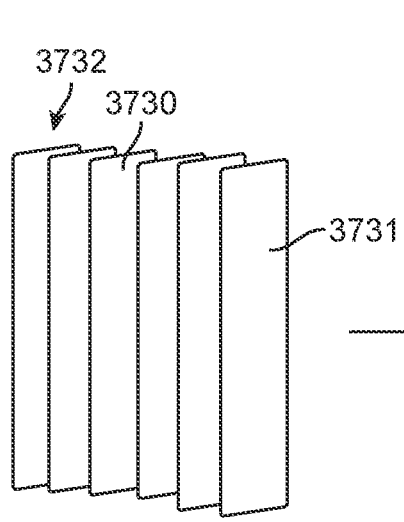
Figure 373B:
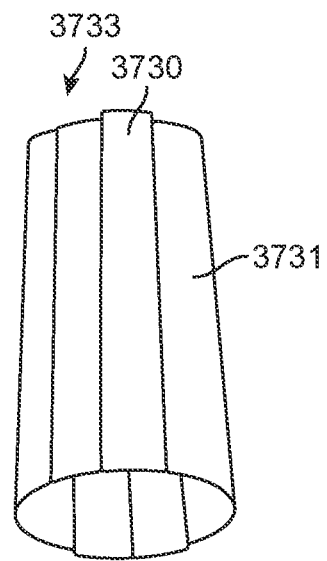

FIGS. 373A-373B illustrate an exemplary embodiment of a forearm barrier comprising sliding longitudinal panels.

Figure 374A:
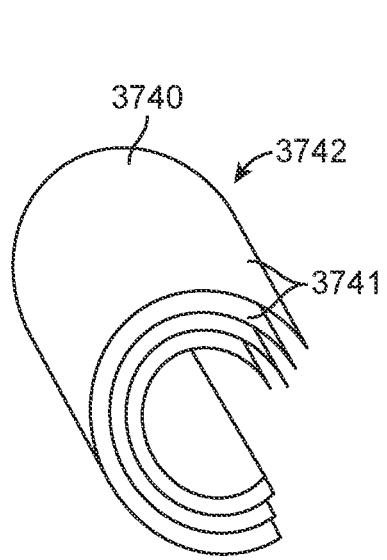
Figure 374B:
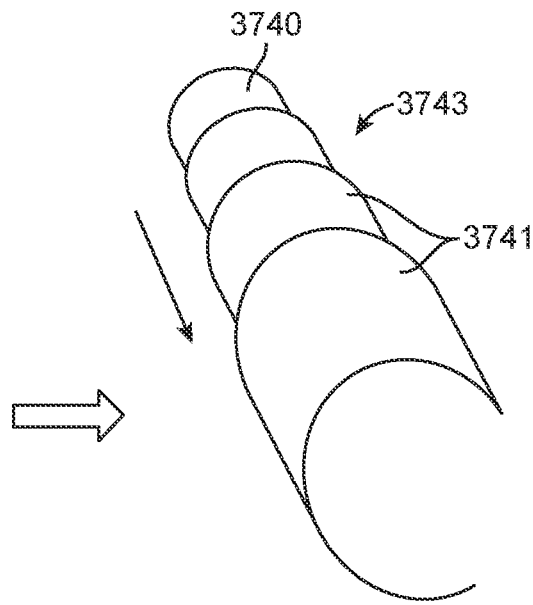

FIGS. 374A-374B illustrate an exemplary embodiment of a forearm barrier comprising sliding c-shaped sections or "bracelets".

Figure 375:
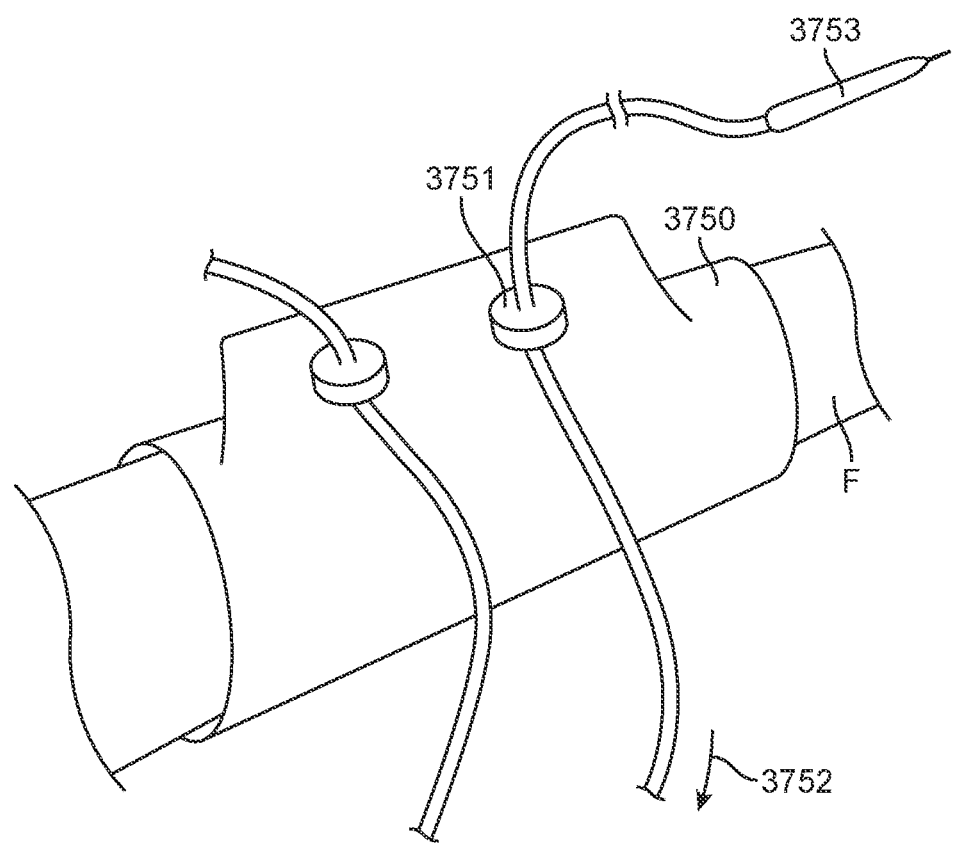

FIG. 375 illustrates a barrier comprising one or more plug-ins for electrically powered surgical tools.

FIGS. 376A-376D illustrate a barrier comprising one or more tool loops for supporting one or more surgical tools.

Figure 377A:
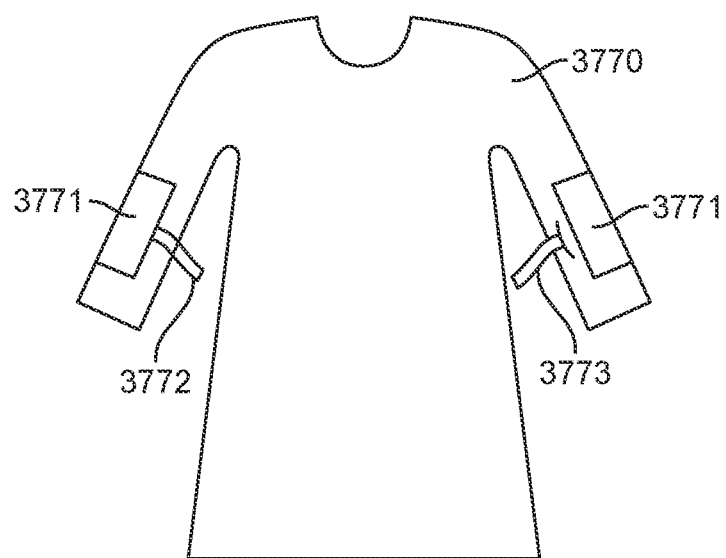
Figure 377B:
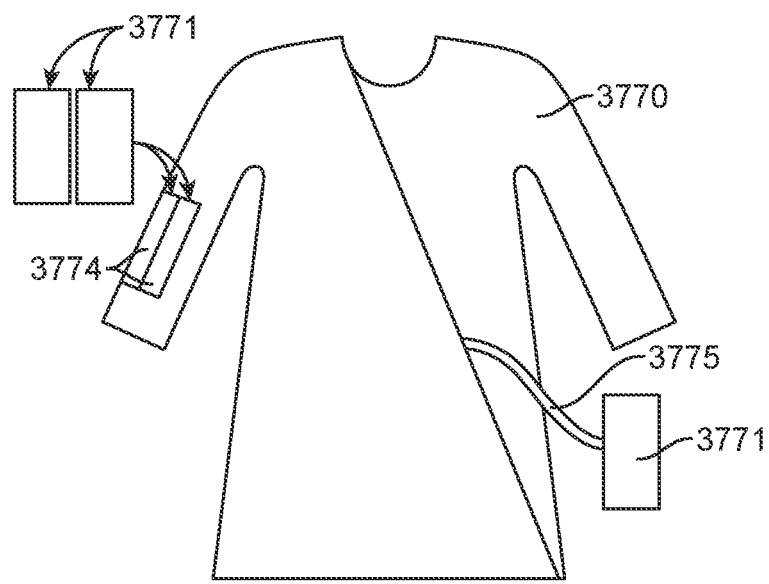

FIGS. 377A-377B illustrate exemplary embodiments of surgical gowns comprising integrated forearm barriers.

Figure 378A:
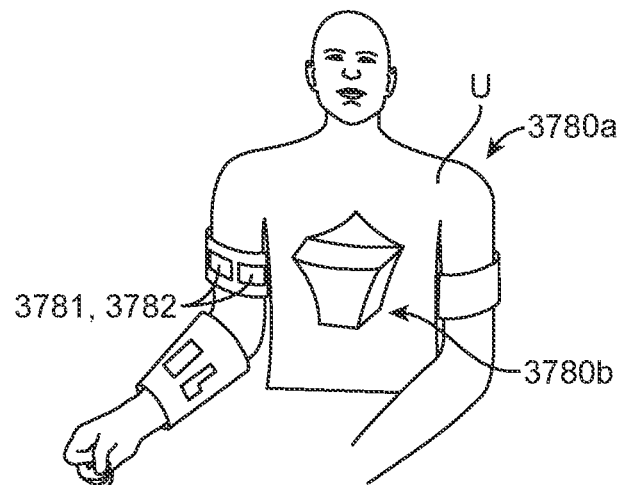
Figure 378B:
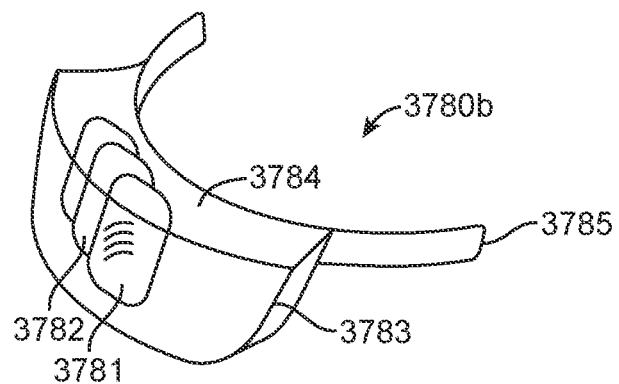

FIGS. 378A-378B illustrate exemplary staging devices suitable for incorporation with the needle handling systems as described herein.

Figure 379A:
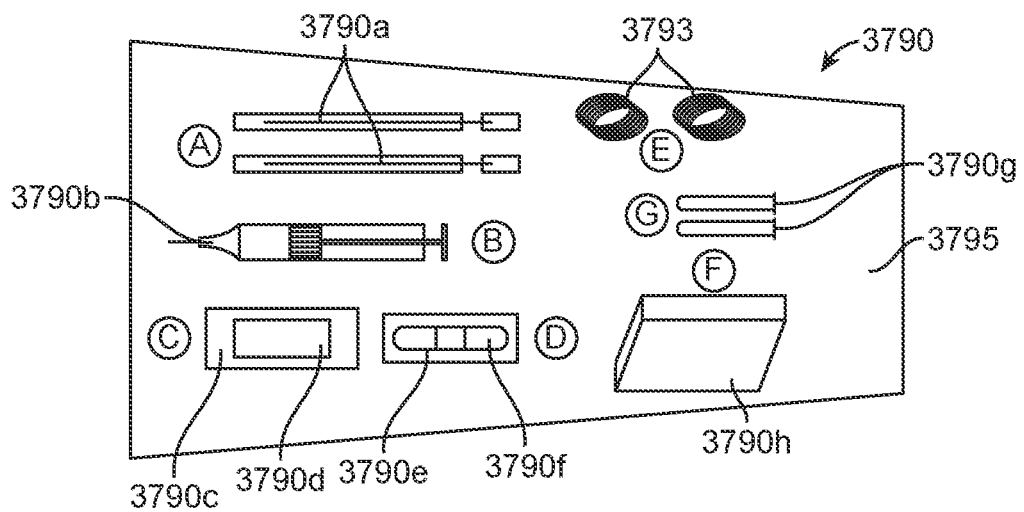
Figure 379B:
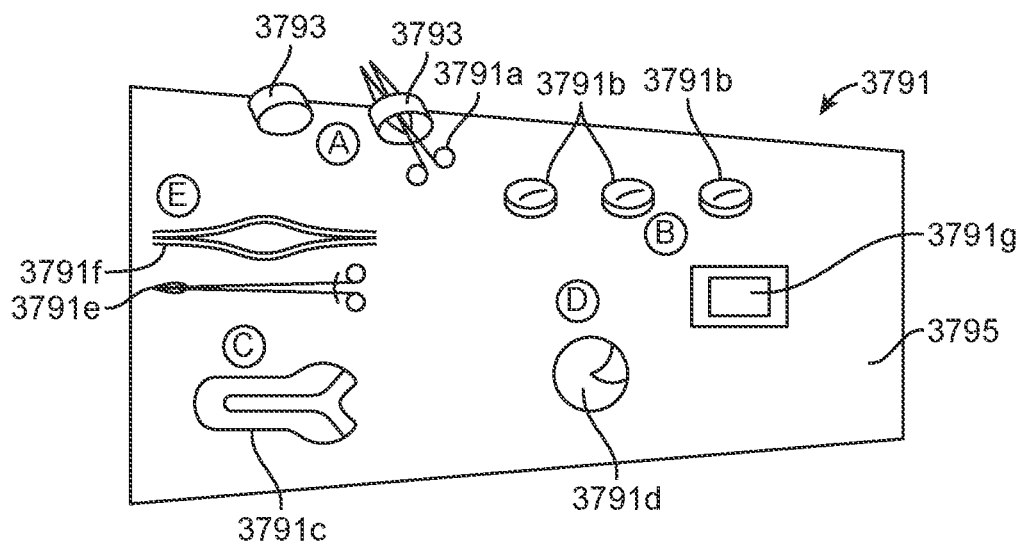
Figure 379C:
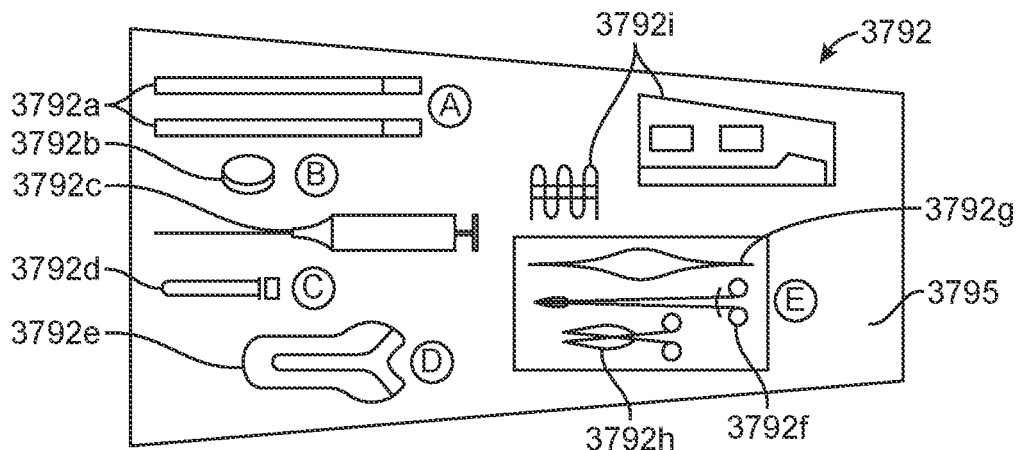

FIGS. 379A-379C illustrate exemplary kits for suture handling systems.

Figure 380A:
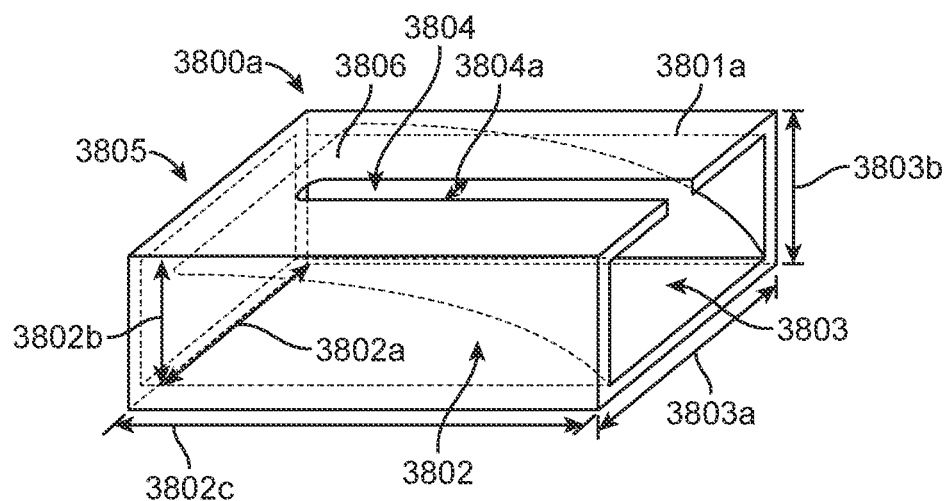
Figure 380B:
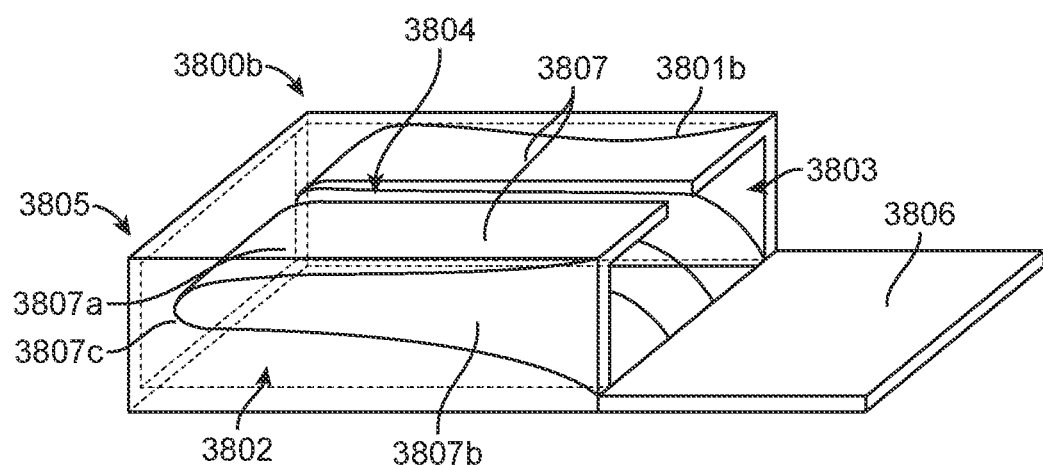

FIGS. 380A-380B illustrate exemplary needle receptacles suitable for incorporation with the needle handling systems as described herein.

Figure 381A:
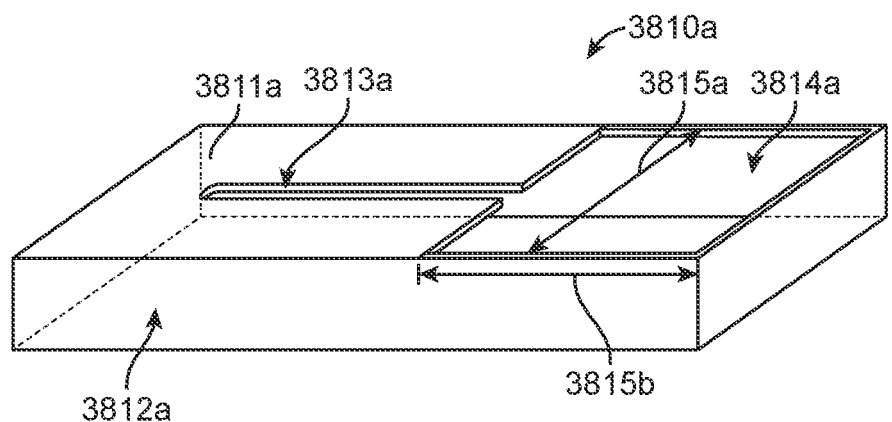
Figure 381B:
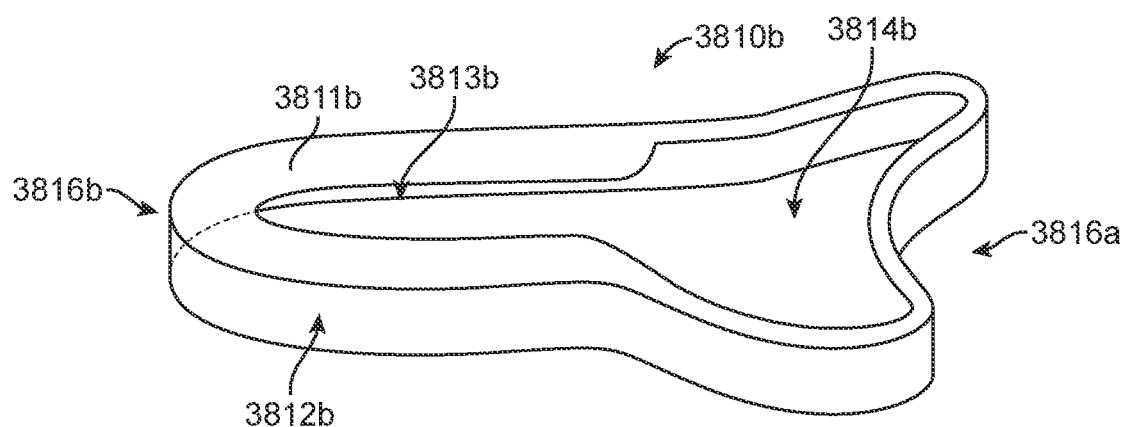

FIGS. 381A-381B illustrate exemplary needle receptacles suitable for incorporation with the needle handling systems as described herein.

FIGS. 382A-382D illustrate optional configurations of a needle receptacle as in FIGS. 380A-381B.

Figure 383A:
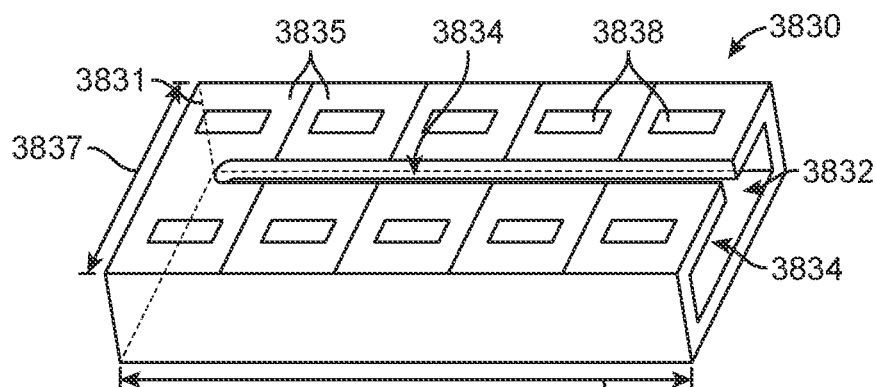
Figure 383B:
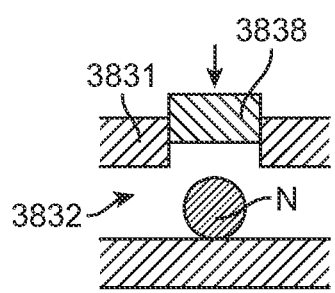
Figure 383C:
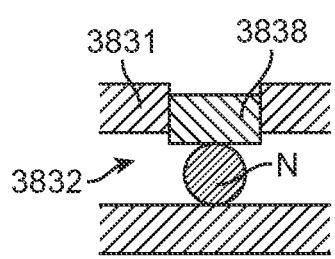

FIGS. 383A-383C show an exemplary needle receptacle configured to store a plurality of needles in an ordered array.

Figure 384A:
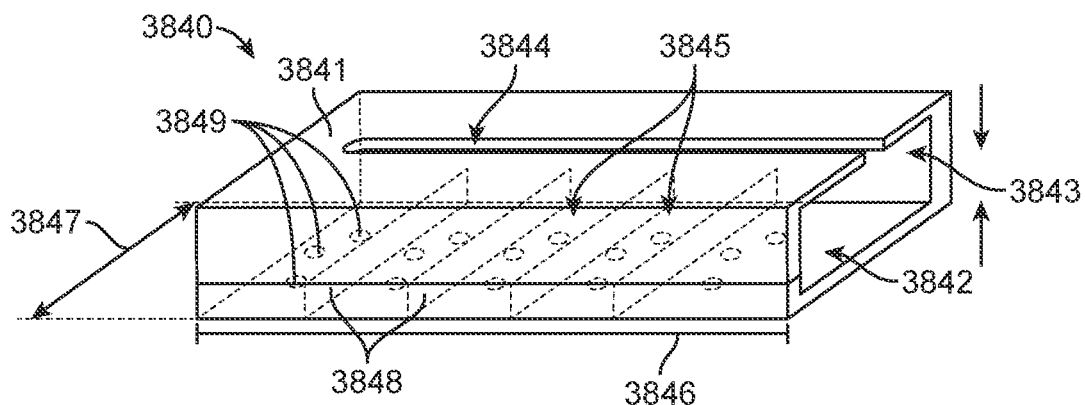
Figure 384B:
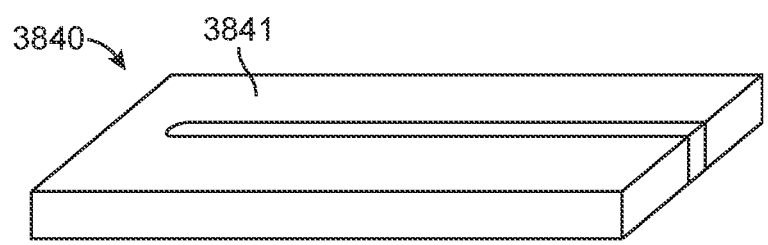

FIGS. 384A-384B show another exemplary needle receptacle configured to store a plurality of needles in an ordered array.

Figure 385A:
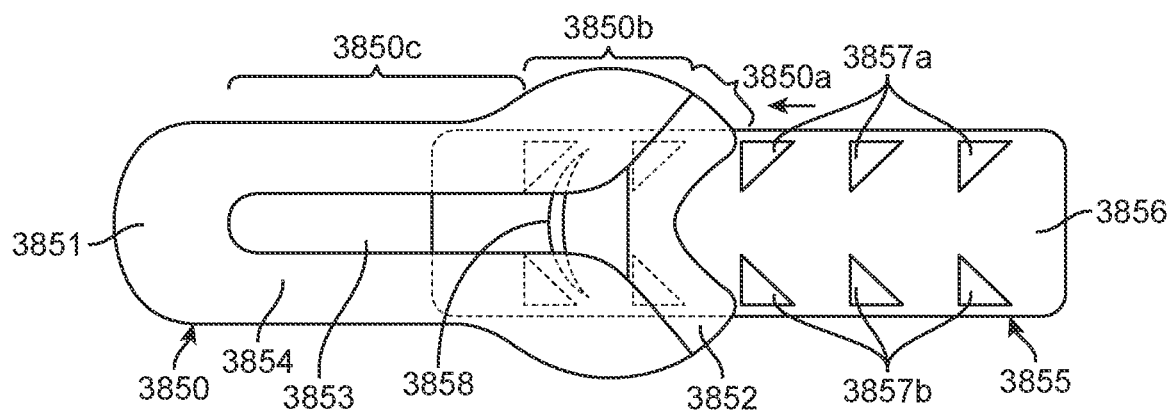
Figure 385B:
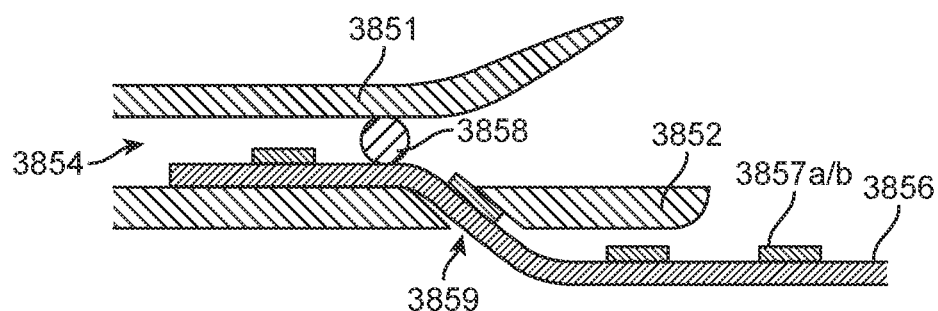

FIGS. 385A-385B illustrate an exemplary embodiment of devices for securing a plurality of needles, in accordance with many embodiments.

Figure 386A:
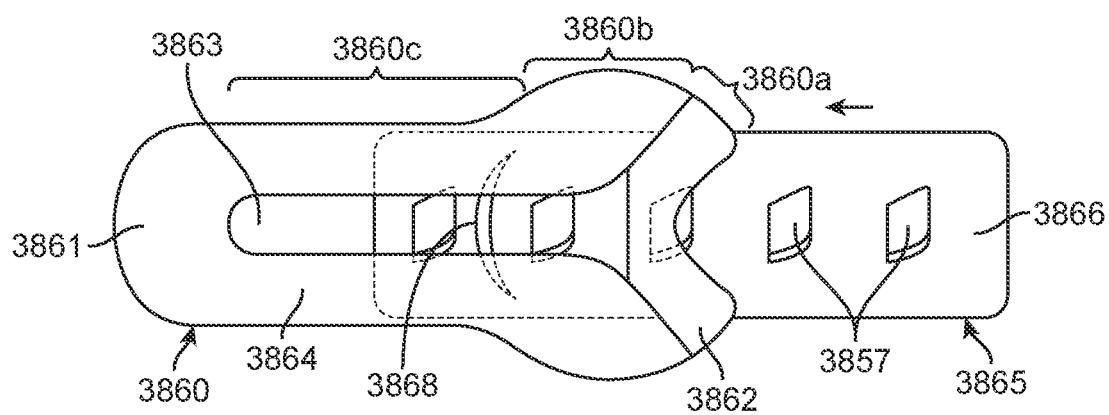
Figure 386B:
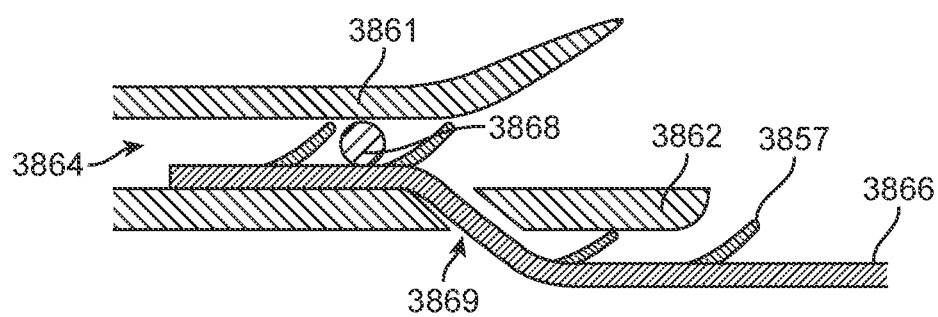

FIGS. 386A-386B illustrate an exemplary embodiment of devices for securing a plurality of needles, in accordance with many embodiments.

FIGS. 387A-387D illustrate longitudinal cross-sectional views of exemplary internal spring dividers suitable for incorporation with the needle handling systems as described herein.

Figure 388:
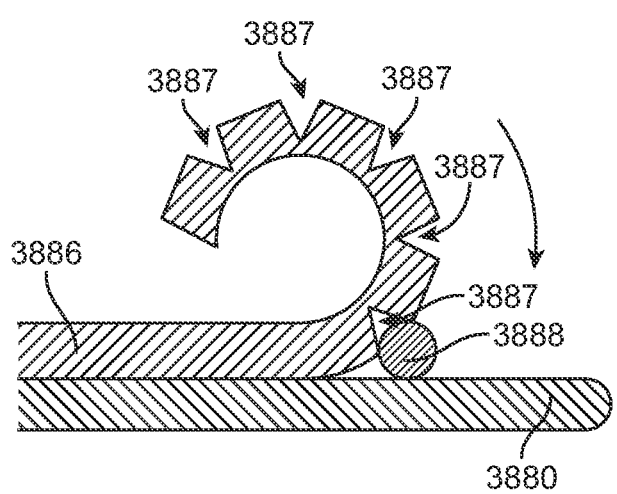

FIG. 388 illustrates a longitudinal cross-sectional view of an exemplary embodiment of a device for securing a plurality of needles, suitable for incorporation with the needle handling systems as described herein.

Figure 389A:
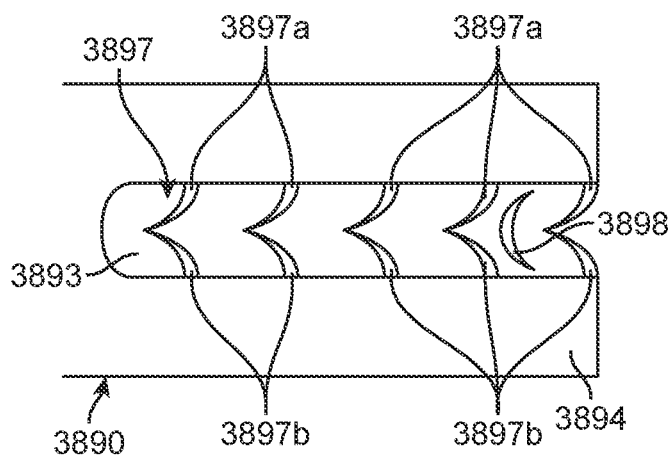
Figure 389B:
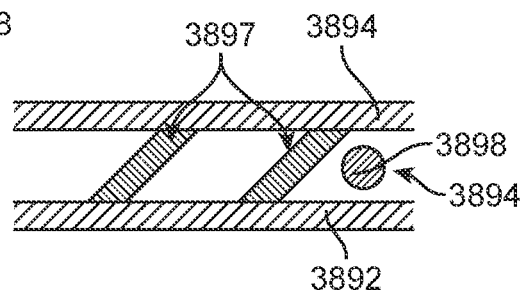

FIGS. 389A-389B illustrate an exemplary embodiment of a device for securing a plurality of needles comprising internal filaments, in accordance with many embodiments.

FIGS. 390A-390E illustrate exemplary embodiments of needle driver slot covers suitable for incorporation with the needle handling systems as described herein.

Figure 391A:
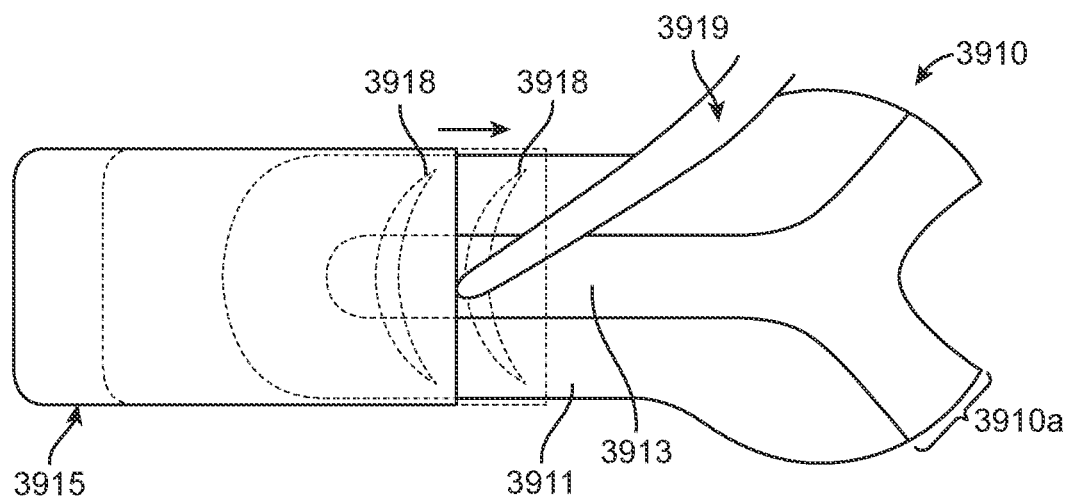
Figure 391B:
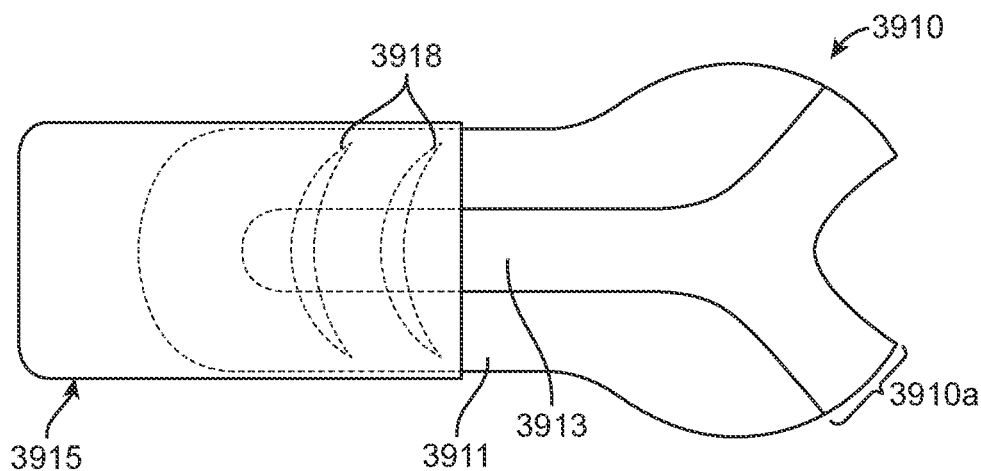

FIGS. 391A-391B illustrate exemplary embodiments of devices for securing a plurality of needles with a ratcheting cover, in accordance with many embodiments.

FIGS. 392A-392F illustrate exemplary embodiments of devices for securing a plurality of needles, in accordance with many embodiments.

Figure 12:
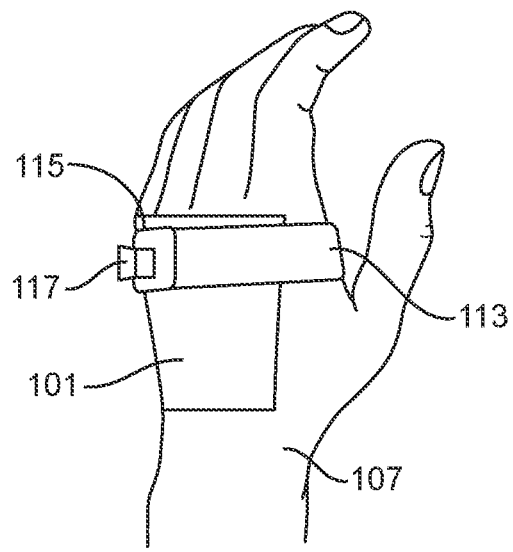
FIG. 12 illustrates a side view of a "C" shaped suture package holder with a suture package worn over a glove.
Figure 392A:
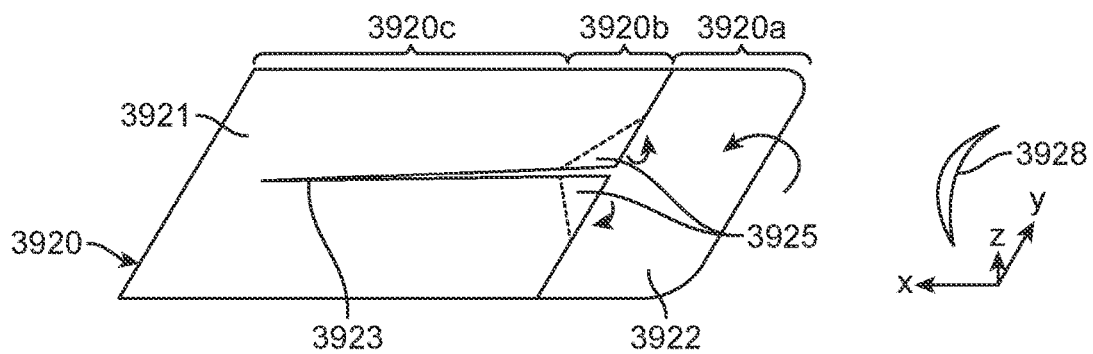

FIGS. 392A1-392A12 illustrate exemplary embodiments of devices for securing a plurality of needles, in accordance with many embodiments.

Figure 5:
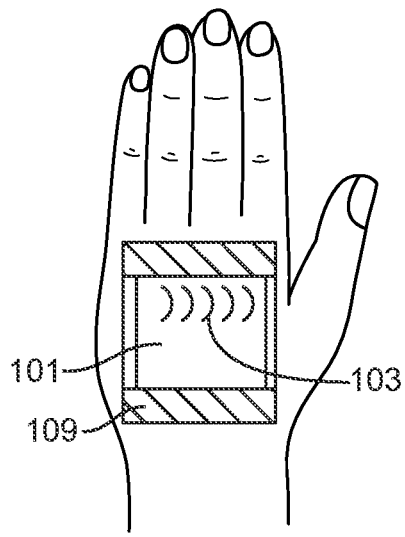
FIG. 5 illustrates a top view of a suture package with adhesive regions for holding the perimeter of the suture package to a glove.
Figure 392B:
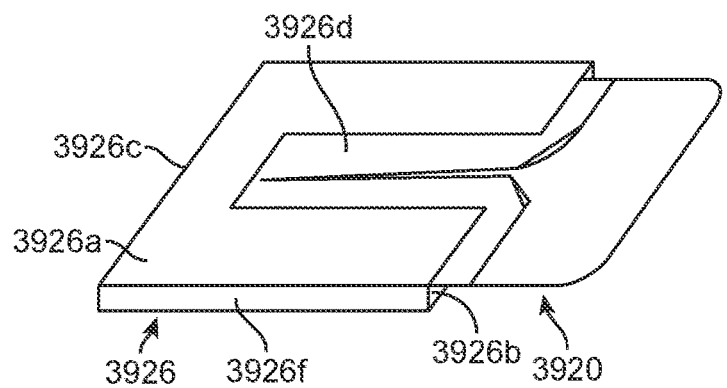

FIGS. 392B1-392B5 illustrate exemplary embodiments of devices for securing a plurality of needles, in accordance with many embodiments.

Figure 393A:
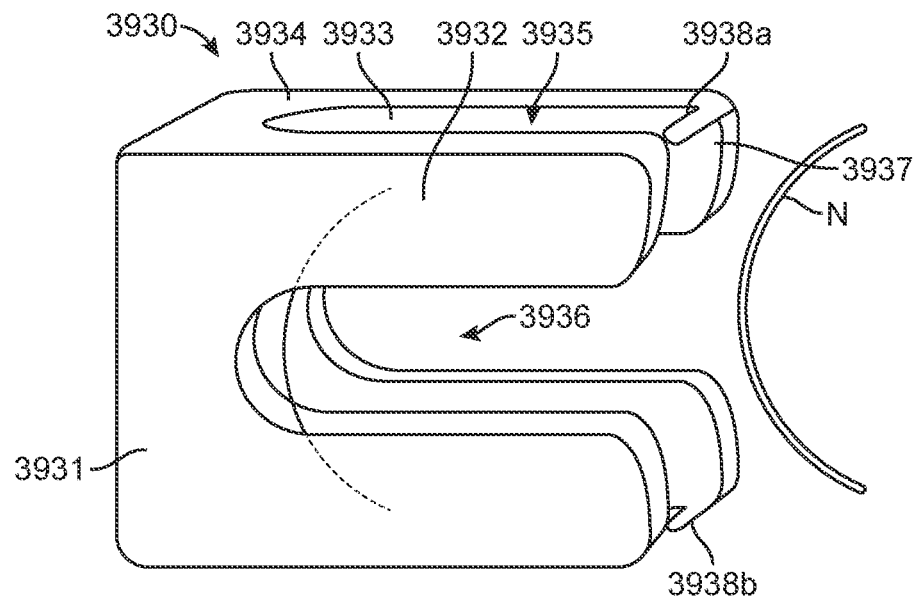
Figure 393B:
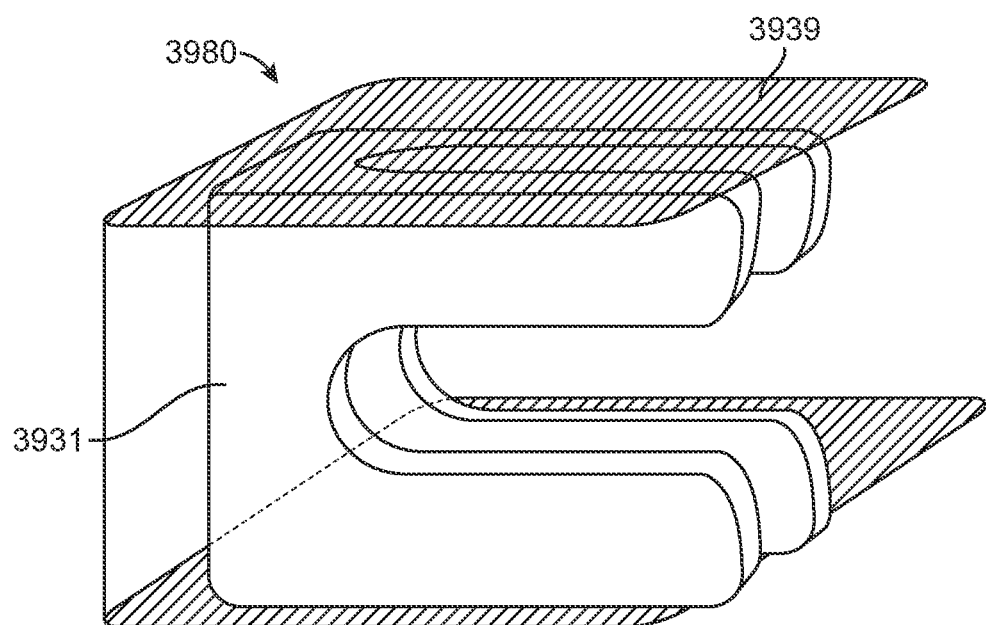

FIGS. 393A-393B illustrate an exemplary embodiment of a device for securing a plurality of needles, in accordance with many embodiments.

Figure 394:
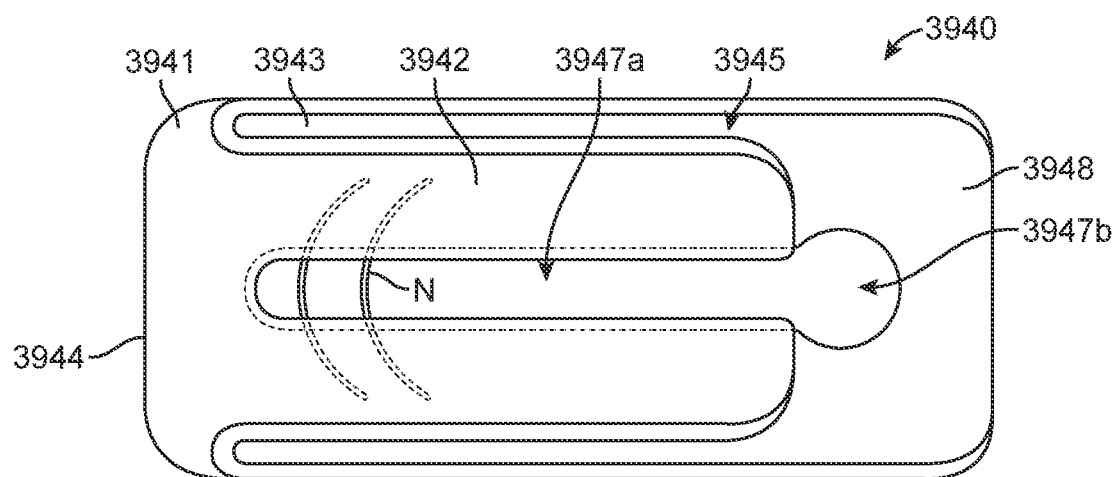

FIG. 394 illustrates an exemplary embodiment of a device for securing a plurality of needles, in accordance with many embodiments.

Figure 395:
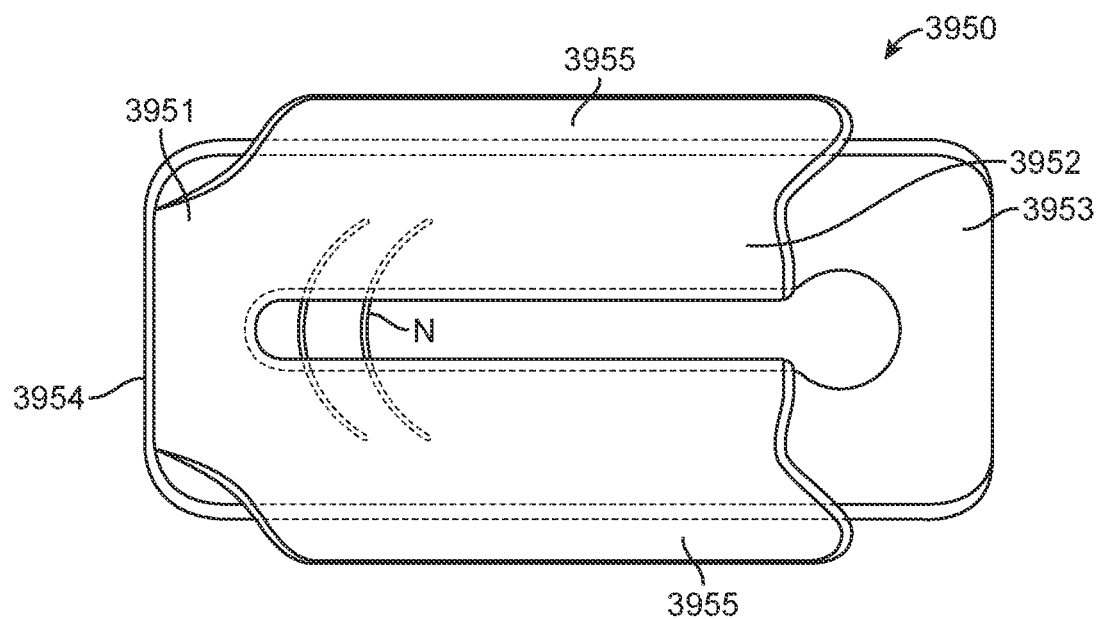

FIG. 395 illustrates an exemplary embodiment of a device for securing a plurality of needles, in accordance with many embodiments.

Figure 396:
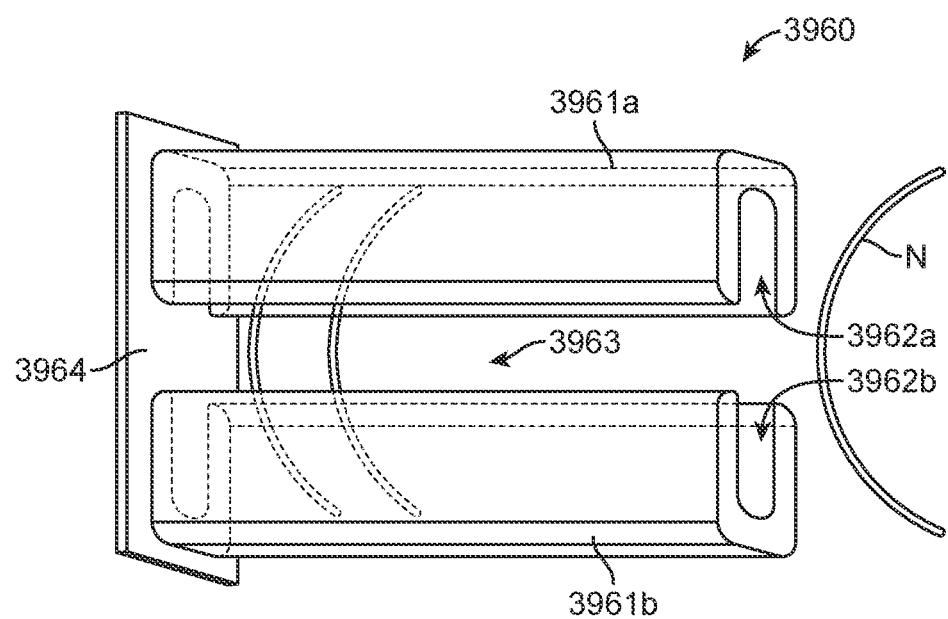

FIG. 396 illustrates an exemplary embodiment of a device for securing a plurality of needles, in accordance with many embodiments.

Figure 397A:
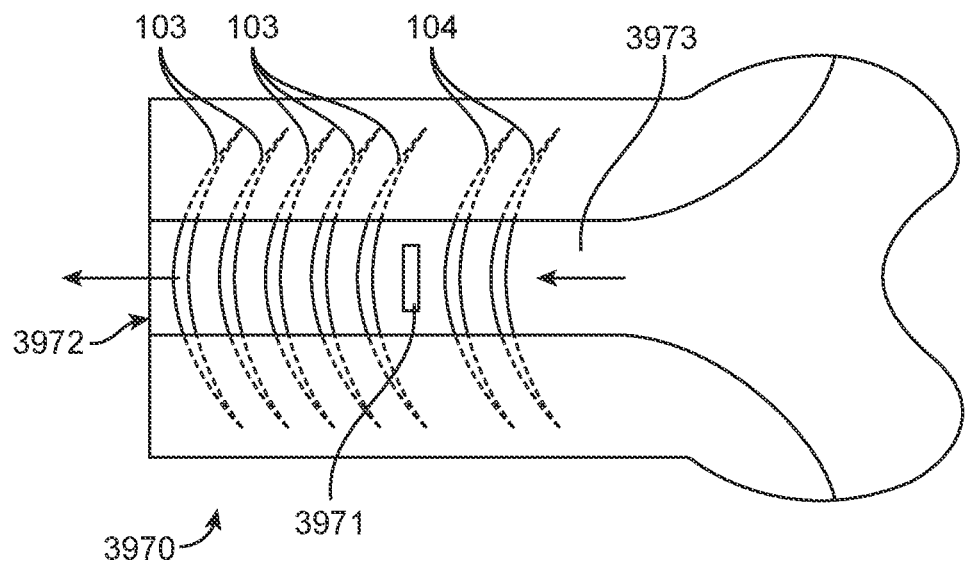
Figure 397B:
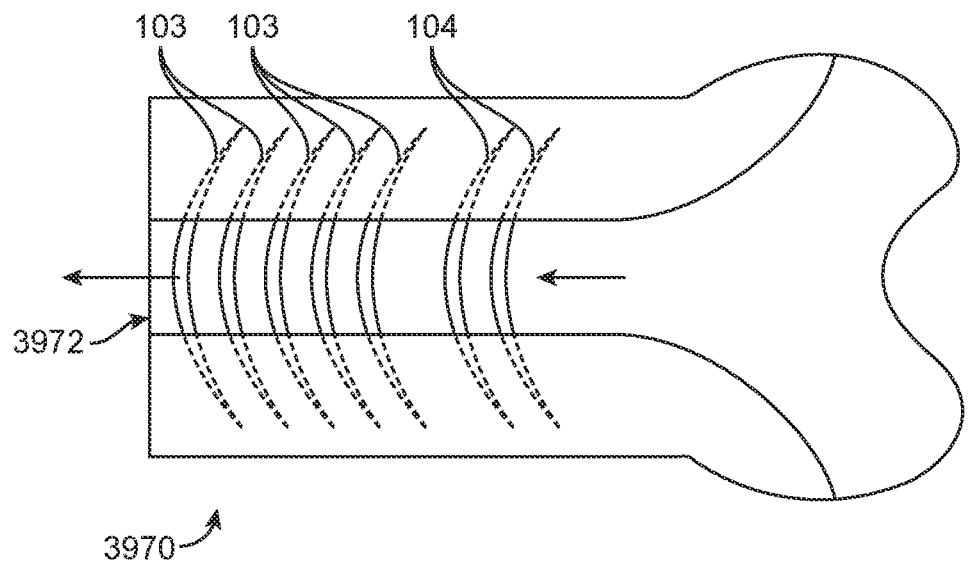

FIGS. 397A-397B illustrate exemplary embodiments of a device for dispensing and securing a plurality of needles, in accordance with many embodiments.

FIGS. 398A-398D illustrate exemplary embodiments of a barrier mounting base with a needle dispenser and needle trap mounted to a barrier for dispensing and securing a plurality of needles, in accordance with many embodiments.

FIGS. 399A-399D illustrate exemplary embodiments of a device for dispensing one or more swaged needles, in accordance with many embodiments.

FIGS. 400A-400D illustrate exemplary embodiments of a device for dispensing one or more swaged needles, in accordance with many embodiments.

FIGS. 401A-401C illustrate exemplary embodiments of a base for mounting one or more devices for dispensing and/or securing a plurality of needles, in accordance with many embodiments.

FIGS. 402A-402C illustrate exemplary embodiments of a base for mounting one or more devices for dispensing and/or securing a plurality of needles, in accordance with many embodiments.

FIGS. 403A-403C illustrate exemplary embodiments of a base for mounting one or more devices for dispensing and/or securing a plurality of needles, in accordance with many embodiments.

FIGS. 404A-404C illustrate exemplary embodiments of a base for mounting one or more devices for dispensing and/or securing a plurality of needles, in accordance with many embodiments.

Figure 405A:
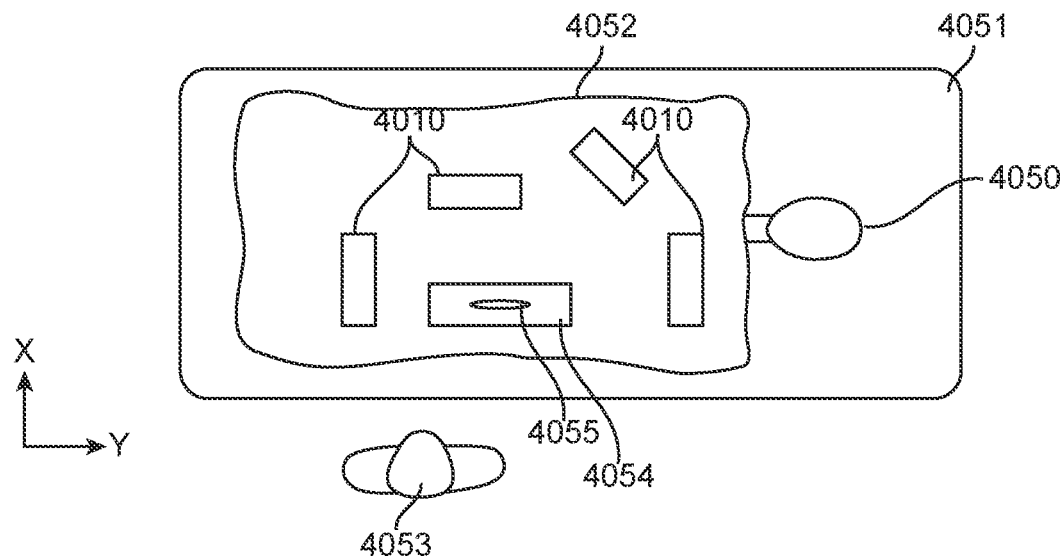
Figure 405B:
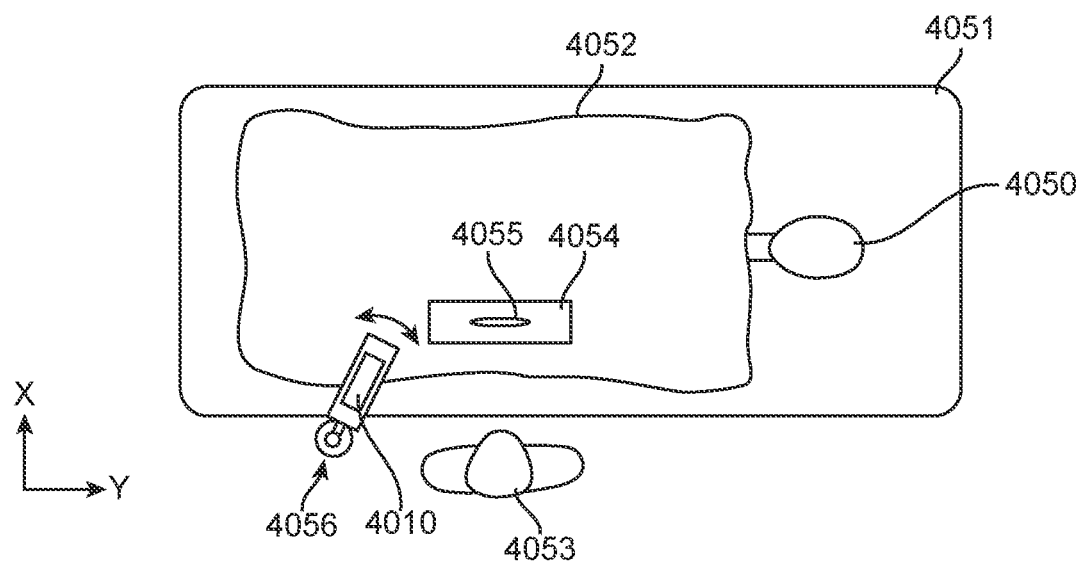

FIGS. 405A-405B illustrate exemplary mounting positions of a base for mounting one or more devices for dispensing and/or securing a plurality of needles, in accordance with many embodiments.

Figure 406A:
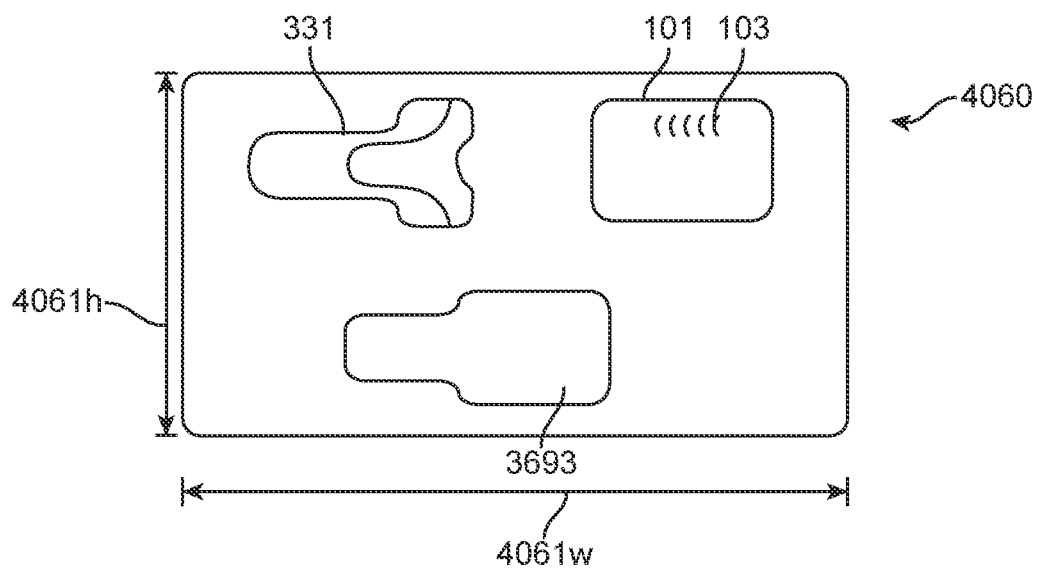
Figure 406B:
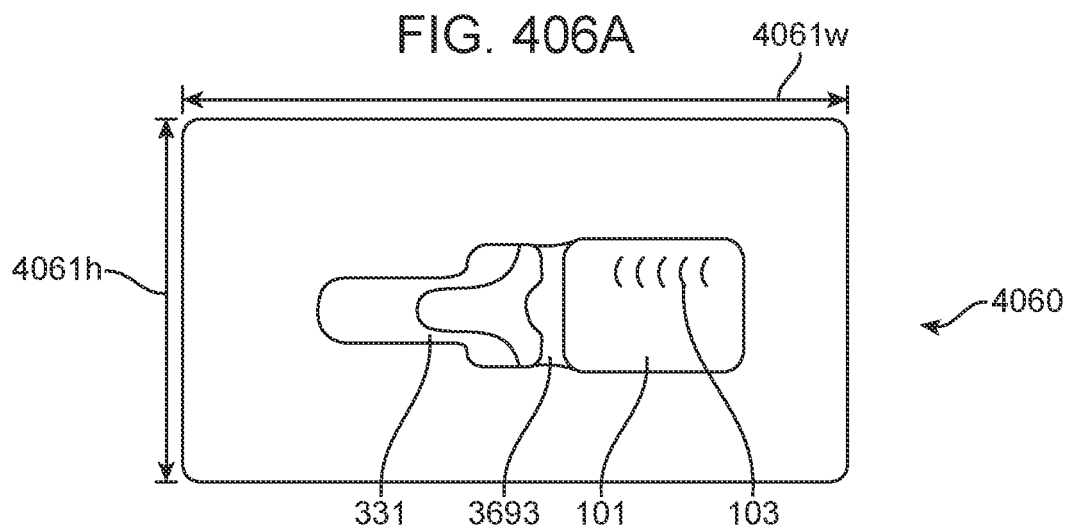
Figure 406C:
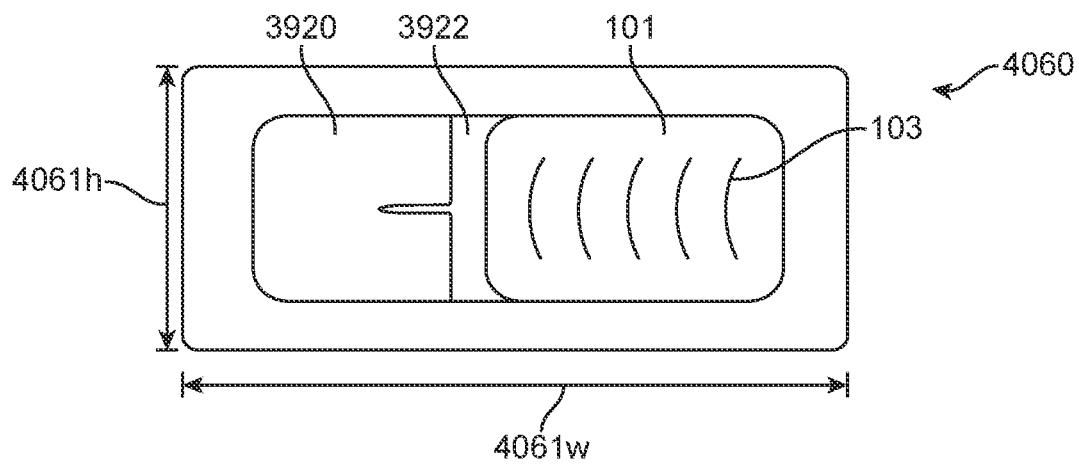

FIGS. 406A-406C illustrate exemplary kits including one or more devices for dispensing and/or securing a plurality of needles, in accordance with many embodiments.

FIGS. 407-413 illustrate an exemplary embodiment of needle receptacle, in accordance with many embodiments.

FIGS. 414-418 illustrate an exemplary embodiment of needle receptacle, in accordance with many embodiments.

DETAILED DESCRIPTION

The present invention is directed towards systems and methods for improving the efficiency of operating rooms. The embodiments disclosed herein are well suited for combination with many prior systems and methods, such as prior suture packs, prior needle holders, and prior operating rooms and personnel.

Although specific reference is made to the placement of used needles in a used needle container, the embodiments disclosed herein are well suited for use with needles dispensed from a suture pack and placed in a used needle container without suturing the patient, for example.

Definitions

Secure—The needle is secure means that the tip of the needle is prevented from compromising sterility or coming into contact with skin of the patient or surgical staff. When used with the sharps container, the used needle is physically secured from falling out of container. Sharps can include needles and tools or other objects which have one or more sharp surfaces that can puncture the skin of the patient or surgical staff.

In many embodiments, a secure needle as described herein is secured to prevent both the leading and trailing ends or tips of the needle from coming into contact with skin, gloves, surgical apparel of the surgical staff, surgical drape, or patient.

As used herein like characters such as letters and numerals refer to like elements.

As disclosed herein, a used suture needle encompasses a suture needle dispensed from a suture pack.

As used herein the terms "needle driver" and "needle holder" are used interchangeably.

As used herein the terms "armed sutures" and "armed needles" are used interchangeably.

As used herein the terms "used needle holder", "needle receptacle", "used needle receptacle, "used suture needle receptacle", "sharps container", "needle trap", and "needle receptacle means" are used interchangeably.

As used herein the terms "suture package", "suture pack" and "suture package means" are used interchangeably.

As used herein the terms "barrier" and "barrier means" are used interchangeably.

As used herein the terms "support" and "support means" are used interchangeably.

As used herein the terms "platform" and "platform means" are used interchangeably.

As used herein "secure" means fixed or fastened so as not to give way, become loose, or be lost.

As used herein "innocuous" means incapable of contact with a human finger.

One approach for improving operating room efficiency is to reduce the dependence of the surgeon on the surgical assistant. For example, a surgical procedure can include performing a surgical procedure and then closing a patient's surgical incisions after the procedure is completed. The closing generally includes installing surgical sutures to hold the patient's body tissue together after the surgery. This surgical suture procedure can include needles loaded with sutures that are stored in a needle package and a needle driver. When needed, the surgeon uses a needle driver to grasp and remove a needle from the suture package. The needle point is pressed into the flesh, advanced along the trajectory of the needle's curve until it emerges, and pulled through. The trailing thread is then tied into a knot, usually a square knot or surgeon's knot. Ideally, sutures bring together the wound edges, without causing indenting or blanching of the skin, since the blood supply may be impeded and thus increase infection and scarring. Placement varies based on the location, but the distance between each suture generally is equal to the distance from the suture to the wound edge. The most common stich is a simple interrupted stitch with the suture thread cut between each individual stitch. Because each stitch may require a separate needle and the patient may require many stitches, the surgeon may need to handle many different needles. The size and shape of the needles may also vary depending upon the patient's needs.

An embodiment, the present invention is directed towards a system for improving efficiency by eliminating the need for the assistant to provide needles to the surgeon when closing a patent's surgical wounds. Eyed or reusable needles are needles with holes or eyes, which are supplied separate from their suture thread. The suture must be threaded on site, as is done when sewing at home. The advantage of this is that any thread and needle combination is possible to suit the job at hand. Swaged, or atraumatic, needles with sutures comprise a pre-packed eyeless needle attached to a specific length of suture thread. The suture manufacturer swages the suture thread to the eyeless atraumatic needle at the factory. The chief advantage of this is that the doctor or the nurse does not have to spend time threading the suture on the needle, which may be difficult for very fine needles and sutures. Also the suture end of a swaged needle is narrower than the needle body, eliminating drag from the thread attachment site. In eyed needles, the thread protrudes from the needle body on both sides, and at best causes drag. When passing through friable tissues, the eye needle and suture combination may thus traumatize tissues more than a swaged needle, hence the designation of the latter as "atraumatic".

There are several shapes and sizes of surgical needles. These include: Straight, ¼ circle, ⅜ circle, ½ circle, ⅝ circle, compound curve, half curved (also known as ski), half curved at both ends of a straight segment (also known as canoe), etc. Subtypes of the ½ circle needle shape include, from larger to smaller size, CT, CT-1, CT-2 and CT-3. The ski and canoe needle design allows curved needles to be straight enough to be used in laparoscopic surgery, where instruments are inserted into the abdominal cavity through narrow cannulas. Needles may also be classified by their point geometry, examples include: taper (needle body is round and tapers smoothly to a point), cutting (needle body is triangular and has a sharpened cutting edge on the inside curve), reverse cutting (cutting edge on the outside), trocar point or tapercut (needle body is round and tapered, but ends in a small triangular cutting point), blunt points for sewing friable tissues, side cutting or spatula points (flat on top and bottom with a cutting edge along the front to one side) for eye surgery, etc. Atraumatic needles may be permanently swaged to the suture or may be designed to come off the suture with a sharp straight tug. These "pop-offs" are commonly used for interrupted sutures, where each suture is only passed once and then tied.

In an embodiment, operating room efficiency can be improved by allowing the surgeon to load suture needles to a needle driver. A surgeon may use a dominant hand to hold the needle driver and one or more suture packets can be attached to the non-dominant limb of the surgeon. The surgeon can then grasp the new suture needles from the suture packet on the non-dominant limb.

For example, if the user is right handed, the surgeon may attach the suture package to the left arm or hand and use the right hand to handle a needle driver. The user can grasp a portion of a needle with the needle driver and remove the needle from the suture package. The user can then use the needle driver to press the needle point into the flesh of the patient. The needle is advanced along the trajectory of the needle's curve until it emerges from the flesh, and the needle and suture are pulled through. The trailing thread is then tied into a knot, usually a square knot or surgeon's knot.

It has been estimated that there are over one billion passages of needles per year in the US. This high needle use results in a serious risk of injury. The inventive system reduces this risk because the needles are only handled by the surgeon. Because there is a reduced number of passes of sharp needles between surgical personnel there are fewer chances of having accidentally dropped needles, drape penetration or retained foreign objects within the patient.

Figure 1A:
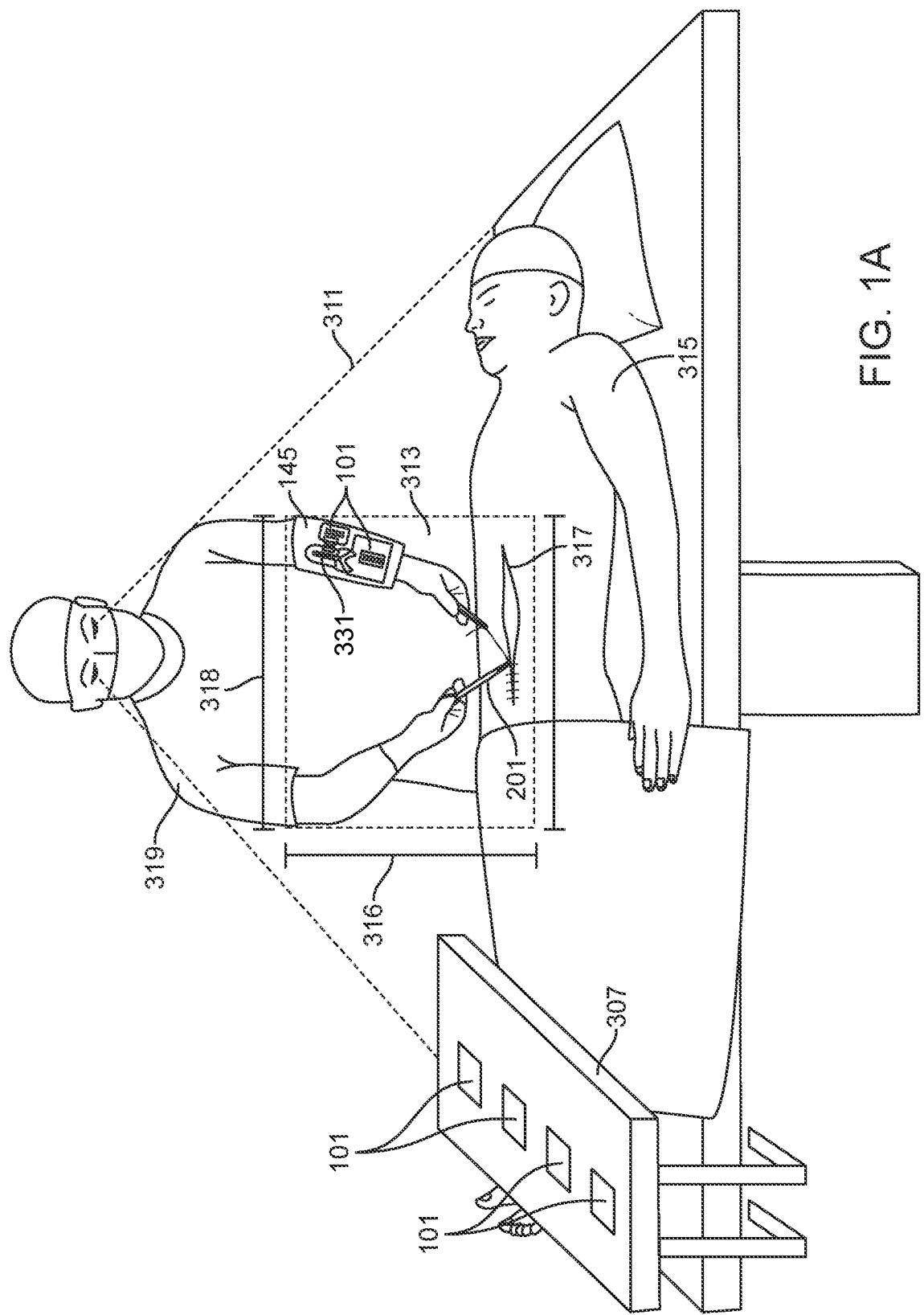
FIGS. 1A and 1B illustrate a surgical field and a near surgical field.
Figure 1B:
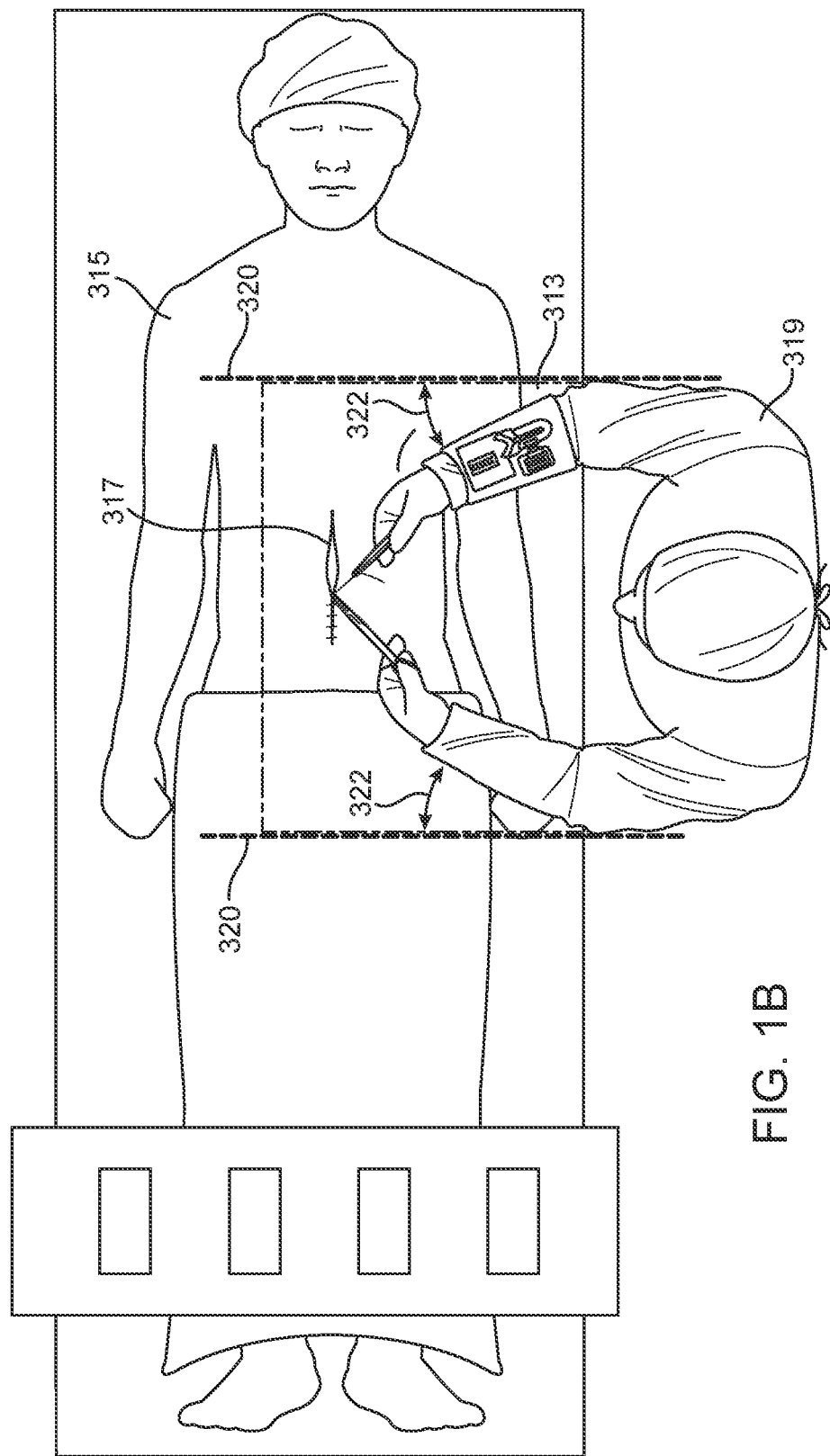

FIGS. 1A and 1B illustrate a surgical field and a near surgical field. FIG. 1A illustrates a perspective view and FIG. 1B illustrates a top view of a surgeon performing an operation within the near surgical field, using methods and apparatuses in accordance with embodiments. The surgeon of FIG. 1A is shown holding a needle driver with his dominant right hand, while holding a tissue forceps with his non-dominant left hand. A suture handling apparatus in accordance with embodiments is shown mounted on the surgeon's non-dominant left forearm. The surgeon of FIG. 1B is shown holding a needle driver with his dominant left hand, while holding a tissue forceps with his non-dominant right hand. A suture handling apparatus in accordance with embodiments is shown mounted on the surgeon's non-dominant right forearm. As shown in FIGS. 1A and 1B, the suture handling apparatus as described herein can be supported on a surgeon's non-dominant limb so that the surgeon may perform maneuvers for an operation using his dominant hand, regardless of whether the surgeon is right-handed or left-handed. This configuration can allow the surgeon or other user to move the needle less than two feet from the suture pack to the wound (such as a surgical incision) and less than two feet from the wound to the needle receptacle. This decreased range of travel of the suture from dispensing to suturing to secure provides improved safety.

A "surgical field" can include a space within an operating room where the patient and surgeon are located during surgery. A "near surgical field" 313 can be a much smaller space that is in close proximity to the incision 317 on the patient 315 and the surgeon. The near surgical field 313 may comprise a space disposed between the surgeon 319 and the incision 317. For example, the near surgical field can comprise a length 316 extending between a surgeon and an incision of a patient and a width 318 extending transverse to the length, the width comprising no more than about 24 inches (61 cm) across. The entire near surgical field can also be within the field of view 311 of the surgeon 319.

The near surgical field may be conceptualized as the space bound by the neutral planes 320 of the surgeon's arms, such that no external rotation of the arms or the shoulders beyond a position of neutrality is necessary for the surgeon to reach an object positioned within the near surgical field. For example, the near surgical field can comprise a space wherein the surgeon's arms retain some degree of bending and can rotate internally from the neutral planes 320 (in the direction shown by arrows 322 in FIG. 2B). Frequently, a surgeon's arms may be in a neutral position, for example with the arms positioned at the sides and the elbows bent at about 90 degrees. From this neutral position, the near surgical field 313 can comprise the space between the edges of the elbows to the tips of the fingers, and about 6 inches beyond the tips of the fingers. Generally, the surgeon does not have to engage gross motor control in order to reach an object positioned within the near surgical field. On the other hand, to reach for an object positioned outside the near surgical field, a surgeon would generally be required to engage gross motor control. Since a surgeon usually engages only fine motor control during the performance of a surgical operation, it is desirable that the surgeon not be required to reach for an object positioned outside of the near surgical field during the operation, in order to prevent interruptions to the surgeon's workflow. The practice of passing individual suture needles between a surgeon and an assistant often requires the surgeon to reach outside of the near surgical field, therefore breaking the surgeon's workflow, in addition to exposing both the surgeon and the assistant to risks of needle-stick injury during the passing of the needles.

As shown in FIGS. 1A and 1B, the embodiments described herein can allow a surgeon 319 to work within the near surgical field 313 without having to pass individual suture needles in and out of the near surgical field. The surgeon can be provided with a support comprising platform 145 as described herein, shown mounted on the volar forearm of the surgeon 319 in FIGS. 1A and 2B. Platform 145 can support a suture pack 101 and a dispensed needle receptacle 157, for example. In many embodiments, when the platform 145 is used by the surgeon 319 to install sutures, the platform 145, incision 317 and the surgical tools 201 will all be within the near surgical field 313 and the field of view 313 of the surgeon 319, for example. In many embodiments, the near surgical field 313 is within about 2 feet of the incision 317. Alternatively or in combination, the near surgical field 313 can be within about 1.5 feet of the incision 317. The near surgical field 313 can be within 1 foot of the incision 317, for example. According to present embodiments, the surgeon can perform procedures requiring the use of suture needles by dispensing suture needles from the suture pack 101 mounted within the near surgical field 313 (e.g., on surgeon's forearm), and securing dispensed needles in a needle receptacle 157 also mounted within the near surgical field.

In many embodiments, a needle trap or needle receptacle as described herein is configured such that a user can slide a needle into the receptacle and have the needle be secured the moment the needle is released from the needle driver. The needle can be released using a single maneuver, and the needle can be immediately secured within the needle receptacle.

FIGS. 1C-1F illustrate a method of using a suture handling apparatus 305 in accordance with embodiments. FIG. 1C shows a surgeon grasping an unused suture needle 103 from a suture pack 101, using a needle driver 327 usually held with the user's dominant hand. FIG. 1D shows the needle driver 327 holding the dispensed suture needle 104, having suture 155 attached to the trailing end 325 of the suture needle. The leading end 323 of the suture needle can be inserted into the tissue 321 near the site of an incision 317, to install the suture and therefore close the incision. FIG. 1E shows the suture needle 104 having been advanced into the tissue 321 through the incision 317, to install the suture 155 in the tissue. The needle driver 327 can be used to grasp the leading end 323 of the suture needle 104 as the needle emerges out from the tissue, and pull the needle up and out of the tissue. FIG. 1F shows the surgeon securing the suture needle 104, held by the needle driver 327, into a needle receptacle 331. For example, the user can place the needle 104 in an entry zone 333 of the needle receptacle 331, align the tip of the needle driver 327 with a slot 343 in the needle receptacle 331, then move the needle 104 into a secure zone 337 of the needle receptacle by moving the needle driver 327 in the direction shown by arrow 329. As shown by the workflow illustrated in FIGS. 1C-1F, using the apparatus 305, a surgeon can dispense a suture needle and securely store the dispensed suture needle by himself, without having to receive a fresh needle passed from, or pass the used needle back to, an assistant located outside the near surgical field.

In addition to the improved safety, the inventive system improves the efficiency of surgical procedures, which can result in reduced time for procedures in the operating room. For example, the time of the surgical procedures can be reduced because the scrub tech no longer needs to assist the surgeon with needle loading/unloading, providing needle holders and scissors. Rather than assisting the surgeon, the scrub tech can perform other tasks reduce the time needed in the operating room. For example, the scrub tech can perform a sponge count with the circulating nurse or begin the breakdown of the back table to facilitate a faster operating room turnover thereby decreasing the time spent between surgical procedures. This extra free scrub tech time may also lead to more accurate and reliable sponge count thereby decreasing the risk of retained foreign object. The overall effect of the inventive system and apparatus is faster time of closures (room turnover from one surgical case to the next) because the scrub tech is also now free to begin "breaking down" the back table where instruments are kept). The work flow in the operating room is more efficient because there are fewer steps and no reliance on the support of a scrub tech. Rather than coordinating the movement of the needles and tools, the surgeon can simply reach for the needed objects without having to wait for anyone else. There is no need to reach for tools and there is no transfer of sharp objects. The platform can be configured with the proper instruments and/or with needles in an optimum position for removal from the suture packs.

Because the surgeon does not need to worry about the coordination of transferring tools and needles, the surgeon can maintain eye contact on surgical field. Time lost to looking away from the surgical field or refocusing the eyes to see where the tools and needles are located during an object transfer can be reduced. Body rotation of the surgeon can be decreased, as well as crossover of one forearm over the other. The movements can be more circular, of lesser excursion. Thus, the micro-ergonomics can be improved.

Further, the present embodiments can allow the surgeon to track his own needle usage and inventory, since the surgeon himself can dispense fresh needles and secure used needles. When needles are passed back and forth between a surgeon and an assistant, it can be difficult for the surgeon to know how many more suture needles remain inside an opened suture pack, how many suture packs are opened, etc., while it can be similarly difficult for the assistant to know how many and/or what types of needles have been used by the surgeon. Such lack of clarity regarding the inventory of available needles can necessitate an ongoing dialogue between the surgeon and the assistant, which can be distracting, inefficient, and prone to producing errors. By contrast, when the surgeon is able to track his own needle usage, as with the methods described herein, he can easily determine when a particular suture pack needs to be replaced, and communicate his needs to his assistant in a more precise manner. Referring again to FIGS. 1A and 1B, preferably, one or more new suture packs 101 may be provided on an instrument tray 307 (e.g., Mayo stand) located just outside the near surgical field 313. The suture packs may be labeled or color-coded to facilitate the identification of their contents, so that a surgeon can precisely point out to the assistant which suture pack he needs. The assistant can then readily hand the requested suture pack to the surgeon, or the surgeon may reach for and grab the necessary suture pack himself.

Figure 2A:
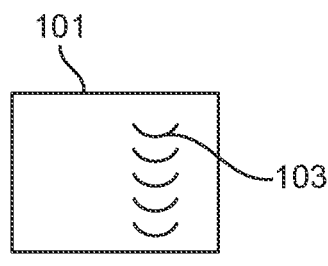
FIG. 2A illustrates a top view of a suture package with needles.
Figure 2B:
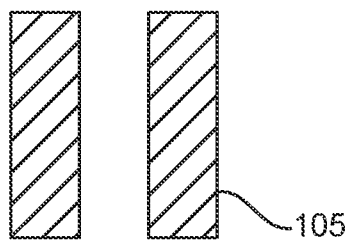
FIG. 2B illustrates adhesive strips.
Figure 3:
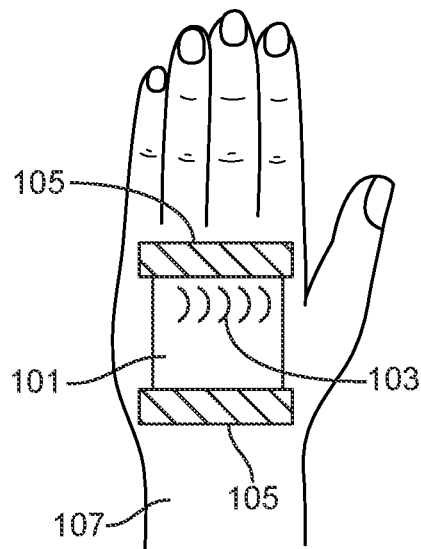
FIG. 3 illustrates a top view of a suture package attached to a glove with adhesive strips.

With reference to FIG. 2A, a top view of a suture package 101 is illustrated. The suture package 101 can contain needles 103 threaded or swaged to sutures. The needles 103 can be releasably attached to suture package 101 that can include a flat surface that can be flexible to bend to a contour that matches a portion of the user's limbs. FIG. 2B illustrates steri-strips which can be adhesive tape 105 or film that can be used to secure the suture package 101 to a glove 107 of a user as shown in FIG. 3 which illustrates a top view of a glove 107 and FIG. 4 which illustrates a side view of the suture package 101 on the glove 107. The adhesive side of the tape 105 can be attached over the edges of the suture package 101 and portions of the glove 107.

Figure 6:
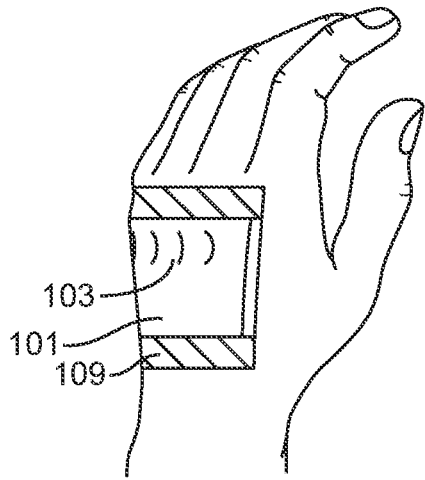
FIG. 6 illustrates a side view of a suture package with adhesive regions for holding the perimeter of the suture package to the glove.
Figure 7:
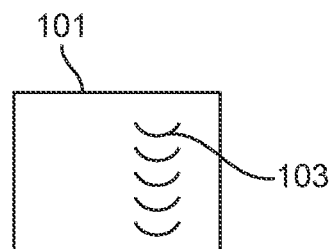
FIG. 7 illustrates a top view of a suture package with needles.
Figure 8:
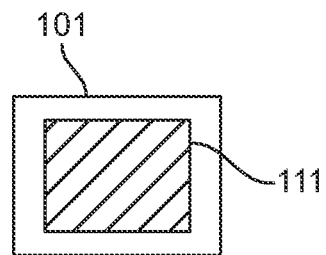
FIG. 8 illustrates a bottom view of a suture package with an adhesive.

With reference to FIGS. 5 and 6 another embodiment of the suture package 101 is illustrated. In this embodiment, a film adhesive or an adhesive 109 applied to the back surface perimeter of the suture package 101. FIG. 5 illustrates a top view and FIG. 6 illustrates a side view of the glove 107 and at least a portion of the perimeter of the suture package 101 attached to the glove 107 with the adhesive 109. Alternatively with reference to FIGS. 7 and 8, an adhesive 111 can be applied directly to the back of the suture package 101. FIG. 7 illustrates a top view of the suture package 101 and FIG. 8 illustrates a bottom view of the suture package 101 with the adhesive 111 applied. In all of these examples, the adhesive that can be used to attach the suture package 101 directly to the glove 107.

Figure 9:
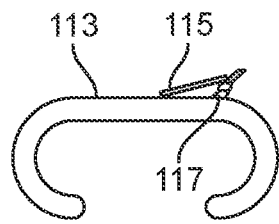
FIG. 9 illustrates a side view of a "C" shaped suture package holder.
Figure 10:
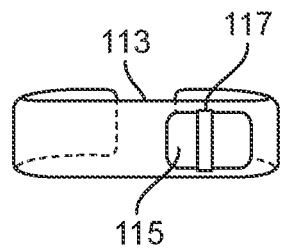
FIG. 10 illustrates a top view of a "C" shaped suture package holder.
Figure 11:
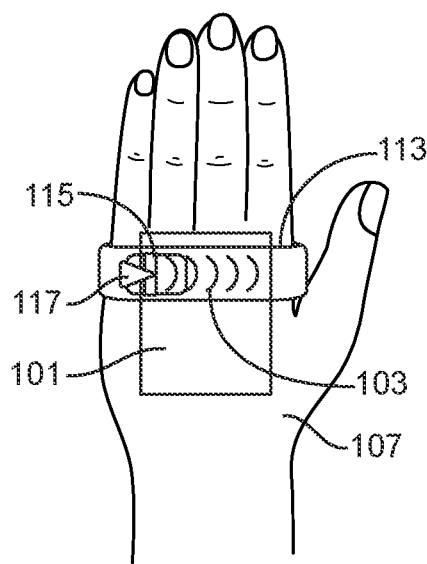
FIG. 11 illustrates a top view of a "C" shaped suture package holder worn over a glove.

FIG. 9 illustrates a front view and FIG. 10 shows a top view of an embodiment of a "C" shaped holder 113 that can be used to hold suture packets 101. The "C" shaped holder 113 can wrap around a portion of the user's hand as shown in FIGS. 11 and 12. FIG. 11 shows a top view and FIG. 12 illustrates a side view of "C" shaped holder 113 on a glove 107 on the user's hand. The holder 113 can be made of a flexible material that inherently retains its C shape and includes a clip 115 on an outer surface. The holder 113 can be placed on the hand and a suture package 101 can be attached to the clip 115, which can include a spring and a hinge 117. The clip 115 can hold the suture package 101 in place so that the needles 103 can be grasped with the needle driver as described above. If the user runs out of needles 103, the original suture package 101 can be removed from the clip 115 and replaced with a new suture package 101 with additional needles 103.

Figure 13:
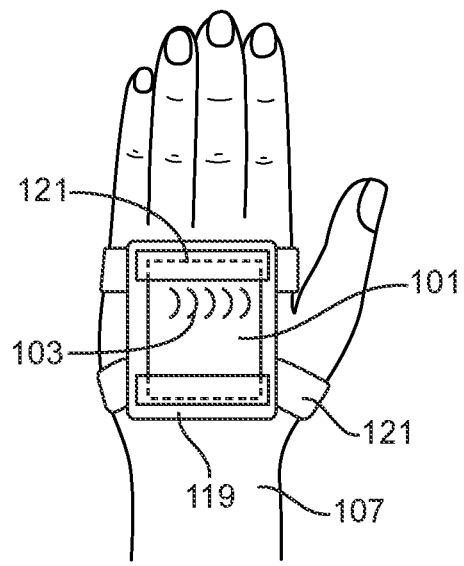
FIG. 13 illustrates a top view of a platform holding sutures attached with straps to a glove.
Figure 14:
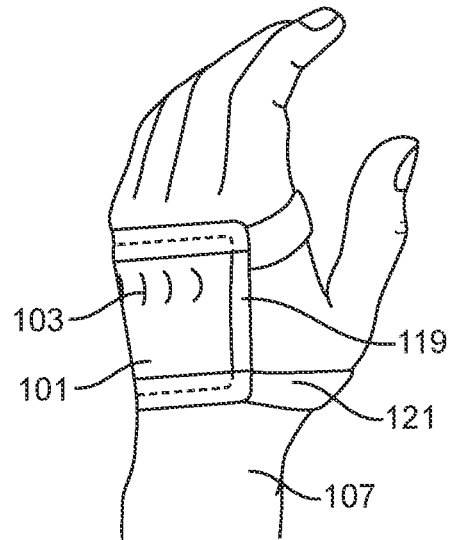
FIG. 14 illustrates a side view of a platform holding sutures attached with straps to a glove.

FIGS. 13 and 14 illustrate another embodiment of the suture package 101 system, which can include a platform 119, and straps 121 that wrap at least partially around the glove 107 on the user's hand. FIG. 13 shows a top view and FIG. 14 illustrates a side view of the platform 119, and straps 121 that wrap at least partially around the glove 107. The suture package 101 can be attached to the platform 119 in various ways, such as with an adhesive, straps, etc. The needles 103 can be grasped as described above. If the user runs out of needles 103, a new suture package 101 can be attached to the platform or the used platform can be replaced with a new platform having additional needles 103.

Figure 15:
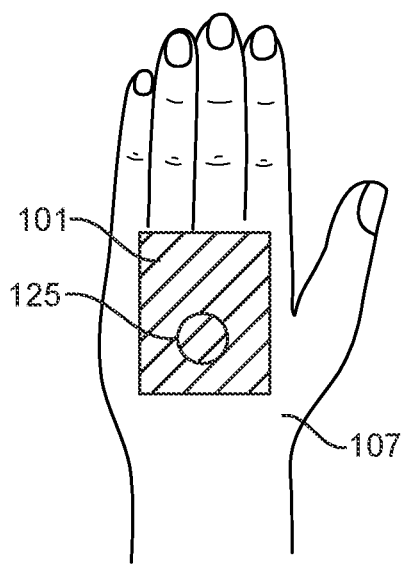
FIG. 15 illustrates a top view of a magnetic platform attached to a glove.
Figure 16:
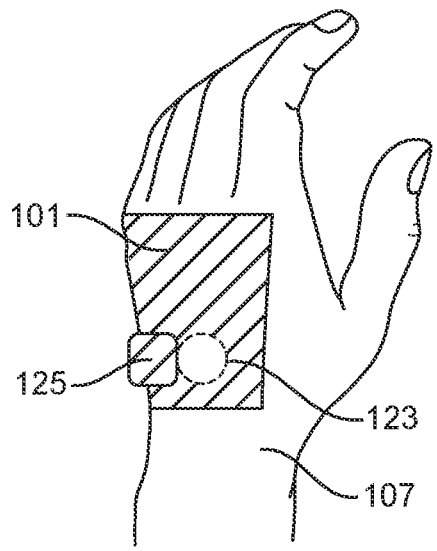
FIG. 16 illustrates a side view of a magnetic platform attached to a glove.

With reference to FIGS. 15 and 16, in another embodiment, a magnetic system can be used to secure the suture pack 101 to the glove 107. FIG. 15 shows a top view and FIG. 16 illustrates a side view of the magnetic system used to secure the suture pack 101 to the glove 107. A first permanent magnet 123 can be secured to the glove 107 and a corresponding polarity permanent magnet 125 can be attached to the suture pack 101. The polarities of the permanent magnets 123, 125 can be arranged so the back of the suture pack 101 is attracted to the glove 107. The magnets 123, 125 can be attached to the glove 107 and suture package 101 with any suitable connection mechanism including adhesives, pockets, clips, etc. When the suture pack 101 runs out of suture needles, the surgeon can remove the empty suture pack 101 by pulling the suture pack 101 with a force greater than the magnetic force and placing a new full suture pack 101 on the magnet 125.

Figure 17:
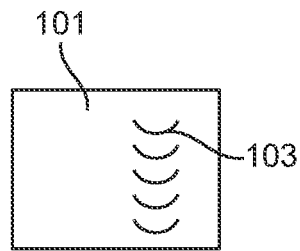
FIG. 17 illustrates a top view of a multi-layer suture package.
Figure 18:
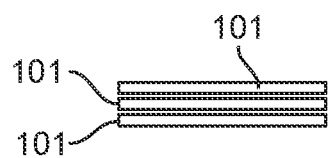
FIG. 18 illustrates a side view of a multi-layer suture package.
Figure 19:
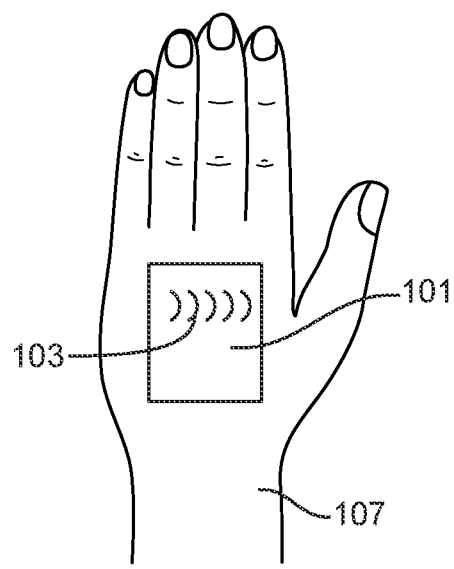
FIG. 19 illustrates a top view of a multi-layer suture package attached to a glove.
Figure 20:
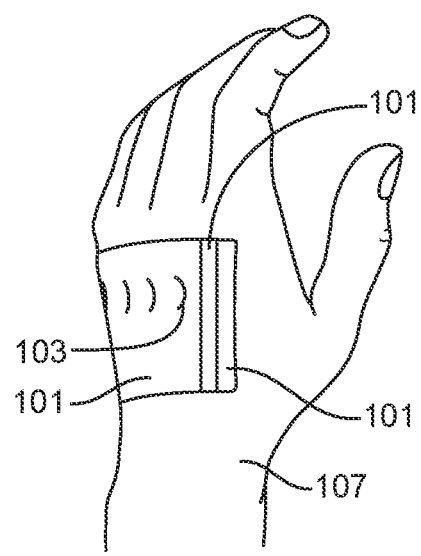
FIG. 20 illustrates a side view of a multi-layer suture package attached to a glove.

With reference to FIGS. 17 and 18, the suture pack 101 can include multiple layered sheets of materials with each sheet holding a set of needles 103 and sutures. FIG. 17 illustrates a top view and FIG. 18 illustrates a side view of the multiple layered suture package 101. This multiple layer suture package 101 can be attached to the glove 107 as shown in FIGS. 19 and 20 in any manner described above. FIG. 19 illustrates a top view and FIG. 20 illustrates a side view of the multiple layer suture pack 101 attached to the glove 107. The user can use the needles 103 on the top layer of the suture package 101. When these first layer needles 103 are used, the user can remove and discard the depleted top layer suture package 101. The underlying layer can then be exposed and the needles 103 stored on the second layer of the suture package 101 can be used. This process can be repeated until all of the layers of the suture package 101 are used.

Figure 21:
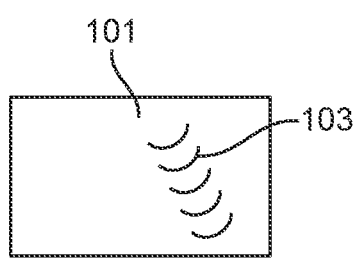
FIG. 21 illustrates a top view of a multi-layer suture package with a hook and loop attachment mechanism.
Figure 22:
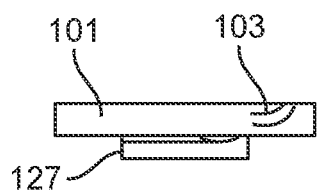
FIG. 22 illustrates a side view of a multi-layer suture package with a hook attachment mechanism.

In an embodiment shown in FIGS. 21-24, a suture pack 101 can have a hook and loop connection mechanism to couple the suture pack 101 to the glove 107. FIG. 21 illustrates a top view of the suture pack 101 and FIG. 22 illustrates a side view of the suture pack 101. In this embodiment, a hook or loop material can be attached to the back of the suture package 101 and a corresponding loop or hook material can be attached to the outer surface of the glove where the suture package 101 is to be attached. In the illustrated embodiment, the hook material 127 is attached to the bottom of the suture package 101. FIG. 23 illustrates a side view of the loop material 129 and FIG. 24 illustrates a bottom view of the loop material 129 with an adhesive 131 applied to the back of the loop material 129. FIG. 25 illustrates a top view and FIG. 26 illustrates a side view of the suture pack 103 attached to the glove 107 with the hook and loop connection mechanism. When the needles 103 in the suture package 101 are depleted, the suture package 101 can be replaced.

Figure 28:
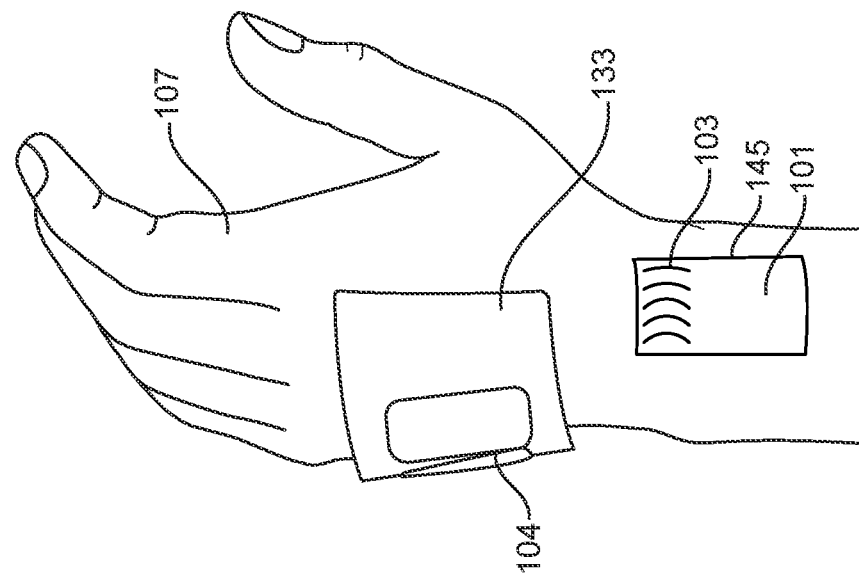
FIG. 28 illustrates a side view of a used suture container and a suture package attached to a glove.
Figure 27:
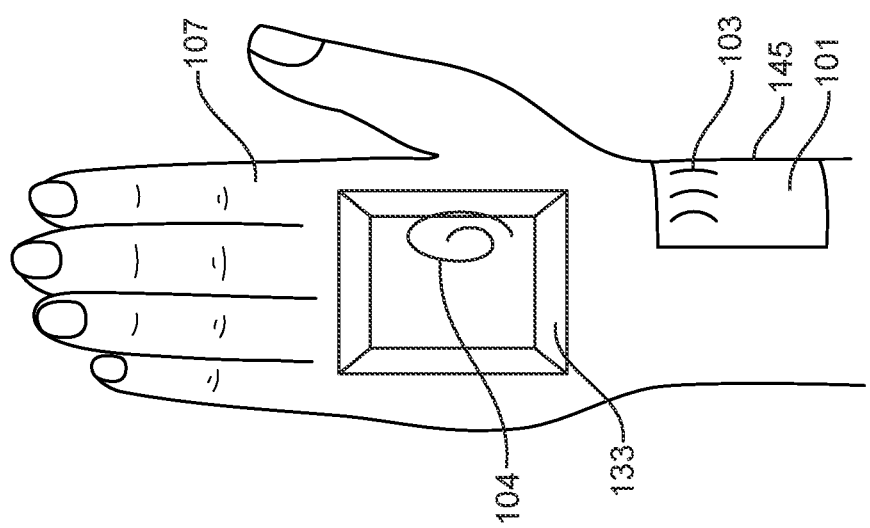
FIG. 27 illustrates a top view of a used suture container and a suture package attached to a glove.

In an embodiment shown in FIGS. 27 and 28, a needle storage unit 133 can be secured to the hand in addition to the suture package 101. The operating efficiency can be further improved by having the suture packs 101 and used needle storage unit 133 in close proximity to the surgeon. The platform 145 can be attached to the non-dominant limb of the surgeon. The surgeon can then grasp a needle 103 and suture from a suture packet 101 on the platform 145. The surgeon can install the suture on the patient and then place the used needle 104 in the used needle storage unit 133. The surgeon can then grasp the new suture needles 103 from the suture packet 101 on the platform 145 worn on the non-dominant limb.

The needle storage unit 133 can hold the used needles 104 after the suture has been knotted and the needle is no longer needed. The needle storage unit 133 eliminates the need to place the used needle 104 in the neutral zone and picked up by the surgical staff after it has been used. The user can simply complete the suture stitch, cut the suture and place the used needle 104 in the needle storage unit 133 with the needle driver. The user can then grasp the next needle 103 from the suture package 101. The needle storage unit 133 can greatly increase the efficiency of the surgical procedure. In an embodiment, the needle storage unit 133 can include an internal volume and internal walls with a hole or slot for inserting the used needles 104. The housing may be transparent so the user can see that the used needles 104 are fully inserted and trapped within the needle storage unit 133.

With reference to FIGS. 29 and 30 elastic bands 135 can be used to secure the suture package 101 to the glove 107 or wrist of the user. The elastic bands 135 can be a uniform loop or elongated structures that have a connection mechanism such as a strap buckle or a hook and loop connection so that the tension of the elastic bands 135 can be adjusted around the user's hand and/or arm. The bands 135 can be attached to opposite edges of the suture package 101 as shown in FIGS. 31 and 32.

In an embodiment, the suture package 101 can be held in a pocket 137 in the glove 107 as shown in FIGS. 33 and 34. The suture package 101 can be placed into the pocket 137 through a slot 139 so that at least the pocket material covers some of the suture package 101. A window 141 or windows can be formed in the pocket so that the needles 103 are accessible. The pocket 137 can securely hold the suture package 101 and allow a user to remove the needles 103 from the suture package 101 as described above. If additional needles 103 are required, the suture package 101 can be removed from the glove pocket 137 and replaced with a new suture package 101.

Figure 35:
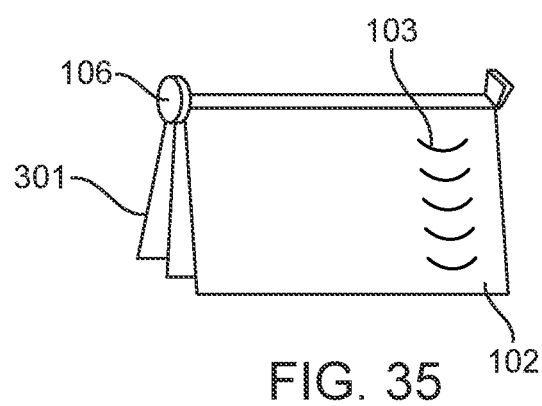
FIG. 35 illustrates a front view of a flip pack suture package.
Figure 36:
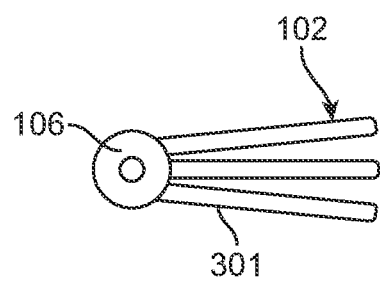
FIG. 36 illustrates a side view of a flip pack suture package.
Figure 37:
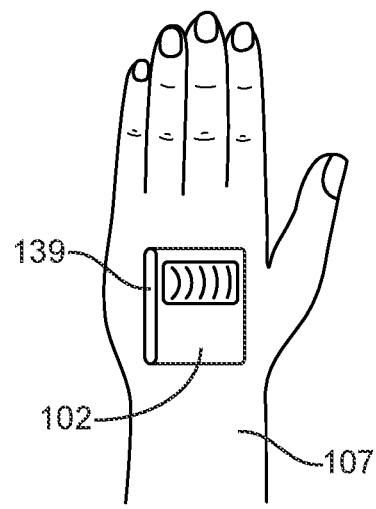
FIG. 37 illustrates a top view of a glove holding a flip pack suture package.

In an embodiment shown in FIGS. 35 and 36, the suture package 103 can include multiple layers that each holds a set of needles 103. The layers can be attached to a hinge unit 106 so that the user can flip through the different layers like a "Rolodex." As discussed above, there are many different types and shapes of needles 103. In an embodiment, different needles 103 can be stored on the different layers of the suture package 102. With reference to FIG. 37, the multi-layered suture package 102 can be attached to the glove 107 in any of the ways described above. For example, a bottom layer of the suture package 101 can be held in a slot 139 pocket formed in the glove 107. A mechanism such as a hook and loop connection can be used to hold the bottom layer in the pocket.

As discussed above with reference to FIGS. 13 and 14, a platform having a suture package can be attached to a glove on a hand. In other embodiments, the platform can include various other components including: tool holders, suture packs and used needle holders. For example with reference to FIG. 38 a top view of a multiple component platform 145 is illustrated. The platform 145 can include a first tool holder 147 for holding a first tool 151 and a second tool holder 147 for holding a second tool 151. During a procedure the surgeon can insert a first tool 151 into a first tool holder 147 and remove a second tool 151 from a second tool holder 147. Because the first and second tools 151 are easily accessible, there is no need for an assistant to handle the tools 151 as the surgeon switches between the tools 151. A suture pack 101 holding suture 103 and a used needle storage unit for storing used needles 104 can also be attached to the platform 145.

In an embodiment, the tools 151 can be needle drivers that have handle at a proximal end and a thin tip at a distal end. The tool holders 147 can be holes or slots that are wider than the distal portion of the tool 151. The distal ends of the tools 151 can be inserted into the holders 147 in the platform but the handle portions of the tools 151 can be wider than the holes or slots. The center of balance of the tools 151 can be inserted through the holes or slots so that when the platform is upright, the tools 151 will be held in the tool holders 147. In an embodiment, the slots can be between about 0.5 to about 2.0 inches in width.

A surgeon can use a platform for holding suture packages during a medical procedure. The suture holders can be attached to a platform 145 that is secured to the glove 107 around the hand/arm 143 of the user. In an embodiment, the platform 145 can be much larger than a single suture package 101. In these embodiments, multiple suture packages 101 can be attached to different areas of the platform 145. A surgeon can have a plurality of suture packages 101 on the dorsal surface of the left hand glove 107. The right hand is holding a needle driver, which is holding a needle. The right hand is also holding a tool. The surgeon can complete a stitch and then release the needle. The needle driver can grasp a new needle from the suture package 101.

Figure 38:
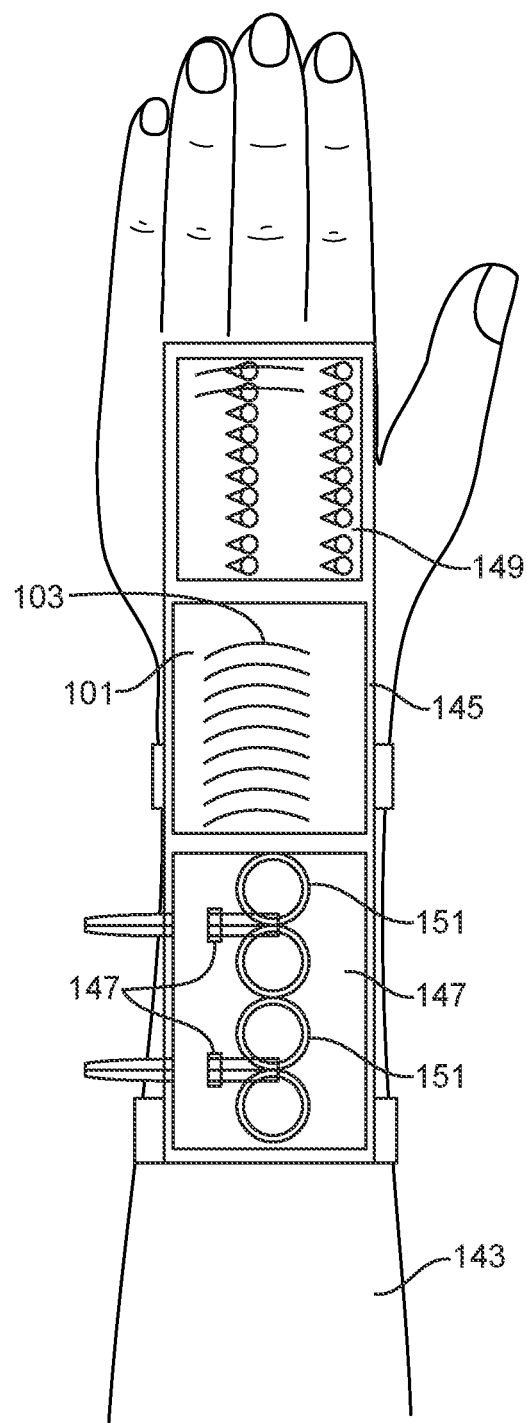
FIG. 38 illustrates a top view of a platform that includes: tool holders, suture packages and a used needle holder.
Figure 39:
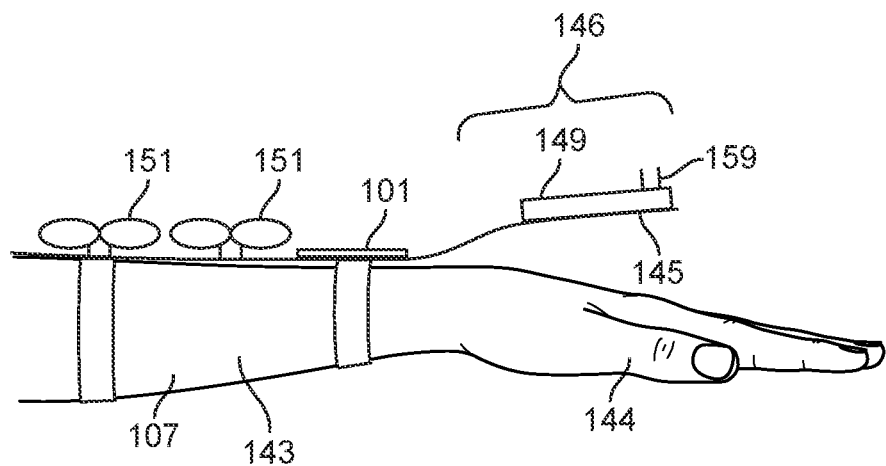
FIGS. 39 and 40 illustrate side views of different embodiments of platforms having modular attachments.
Figure 40:
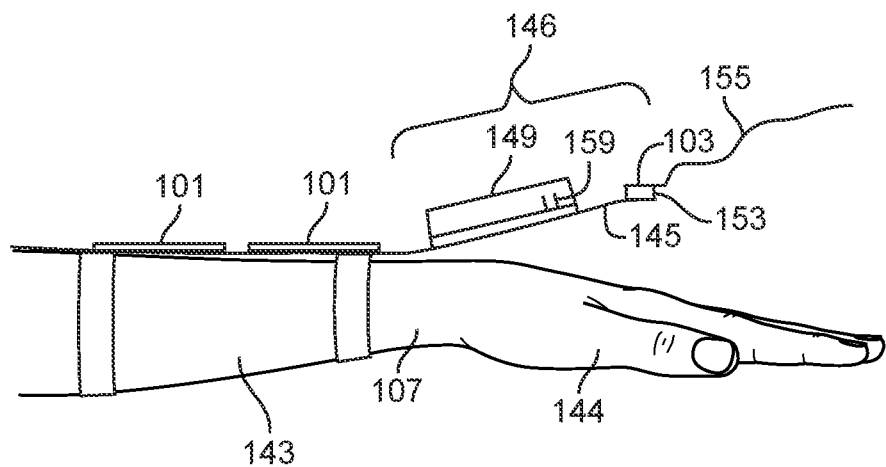
Figure 41:
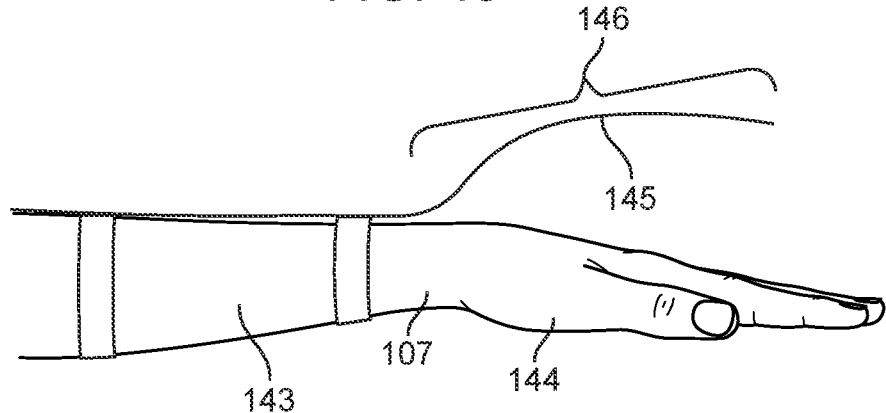
FIG. 41 illustrates a side view of a platform with an enlarged hand portion.

FIG. 38 illustrates a top view of an embodiment of a platform 145 secured around an arm that includes modular attachments. In this example, a tool holder 147, suture package 101 and a used needle holder 149 are mounted on the platform 145. FIGS. 39-41 illustrate side views of different embodiments of platforms 145 that are secured to arms 143 of surgeons. FIG. 39 illustrates a side view of an embodiment of the platform 145 with the tool holder 147, suture package 101 and a used needle holder 149 are mounted on the platform 145. The platform 145 can be a thin structure that can have planar surfaces for mounting the modular attachments in any locations desired by the surgeon. The portion of the platform 145 that is on the forearm 143 can be secured close to the dorsal surface up the wrist portion of the arm 143. However, the platform 145 may also include a wrist and hand portion 146 that is angled away from the upper dorsal surface of the hand 144. This spaced configuration allows the user to move the hand 144 freely without contacting the bottom surface of the platform 145. In an embodiment, the bottom surface of the platform 145 can be between about 1 to 4 inches away from the upper surface of the hand 144 in the normal straight position.

FIG. 40 illustrates a side view of a platform 145 with a first suture package 101, a used needle holder 149, a second suture package 101 and a swaged needle holder 153 with an attached suture. In this example, the swaged needle holder 153 can be include a permanent magnet that holds the needle temporarily and the end of the needle 103 can protrude from the needle holder 153 so the needle 103 can be easily grasped again. The surgeon can place the needle 103 on the swaged needle holder 153, release the needle 103 and tie the suture 155. The surgeon can then grasp the needle 103 with the needle driver and insert another stitch through the patient and repeat the described process. The platforms 145 can have various different curvatures so that a surgeon can select a platform 145 that best suits the personal preference. FIG. 41 illustrates a side view of a platform 145 having a substantially different size and curvature shape.

Different structures can be mounted on the platforms 145 depending upon the preference of the surgeon. For example with reference to FIG. 40, the platform 145 can include a two suture packages 101 arranged side by side and a needle container 149 on the hand portion of the platform 145. Using the illustrated platform, the surgeon can select different types of needles and then place the used needles 104 in the needle container 149 after each is used. The surgeon can then grasp additional needles as they are needed. Alternatively in other embodiments, the platform 145 can include a suture package area on the proximal portion of the platform 145, a tool holder at a wrist portion of the platform 145 and a needle container 149 on the hand portion 146 of the platform 145.

As discussed above, the surgeon can place used needles 104 into the needle container 149 and then use a second tool as needed. FIGS. 42-47 illustrate different embodiments of the used needle holders. It is extremely important to account for all needles during the surgical procedure. If a needle becomes lost during the surgery, the needle must be found and it may become necessary to x-ray the patient to determine if the needle has been left within the body. The used needle holder can provide various features, which can make the used needle count easier.

Figure 42:
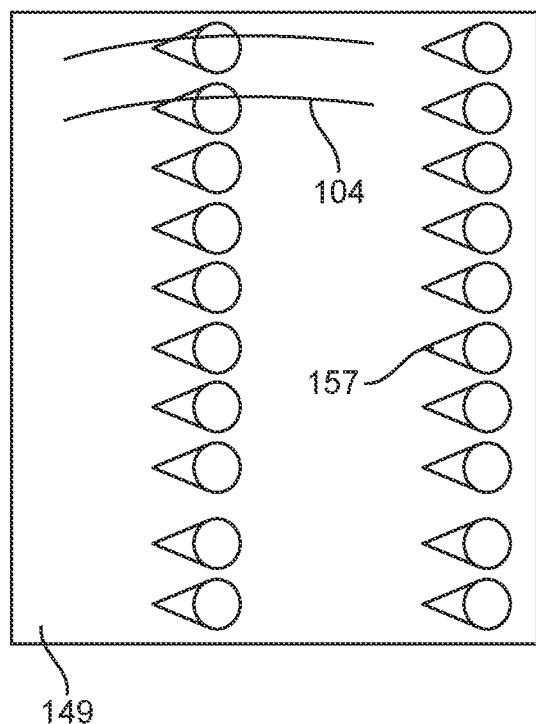
FIG. 42 illustrates a top view of an embodiment of a used needle holder.
Figure 43:
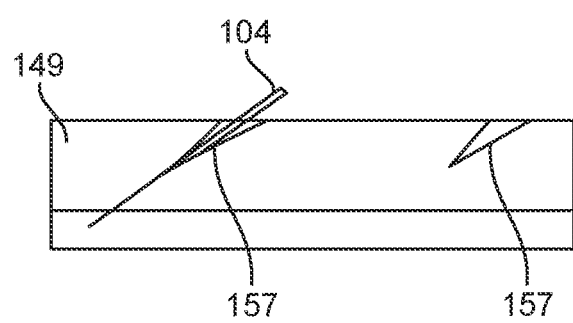
FIG. 43 illustrates a side view of an embodiment of a used needle holder.

FIG. 42 illustrates a top view and FIG. 43 illustrates a side view of an embodiment of a used needle holder 149 having a plurality of individual needle receptacles 157. Each receptacle 157 can include a conical hole that can easily accept the tip of the needle 104. The lower portion of the conical hole can clam around the sides of the needle 104. This mechanism can allow the needle 104 to be inserted but prevent the needle 104 from being removed. The needle holder 149 can also include an elastic material that can allow a needle 104 to be pressed into the material but may resist the movement/removal of the needle 104. The needle holder 149 may also include a magnet, which can attract the needle 104. These features can be mixed and matched or omitted in any combination to provide an effective means for holding used needles 104. The surgeon can press the needles 104 fully into the used needle holder 149 and release the needle 104. Once fully inserted the needle holder 149 will not release the used needles 104. The surgeon can preferably insert the used needles 104 sequentially. The number of needles 104 can easily be counted. In this example, needle receptacles 157 are arranged in two rows of 10 receptacles 157. In other embodiments, any other receptacle configuration can be used and the receptacles 157 can be labeled with numbers.

Figure 44:
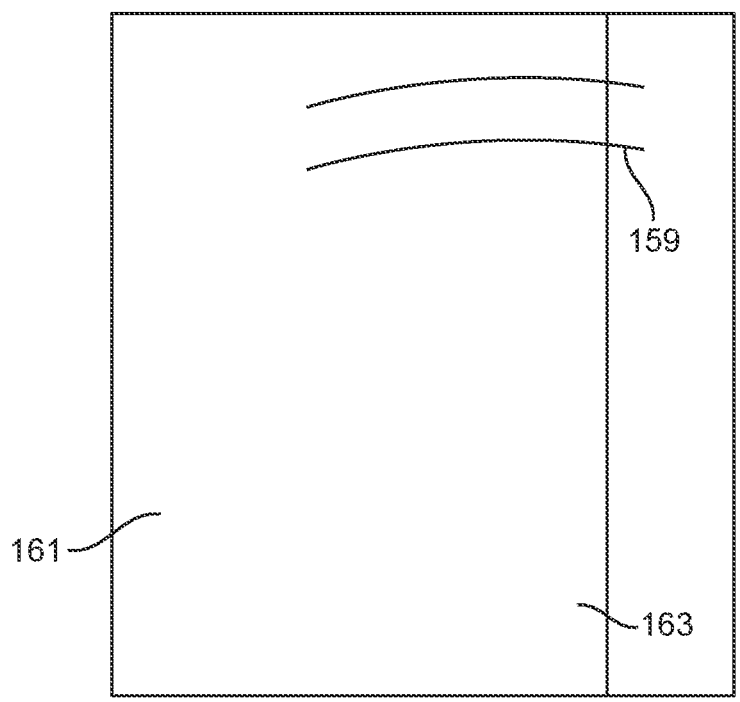
FIG. 44 illustrates a top view of an embodiment of a used needle holder.
Figure 45:
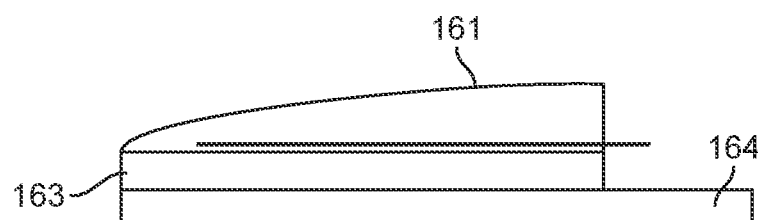
FIG. 45 illustrates a side view of an embodiment of a used needle holder.

FIG. 44 illustrates a top view and FIG. 45 illustrates a side view of an embodiment of a used needle holder having a tapered needle receptacle 161 and a permanent magnet 163 mounted on a base 164. The needles 104 are held at a proximal end with a needle driver and the surgeon can place the tips of the used needles 104 into the side opening of the used needle holder. The needles 104 can be placed flat against the permanent magnet 163. The magnet 163 can provide a raised needle holder surface so that the proximal end can be held until the needle 104 is held flat against the permanent magnet 163. The surgeon can then release the needle 104 knowing that the used needle 104 is securely in the used needle holder 161. The used needle holder 161 can be constructed of clear plastic so that the number of used needles 104 in the used needle holder 161 can be seen and counted.

Figure 46:
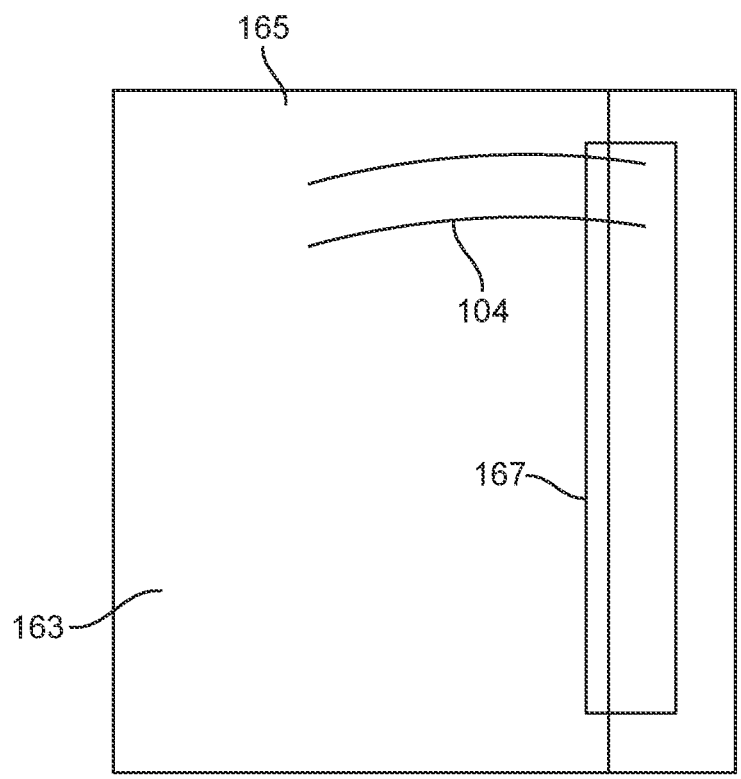
FIG. 46 illustrates a top view of an embodiment of a used needle holder.
Figure 47:
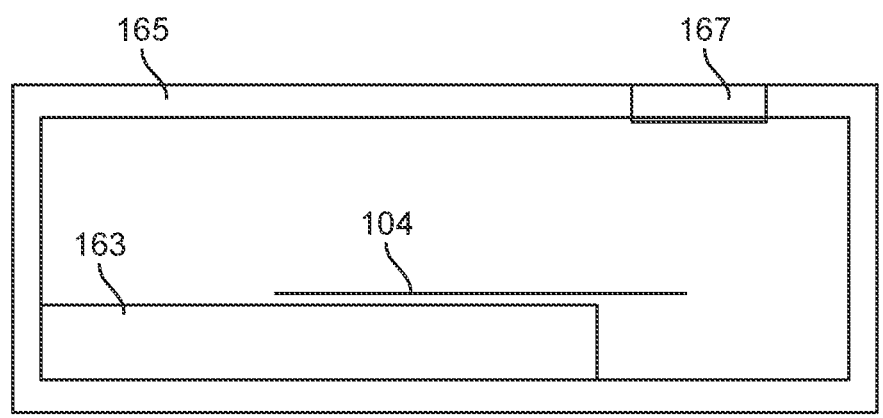
FIG. 47 illustrates a side view of an embodiment of a used needle holder.

FIG. 46 illustrates a top view and FIG. 47 illustrates a side view of another embodiment of a used needle holder 165. The needle holder 165 can include a housing that has an interior volume and a needle slot. The surgeon can align the used needle 104 with the slot 167 and insert the needle 104 into the housing with the needle driver approximately perpendicular to the length of the slot 167. The surgeon can then rotate the used needle 104 so that it is out of alignment with the slot 167 and place the needle 104 against a permanent magnet 163 within the housing. The magnet 163 can provide a raised needle holder surface so that the proximal end can be held until the needle 104 is held flat against the permanent magnet 163. The surgeon can then release the used needle 104 and remove the needle driver. The used needle 104 will be held against the permanent magnet 163 and even if the needle 104 comes loose it will be held within the needle holder 165 housing.

In an embodiment, a platform can be used by the surgeon to hold tools, sutures, needles, suture packs, sharps container, etc. The platform can be secured to a forearm and/or hand and/or forearm and/or fingers on one or more dorsum surfaces of the surgeon so that the objects can be easily accessed without the need for any interaction with anyone else such as a scrub technician. Thus, when using the platform, the surgeon does not need to interact with anyone else. The surgeon can remove objects from the platform that are needed and place and store objects on the platform that are no longer needed. The elimination of interaction between multiple individuals to handle the sharp objects simplifies the surgical procedure and reduces the chances of cuts or other injuries such as lacerations, punctures, abrasion, break in the skin, etc.

Figure 48:
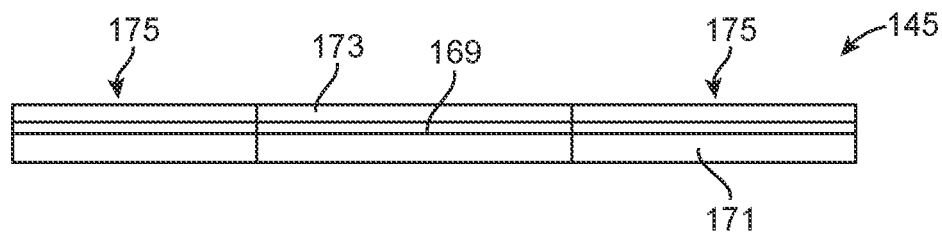
FIG. 48 illustrates a front view of an embodiment of a multi-layer platform.
Figure 49:
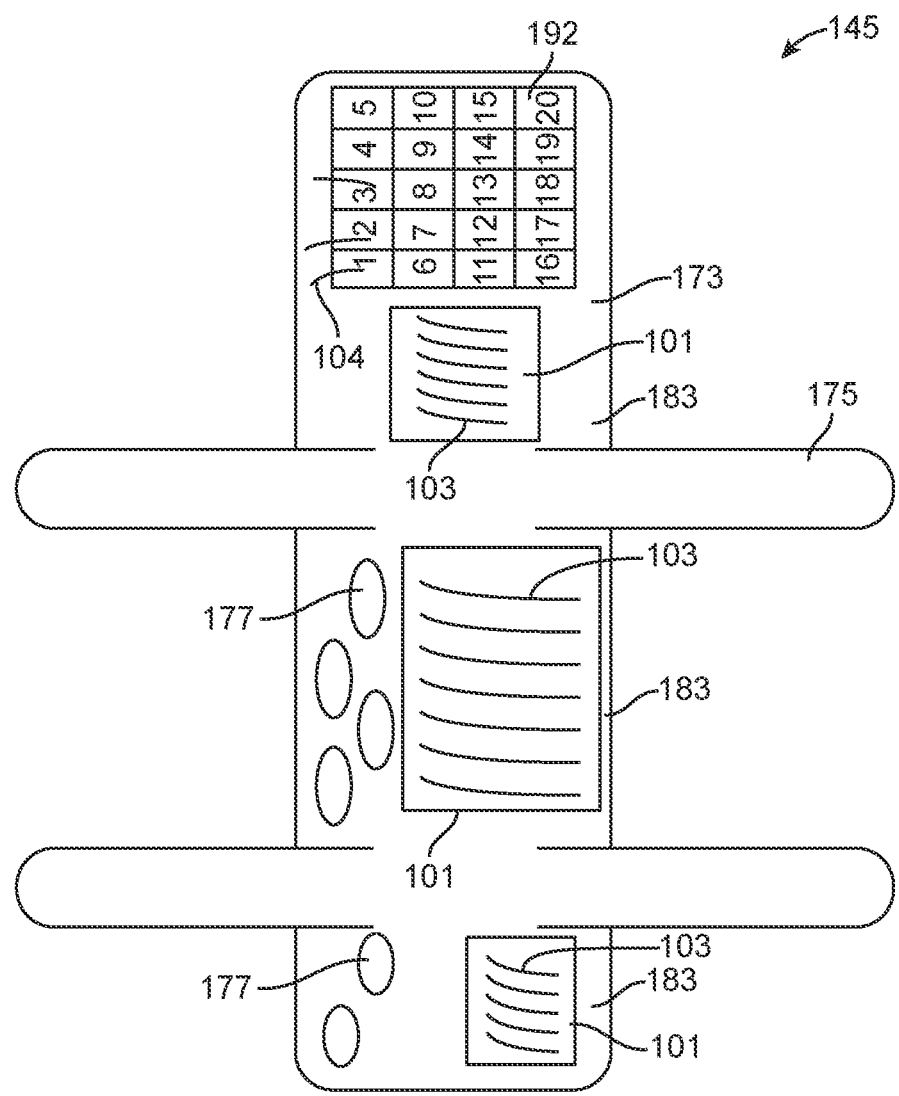
FIG. 49 illustrates an embodiments of a platform holding a plurality of suture packs, a used suture needle receptacle and tool holders.
Figure 50:
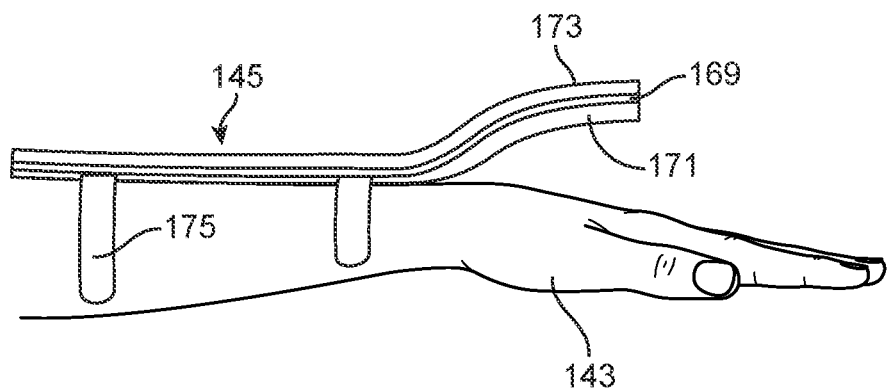
FIGS. 50-52 illustrate side views of different embodiments of multi-layer platforms.
Figure 51:
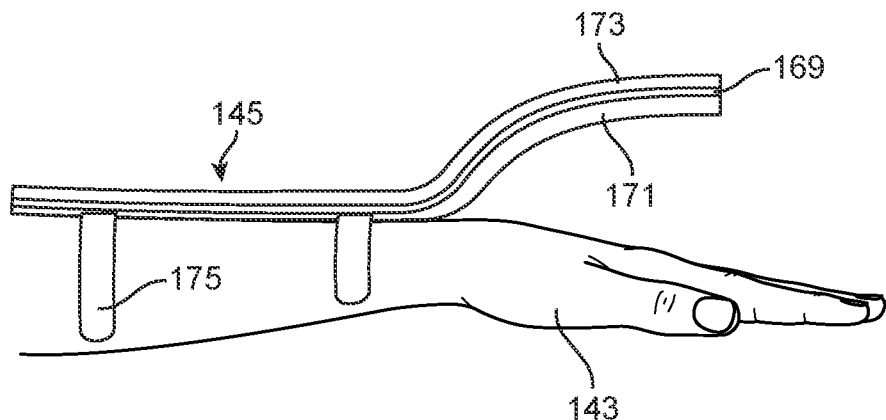
Figure 52:
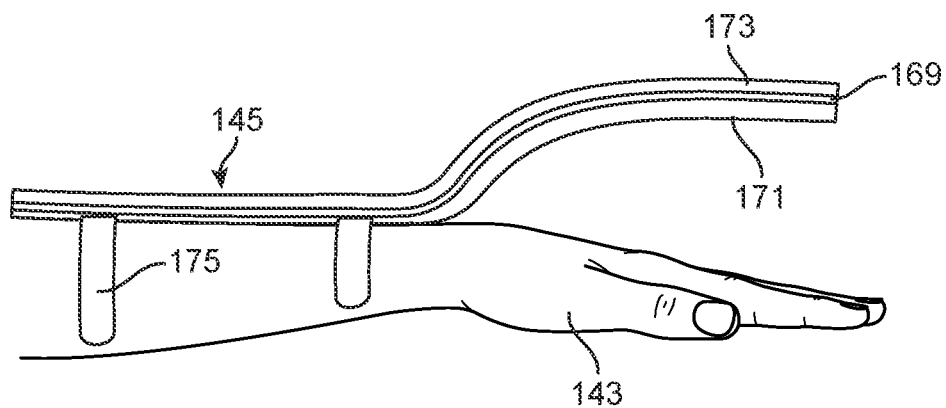

In an embodiment with reference to FIGS. 48 and 49, the inventive platform 145 can have a multi-layered construction. The main structural element can be a structural layer 169 which can be malleable and may also function as a barrier. The ability to plastically deform the structural layer 169 can allow the surgeon to easily adjust the shape of the platform 145 to provide any desired fit and configuration. An example of a suitable structural layer 169 material can be aluminum and aluminum alloys which provides a durable, lightweight, ductile and malleable metal material. The thickness of the aluminum structural layer 169 can be between about 0.01 and 0.10 inches. Any portion of the aluminum structural layer 169 can be easily bent by hand into the desired shape resulting in plastic deformation so the structural layer 169 will retain the bent shape. In other embodiments, any other material that has similar characteristics can be used.

In addition to providing a stable platform 145 for tools and objects, the structural layer 169 can also provide a protective barrier for the surgeon from sharp objects. If a surgeon accidentally directs a sharp object towards the dorsum of the forearm, the structural layer 169 of the platform 145 will block the sharp object and prevent any injury to the portions of the forearm and wrist and hand covered by the platform 145. Aluminum is a material that is softer than steel. Thus, a tool or sharp object that is pressed against the structural layer 169 will tend to not be scratched or otherwise damaged by the contact with the softer structural layer 169 material.

FIG. 48 illustrates a side view of a multi-layer platform 145. A lower or inner surface of the structural layer 169 can be bonded to an inner elastic foam layer 171. When the platform 145 is attached to the forearm of the surgeon, the inner foam layer 171 can be placed on the forearm and hand dorsum of the surgeon. The inner foam layer 171 can have a porous open cell structure. Because the foam does not contain gas bubbles, it can be more compressible than closed cell foams. However, both closed and open cell foams can be used. The inner foam layer 171 can provide improved comfort and conformability. The elasticity of the inner foam layer 171 allows the structural layer to be bent as described above. A suitable inner foam material is natural rubber latex.

As shown in FIGS. 48 and 49, the structural layer 169 can include bendable legs 175 that extend outward from the sides of the platform 145. These legs 175 can be bent to wrap around the forearm of the surgeon. The inner foam layer 171 provides a conforming fit to variable anatomy that is securely attached to the forearm. The inner foam layer 171 also provides a comfortable padded surface that disperses the compressive forces of the legs on the forearm. Because the malleable structural layer 169 is plastically deformed to any shape, the legs of the platform 145 can be accurately fitted to any forearm. Because there can be various configurations and sizes that best suit specific applications, the size and shape of the platform 145 can be any suitable dimensions. The inventive platform is not limited to the illustrated embodiments.

Figure 53:
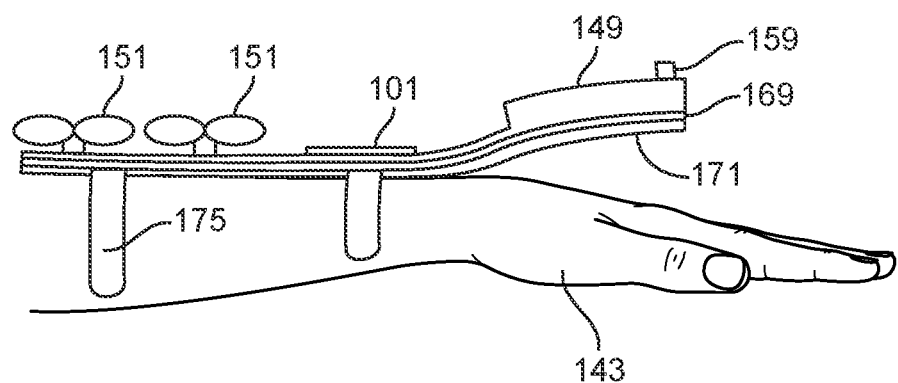
FIG. 53 illustrates a side view of an embodiment of a multi-layer platform having modular attachments.

With reference to FIGS. 50-53, various shape multi-layer embodiments of the platform 145 are illustrated. These multi-layer platforms 145 include a structural layer 169 secured to an inner layer 171 and an outer layer 173. Legs 175 can extend from the platforms 145 and wrap around the surgeon's arm 143. In the illustrated embodiments, the surface area and shape of the platform 145 over the hand portion of the arm 143 can vary dramatically. The inventive platform 145 is not limited to the illustrated embodiments. With reference to FIG. 53, the multi-layer platform 145 with legs 175, an inner layer 171, a structural layer 169 and an outer layer 173. The platform 145 is illustrated with a tool holder for holding tools 151, suture pack holder for holding suture packs 101 and a used needle holder 149 for holding used needles 104.

Although the inner elastic foam layer has been described as being bonded to the structural layer, there can be portions of the inner foam layer that are not bonded to the structural layer. For example, in some embodiments, the platform can include tool holders that are located at holes formed in the structural layer. The tools such as needle drivers can be placed in the holes with the thin body of the needle driver distal to the tool finger holes. The thin body can be placed through the hole while the handle finger holes of the needle driver cannot pass through the hole because it is wider than the diameter of the hole. Thus, the handle will hold the tool in place and prevent it from passing completely through the hole. The holes can be oriented such as to properly orient the tools for easy grasping by the contralateral hand. For example the holes may be oriented as slots with the long axis parallel or at a specific angle to the long axis of the forearm such that the finger loops of the needle holder can be easily grasped by the contralateral hand without the need for contralateral forearm motion. In an embodiment, the tools are held in the tool holders of the platform with the structural layer between the center of gravity of the tool and the handle or finger hole portion of the tool. As discussed, the inner and/or outer foam layers that are bonded to the structural layer can provide friction which can prevent the movement of the tool. Thus, the tools can be held in the tool holders by a combination of gravity and friction.

Figure 54:
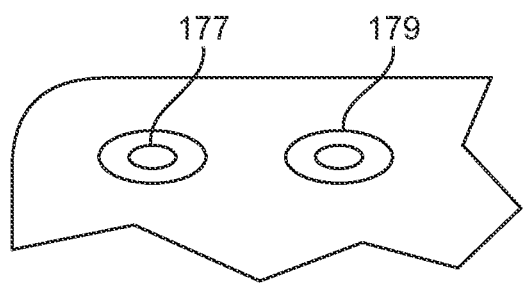
FIGS. 54-57 illustrate top views of embodiments of tool holders on multi-layer platforms.

In some embodiments, the upper and lower foam material adjacent to the holes is removed. However, in other embodiments, the foam layers can be left over the holes. For example with reference to FIG. 54, in the inner foam of the tool holder holes, a smaller hole 177 can be formed within an hole 179 in the barrier material. The tool can be pressed through the smaller hole 177 and because the inner foam is elastic, the smaller hole 177 can expand as the tool is pressed through the hole 177. The static friction of the expanded foam hole 177 circumference which is in tension against the sides of the tool can prevent accidental removal of the tool from the platform. The foam can also act as a dampening device that prevents the tools from knocking or sliding against the inner diameter of the hole 179 in the structural layer which can create noise and vibrations. This dampening feature can be important during delicate surgical procedures.

Figure 55:
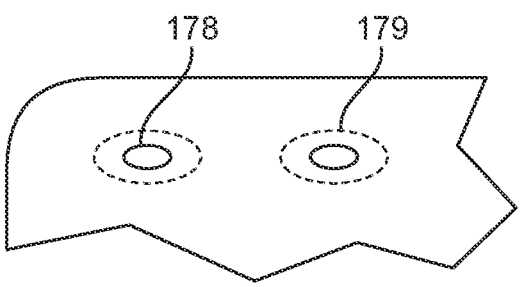
Figure 56:
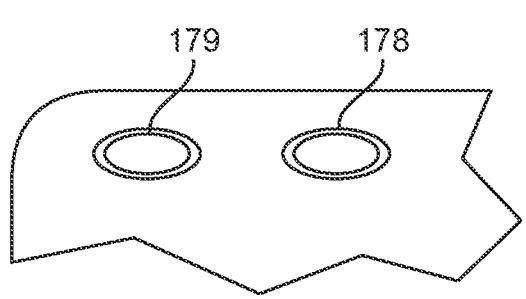
Figure 57:
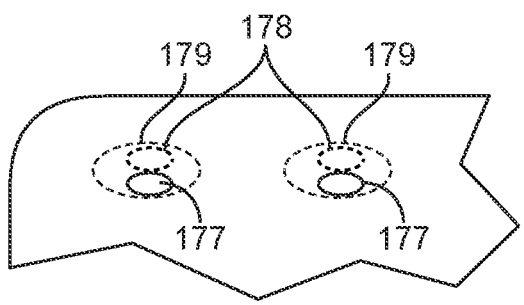

It is also possible to have a smaller hole 178 (FIG. 55) or larger hole 178 (FIG. 56) formed in the upper outer layer foam over the tool holes 179 in the barrier layer. Again, the upper layer foam can provide a friction force that can hold the tools in the tool holes 179. In yet other embodiments with reference to FIG. 57, the upper and lower foam layers may have smaller holes 177, 178 that are not aligned with each other. By offsetting the alignment the foam layers can cause the tools to be angled relative to the platform. This can provide more clearance so the ends of the tools are not rubbing against the forearm of the surgeon.

In other embodiments the inventive surgical platform can include another outer elastic foam layer that is bonded to the outer surface of the structural layer opposite the inner surface. The outer foam layer can have different physical properties than the inner foam layer. As discussed above, the platform can be used to hold tools, sutures, suture packs, needles, sharps containers, etc. The sharps containers can include various embodiments including: sponges, enclosures, magnetized surfaces and/or combinations of different embodiments. In an embodiment the outer foam layer can have physical characteristics that will improve the connection between the objects and the platform. For example, the outer surface of the outer foam layer can have a greater surface area for better anti-slip surface that provides a high static coefficient of friction with the objects that effectively grip the contact surfaces of the object.

In an embodiment with reference to FIGS. 58-63, the structural layer 169 can have tabs 181 that can be bent upward from the plane of the structural layer 169. An object 108 such as a suture pack can be placed adjacent to one or more of the tabs 181 and the tabs 181 can be bent over an exposed surface of the object 108 to hold the object 108 against an edge of the outer foam layer 173. As discussed, the malleable structural layer 169 material may be plastically deformed and the bent tabs 181 can hold the object 108 against the platform 145. The horizontal force of the tab 181 against the object 108 can cause a compressive force between the object 108 and the outer foam layer 173 as shown in FIG. 64.

It can be very important to hold objects 108 in a secure manner to the platform 145. In an embodiment, the outer foam layer 173 can be a high friction material that prevents or resists movement between the object 108 and the outer layer 173. The friction force between the objects 108 and the outer surface of the outer foam layer 173 can be described or quantified based upon the static coefficient of friction (COF), which can be symbolized by the Greek letter µs. The static COF is a dimensionless scalar value that describes the ratio of the force of friction between two bodies and the force pressing them together. The coefficient of friction depends on the materials used. For example, slippery materials such as Teflon on smooth surfaces can have a low coefficient of friction, while rubber on a suture package surface can have a higher coefficient of friction. Coefficients of friction range from near zero to greater than one. In an embodiment, the static coefficient of friction between the outer surface of the outer layer 173 of foam and the object 108 coupled to the platform is greater than 0.3. The friction force is quantified by the static friction=µs×compression force.

The compression force can be applied by a clamp, a tab 181, elastic material, a clip, a spring and/or any other suitable mechanical device. The compression force can also be provided by the foam. The compression force can be stored in the foam material by manually bending the tab 181 over and onto the suture packet. The compressed foam will try to expand and this foam expansion force can help to hold the suture packet in place. The compression force can prevent any vertical movement of the suture packet and the friction force can prevent any horizontal movement relative to the platform surface. In an embodiment, the compression mechanism is attached to the platform and applies a force to compress the object against the outer foam layer. The compressive force results in a friction force that prevents a sliding movement of the object over the surface of the outer foam layer.

With reference to FIG. 49, in an embodiment, the outer foam material 173 can provide a functional structure. For example, after needles are used they must be stored and accounted for. In an embodiment, a portion such as the used suture needle region 192 of the outer foam 173 can be marked with individual needle regions. Each of the individual needle regions can be marked with a number 259 and adjacent needle regions can be marked with sequential numbers 259. As the needles 103 are used, the surgeon can place the used needles 104 in the used needle region 192. A first used needle 104 can be placed in a region marked 1, a second used needle 104 can be placed in a region marked 2, etc. The outer foam 173 can be made of a thick material that allows the needles 104 to be securely captured until the surgical procedure is completed. Because the needles 104 are placed in numbered 259 regions, it is easy to visually account for all needles 104 used during the surgery by simply looking at the numbers 259 in the used needle regions 192.

The described sharps container 255 can provide various benefits to the users. The sharps container 255 is easily accessed and secured to any portion of the platform 145 over the forearm and hand. The used needles 104 are highly visible in the repository for easy used needle 104 counting. The demarcations can assist in the counting of the used needles 104. The foam 173 in the sharps container securely holds the tips of the needles 104. The tips are also adjacent to the structural layer 169 and cannot cause damage even if the needles 104 are accidentally contacted or pressed further into the foam 173. The used needles 104 can be secured, treated and maintained in control of the surgeon until a "group transfer" occurs. More specifically, the used needles 104 are secured to the sharps container 255. The used needles 104 can also be treated by mechanically cleaning the distal portions and chemically disinfected. The securing of the used needles 104 can be in constant contact and can be maintained in control of the surgeon until a "group transfer" occurs. The "group transfer" can include the transfer of a group of surgical tools from the surgeon to the scrub tech. The surgical tools in the group transfer can include: the needle driver, the forceps, the used sharps container, the sharps container and other objects.

In an embodiment, outer foam layer 173 can include different areas that have different physical properties. For example, first area may be designed to support suture packs 101 and a second area may be designed to function as a sharps container 255 as described above. The first area that supports the suture packs 101 can be made of a thinner less elastic foam material with a higher COF exposed surface than the second area. The suture packs 101 can be compressed against the first area and the high COF can prevent movement of the suture packs. This feature can be important because the surgeon must manually place the proximal ends of the needles 103 in needle driver. Any unwanted movement of the needles 103 can make this task more difficult.

Figure 58:
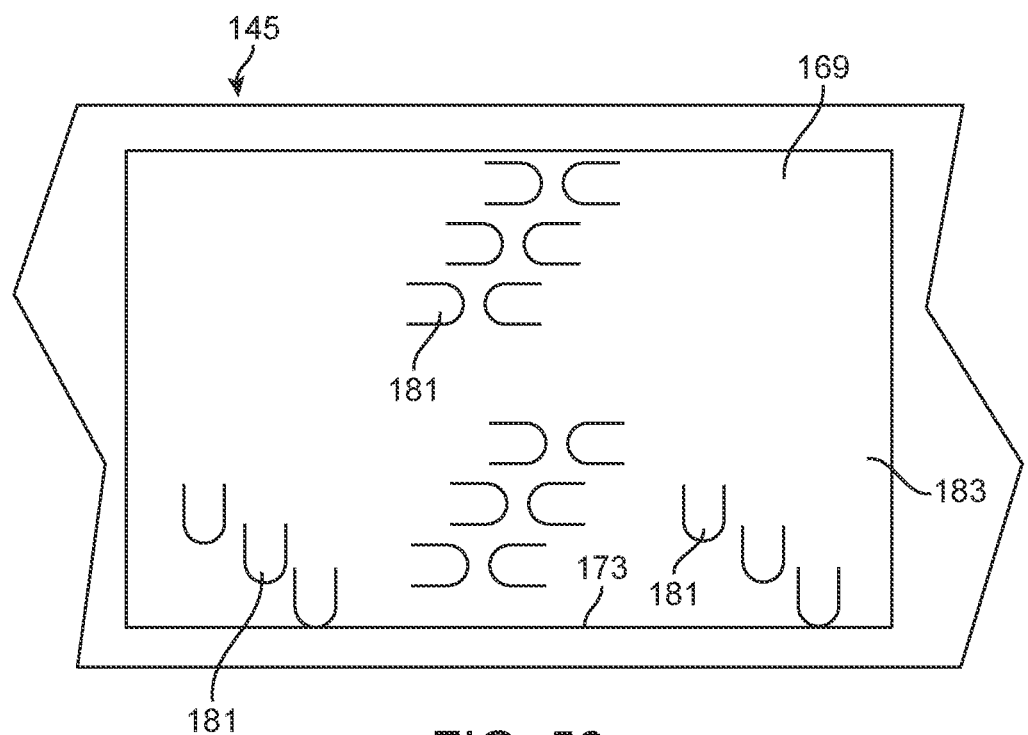
FIGS. 58 and 59 illustrate a top view of an embodiment of a suture pack carrier on a multi-layer platform.
Figure 59:
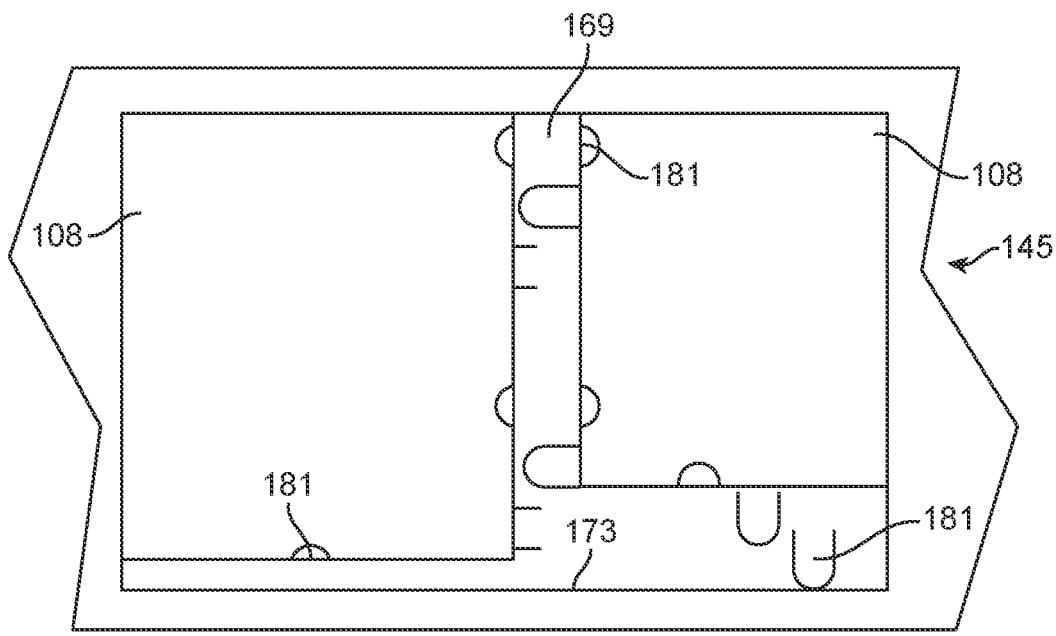

With reference to FIGS. 58-59 in an embodiment, the structural layer can have one or more tabs 181 that can be used to secure objects to the platform 145. The outer foam layer 173 can be removed from the structural layer 169 which can be exposed. Bendable tabs 181 can be formed in a suture pack carrier 183 area of the exposed structural layer 169. These bendable tabs 181 can be cut in the structural layer 169 and can remain planar with the structural layer 169 before being used. The tabs 181 can be arranged in a staggered manner so that objects such as suture packs can be secured to the suture pack carrier 183 area of the structural layer 169 with the tabs 181 that most closely fit the objects.

FIG. 58 illustrates a suture pack carrier 183 before suture packs 101 are secured and FIG. 59 illustrates a suture pack carrier 183 after suture packs 101 have been secured. For example, a suture pack or suture packs 101 may be substantially planar rectangular structures that are held to the platform with the tabs 181. The suture packs 101 can be placed on the platform 145 and the tabs 181 can be bent up and over one more side edges of the suture packs 101. The suture packs 101 can come in various different sizes. Thus, the suture pack carrier 183 on the platform 145 can have multiple tabs 181 can be set in different locations to accommodate the variety of suture pack 101 sizes.

Figure 60:
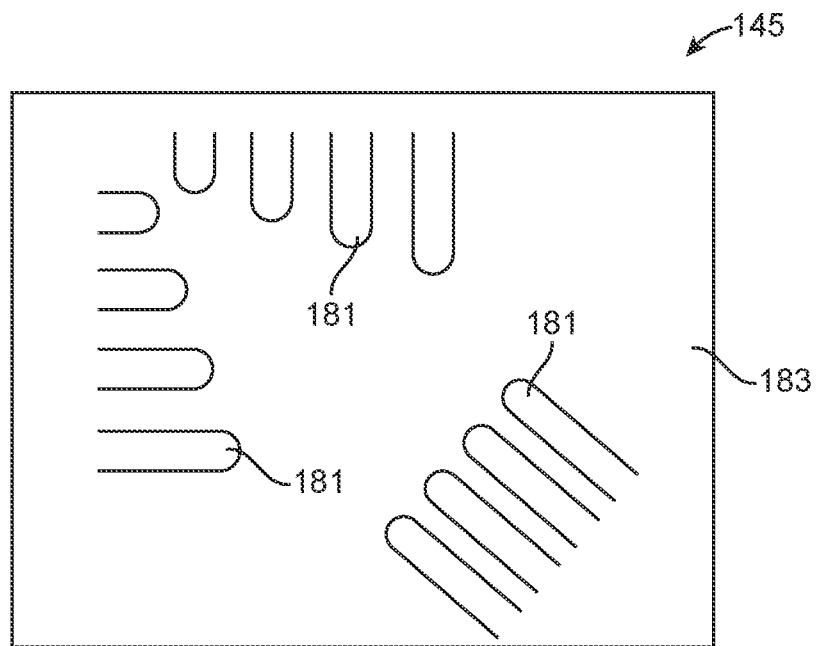
FIGS. 60-63 illustrate top views of an embodiment of a suture pack carrier for holding multiple stacked suture packs.
Figure 61:
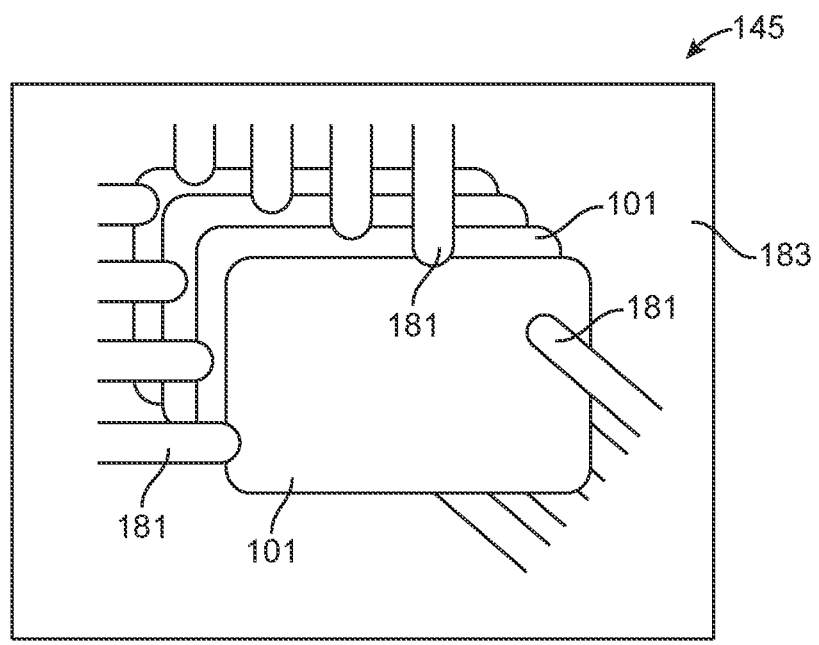
Figure 62:
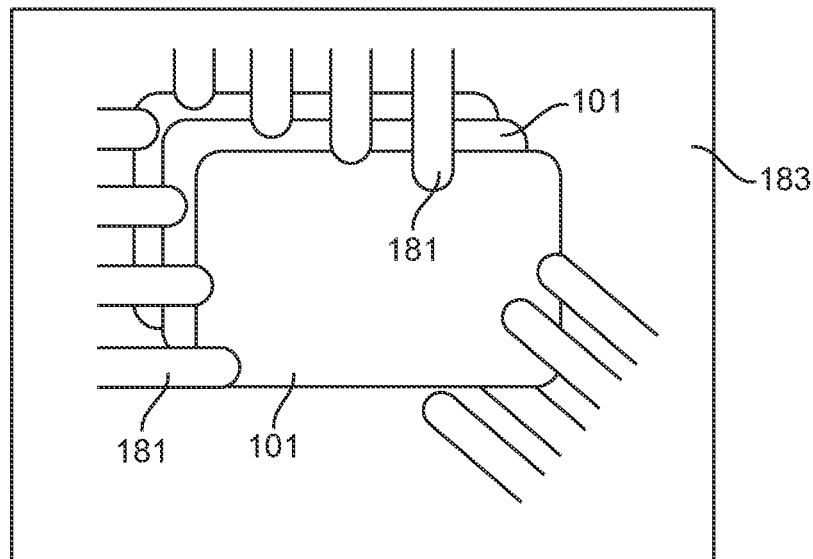
Figure 63:
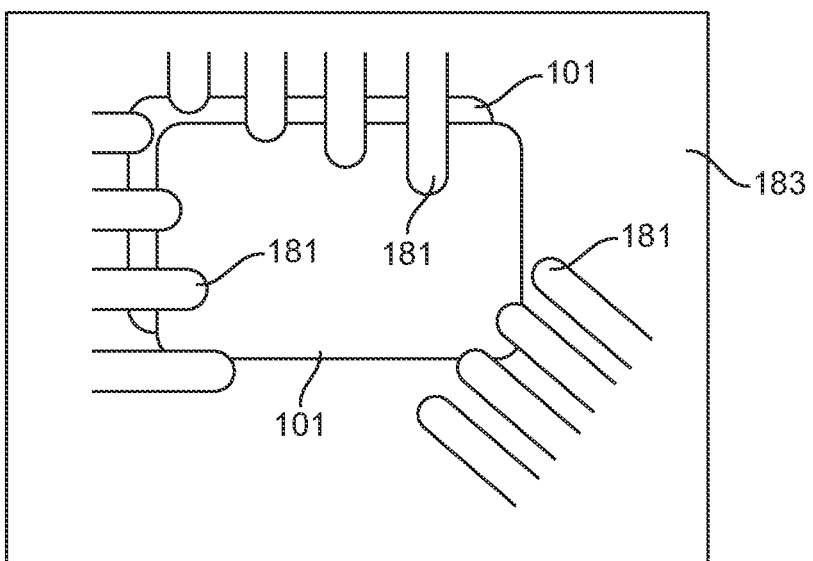
Figure 64:
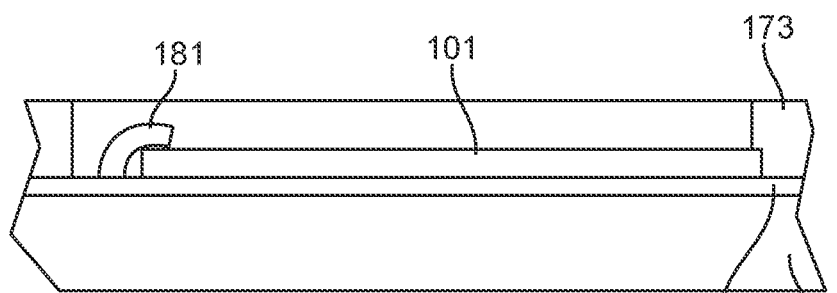
FIGS. 64-67 illustrate side views of embodiments of suture pack carriers on multi-layer platforms.

With reference to FIGS. 60-63 in other embodiments, multiple suture packets 101 can be stacked over the same suture packet carrier 183. FIG. 60 illustrates a suture pack carrier 183 before suture packs 101 are secured and FIG. 61 illustrates a suture pack carrier 183 after multiple layers of suture packs 101 have been secured. FIG. 62-63 illustrate a suture pack carrier 183 after multiple layers of suture packs 101 have been secured and some suture packs 101 have been removed. Different tabs 181 can be used to hold each of the layered suture packets 101. After all needles 103 of a suture packet are removed, the suture packet 101 can be removed to expose the underlying suture packet 101. In a preferred embodiment, the surgeon can grasp a side of upper depleted suture packet 101 with the needle driver and remove it from the suture packet carrier 183. The underlying suture packet 101 will then be exposed and the needles 103 will be accessible to the surgeon. This process can be repeated until the bottom suture packet 101 is exposed and all necessary needles 103 are used by the surgeon.

In the illustrated embodiment, the tabs 181 hold one or more of the suture packs 101 to the platform 145. Some of the tabs 181 are oriented to be substantially perpendicular to the edges of the suture packets 101 while other tabs 181 can be oriented at various other angles. In the illustrations, the tabs 181 on the lower right are oriented to be about 45 degrees to the side edges of the suture packets 101.

In an embodiment, the multi-layer platform can have a suture pack carrier. FIGS. 64-67 illustrates side views of various suture pack carriers 183. With reference to FIG. 64, the upper foam layer 173 can be partially removed from some areas of the platform which can expose the structural layer 169. The objects, such as a suture pack 101, can be pressed against the edges of the upper foam layer 173. This force on the object can compress the object into side of the upper layer foam 173. The compression force creates a friction force that can hold the edge of the object to the platform adjacent to the structural layer 169. One or more sides of the object can be compressed into different surfaces of the upper foam layer 173. One or more tabs 181 can be secured over the sides of the object opposite the side of the object pressed into the upper layer foam 173.

In the illustrated embodiments, the suture pack retaining structures can adapt to wide range of suture pack 101 sizes. Suture packs 101 can vary in size from about 1"×3" to about 3"×4". The suture packs 101 can have a "flat" conformation. The tabs 181 can provide an easy and secure system for attaching or locking the suture packs 101 onto the barrier platform. The platform can accommodate multiple suture packs 101 and the packs can also be easily removed from the platform.

Figure 65:
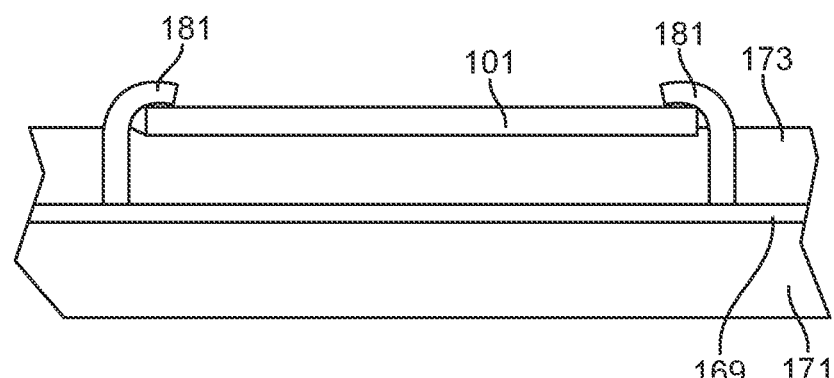
Figure 66:
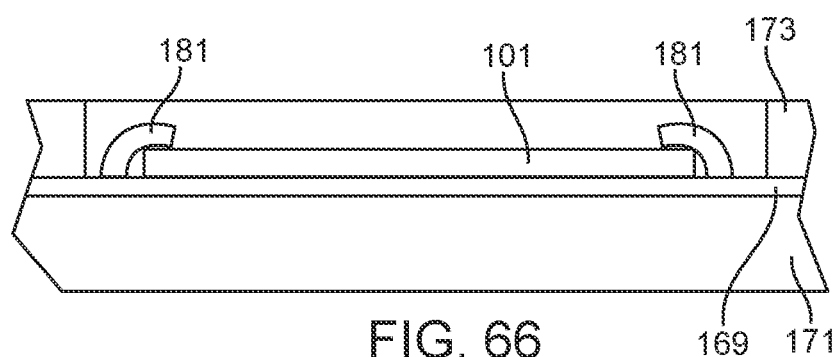

With reference to FIG. 65, in an embodiment, the tabs 181 can extend through the upper foam layer 173. The suture pack 101 can be placed between the tabs 181 and the ends are bent over the edges of the suture pack 101 to hold it against the upper foam layer 173. With reference to FIG. 66, in an embodiment, the upper foam layer 173 can be partially removed. Tabs 181 can be wrapped over the edges of the suture pack 101 to hold it against the structural layer 169.

Figure 67:
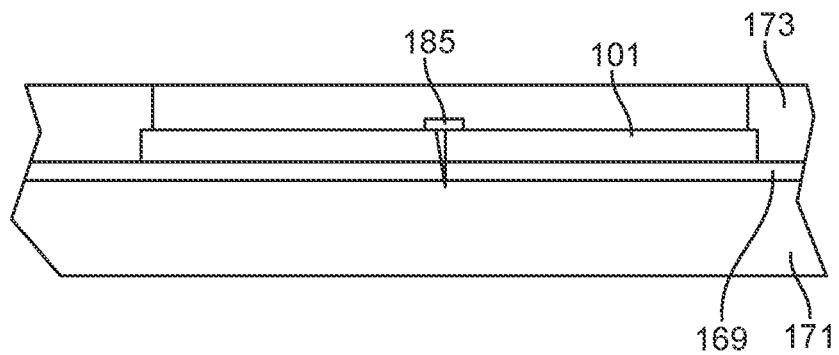
Figure 68:
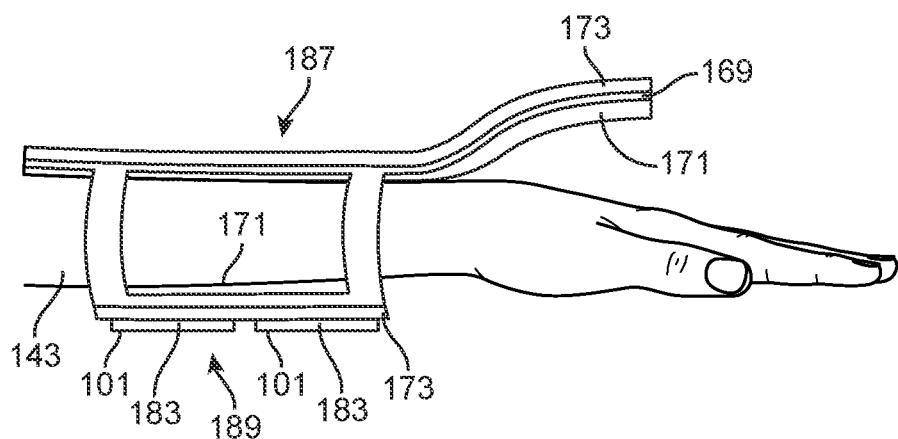
FIGS. 68-70 illustrate side views of embodiments of multi-layer apparatus that include a dorsum platform and a volar platform.
Figure 69:
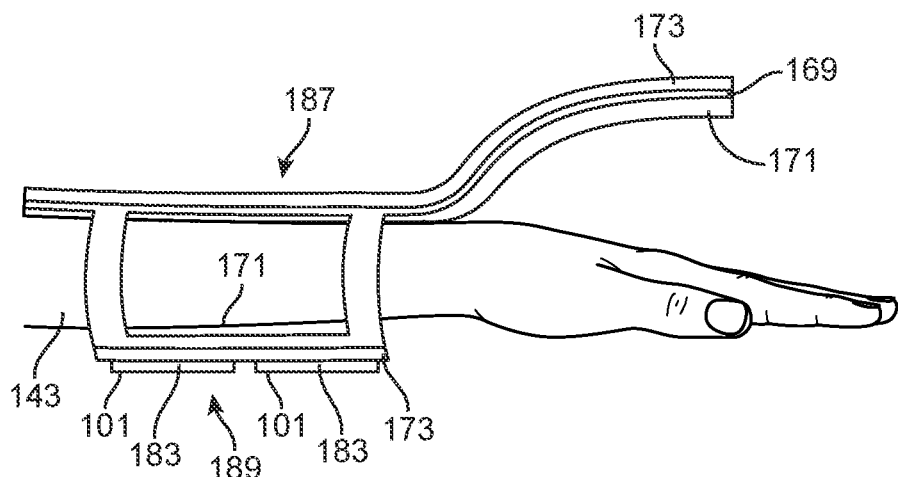
Figure 70:
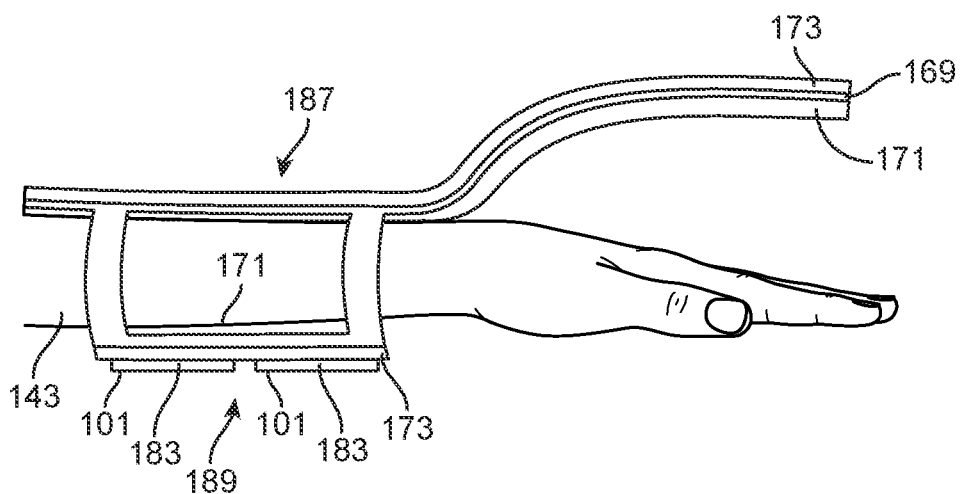
Figure 71:
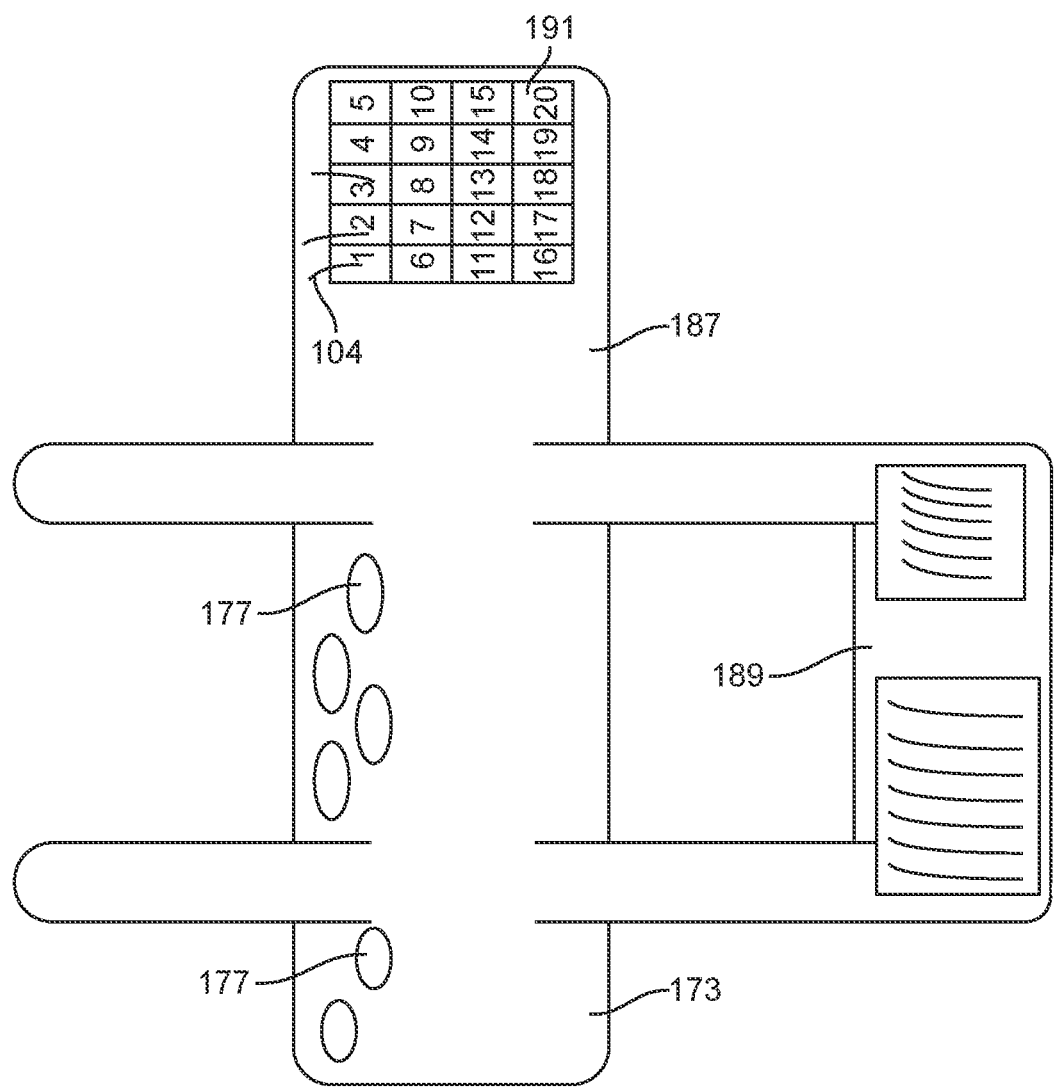
FIG. 71 illustrates a top view of an embodiment of a multi-layer apparatus that include a dorsum platform and a volar platform.

With reference to FIG. 67, in yet another embodiment, holes that are slightly smaller than the perimeter shape of the suture packs 101 are formed in the upper foam layer 173. The suture packs 101 can be pressed into the holes until they are against the structural layer 169 or the lower surface of the hole. The compression of the suture packs 101 may cause them to bow upward. In order to prevent this motion, fasteners 185 can be placed in a center portion of the suture pack 101 to hold it in place. In other embodiments, where the suture pack 101 is made of a stronger material that does not deform under compression, the fastener 185 may not be necessary.

The inventive platform has been described with various system components: tool holders, tools, suture pack holders, suture packs, armed needles, used and sharps containers, all mounted on a platform. Although these components can be set at predetermined locations on the platform, in other embodiments, the inventive system can have a modular configuration. In these embodiments, the system components: tool holders, tools, suture pack holders, suture packs, armed needles 103, sharps container can be independent and modular. The user can mix and combine these individual components and place them in any desired positions on the apparatus and platform. The individual components can have various connection mechanisms such as: hook and loop (Velcro), snaps, tack features, screw fasteners, tabs, or any other suitable connection mechanisms such as elastic bands and adhesives. Once the surgical procedures are completed, the system components can be removed from the inventive platform. It may be possible to clean and sterilize the platform, attach new modular components and reuse the platform.

The present platform invention can address several operating room issues including improved safety and efficiency. As discussed, the structural layer of the platform can create a barrier that prevents needle sticks to forearm and dorsum of hand. Thus, both the surgeon's hand and forearm can be protected. The platform can be held against the forearm but can be spaced away from the hand, which may allow for full movement of the surgeon's (wrist, hand, fingers) hand. The platform also does not interfere with the elbow range of motion.

The inventive platform system provides various benefits. The bendable legs allow the platform to adapt readily and securely to variable forearm sizes. The platform allows the surgical tools and needles to be oriented in any desired position. Ideally, the system can minimize unnecessary forearm motion. The suture pack(s) can be placed on any portion of the platform including the radial border of forearm and the volar forearm. The platform provides a protective barrier to the hand and forearm while still allowing full hand range of motion. The angle of the hand cover portion of the platform relative to forearm portion can be about 10-45 degrees. However, the hand element can be flexible and the angle and shape of the hand element can be adjusted to any desired shape. The inflection point may be: a living hinge, a mechanical hinge or any other suitable articulation movement mechanism.

Figure 88:
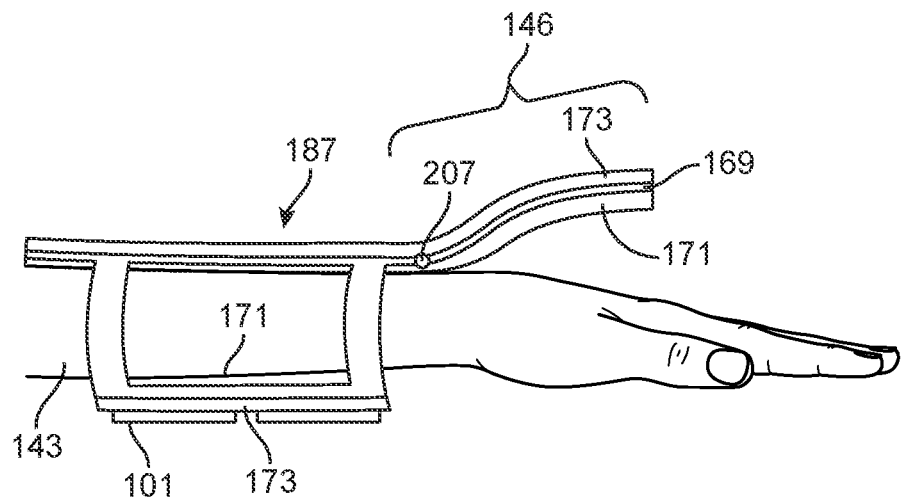
FIGS. 88 and 89 illustrate side views of an embodiment of a platform with an inflection point on an arm.
Figure 89:
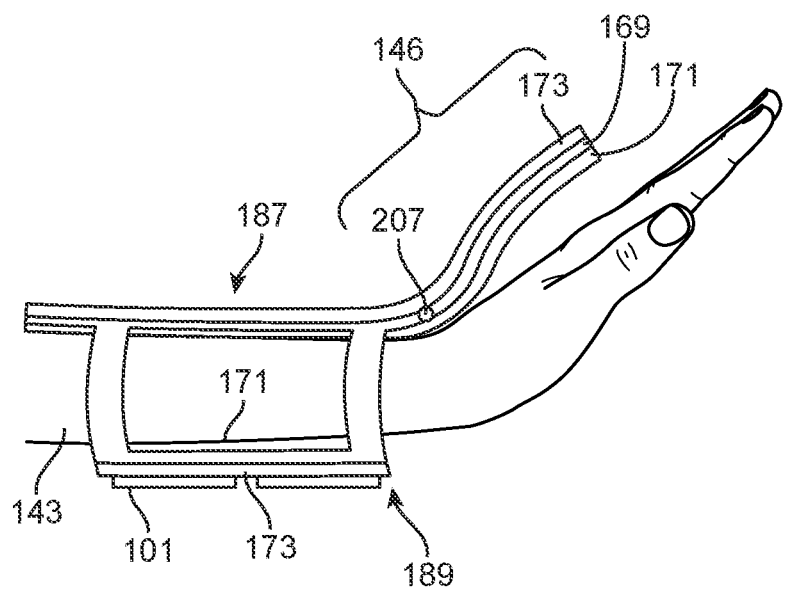

For example, with reference to FIGS. 88 and 89, a multi-layer platform is illustrated that includes a movable inflection point 207. When the hand is in a straight position, the platform can assume a normal shape. However, then the hand is moved up relative to the forearm, the hand can contact the bottom of the portion of the platform and the hand portion 146 of the platform can rotate with the hand as shown in FIG. 89.

In preferred embodiments, the sharps container can be physically adjacent to or in close proximity with the suture packet holder and the suture packets. The sharps container and the suture packets can be on the same support structure such as a platform. This configuration facilitates improved surgical work flow and condenses several complex coordinated motions into more streamlined simplified actions performed by the surgeon. As discussed, the platform with the suture packet holders secured to suture packets and the sharps container can be on the same platform apparatus mounted on a non-dominant arm of the surgeon. When a suture is required, the surgeon can grasp an armed needle having an attached suture from the suture packet and use the suture on the patient. When the stitch is completed, the surgeon can then place the used needle in the sharps container and then easily grasp a new armed needle from the suture packet.

Various sharps container designs can combine with the inventive system. In an embodiment, the sharps container can be a soft open or closed cell elastic material such as foam or a sponge which can be marked with a sequence of numbered regions. The used needles can be inserted into the soft cell material which will hold the used needles in place. In an embodiment, the sharps container cell material can be adjacent or bonded to one or more layers of a thin elastic homogeneous material such as a soft plastic or rubber that can be easily pierced by the used needles without substantially deforming the soft elastic cell material. The homogeneous material can provide a friction force that can increase the resistance to inserted needle movement that can further prevent the accidental removal of the used needles from the sharps container. It can also be easier to print the number markings on a solid rubber material than on a soft elastic cell material such as foam.

A potential problem with used needles is their ability to transmit viruses when a used needle accidentally breaks the skin on an operating room surgical member. However, if the used needle is cleaned and/or disinfected the used needles are much less likely to spread viruses. In yet another embodiment, the soft open or closed cell elastic material can be coated and/or saturated with a disinfectant such as bleach or other antimicrobial materials. The disinfectants can be in the form of a high viscosity gel that can be held within the foam material but will not easily be removed from the elastic cell material. In an embodiment, a portion or all of the soft open or closed cell elastic material of a sharps container can be surrounded by a layer(s) of the thin elastic homogeneous material in order to help retain a disinfectant liquid within the soft cell sharps container material (may need to elaborate, clarify).

Figure 102:
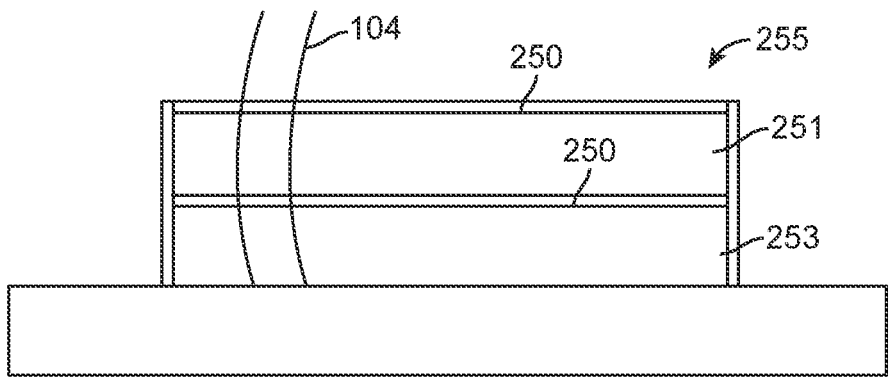
FIGS. 102 and 103 illustrate side views of embodiments of sharps containers with perpendicular orientation needles.
Figure 103:
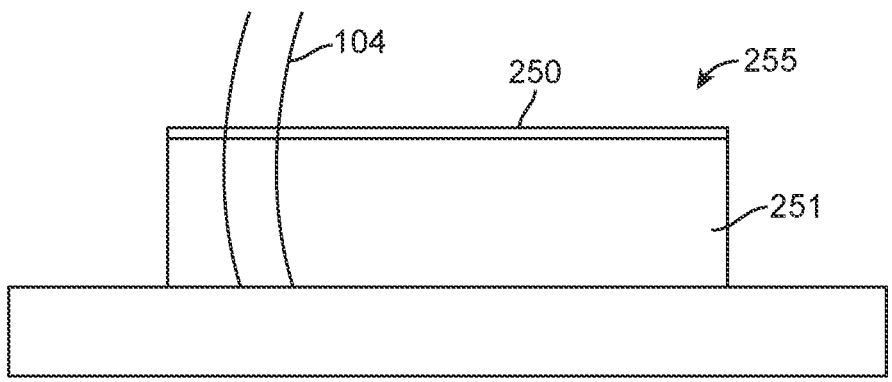

With reference to FIGS. 102, 103 the inventive system can clean and disinfect the used needles 104 as they are inserted into the soft open or closed cell elastic material 251, 253. As the used needles 104 pierce the soft cell material 251, 253 and/or the solid elastic material layer(s) 250, 252, that can be cleaned by wiping the outer surfaces against these materials. The used needles 104 can be disinfected when they are exposed to the disinfectant. Thus, if any of the used needles 104 are accidentally removed from the described sharps container 255, they are cleaned and disinfected and are much less likely to spread viruses.

With reference to FIGS. 96-99 in other embodiments, the sharps container 235 can include an enclosure having a door mechanism 237 that is opened to received used needles and closed to prevent used needles from exiting the sharps container 235. Different mechanisms can be used to control the position of the door 237. For example, in an embodiment, the position of the door 237 can be manually controlled with a switch mechanism. The door control mechanism can be coupled to a spring 245 which can hold the door 237 in the closed position and a manual actuator such as a lever 243. When user presses against the lever 243, the spring 245 can be compressed and the door(s) 237 can be open. The user can drop the used needles into the repository and the release the lever 243 to close the door 237.

In the illustrated embodiment, the door 237 mechanism is coupled to a pair of rotational members 246 on opposite sides of the sharps container 235. A lever 243 can extend away from the receptacle housing. When no force is applied to the lever 243, a torsional spring 245 or any other suitable spring mechanism can exert a counter clockwise torque about one or both of the rotational members 246. This torque can hold the door 237 in the closed position against a stop 247. When a downward force is applied to the lever 243, a clockwise torsional force can be applied to the door 237 mechanism that is greater than the counter clockwise spring 245 force. The door 237 mechanism can rotate clockwise and open to allow used needles 104 to be deposited in the receptacle 235. Once the used needle 104 is captured, the use can release the lever 243 and the door 237 can return to the closed position against the stop 247.

The manually controlled door configuration can allow the user to carefully control the door 237 to prevent used needles from escaping the sharps container 235. The repository housing can include an opening at the top surface and the door 237 mechanism can be mounted on two rotational members 246 on opposite sides of the housing that define a rotational axis. The doors 237 can be above the rotational axis 246 and a spring 245 can normally hold the door 237 in a closed position against a rotational stop 247. The lever 243 can be coupled to the door 237 mechanism and exit a side of the housing that is easily accessible to the user such as the side of the housing closest to the user. Actuating the lever 243 can cause the door 237 mechanism to rotate about the rotational axis and open. When the lever 243 is released, the spring 245 will rotate the door 237 mechanism back to the closed position.

Figure 100:
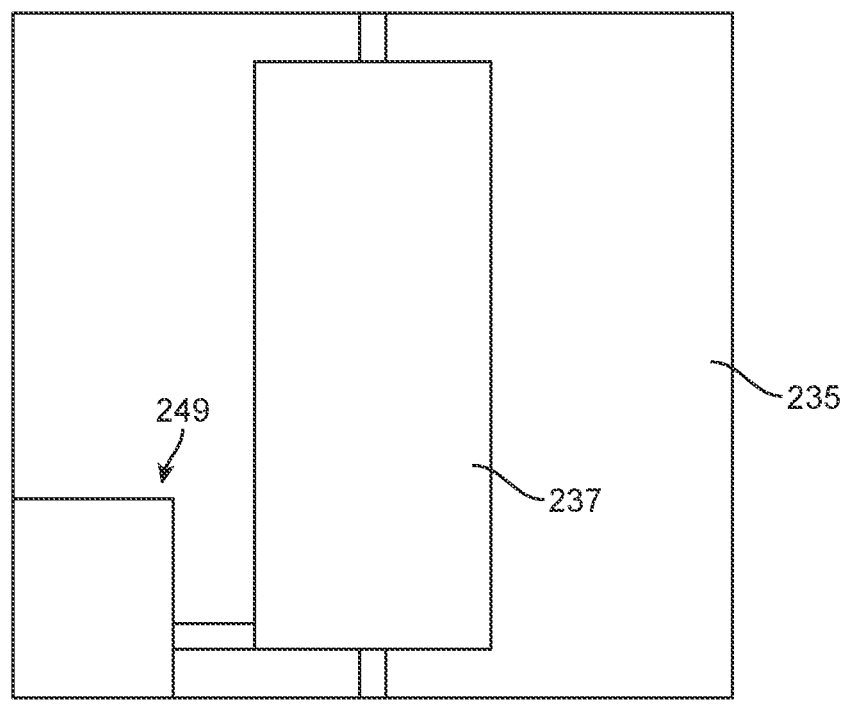
FIG. 100 illustrates a top view of an embodiment of a repository housing.
Figure 101:
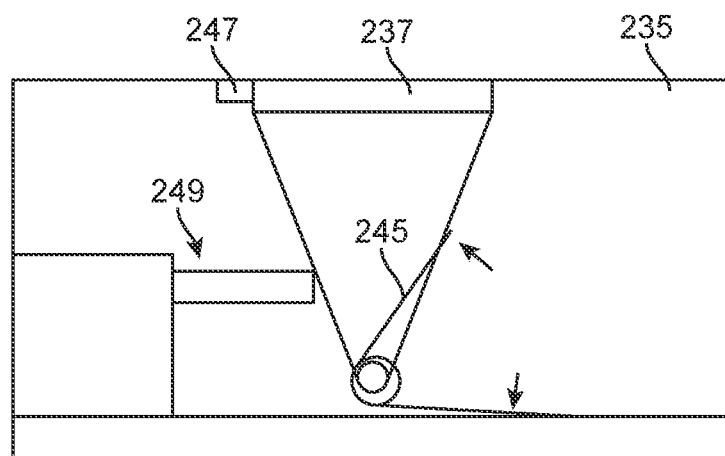
FIG. 101 illustrates a side view of an embodiment of a repository housing.

With reference to FIGS. 100 and 101 in an embodiment, the door 237 can be coupled to an automatic control system 249 which includes an accelerometer(s), a processor, a power supply and an actuator. The accelerometer(s) can detect the orientation of the needle receptacle 235 based upon the gravitational forces. When the accelerometers detect that the needle receptacle 235 is substantially upright in position, the processor can control the actuator to open the door 237 and when the needle receptacle is not properly oriented, the processor control the actuator to close the door 237. In an embodiment, the system can be programmed or set to open the door 237 at a specific range of orientations that can correspond to the optimum limb or tool positions which can allow for the needle to be dropped into the receptacle 235. The system can also detect abnormal situations which can indicate an accident. For example, if the detected acceleration is significantly greater than the gravitational force, the system can interpret this as an accidental impact with the sharps container and the processor can control the actuator to close the door 237.

Alternatively the position of the door can be automatically controlled by gravity. When the sharps container is used on a forearm-mounted platform, the door can be at the top of the repository and open when the repository is in an upright position. However, when the sharps container is rotated, the doors can close to prevent used needles from exiting.

FIGS. 92-95 in an embodiment, the repository housing 235 can include an opening at the top surface. The door 237 mechanism can be mounted on two rotational members 246 on opposite sides of the repository housing 235 that define a rotational axis. The doors 237 can be above the rotational axis and a counter weight(s) 239 below the rotational axis. The door 237 mechanism can open when the repository housing 235 is upright relative to the rotational axis within a range of about 0 to 30 degrees. At rotational positions greater than 30 degrees or more away from vertical alignment, the doors 237 can close to prevent used needles 104 from escaping the repository 235. In use, the repository 235 can be vertically oriented relative to the rotational axis to open the door and the used needle 104 can be dropped in the repository 235 through the open door 237. The surgeon can then rotate the forearm out of vertical alignment to close the door 237 and grasp a new needle from the suture packet. The process can be repeated after the needle is used.

Because the suture packets and the sharps container are in close proximity, the surgeon's movement of releasing a used needle 104 and picking up a new needle is simple and short. Thus, this configuration has micro-ergonomic benefits over other suture packet and sharps container methods. As discussed above, the sharps container can be an elastic foam or other material into which used needles 104 are inserted with the sharp points directed towards a structural layer which blocks the needle from further movement and protects the surgeon's forearm from the used needle. It has also been found that mounting the used needle 104 on the dorsum on the forearm can also resist injury to the surgeon from the exposed suture ends of the needles. The dorsum of the forearm can rotate with the hand. However, the forearm is not easily moved into a position where the dorsum of the forearm faces the body. The forearm is inherently configured with the volar and palmar surfaces facing the body while the dorsum faces away from the body. This human anatomy limitation provides another safety feature for the inventive forearm mounted platform with sharps container.

With reference to FIGS. 68-71 in an embodiment, the platform apparatus may include a platform 187 on the dorsum of the forearm onto which a sharps container is mounted and suture packet holders 183 mounted on a surface or platform 189 of the apparatus on the volar side of the forearm 143. In this configuration, the surgeon can supinate the non-dominant assisting limb to rotate the suture packet mounted on the volar side into any desired orientation before grasping a new armed needle. As discussed, the human anatomy allows for a wider range of natural movement when the volar side of the forearm 143 is facing the body. Thus, the surgeon can more easily and precisely move the needle to the desired position before grasping the new needle with the needle holder. The needles are securely attached to the suture packs 101 and require a physical force to be removed. Gravity will not cause the needles to come loose from the suture packs 101 and the placement of the suture packs 101 below the forearm 143 will not cause new armed needles to be accidentally released. In contrast, it may not be desirable to mount the tool holders and sharps container on the volar side of the limb.

With the used sharps container on a dorsal side and suture packs 101 on the volar side, the movement and micro-ergonomics are slightly different because the surgeon will rotate the forearm 143 after the used needle is placed in the sharps container and while the new armed needle is being grasped. However, because the suture packet 101 and sharps container are still in close proximity, for example within less than 7 inches, the movement of the surgeon is still very efficient. This configuration also has the benefit of a safe used needle 104 position and a more adjustable suture packet 101 position.

Figure 90:
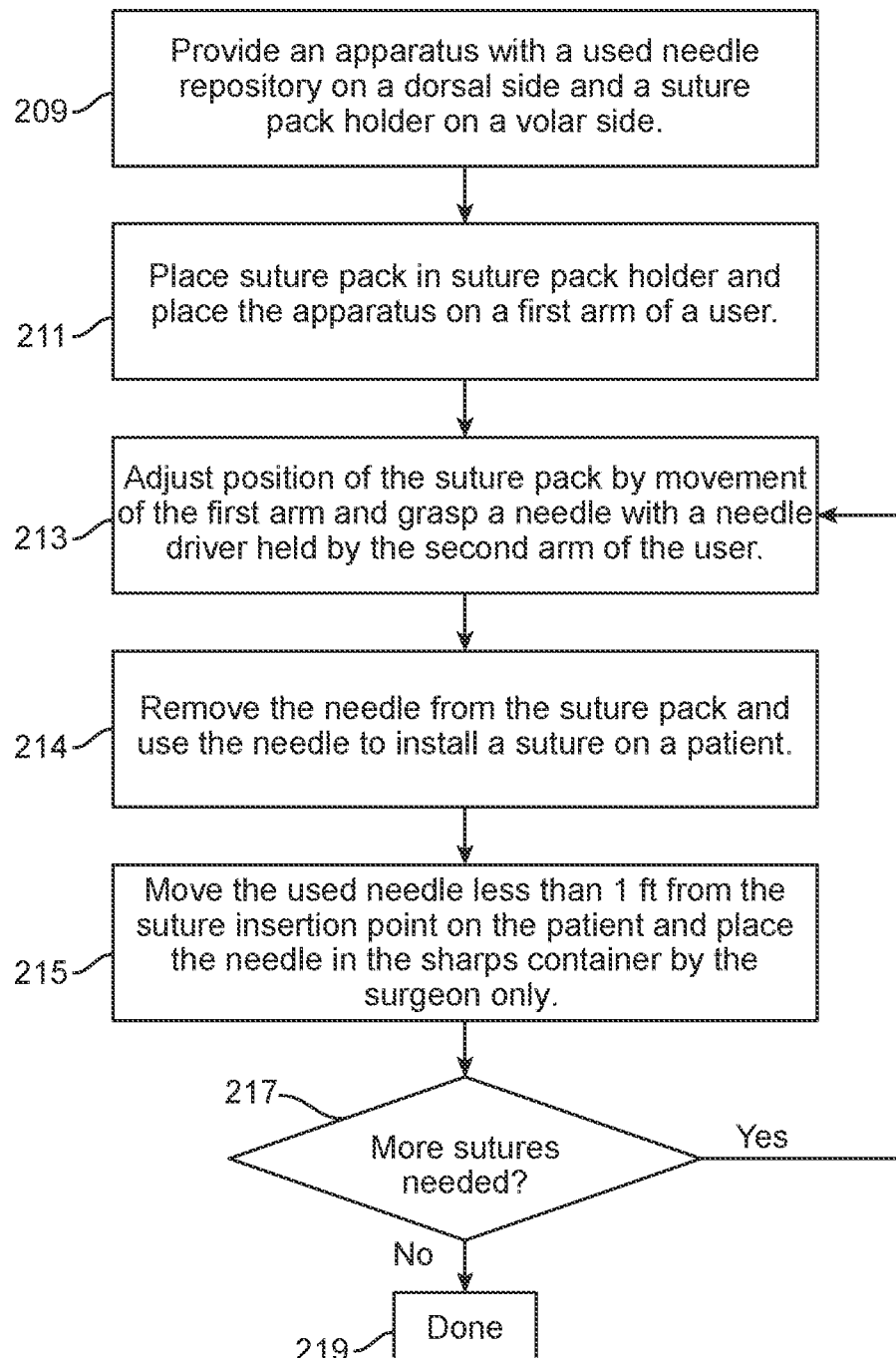
FIG. 90 illustrates a flow chart of a process for using an arm mounted platform apparatus that includes a suture pack and a needle sharps container.

The described process used with a medical apparatus on a forearm of a user can be illustrated with reference to flow chart shown in FIG. 90. A medical apparatus can have a platform on a dorsal side of the forearm and a volar platform on the volar side of the forearm. A used needle repository can be attached to the dorsal platform on the dorsal side of the medical apparatus and a suture pack holder can be attached to the volar side of the medical apparatus 209. A suture pack can be placed in the suture pack holder and the medical apparatus can be worn on a first arm of a user who can be surgeon, which can be the non-dominant arm 211. The user can move the first arm to adjust the position of the suture pack and the user can grasp a suture needle with a needle driver held by the second arm of the user which can be the dominant arm 213. The user can then remove the suture needle from the suture pack and use the needle to install a suture on a patient 214. Once the suture is installed and possibly knotted, the user can move the used needle less than one foot from the suture insertion point on the patient and place the used needle in the sharps container by the surgeon only 215. The surgeon can determine if additional sutures are needed 217. If more sutures are needed, the steps 213, 214 and 215 can be repeated until all sutures have been installed on the patient. Once no more sutures are needed this process is done 219. As discussed, the benefit of this process is that only the surgeon handles the sutures and needles and the movement of the needle can be, for example, within one foot from the suture insertion point which can improve efficiency and prevent injury from sharps.

The sutures and needles can remain within the near surgical field during the installation of the sutures.

In yet another embodiment, the suture packet holder (with a suture packet) and a sharps container can be mounted on a surgical tool on the same plane, facing the same direction, or on opposite planes. The suture packet holder and the sharps container can be held by the surgeon's non-dominant hand. In the illustrated examples shown in FIGS. 81 and 83 the suture packet 101 and the sharps container 191 can be mounted on opposite sides of a surgical tool 201 such as forceps. When the suture packet holder 183 and the sharps container 191 are mounted opposite each other, the surgeon can rotate the suture packet 101 toward the needle driver so a new armed needle can be grasped. When the suture has been installed, surgeon can rotate the tool between about 90-270 degrees so the sharps container 191 faces the used needle and the surgeon can deposit the used needle in the sharps container 191. The surgical tool can be rotated between about 90-270 degrees back to its original position so a new armed needle can be grasped and the process can be repeated. In other embodiments, the suture packets and sharps container can also all be on same plane, facing the same direction with the unused and used needles side by side.

Figure 91:
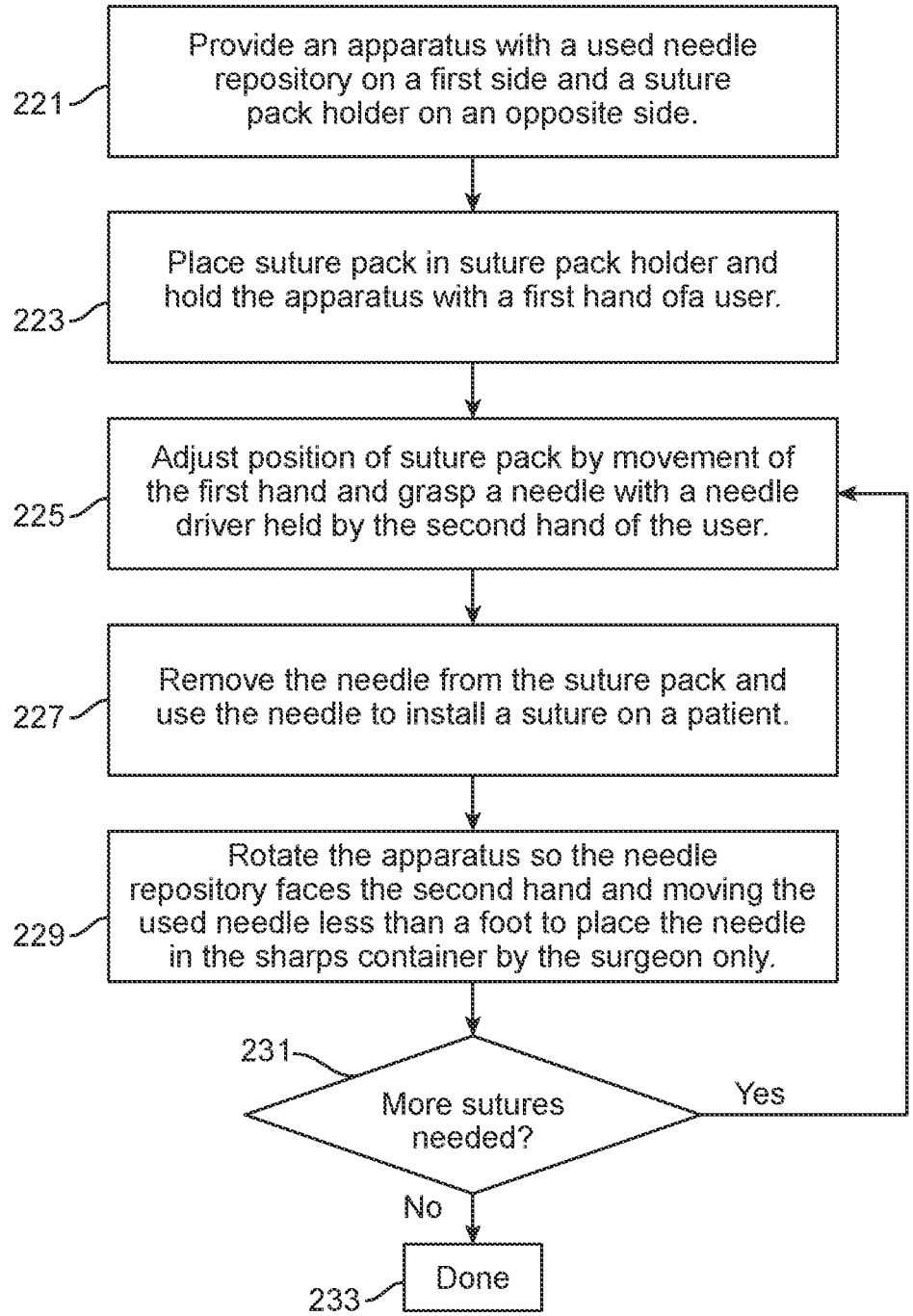
FIG. 91 illustrates a flow chart of a process for using a tool mounted platform apparatus that includes a suture pack and a needle sharps container.
Figure 92:
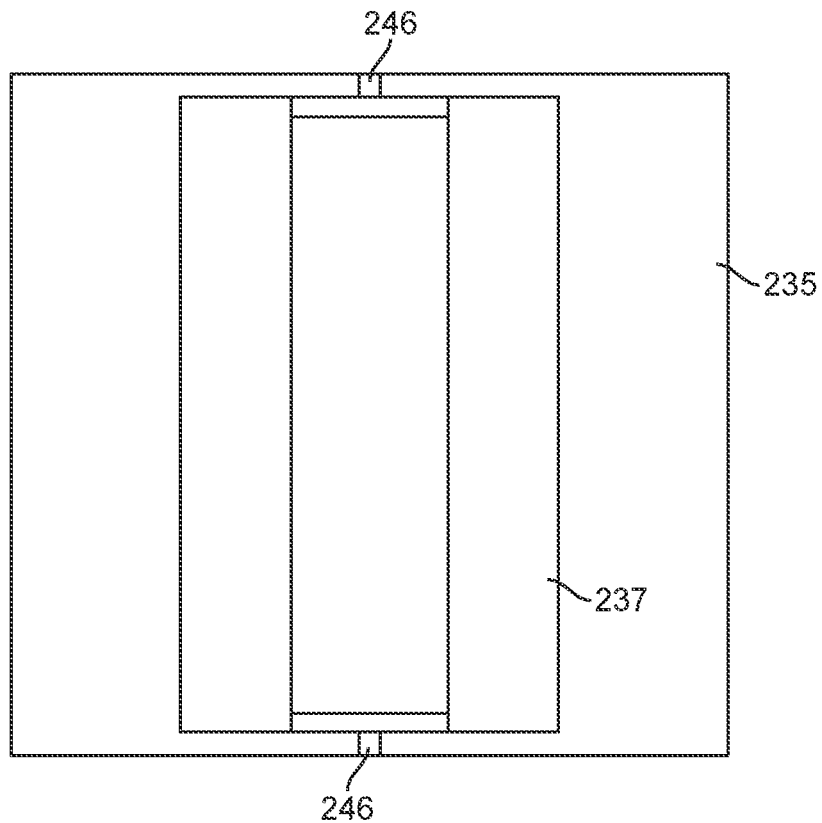
FIG. 92 illustrates a top view of an embodiment of a repository housing.
Figure 93:
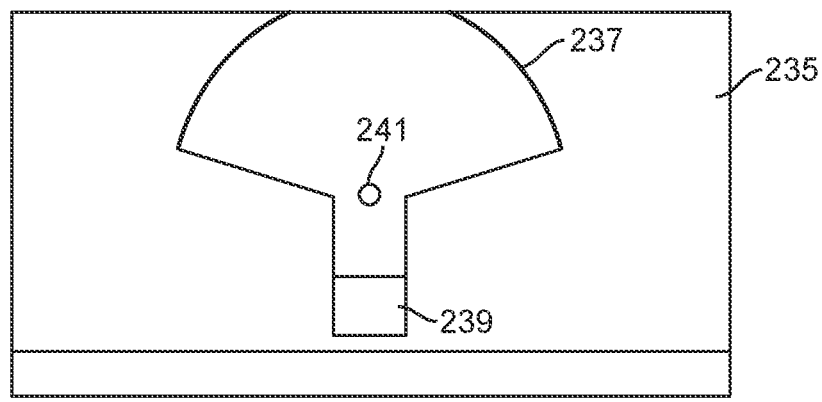
FIGS. 93-95 illustrate side views of an embodiment of a repository housing.
Figure 94:
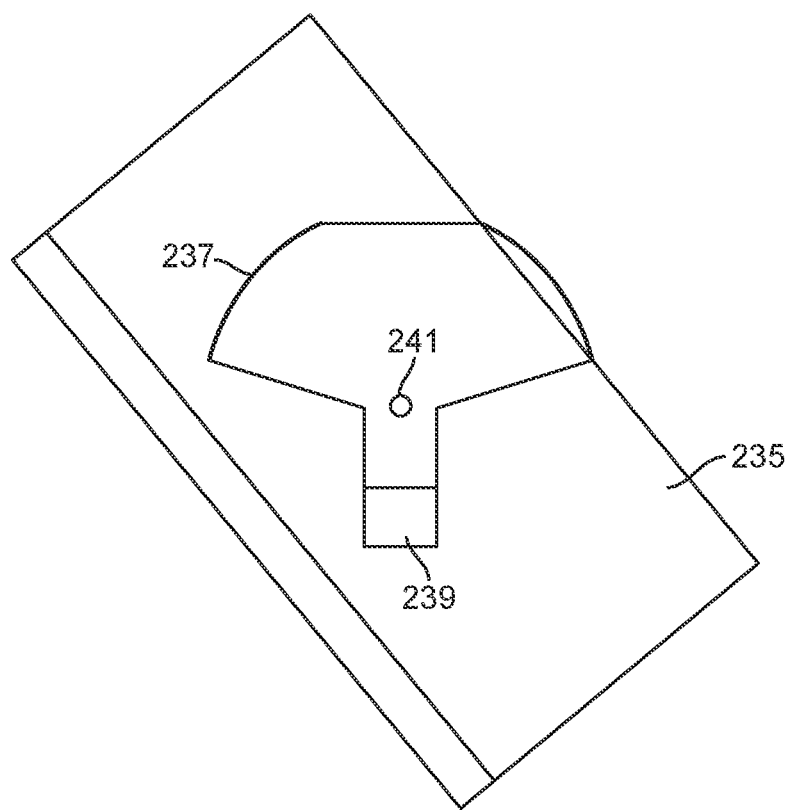
Figure 95:
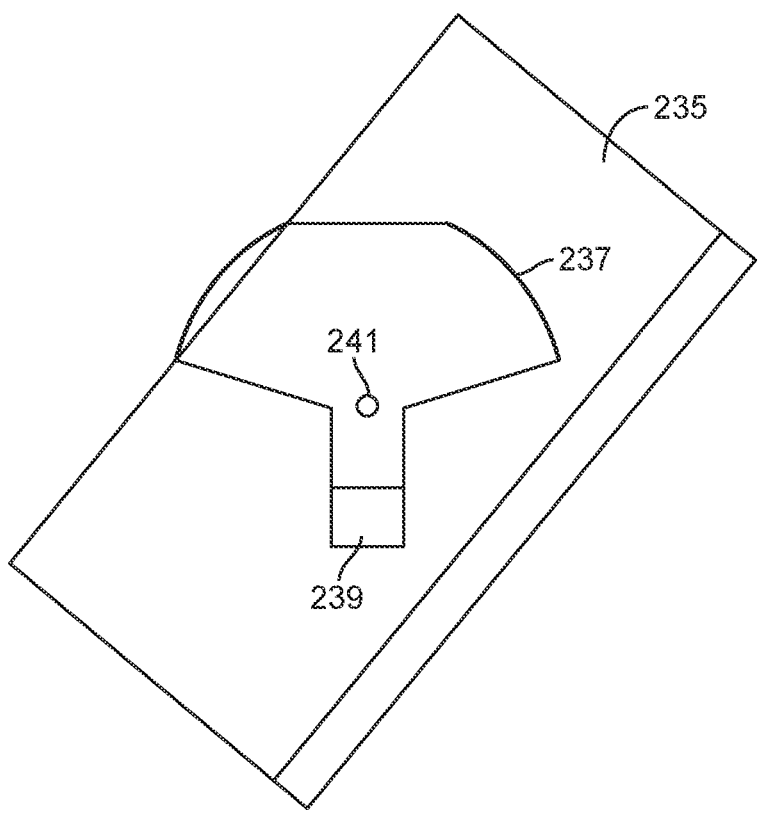
Figure 96:
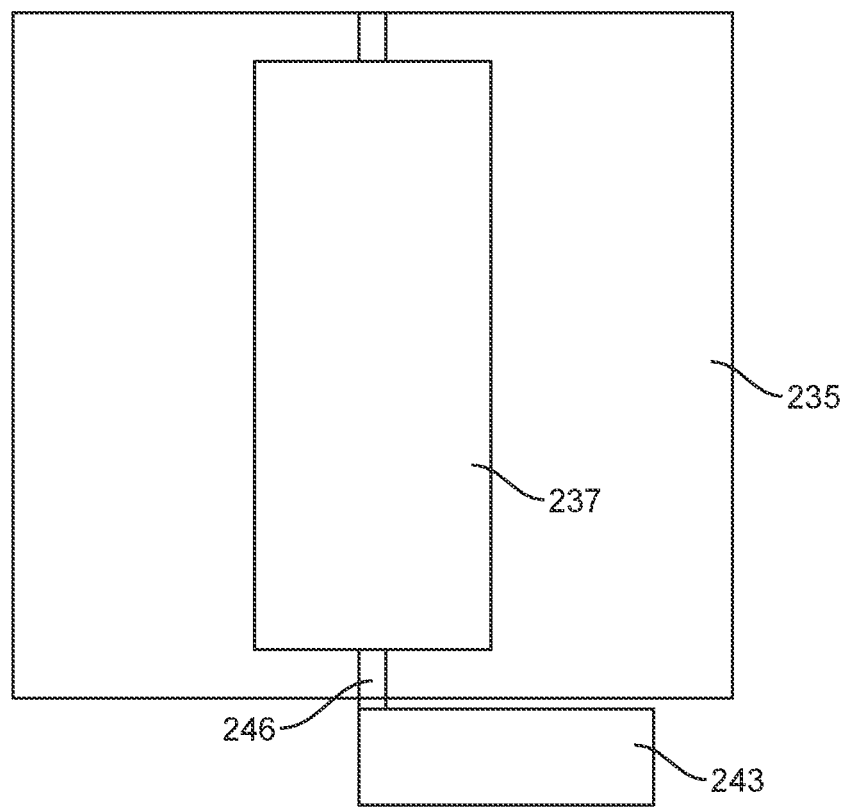
FIG. 96 illustrates a top view of an embodiment of a repository housing.
Figure 97:
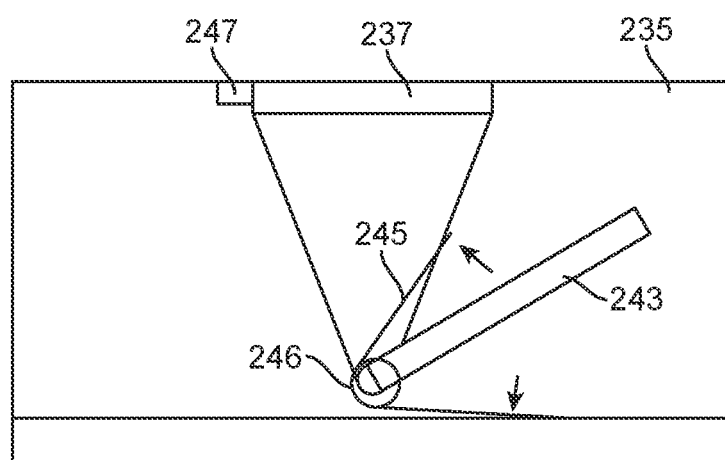
FIG. 97 illustrates a side view of an embodiment of a repository housing.
Figure 98:
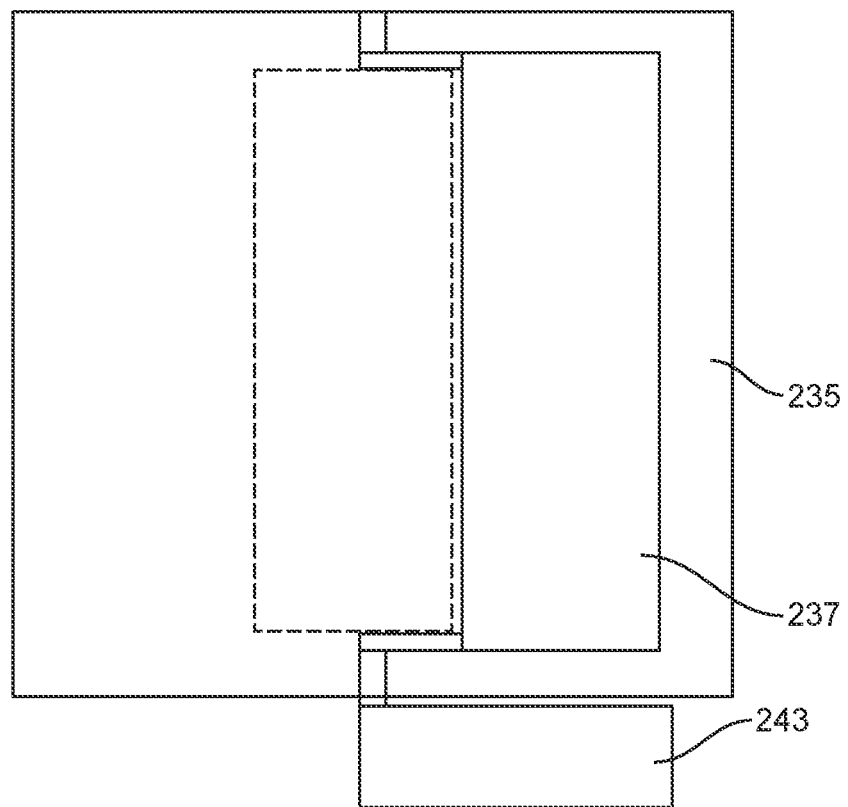
FIG. 98 illustrates a top view of an embodiment of a repository housing.
Figure 99:
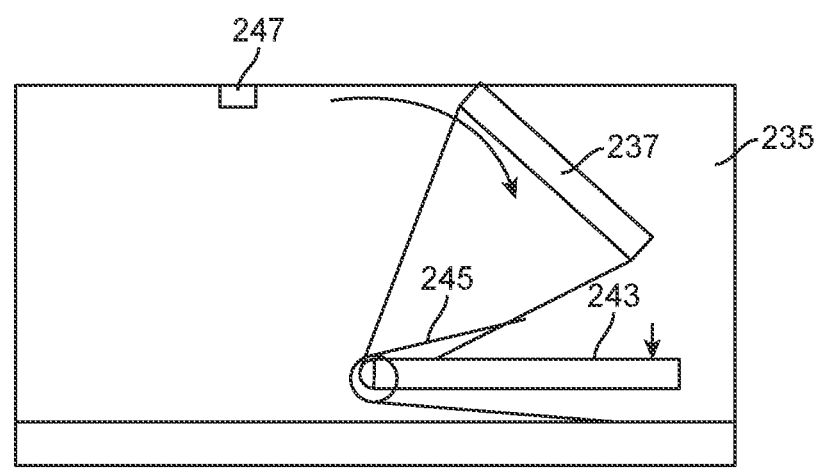
FIG. 99 illustrates a side view of an embodiment of a repository housing.

An embodiment of this process can be illustrated with reference to the flow chart shown in FIG. 91. A medical apparatus such as forceps can have a used needle repository on a first side of a proximal end portion and a suture pack holder on an opposite side can be provided to a user who can be surgeon 221. A suture pack can be placed in the suture pack holder and the medical apparatus can be held with a first hand of the user 223. The user can adjust the position of the suture pack by movement of the first hand and the user can grasp a needle with a needle driver held by the second hand of the user 225. The user can then remove a needle from the suture pack and used the needle to install a suture on a patient 227. Once the suture has been installed, the user can rotate the medical apparatus so that the needle repository faces the second hand and the used needle moves less than a foot to place the needle in the used needle repository which can be a sharps container by the surgeon only 229. If more sutures are needed, the steps 225, 227 and 228 can be repeated until all sutures have been installed on the patient. When no more sutures are needed this process is done 233. Again, this process can be performed by only the surgeon and the needles may move less than one foot from the incision which can improve efficiency and prevent injury from sharps.

In other embodiments, various types of sharps containers can be used to hold used needles. For example with reference to FIG. 150, the sharps container 255 can have a door 237 that is coupled to a lever 243. When the lever 243 is actuated, the door 237 can open to allow a used needle to be inserted into the sharps container 255. When the lever 237 is released, the door 237 can close to prevent the used needles from escaping. In an illustrated embodiment, the user can simultaneously hold the forceps 201 and actuate the lever 243 to open/close the door 237 to the sharps container 255. For example, the user can hold and actuate the forceps 201 between the thumb and long finger. The index finger can independently contact and actuate the lever 243 to open the door 237. The index finger can also allow the user to apply additional downward force to the forceps 201 if necessary.

Figure 77:
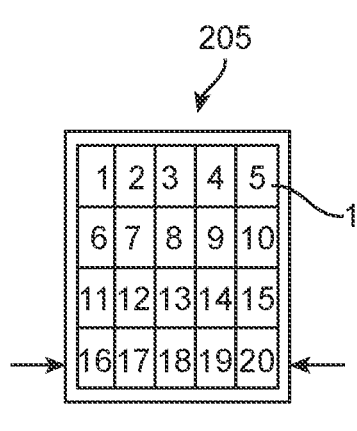
FIG. 77 illustrates a front view of an embodiment of a needle receptacle and suture packet assembly.
Figure 78:
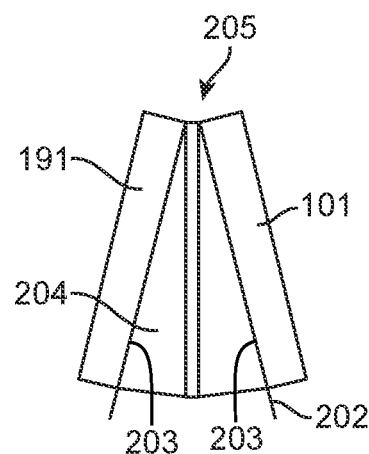
FIGS. 78-79 illustrate side views of an embodiment of a needle receptacle and suture packet assembly.
Figure 79:
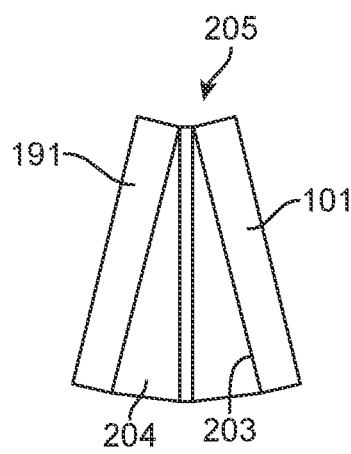
Figure 80:
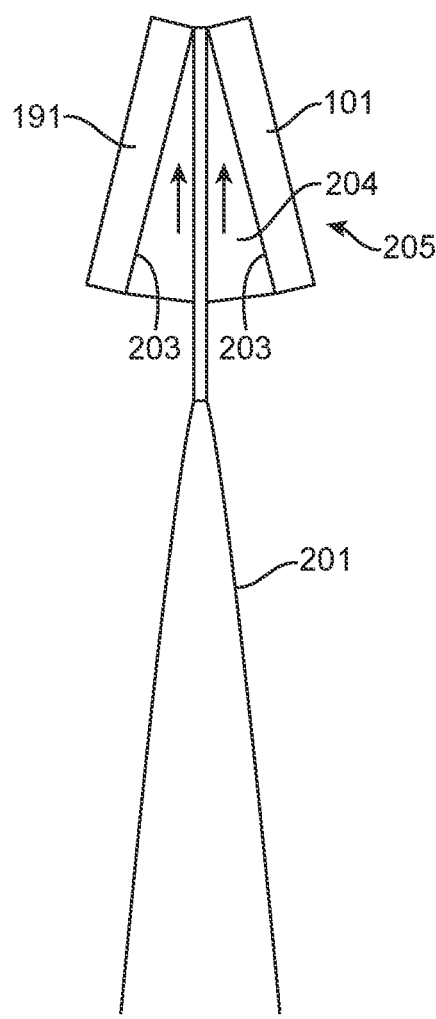
FIGS. 80-81 illustrate side views of an embodiment of a needle receptacle and suture packet assembly on a surgical tool.
Figure 81:
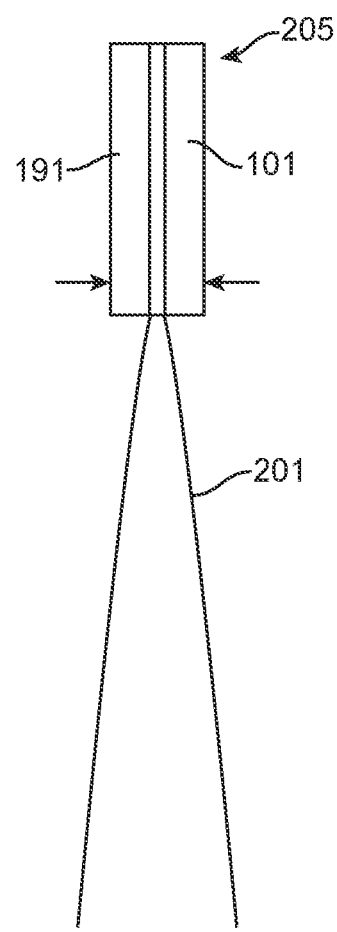

With reference to FIGS. 77 and 78, in the illustrated embodiment, the suture pack 101 and sharps container 191 are coupled to each other along a top side and two vertical sides to form a needle receptacle and suture pack assembly 205. The bottom edge can be open so that the structure forms a tool attachment pocket 204. The inner sides of the suture pack and sharps container can be coated or attached to an adhesive layer 203 that is covered with a release paper 202 prior to installation on a tool. The user can squeeze the two vertical sides of the suture pack 101 and sharps container assembly as shown in FIG. 77 to open the pocket shown in FIG. 78. The user can then remove the release paper 202 to expose the adhesive 203 as shown in FIG. 79. A tool 201 such as a proximal end of forceps can be inserted into the pocket 204 against the adhesive surfaces 203 as shown in FIG. 80. The suture pack 101 and sharps container assembly 191 can be pressed together to secure the device to the end of the tool 201 as shown in FIG. 81. Because the inventive structure is being attached to a surgical instrument 201, it can be important to use lightweight materials so that the feel and balance of the tool is not significantly reduced when the system is used. In many embodiments, the weight of the structure is less than 0.100 lbs or 45 grams.

Figure 82:
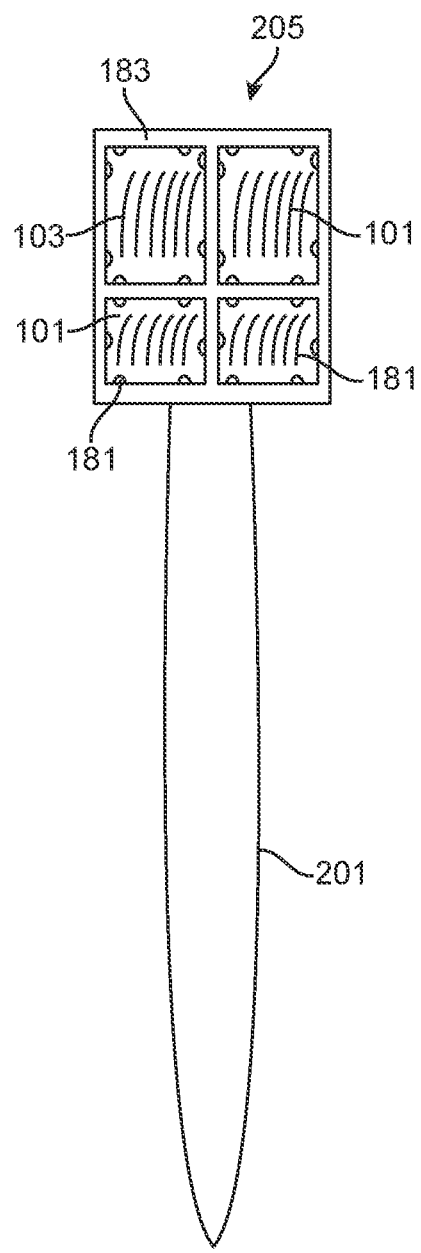
FIG. 82 illustrates a back view of an embodiment of a needle receptacle and suture packet assembly on a surgical tool.
Figure 83:
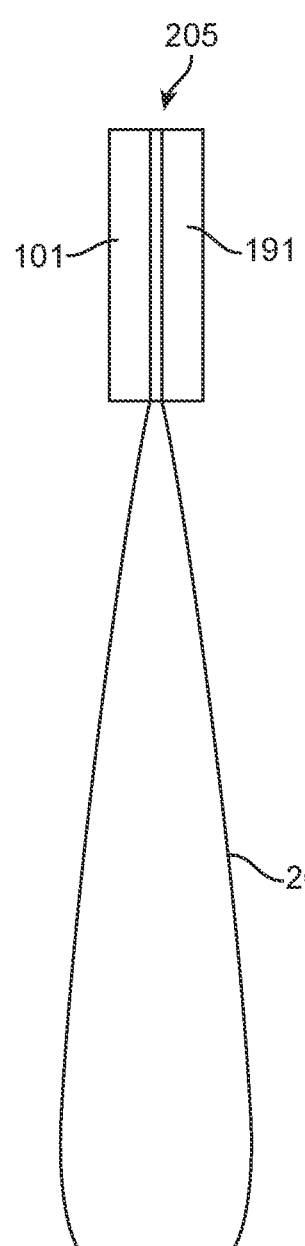
FIG. 83 illustrates a side view of an embodiment of a needle receptacle and suture packet assembly on a surgical tool.
Figure 84:
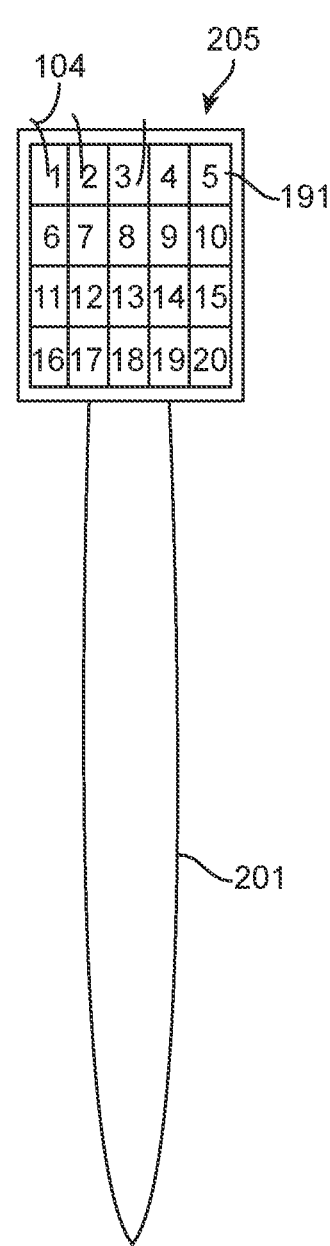
FIG. 84 illustrates a front view of an embodiment of a needle receptacle and suture packet assembly on a surgical tool.

With reference to FIGS. 82-84 various view of a needle receptacle and suture pack assembly 204 mounted on a surgical tool 201 are illustrated. FIG. 82 illustrates a front view of the needle receptacle and suture pack assembly 205 with the suture holder 183 with a plurality of suture packs 101 holding suture needles 103 is illustrated. The suture packs 101 can be held to the suture holder 183 with tabs 181. With reference to FIG. 83, a side view of the needle receptacle and suture pack assembly 205 is illustrated with the suture packs 101 on a front side and the used needle receptacle 191 on the opposite side. With reference to FIG. 84, a back view of the needle receptacle and suture pack assembly 205 with used needles 104 placed in the needle receptacle 191.

Figure 85:
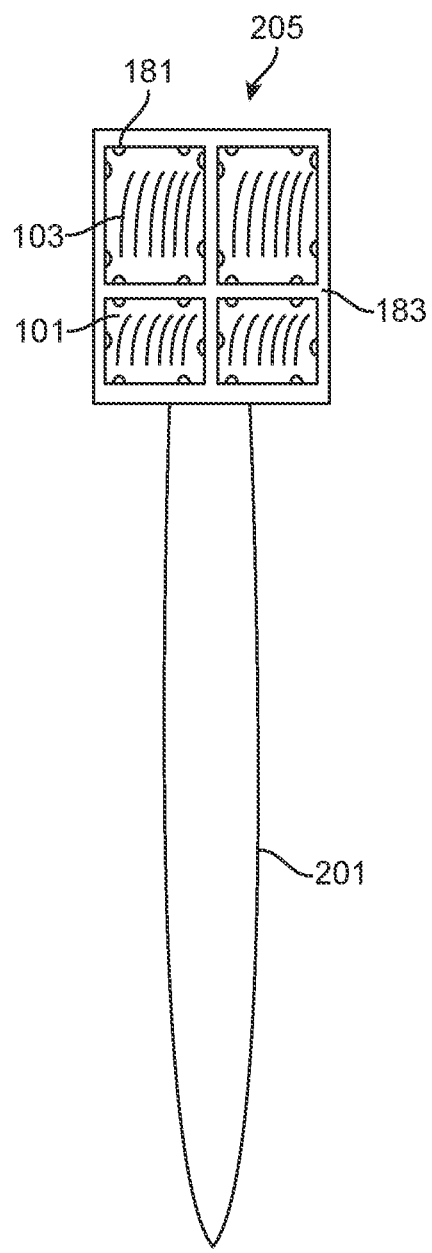
FIG. 85 illustrates a front view of an embodiment of a needle receptacle and suture packet assembly on a surgical tool.
Figure 86:
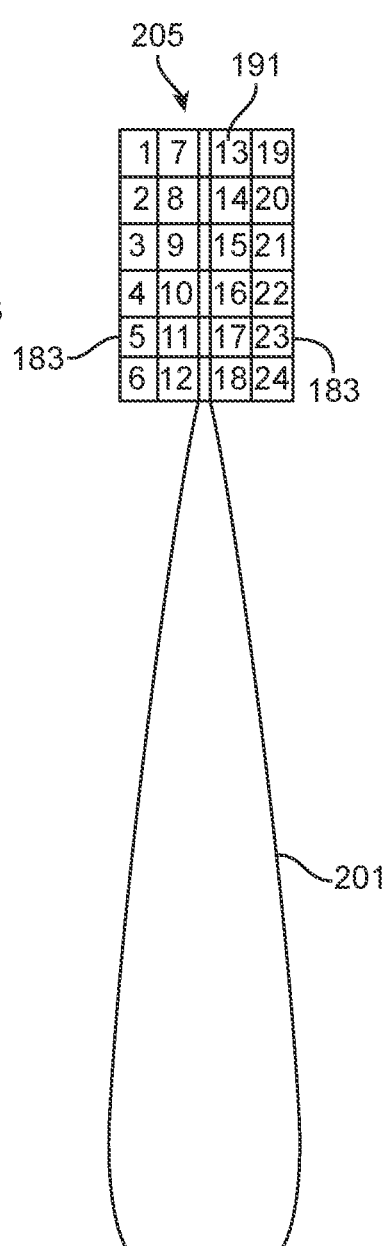
FIG. 86 illustrates a side view of an embodiment of a needle receptacle and suture packet assembly on a surgical tool.
Figure 87:
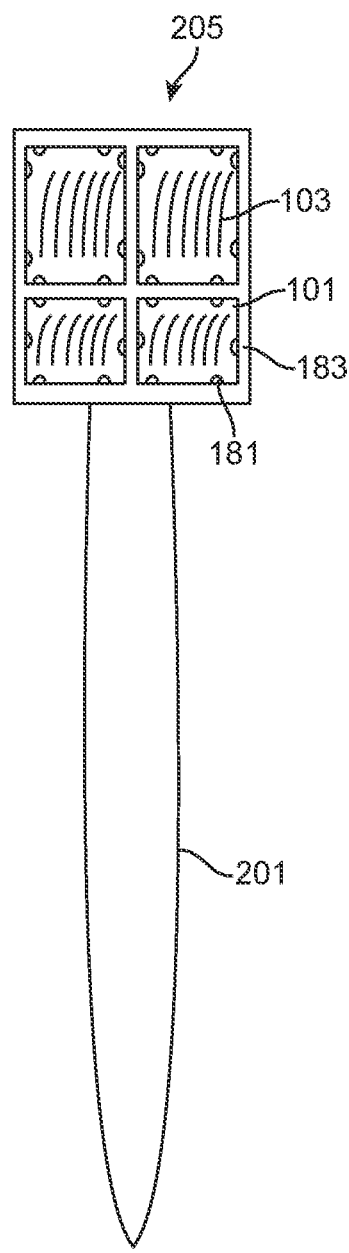
FIG. 87 illustrates a back view of an embodiment of a needle receptacle and suture packet assembly on a surgical tool.

In an alternative embodiment, the back surfaces of the suture packets can be attached to a foam needle repository and the opposite side of the needle repository can be attached to the tool. In yet another embodiment of a needle receptacle and suture pack assembly 205 as shown in FIGS. 85-87, the tool 201 can be attached to one or between two foam needle repositories 191 that are sandwiched between two suture pack holders 183. In this embodiment, the used needles 104 are inserted into the exposed sides of the foam needle repository 191. This provides a much deeper used needle 104 insertion because the foam extends across the entire width of the structure rather than the thickness. In the illustrated embodiment, the needle areas can be marked with a sequence of numbers so that the used needle 104 count can be easily performed. FIG. 85 illustrates a front view of the needle receptacle and suture pack assembly 205 facing one of the suture pack holders 183. FIG. 86 illustrates a side view of the needle receptacle and suture pack assembly 205 facing one of the foam needle repositories 191 and FIG. 87 illustrates a back view facing the second suture pack holder 183.

Figure 72:
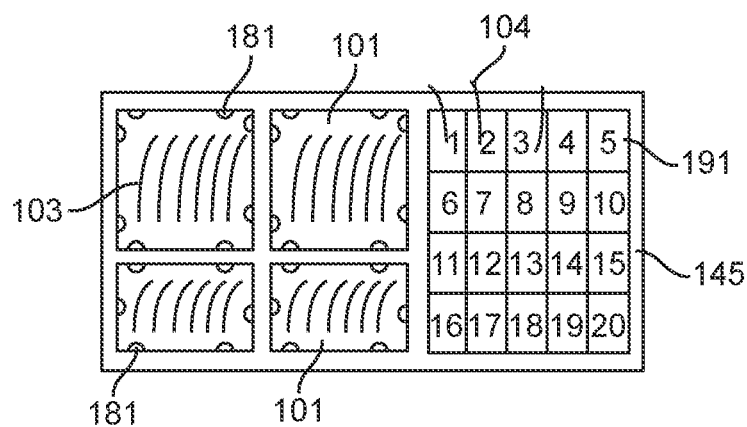
FIG. 72 illustrates a top view of an embodiment of a platform that includes a suture pack holder and a used needle receptacle.
Figure 73:
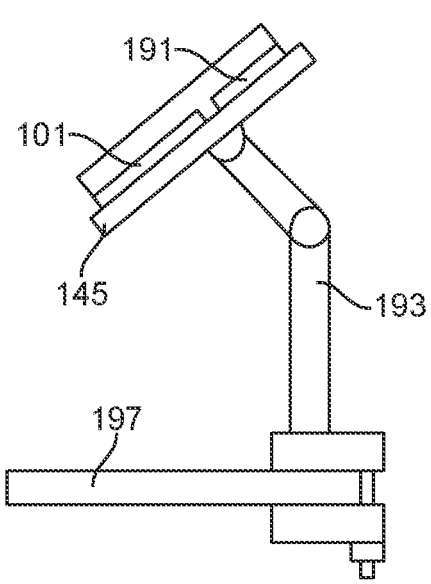
FIG. 73 illustrates a side view of an embodiment of a platform coupled to an arm having an adjustable joint.
Figure 74:
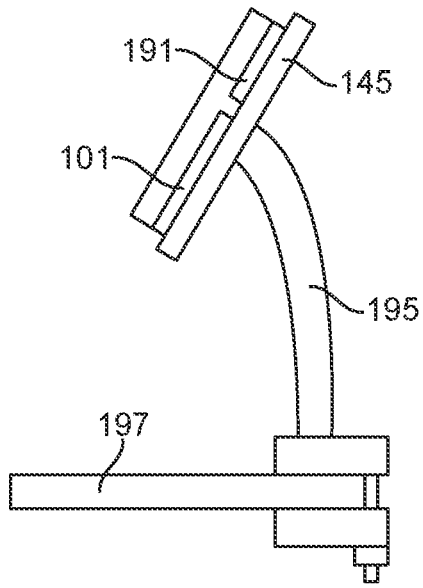
FIG. 74 illustrates a side view of an embodiment of a platform coupled to a flexible arm.
Figure 75:
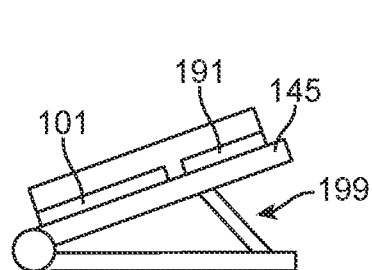
FIGS. 75 and 76 illustrate side views of an embodiment of a platform coupled to an "A" frame structure.
Figure 76:
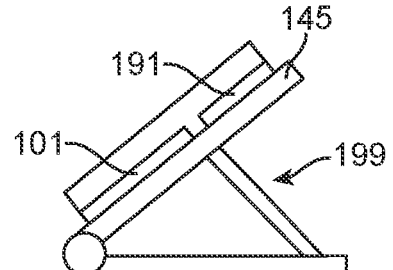

With reference to FIGS. 72-76, in other embodiments, a platform 145 with suture packet holders 183 that can include tabs 181 for holding suture packets 101 and a sharps container 191 can be mounted on a mechanical arm at a fixed or movable location in the surgical field. For example, the platform 145 can be a separate structure mounted to an arm having an adjustable joint 193 as shown in FIG. 73 or a flexible arm 195 that can be moved to any desired position as shown in FIG. 74. The base of the arms 193, 195 can be clamped to a fixed surface 197 such as a table.

In other embodiments a solid platform is secured to the surgical drape on the fringe of the surgical incision. In an embodiment the device is mounted opposite the surgeon if the surgeon has no assistance or on the adjacent side to the surgeon's dominant hand. In an embodiment illustrated in FIGS. 75 and 76, the platform 145 with suture packet holders holding suture packets 101 and a sharps container can be mounted on an "A" frame structure 199 that allows the angle of the platform 145 surface to be adjusted. For example, the platform 145 can mount the suture packets 101 and suture repository 191 at an angle to the surface of about 0-50 degrees that most easily facilitates the grasping of the new armed needles and used needle deposition motions. The platform structure 199 can be attached to the surgical drape with staples or tape. A platform 145 with the suture packet(s) 101 and sharps container 191 adjacent to the needle holder securely mounted to the within the surgical field will facilitate the improved and more efficient surgical workflow. In this embodiment as illustrated in FIG. 72, the proximity of the suture packet holders holding suture packets 101 and a sharps container 191 can be within about 4 inches.

A common feature among the inventive devices described above is that they combine armed and/or unarmed needle and/or suture pack(s) with a used needle retention device on the same structure. The armed and/or unarmed needle and/or suture pack(s) with a used needle retention device can be fixed to the structure permanently and/or in frangible association. This configuration allows for improved micro-ergonomics. The surgeon can hold a needle driver in one hand and another tool such as forceps in the second hand. The surgeon does not have to let go of the needle driver or the forceps when needles are removed from the suture packs or when the used needles are placed in the used needle retention device. Since the surgeon does not have to remove the fingers from the instruments, the procedures can be a more efficient and safer since there is much less likelihood of accidentally dropping an instrument.

The use of the forearm for needles and used retained needles can provide improved efficiency, safety, and better micro-ergonomics. Using such a system, the surgeon always knows where used needles are located. It is also is very difficult to accidentally jab the surgeon's body with the used needles unless the surgeon crosses forearms to appose the dorsum of non-dominant forearm to another part of your body. If used needles are on the surgical field it is much easier for the surgeon's hand to accidentally be placed on them. Having the new and used needles on the in close proximity allows for apposition. The installation of sutures in a patient is done with a circular motion by the surgeon. The surgeon can more easily, drop a used needle off in the sharps container and grab the next new needle.

As illustrated in the top view of an embodiment of the inventive platform shown in FIG. 49, the system can include tool holders 177, suture pack holders 183 and a sharps container 191. In an embodiment, one of the tools stored in the tool holder 177 can be a bulb irrigator, which can be a hollow container that stores saline for irrigation of the surgical wound. The surgeon can point the nozzle of the bulb irrigator at the wound and squeeze the bulb portion to control the flow and direction of the saline. By storing the bulb irrigator on the platform 145, the surgeon can access this tool at any time. The scrub tech who is observing the surgery can assess, and thereby anticipate that the next step might be: bone wax or gelfoam application (as required during certain procedures, such as lumbar decompression) or cottonoid in that stepwise function. For example, the surgeon can reach for the bulb irrigator, perform the irrigation and upon placing it back on the platform 145 the scrub tech can know to be ready with the next step. Since the surgeon is handling the bulb irrigator, the surgeon will know how much saline is left in the bulb. The surgeon can feel and see the quantity of saline in the bulb irrigator and ask for more saline when a refill is needed. Alternatively, the scrub tech can spend more time watching the surgeon and less time passing objects to the surgeon. By watching the surgeon handle the bulb irrigator, the scrub tech can see when the fluid level is running low and anticipate the need for more saline. Because the actions of the surgeon and scrub tech are more independent, all parties can be more focused on the surgery and communications can be improved. These same benefits would apply to the needle handling processes of the inventive system described above.

Figure 104:
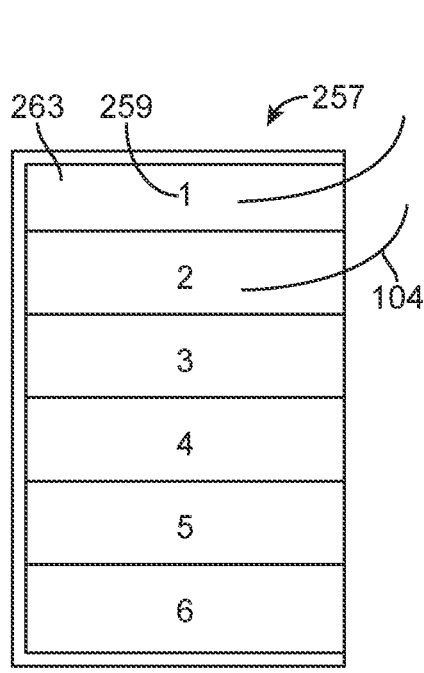
FIG. 104 illustrates a top view of an embodiment of a used needle receptacle with parallel orientation needles.

In some of the illustrated embodiments, the used needles are inserted into a foam sharps container coupled to a planar mounting surface such as a platform with the lengths of the needle approximately perpendicular to the mounting surface as shown in FIGS. 102 and 103. In other embodiments with reference to FIG. 104, the sharps container 257 can be oriented so that the used needles 104 are inserted into sides of the sharps container 257 so that the needles 104 are more parallel to the mounting surface. In an embodiment, sides of a container 257 structure can surround the foam, except for the used needle insertion side of the container 257. The container 257 can be made of a clear material and marked with numberings 259 for needle counting. The container 257 can prevent the sharp tips of the needle 104 from exiting the sharps container 257 and the increased insertion depth prevents the needles from escaping. Both of these features increase the safety of the device.

Figure 105:
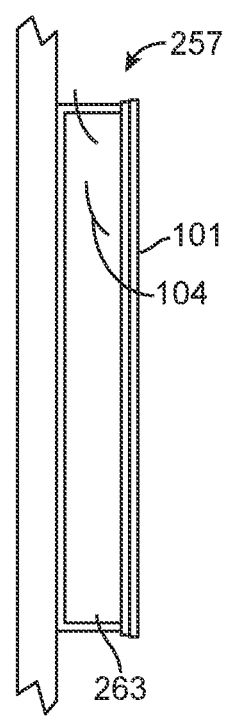
FIG. 105 illustrates a side view of an embodiment of suture packs attached to a used needle receptacle.
Figure 106:
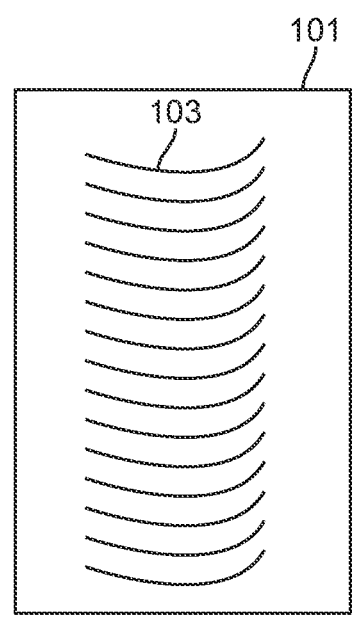
FIG. 106 illustrates a top view of an embodiment of suture packs attached to a used needle receptacle.

In other embodiments, suture packs 101 can be placed on the upper surface of the sharps container 257. With reference to FIG. 105 a side view of the sharps container 257 with suture packs 101 mounted on a front surface are illustrated. FIG. 106 illustrates a front view of the suture packs 101 holding sutures 103 mounted on the sharps container 257.

Figure 107:
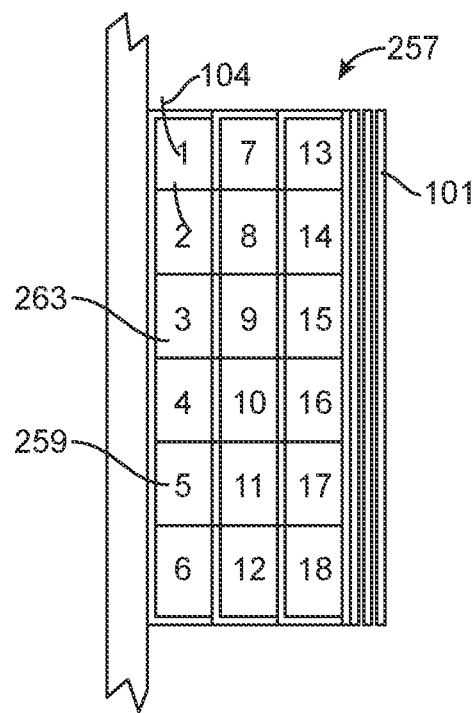
FIG. 107 illustrates a side view of an embodiment of suture packs attached to a multi-layer used needle receptacle.

In an embodiment with reference to FIG. 107, multiple layers of needle repositories 257 can be stacked together with the inner repository 257 attached to a mounting surface which can be on a protective platform or a tool. The opposite exposed side of the sharps container can be used to mount one or more stacked suture packets 101 that can be held together with an adhesive. Needles can be removed from the outermost suture packet and the used needle 104 can be inserted into the side of the sharps container 257. The used needles 104 can be inserted into the side of the sharps container 257 into a foam material 263 that can be marked with numberings 259 for needle counting. When the suture packet 101 is out of needles it can be removed to expose an underlying suture packet 101. Because the suture packets 101 and sharps container 257 are in very close proximity, the micro-ergonomics of the surgical procedure are improved.

Figures 108, 109:
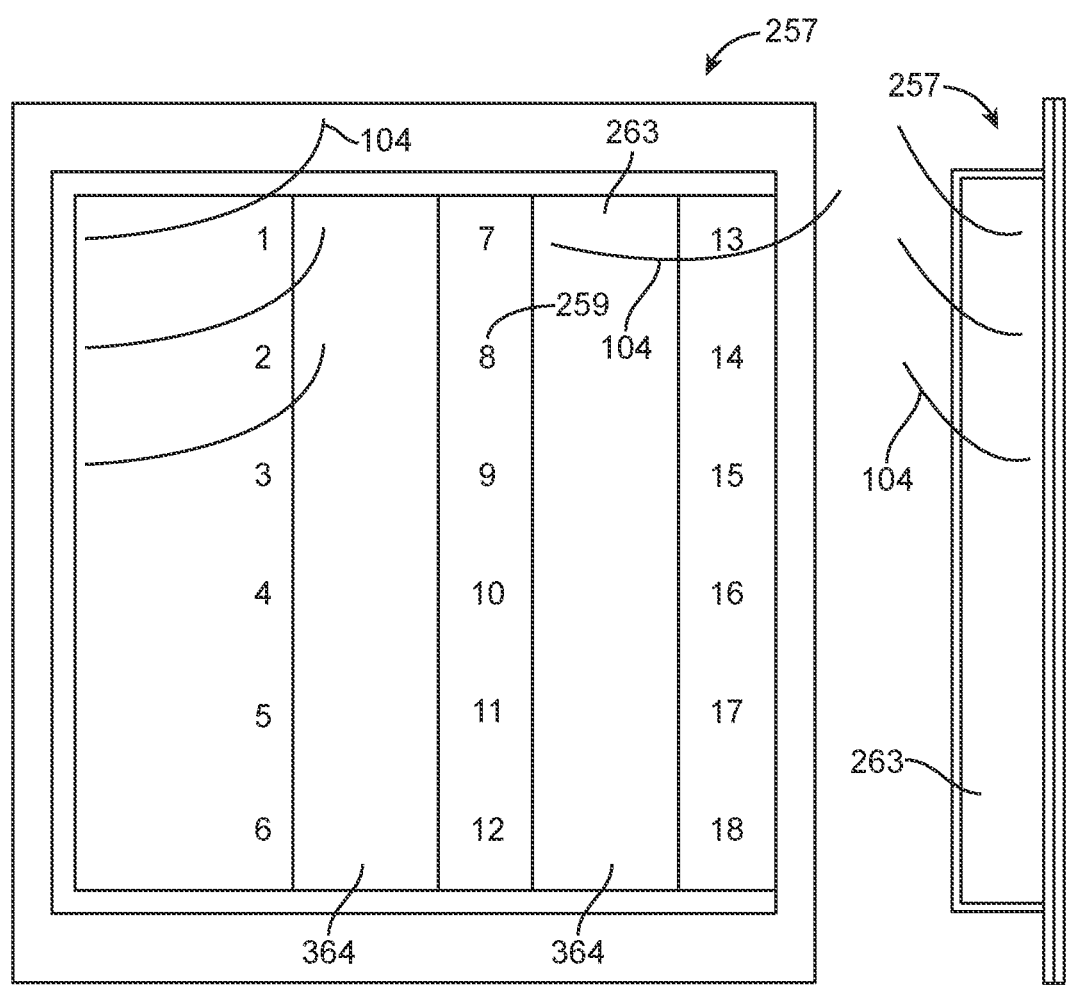
FIG. 108 illustrates a top view of an embodiment of a sharps container.
FIGS. 109 and 110 illustrate side views of an embodiment of a sharps container.
Figure 110:
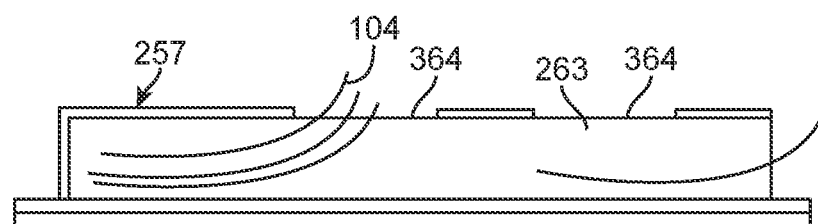

In an embodiment with reference to FIGS. 108-110, the sharps container 257 can include a material that the used needles 104 are inserted into a single piece needle holding material through multiple surfaces. In the illustrated example, a foam material 263 can be placed within a container structure 257 which includes a plurality of elongated openings 364 and numerical markings 258. The used needles 104 can be inserted into an exposed top surface as well as a side surface. The used needles 104 inserted through the top surface can be oriented at a shallow diagonal angle relative to the mounting surface and the used needles 104 inserted through the side surface can be more parallel to the mounting surface. In another embodiment with reference to FIGS. 111-113, dividers 261 can be placed in the container structure 257 which separate the adjacent needle holding material pieces. In this embodiment, each used needle 104 is inserted into a specific used needle passageway which can help to improve needle count accuracy.

With reference to FIGS. 114-116 in other embodiments, the sharps container 257 can be configured with access only through the side surfaces with multiple layers so that the used needles 104 are placed in multiple planes and mounted between one or more stacked suture packets 101 and a mounting surface. The assembly components can be held together with an adhesive and the assembly can be attached to the mounting surface with an adhesive. The mounting surface can be a tool surface or a platform surface. The new needles 103 can be removed from the outermost suture packet 101. When all needles 103 are removed from the outermost suture packet 101, the user can peel away the depleted suture packet 101 to exposed a full underlying suture packet 101.

In other embodiments, the suture packet 101 and used needle receptacle 257 can be configured in a diagonal manner like layered shingles. In the illustrated example shown in FIGS. 117-119, a plurality of suture packets 101 are stacked on a left side of the assembly 205. Needles 103 are removed, used and then placed in the needle receptacle 257. The suture packets 101 can be held in place with an adhesive and when the needles 103 are depleted, the outermost suture packet 101 can be peeled away and discarded to expose the next suture packet 101. The used needle receptacle 257 can have a single piece foam structure or multiple foam 263 pieces which can have a plurality of diagonally oriented dividers 261 separating the multiple foam 263 pieces. The dividers 261 can direct the needles 104 in a diagonal direction relative to the lower mounting surface. This diagonal configuration increases the insertion depth and allows the user to view the insertion points on an upper surface of the assembly 205. The exposed surfaces of the sharps container 257 can be numbered 259. In addition to the upper surface insertion points, the used needles 104 can also be inserted into one or more layers through a side surface. In an alternative embodiment shown in FIGS. 120-122, the dividers 261 between the different layers of the sharps container 257 can be curved so that they can be similar to the curvature of the used needles 104. This can improve the used needle insertion since the used needles 104 can follow the curvature of the dividers 257 and are less likely to collide with the dividers 257.

Figure 123:
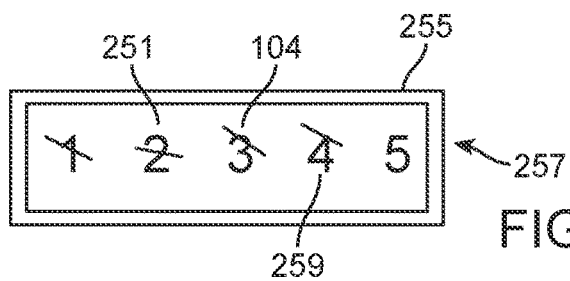
FIG. 123 illustrates a top view of an embodiment of a sharps container.
Figure 124:
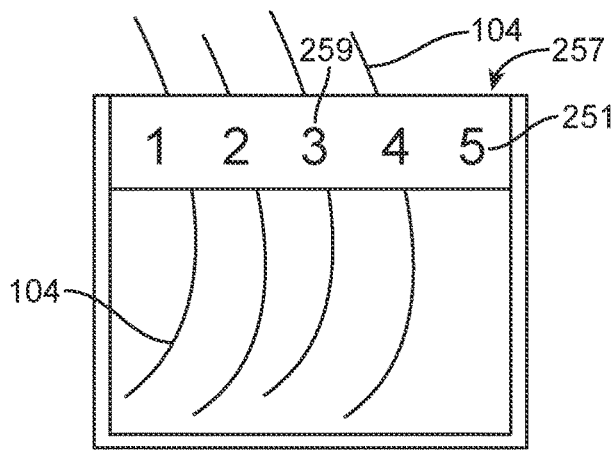
FIG. 124 illustrates a front view of an embodiment of a sharps container.
Figure 125:
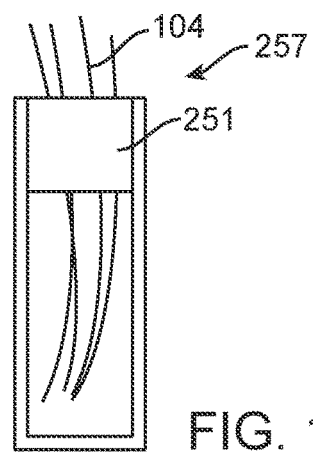
FIG. 125 illustrates a side view of an embodiment of a sharps container.

With reference to FIGS. 123-125, as discussed potential safety problem with used needles 104 is their ability to transmit viruses when a used needle 104 accidentally breaks the skin on an operating room surgical member. If the used needle 104 is cleaned and/or disinfected the used needles 104 are much less likely to spread viruses. In an embodiment with reference to FIGS. 123-140, the used needle receptacle 257 can include a disinfectant fluid container 264 encapsulated within a portion of the sharps container 255. The disinfectant fluid can be a liquid, gel, powder or any other suitable antimicrobial material 266. The portion of the sharps container 255 used to contain the antimicrobial material 266 can be a clear plastic and other transparent material. An elastic material 251 can be attached to the portion of the disinfectant fluid container 264 that can seal the antimicrobial material 266 in the disinfectant fluid container 264 portion of the sharps container 255. The elastic material 251 can be foam, rubber, plastic or any other suitable material that can be punctured by the used needles 104.

When a needle 104 is placed in the sharps container 255, the surgeon can drive the sharp tip of the needle 104 through the elastic material 251. The needle 104 can be covered with body fluids and may be contaminated with bacteria and/or viruses. The used needle 104 tip can pass through the elastic material 251 and into the antimicrobial material 266 in the container 264 portion. Since the container material can be transparent, the user to see the used needle 104 tips in the antimicrobial material 266. The elastic material 251 may create a tight seal around the perimeter of the used needle 104 which can prevent the antimicrobial liquid 266 from escaping from the fluid container 264 portion of the needle receptacle 257.

The portions of the used needles 104 that are inserted into the antimicrobial material 266 are cleaned and disinfected. Thus, these used needles 104 are properly treated by the act of inserting the used needles 104 into the receptacle 257. These disinfected treated needles 104 pose much less of a threat of transferring an infection or disease in the event of subsequent human contact. If the used needle 104 is accidentally removed from the used needle receptacle 257, the surface of the needle 104 will slide against the elastic material 251 which will further clean the needle 104 as it is removed from the needle receptacle 257 further reducing the risk of spreading an infection or disease compared to untreated used needles 104.

After sutures are used to close a patient, the surgical team must perform a needle count to insure that none of the used needles 104 are in the patient. In an embodiment the used needle receptacle 257 can have a sequential series of number markings 259. The numeric markings 259 can be on the elastic material 251 or on any other suitable portions of the receptacle 257. The surgeon can place the used needles 104 in the numbered spaces in the marked sequence. During the needle count, the counter can easily perform the count by looking at the last numbered area of each receptacle 257 having an inserted used needle 104.

Figure 126:
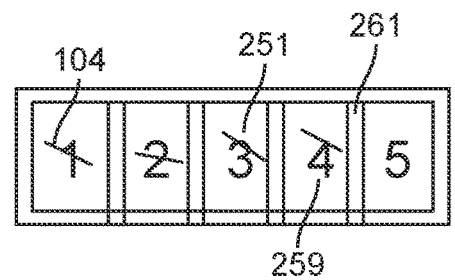
FIG. 126 illustrates a top view of an embodiment of a sharps container.
Figure 127:
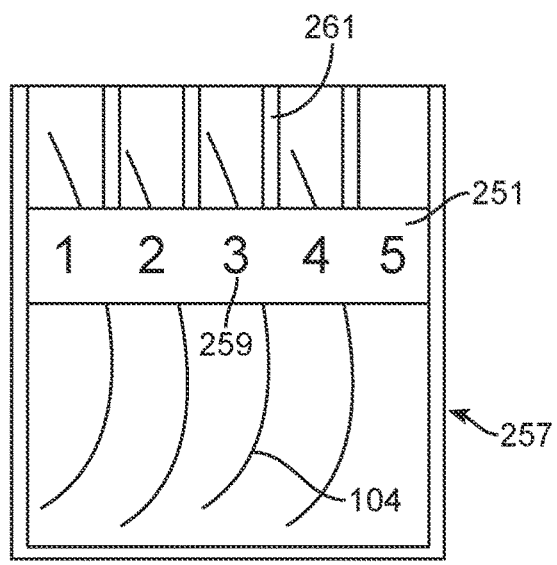
FIG. 127 illustrates a front view of an embodiment of a sharps container.
Figure 128:
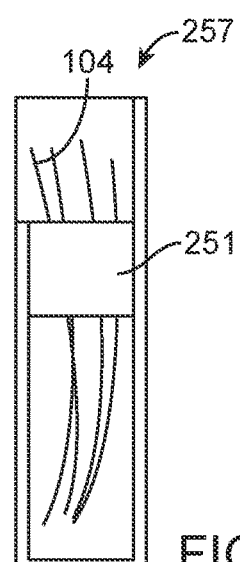
FIG. 128 illustrates a side view of an embodiment of a sharps container.

The used needles 104 should be placed as far as possible into the used needle receptacle 257. However, the proximal end will normally be exposed after the used needle 104 is inserted into the receptacle 257. These proximal ends are not as sharp as the distal ends but can still be sharp enough to cause injury to people. With reference to FIGS. 126-128, In order to reduce the risk of injury, the used needle receptacle can include barriers 261 that are adjacent to the can extend outward from the elastic material 251. The barriers 261 can create channels that can surround the proximal ends of the needles 104 inserted into the receptacle 257. The channels can be open on two sides and the widths of the channels can be wide enough for the needle driver to easily insert the used needle 104 through the elastic material 251. These channels can also prevent injury to the surgical staff. Even if the used needle receptacle 257 is pressed against a body, walls of the channels can prevent the exposed proximal ends of the needles 104 from causing injury. If the proximal end of the used needle 104 extends past the outer edge of the channels, physical contact with a proximal end will tend to safely push the needle 104 deeper into the elastic material 251 and move the proximal end into channels.

Figure 129:
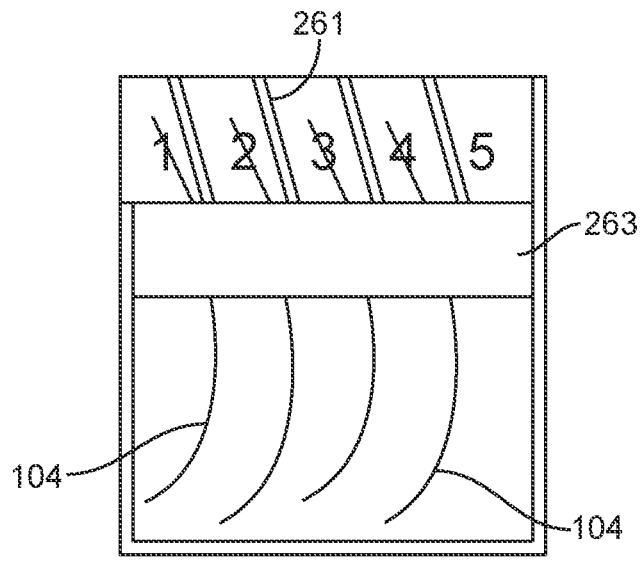
FIG. 129 illustrates a front view of an embodiment of a sharps container.
Figure 130:
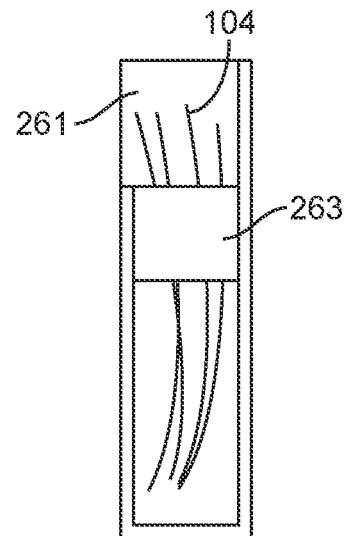
FIG. 130 illustrates a side view of an embodiment of a sharps container.
Figure 131:
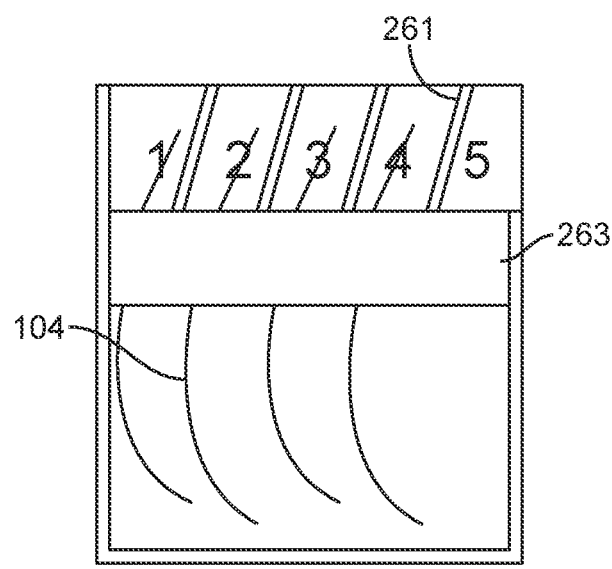
FIG. 131 illustrates a front view of an embodiment of a sharps container.
Figure 132:
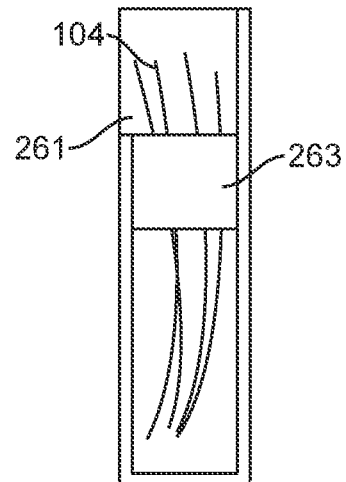
FIG. 132 illustrates a side view of an embodiment of a sharps container.
Figure 133:
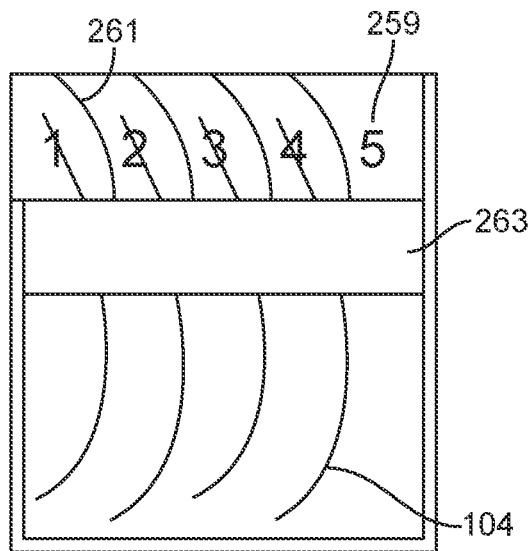
FIG. 133 illustrates a front view of an embodiment of a sharps container.
Figure 134:
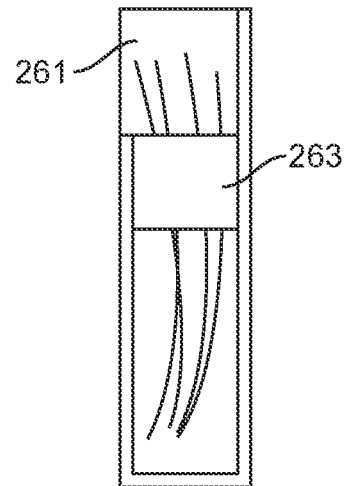
FIG. 134 illustrates a side view of an embodiment of a sharps container.
Figure 135:
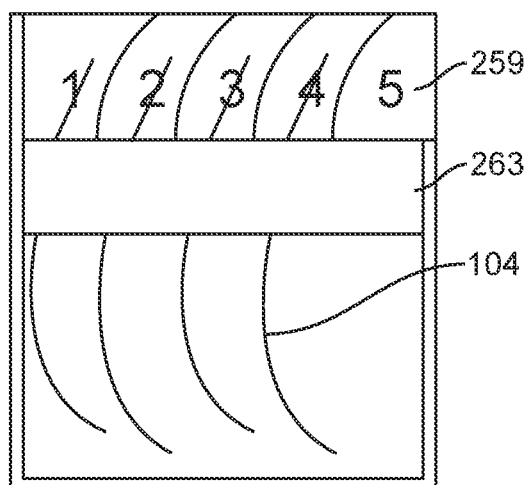
FIG. 135 illustrates a front view of an embodiment of a sharps container.
Figure 136:
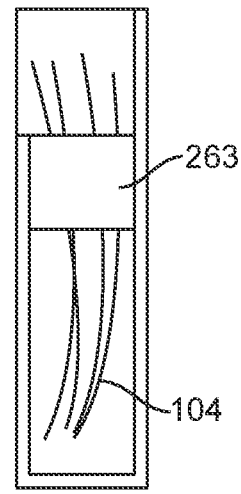
FIG. 136 illustrates a side view of an embodiment of a sharps container.
Figure 137:
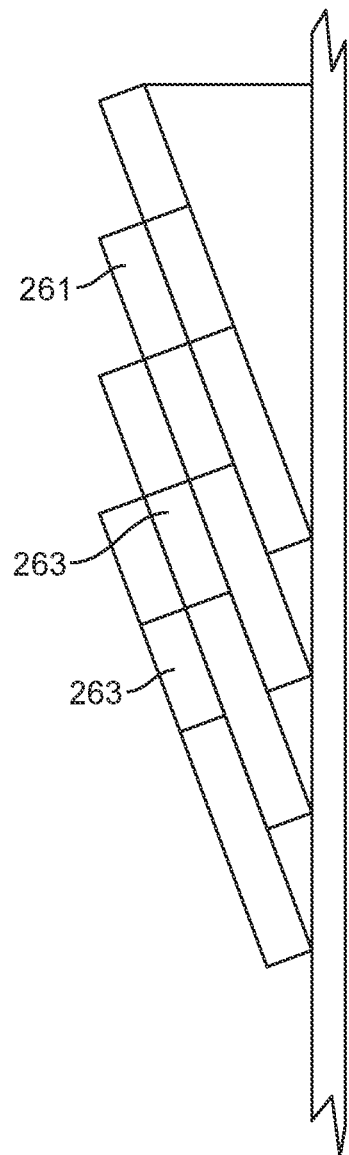
FIG. 137 illustrates a side view of an embodiment of a sharps container.
Figure 138:
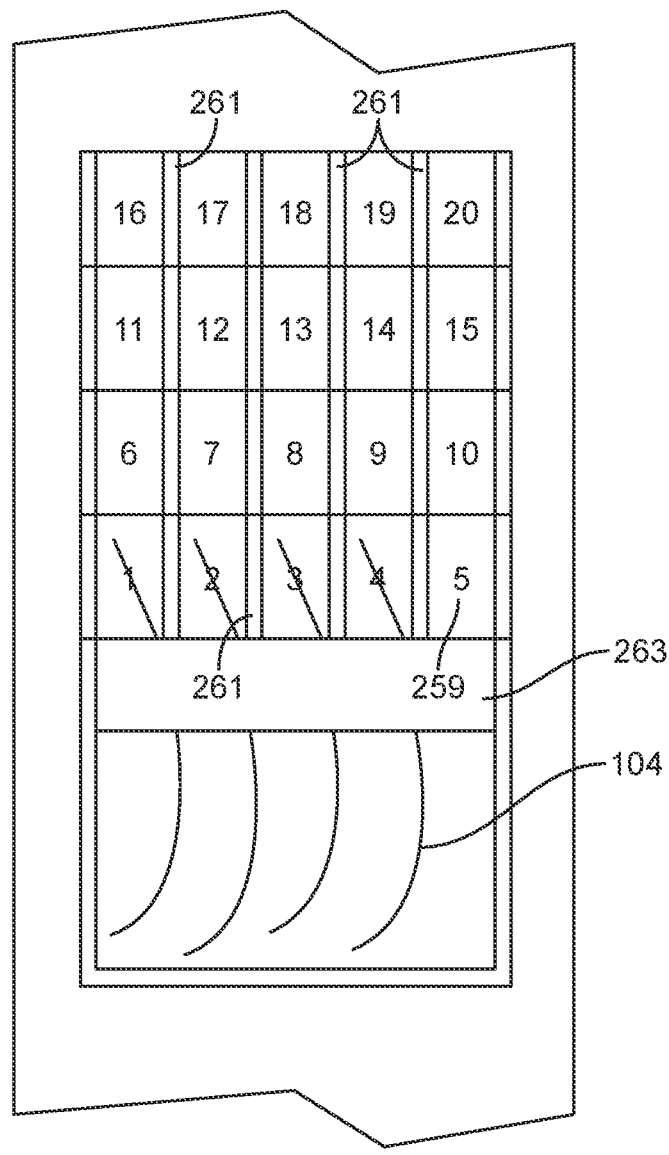
FIG. 138 illustrates a top view of an embodiment of a sharps container.

The suture needles 104 are generally curved in shape. Thus, it may be easier to insert the used needles 104 into the used needle receptacle if the channels are also curved or angled as shown in FIGS. 129-136. In these configurations, the surgeon can insert the used needles 104 with the convex curvature side of the needle facing the concave or inward curvature of the channel walls. When the used needle 104 is fully inserted, the ends of the used needle 104 can be aligned rather than being offset. Different users may prefer different channel angles or curvatures. For example, a right handed surgeon may prefer channels that have top ends that are angled to the left as shown in FIGS. 129 and 130 or curved to the left as shown in FIGS. 133 and 134. In contrast, left handed surgeons may prefer channels that have top ends that are angled to the right as shown in FIGS. 131 and 132 or curved to the right as shown in FIGS. 135 and 136.

Figure 139:
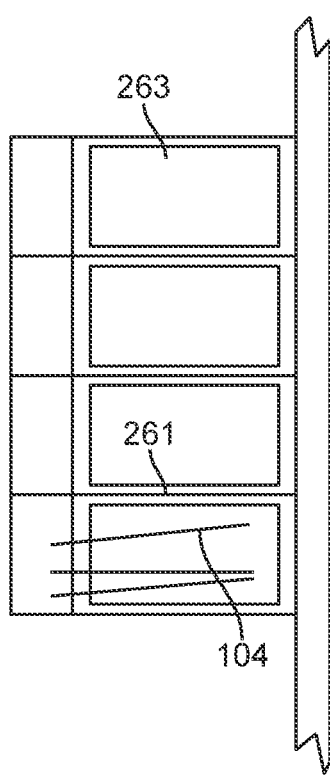
FIG. 139 illustrates a side view of an embodiment of a sharps container.
Figure 140:
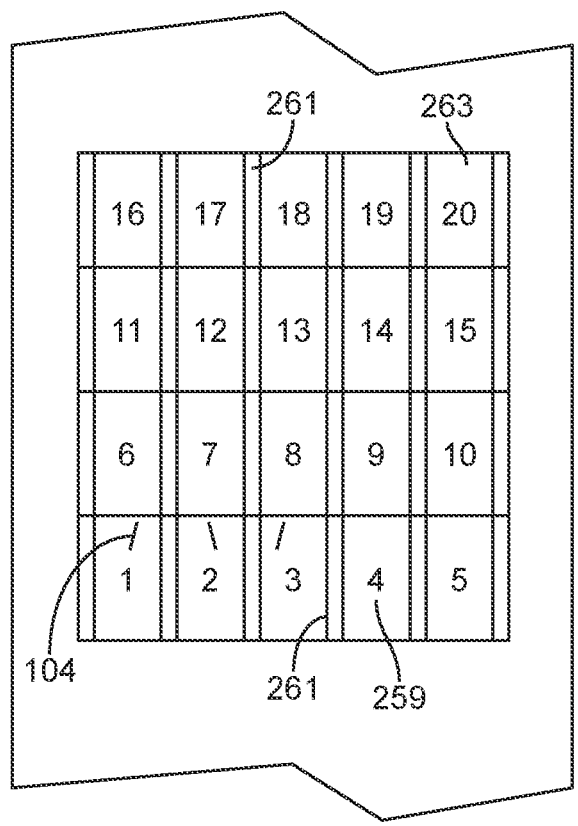
FIG. 140 illustrates a top view of an embodiment of a sharps container.

In some embodiments, multiple used needle sharps containers can be used together to hold a greater number of used needles 104. In an embodiment shown in FIGS. 137 and 138, the used needle sharps containers 255 can be arranged in an overlapping configuration with the channel portions of each of the sharps containers 255 exposed. The sequential numbering 259 on the channels can be clearly visible when the surgeon places the used needles 104 into the sharps containers 255. The tip of the needle driver can fit within the channels so the proximal ends of the used needles 104 will be completely within the protective channels. It is also possible to place one or more suture packets 101 on the uncovered surface of the first sharps container 255 as described previously. In other embodiments as shown in FIGS. 139-140, the sharps containers 255 can be arranged in a vertical manner with only the used needle input ends exposed. The number markings 259 can be seen on the exposed elastic layer 251 by the surgeon.

Figure 153:
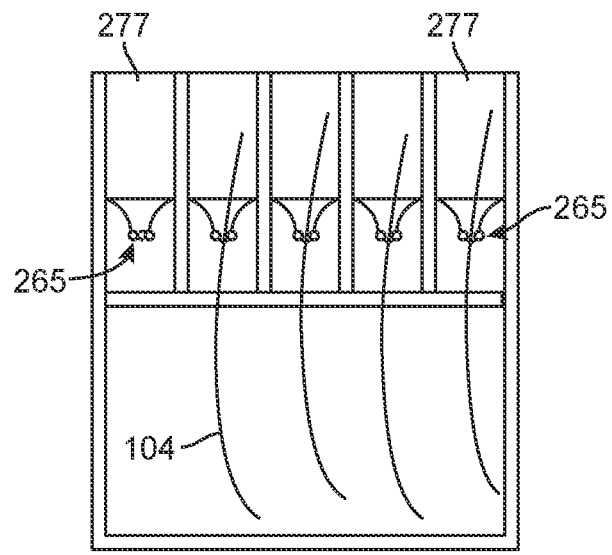
Figure 154:
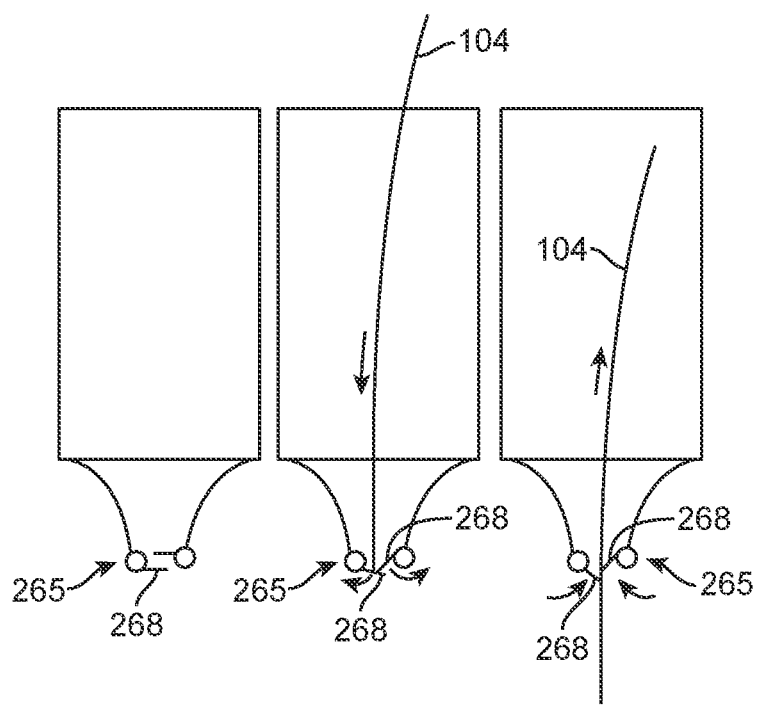

In some embodiments of the present invention, locking mechanisms 265 can be used with the sharps containers 255 as shown in FIGS. 153 and 154. The locking mechanisms 265 can allow the needles 104 to be inserted but may prevent the used needles 104 from being removed. In an embodiment, a locking mechanism 265 can be located within each of the channels of a sharps container 255. The walls of the channel can taper to guide the tip of the needle 104 to the locking mechanism 265 and the locking mechanism 265 can include one or more hinged arms 268 that can be overlapping on opposite sides of the channel. With reference to FIG. 154, when the needle 104 is pressed into the locking mechanism 265, the arms 268 can deflect downward so that the arms 268 are pressed against opposite sides of the used needle 104. The arms 268 will then clamp down on the needle 104 to prevent it from being removed from the channel thus looking the used needle 104 into the sharps container 255.

Figure 155:
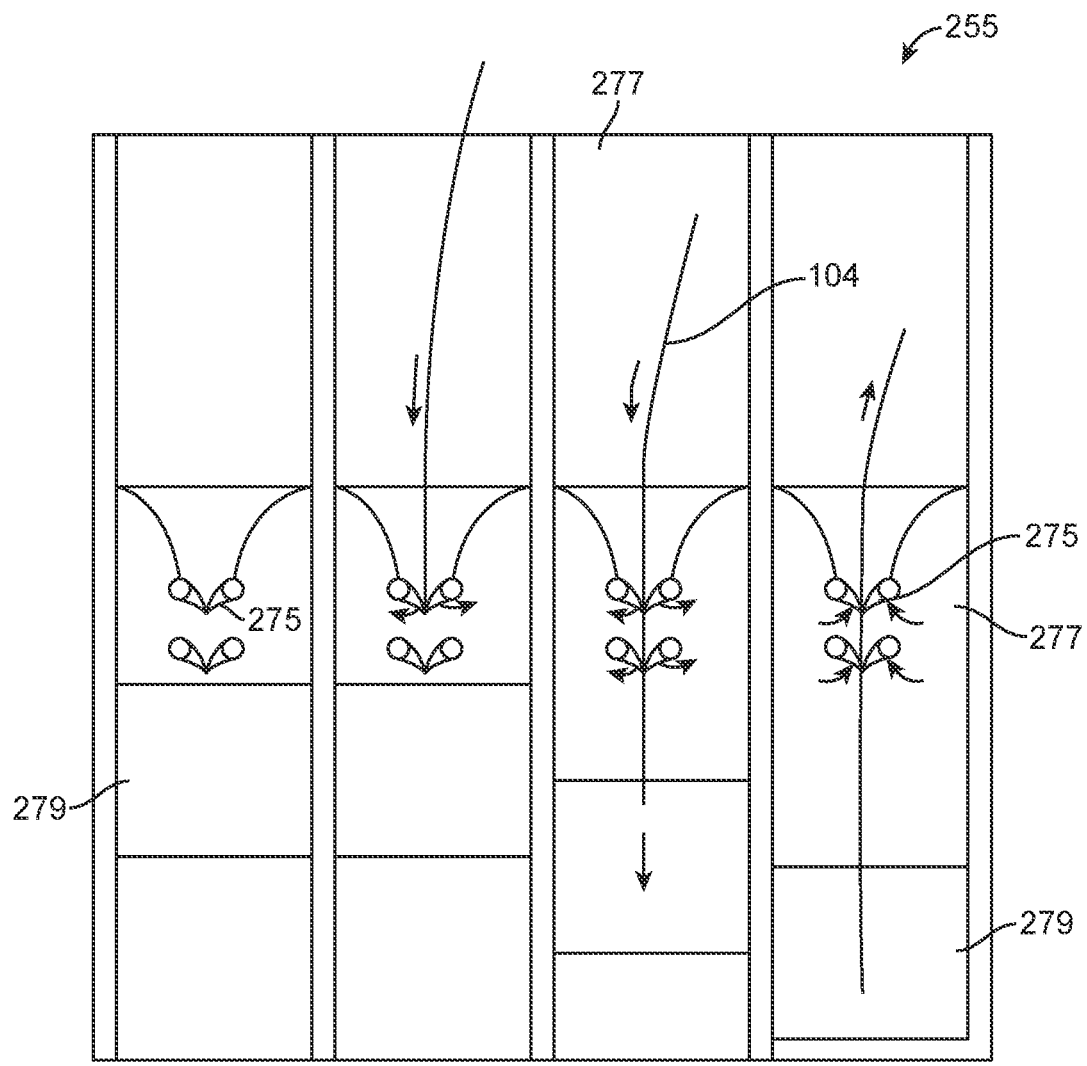
Figure 156:
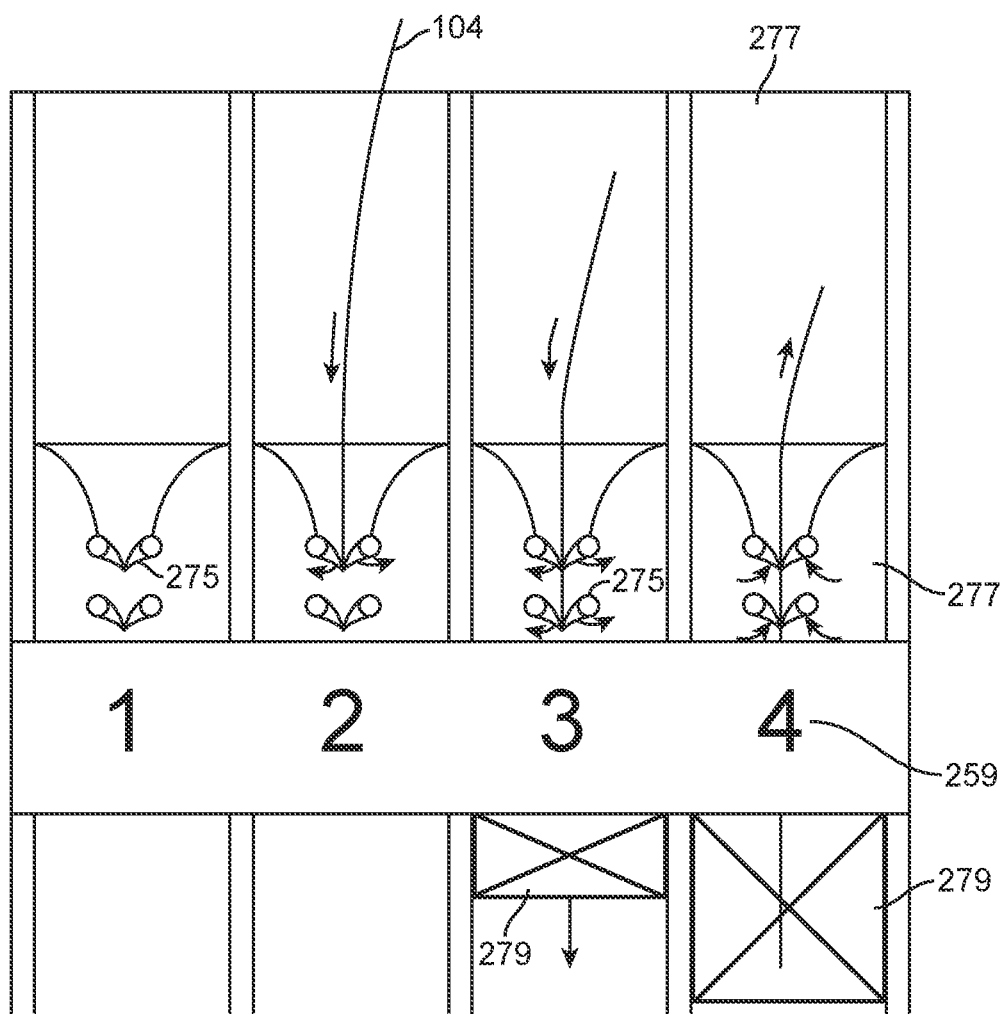

In other embodiments with reference to FIGS. 155 and 156, the locking mechanism 265 can include multiple cams 275. The used needles 104 can be pressed through multiple cams 275 which are mounted on opposite sides of the channel 277. The cams 275 can rotate downward to allow the needles 104 to enter the sharps container 255. If an upward force is applied to the needles 104, the cams 275 will rotate upward and clamp the opposite sides of the needle 104 at each cam 275 to prevent the needles 104 from being removed. In other embodiments, various other locking mechanisms can be used to prevent the used needles 104 from being removed from the sharps container.

In an embodiment, the sharps containers 255 can have indicators that indicate that the needle is properly placed in the channel 277 of the sharps container 255. In the illustrated example, foam indicator blocks 279 can be mounted just below each of the cams 275. The friction force of the foam 279 against the sides of the channel 277 can hold the blocks 279 in place. After the needle 104 tip passes through the cams 275, it contact the upper surface of the foam indicator block 279 and the downward force of the needle 104 can move the foam block 279 to a lower portion of the channel 277. Eventually, the foam block 279 may contact the bottom of the channel 277 and the used needle 104 can be further inserted into the foam block 279 without any additional movement of the block 279. In an embodiment the foam block 279 can be concealed in the upper position and visible in the lower position so that users can easily see if the channel 277 of the sharps container 255 is filled with a used needle 104. FIG. 155 illustrates the sharps container 255 with the foam blocks 279 in the upper positions covered with numerical markings 259.

Figure 151:
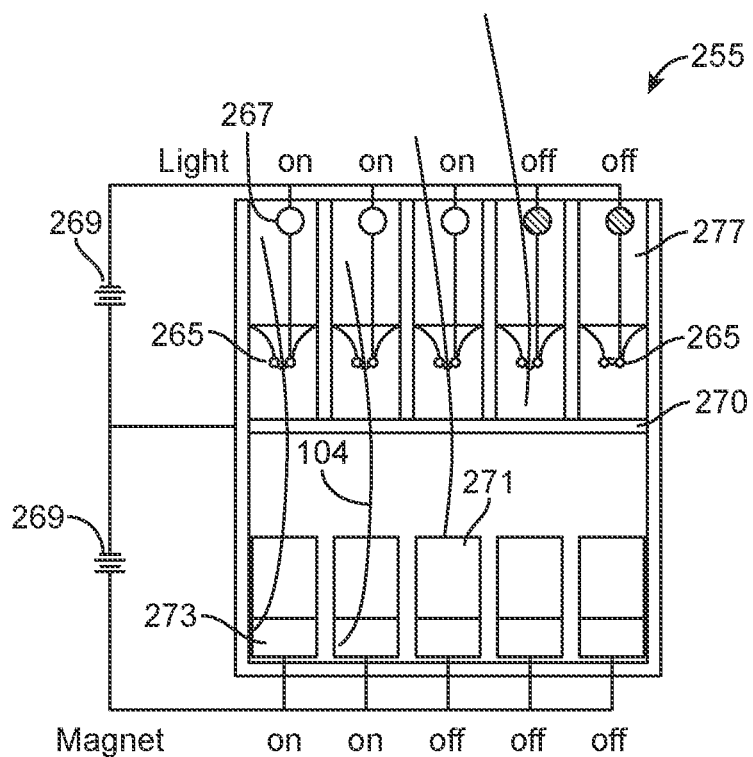
Figure 152:
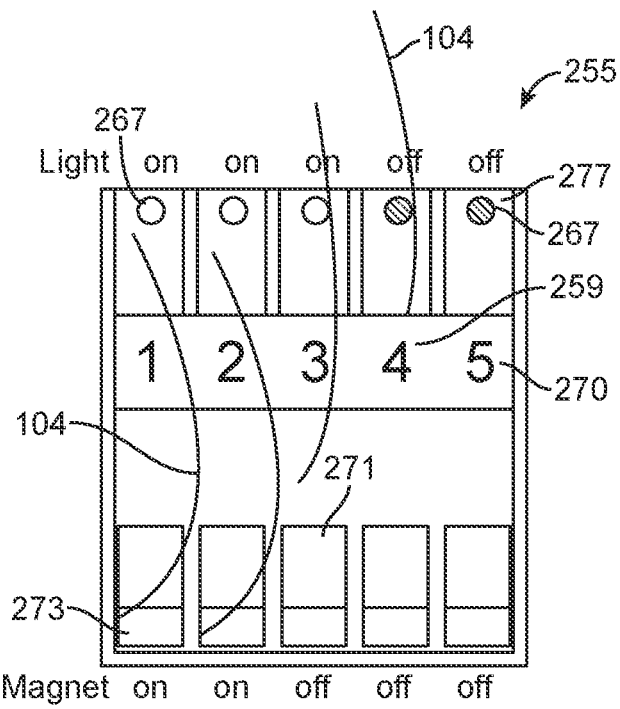

In other embodiments, other types of locking mechanisms and indicators can be used with the sharps container. In an embodiment illustrated in FIGS. 151-152, the used needles 104 can be electrically conductive and magnetic. FIG. 151 illustrates sharps container 255 with the electrical circuitry and locking mechanism 265 visible. FIG. 152 illustrates the sharps container 255 with the electrical circuitry and locking mechanism 265 covered with numerical markings 259. The channels 277 can have an upper electric circuit for a light indicator system. The upper light indicator circuit is normally open with the light 267 off. The needle 104 is placed into the locking mechanism 265, which is electrically connected to light 267 and a positive or negative lead of the battery 269. When the needle 104 is pressed through the locking mechanism 265 to a lower conductor 271 the electrical contact of the used needle 104 closes the circuit illuminating the channel light 267. Because the needle 104 is locked in place, the light 267 will remain illuminated.

In the illustrated embodiment, the lower circuit turns on the electromagnet 273 when the tip of the needle 104 is adjacent to the electromagnet. In this embodiment, the lower circuit is completed when the needle 104 which is in contact with the middle conductor 270 also touches the lower conductor 271. This electrical connection between the middle conductor 270 and lower conductor 271 completes the circuit and causes the electromagnet to energize pulling the needle against the electromagnet 273. It would be easy to slide the needle 104 against a charge electromagnet 273 so it should be energized once the needle 104 is in the proper position. In this embodiment, the electromagnet 273 provides a locking mechanism that prevents the needle 104 from being removed from the sharps container 255. The electromagnetic 273 locking mechanism can be used alone or in combination with other locking mechanisms.

In other embodiments, the sharps container 255 can have battery 269 and control electronics that senses presence of needle 104 and keeps ongoing count and has indicator lights 267 or display that lets operator know the relative or absolute absence of needle same device can contain transmitter to communicate wirelessly with other devices and electronics including via Bluetooth or low frequency low energy transmitter including tablets, computers, mobile phones etc. Sensors may sense impedance changes, weight, electrical resistance, volumetric, etc. The sensor information can be used to indicate the number of used needles 104 in the sharps container for the purpose of providing an accurate used needle 104 count. The electromagnet 273 can work through a plastic layer. Therefore in some embodiments, the used needles 104 are not in direct contact with the electromagnets 273. When the used needles 104 need to be removed from the sharps container 255, the electromagnets 273 can be turned off. In an embodiment, electromagnet 273 can be used to secure the sharps container 255 to a magnetic forearm platform.

Figure 141:
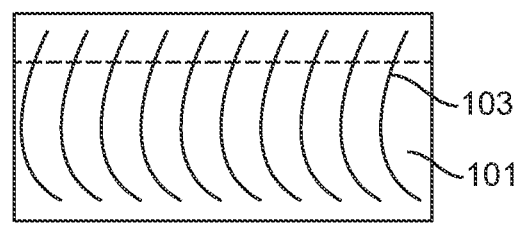
FIG. 141 illustrates a top view of an embodiment of a suture pack.
Figures 142, 143:
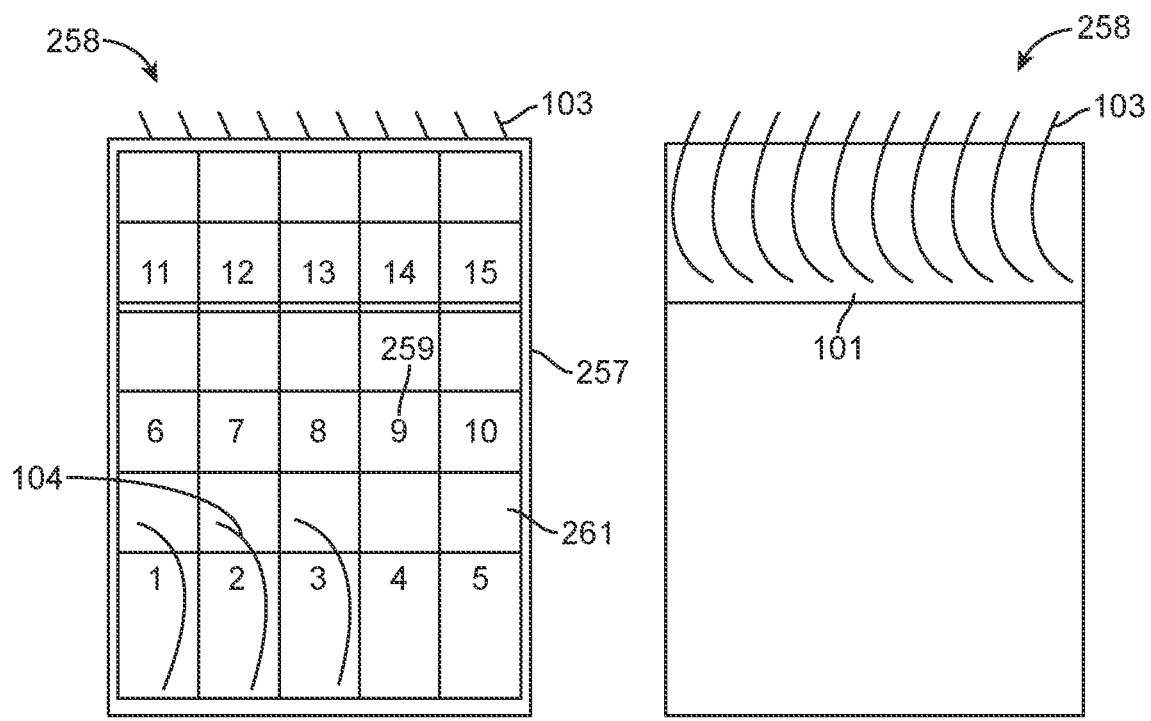
FIG. 142 illustrates a front view of an embodiment of a sharps container coupled to a suture pack.
FIG. 143 illustrates an embodiment of a sharps container coupled to a suture pack.
Figures 144, 145, 146:
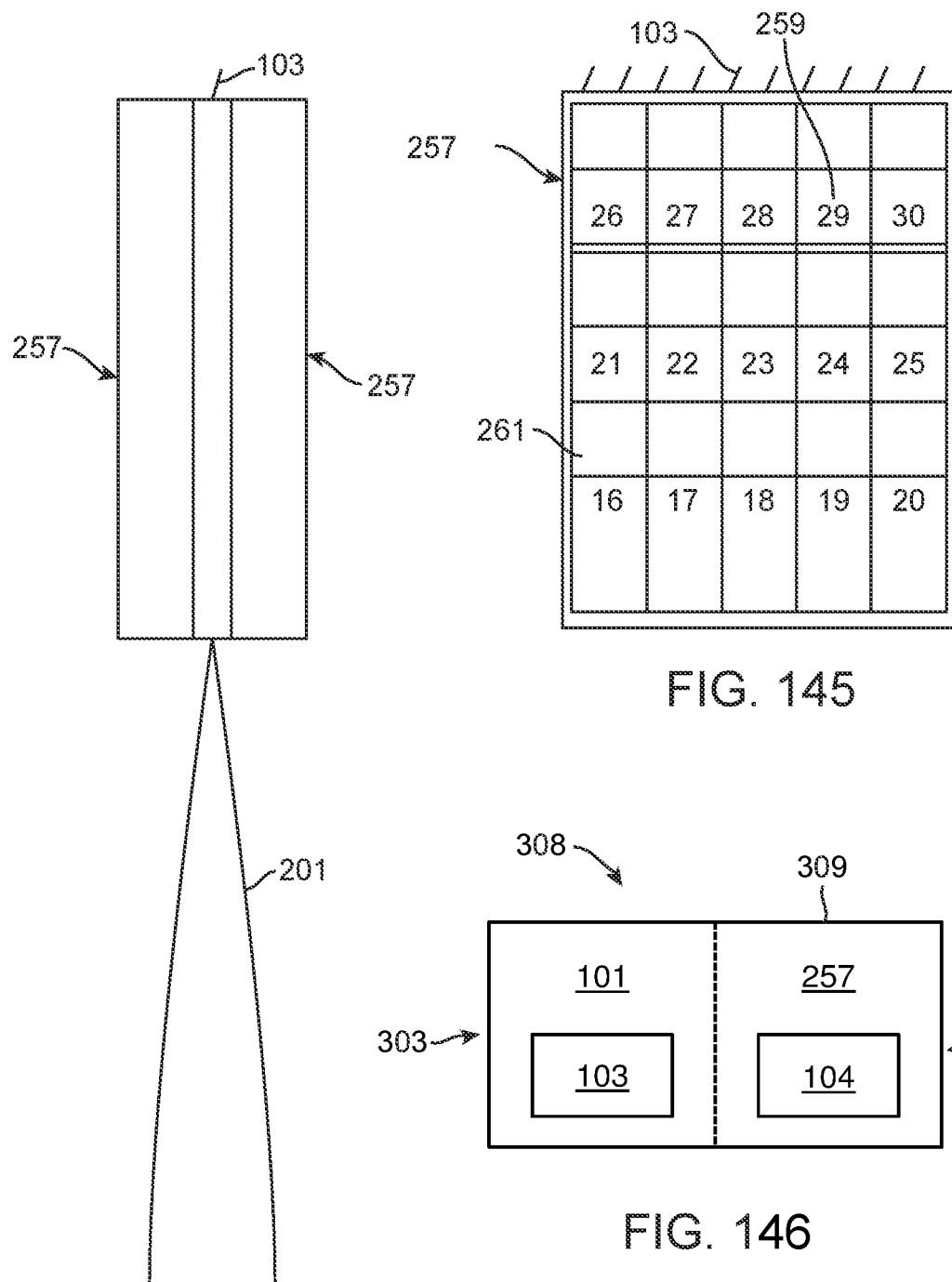
Figure 147A:
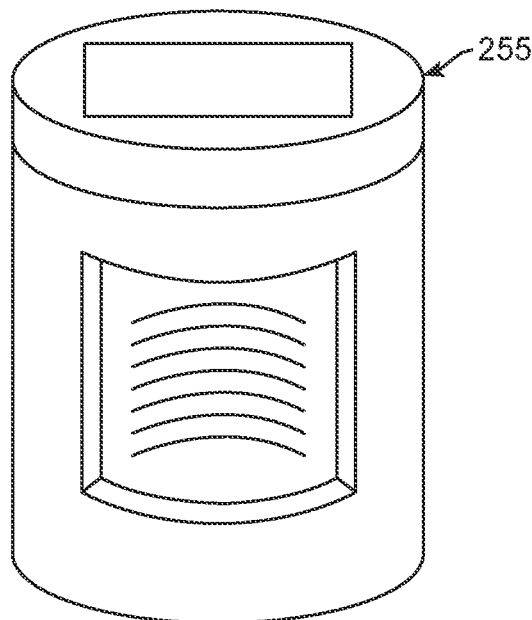
Figure 147B:
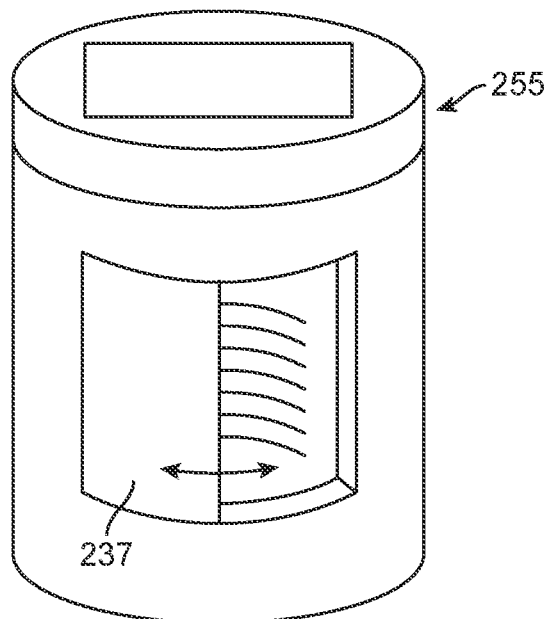
Figure 148:
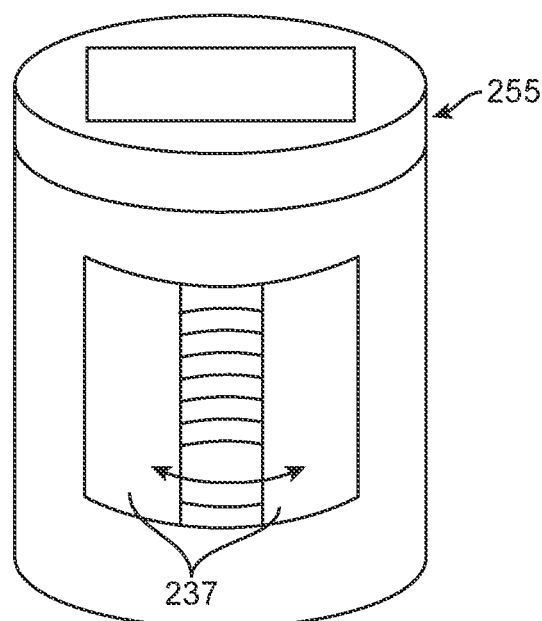
Figure 149:
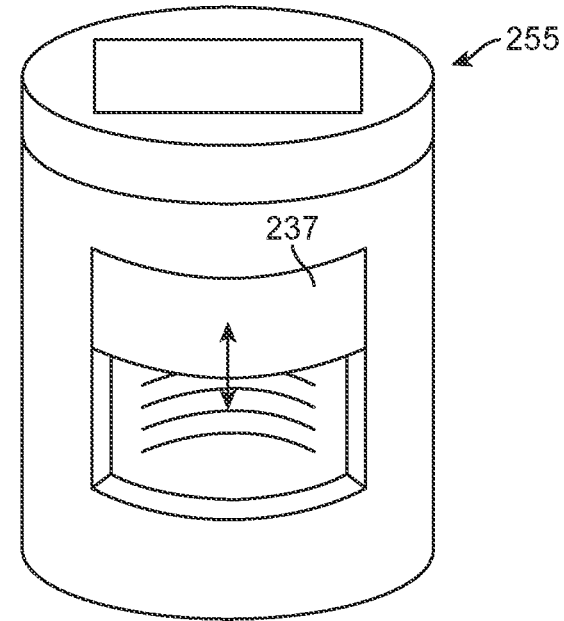

As discussed above, the needle receptacle and suture packet assembly can be placed on the end of a surgical tool. The prior example illustrated suture packets on the exposed sides and a used needle receptacle along the edge of the assembly. In other embodiments as illustrated in FIG. 142, it is also possible to have the used needle receptacles on the exposed sides and the suture packets placed on the edge of the assembly between the used needle receptacles. In the illustrated example, the proximal ends of the new needles 103 in the suture packets 101 can be exposed and extend away from the edges of the used needle receptacles 257. In an embodiment with reference to FIG. 141, the portion of the suture packet 101 adjacent to the proximal ends of the new needles 103 can be bent or removed to expose the proximal ends along the dashed line. With reference to FIGS. 144 and 145, the suture packet 101 and the proximal end of a surgical tool 201 can then be positioned against the backs of the used needle receptacles 257 to form a used needle receptacle and suture pack assembly 258. The used needle receptacles 257 can be secured to the proximal end of the tool 201 with an adhesive or any other suitable coupling mechanism.

The surgeon can grasp a proximal end of a new needle 103 from the used needle receptacle and suture pack assembly 258 and install the suture. The surgeon can then insert the used needle 104 in the next sequential space in the used needle receptacle 257. The surgeon can then grasp another new needle 103 and repeat the process. This process is more efficient because the surgeon does not need to reply upon a scrub tech to handle needles and needle drivers. This process is also safer because there is limited, or no coordinated handling of needles between the surgeon and the scrub tech reducing the risk of mishandling.

Embodiments of the present invention are directed towards sharps containers that can provide a lightweight structure that securely store between about 2-20 used needles in the immediate proximity of the surgeon. The sharps container can be less than approximately 4 inches in height or length, 4 inches in width and 3 inches in thickness and can be held on a surgical tool, a platform supported by the surgeon or any other movable structure controlled by the surgeon. The inventive sharps container can have an internal volume for storing the used sharps and in an embodiment, the container can have a movable door that can be open to insert the used sharps and closed to prevent the used sharps from escaping. The shape of the sharps container can be cylindrical, box shaped or any other suitable shape that has an internal volume that is large enough to store about 2-20 used needles 104. Because the used sharps container can be on the end of a surgical tool, the weight of the used sharps container is preferably less than 0.100 lbs. or 45 grams.

In many embodiments, the surgeon takes responsibility for securing the needle or group of needles prior to passing to the assistant. The suture needles can be curved solid needles that pass through tissue. Thus, these needles pass through very small holes in the tissue and the needles cannot have adaptions on the back end of the needle to slide over the needle to safely secure the sharp used needle tip in at least some embodiments.

In an embodiment, the present invention provides a means for safely securing the used surgical needle in the surgical field with the shortest route for the contaminated needle from tissue to a used sharps container. The process is substantially shorter because the needle only travels a short distance that is normally less than one foot, for example within the near surgical field.

The design and use of the inventive sharps container as described and illustrated has physical properties that do not interfere with the surgeon's workflow in closing patient wounds. Work in relation to embodiments suggests that securing used needles to a sharps container positioned on the instrument or on the surgeon's forearm or hand actually expedites the procedure, in addition to making the procedure safer. There can be no shorter physical path for the needle to a sharps container that is attached to hand/forearm or back of surgical tools on the surgeon's anatomy. Thus, the inventive system also minimizes the distance that the used needles must travel and eliminates unnecessary movement of the used needles, which increases the efficiency and reduces the required time. The inventive process has the benefits of only requiring the surgeon to perform the entire task, which minimizes the handling of a used sharp needle which increases the safety of the inventive system.

FIG. 146 is a block diagram of an apparatus 308 comprising an integrated suture packet and needle receptacle, in accordance with embodiments. In an embodiment of the present invention, a plurality of new needles 103 can be packaged with a sharps container or needle receptacle 257 as a single integrated unit 308 that can share the same housing 309. The needle receptacle may comprise any sharps container or needle receptacle as described herein (e.g., used needle receptacle 191, sharps container 257, needle trap 331, etc.), configured to secure a plurality of dispensed suture needles 104. The integrated suture packet and sharps container can include a predetermined number of new needles and a sharps container that includes sufficient room for at least the predetermined number of used needles. For example, in an embodiment the integrated suture packet and sharps container can contain five new needles in the suture packet within or mounted on a first portion of the housing with an optimized sharps container for the used needle that can accept between about five to seven used needles. In other embodiments, the integrated unit can have any other number of needles, for example, 10 or 20 or more. However, the integrated sharps container is preferably able to hold an equal number or more used needles than new needles.

In some embodiments, the integrated suture packet and sharps container 308 share a housing 309, with the new armed needles 103 accessible from a first side 303 of the housing, and the sharps container 257 disposed on a second side 304 of the housing. For example, in a first embodiment the surgeon may use a needle driver to grasp an armed needle from a first side of the housing. The surgeon can use the suture and place the used needle in the sharps container through a door in a second side, such as the top surface, of the housing. The user can open the door to insert the used needle and then close the door to prevent the used needle from escaping.

In other embodiments, a protective door can be closed to shield the armed needles. This can be useful if the integrated suture packet and sharps containers are placed in storage to protect the needles. In different embodiments, the protective doors can be opened in various different ways. In an illustrated embodiment, the door may slide side to side or up/down so that the surgeon can easily open the door to access new armed needles. In other embodiments, multiple doors can open to allow access to the armed needles. In some embodiments, the protective door can be manually operated. In other embodiments, an actuator can be used to control the position of the protective door. The housing can also have an outer surface which can be used for labels or markings to provide needle and/or housing information.

Such an integrated configuration of a suture pack and a needle receptacle can provide improved safety and efficiency benefits described herein. Sharps containers can have many different varieties including: foam with demarcations that allow for multiple needles, foam encased in an outer shell such that needles cannot pass out the sides of the shell, foam encased in the outer shell having an aperture for introducing the used needles, the aperture is more narrow that the width of the housing such that with the bend of the needle, the housing will capture the needle tip. The foam represents a reservoir type vehicle for capturing needles in which the surgeon has flexibility on the orientation and location to place the used needles.

Another sharps container embodiment includes specific holes into which the needles are place by the surgeon. The used needles can go in but the mechanism captures the needle and does not allow removal of the used needles 104. Such mechanisms can include a cone with tapered tip and malleable leaves that bend to allow needle passage but prevent removal-similar in shape to lobster trap. Another mechanism is a cam or several cams with ratchet. As a used needle is introduced the cams rotate and compress the tip of the needle. Rotation of the cams can also expose side of the cam with a color change indicating the presence of the needle. There many potential mechanisms for capturing individual needles at fixed location.

Figure 150:
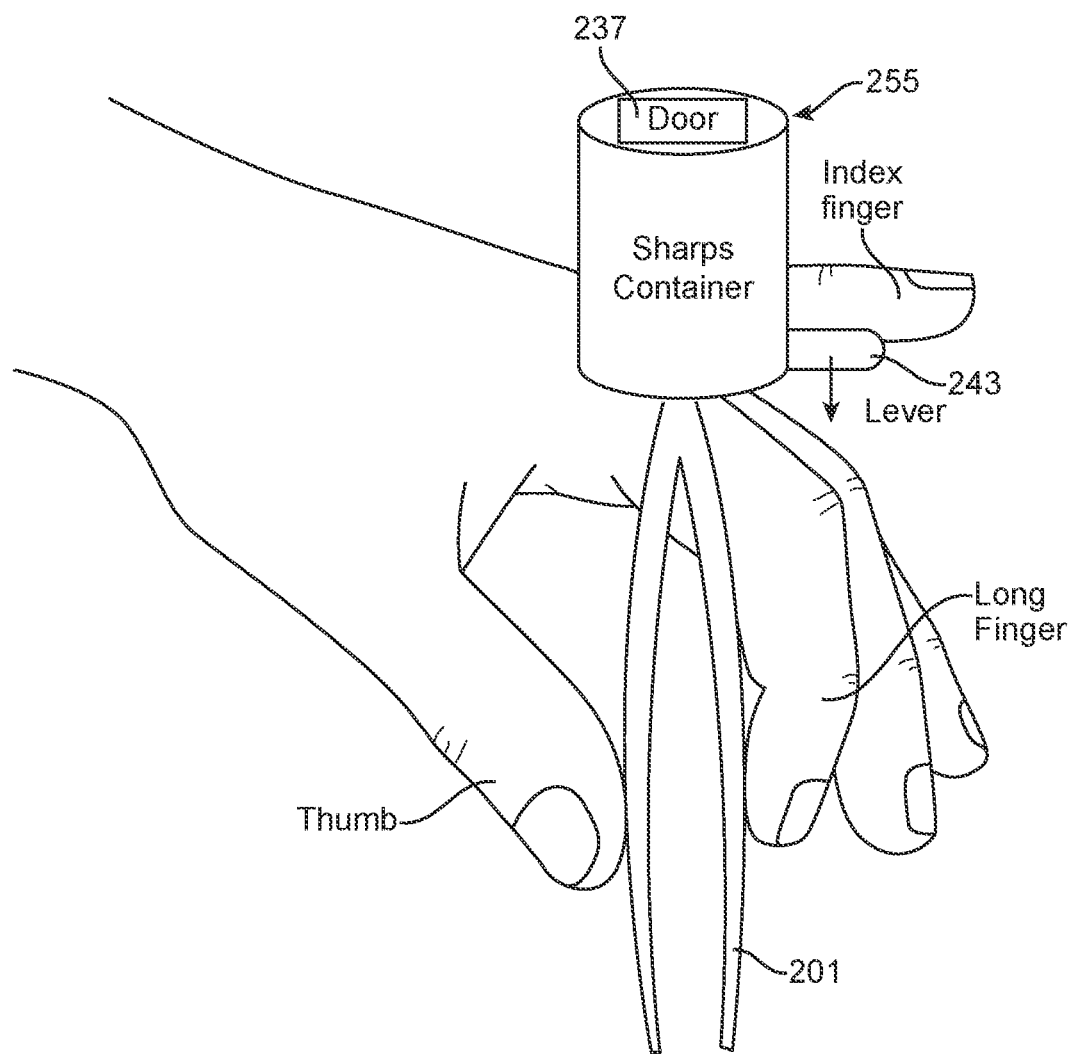

FIGS. 147A-149 illustrates exemplary embodiments of a sharps container in the form of a cartridge. The cartridge can be attached to the instruments that are typically used in the non-dominant hand such as the surgical pickups, Adsons, Bonneys, etc. The cartridge can be designed to be secure to the pickups and can include a mounting mechanism that can allow the cartridge to be easily attached and detached from the tool or structure. In addition to the sharps container, the cartridge can also include one or more needle packages and broad labeling on an outer surface of the housing that can be easily visible to the surgeon. FIG. 150 illustrates an embodiment of a sharps container 255 coupled to a surgical instrument 201.

Figure 157:
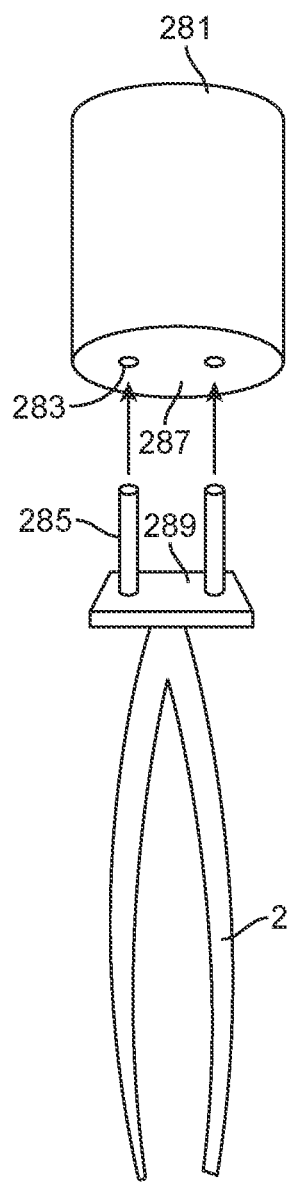

In an embodiment, the cartridge can include an attachment mechanism(s). The attachment mechanism can be used to couple the cartridge to another object such as a tool or a platform. In an embodiment the attachment mechanism can be a slot or slots or holes in the cartridge into which the non-surgical end of the pickup attaches, or can incorporate and adaption of the surgical pickup. In other embodiments, the attachment mechanisms can include permanent magnets which can be used to secure the cartridge to the tool. With reference to FIG. 157 in the illustrated example, the cartridge 281 has two holes 283 which correspond to two elongated rods 285 that extend from the proximal end of a forceps tool 201. Permanent magnets 287 can also be mounted at the proximal end of the forceps tool 201 so that the magnets 287 in the cartridge 281 will be attracted to magnets 287 in the forceps tool 201 and the magnetic attraction will hold the cartridge 281 in place. The cartridge 281 can be separated with a force greater than the magnetic attraction force is applied.

Figure 158:
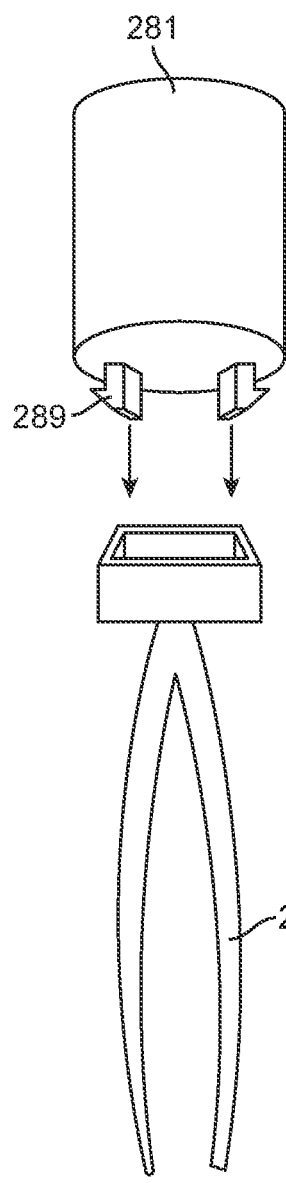
Figure 159:
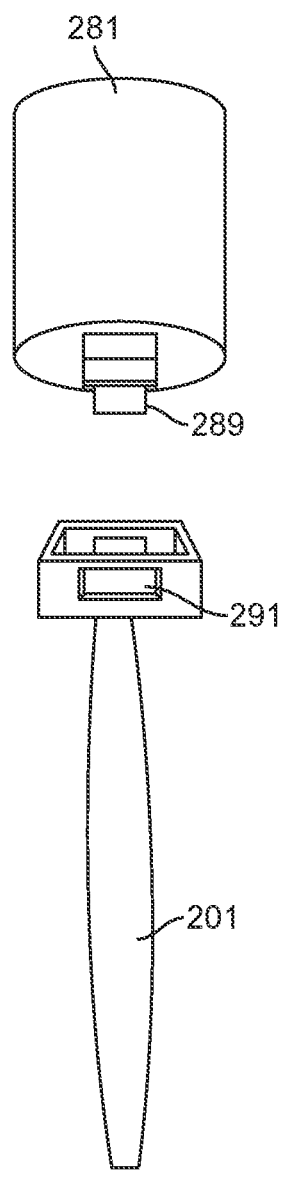

In other embodiments, a pure mechanical locking mechanism can be used to secure the cartridge to another object. In an illustrated example FIGS. 158-159, the bottom of the cartridge 281 has two tabs 289 which can engage corresponding recesses 291 in a coupling. When pressed together, the tabs 289 can deflect inward so that the outer surfaces of tabs 289 slide against the inner surfaces of the coupling. The tabs 289 can then engage the slots 291 in the inner surfaces of the coupling to rigidly secure the cartridge 281 to the top of the forceps tool 201. The user can squeeze the tabs 289 inward through the slots 291 to disconnect the cartridge 281 from the forceps tool 201.

In different embodiments, the fresh needle side of the cartridge can have a protective cover or door that moves or slides to expose the armed needle. The protective cover or door mechanism can be actuated in any direction, up down or sideways.

The cartridge can have an oval cross section with the fresh needles recessed from the face. Once the cover or door is open, the fresh needles are accessible to the surgeon.

The sharps container can be closed cell foam on the contralateral side that also is marked and has an aperture on the face. The foam may extend to the full border of the face to facilitate the capture and retention of the used needles 104. The walls of the cartridge are not penetrable by the needle to protect the needle from coming out of the side of the housing.

The sharps container can have a magnetic base that can help to prevent used sharps from accidental removal and the sharps container can also be a clear transparent structure that can allow the used needles 104 to be more easily counted. The sharps container can have a dome coverage that allows used needles 104 to pass through by rotating the needle through a small aperture so needle can enter the sharps container at any angle. The sharps container may include a magnetic base with covers that lock in place as needle placed in the container. Locking or closing the sharps container lid may expose the next new armed needle(s) or actuate and open the door covering the new needles.

With reference to FIGS. 160-166 in yet another embodiment of the sharps container, a hole 293 is a housing 295 can be covered with a thin layer of elastic foam 263. A larger width volume of the sharps container can be located under the hole 293. Thus, when a needle 104 is placed into the foam 263 over the hole 293, the needle 104 will pass through the foam 263 and the middle portion of the needle 104 may be positioned within the hole 293 and the sharp tip can be within the wider volume below the hole 293. In an embodiment, this embodiment of the sharps container can include a layer of elastic foam 263 that can be between about 1-10 mm thick covering an underlying hole 293 that can be between about 2-50 mm in diameter or wide. The hole 293 depth can also be between about 2-50 mm. The foam material 263 can be bonded to the top of the housing 295 and can cover the hole 293 like a drum. This configuration can have several benefits. The needle 104 tip can more easily pass through the foam 263 layer with less force than a thicker foam layer. However, the thinner foam 263 layer still provides enough sliding resistance to prevent the used needles 104 from becoming dislodged by gravity. The proximal aspect of the needle 104 will still remain above the foam layer 263.

Forces on the proximal aspect of the needle 104 do not need to be very large to cause the needle 104 to be further advanced through the foam 263 layer or rotate the needle 104 within the foam 263. The foam 263 can also allow for low force angulatory displacement of the needle 104 relative to the plane of the foam 263. Thus, if a side force is applied to the exposed proximal portion the needle 104 will simply bend relative to the plane of the foam 263. Under the foam 263, there is a sufficient volume for the distal tip of the needle 104 to move around within the sharps container housing 295. Because the foam 263 can allow for movement of the needle 104 even after it has been inserted, there is a reduced risk of injury to human skin by the proximal aspect of the needle 104. As discussed, a downward force on the needle 104 will cause it to be pushed further through the foam 263 into the sharps container and a horizontal force will cause the needle 104 to rotate about the foam 263 entrance point.

In different embodiments, the hole 293 size and the foam 263 thickness can both be variable. The size and physical properties of the foam 263 and hole 293 can be selected to provide optimized functionality based upon the types of needles 104 being used. Smaller needles 104 are lighter weight can use thinner lower density foam 263 over a smaller hole 293 while longer needles 104 may need thicker higher density foam 263 over a larger hole 293. The shape of the underlying volume of the container will need to be optimized to allow for maximal needle 104 tip excursion.

Figure 160:
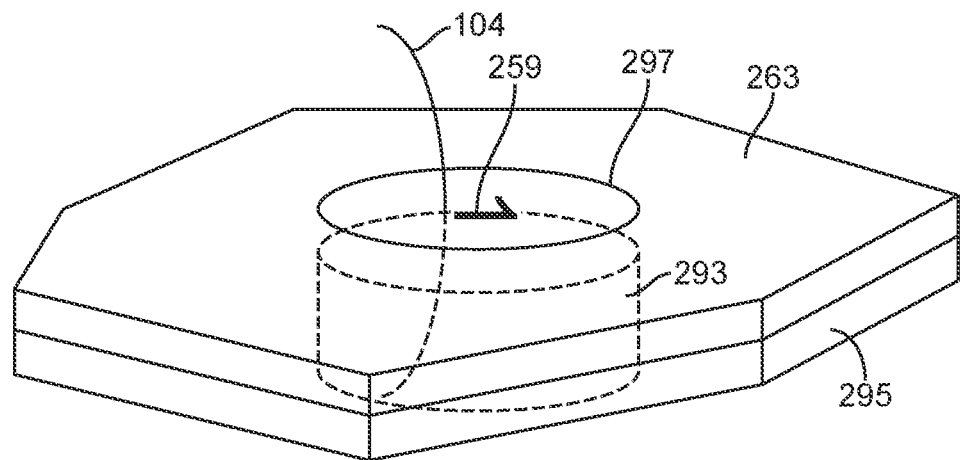
Figure 161:
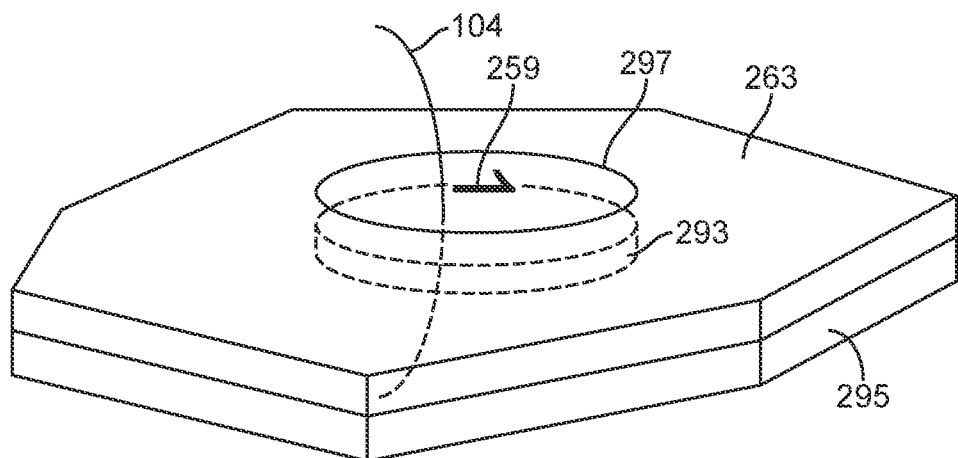
Figure 162:
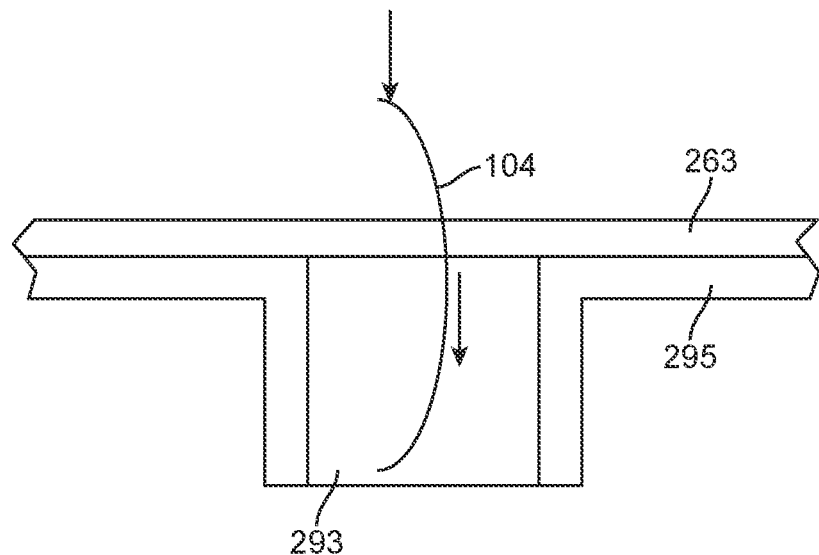
Figure 163:
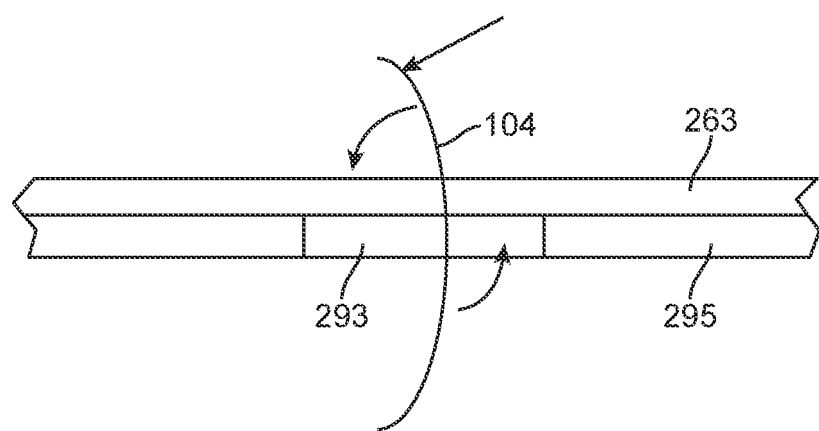

In an embodiment, the position of the holes 293 can be indicated by corresponding circular markings 297 on the exposed side of the foam 263 so that the user can easily locate the holes 293 under the foam 263 layer. The holes 293 can be numerically marked 259 so to help with needle 104 counts. The hole 293 can be part of a tubular structure that extends into the housing 295 as shown in FIGS. 160 and 162. Alternatively, the hole 293 can be planar with the wall of the sharps container structure housing 295 as shown in FIGS. 161 and 163.

Figure 166:
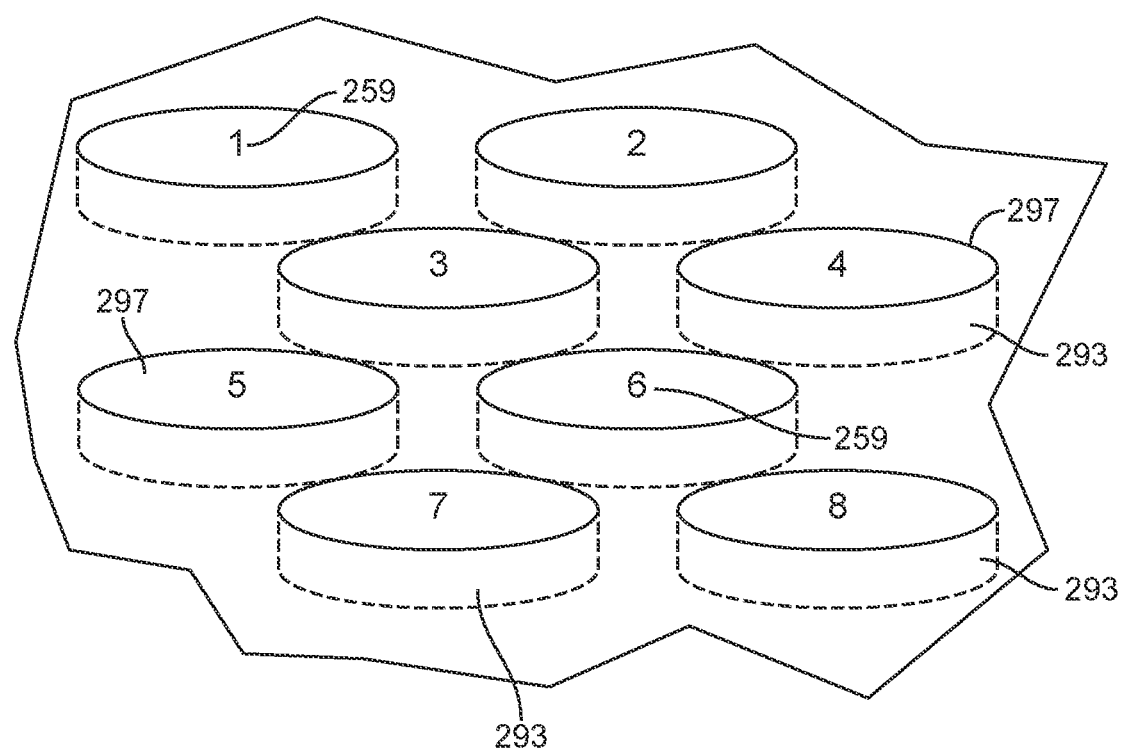

With reference to FIG. 166, in an embodiment, the sharps container can include many holes 293 that are each covered with a foam 263 layer. Each of the holes can be marked with a circular marking 297 to visually indicate the locations of the holes 293. A sequence of numerical markings 259 can also be placed within each of the circular markings 297 to aid with the needle count. The used needles can be sequentially placed in different circular markings 259 through the foam 263 in the order of the numerical markings 297 which can simplify the counting of the used needles.

Figure 164:
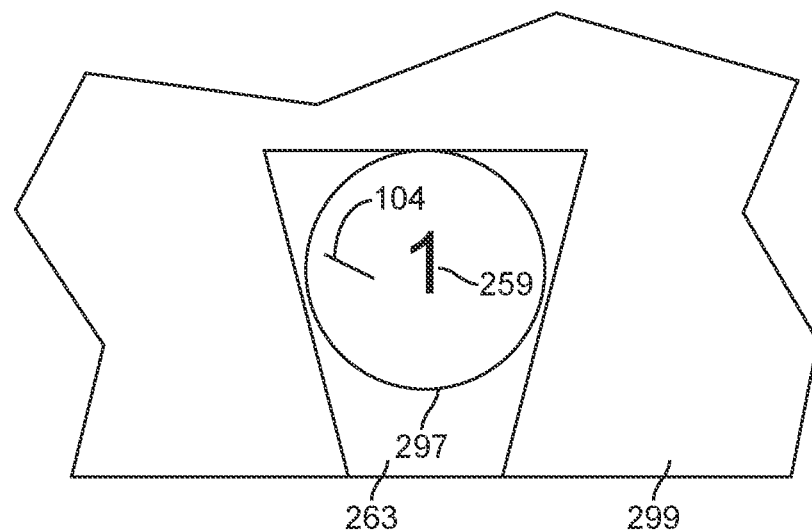
Figure 165:
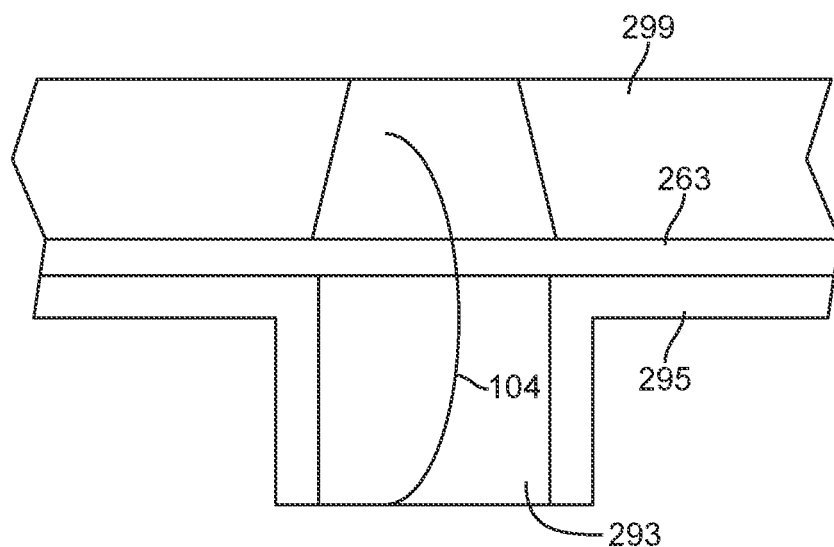

In other embodiments with reference to FIGS. 164 and 165, it is possible to modify the device above the plane of the foam 263 to further limit access to the proximal aspect of the needle 104. For example, in an embodiment, sharps container can include protective structures 299 on opposite sides of the needle insertion hole. For example, the protective structure 299 can have two trapezoidal openings orthogonal to one another. The user can insert the used needle 104 into the trapezoidal openings, through the foam layer 263 and into the underlying hole 293. It is also possible to have a large number of used needle holes 293 in the sharps housing 295 that are each similar to the described used needle 104 hole structures. Again, the position of the hole 293 can be visually indicated by the circular marking 297 and the numeric sequence of the hole 293 can be indicated by the numeric marking 259.

In an embodiment, a modular medical device comprising a forearm-mounted puncture barrier functions as a platform upon which one or more used needle repositories and/or one or more suture packs or suture pack carriers can be mounted. The used needle repositories and the suture packs/carriers can be coupled to the forearm mounted puncture barrier by any of the coupling mechanisms described above or by any other suitable method. The used needle repositories can include various needle trap devices and the suture pack carriers can include a clip for holding a suture pack to the forearm mounted puncture barrier. The needle trap can be removable from the forearm mounted puncture barrier and is intended for replacement when the device has secured the intended number of contaminated needles.

Figure 168:
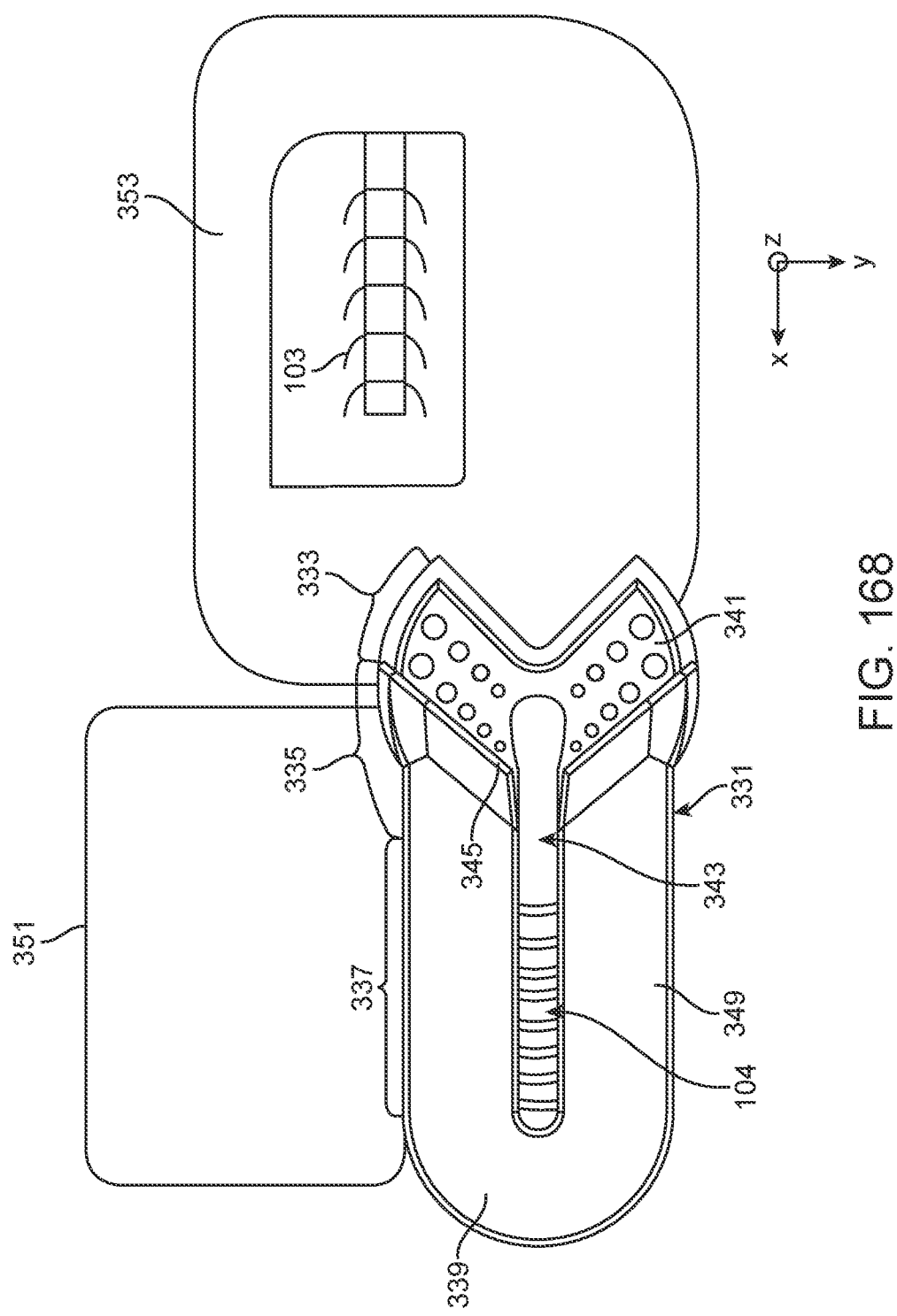

An embodiment of a used needle trap is illustrated in FIG. 168, which is a top view of the needle trap 331 with suture pack holder 351, which can hold suture pack 101, and suture pack 353. In the illustrated embodiment, the needle trap 331 can be a planar device that is comprised of several zones: 1) an entry zone 333, 2) an entryway or transition zone 335 and 3) the secure zone 337. The needle trap 331 can include an upper structure 339 and a lower structure 341 that are securely coupled together around an outer portion of the needle trap 331. The needle trap 331 can have a needle driver slot 343 extending through both the upper structure 339 and a lower structure 341, the needle driver slot configured to provide clearance for the needle driver along the entire length of the needle translation from entry zone 333 to secure zone 337. The needle trap can further comprise a needle slot 349 that constrains the secured needles into a single needle depth array, to minimize overall depth profile and facilitate needle counting. The configuration of the needle trap 331 can be described with reference to an X axis that extends from left to right and Y axis extends up and down when viewing the front or top of the needle trap 331 from the perspective of the surgeon, and a Z axis which defines a depth position.

In an embodiment, the entry zone 333 of the used needle container 331 can be a partially circular flat zone or area in the X-Y plane that is an exposed part of the lower structure 341. The surgeon can hold the used needles 104 with a needle driver and place the used needles 104 on an upper surface of the entry zone 333. The contact and/or force of the needle 104 against the entry zone 333 can cause the curvature of the used needles 104 to be moved into a planar orientation flat against the landing zone surface X-Y plane with the convex mid-portion of the curved needle 104 facing or pointing towards the transitional zone 335.

The entry zone 333 can be wider (y-axis) relative to needle slot 349 and the perimeter around the entry zone 333 can have a contrasting color to aid visual recognition. The upper surface of the entry zone 333 surface can include a low friction material. Graphic guides on the entry zone 333 surface can help to reinforce needle 104 rotational orientation. The needle driver slot 343 can extend into the entry zone 333 and the width of the needle driver slot 343 can be greater or oversized in the entry zone to facilitate fast location of the entrance to the needle trap with the needle driver. The needle driver slot can taper as it extends through the transition zone 335 towards the secure zone 337, to provide a self-centering close fit with the tip of the needle driver in the transition zone 335 and secure zone 337.

The transition zone 335 is disposed between the entry zone 333 and the secure zone 337. In the transition zone, the compressive side load on the needles ends may be increased and the depth (z-axis) of the needle slot can narrowed as the secured needles are translated through the transition zone, constraining the needles to a single needle deep array extending longitudinally along the secure zone 337.

The secure zone 337 comprises the region adjacent to the transition zone 335, in which full compressive side loading is applied to the needle ends to prevent unintentional removal or dislodging of the needles.

The boundary 345 may be concave, wedge or "V" shaped, with the apex of the "V" shape pointing towards the secure zone 337 to promote proper orientation of the needles 104.

In an embodiment, the transition zone 335 can include a concave, wedge or "V" shaped boundary on a side of the entry zone 333 in the upper structure 339 with the apex of the "V" shaped boundary pointing towards the secure zone 337 to promote proper orientation of the needles 104. The secured needle 104 in the needle trap 331 can be configured to have the convex side of the needle 104 facing the secure zone 337 and the concave side, sharp point and tail of the needle 104 facing towards the entry zone 333. Thus, the needle trap 331 can be configured to have the sharp leading and trailing ends of the needle 104 pointing away from the direction of motion, thereby reducing the risk of needle-stick injury. The transition zone 335 can have a flared cowling over a portion of the landing zone and tapered surfaces in both the Y-axis and the Z-axis, to reduce the width and height from the entry zone 337 to a single needle height and width in the used needle slot 349 as the needle 104 is moved along the longitudinal X-axis path from the transition zone 335 to the secure zone 337. The needle driver slot 343 can intersect a portion of the needle slot 349, such as a middle portion of the needle slot, and can be in the midline of the used needle trap 331 in the X-axis such that the distal tip of the needle driver can translate the needle 104 along the X-axis of the used needle trap 331. Alternatively, the needle driver slot 343 can intersect the needle slot 349 off the midline or asymmetrically, such that the needle driver slot extends along an axis substantially parallel to, but not overlapping, the X-axis of the used needle trap 331. The needles 104 can slide within the needle slot 349 deeper into the secure needle zone 337 without excessive resistance or sensitivity as to how the needles 104 are grasped by the needle holder. In an embodiment, the secure zone 337 can prevent used needles 104 from being removed from the used needle trap 331.

In a preferred embodiment, the needle 104 is moved into contact with the entry zone 333 of the lower structure 341 by the surgeon manipulating the tip of the needle driver in the needle driver slot 343. The needles 104 can be pushed against the entry zone 333 and become aligned with the X-Y plane of the used needle trap 331. The needles 104 can then be moved in translation along the longitudinal X-axis of the used needle trap 331 from the entry zone 333 into the transition zone 107 where the needles 104 slide into the used needle slot 349 with the convex side facing the secure zone 337 and the sharp tip and tail of the needle 104 facing the entry zone 333. The needle driver can move the used needles 104 into the used needle slot 349 in the secure zone 337 until the needle driver runs into the end of the needle slot 349 or the last inserted used needle 104, or the needle 104 contacts the end stop 363 of the needle slot 349.

In an embodiment, the distal tip of the needle driver holding a needle 104 can have an elongated cross section and the width of the needle driver slot 343 can narrow in the secure zone 337 so that the distal tip of the needle driver must be oriented with the longer cross section dimension aligned with the needle driver slot 343. This needle driver orientation can also cause the needle 104 properly aligned across the width of the secure zone 337 within the needle trap 331. Thus, the narrowing of the needle driver slot 343 can force the needle driver to properly orient the needles 104 in the secure zone 337 as the needle driver slides against the sides of the needle driver slot 343 in the secure zone 337.

FIG. 168 illustrates a top view of an embodiment of a needle trap 331. In different embodiments, the needle trap 331 can have different dimension depending upon the size of the needles 104 being stored. Thus, a small needle trap 331 used to store smaller needles 104 can have smaller dimensions than a large needle trap 331 used to store larger needles. With reference to TABLE 1 below, the ranges of dimensions of embodiments of a small and a large needle traps 331 of different sized embodiments are listed. The length can extend along the X-axis, the width can extend along the Y-axis and the thickness can extend along the Z-axis. The entry zone 333 can have a circular portion and the "entry zone radius" can be the radius range of the circular portion. The needle slot thickness can be the range of distances between the lower surface of the upper structure 339 (not including the protrusions 361) in the secure zone 337 and the upper surface of the compressible members 347. In other embodiments, the needle traps 331 can have any other dimensions which will allow the storage of needles 104. The dimensional ranges in table 1 are in inches.

TABLE 1

| Size | Length | Width | Thickness | Entry zone radius | Needle slot thickness |
| --- | --- | --- | --- | --- | --- |
| Small | 2.5 to 4.5 | 0.8 to 2.0 | 0.1 to 0.5 | 0.5 to 1.0 | 0.01 to 0.05 |
| Large | 3.0 to 5.5 | 1.0 to 3.0 | 0.2 to 0.8 | 0.7 to 1.5 | 0.02 to 0.10 |

In the secure zone 337 the Z-axis depth of the needle slot 349 narrows so as to compress against and orient the used needles 104 in parallel alignment with the needles 104 positioned across the width of the needle slot 349 and center portions of the used needles 104 spanning across the needle driver slot 343. Once the needle 104 has been fully inserted into and can proceed no further in the X direction the surgeon can release the used needle 104 in the secure zone 337 and this process can be repeated for the next used needle. The tip and trailing ends of the used needles 104 can be secured within the used needle slot 349 in the secure zone 337 between the lower structure 341 and the upper structure 339. Once the surgery is completed or when the used needle trap 331 is full or during a medical procedure, the used needles 104 stored in the needle trap 331 can be easily counted. In FIG. 168, seven used needles 104 are shown in the secure zone 337.

FIG. 169 illustrates a top perspective exploded view of the needle trap 331 with a suture pack 101, FIG. 170 illustrates a side perspective exploded view and FIG. 171 illustrates a bottom perspective exploded view. The needle trap 331 may comprise an upper structure 339, lower structure 341, compressive members 347, foam connectors 357, entry zone suture pack holder 351, and adhesive pad 355. A plurality of used needles 104 may be secured in the needle trap, and one or more suture packs, such as suture pack 101 holding one or more suture needles 103, may be coupled to the suture pack holder 351 and/or the adhesive pad 355.

The upper structure or front cover shell 339 comprises the top half portion of the needle slot 343, and can be joined to the lower structure 341 by adhesive bonding or ultrasonic welding. The upper structure may comprise an injection molded clear polycarbonate, or other optically transparent material. The inner surface of the upper structure may have protrusions or nubs 361, also referred to as tactile bumps, intended to provide separation between secured needles, to increase resistance against the removal of secured needles, and to provide tactile feedback during translation of needles from entry or transitional zone into the secure zone. The upper structure may includes 2-20 tactile bumps, 5-8 tactile bumps, or 3-10 tactile bumps. The inner surface of the upper structure may have a protruding needle stop 363, intended to prevent needles from being translated beyond the needle driver slot which would prevent accurate visual counting. The upper structure that covers the transition zone 335 is flared at the boundary 345 toward the entry zone 333 to present a deeper (z-axis) spatial target for fast location of the entrance to the trap with the needle driver.

The lower structure or rear shell 341 comprises the bottom half portion of the needle slot 343, and can be joined to the upper structure 339 by adhesive bonding or ultrasonic welding. The inner surface of the lower structure may have wells or recesses 359 within which the compressive members 347 may be adhesively attached. The recesses may decrease in depth within the transition zone from the entry zone to the secure zone to increase compressive side load on needle ends. The deeper recesses at the boundary of the entry and transition zones can prevent the end of the compressive members from being displaced by the needles during translation. The outer surface of the lower structure can incorporate recesses within which the foam connectors 357, adhesive pad 355, and secure zone suture pack holder 351 may be adhesively attached. The walls of the recesses can provide a standoff to provide separation between the needle trap and barrier mounting surface for the needle driver tip. The lower structure may comprise injection molded colored polycarbonate, or a material similar in composition to the material of the upper structure.

Compressive members 347 can comprise open cell urethane foam strips adhesively bonded to the lower structure 341. The compressive members can provide side load compression on the ends of the used needles along the secure zone.

The foam connectors 357 can provide an attachment interface between the needle trap 331 and a barrier or platform as described herein. The foam connectors may be adhesively attached within recesses to the outer surface or underside of the lower structure 341. Loop connectors may be adhesively attached to the exposed foam surface, which can extend above the recess walls and provide a means of attachment to corresponding hook connector adhesively attached on the exterior barrier surface.

The secure zone suture pack holder 351 can provide a means to permanently attach a suture pack 101 next to the needle trap 331, providing a means for proximity reconciliation in real time by both the surgeon and operating room assistants in the near surgical field. The suture pack holder may comprise a closed cell foam pad, adhesively bonded to the outer surface of the lower structure 341. The exposed top surface of the holder may be covered with pressure sensitive adhesive for attachment to the rear surface of a suture pack. Loop connectors can be adhesively attached to a raised surface 344 on the bottom surface of the suture pack holder, and provide a means to attach to a hook connector on a barrier or platform as described herein.

Figure 167:
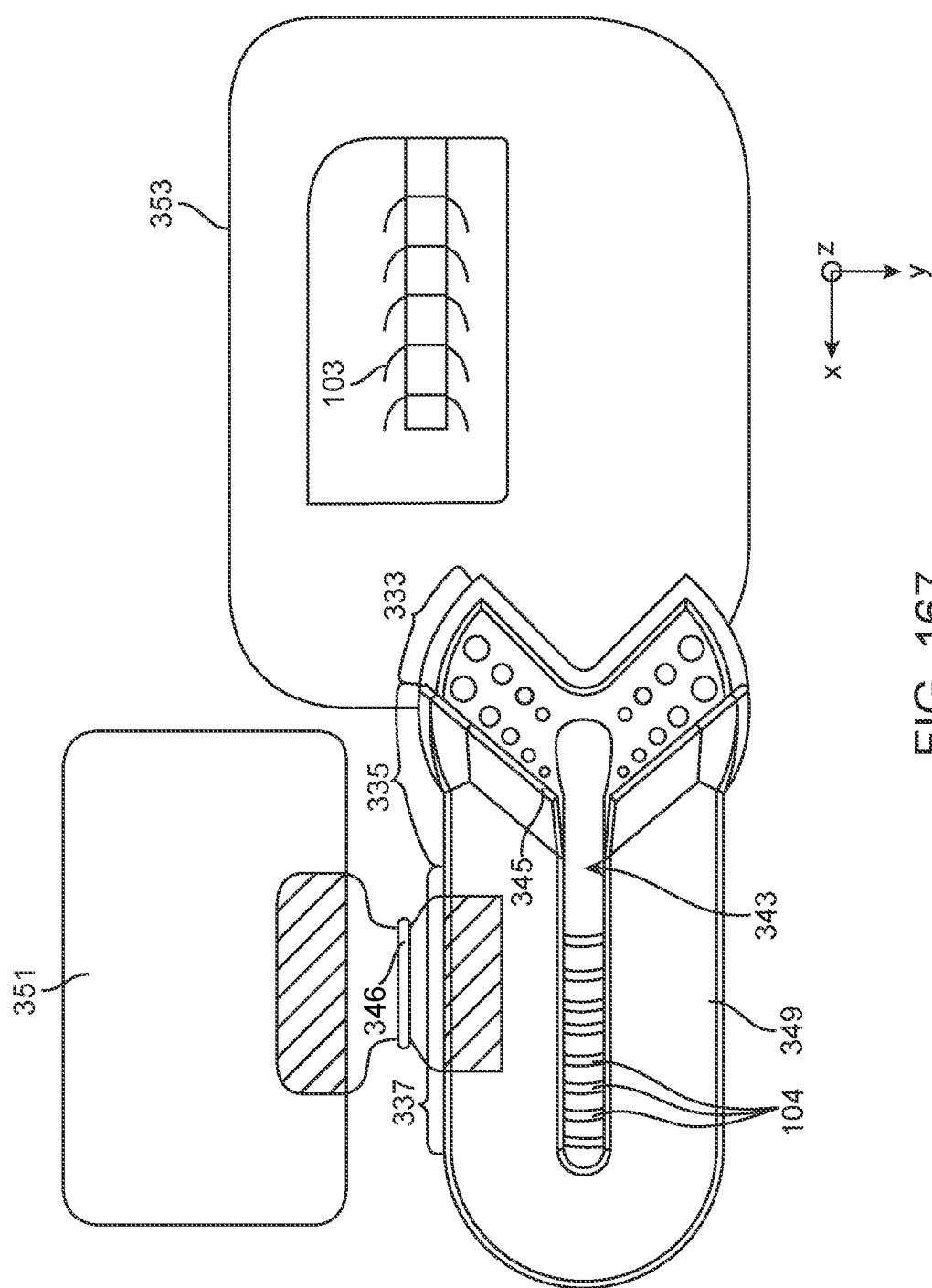

The suture pack holder can be configured to flex between the needle trap and attached suture pack to enable the combined assembly to assume a lower profile when mounted on the forearm by "tenting". Alternatively or in combination, the suture pack holder can be coupled to the needle trap via a hinge 346, as shown in FIG. 167. The hinge can reduce the profile of the assembly, by allowing the suture pack holder to "tent" about the hinge rather than extend straight up.

The adhesive pad 355 can be attached to the outer surface or underside of the lower structure 341, underneath the entry zone. For example, the adhesive pad may be attached to the lower structure with pressure sensitive adhesive. The exposed surface of the adhesive pad can be covered with pressure sensitive adhesive providing a means to attach a suture pack 353 under the entry zone of the needle trap, along the longitudinal axis of the forearm (x-axis). An additional piece of loop connector may be attached to the underside of the suture pack 353, to enable additional stabilization of the suture pack by attaching to a hook connector on a barrier or platform as described herein.

The used needles 104 can be held in the needle slot 349 between an upper structure 339 and a lower structure 341. Compressive members 347 can be placed on the lower structure 341 below the needles 104 in the secure zone 337. In an embodiment, an elastic and/or compressible member 347 material can be foam, rubber, elastic plastic or any other suitable material or mechanisms that can be attached to the inner surfaces of the lower structure 341 facing the needle slot 349. In the illustrated example, compressible member 347 can have a uniform thickness and leading edges of the compressive members 347 can be bend downward at the leading edge (towards the entry zone 333). In the illustrated embodiments, the compressive members 347 can fit within recesses 359 in the lower structure 341. The leading edges of the recesses 359 can be deeper than the other portions of the recesses 359 and this curvature of the compressible member 347 can provide a gradual narrowing of the needle slot 349 as the used needles 104 slide over the compressible member 347 into the secure zone 337.

With reference to FIG. 171 a series of protrusions 361 can extend downward from the upper structure 339 on both sides of the needle driver slot 343. As the needles 104 are inserted into the needle trap 331, the compressible member 347 can press the needles 104 against the protrusions 361. The protrusions 361 can resist the movement of the needles 104 along the X-axis and prevent the needles 104 from accidentally sliding out of the secure zone 337 of the needle trap 331. A needle stop 363 can be positioned close to the end of the needle driver slot 343. The needle stop 363 can prevent the needles 104 from being placed away from the needle driver slot 343.

In different embodiments, the secure zone 337 can incorporate other types of retention systems. For example, the retention system can include a compressible member 347 which can be fabricated from: foam, Velcro loop or any other suitable media. The compressible member 347 can be compliant and can compress the needles 104 against the bottom side of the upper structure 339 between retention features. The compressible member 347 can have a dimensional interference with the protrusions 361. In an embodiment, the density of the retention media material can be less than or equal to 4 lb. For example, the retention media material can be polyethylene or polyurethane foam which can provide a low coefficient of friction against a sliding needle 104.

In the illustrated embodiment, a suture pack 101 can be attached to a suture pack holder 351 that can be can be attached to the secure zone 337 portion of the needle trap 331 with an adhesive. In another embodiment, another suture pack 353 with sutures 103 can be attached to the entry zone 333 with an adhesive 355. The suture pack holder 351 and/or suture pack 353 can provide a rigid base under the suture pack 101 which can prevent the suture pack 101 from being bent while attached to a forearm barrier or any other structure. Bending of the suture pack 101 can result in loosening of needles 103 in their mounts which can potentially result in a lost needle 103. The suture pack holder 351 and/or suture pack 353 can be designed to either extend from or be attach as separate pieces to the needle trap 331. In an embodiment, the suture pack holder 351 and/or suture pack 353 and the trap 331 can be manipulated into a compact or flat space saving configuration for shipping and storage and then expanded into the illustrated configuration prior to use.

In an embodiment, the needle trap 331 and suture pack holder 351 and/or suture pack 353 can be attached to another structure such as a protective barrier worn on a forearm of a surgeon using various different types of connection mechanisms. For example, the needle trap 331, suture pack holder 351, and suture pack 353 can be attached to another structure such as a protective barrier with a hook and loop connection mechanism. At least a portion of the protective barrier can be covered with a hook material which can be adhesively bonded to the protective barrier and back portions of the needle trap 331, suture pack holder 351, and suture pack 353 can be adhesively bonded to a loop material. In another embodiment, the needle trap 331 can be attached to a barrier or any other object with adhesive backed foam 357. In an embodiment the needle trap 331 can include one or more pieces coupled to a back surface of the lower structure 341.

Although the needle trap has been described and illustrated as having a specific configuration, in other embodiments various other configurations of components can be used to hold the needles in the needle trap. For example in an embodiment, the compressive members 347 illustrated in FIG. 176 can be replaced with elastic strips that are secured in the secure zone on either side of the needle driver slot. The elastic strips can include a plurality of elastic protrusions, which can extend up towards the upper structure. When the used needles are moved across the exposed surfaces of the elastic strips with the needle driver, the protrusions can push the needles up against the upper structure and the protrusions extending inward from the upper structure. These forces and protrusions can prevent the used needles from moving freely within the secure zone of the needle slot.

In other embodiments, other mechanisms can be used to keep the used needles in the secure zone of the needle trap. For example, the used needle container can include magnets mounted on the upper structure and/or the lower structure on opposite sides of the needle driver slot. The needle driver can be used to move the used needles into the needle slot and when the needles are released, the magnets can hold and secure the needles within the secure zone.

With reference to FIG. 177, a front view of an embodiment of a needle trap 331 is illustrated. In the illustrated embodiment, the needle trap 331 can include elastic materials 365 such as foam or other elastic materials coupled to the upper structure 339 and the lower structure 341 on either side of the needle slot 349. When the needles 104 are placed in the needle slot 349 the elastic foam can contact opposite sides of the needles and prevent the needles from moving within the secure zone of the needle trap 331.

Although the elastic material 365 is illustrated as having flat inner surfaces, in other embodiments, the elastic material 365 can have various surface features. For example with reference to FIG. 178 a cross section side view of the needle slot 349 of the needle trap 331 is illustrated. The surfaces of the elastic material 365 that face the needle slot 349 can include depressions or protuberances on the surface facing needle slot 349 in the secure zone 337. In the illustrated example, the surfaces of the elastic material 365 can have ramped surfaces which can be configured to allow the needle 104 to more easily be moved into the secure zone 337 and resist the remove of the needles 104 from the secure zone 337. The depressions and/or protuberances can cause the needles 104 to have a predisposition to seat at the proper interval positions in the secure zone 337. The depressions and protuberances can provide positional cues for the surgeon with the subtle force reduction to place and secure needles 104 at that the designated location.

With reference to FIG. 179 a top view of the secure zone 337 portion of the lower structure 341 in an embodiment of the needle trap 331 is illustrated. In the illustrated embodiment, the opposite sides of the needle slot 349 can be lined with angled bristles 365 on opposite sides of the needle driver slot 343. The bases of the bristles 365 can be attached to the outer side portions of the needle slot 349 and the remaining portions of the bristles 365 can bend relative to the bases. The arcuate needles 104 are moved through the secure zone 337 between the bristles 365 and the bristles 365 can bend inward away from the needle slot 349 to allow the needles 104 to be inserted into the secure zone 337. However, the bristles 365 can prevent the needle 104 from moving in the opposite direction because the bristles 365 would engage the ends of the needle 104 which would move inward towards the needle slot 349 and resist the movement of the needle 104 out of the secure zone 337. Thus, the bristles 365 result in less force to translate the needle 104 from the entry zone 333 into the secure zone 337 than the force required to remove the needle 104 from the secure zone 337.

A feature of the needle trap 331 is the ability to easily count needles that are placed in the secure zone 337. As illustrated in FIGS. 168 and 172, the used needles 104 in the secure zone 337 of the needle trap 331 are visible through the needle driver slot 117 and can be easily counted. In other embodiments, the upper structure 123 can be made of a transparent or translucent material so that the used needles 104 can be viewed through the upper structure 123. In an embodiment, the used needles 104 can be counted by a second individual (other than the surgeon) who is responsible for keeping track of the used needles 104. The needle trap 331 can allow the secured needles 104 to be visible from a distance so that the second individual can easily count the number of needles 104 in the needle trap 331. As discussed, the used needles 104 can be positioned in parallel in the secure zone 337 with a spacing of about 3 mm to 10 mm between adjacent needles 104 to facilitate accurate needle counting. In an embodiment, the needle trap 331 can have a chamfered or filleted needle driver slot 343 edges can be colored or painted to maximize reflectivity and provide a visual contrast to needles 104 visible through the needle driver slot 343. For example, the edges of the needle driver slot 343 can be white.

FIGS. 172B-172D show top, side and end views, respectively, of the needle trap 331 of FIG. 172A. Needle trap 331 comprises a housing 340 to contain dispensed needles. The housing 340 comprises upper and lower structures as described herein.

Housing 340 defines needle slot 349, which comprises channel slot 349 having an elongate cross section sized to receive the plurality of needles. The housing 340 comprises an overall length L, an overall thickness T, and a first width W1 comprising an overall width, and a second width W2. The needle driver slot 343 comprises a width S to receive needles. The driver needle slot comprises a length dimensioned larger than a width of the slot to allow placement of a plurality of needles in the secure zone. The needle driver slot comprises a guide to guide the needle driver as the needle driver and needle are advanced along the slot. An upper flange portion F1 and a lower flange portion F2 extend from the housing 340. The upper flange portion F1 can be flared upward to facilitate needle placement in the slot. Alternatively or in combination, the lower flange portion can be flared downward. The upper and lower flange portions may define a landing zone to receive needles from a needle driver.

The transition zone of the needle slot is dimensioned larger than the secure zone to facilitate placement of the needles in the needle slot. The elongate needle channel slot comprises a first elongate width CW1 near an opening of the needle slot 349, and a second elongate width CW2 in an interior secure zone of the needle slot. The elongate needle channel slot comprises a first thickness CT1 near an opening of the needle channel slot 349, and a second thickness CT2 in an interior secure zone of the needle slot. The first thickness CT1 can be at least about twice as thick as the second thickness CT2, for example.

The transition zone of the needle slot comprises a guide in order to facilitate placement of the needles in the needle slot. The first channel width CW1 is dimensioned larger than the second channel width CW2 in order to provide a larger entry zone to receive needles and facilitate placement of needles in the secure zone. The second channel width CW2 is dimensioned to receive the plurality of needles arranged in a row in the secure zone. The needle slot channel comprises a first thickness CT1 and a second thickness CT2. The first channel thickness CT1 is dimensioned larger than the second thickness CT2 in order to facilitate placement of needles in the secure zone comprising second thickness CT2. The second thickness CT2 can be dimensioned smaller than a thickness of the needles as described herein in order to contain the needles with at least some mechanical resistance and deformation of one or more interior structures, such as a surface or protrusions of the interior surface. The first thickness CT2 is dimensioned larger than the thickness of the needles placed therein in order to easily place the needles in the transition zone.

In many embodiments, the needle trap is configured to provide at least some resistance to the needle sliding along the needle slot in the secure zone, in order to stabilize and render innocuous the needle in the secure zone, such that the needle is secured. One or more of the upper or lower structures of the needle slot can be configured to deflect when the needle is advance into and placed in the secure zone, for example. Alternatively or in combination, the interior of the needle slot channel may comprise structures configured to one or more of deflect, deform, stretch or bend within the secure zone in order to stabilize the needles within the secure zone.

In some embodiments, the resistance of the needle driver along the needle driver slot is less than the resistance of the needle along the needle slot when the needle is advanced along the slot with a needle driver.

In some embodiments, the resistance of the needle receptacle against the needle driver is less than the resistance of the needle receptacle against the needle.

In some embodiments, the force imparted by the needle driver slot against movement of the needle driver is less than the force imparted by the needle slot against movement of the needle.

In some embodiments, the force imparted by the needle receptacle against movement of the needle driver is less than the force imparted by the needle receptacle against movement of the needle.

In some embodiments, the friction force between the needle driver slot or slit and the needle driver is less than the friction force between needle slot and the needle.

In some embodiments, the friction force between the needle receptacle and the needle driver is less than the friction force between the needle receptacle and the needle.

Although reference is made to dimensions of the needle trap having a substantially flat configuration, the needle trap can be configured in many ways. For example, the needle trap 331 may comprise a conformal material that allows the needle trap to be bent or curved, for example.

In other embodiments, additional devices can be used with the needle trap 331 to facilitate remote counting and tracking of needles. With reference to FIGS. 180 and 181, in other embodiments, the needle trap can include an electronic needle counter that can be powered by a battery 373 such as a lithium ion battery or any other suitable electrical power source. Conductive elements 371 can be mounted in the needle slot on the compressive members 347 on opposite sides of the needle driver slot. The conductive elements 371 can be pressed into physical contact with each needle 104 that is placed in the secure zone 337 by the compressive members 347. The electrical counter mechanism can include control circuitry 375 and a visual display 377 coupled to the control circuitry 375.

The electrical counter mechanism can comprise an electrical circuit with electrical current flowing through the needles 104 in the secure zone and the control circuitry 375. The electrical resistance changes based upon the number of needles 104 stored in the secure zone in contact with both of the conductive elements 371. The electrical circuit can have a higher electrical resistance with fewer needles 104 in the secure zone. The electrical resistance can decrease with more needles 104 in the secure zone. Each of the used needles 104 can each have an electrical resistance between the conductive elements 371 that is substantially the same. Thus, each of the used needles 104 can function as a resistor in the electrical circuit and multiple used needles 104 in the secure zone can function as a plurality of parallel resistors.

The basic electrical circuit equation is V=I R where V is voltage, I is current and $R_{total}$ is the cumulative needle resistance. The cumulative electrical resistance can decrease with each additional stored needle in the secure zone. The equation for parallel resistors is $1/R_{total}=1/R_1+1/R_{2+1}/R_3$ . . . . However, the resistances of the needles can all be substantially equal, i.e. $R_1=R_2=R_3$ where $R_1$ is the electrical resistance of each used needle. The cumulative electrical resistance needles equation becomes $1/R_{total}=N/R_1$ or $R_{total}=R_1/N$ where N=number of needles. Thus, the number of needles can be calculated with the electrical circuit by V=I $R_1$/N or N=I $R_1$/V. Changes in the cumulative resistance and impedance of the parallel needles can alter the electrical current flowing through the electrical circuit. The voltage V and $R_1$ values can be substantially constant. Thus, changes in the electrical current (I) are based upon the number of parallel needles in the secure zone. The control circuitry 375 can include an ammeter that measures the electric current (I) in the circuit and based upon the measured current, the control circuitry 375 can calculate the number of needles in the secure zone. The control circuitry 375 can output a signal to the visual display 377 that corresponds to the number of needles in the secure zone. In an embodiment, the number of needles N can be displayed on the visual display 377. With reference to FIG. 180 the visual display 377 can display the number "1" which corresponds to the single needle 104 between the conductive elements 371. With reference to FIG. 181, the visual display 377 can display the number "5"

which corresponds to the five needles 104 between the conductive elements 371. In other embodiments, the visual display 377 can output any other display that can indicate the number of needles in the secure zone. For example, the display can use individual lights to represent each needle. Each needle in the secure zone can be represented by a single corresponding illuminated light.

With reference to FIGS. 182-184, in an embodiment, mechanical counter devices can be used with the needle trap 331 to facilitate needle counting. In the illustrated embodiment, an arm can be actuated to cause a numerical indicator to advance the number displayed. In FIG. 182, a single needle 104 has been placed in the needle trap 331 and the visual display 377 shows "1". With reference to FIG. 183, a second needle 104 can slide through the needle slot 349 and contact the arm 379 which rotates about an axis and actuates the visual display 377 to advance the displayed number. With reference to FIG. 184, after the second needle 104 passes the arm 379, the display 377 has changed to "2" and the arm 379 has reset to its normal position detect the next needle 104.

As discussed, the middle portions of each of the needles in the secure zone 337 of the needle container 201 are visible through the needle driver slot 343 which can also function as a window. Counting of needles 104 can be improved by fabricating a needle container 201 from a clear casing and clear foam materials an embodiment of which is shown in FIG. 185. Depressions 379 in the needle slot 349 boundary surface compressive members 347 can provide individual locations for each of the used needles. In different embodiments, the compressive members 347 can be foam or any other suitable materials. The used needles 104 can sit in the depressions 379 which can be used as a visual indicator(s) of the number of needles 104 stored in the secure zone 337. A dye may be applied such that with compression of the compressive members 347 when a needle 104 is stored can cause the color of the compressive members 347 in the compressed area in contact with or adjacent to the needles 104 to change. In the illustrated example, the needles 104 in the depressions 379 can result in a red color marking. A portion of foam or material may be normally hidden in the compressive members 347 but as the needle 104 presses against the dyed material in the depressions 379, the dye(s) can be released, combined, actuated or any other process that can cause the surface of the depressions 379 where needles 104 are stored to be colored and become visible.

In another embodiment, a visible red dot can appear wherever a needle is present in the secure zone and each dot can represent a different needle in the secure zone. In other embodiments, different color dyes can be used with some or all of the needle depressions. It can be easier to count different colored dye markings or alternatively, if the dyes are arranged in a repeating sequence. For example a first needle position depression can be red, a second needle depression can be blue, a third needle depression can be green, a fourth needle depression can be purple and a fifth needle depression can be yellow. This color sequence can repeat for all subsequent depressions in groups of five or any other numeric interval of depressions. Thus, a sixth needle and eleventh needle depressions can be red, a seventh and twelfth needle depressions can be blue, etc.

In an embodiment with reference to FIG. 186, an optical counter mechanism can be used with the needle trap to indicate the number of store needles 104. An optical scanner (s) 381 can be used to detect the number of needles 104 that are stored in the secure zone 337 of the needle trap 331. The scanner 381 may also be designed to operated in other areas of the radio frequency spectrum such as infrared, UV, radar etc. for the counting function. In another embodiment, a reflective scanner can be used to quantify amount of metal from strength of reflected or transmitted optical signal. In an embodiment an infrared image can detect needles in the needle trap 331 with better accuracy than visual counting from a standard optical image of the needle trap 331. The plastics and foam components of the needle trap 331 can transmit infrared energy whereas the metal needles 104 can reflect the infrared energy. The optical scanner 381 can transmit scanned needle information to a processor 383 that can convert the scanned signal into a number representing the number of needles 104 in the secure zone 337 of the needle trap 331. The processor 383 can be coupled to a visual display 377 that can be controlled to display the number of detected needles in the secure zone 337 of the needle trap 331.

With reference to FIG. 187, a camera(s) 385 can be used to detect the number of needles 104 that move into the secure zone 337 of the needle trap 331. The cameras can be coupled to a processor 383 that receives needle count signals as each needle 104 passes over the camera(s) 385. The processor can count and store the needle count signals and output a needle count signal to the visual display 377 which can display the number of detected needles 104 in the secure zone 337 of the needle trap 331. In different embodiments, different types of cameras 385 can be used. For example, the needles 104 can be more visible to an infrared sensor than a visual wavelength optical camera. Thus, an infrared camera 385 may more accurately detect the movement of needles 104 into the secure zone 337.

With reference to FIG. 188, in an embodiment the system can detect the number of needles in the secure zone 337 of the needle trap 331 based upon pressure measurements detected by transducers 387. In the illustrated embodiment, the needle trap 331 transducers can detect compressions in the compressive member 347 caused by the needles 104. The transducers 387 can be positioned along the length of the secure zone 337 and the protrusions 361 can create individual needle storage areas. By measuring the increased pressure in each of the needle storage areas, the number of needles 104 in the secure zone 337 can be determined. The transducers 387 can be coupled to a processor 383 which can determine the number of used needles 104 in the secure zone 337 based upon the transducer 387 signals and the processor 383 can transmit a needle count number signal to the visual display 377 which can display the needle count number. In different embodiments, different types of transducers 387 can be used to detect the needle pressure. For example, the transducers 387 can be can be piezoelectric devices that can also be used in which pressure applied to compressive member 347 and records the presence of each needle 104. Alternatively, the transducers 387 can include a series of strain gages that may be utilized to sense the presence of needles 104 in the secure zone 337 or any other suitable pressure detecting mechanisms.

With reference to FIG. 189, in other embodiments, the needle trap 331 can be used with other components to perform needle counting. In the illustrated example, the needle trap 331 can be mounted on a barrier 403 that can be placed on a forearm of a surgeon. A needle sensor 389 can detect needle count signals and the needle count signals can be transmitted by a transmitter 391 to a receiver(s) 393 which can be coupled to a processor(s) 383 which can output needle count information to an output device 395 which can indicate the number of needles in the needle trap 331. In the illustrated embodiment, the needle sensor 389 can be a small camera with an integrated radio frequency (RF) transmitter 391 which transmits image and/or video RF signals to receivers 393. A processors 383 coupled to the receivers 393 can output image and/or video signals to visual displays 337 which can display the needle driver slot 343 to allow the needles 104 to be visually counted remotely. The needle sensor 389 and transmitter 391 can be within the near surgical field. In contrast, the receivers 393, processors 383 and visual displays 337 can be well outside the near surgical field.

The camera can face the needle trap 331 and also possibly the suture pack(s) 101. The images of the needle trap 331 can be transmitted to the visual display(s) 337 which can be visible to another person. For example, the remote visual display(s) 337 can be a video display mounted on an operating room wall. As discussed, a portion of each of the needles 104 is visible from the upper surface of the needle trap 331 through at least the needle driver slot 343. Thus, a displayed image of the needle trap 331 on the surgeons forearm can show the number of used needles 104 in the needle trap 331 and new suture needles 103 in the suture pack 101. A surgical assistant can view the display 337 and see the suture pack(s) 101 and the needle trap 331 with the secured needles 104 to track in real time. The surgical assistant can then provide additional suture packs 101 if additional needles 103 are required and provide new empty needle traps 331 as the barrier mounted needle traps 331 become full of used needles 104 and needs to be replaced. Also, if a needle 104 is lost the error can immediately be detected by someone monitoring the surgical procedures or by the processor which can detect the sequential removal of new needles 103 from the suture pack and the deliver of the used needles 104 to the needle trap 331. Although an exemplary set of system components has been described, in other embodiments, the needle count components can include but are not limited to: dedicated receivers, electronic watches, smartphones, tables, computers, headsets, earpieces, displays, or any other suitable device for the purpose of tracking the needles.

As discussed, mid-bodies of needles 104 are visible through the needle driver slot 349 in the needle trap 331. In an embodiment, the processor 393 can run a software program that can interpret the visual display signals from the needle sensor 389 (camera) and determine the number of needles 104 in the needle trap 331 as well as the needles 103 in the suture pack 101. The processor 393 can then output this needle count number on the visual display 377 which can help with the needle counting process. In other embodiments, the needles 104 can include markings 397 or transmitters that can help track the needles 104. In an embodiment, the markings can visual codes such as bar codes, quick response (QR) codes, color codes, numeric markings or any other markings which can provide at least some identification information about the needles 104. The markings can be placed on the middle body portion of the needles 104. When the needles 104 are placed in the needle trap 331, the markings can be visually detected through the needle driver slot 349 in the needle trap 331 by an optical sensor such as a scanner or a camera. In an embodiment, an optical needle sensor 389 can detect the markings and the processor 383 can interpret the markings and determine the identifications of the needles 104 based upon the markings. This identification information can then be used for needle tracking and needle reconciliation. The identification information can also be output to the visual display 377.

In other embodiments, other mechanisms can be used for needle tracking. For example, in an embodiment the needles 104 can include embedded electronic components such as a radio frequency transmitter such as a radio frequency identification tag (RFID) which can transmit an RF identification signal in response to exposure to an interrogating radio wave. In an embodiment with reference to FIG. 189, the needle sensor 389 can include an interrogating radio wave transmitter and an RF receiver. When exposed to the interrogating RF waves, the RFID tags on the needles 104 can emit RFID signals that can be detected by the RF receiver. The RFID information can be transmitted to the processor 383 which can then identify each needle in the needle trap 331.

In other embodiments, the suture packs 101 can also have integrated tracking mechanisms. For example, the suture packs can include an active electronic sensor that can be activated when suture pack is opened. This active signal can be transmitted to a processor off the surgical field that can monitor the use of the suture packs and know which needles must be reconciled after the suture pack is used. In an embodiment, these active signals can be transmitted wirelessly from a suture pack or a suture pack sensor to a remote receiver. These active signals can be processed by a processor as described above. This feature can allow the needles to be tracked from the suture packs to the needle trap in a closed loop manner to further insure that all needles are accounted for.

In another embodiment, the tracking of the needles can be done more locally on the barrier which can be mounted on the forearm of the surgeon. In this embodiment, a processor can be mounted on the barrier and the processor can keep track of the locations of all needles through out the surgical procedure. An active signal can identify a suture pack that is being opened and the identities of all of the needles in the newly opened suture pack. The system can identify the movement of each of the needles from the suture pack through a patient and into the needle trap. If a needle is lost the processor that can output an error signal to an output device such as a visual display or audio output device can immediately detect the error. If possible, the surgical procedure can be temporarily stopped until the lost needle is found. The described needle tracking can also provide useful needle tracking information that can be stored in a data center and the number of needles in the near surgical field can be automatically reconciled in real time. As needles are secured in the needle trap, the system can broadcast correlation information for needle reconciliation.

In another embodiment, the suture dispenser and needle trap can be combined onto a single mount that attaches to the proximal end of a surgical tool such as forceps. Such configurations can allow attachment to the slotted shape of the forceps with adequate mechanical integrity such as to avoid displacement with the mechanical forces anticipated during manipulation of the tools against the needle trap.

In an embodiment the suture dispenser and needle trap can be attached to the surgical tool with a mechanical clip that secures a sufficient length of the suture dispenser and needle trap to the tool (forceps) base to provide rotational and translational stability. In another embodiment, the clip can contain adhesive mounts. In another embodiment, magnets can augment the secure attachment of the suture dispenser and needle trap to the forceps.

In other embodiments, the needle trap and/or suture dispenser can be attached to the surgical drapes covering the patient and can be positioned adjacent to the wound. In an embodiment the suture dispenser and needle trap are mounted on a protective platform that secures position on drapes and the platform can be secured to the drapes with an adhesive or any other suitable coupling mechanism.

The suture pack dispensers can have multiple configurations and designs. In an embodiment, suture pack dispensers can secure existing suture packs to the barrier. In other embodiments, needles with attached suture are secured in a structured array for easy access by the surgeon. In another embodiment, non pop-off suture needles are compatible with the suture packs and suture pack dispensers. The non pop-off needles can include but are not limited to swaged on needles, running suture needles, barbed running suture needles, etc. These needles can be used for creating multiple surgical knots and/or for running suture application that can be dispensed as single or double needles.

In an embodiment, a spool can be attached to the forearm mount or barrier for securing the running needle. This embodiment can include multiple spool mounts attached to the barrier for the forearm configuration, or to the instrument clip construct for the forceps attached device. In an embodiment the suture spools can be stack together for lower profile. In another embodiment the spool can allow for rotation for easier dispensing of the suture. Multiple mechanisms for securing the needle, which is attached to the thread wound around the spool, can includes mechanical, adhesive, magnetic mechanisms and multiple needle enclosure designs.

Used Needle Receptacles

In many embodiments, various types of used needle receptacles can be mounted on any of the disclosed barriers and platforms. With reference to FIG. 190, a used needle receptacle 257 can be an open top box 260 with a foam 263 layer having numeric markings 259 secured within the box 260. Used needles 104 can be placed in the foam 263 in a sequence and areas that correspond to the numeric markings 259. There are various problems with this type of used needle receptacle 257. While the distal ends of the needles 104 are placed in the foam 263, the proximal end of the needles 14 are exposed and can be dangerous. The foam 263 can have a durometer or density that is still enough to resist displacement of the needles 104 (angulatory and/or translatory) which potentiates injury. The needles 104 can protrude beyond the upper edge height limit of the open top box 260 container which can create a safety issue. If the container walls are higher than the needles 104, this higher height can make the placement of the needles 104 more challenging especially when the box 260 is against a lateral wall. If an open top box 260 used needle receptacle 257 were placed on the user's arm without a barrier, the downward motion needed to stick the needle 104 into the foam 263 could potentiate injury and this potential injury can be more likely if the surgeon tends to "swipe" the needle 104 into the surface, foam 263. A swipe needle 104 insertion can include a combination of horizontal translation, rotation and downward forces. The numeric markings 259 can be small target areas that not optimal or easily hit with a used needle 104 if a surgeon is trying to expedite the insertions of used needles 104. Further, the small target areas associated with the numeric markings 259 can be easily missed. There can also be a tendency to insert a used needle 104 wherever there is an open spot on the foam 263 layer rather than the designated locations. It may be better to segregate the used needle areas on the foam 263 into limited and distinct zones that may contain five needles 104 at most.

In an embodiment with reference to FIG. 191, it can be possible to improve the safety of open top box 260 used needle receptacles 257 by adding a transparent dome 262 that can be coupled to multiple sides of the open top box 260 as well as open sides which can allow the placement of needles 104 into the foam 263. The transparent dome 262 can provide many benefits over a normal open top box 260 design. The transparent dome 262 can prevent or reduce the risk of inadvertently contacting proximal needle 104 ends which are sharp enough to tear a glove. Transparent dome 262 can also enable visual counting of the used needles 104. If needles 104 are not fully fixed into the foam 263, the partial surrounding container provided by the dome 262 makes losing a loose needle 104 less likely. Because needles 104 are covered it can be possible to insert a crimped proximal end of the used needle 104 into the foam 263 (depending on durometer or density) and the dome 262 would prevent the sharp distal end of the needle 104 from causing injury.

In an embodiment, the box 260 with transparent dome 262 could be mounted on a platform or barrier on a forearm of a surgeon. When the used needle 104 is used to install a suture and is then placed in the used needle receptacle 257, the surgeon can hold the used needle 104 with a needle driver, place the needle 104 into the used needle receptacle 257 though an opening under the dome 262. The surgeon can then insert the needle 104 into the foam 263 and rotate the needle driver and needle 104 to fully insert the needle 104. The initial motion of inserting the needle 104 can be tangential to the forearm and there can be a lower likelihood of missing the foam 263 and causing injury. However, there can be problems with this configuration. Because the dome 262 makes the foam 263 less accessible, it can be difficult to properly place the needles 104 in an organized manner unless significant effort and attention to needle 104 placement is performed by the surgeon. Also, the needles 104 placed closest to the dome 262 opening may possibly project the proximal ends out of the needle receptacle 257 from the opening which can potentiate injury since they may not be covered by the dome 262.

In another embodiment as illustrated in FIG. 192, a used needle receptacle 257 can have an open top box 260 that has a smaller foam 263 area and can be covered by a transparent dome 262. This smaller box 260 size may only allow a limited number of needles 104 to be placed in the receptacle 257. In an embodiment, the smaller box 260 size may be limited to storing a maximum number of used needles 104, such as 5-10 used needles 104. The smaller size can also allow for a Lower profile dome 262. When this used needle receptacle 257 is used, the needle 104 can be placed through the opening on the side of the dome 262 and rotated to drive the needle 104 into the foam 263. This insertion and rotation motion can improve safety particularly when the used needle receptacle 257 is mounted on a forearm of a surgeon. However, the smaller size can limit the number of needles 104 that can be contained before the used needle receptacle 257 becomes full. Proximal ends of needles 104 that are stored close to the dome 262 opening can be exposed if the needle 104 is inserted at an angle into the foam 263. Depending on the durometer or density of the foam 263 it may or may not be possible to insert the needles 104 proximal crimped end into the foam 263 given that the needle 104. The clear dome 262 can allow the needles 104 to be easily counted.

With reference to FIGS. 193 and 194, another embodiment of a used needle receptacle 257 is illustrated. In this embodiment, an open top box 260 is placed within a dome 262 that is at least partially transparent. Rather than having open sides, the dome 262 can have an elongated opening 256 that can be longer than the length of the longest needle 104 to be stored. Needles 104 can be held with a needle driver and inserted through the elongated opening. The needle 104 can then be positions above the foam 263 and rotated to drive the distal end of the needle 104 into the foam 263. Once the needle 104 is securely placed in the foam 263, the needle 104 can be released and the needle driver can be removed from the elongated opening 256.

With reference to FIG. 195, an embodiment of a used needle receptacle 257 can include an open top box 260 and magnets 287 mounted on a floor of the box 260. In the illustrated example a plurality of discrete disk magnets 287 can be mounted a transparent base of the box 260 which can enable easier needle 104 counting. The spacing between adjacent magnets 287 can enable magnet-free zones so that needle driver contact magnetization is minimized. In an embodiment, the polarities of the magnets 287 poles facing outward can be alternated to also minimize magnetization of needle drivers. When inserted, the needles 104 lie flat or horizontal relative to the floor of the box 260 rather than in perpendicular orientations which can be safer because the ends of the needles 104 may not protrude above the upper edges of the box 260. Since there is not an opening to insert the needle 104 though, this used needle receptacle 257 can accept all needle 104 sizes. It can also be easy to use by quickly dropping needles 104 onto the magnet 287 which will retain the needles 104 with magnetic attraction. However, because the needles 104 may not be stored in any order or pattern, there can be a lack of needle 104 organization making it more difficult to count the stored needles 104. When the used needle receptacle 257 a scrub technician might need to take time to rearrange the needles 104 for counting which can require additional time and more needle 104 handling. There can be additional risks of needle 104 sticks with additional handling. The needle 104 can often be relatively orthogonal to the needle driver and it may be hard to appose the needles 104 with the box 260. In an embodiment, the used needle receptacle 257 can be mounted on the non-dominant forearm of a surgeon and the used needle receptacle 257 can be positioned in space to facilitate needle 104 placement onto the surface of the magnets 287.

In other embodiments, a used needle receptacle 257 can include both magnets 287 and foam 263. In an embodiment with reference to FIGS. 196 and 197, the used needle receptacle 257 can also be oriented vertically relative to a forearm barrier or platform with the open top of the box 260 facing proximally. In this orientation, the needle driver can place the needle 104 substantially parallel to a planar floor of the box 260 while being held by the surgeon. The needle driver can then easily rotate so the sharp distal end of the needle 104 is driven into the foam 263. The magnets 287 can allow the needles 104 to lie flat within the box 260 in vertical orientation. The needles 104 can be inserted and rotated into the foam 263. In different embodiments, the used needle receptacle 257 can include any combination of magnets and foam. For example, a first embodiment can only include magnets 287, a second embodiment, can only include foam 263 and a third embodiment can include both magnets 287 and foam 263. The vertical orientation of the box 260 of a forearm barrier can have an improved safety aspect because the forces and motions are not directed toward the forearm. The needles 104 are I insert into the box 260 and then rotated and translated into the foam 263. The box 260 can be made of a clear material and the clear floor of the box can allow for needle counting from both sides of the box 260.

With reference to FIG. 198, an embodiment of a used suture needle receptacle 257 can include a combination of magnets 287 and foam 263 in vertical orientation. In the illustrated embodiment, the box 260 can be divided into two adjacent areas. In other embodiments, the used suture needle receptacle 257 can include 3 or more adjacent needle storage areas. In other embodiments, the foam 263 can be angled to optimize ergonomics of the needle 104 rotation and fixation. In an embodiment, a needle 104 can be placed on each of the spaced magnets 287 and each of the magnets 287 can be numbered in order to maintain needle 104 organization and to facilitate needle 104 counting.

With reference to FIGS. 200 and 201 another embodiment of a used suture needle receptacle 257 is illustrated which can include a half cylindrical housing 295 which can be made of a transparent material. The housing 295 can have a half circle shaped insertion slot. The needles can be placed in the used suture needle receptacle 257 in a low profile array of needles extending front to back. The used suture needle receptacle 257 can incorporate an insertion offset zone between outer opening and foam 263 inside container housing 295. The insertion zone can be offset from foam 263 to ensure that the entire needle 104 including the proximal end is fully enclosed within the housing 295. If the needle 104 is inserted at an angle into the foam 263, the proximal end of the needle 104 is less likely to extend out of the housing 295 when there is a sufficient insertion offset zone.

The used suture needle receptacle 257 can be mounted on a platform with the opening facing away from the platform. The cylindrical geometry of the used suture needle receptacle 257 enables the housing 295 to be rotated in the mounting plate to present the foam 263 at optimal angle for both forehand and backhand needle driver rotation which can be easily used by both left and right handed users. The size of the opening may provide safety features. A hand or a fingertip is less likely to be accidentally inserted into a smaller opening than a larger opening and injury is less likely. In an embodiment, it is possible to have a larger number of smaller containers with each container limited to 5 needles per housing 295. The illustrated design of the housing 295 can allow either end of the needle 104 to be inserted into the foam 263.

With reference to FIG. 202 another embodiment of a used suture needle receptacle 257 is illustrated. An opening in the housing 295 can have an oval entry slot that can decrease the profile of the used suture needle receptacle 257 which can require the needle 104 to be tilted to enter the housing 295. The illustrated embodiment can incorporate a needle entry offset zone between outer opening and foam 263 inside housing 295. The foam 263 can be mounted on a top portion of the housing that enables needle 104 rotation and fixation from either side of the foam 263. Foam 263 material can be used that has a consistency and hardness that can allow for penetration by proximal or distal ends of the needles 104. The needles 104 can be inserted into the used suture needle receptacle 257 in an upside down orientation. Because the exposed end of the needle 104 will be below the upper surfaces of the housing 295 and close to the barrier or platform the chances of user contact with the needle 104 are minimal. Even if a proximal end of the needle is projecting from the housing 295 a hand would normally strike the needle with a downward motion and there would be little counterforce to cause the needle 104 to penetrate through a glove because the needle 104 is suspended in air. This isolation of the needle can allow lower durometer or density foam to be used which can be easier for the needles 104 to penetrate. This configuration can allow more needles 104 to be held by the used suture needle receptacle 257 because needles 104 can be inserted into opposite sides of the foam 263 rather than just through one side. Although the opening is illustrated as an oval shape, in other embodiments, the opening could be more triangular, tear drop or a keyhole. The wider base of the illustrated embodiment can provide greater stability and in different embodiments, the used suture needle receptacle 257 can be mounted on the forearm or on the surgical field, on the patient.

With reference to FIGS. 203 and 204, an embodiment of a used suture needle receptacle 257 is illustrated that can have a slot slide box housing 295, a needle slot 349, a needle driver slot 343, a layer of top foam 263 and a lower of bottom foam 263 on opposite sides of the needle slot 349 and an opening for inserting the used needles 104. In this embodiment, the user can grasp the needle 104 and place the needle 104 through the opening. Once the plane of the needle 104 is adjacent to the lower needle slot 349 surface the user can slide the needle 104 into the covered portion of the needle slot 349 with the needle driver moving through the needle driver slot 349. The needle 104 can be compressed and held in the needle slot 349 by the top foam 263 and bottom foam 263. The foam 263 on the top and bottom surface of the slot can enable insertion by both forehand and backhand needle driver rotation and either left- or right-handed needle driver use. The used suture needle receptacle 257 can incorporate an insertion offset zone between outer opening and foam 263 inside container. Like the needle trap embodiments, the needles 104 can be organized and stored in an array in side-side orientation allowing for thin profile. Although the opening is illustrated as being large and round, in other embodiments, the opening can be narrower keyhole shape that requires insertion and rotation through the opening before moving the needle 104 into the more secure needle slot 349. The illustrated left and right needle slot 349 configuration can allow the needles 104 to be more easily aligned and moved into the needle slot 349.

With reference to FIG. 205, another embodiment of the used suture needle receptacle 257 is illustrated. In this embodiment, the needle 104 can be placed through a slot 256 in a housing 295 so that the distal sharp end is pressed into foam 263. The housing 295 can be coupled to an angled structure that can help to guide the needle 104 into the foam 263. Magnets 287 can be mounted under a planar structure adjacent to the slot 256 which can hold the proximal end of the needle 104 against the planar structure so avoid having proximal end of the needle 104 positioned in space which can FIGS. 223-224 illustrate an embodiment of a used suture needle receptacle 257 that can include a cylindrical housing 295 having an opening 256 on one end. An elongated foam 263 structure can be mounted to a bottom portion of the cylindrical housing 295. To store a needle 104 in the receptacle 257, the needle driver can insert the needle 104 into the housing until the needle is adjacent to the foam structure 263. The needle driver can then rotate the needle 104 to insert the needle 104 into the foam structure 263. Once the needle 104 is securely held by the foam 263, the needle driver can release the needle and the surgeon can remove the needle driver from the housing 295. This insertion process can be described very generally as "insert and rotate" meaning that the needle is first inserted and then rotated to secure the needle 104 to the foam 263 in the receptacle 257. FIG. 225 illustrates a side view of the housing 295. The foam 263 can be recessed within the housing 295 away from the end opening 256. This offset space between the outer opening 256 and the foam 263 can be known as an "insertion offset zone". If the needle 104 is inserted at an angle into the foam 263, the proximal end of the needle 104 is less likely to extend out of the housing 295 when there is a sufficient insertion offset zone.

FIGS. 226-228 illustrate an embodiment of a used suture needle receptacle 257 that is very similar to the embodiment illustrated in FIGS. 223-225. FIGS. 226 and 227 illustrate front views of the receptacle 257 and FIG. 228 illustrates a side view. In the illustrated embodiment, the foam 263 if mounted on an upper inner surface of the housing 295. Thus, the needle 104 must be positioned so that the insertion end of the needle 104 is adjacent to the upper foam 263. The placement of the foam 263 on the upper portion of the housing 295 can have some safety benefits. If the receptacle 257 is normally in the upright position, the needles 104 in the foam 263 will dangle downward and gravitational forces on the needles 104 will tend to maintain this needle orientation. If a portion of a needle 104 extends out through the opening 256 of the housing 295, contact with the needle 104 can normally be a downward impact which can cause the needle 104 to rotate into the downward orientation and possibly move the exposed end of the needle 104 into the housing 295. In contrast, if a portion of the needle 104 is exposed in the "lower foam" 263 embodiment, a downward impact with an exposed end can cause the needle 104 to rotate further out of the housing 295. Further, because the portion of the needle 104 in the foam 263 can provide resistance to a downward impact, contact with the exposed portion of the needle 104 can cause injury to the object that contacts the needle 104.

With reference to FIG. 229 a front view of another embodiment of a used suture needle receptacle 257 is illustrated. In this embodiment, the housing 295 can include a transparent dome 262 and foam 263 pieces on opposite sides of the transparent dome 262. The foam 263 can include multiple surfaces into which the needles 104 can be inserted. Thus, the needles 104 can be inserted into any exposed surface of the foam 263 pieces with either the concave or convex sides facing up. With reference to FIG. 230 a top view of the embodiment of the used suture needle receptacle 257 is illustrated. The foam 263 can be offset inward from the opening 256 in the housing 295 by the insertion offset zone for the safety reasons described above.

With reference to FIG. 231 a side view of an embodiment of a used suture needle receptacle 257 which can have a cylindrical housing 295 with one closed end and an opening 256 which is an open end of the housing 295. FIG. 232 illustrates a front view of the embodiment of the receptacle 257. An elongated strip of foam 263 can be attached to an inner surface of the housing 295 along the length of the housing 295. In the illustrated embodiment, the foam 263 extends out of the housing 295 and wraps around the edge of the opening 256 and along a portion of the outer surface of the housing 295. To use the receptacle 257, a needle can be held with a needle driver such that the curvature of the needle can be aligned with the curvature of the housing. The needle driver can insert the needle through the opening and into the housing 295 with an end of the needle facing the foam 263. When the needle is positioned at the desired insertion point, the needle driver can be rotated to drive the needle into the foam 263. Once the needle is securely held by the foam, the needle can be released by the needle driver which can then be removed from the receptacle.

The needle traps 331 illustrated and described with reference to FIGS. 223 to 232 can all utilize an insertion process can be described very generally as "insert and rotate." Each of the illustrated needle receptacles 257 can have a housing 295 having a longitudinal axis that can extend from the opening 256 through the center of the housing 295. A needle can be held with a needle driver in an orientation that is roughly perpendicular to the longitudinal axis of the needle receptacle 257. The needle 104 insertion movement into the housing 295 can be substantially parallel to the longitudinal axis. The needle 104 can be inserted until a tip of the needle 104 is aligned with a desired insertion point on the elastic member 263 which can be made of foam or any other suitable material. At the insertion point, the needle 104 can be rotated about the longitudinal axis, meaning that the axis of rotation of the needle 104 can be parallel to the longitudinal axis of the needle receptacles 257. The needle 104 can be inserted into the elastic member 263 to secure the needle 104 within the receptacle 257 and the needle driver can release the needle 104.

Figure 206:
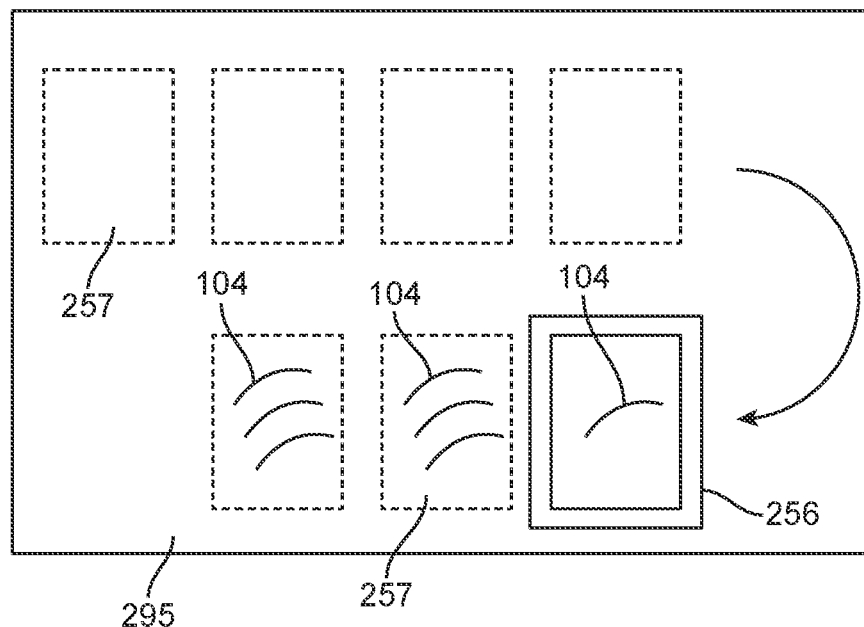

With reference to FIG. 206, a plurality of used suture needle receptacles 257 can be coupled to a movement control mechanism within a housing 295. The housing 295 can have an opening 256 so that at least one of used suture needle receptacle 257 can be accessible through the opening 256. In the illustrated example, the receptacles 257 move in a linear manner with the upper row moving right and the lower row moving left. The movement can be controllably moved so that the surgeon will always be able to place used suture needles in an empty or only partially full used receptacle 257 that is accessible through the opening 256. When the exposed receptacle 257 becomes full, the movement control mechanism can be actuated to move an empty receptacle 257 under the exposed opening 256. This movement also causes the full receptacle to move the used needles under a protective housing 295. This movement of the movement control mechanism can be manually powered or powered by any other movement device such as but not limited to: electric motors, pneumatic power, etc.

The movement of the receptacles 257 can be triggered or actuated by various means including forces effected by the same appendage as the one upon which it is being worn such as: elbow, wrist, hand, finger motion, etc.

Figure 207:
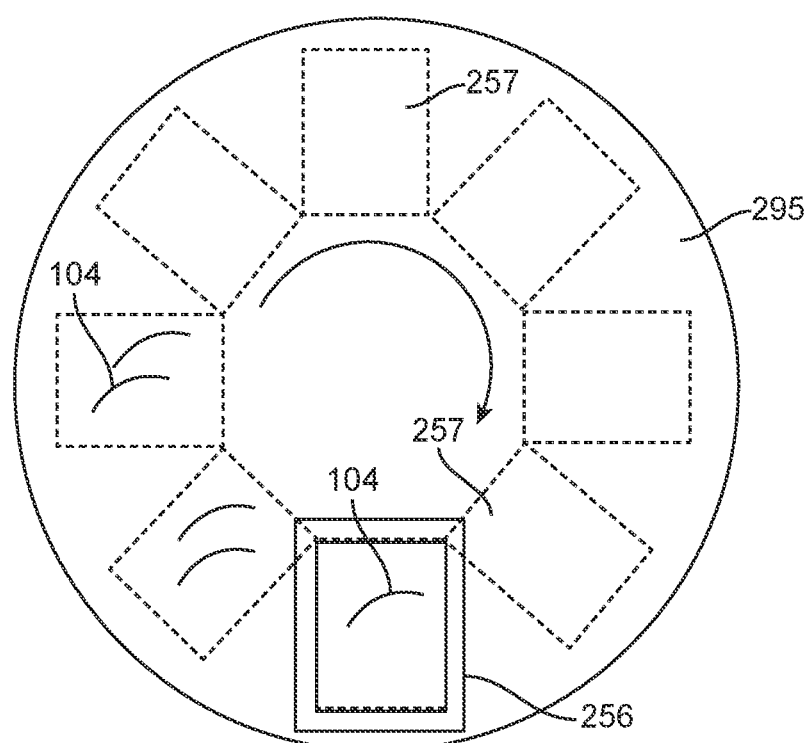
Figure 208:
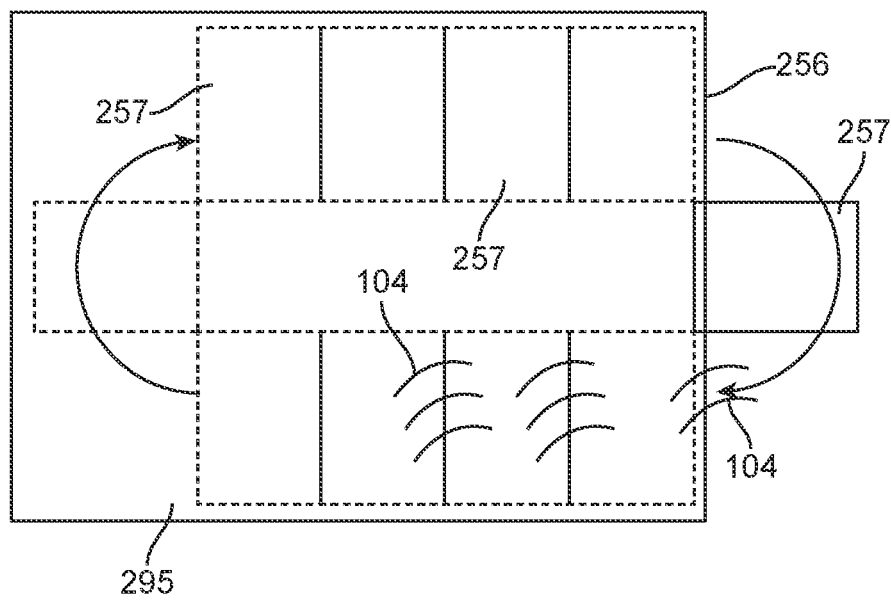

With reference to FIG. 207, in another embodiment, the housing 295 can have a cylindrical shape and the movement of the receptacles 257 can be rotational. The housing 295 can have an opening 265 through which needles 104 can be inserted into the receptacles 257. When the exposed receptacle 257 under the opening 265 is full, an empty receptacle 257 can be rotated under the opening and the needles 104 can be moved to a position completely within the housing 295.

In other embodiments, the needles 104 can be inserted into different surfaces of the used suture needle receptacles 257. For example, with reference to FIG. 208, in an embodiment, the receptacles 257 can move in translation and rotation within the housing 295. Needle insertion surfaces of the receptacles 257 can be accessible through an opening 256 on the right side of the housing 295. Needles 104 can be inserted into exposed surfaces of the receptacle 257. When the receptacle 257 is full, the system can move the receptacles to expose a surface of an empty receptacle 257 and the filled receptacle 257 can be moved within the housing 295. In an embodiment, the receptacles 257 can be pressed against each other to fully contain inserted needles 104 and this containment can prevent injury.

Figure 209:
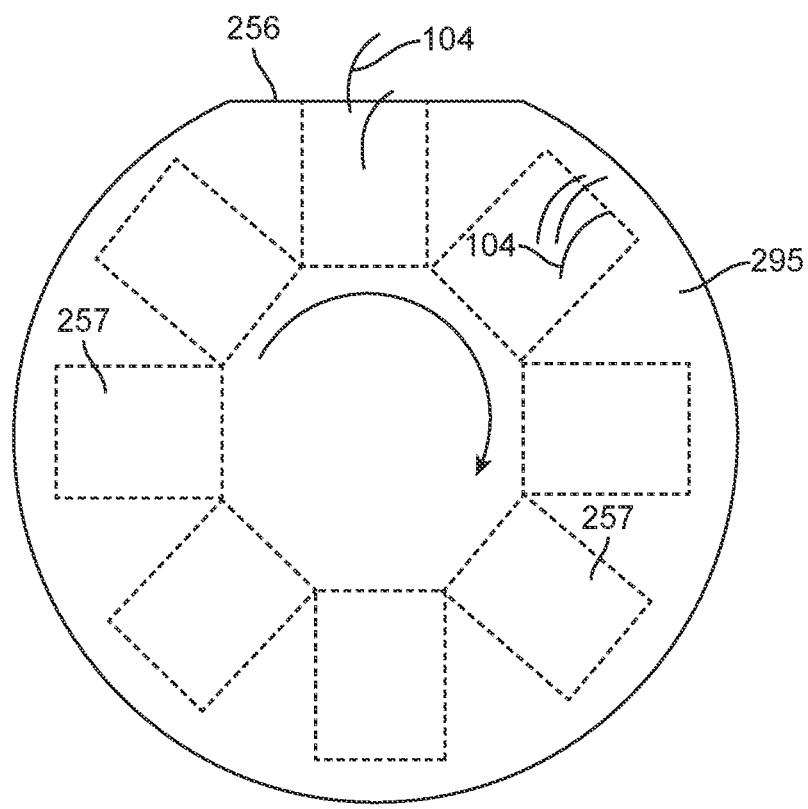

With reference to FIG. 209, in the illustrated embodiment a circular housing 295 can have an opening 265 on an upper surface. Needles 104 can be inserted into an exposed surface of a receptacle 257. When the exposed receptacle is full of needles 104, an empty receptacle 257 can be rotated to be aligned with the opening 256 and the needles previously inserted into the full receptacle 257 can be rotated to be positioned completely within the housing 295 which can prevent the needles 104 from causing injury or being lost.

Figure 210:
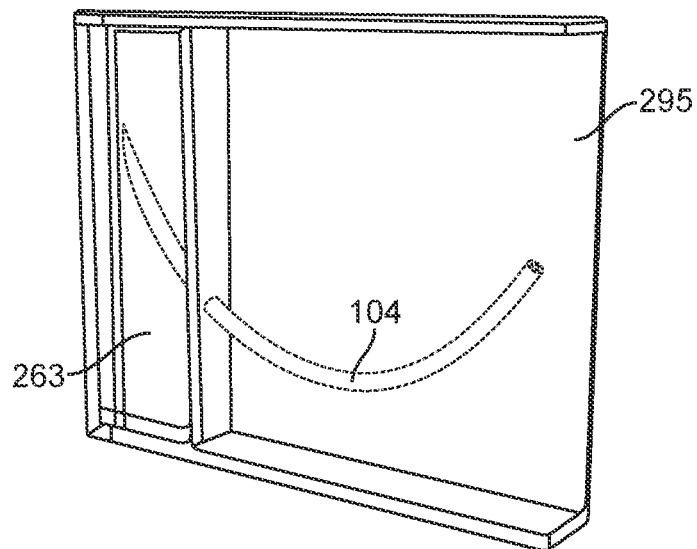
Figure 211:
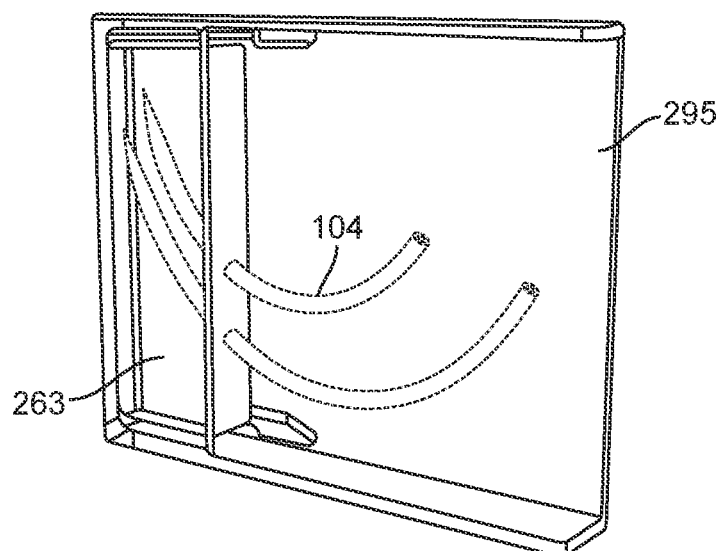

With reference to FIGS. 210-214 another embodiment of a used suture needle receptacle 257 is illustrated. In this embodiment, the used suture needle receptacle 257 can have a modular design with each unit having a low profile and holding one or two needles 104. The housings 295 of each used suture needle receptacle 257 can be transparent and foam 263 can be secured to one side of the housing 295. In FIG. 210, one needle 104 has been inserted into the foam 263 at one end of the housing 295 and in FIG. 211, two needles 104 have been inserted into the foam 263.

Figure 212:
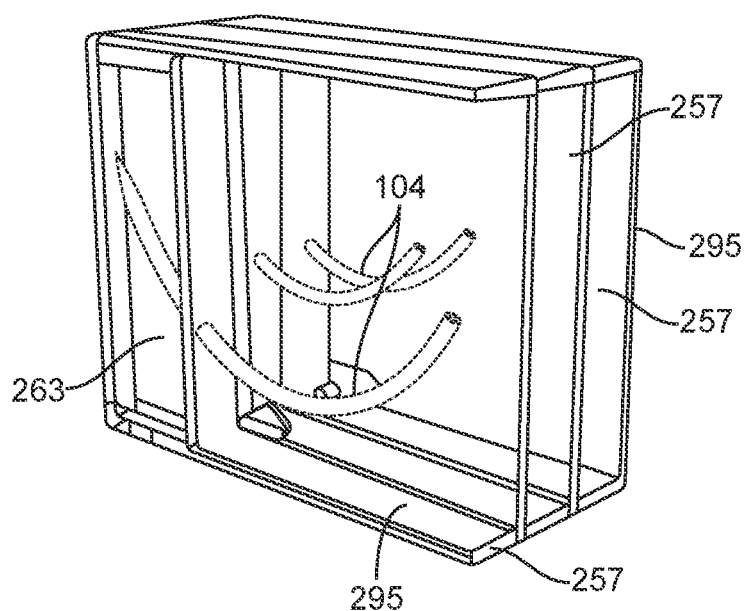
Figure 213:
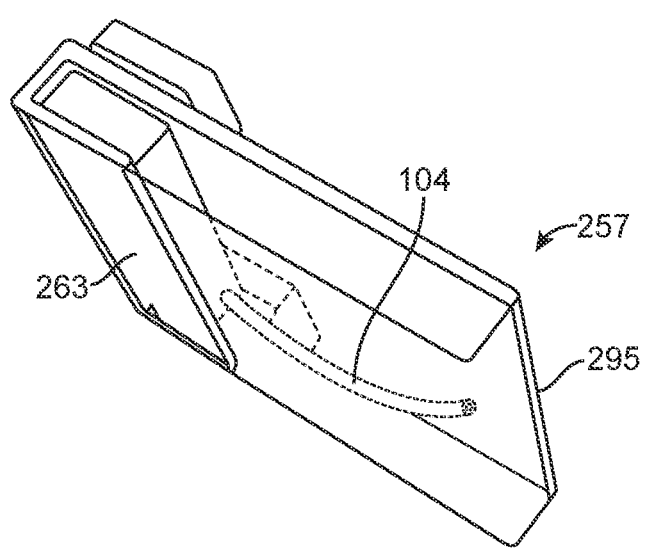
Figure 214:
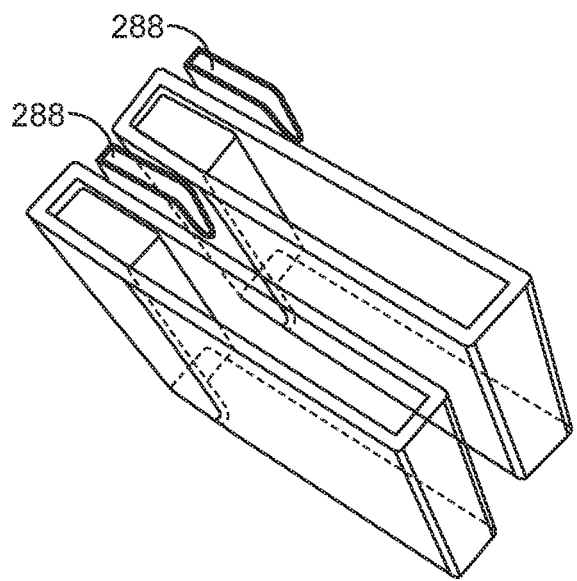

With reference to FIG. 212, once a first receptacle 257 has been filled, a second receptacle 257 can be placed against the open side of the first receptacle 257 and once the second receptacle 257 is filled, a third receptacle 257 can be placed against the open side of the second receptacle 257. The back surface of each receptacle 257 can be placed against the open side of the prior filled receptacle 257 and can function as a closing lid that contains the used needles 104 between the adjacent housings 295 so that the only exposed needles 104 are in the outermost receptacle 257. In an embodiment illustrated in FIGS. 213 and 214, the housings 295 of the adjacent receptacles 257 can be coupled with hinges 288 that can be coupled to the foam 263 side edges of the housings 295. When the receptacle 257 is filled, the next empty receptacle 257 can rotate about the hinge 288 until it is parallel and adjacent to the filled receptacle 257. This rotational motion can press or flatten the position of the needle 104 into the space within the housing 295 and the needle 104 can be contained by the adjacent receptacle 257.

With reference to FIGS. 215 and 216 in another modular embodiment of a used suture needle receptacle 257 is illustrated. In this embodiment an open sided box 260 which can have transparent walls and can be coupled to an elastic material 251 that covers the open side of the box 260. Needles 104 can be pressed through the elastic material 251 into a chamber behind the elastic material 251. The elastic material 251 can be made of sponge, foam or any other suitable elastic material that can support needles 104. When the maximum number of needles 104 have been inserted into the elastic material 251 of the exposed receptacle 257, an empty receptacle 257 can be paced over the elastic material 251 of the full receptacle 257. The bottom surface of the box 260 of the empty receptacle 257 can be pressing against the elastic material 251 of the full receptacle 257. This compression can secure the needles 104 to the receptacle 257 and allows the empty elastic material 251 to be available for more needles 104. With reference to FIG. 217 a plurality of adjacent receptacles 257 are illustrated. In this example, three receptacles 257 have been filled with needles 104 and needles 104 can be inserted into the elastic material 251 of the fourth receptacle 257.

With reference to FIG. 218, an embodiment of a used suture needle receptacle 257 is illustrated which can include a transparent dome 262, a magnetic 287 base and a needle slot 349 formed in an upper portion of the transparent dome 262. The needle slot 349 can match the curvature of the needle 104 and the needle slot 349 can have a larger cross section than the needle 104. The used needles 104 can be inserted through the needle slot 349 with a needle driver and released. The needles 104 can fall to the base of the needle receptacle 257 and magnets 287 in the base can hold the needles 104 at the bottom of the receptacle 257. Needles 104 in the receptacle can be counted visually through the transparent dome 262.

With reference to FIG. 219, another embodiment of a used suture needle receptacle 257 is illustrated. The illustrated receptacle 257 can include a transparent dome 262, an internal foam 263 structure, a needle slot 349 and a needle driver slot 343. The needles 104 can be inserted through the needle slot 349 in the transparent dome 262 and the distal end of the needle driver can be inserted through the needle driver slot 343. The needle driver can then press the needle 104 into the cylindrical foam 263 that can be mounted at the center axis of the transparent dome 262. In other embodiments, the foam 263 can be any other shape and mounted in any other suitable location within the transparent dome 262. Once the needle 104 is secured to the foam 263, the needle driver can be removed from the transparent dome 262. In an embodiment, the foam 263 may be able to rotate relative to the needle slot 349 and a needle driver slot 343 so that needles 104 can be inserted around the entire perimeter of the cylindrical foam 263 structure.

With reference to FIG. 220, an embodiment of a needle receptacle 257 is illustrated that has a circular housing 295 having an opening 256 and a foam disk 252 that can rotate within the circular housing 295. Needles 104 can be inserted into portions of the foam disk 252 that are exposed through the opening 256. As the exposed area of the foam disk 252 are filled with needles 104, the disk can be rotated within the housing 295 to expose fresh portions of the foam disk 252. The used needles 104 inserted into the foam disk 252 can be moved to positions that are completely surrounded by the housing 295 which can prevent the enclosed needles 104 from causing injury. In an embodiment the housing 295 can be transparent so that the needles in the housing 295 can be easily counted.

With reference to FIGS. 221 and 222, another embodiment of a needle receptacle 257 can include housing 295 with an opening 256 and a spool 453 upon which a roll of foam 265 is stored. With reference to FIG. 221, the foam 263 can be unrolled from the spool 453 and moved in close proximity to the opening. Needles 104 can be inserted into the housing 295 through the opening 256 and pressed into the exposed foam 263 which can securely hold the needles 104. When exposed area of foam 263 is filled with needles 104, the spool 453 can rotate to move the needle 104 filled foam 263 into the housing 295 and expose clean foam 263 as shown in FIG. 222. The illustrated process can continue until all of the foam 263 has been unrolled from the spool 453.

Barrier

As discussed, the efficiency of suture installation processes can be improved by placing used suture needles in a used needle receptacle or a used needle trap within the near surgical field. In an embodiment with reference to FIGS. 233 and 234, a used needle receptacle can be attached to a barrier 403 wrapped around a forearm of a surgeon. In this example, the barrier 403 can be a layer of puncture resistant material that has a coupling mechanism on an inner surface of an end of the barrier 403. The coupling mechanism can be attached to the outer surface of the barrier 403 so that the barrier 403 is securely wrapped around the forearm. FIG. 233 illustrates a top view of the forearm with the needle receptacle 257 attached to the barrier 403 adjacent to the dorsal portion of the forearm. FIG. 234 illustrates a side view of the forearm with the needle receptacle 257 attached to the barrier 403 adjacent to the dorsal portion of the forearm and a suture pack 101 attached to the barrier 403 adjacent to the volar portion of the forearm. In this configuration, a surgeon can remove a needle and suture from the suture pack 101 with a needle driver, install the suture in the patient and place the used needle into the needle receptacle with out having the needle 104 leave the near surgical field.

The barrier can function as a protective layer for a user and can be made of various materials and can have various different shapes. The barrier can be worn over a limb of the user and can be made of any material that can prevent needles from passing through the barrier and contacting the covered limb of the user. With reference to FIG. 235 a top view of an embodiment of a barrier 403 is illustrated. The barrier 403 can include a structural barrier layer 169 that can be made of a malleable and puncture resistant material such as aluminum. Grooves 404 added to surface of the structural barrier layer 169 to control bending along preferential lines to facilitate conformability to a forearm of a user. The structural barrier layer 169 can be fabricated from a flat sheet of barrier material. This flat configuration of the barrier 403 can be useful for storage and shipping because the barriers 403 can be stacked and a minimal volume of space is required for each barrier 403.

When the barrier 403 is used, a user can wrap the barrier around the limb to be protected. In this example, the barrier 403 is designed to protect a forearm. With reference to FIG. 236, the barrier 403 is illustrated after it has been bent to wrap around the forearm of a user. In this example, the grooves 404 can be substantially perpendicular to the curvature of the bend(s). In the illustrated embodiment, a tool holder 147 is attached to the barrier 403.

With reference to FIG. 237, bottom view of an embodiment of a barrier 403 is illustrated. The barrier 403 can include a structural barrier layer 169 and an inner foam layer 171 can be attached to an inner surface of the structural barrier layer 169. The inner foam layer 171 can be compressed against the limb of the user and this compression can cause the barrier 403 resist sliding against the limb.

With reference to FIG. 238, in an embodiment the barrier 403 can be fabricated from a plastic material and the shape of the barrier 403 can be formed into a generally cylindrical configuration. In the illustrated embodiment, the barrier 403 has a cylindrical forearm portion 415 that fits around a forearm of a user. The hand portion 417 of the barrier 403 can have a thumb hole 419. A thumb can be placed through the thumb hole 419 to improve the securement of the barrier 403 on the forearm and prevent rotation movement of the barrier 403 around forearm.

In addition to providing protection, the barriers can also provide mounting surfaces for various surgical components. With reference to FIGS. 239-241, an embodiment of a barrier 403 is shown upon which a needle trap 331 and suture packs 101 are mounted. Various mounting mechanisms can be used to attached the needle trap 331 and suture packs 101 to the outer surface of the barrier 403. In different embodiments, the mounting mechanisms for the needle trap 331 can be flat, low profile mounting interfaces which may be hook and loop, adhesive backed foam tape, a simple dovetail mount, clasps, barbed insert, pressure sensitive adhesives or any other suitable coupling mechanism. In some embodiments, these same mounting mechanisms can be used to secure the suture packs 101 to the barrier 403. However, in different mechanisms, different mounting mechanisms can be used for the suture packs 101. For example, the suture packs 101 may be held to the barrier 403 with clips or any other suitable mechanical devices.

With reference to FIGS. 242-244 another embodiment of a barrier 403 is illustrated. In the illustrated embodiment, the barrier can have a cylindrical curvature. A thumb loop 420 can be attached to a distal end of the barrier 403 and a strap 121 can be attached to facing edges of the barrier 403. The user can place the barrier 403 on a forearm and place a thumb through the thumb loop 420. The strap 121 can be an elastic structure that can provide sufficient tension to hold the barrier 403 to the forearm. Needle receptacles 257 cam be mounted on a dorsal portion of the barrier 403. In the illustrated embodiment, the needle receptacles 257 can be positioned with the openings 256 facing towards the user. Thus, the illustrated barrier 403 can be configured to be worn on a user's left forearm. Clips 115 for holding suture packs can be attached to the volar portion of the barrier 403. In the illustrated embodiment, a tool holder 147 for holding a tool 201 can be attached to a side of the barrier 403 that faces away from the user.

With reference to FIG. 249, a flat pattern for an embodiment of a forearm mounted puncture barrier 403 is illustrated. The barrier 403 can have a distal portion that includes legs 175 that can be wrapped around a limb of the user. The width of the barrier 403 can expand towards the proximal portion of the barrier 403. The barrier 403 material can be made of a plastic material that is flexible but the thickness and density of the plastic material can be sufficient to prevent the sharps such as used needles, tools or other objects which have one or more sharp surfaces that can puncture the skin of the patient or surgical staff.

In an embodiment, the barrier 403 is needle puncture resistant, unobtrusive and conformal. The barrier 403 design and fabrication can be an optimized combination of hardness and thickness. More specifically, the barrier 403 can be hard enough to resist puncture and thin enough to remain adequately flexible to be comfortable during use. In a an embodiment, the barrier 403 can be fabricated from extruded Polyethylene terephthalate glycol-modified (PETG) or polycarbonate which can be between about 0.010-0.04 inch in thickness. The hardness of the barrier 403 can have a hardness between about 45A and 65D (Shore hardness scale A and D, respectively). In an embodiment, the barrier 403 can be die cut from flat sheet of puncture resistant material. In another embodiment, the barrier 403 can be thermoformed in an anatomically conformal, semi-conical shape that can be attached to the forearm and adjusted to optimize fit with a single hand. In an alternative embodiment the barrier 403 can be blow-molded and rotationally laser cut into the designed shape. In different embodiments, barriers 403 can be fabricated using various other manufacturing processes. In an embodiment, a conformal foam layer can be mounted on inner surface of the barrier 403. This foam forearm interface surface added to the barrier can improve comfort. In some embodiments, the barriers 403 can be packaged in a flat form. However, in other embodiments, the barriers 403 can be packaged in a rolled up configuration. The barriers 403 can be packaged with one or more needle traps.

With reference to FIGS. 250-252 illustrate an embodiment of a method for placing a barrier 403 on a left forearm of a user. With reference to FIG. 250, the barrier 403 can be placed over the user's forearm and the legs 175 can be wrapped around the user's wrist. The legs 175 are secured around the wrist and the barrier 403 can wrap around the forearm as shown in FIG. 251. The legs 175 can be secured to each other on a volar side of the wrist as shown in FIG. 252.

With reference to FIGS. 253-256 an embodiment of the barrier 403 that is placed over a volar side of the forearm and uses hook material 127 and loop material 129 as a coupling mechanism that used to secure the barrier 403 to the forearm. With reference to FIG. 253, a top view of the outer surface of the barrier 403 is illustrated. A needle trap 331 and suture pack carriers 183 that hold a suture pack 101 containing suture needles 103 are attached to the barrier 403. In an embodiment, various mechanisms can be used to attach the needle trap 331 and/or suture pack carriers 183 to the barrier 403. The coupling mechanisms can include pressure sensitive adhesive (PSA) backed hook and/or loop fasteners attached to the barrier 403 to provide mounting interfaces for the needle trap 331, suture pack mount 183, etc.

The suture pack mounts can be integrated with or coupled to the needle trap. In different embodiments, the suture pack mounts can be positioned in two orientations. A suture pack mount 183 can be positioned above the needle trap 331 towards the radial aspect of the forearm. In another embodiment, a suture pack mount 183 can be positioned under the needle trap 331 in a longitudinal configuration. In an embodiment, a die cut foam mount can be attached to an underside of the needle trap 331 with PSA. A hook or loop fastener on an underside of the foam mount can be attached to a mating fastener on the barrier 403 to increase stability of a suture pack 101. Alternatively, the suture pack 101 can be attached to the needle trap 331 by means of PSA on underside of needle entry zone 333. In an embodiment, a hook or loop fastener can be attached by to the bottom of the suture pack 101 which in turn attaches to a mating fastener on the outer surface of the barrier 403.

Legs 175 or straps can extend outward from the barrier 403 at a distal portion and loop material 129 can be attached to an upper surface of one of the legs 175. With reference to FIG. 254, a bottom view of the inner surface of the barrier 403 is illustrated. Hook material 127 can be attached to the inner surface of one of the legs 175 or straps.

With reference to FIG. 255, a top view of the carrier surface supporting the needle trap 331 and suture pack carriers 183 on the barrier 403 positioned over a volar surface of a forearm is illustrated. The legs 175 can wrap around the wrist to the dorsal side of the wrist. FIG. 256 illustrates a bottom view of the dorsal side of the forearm over the barrier 403 positioned over a volar surface of a forearm is illustrated. The legs 175 can be wrapped around the wrist and the loop material 129 can be coupled to the hook material 127 to secure the barrier 403 to the forearm. The overlapping distal barrier strap surfaces can enable adjustment for range of forearm sizes and fit tightness.

Figure 245:
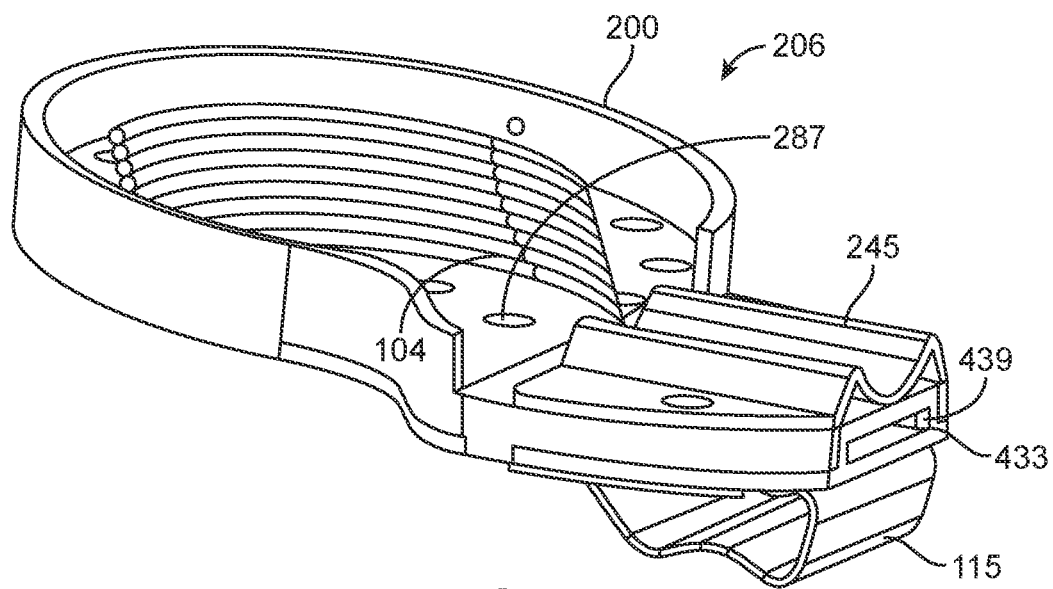
Figure 246:
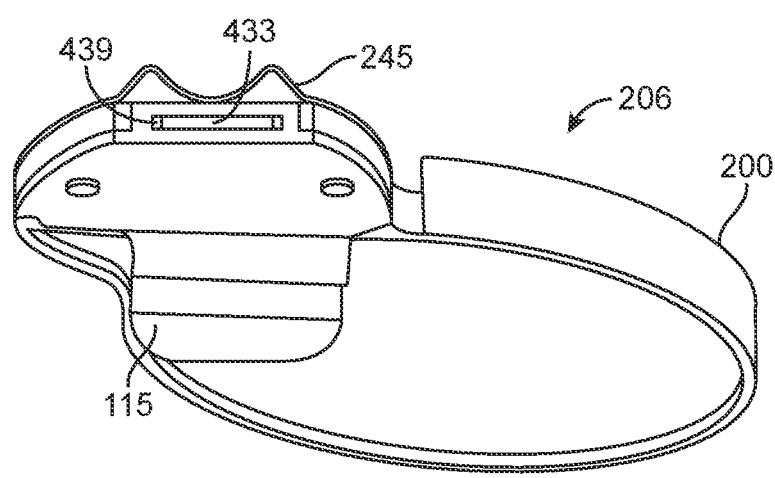
Figure 247:
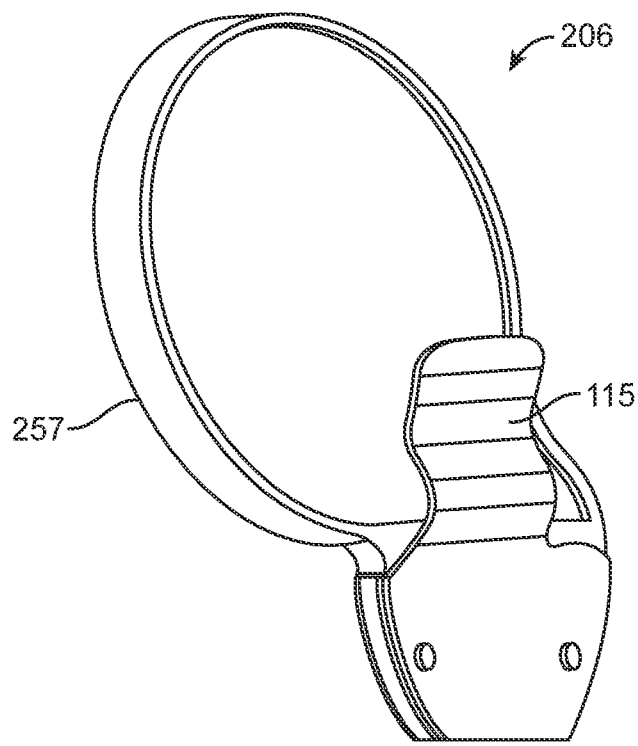
Figure 248:
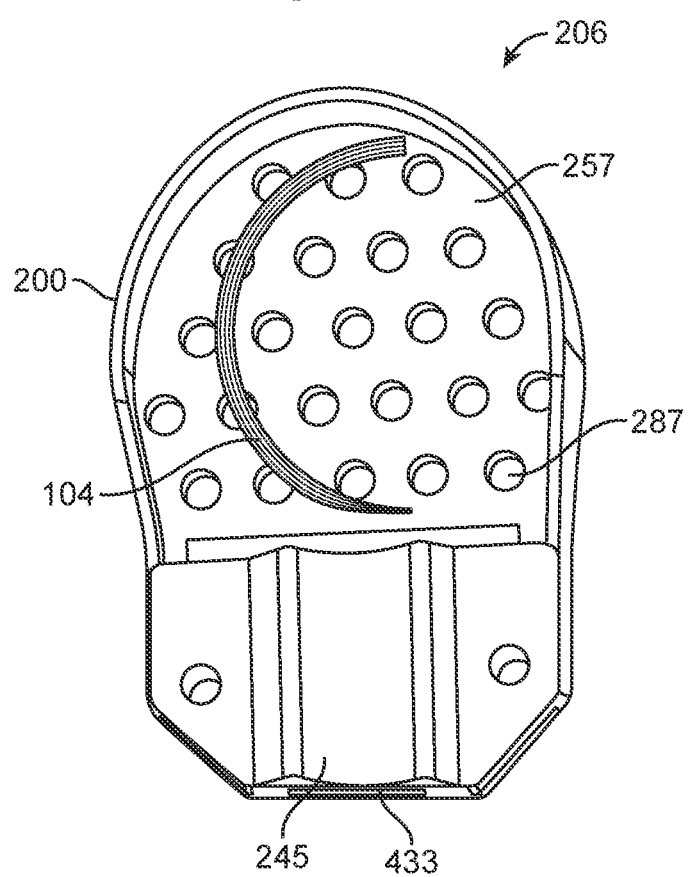

In other embodiments a needle receptacle 257 and/or a needle trap 331 can be attached to a surgical tool 201. With reference to FIGS. 245-248 an embodiment of a needle receptacle 257 and suture pack clip 115 assembly 206 is illustrated. FIGS. 245 and 248 illustrate perspective views of the needle receptacle 257 side of the assembly 206. The needle receptacle 257 can include a recessed surface that can include embedded magnets 287 that can be surrounded by a wall 200. Needles can be placed on the magnets 287 and the magnets 287 can hold the needles 104 on the recessed surface below the outer edge of the wall 200. A suture clip 115 can be mounted on the opposite side of the needle receptacle 257. With reference to FIGS. 246 and 247 illustrate bottom perspective views of the needle receptacle 257 and suture pack clip 115 assembly 206. The suture pack clip 115 can extend inward to secure a suture pack over the back surface of the needle receptacle 257.

The needle receptacle 257 and suture pack clip 115 assembly 206 can also include a tool mounting interface 433 illustrated in FIG. 245 that can include a tool slot 439 and a spring 245. A proximal end of a tool can be inserted into the tool slot 439 and the spring 245 can compress the tool slot 439 against the proximal end of the tool secure the end of the tool to the needle receptacle 257 and suture pack clip 115 assembly 206.

In other embodiments, other types of needle receptacles can be attached to surgical tool 201. An embodiment of needle trap 331 attached to a proximal end of a surgical tool 201 is illustrated in FIGS. 257-260. FIG. 257 illustrates a perspective view of a needle trap assembly 332 that includes needle traps 331 that can be coupled to a tool mounting interface 433 that is attached to a proximal end of a surgical tool 201. FIG. 258 illustrates a front view of the needle trap assembly 332. The needle traps 331 in the assembly 332 can function in substantially the same ways that the needle trap 331 described above with reference to FIG. 168. The illustrated needle trap 331 can be angled towards the left relative to the axis of the tool 201. When needles are inserted into the needle trap 311 the needle insertion force can apply a rotational and translational force on the tool 201. With reference to FIG. 259 a side view of the needle trap assembly 332 is illustrated. In this embodiment, the needle traps 331 can be mounted on opposite sides of the tool mounting interface 433 with the entry zones 333 of the two needle traps 331 facing in opposite directions. When a needle trap 331 is being used, the needle trap assembly 332 can be rotated so that the target entry zone 333 faces the needle being inserted.

With reference to FIG. 260, an exploded view of the needle trap assembly 332 is illustrated. The needle traps 331 can each include a front (upper) structure 339 and a back (lower) structure 341. Rotational mounting components 367 can be used to attach the needle traps 331 to the tool mounting interface 433. In the illustrated example, the rotational mounting components 367 can be fastened to the holes 342 in the lower elements 341 as well as the hole 434 extending through the tool mounting interface 433. In an embodiment, the needle traps 331 can rotate relative to the tool 201 about the holes 342 in the lower elements 341. Once the desired angular orientation of the needle traps 331 is determined, the rotational mounting components 367 can be tightened to lock the needle traps 331 in the desired angular orientation. In an embodiment, the needle traps 331 can have clips on portions of the needle traps 331 that are opposite the entry zones 333.

In the illustrated embodiments, the needle traps 331 can be configured in a back-to-back orientation. The needle traps 331 can be positioned at right angles to each other, 45 degrees off set from an axis of the surgical tool 201. Although the tool mounting interface 433 illustrates a tool slot 439 attached to the surgical tool 201, in other embodiments the needle trap assembly 332 can be connected with any other types of connection mechanisms such as but not limited to: hook and loop, tabs, adhesives or foam etc. These various mechanisms can be used to secure the needle trap assembly 332 to various forceps geometry.

For clarity, all components of the needle traps 331 are not illustrated in FIGS. 257-260. However, in different embodiments, the needle traps 331 and associated components described with reference to FIGS. 168-189 can also be used with the needle trap assembly described with reference to FIGS. 257-260, for example.

The weight of the combined needle traps and mounting structure can be within a range from about 5 grams to about 80 grams, for example within a range from about 10 grams to about 40 grams, for example. The weights within these ranges can provide balance to the surgical tool on which one or more needle traps are placed.

The needle trap as shown in FIGS. 257 to 260 can be configured in many ways, and may be combined with a suture pack for ease of use, for example as described with reference to FIGS. 80-84. A needle trap and suture pack can be combined with an opposing configuration in which the suture pack is located on an opposite side from the needle trap. For example, one or more of the needle traps 331 can be replaced with one or more of the suture packages as described herein. The trap and suture pack can be mounted in an opposing configuration on the proximal end of the forceps, similar to the pair of needle receptacles. The weight of the combined needle trap and receptacle and mounting structure can be within a range from about 5 grams to about 80 grams, for example within a range from about 10 grams to about 40 grams, for example. The weights within these ranges can provide balance to the surgical tool on which the needle pack and traps are placed.

Alternatively, a pair of opposing suture packs can be mounted on the instrument, and used needles stored elsewhere such as the volar forearm as described herein, and for example as described with reference to FIGS. 80-84, and which may incorporate components of the mounting assembly of FIGS. 257-260. The weight of the combined used needle receptacles and mounting structure can be within a range from about 5 grams to about 80 grams, for example within a range from about 10 grams to about 40 grams, for example. The weights within these ranges can provide balance to the surgical tool on which the needle packs are placed.

Surgical Gown

In an embodiment, a surgical gown can be constructed with barrier or multiple barriers built into the sleeves of the gown. Typically the sleeves of the gown are manufactured of lightweight fabric that is impenetrable to fluids to protect surgeon and patient from cross contamination. These gown materials however may not protect a surgeon from needle or sharps penetration or tearing. In an embodiment, the gowns can be created with barrier zones on the forearms that can be impenetrable to needle perforation and can prevent tearing.

In an embodiment with reference to FIG. 261, a surgical gown 401 can have a barrier 403 is created on the dorsal radial aspect region of the surgical gown sleeve 402. The barrier 403 can have a curvilinear cross section that can conform to the outer curvature of the forearm.

In another embodiment with reference to FIG. 262, sleeves 413 that include barriers 403 can be separate components that can be placed over and can be removed from the gown 401. The sleeves 413 can have one or more circumferential elastic elements 405 on the sleeve 413 in the area of the barrier 403 that renders the sleeve conformal in the region of the zone and prevent rotation of the barrier 403 around the limb that the sleeve 403 is worn on. An elastic element 405 can also be placed around the proximal edge of the sleeves 413 to hold the proximal portion of the sleeves 413 to the gown 401. Such elastic elements 405 can stabilize the sleeve 413 and the barrier 403 reducing movement and displacement as the surgeon moves.

In another embodiment the barrier 403 can be a flexible plastic shield that is substantially flat or slightly curved and conforms to the arm when the barrier 403 is attached to the forearm over the surgical gown 401. In other embodiments, additional straps and/or tabs can be additionally used to augment the coupling of the forearm sleeve 413 to the barrier 403 and improve the connection security. For example, Velcro, wet and dry adhesives, magnets and mechanical locks or any other suitable types of connection mechanisms such tabs and straps can be used to secure the sleeve 413 and barrier 403 to the user's forearm.

In an embodiment, the surgical gowns can be constructed of multiple pieces, panels and/or sheets of thermoplastic materials. These pieces can be seamlessly welded together to create the surgical gowns. Such thermoplastics gown materials can be used to create zones of increased material thickness that can act as barrier zones. In an embodiment, the barrier is comprised of a thickened layer and/or multiple layers of the gown material that can be thermally heated and compressed such that the material properties of the barrier prevent needle penetration with forces that one reasonably may anticipate in surgery.

With reference to FIGS. 263-265, side views of the barriers in gown sleeves 402 or separate sleeve 413 structures. With reference to FIG. 263, a cross section of a barrier can be a thicker material 407 area of the sleeve, where the same surrounding gown material 411 is used to create a thicker more puncture resistant thicker material 407 which functions as a barrier 403.

With reference to FIG. 264, in another embodiment the barrier 403 can be made of a different material than the gown and the barrier 403 can be thermally welded 409 to the gown or sleeve material 411. For example, in different embodiments the barrier can be made of plastic, metal or any other suitable barrier materials. The barrier 403 can be attached with adhesive to the gown sleeve material or can be mechanically attached with seams to the surrounding sleeve material. In this example, the intersecting edges of the barrier 403 material and the gown or sleeve material 411 material are thermally welded 409 to each other. In other embodiments with reference to FIG. 265, the barrier 403 material can be thermally welded to the outer surface of the gown or sleeve material 411.

In other embodiments, the barriers 403 illustrated in FIGS. 263-265 can be used as platforms for mounting other surgical devices such as needle traps, suture packs, tool holders and other objects. These components can be attached to the barriers with various types of connection mechanisms such as: adhesives, magnetic mechanisms, mechanical connectors such as hook and loop materials, etc. For example, in an embodiment, a hook material can be attached to the bottom surface of a needle trap and a loop material can be attached to an outer surface of the barrier 403. This configuration can allow the needle trap to be releasably coupled to the barrier on a gown or a sleeve on the forearm of a surgeon.

In other embodiments, various mechanisms can be used to mechanically attach one or more suture packages to the barrier mounted on the forearm of a surgeon. With reference to FIG. 189, suture packs 101 and a needle trap 331 are illustrated mounted on the barrier. In similar embodiments, the barrier upon which the suture packs 101 and a needle trap 331 are mounted can be a barrier that is integrated with a sleeve or gown.

In different embodiments, the surgical gowns with barrier zones can be disposable gowns or reusable fabric gowns. Alternatively, the gown can be constructed of a disposable gown material with the barrier device attached to the forearm of the gown. However, after use, the barrier can be removed from the disposable gown and reused. In these embodiments, the barrier can be attached to the sleeve with an adhesive, hook and loop coupling, or any other suitable releasable attachment components.

In an operating room, sterile sleeves 413 as illustrated in FIG. 262 can be available to operating room personnel. If surgeon either tears or contaminates the sleeve of a surgical gown, such an extra sleeve 413 can be rolled onto the surgeon's arm. Such an overlay sleeve 413 preserves sterility and covers any potential breach of the gown. The alternative to the overlay sleeve 413 can be for the surgeon to "regown" which is a process in which the gown and multiple layers of gloves are removed, a new gown applied followed by new gloves. The overlay sleeve 413 thus saves time and is an efficient device where surgically appropriate. As discussed, the overlay sleeve 413 can have a barrier 403 in the region of the forearm. Such an overlay sleeve 413 can allow a barrier 403 to be rapidly secured to operating room personnel.

Glove Extensions

In the operating room the surgeon can wear an operating gown that extends to the wrist or palm of the surgeon. The surgeon can then place a glove or multiple layers of gloves on the fingers and hand can then pulled proximally to cover the distal extent of the sleeve of the gown. Thus, a distal portion of the sleeve of the gown can be covered a proximal portion of the gloves.

FIGS. 286-289 illustrate different embodiments of surgical gloves 480. FIG. 286 illustrates a top view of an embodiment of a glove 480 having a glove portion 481 made of a latex type material that extends from the fingers to a middle portion of the forearm. A glove extension 483 can be attached to the proximal edge of the glove portion 481 and can extend from the forearm to a position that covers the elbow of the surgeon. The glove extension 483 material can be made of surgical gown material or any other suitable material. FIG. 287 illustrates a top view of an embodiment of the glove 480 that has a glove portion 481 made of a latex type material that extends from the fingers to the wrist and a glove extension portion 483 that extends from the wrist to a position that covers the elbow of the surgeon. With reference to FIG. 288, a top view of a glove 480 having a glove portion 481 made of a latex type material that extends from the fingers to the wrist and a glove extension portion 483 that extends from the wrist to a position that covers the elbow and a barrier 403 attached to a portion of the glove extension 383. FIG. 289 illustrates a top view of a glove 480 having a glove portion that extends from the finger to an elbow and a barrier 403 coupled to a portion of the glove portion 481. As discussed, the barriers 403 can protect the portions of the forearm that are covered by the barriers 403. In an embodiment, surgical components such as needle traps, needle receptacles, suture pack carriers, tool holders, etc.

Embodiment of the present invention can include surgical gloves 481 designed to extend proximally up the surgeon's forearm. Gloves 480 may include a glove portion 481, a glove extension 483 and a barrier 403. The glove portion 481 can be fabricated with latex or latex like polymers such as but not limited to: nitrile, isoprene, or vinyl. In an embodiment, a sleeve extension 483 can be coupled to the glove portion 481 and the sleeve extension 483 can be made of a material that is different than the glove portion 480 material covering the fingers. More specifically, the fingers of the glove 481 can be made of a different material than the rest of the glove. Such glove finger materials can include but are not limited to materials usually encountered in the sleeves of gown. Such materials include fabrics and thermoplastic materials.

In an embodiment, a glove can have a proximal extension 483 that includes a barrier 403 zone having a barrier material that can resist and/or prevent sharps from penetrating the barrier 403 and contacting the flesh under the barrier 403. In an embodiment the glove barrier can also allow any of the described components to be attached. For example, needle trap(s) and/or suture pack(s) can be attached to the glove barrier using any of the described attachment mechanisms such as but not limited to: adhesives, hook and loop connectors, magnets, mechanical couplings, etc.

In an embodiment, the glove with an integrated barrier can cover the hand and further comprise a proximal extension that extends over at least a portion of the forearm and may possibly extend to the elbow. The proximal extension can contain a barrier that can orient to the radial border of the forearm. Such a barrier can also contain one or more zones for attachment of a needle trap(s) and/or suture pack(s).

In an embodiment, the barrier 403 on the forearm and integrated with the glove can comprise one or more devices that can function to provide a barrier 403 for the wearer of the glove 480. The barrier 403 material integrated with the glove 480 can be made of plastic, metal, fabric, or any other suitable material(s). In an embodiment the barrier 403 can be attached to an inside portion of the glove 480 which can be along the forearm. In another embodiment the barrier 403 sandwiches the glove between an inner and outer layer of the glove material.

Surgeon-Controlled Suture Cutting

Sutures are sometimes swaged into the trailing end of the needle and must be cut at the conclusion of a stitch. A scrub technician may traditionally cut the sutures from the needles. However, enabling the surgeon to cut the sutures can eliminate the need for a third party scrub technician to cut the suture. This procedural change can improve efficiency and safety. Ideally, the suture can be cut without imparting tension on the suture during the cutting.

In an embodiment with reference to FIGS. 266-268, scissors or a blade can be worn on the surgeon's fingers like a ring. FIG. 266 illustrates a front view of a ring cutter 412 and FIG. 267 illustrates side view of embodiments of the ring cutter 412. The ring cutter 412 can have a ring 423 and a cutting blade 425 that can be oriented with the blade aligned with the finger wearing the ring cutter 412. When a suture needs to be cut, the surgeon can press the blade 425 against the suture to cut the suture. The excess suture can be removed from the near surgical field and the ring cutter 412 can be used again when the next suture needs to be cut. In other embodiments, a suture cutter may be incorporated into the needle trap, or the barrier.

With reference to FIG. 268, an alternative embodiment of a finger-mounted blade 425 is illustrated. In this embodiment, the blade 425 can be mounted on a distal portion of a rod 427 that can be coupled to multiple rings 423 that can be placed on a finger 429. The sutures can be cut by pressing the blade 425 against the sutures.

With reference to FIGS. 269-271, in an embodiment, a tool-mounted cutter 437 can be permanently or removably attached to a proximal portion of a tool 201 such as a forceps or needle driver. With reference to FIG. 269, the tool-mounted cutter 437 can have a tool cap 433 that has a recess that can closely fit over the proximal portion of the tool 201. The blade housing 435 can have two portions that extend proximally that define a recessed area within the housing 435 where a blade 431 is mounted. In the illustrated embodiment, the blade 435 can have a "V" shaped cutting surface. With reference to FIGS. 270 and 271, the blade 435 can be aligned with the length of the tool 201. When a suture needs to be cut, the surgeon can push the "V" shaped cutting surface against the suture to perform the cut.

In an embodiment with reference to FIGS. 272 and 273, a surgical tool 201 can have an integrated cutter. In this example, standard blades 441 can be mounted to the blade housing 445. The standard blades 441 can include mounting holes and the blades 441 can be secured to the blade mounts 443 to rigidly secure the blades 441 to the blade housing 445. In this embodiment, the blades 431 can be removably attached to a proximal portion of a tool 201 which can be forceps, a needle driver or any other surgical tool. When the blades 441 are worn and/or need to be replaced, the blades 431 can be removed from the blade mounts 443 and replaced.

With reference to FIG. 274, in an embodiment scissors can be mounted on the end of the surgical tool 201. In this embodiment, the blade housing 435 can include hinges 445 that can be living hinges that can allow the blades 431 to rotate and function as scissors for cutting sutures. The hinges 445 can normally assume a straight shape so that when the scissors are normally open. In this embodiment, when the surgeon wants to cut the suture, the suture can be placed between the blades 431. The surgeon can then squeeze to apply a compressive force to the sides of the housing 435 to move the blades 431 towards each other cut the sutures. When the compressive force applied to sides of the housing 435 is released, the blades 431 of the scissors can separate and open.

Figure 275:
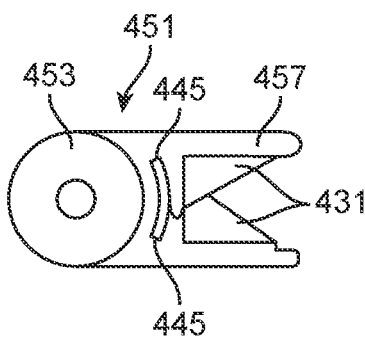
Figure 276:
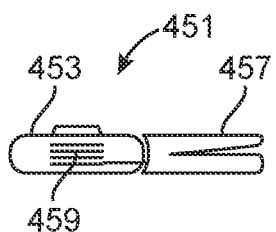

With reference to FIGS. 275-278, an embodiment of a retractable cutter system 451 is illustrated. The retractable cutter system 451 can include a cutter 457 which can be a fixed blade 431. FIG. 275 illustrates a top view and FIG. 276 illustrates a side view of the retractable cutter system 451 in the retracted position. In the illustrate embodiment, the cutter 457 can have hinges 445 that allow the blades 431 to move and function as scissors 447. The cutter 457 can be coupled to an end of a retractable cable 455 that can be partially wrapped around a spool 453 that can be coupled to a rotational spring 459. In a retracted position, the retractable cable 455 can be wrapped around the spool 453.

Figure 277:
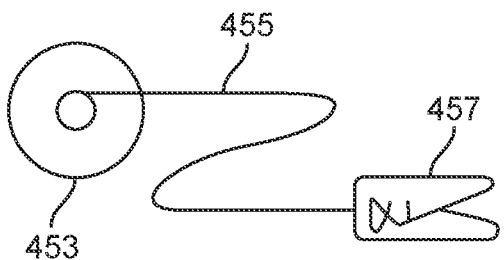
Figure 278:
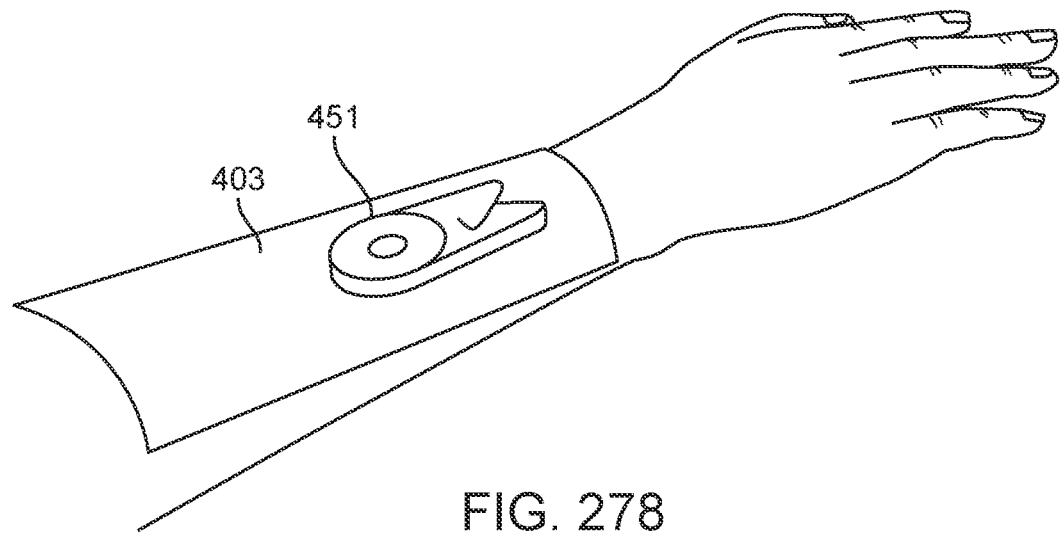

With reference to FIG. 277, the cable 455 can be pulled and the spool 453 can rotate to allow the cable 45 to extend away from the spool 453. In an embodiment illustrated in FIG. 278, the retractable cutter system 451 can be mounted to a barrier 403 on a forearm of the surgeon. When the surgeon wants to cut a suture, the cutter 457 can be pulled from the spool 453 and press the blades 431 against the suture. When the suture is cut, the surgeon can release the cutter 457 and the spring 459 can retract the cable 455 onto the spool 453.

In other embodiments with reference to FIGS. 279 and 280, sutures can be cut with a barrier-mounted cutter 461 that can be integrated with a forearm-mounted barrier 403. FIG. 280 illustrates an enlarged view of the embodiment of the cutter 461. The cutter 461 can have a housing 463 and a recessed blade(s) 431 on a distal portion of the housing 463. The blade(s) 431 can be configured in a perpendicular orientation to the surface of the barrier 403. When the surgeon needs to cut a suture, the surgeon can pull the suture proximally to press the blade(s) 431 against the suture. In another embodiment, the barrier-mounted cutter 461 can function as scissors. In this embodiment, the housing 463 can be compressed against the barrier 403 to cause the blade(s) 431 to move and function as scissors. When the surgeon needs to cut a suture, the surgeon can place the suture between the blade(s) 431 and the surgeon can compress the housing 463 to actuate the scissors and cut the suture.

In other embodiments, the scissors can be actuated with a pneumatic pressure. In these embodiments, the scissors can be coupled through a pneumatic hose to a control button which can be a valve and a pneumatic pressure source. The scissors can be normally open when the control button is not actuated. For example, when the control button is pressed the air pressure can be directed through a hose to actuate the pneumatic scissors and cut an object between the blades of the scissors. When the control button is released, the air pressure can be vented and the pneumatic scissors can open the blades of the scissor.

In another embodiment with reference to FIG. 281, the blades 431 on a distal portion of scissors 447 can be mounted within a safety guard 465 which can surround the sharp tips of the scissor blades 431 but also have a slot that can allow the suture to be positioned between the blades 431. The scissors 447 can be actuated by applying a compressive force which can cause the blades 431 to cut sutures in the slot 469 of the guard 465. In an embodiment, the scissors 447 can be actuated by compressing opposite sides of the scissors 447. Alternatively, in other embodiments the scissors can be actuated by other means such as but not limited to: pneumatic foot pedal coupled to a piston, electronic signal from foot pedal, proximity sensing of suture within cutting zone. If the scissors 447 are actuated by pneumatic pressure, the pneumatic scissors 447 could be coupled to a pressure source 475 and a control valve 477 with a pneumatic hose.

Figure 282:
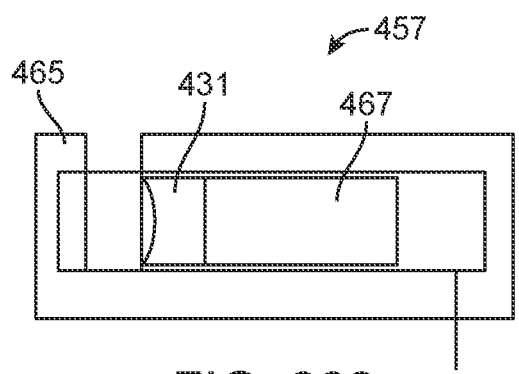
Figure 284:
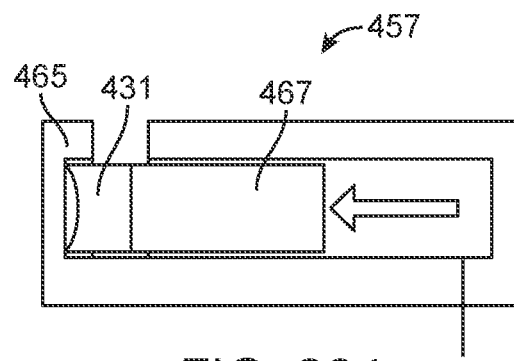
Figure 283:
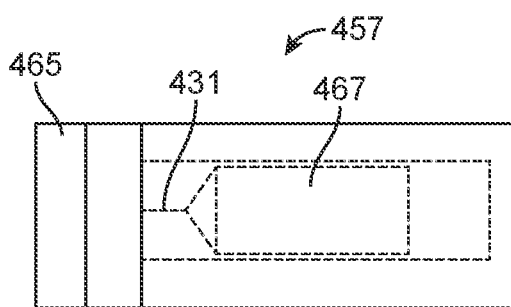
Figure 285:
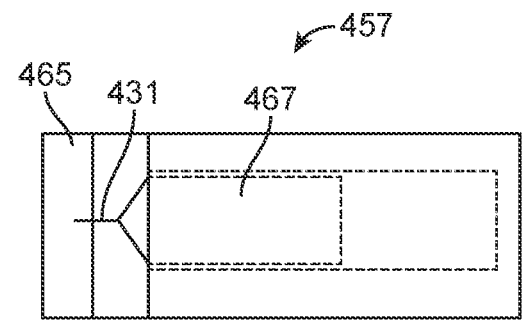

With reference to FIGS. 282-285, an embodiment of a cutter 457 that can be used to cut sutures is illustrated. FIG. 282 illustrates a side view and FIG. 283 illustrates a top view of the cutter 457 in the open position. FIG. 284 illustrates a side view and FIG. 285 illustrates a top view of the cutter 457 in the closed position. The cutter 457 can include a blade 431 coupled to a moveable piston 467 that slides within the guard 465. The guard 465 can have a hook or "J" shaped distal end portion that the blade 431 can contact to cut sutures placed into the cutting slot. The piston 467 can be normally retracted which moves the blade 431 away from the distal end portion and opens the cutting slot between the blade 431 and the inner end of the hook or "J" shaped distal portion. When the piston 467 is actuated the blade 431 can move into a close fitting slot in the hook or "J" shaped distal end and a suture placed in the cutting slot can be cut. The piston 467 can be a pneumatic actuator that is actuated by applied air pressure supplied by a pneumatic hose. Alternatively, the piston 467 can be an electrical device such as a solenoid that can use electromagnetic forces to actuate the piston 467. In other embodiments, the piston 467 can be actuated by pure mechanical means.

In various embodiments the actuation of the described cutters and scissors can be accomplished by manually squeezing the scissors as discussed above, or by other means such as but not limited to: pneumatic foot pedal coupled to a piston, electronic signal from foot pedal, proximity sensing of suture within cutting zone.

Needle Traps

Surgeons often pull the needle from the tissues after the "last throw" of the needle by grasping the tip portion of the needle. This practice is common as the tip is the portion of the needle showing from the tissues and therefore the needle tip is the easiest portion of the needle to grasp. The needle may not need to be regrasped (in a center portion) after the last throw and therefore grasping of the tip of the needle with the needle driver can provide the safety benefit of securing the tip of the needle within the jaws of the needle driver. If the needle driver and needle are handed to a scrub tech, the needle tip may not be exposed and the needle handling can be less dangerous to the scrub tech and the surgeon. However, in embodiments, the used needles can also be deposited in needle traps that can be configured to receive needles held by their tips by a needle driver.

With reference to FIGS. 290-294 an embodiment of a needle trap 331 is illustrated. FIG. 290 illustrates a cross sectional view and FIG. 291 illustrates a front view of the needle trap 331. The illustrated needle trap 331 includes a housing 295 that is configured with a needle driver slot 343 that asymmetrically intersects one side of a needle slot 349, rather than the center of the needle slot 349. The needle slot 349 can have compressible members 347 attached to one or both sides of the needle slot 349. In an embodiment, the compressible members 347 can be foam. However in other embodiments, the compressible members 347 can be made of any other suitable material. Further, the needle trap can utilize any other type of needle retention systems such as those described above with reference to FIGS. 172-179.

Figure 294:
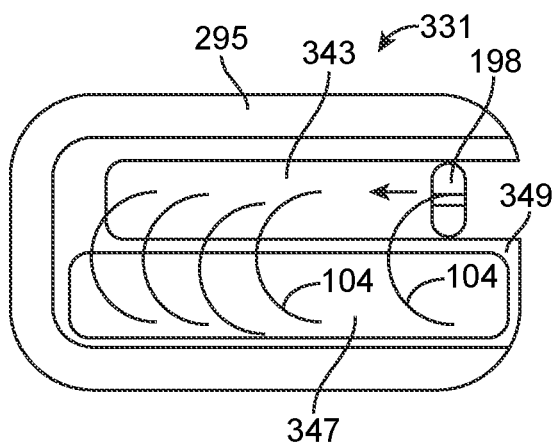

With reference to FIGS. 292 and 293 a tip of a needle driver 198 can be used to insert the needle 104 into the needle slot 349. The needle driver 198 can be moved to the end of the needle slot 349 and in the location the needle driver 198 can release the needle 104. Although the needle driver 198 is illustrated with the tip portion held by the needle driver 198 can be substantially parallel with the needle driver slot 343, in other embodiments the tip portion can be moved through the needle driver slot 343 in any directional orientation. With reference to FIG. 294, illustrates the needle trap 331 after a plurality of needles 104 have been inserted into the needle slot 349.

Figure 295:
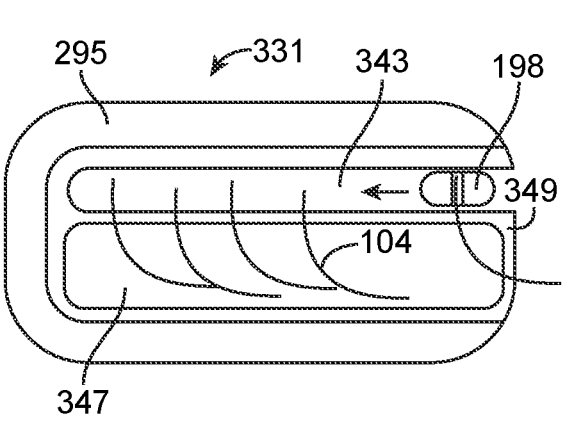

With reference to FIG. 295 another embodiment of a needle trap 331 is illustrated. In this embodiment the needle driver slot 343 can be narrower. The tip of the needle driver 198 can have a cross section with a width that is longer than the thickness. When the needle driver 198 holds a needle 104, the tip of needle driver 198 can fit within the needle driver slot 343. However, the needle driver slot 343 can be narrower than the width of the tip of the needle driver 198 so that the needle driver 198 cannot freely rotate within the needle driver slot 343. By forcing the needle driver 198 to assume a specific rotational orientation, the rotational positions of the needles 104 within the needle slot 349 can also be controlled. In an embodiment, the uniform positions of the needles 104 can increase or optimize the number of needles 104 that can be stored in the needle trap 331. With reference to FIG. 295 a side view of the needle trap 331 is illustrated where the needle driver 198 has pulled a plurality of needle 104 into the needle slot 349.

Figure 296:
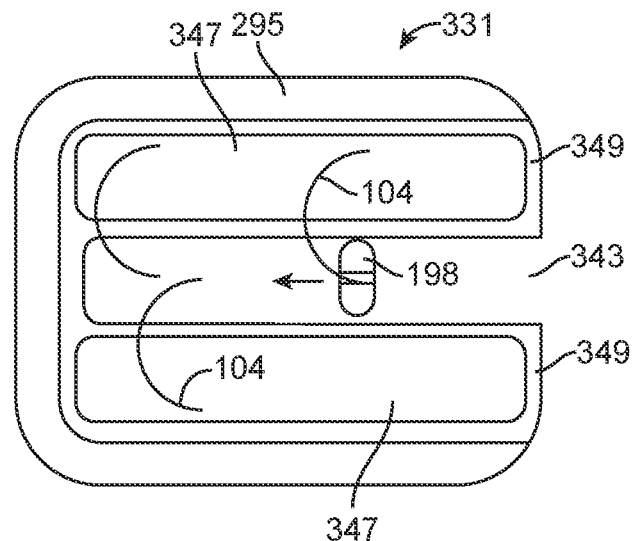

Another embodiment of a needle trap 311 is illustrated in FIG. 296. In this embodiment, two separate needle slots 349 can be formed in the housing 295 with the needle slots 349 positioned on opposite sides of the needle driver slot 343. Compressible members 347 can be secured to the housing 295 and adjacent to each of the needle slots 349. The needles 104 can be inserted into either of the needle slots 349 by sliding a needle driver 198 that is grasping a needle 104 through the needle driver slot 343.

Figure 297:
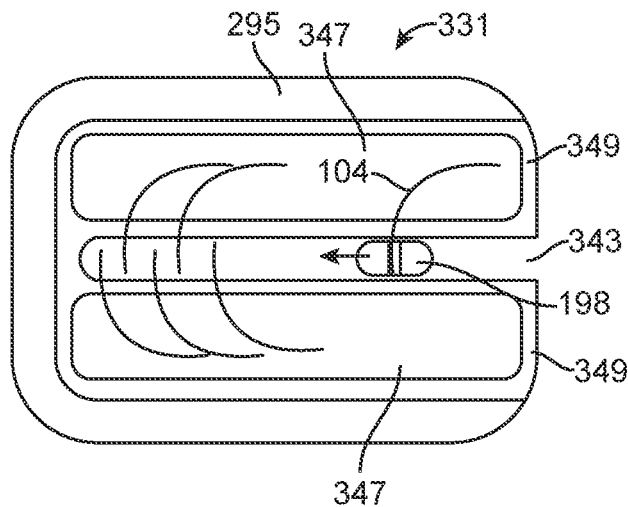

FIG. 297 illustrates another two needle slot 349 embodiment of the needle trap 331. In this embodiment, the needle driver slot 343 is narrower to that the needle driver 198 cannot rotated which can cause the needles 104 to be positioned uniformly within the needle slots 249. FIG. 298 illustrates a front view of the needle trap 331.

In another embodiment with reference to FIGS. 299-306, the needle trap 311 can have a circular or spiral configuration. With reference to FIG. 299, embodiments of the needle driver slot 343 can be curved in a circular or spiral shape. The needle driver slot 343 can be concentric to the needle slot 349. In the illustrated example, the needle driver 198 can enter the needle driver slot 343 with a needle 104. The needle driver 198 can slide through the needle driver slot 343 and pull the needle 104 though the needle slot 343. FIG. 300 illustrates a front view of the needle trap 331 with the needle driver 198 in the needle driver slot 347 and the needle 104 in the needle slot 349. With reference to FIG. 301, when the needle driver 198 has moved to the end of the needle driver slot 343 where the needle 104 can be released and the needle driver 198 can be pulled away from the needle trap 331. With reference to FIG. 302, additional needles 104 can be inserted into the needle slot 343 in the described manner.

Another embodiment of a circular needle trap is illustrated with reference to FIGS. 303-306. In this embodiment, the width of the needle driver slot 343 can prevent free rotation of the needle driver 198. The needle driver slot 343 can be slightly wider than the width of the tip of the needle driver 198. This configuration can allow a torque to be applied between the housing 295 and the needle driver 198 which can drive the needle driver 198 through the circular portion of the needle driver slot 343. With reference to FIG. 303, the needle driver 198 can enter the needle driver slot 343 pull the needle 104 into a straight portion of the needle slot 349. FIG. 304 illustrates a front view of the needle trap 331. With reference to FIG. 305, once the needle driver 198 reaches the curved portion of the needle driver slot 343, a torque can be applied between the needle driver 198 and the needle trap 331. More specifically, a clockwise torque or rotational force can be applied to the needle driver 198 which can be resisted by a counter clockwise torque applied to the housing 295. The torque can cause the needle driver 198 to rotate and slide in a clockwise motion through the needle driver slot 343 which can cause the needle 104 to similarly rotate and slide within the needle slot 349. With reference to FIG. 300, once the needle driver 198 has reached the end of the needle driver slot 343, the needle 104 can be released and the needle 198 separated from the needle trap 331. With reference to FIG. 306, the described rotational insertion process can be repeated for additional needles 104 until the needle trap 331 is full.

For all of the needle trap embodiments illustrated in FIGS. 290-306, entrances to the needle slots 349 and needle driver slots 343 can be flared to assist with aligning the needles 104 with the needle slots 349. When the needles 104 are placed in the needle slots 349, the tips of the needles 104 can be exposed within the needle driver slot 343, which is visible from either side of the needle trap 331. However, because a portion of the housings 295 is adjacent to the tips of the needles 104, the needle trap 331 can prevent physical contact and injury. The needle traps 331 can also provide grooves in the housings adjacent to the tips of the needles 104 as illustrated in FIG. 294 and in an embodiment, the tips of the needles 104 can be placed in these grooves to further prevent physical contact and injury.

In the illustrated embodiments, the number of needles stored in the needle slot 349 can be determined by counting the needles within the needle driver slot 343. In an embodiment, some or all of the housing 295 components can be made of a transparent material so that a larger portion of the trapped needles 104 can be visible. In still other embodiments, any of the compatible needle counting systems disclosed with reference to FIGS. 180-189 can also be used with the needle trap 331 embodiments illustrated in FIGS. 290-306 to perform needle counting.

In many embodiments, the needle trap 331 embodiments illustrated in FIGS. 290-306 can be secured to platforms and barriers that can be mounted or worn on limbs of surgeons. The coupling mechanisms described for securing the needle traps and needle receptacles to platforms and barriers can also be applied to the needle trap 331 embodiments illustrated in FIGS. 290-306.

FIG. 307 illustrates an exemplary embodiment of an integrated suture needle dispensing and securing apparatus 308. The apparatus 308 comprises a needle dispensing portion 102 and a needle receptacle portion 334, supported with the same housing 309. The housing may comprise a single structure, such as a single molded plastic piece, or the housing may comprise a base 310 coupled to one or more covers 312. The covers may comprise separate covers for each of the needle dispensing portion 102 and the needle receptacle portion 334. Alternatively, the cover may comprise a single cover for both the needle dispensing portion and the needle receptacle version. The covers, or the upper portion of the housing, can comprise an optically transparent material, such that the user can easily see the number of fresh needles 103 or secured needles 104 supported by the apparatus 308. The needle dispensing portion 102 can be configured to support one or more fresh suture needles 103, for example via a foam member 110. The new suture needles 103 may be pre-loaded with sutures 155, and the sutures may be disposed within a pocket 324 of the housing 309. The needle receptacle portion 334 can be configured to receive a plurality of suture needles 104, for example using the mechanisms described herein in relation to needle receptacle 331. In many embodiments, the apparatus 308 is sterile, and can be self-supporting and/or coupled to another support such as a platform or a surgical tool as described herein. Providing a single device that integrates the functions of suture needle dispensing and securing/storage can have the advantage of providing a highly compact system for suture needle handling.

FIG. 308 is a block diagram of a sterile suturing kit 500 in accordance with embodiments. The sterile suturing kit 500 comprises a sterile enclosure 505 containing a sterile package 101 of sterile sutures 103, and a sterile apparatus 331 for receiving at least one contaminated surgical suture needle 104. The sterile apparatus 331 may comprise any needle receptacle or sharps container as described herein, for example. The sterile needle receptacle 331 comprises a sterile housing 340 having a top and a bottom. The needle receptacle 331 further comprises at least one opening 350 between the top and the bottom of the housing 340, configured and dimensioned to receive a contaminated surgical needle 104 inserted through the opening. The needle receptacle 331 further comprises a secure zone 337 within the housing, to hold the contaminated surgical needle 104 in a predetermined orientation with the needle tip secured. The sterile surgical kit 500 may further comprise a protective barrier as described herein, configured and dimensioned to support the sterile suture package 101 and sterile needle receptacle 331. The barrier may, for example, be configured to be mounted to a forearm of a surgeon, as described herein.

The materials and structures to stabilize needles as described herein can be configured in many ways. The materials and structures may comprise one or more one or more of a deformable material, an adhesive material or an elastic material, and the material may comprise one or more of a foam, elastic membrane, or an adhesive, for example.

In many embodiments, a needle resistant barrier as described herein can comprise a thin, puncture-resistant material integrated with a flexible web. The barrier can comprise a plurality of bi-stable springs connected by a flexible, in order to accommodate a range of different forearm sizes. The plurality of bi-stable springs can comprise a plurality of stacked bi-stable springs, to adjust a compressive force.

Although the suture handling systems and methods as described herein are presented in the context of a surgeon closing a patient's wound, the systems and methods can be used in any situation involving the handling of suture needles. For example, the systems and methods may be used to safely dispense and dispose of suture needles when the dispensed suture needle is not used to install a suture in a patient. For example, a surgeon may dispense a fresh suture needle, and then decide that he does not want to use the dispensed needle. The surgeon may decide that a needle of a different size would be more appropriate, or that the dispensed needle is not needed after all, for example. The surgeon may accidentally contaminate a freshly dispensed needle before the needle is used (e.g., by touching the tip of the fresh needle against an unsterile surface), and may therefore have to dispose of the needle without using it. A need to attend to another matter may arise after the surgeon has already dispensed a fresh suture needle (e.g., blood splashed on surgeon's gloves necessitating a change of gloves), necessitating the disposal of the fresh needle before it can be used.

As used herein the terms "needle trap" and "needle receptacle" are used interchangeably.

As used herein the terms "shell" and "shell structure" are used interchangeably.

As used herein the terms "panel" and "shell" are used interchangeably.

The present inventors have conducted several experimental studies to determine needle receptacles and barriers that work well in the surgical environment. Several prototypes have been built and tested, and performance metrics measured.

In many instances the needle receptacle is referred to with reference to the receptacle as placed on the volar forearm of the user such as a surgeon. In this regard, the term "distal" may refer to the opening of the needle receptacle that receives the needle from outside the receptacle, and the term "proximal" may refer to the secure zone into which the needle is placed after moving through the distal opening.

The needle receptacle may comprise a front (upper) and back (lower) panel that houses the needles with a secure zone. The needle receptacle may comprise a planar needle slot or groove along which needles are conveyed and within which the needles are housed, partially encased in a parallel, back to back, single layer array, for example. A needle driver slot in the back (lower) panel allows the needle and needle driver to become aligned with the needle slot. The back (lower) needle driver slot can be located distally to the needle slot with an enlarged opening, such that the needle driver can be aligned with the needle slot prior to entry into the needle slot. The experiments of the present inventors have suggested that a back panel landing zone and needle slot having substantially planar configurations may be preferred. For example, the needle slot can be substantially parallel (e.g. generally within about ten degrees) with the front surface of the landing zone, for example coplanar. The inventors have tested a trumpet or funnel shaped landing zone having a tapered concave section, and these experiments indicated that a planar landing zone may provide improved performance. The landing zone can have a distance transverse to the longitudinal axis that defines the width of the landing zone. The maximum distance across of the width of the landing zone can be within a range from about 20 mm to about 60 mm, for example within a range from about 30 mm to about 50 mm. The width of landing zone can taper from the maximum distance to a lesser distance near the needle entry slot, for example adjacent the needle entry slot. The distance across the landing zone near the needle entry slot can be within a range from about 20 mm to about 60 mm, for example within a range from about 20 mm to about 50 mm.

The entry zone of the needle slot can be sized larger than the secure zone of the needle slot. As described herein, the elongate needle channel slot may comprise a first elongate width CW1 near an opening of the needle slot 349, and a second narrower width CW2 within the secure zone of the needle slot. The height of the needle slot above the landing zone can be within a range from about 4-10 mm, for example from about 5-8 mm. The width CW1 can be within a range from about 20 to about 60 mm, for example from about 30 mm to about 50 mm. The entry zone of into the needle receptacle may comprise an upward flare near the edges to provide sufficient clearance for the needle. The upward flare can provide height to the distal opening of the needle slot. The flare can be within a range from about 50 degrees to about 90 degrees relative to the surface of the landing zone. For example, within a range from about 60 degrees to about 80 degrees.

The needle driver slot width is designed to be sufficient to accommodate a needle driver various orientations. The needle driver slot depth of the lower slot is dimensioned to allow protrusion of the needle driver jaws when the needle driver grasps the needle away from the ends.

In accordance with these experiments and contemplated embodiments, the landing zone front face may be substantially planar, and needle slot of the secure zone substantially planar, for example substantially parallel to each other. In some embodiments, the landing zone and needle slot can be substantially parallel with each other. In many embodiments, a plane defined by the landing zone extends through the secure zone of the needle receptacle.

The needle receptacle can suspend the needle/s while protecting the tip and tail end of the needle in a stiff protective container, for example a hard container. The landing zone and secure zone can be arranged to guide the needle and provide tactile feedback to the user.

The needle receptacle may maintain needles along a plane and provides the suspension of the needles such that tip and ends are between the protective stiff cover in front and stiff cover in back, for example hard cover in front and hard cover in back. This can suspend the middle of the needle in air. This configuration allows for counting and allows for access to manipulate and position the needles for counting by visual assessment. The planar orientation can be orthogonal to a user's line of sight when counting and can display the needle in full profile for easy visual assessment. Other planar organization may comprise a needle magnet or a flat adhesive strip, although these do allow for access to the needle, the needle may not be grasp and manipulated as easily.

The thickness of that needle slot in which the needle is housed can be dimensioned appropriately. If the needle slot is too wide, the needle could rotate/twist or come loose. The present inventors have made a limited needle slot groove width between the hard plastic shells and then further reduced this space by using foam compression, which also provides friction component. The arc of the needle can facilitate capture, although straight needles can also be captured. In many embodiments, the needle tip and end are secured within planar recesses such as grooves. Other structures are contemplated and described herein that allow for the suspension or "floating" of the mid portion of the needle, for example in air.

In many embodiments, a slotted structure is configured to allow the tip and tail of the needle to be substantially enclosed while suspending in the slot the mid portion of the needle.

A needle could be contained in the planar recess (Groove) on one end only with the needle tip for instance residing in the longitudinal slot as described herein. The needle tip can be recessed from the frontal surface of the receptacle to provide improved safety.

The lower trap slot can be configured with depth to accommodate the tip of the needle driver that may well extend beyond the needle slot plane. The lower or back slot may comprise a groove of sufficient depth to allow the needle driver to advance the needle along the slot.

The present inventors have conducted experiments to determine suitable amounts of force to advance the needle along the slot or other structure to secure the needle. Structures can be provided to provide a greater amount of force to remove the needle than insert the needle.

While the thickness profile of the needle receptacle can be configured in many ways, the thickness can be less than 2 cm in preferred embodiments, in which the needle receptacle comprises a longitudinal length and a cross-sectional width dimensioned greater than the thickness. The thickness profile can be especially helpful on the volar side of the forearm and other surfaces on the forearm as well. The needle retention device may have a profile above the surface of the barrier of less than 4 cm, for example. The profile can be further reduced by creating a recess in the barrier to accommodate the trap. A cutout can be provided in the barrier, in which the footprint of the cutout corresponds to the trap. Alternatively or in combination when the trap has a solid back wall to the slot and the trap fit with the barrier, the trap can be recessed. The recess may comprise a depth 2 to 5 mm, for example.

The barrier may comprise the receptacle as described herein in order to decrease the profile.

The trap can be configured to facilitate safe handling or transfer between personnel in many ways. The needle landing zone can be used to grasp the needle receptacle. The needle receptacle can be held up to a light source, such that the needles are not obscured by the fingers or hand of the user. The needle receptacle may comprise a material or dye having an orange color, red or other color, for example. The backlight illumination can highlight the profile of the needle when needle visualized through the front face, which can be transparent. The well-defined profile can be helpful for counting, for example by a person or an automated needle counter, such as a video camera coupled to a processor with appropriate software. Any needle receptacle as disclosed herein can be configured with a landing zone that can be used for dual purpose of safe handling and needle placement.

FIG. 309 shows a suture pack 3092 and needle receptacle 3094 coupled to a barrier mounting base 3096. The barrier mounting base comprises a living hinge 3098. A suture pack and a needle receptacle are coupled to the barrier mounting base. The barrier mounting base comprises the living hinge in order to allow the suture pack and needle receptacle to fit onto the barrier on the arm of the surgeon with an angle between a first portion 3096a of the barrier mounting base having the needle receptacle and a second portion 3096b of the barrier mounting base having the suture pack. The first portion of the barrier mounting base and the second portion of the barrier mounting base can be placed on the arm with the living hinge such that they are inclined at an angle with respect to each other. The suture pack and needle receptacle shown with reference to FIG. 309 may comprise many of the structures shown with reference to FIGS. 167 to 179, and a person of ordinary skill in the art will recognize that many of these embodiments are well suited for combination with each other, as well as other embodiments as shown and described herein.

The needle receptacle can be configured with various amounts of resistance in many ways. In many instances, the needle receptacle comprises an amount of force for insertion of the needle and a greater amount of force to remove the needle. The needle receptacle comprises a structure to receive a needle with resistance. The amount of resistance to insertion can be within a range from about 5 grams to 250 grams, for example. The amount of force can be within one or more of the following ranges: about 25 grams to about 100 grams; or about 30 grams to about 90 grams, for example. The needle receptacle may comprise a needle slot, and the amount of force may comprise an amount of force to advance the needle along the needle slot. Alternatively or in combination, the needle receptacle may comprise a needle driver slot, and the amount of force may comprise an amount of force to advance the needle driver along the needle driver slot to secure the needle in the needle slot.

The needle receptacle may be configured to provide an increasing amount of resistance as the needle is advanced along the needle slot. The varying resistance is provided with one or more of a discrete or asymmetric features that protrude into the needle slot, in order to increase compression of the needle and provide tactile feedback as the needle is drawn along the slot.

The needle receptacle may comprise a compressive member configured to secure a needle and provide resistance to movement of the needle against an apposed surface, and wherein the foam structure comprises a gap of less than 2 mm between the foam and the apposed surface.

The needle receptacle comprises a secure zone and can be applied to the forearm and comprises a width of less than 12 cm, and a length of less than 26 cm. The appropriately sized receptacle can be applied to the forearm or a barrier as described herein.

The needle receptacle can also be configured to easily view the needles with various types of illumination. For example, the housing containing the needles may comprise an optically transmissive material. A lower portion of the housing may comprises an optically transmissive material in order to view needles within a secure zone of the receptacle with backlight illumination. Alternatively or in combination, the upper portion may comprise a transparent material to view the needles. The lower portion may comprise a transparent or a translucent material to pass backlight illumination light to the needles. The upper portion may comprise the upper shell, and the lower portion may comprise the lower shell as described herein, for example.

The needle receptacle trap may comprise a landing zone and a secure zone, in which the landing zone is substantially coplanar with the secure zone. The landing zone coplanar with the secure zone can make it easier for a user to place the needles in the trap. The needle can be placed by moving the needle to the landing zone of the needle receptacle and sliding the needle from the landing zone into the secure zone of the needle receptacle.

The needle receptacle may comprise a slotted structure that allows a tip and a tail of the needle to be substantially enclosed while suspending a mid-portion of the needle in the slot.

The needle receptacle may comprise a slot along a secure zone, in which the slot is sized smaller than a finger tip having a size of about 10 mm.

A needle receptacle comprising a needle groove having a thickness small enough to inhibit rotational movement of the needle out of the needle groove.

FIG. 310 shows the needle receptacle as in FIG. 309. FIG. 310 shows a top oblique view of the needle receptacle in a fully assembled configuration. The needle receptacle 3094 is configured to define the direction in which needles are moved to place the needles in the receptacle. The needle receptacle comprises an arrow tip 3101a and an arrow tail 3101b. The arrow tip comprises a generally convexly curved tip in order to define one direction of movement, and the arrow tail comprises a generally concave profile to define the direction of motion. The needle receptacle comprises a top needle driver groove 3102a configured to receive a needle driver holding a needle. The needle receptacle comprises an entry zone 3103 configured for landing of the needle as the surgeon places the needle into the receptacle. The entry zone is sized and shaped to allow the surgeon to place the needle on the entry zone, or land the needle with an arcuate movement of the needle in the needle driver. As the surgeon rotates his or her arm, the needle driver extends with an arcuate motion onto the landing zone and into a secure zone 3104 of the needle trap. The needle trap or receptacle comprises the top needle driver groove 3102a and a bottom needle driver groove 3102b to allow the needle driver to be advanced while the needle enters the secure zone. An elevated flange 3105 extends above the entry zone to receive the needle. The elevated zone defines an entry opening sized larger than the secure zone. The elevated flange guides the needle from the entry zone into the secure zone. The needle receptacle comprises inner protrusions 3106 that engage the needle as the needle is slid along the secure zone toward a needle stop 3107 on a distal end of the receptacle. The needle stop is configured to limit movement of the needle within the secure zone to a most distal portion of the needle receptacle. The inner protrusions may comprise feedback to the user with tactile sensation of the needle with a clicking-type sensation as the needle is drawn into the secure zone to give the user feedback as to the depth of placement into the needle receptacle. Alternatively or in combination, the top needle driver groove and/or the bottom needle driver groove may comprise undulating structures that allow the user to have feedback as the needle driver is advanced along the slot toward the end of the needle secure zone. As the needle driver is drawn along the needle driver grooves and slots, the user is provided feedback by undulation from one side or the other side or both of the needle driver grooves. The lower needle driver slot 3102b comprises an enlarged opening within the landing zone or entry zone, such that the needle driver can be received into the lower needle driver slot as the needle is advanced in the lower needle driver slot comprises a smaller cross-section in the secure zone than in the entry zone. The entry zone of the needle receptacle comprises a bevel 3108 near the arrow tail. The bevel zone facilitates landing of the needle into the entry zone.

The needle receptacle may comprise an upper shell structure and a lower shell structure. The upper shell structure may comprise the top needle driver groove and the undulations in the elevated flange, the needle stop, and a portion of the arrow tip. The lower portion may comprise the entry zone, the lower needle driver slot, the arrow tail, and the bevel. The upper shell structure and the lower shell structure may comprise coupling structures 3109 to couple the upper shell structure with the lower shell structure.

The needle receptacle can be placed on the volar forearm of the user on a barrier as described herein. The needle receptacle can be arranged over the volar forearm to allow easy insertion of a used needle when a hand holding needle holder is slightly supinated or slightly pronated. The needle can be placed in the receptacle with rotation of an arm holding a needle driver with shoulder joint rotation in order to align and place the used needle into an opening of the needle receptacle, for example.

While the needle receptacle can be dimensioned in many ways, the needle receptacle may comprises a longitudinal length, a transverse width and a height. The length may be greater than the width and the height, and the width is greater than the height. The length can be within a range from about 4 cm to about 15 cm, the width is within a range from about 3 cm to about 6 cm, and the height is within a range from about 0.5 cm to about 2 cm, for example. The needle receptacle may comprise an opening to receive the needle, and the opening can be sized larger than the secure zone of the receptacle, such that the opening comprises the maximum height and width of the receptacle.

FIG. 311 shows a top exploded view of the needle receptacle 3094 with needles 3111 coupled to the barrier mounting base 3096. As in FIG. 310, the exploded view shows the top shell structure 3112, needles 3111, a compressive member 3113, a bottom shell structure 3114, an adhesive backing 3115, a barrier mounting base 3096, a living hinge 3098, a suture pack adhesive 3116, and a mounting base adhesive 3117. The compressive member 3113 fits into a recess in the bottom shell structure 3114, and the compressive member may comprise a plurality of compressive members fitting into a plurality of recesses in the bottom shell structure. The compressive member is shown as a first compressive member and a second compressive member disposed on either sides of the needle driver slot. The compressive members urge the needle upward toward the top shell structure, such that the needle engages the top shell in the protrusions of the top shell structure. The compressive member is shown with a generally rounded end near the landing zone or receptacle zone of the bottom shell structure. This rounding of the compressive member or bevel or fillet can facilitate advancement of the needle into the secure zone. The adhesive backing 3115 can be used to couple the bottom shell structure to the barrier mounting base. The adhesive backing may comprise an adhesive on each side of the adhesive backing. The adhesive backing may comprise a plurality of adhesive backings, such as a first adhesive backing and a second adhesive backing disposed on either side of the lower needle driver slot. The bottom shell structure may comprise standoffs on the lower surface, as shown and described in figures herein elsewhere. The adhesive backing positions the bottom shell structure at a distance up above the barrier mounting base, with standoffs on the bottom shell structure to provide the lower needle driver slot sufficient room and depth to receive a needle in the needle driver when the needle is located away from the distal end of the needle driver. The barrier mounting base may comprise a suture pack adhesive 3116. The lower surface of the mounting base may comprise a mounting base adhesive 3117. The barrier mounting base may comprise a first portion 3096a having the needle receptacle placed thereon, and a second portion 3096b having the suture pack adhesive placed thereon, with a living hinge 3098 extending there between. The living hinge allows the first portion and the second portion to be inclined relative to each other when placed on the protective barrier on the forearm of the user.

FIG. 312 shows a bottom exploded view of the needle receptacle 3094 with needles 3111 coupled to the barrier mounting base 3096 as in FIGS. 310 and 311. The top shell structure 3112 of the needle receptacle comprises inner protrusions 3121. The inner protrusions may comprise asymmetric protrusions. For example, the asymmetric protrusions can be shaped such that a needle is more readily advanced into the needle receptacle than drawn from the secure zone of the needle receptacle. The inner protrusions can be sized and shaped in many ways, and may comprise, for example, a ratcheting mechanism one engaged with the needle. The needles engage the compressive member 3113 as the needles are advanced along the receptacle, such that the needles are urged upwards by the compressive members into the inner protrusions. The bottom shell structure 3114 comprises a standout to receive the compressive members and to define the needle driver groove and also to define a recess in which the compressive members are located in the entry zone with the tips of the compressive members deflected downward such that the compressive members do not provide a gap extending upwardly from the entry zone so that the needles can advance smoothly onto the compressive members. The standout may comprise a standout 3122a to receive a compressive member and the standout 3122b for the lower needle drive groove. The upper and lower needle driver grooves extend generally along an elongate axis of the needle receptacle. The standout to receive the compressive member extends generally transverse, for example, perpendicular to the long axis of the needle receptacle. The adhesive backing 3115 is shown disposed on either side of the standout 3122b for the lower needle driver groove. The adhesive backing may comprise a first portion and a second portion, such as a first piece and a second piece. The adhesive backing may comprise a cutout sized and shaped to receive the standout for the compressive member. The barrier mounting base 3096 is shown beneath the adhesive backing that supports the needle receptacle. The barrier mounting base comprises a first portion 3096a supporting the needle receptacle and a second portion 3096b to support the suture pack. The first portion of the barrier mounting base may comprise a plurality of adhesive pads 3123a to support the first portion of the barrier mounting base, and the second portion of the barrier mounting base may comprise a plurality of adhesive pads 3123b. The adhesive pads may comprise a first surface having an adhesive and a second opposite surface having an adhesive. The living hinge 3098 extends between the first portion of the barrier mounting base and the second portion of the barrier mounting base, to allow the first portion of the barrier mounting base and the second portion of the barrier mounting base to be mounted on the protective barrier on the arm at an angle to each other.

FIG. 313 shows a top oblique view of the top shell structure 3112 of the needle receptacle as in FIG. 312. The top shell structure may comprise components as described herein. The top shell structure comprises the upper needle driver groove 3102a and the inner protrusions 3106 and the needle stop 3107 as described herein. The needle protrusions generally face downward as shown in the other views. The upper flange 3105 is shaped to direct the needle driver with the needle toward the needle driver slot or groove on the upper shell structure. The upper flange comprises a first side 3105a and a second side 3105b disposed on opposite sides of the upper needle driver slot. The landing zone end of the first side and second side of the upper flange are inclined at an angle so as to guide the needle driver into the needle driver slot.

FIG. 314 shows a bottom oblique view of the top shell 3112 as in FIG. 313. The top shell structure 3112 comprises the upper needle driver groove 3102a and the inner protrusions 3106 along the lower surface of the upper needle driver slot. The top shell structure also comprises the needle stops 3107 on the lower surface of the top shell structure. The plurality of needle stops is shown on either side of the upper needle driver slot. The inner protrusions are shown symmetrically disposed on each side of the upper needle driver groove. The top shell structure comprises an edge 3141 shaped to engage the bottom shell structure.

FIG. 315 shows a close-up bottom oblique view of the top shell 3112 as in FIG. 314. The plurality of needle stops 3107 are shown symmetrically disposed on either side of the top needle driver slot 3102a. The inner protrusions 3106 are shown symmetrically disposed on either side of the upper needle driver slot. The inner protrusions may comprise asymmetric protrusions. The inner protrusions can be sized and shaped in many ways. For example, the inner protrusions may comprise a ramp with an inclined surface to allow the needle to be advanced toward the needle stop. A second opposite surface of each protrusion may comprise a vertically inclined surface to inhibit movement of the needle away from the needle stop.

FIG. 316 shows a top oblique view of the bottom shell structure 3114 of the needle receptacle as in FIG. 310. The lower needle driver slot or groove 3102b comprises a receiving portion 3161 located within the entry zone 3103. The needle driver slot within the entry zone comprises a cross-sectional dimension sized larger than the lower needle driver slot in the secure zone, in order to facilitate and guide the needle driver into the secure zone. The bottom shell structure comprises filleted recesses 3162 to receive the compressive member. The recesses are dimensioned to urge the needle into the protrusions with the compressive member. The recesses comprise a filleted zone 3163 near the entry zone. The bevel 3108 of the entry zone allows the needle driver to be guided into the needle receptacle. The bottom shell may comprise a raised edge or protrusion 3164 configured to engage the top shell structure to facilitate coupling of the top and bottom shells.

FIG. 317 shows a bottom oblique view of the bottom shell structure 3114 as in FIG. 316. The lower needle driver slot 3102b is shown extending along a long axis of the needle receptacle. Protruding standouts 3122a for the filleted recesses are shown extending transverse, for example perpendicular to the long axis of the needle receptacle. Standouts 3122b for the lower needle driver groove are shown extending along the long axis defined with the needle driver slot. The standouts extend a distance from the surface of the bottom shell structure in order to dimension the lower needle driver slot in the fillets of the recess that receives the compressive member. The standouts for the lower needle driver slot are dimensioned to allow the needle driver sufficient clearance to advance easily along the lower needle driver slot when the needle has been engaged away from the proximal end of the needle driver. The standouts for the filleted recesses extend a distance from the lower surface of the bottom shelf in order for the compressive members to be flush with the entry zone or beneath the entry zone along the upper surface of the compressive member. This configuration of the standout for the filleted recess and the compressive member allows the compressive member to gradually urge the needle upward into the upper shell structure as the needle is advanced toward the stops on the proximal end of the needle receptacle. The standouts for the filleted recesses are symmetrically disposed on either side of the lower needle driver slot. The standouts for the lower needle driver groove are symmetrically arranged on either side of the lower needle driver slot. The standouts for the lower needle driver groove may extend across the midline of the bottom shell structure. The standout for the lower needle driver groove may comprise a curved surface on either end defining the ends of the lower needle driver slot. The standout for the lower needle driver groove may comprise a single standout or plurality of standouts arranged to position in dimension the lower needle driver slot to allow the needle driver to be advanced along the lower needle driver slot when the suture is positioned away from the proximal end of the needle.

FIG. 318 shows a top oblique view of the bottom shell structure 3114 as in FIG. 317 with compressive members 3113 placed thereon. The compressive members are shown disposed on either side of the lower needle driver slot 3102b. The compressive members can be symmetrically disposed on either side of the lower needle driver slot. The compressive members comprise filleted or beveled ends 3181 that extend down into the recess of the lower shell structure. The upper surfaces of the compressive members extend down to the height of the entry zone such that the proximal most ends of the compressive members are the height below the entry zone or flush with the entry zone in order to facilitate movement of the needles toward the needle stop on the proximal end of the receptacle. The inner surfaces 3182 of the compressive members towards the needle driver slot are approximately flush with the needle driver slot. This positioning of the inner surfaces of the compressive members allows the compressive members to engage the needle in the needle receptacle when the needle extends only a little bit into the receptacle from the slot. The inner surfaces of the compressive members are generally positioned within about 2 millimeters, for example, within about 1 millimeter of the lower needle driver slot of the bottom shell structure. This arrangement of the inner surfaces of the compressive members insures that the compressive members engage the needle when advanced into the secure zone.

The compressive members are dimensioned to allow the needle to be readily advanced into the secure zone with decreased amounts of resistance. In this regard the cross-sectional dimensions of the compressive members are sized to provide appropriate amounts of resistance. For example, the compressive members may not extend fully outward toward the full width of the bottom shell structure. The compressive members comprise a generally cross-sectional shape having a rectangle. The rectangular shape of the cross-section may comprise a height and a width from with the height is dimensioned to urge the needle upward toward the upper shell structure and the width dimensioned with the cross-section to provide appropriate amounts of resistance. The wider the compressive member the greater the amount of force to the needle. The narrower the compressive member the less the force.

FIG. 319 shows a longitudinal cross-sectional view of the top and bottom shell structure as in FIG. 310 without the compressive members. The asymmetric inter-protrusions 3106 are shown on the top shell structure 3112. Although these protrusions are shown as asymmetric the protrusions can be symmetrical, for example defined with bumps such as spherical surfaces. The inter-protrusions are shown with an inclined surface that engages the needle as the needle is advanced toward the stop and a vertically extending surface or substantially vertically extending surface on the proximal side of the protrusion to inhibit movement of the needle away from the stop. The filleted recess 3162 to receive the compressive member is shown with a curved surface extending downward toward the lower surface of the bottom shell structure 3114. The filleted recess alternatively may comprise a bevel or plurality of segmented linear surfaces. The recess extends downwardly away from the upper shell structure to receive the compressive member as describe herein.

FIG. 320 shows the fully assembled needle receptacle 3094 with the needle 3111 in a transverse cross-sectional view for the needle receptacle as shown in FIG. 310. The needle 3111 is shown positioned between the upper shell structure 3112 and the lower shell structure 3114. The trailing end 3111a of the needle after the suture has been popped off is also shown. The top shell structure is shown coupled to the bottom shell structure and can be adhered to the bottom shell with adhesive. The top shell and the bottom shell comprise engagement structures 3109 for the top shell to engage the bottom shell with the adhesive. The engagement structures may comprise grooves or protrusions on the top shell and bottom shell such that the bottom shell and the top shell are easily positioned together with the adhesive.

FIG. 321 shows advancement of the needle 3111 positioned into the needle receptacle 3094 as in FIG. 310. The needle is shown to advance into the needle receptacle with a movement that is approximately parallel to the barrier in the user as shown with the arrow 3212.

FIG. 322A shows a top oblique view and FIG. 322B shows a cross-sectional view of the needle 3111 stabilized in the needle receptacle 3094. The lower slot 3102b is shown and the upper slot 3102a is shown with the needle positioned between the upper shell 3112 and the lower shell 3114. The needle stabilizer 3221 may comprise the compressive members and/or the protrusions as described herein.

FIG. 323 shows dimensions of the needle receptacle 3094 as in FIG. 310. The needle receptacle comprises a cross-sectional dimension of the needle driver slot that is shown with dimension A. The user has a finger with the dimension across as shown with dimension B. The dimension across the slot is less than the dimension of the finger of the user. For example, the user may have a typical finger size greater than 10 millimeters across and the dimension of the slot receiving the needle driver on the upper shell may be less than 10 millimeters for example. The landing zone or entry zone of the needle receptacle is generally dimensioned so that the user can easily grasp the needle receptacle with a finger as shown in FIG. 323 away from the area where the needles are securely stored. The entry or landing zone may comprise a flange portion of the lower shell which allows the user to grasp and handle the needle receptacle safely.

FIGS. 324A and 324B show a needle containment groove 3241 defined with a U-shaped housing 3242 having a slot to secure needles, which may comprise some of the structures shown in FIG. 310, such as the needle driver slot 3243 to receive needles on upper and lower portions of the housing. Alternatively or in combination, the housing may comprise a single-piece housing formed of materials such as silicone. The needle containment groove 3241 is dimensioned to receive the needle and the needle driver slot 3243 is dimensioned to receive the needle driver on the upper and lower surfaces. The needle receptacle 3240 comprises the length extending along the needle driver slot and a width extending transverse to the needle driver slot. The needle receptacle also comprises a thickness 3244 as shown in FIG. 324B. The thickness is generally less than about 1 centimeter. The needle receptacle may comprise a U-shaped piece for example. The needle slot may defined with inner grooves on legs of the U-shaped piece, and the grooves may comprise a thickness of no more than about 1 cm, for example. The needle driver slot can be no more than about 2 cm, for example.

The receptacle can be sized to a range of needles, and may comprise a smaller slot for smaller needle drivers, in which the slot comprises a width of no more than a diameter of a largest needle for which the trap is designed to store.

The longitudinal slot for the needle driver may comprise a through and through slot, in which the slot extends though both sides of the receptacle.

The longitudinal slot may comprise a lower solid wall, in which the wall has a recess or groove of sufficient depth to allow the tip of the needle driver to protrude beyond the needle securement slot plane, in which the needle driver groove or slot extends beneath the needle slot plane by a distance within a range from about 0.1 mm to about 10 mm.

The receptacle may comprise a longitudinal slot bounded by a structure to one or more sides of the slot that creates a varying resistance to translation as the needle is drawn along the slot. The varying resistance can be provided in many ways, and may comprise a discrete or asymmetric features that protrude into the needle slot, in order to increase compression of the needle and provide tactile feedback as the needle is drawn along the slot FIGS. 325A-325C show needles placed in a needle receptacle 3240 as in FIG. 324A. FIG. 325A is a top view, FIG. 325B is an end view, and FIG. 325C is a side cross-sectional view of the needle receptacle 3240 holding the needles 3251. The needles are shown extending at various locations across the needle driver slot 3243. The grooved sides 3252 of the needle receptacle safely contain the needles and cover the tips. The upper view of FIG. 325A shows the needles visible to the user. The needles are shown extending across the needle driver slots such that the needles can be counted. The end view of FIG. 325B shows the grooved sides 3252 containing the tips of the needles. The side cross-sectional view of FIG. 325C shows the needles placed in the needle receptacle.

FIGS. 326A-326D show needles placed in a needle receptacle as described herein, for example, with reference to FIGS. 310 and 324. FIG. 326A shows an oblique view, FIG. 326B a side view, FIG. 326C a top view, and FIG. 326D an end view. The needles 3261 are shown contained within a groove 3262 of the needle receptacle. The needle receptacle may comprise walls 3263 such as the upper and lower surfaces of the shells as described herein. The needles are contained between the walls in a secured configuration such that the needle tips are covered. The needles are shown in a planer array arranged in a groove. The longitudinal slot of the receptacle facilitates an organized deposition of the needles in the secure zone between walls of the needle receptacle.

FIG. 327A shows ratcheting 3271 along the groove of the needle driver slot 3272 for example with reference to FIGS. 310 and 324. The ratcheted slot 3272 allows the user to sense the depth at which the needles are being placed along the needle driver slot. The needle driver slot may contain many types of protrusions or undulations along the side of the slot to provide the user with tactile feedback and sensation as the needle driver is advanced toward the stop on the proximal end. This feedback to the user allows the user to position the needles with gross motor skills and to provide a sense of the depth of the needle within the slot. The ratcheted slot may comprise a defined surface such that the needle driver is more easily advanced toward the end of the slot and away from the end of the slot. Although the needle driver slot may be dimensioned larger than the needle driver, the user generally will be guided by the needle driver slot such that the needle driver engages one or both sides of the slot as the needle driver is advanced toward the end of the slot. The sliding movement of the needle driver along the slot can provide a sensation of vibration or varying drag or ratcheting as the needle driver is moved along the slot. The inclined ratcheting surface may comprise a first side for the entry zone which is inclined at an angle and a second side that faces the stop that is inclined at a greater angle away from the axis to inhibit movement of the needle driver away from the end of the slot.

The inner surfaces of the needle driver slot can be configured in many ways to provide the user with feedback as the needle driver is being advanced toward the proximal end. For example, one or more of the upper shell or the lower shell may comprise undulating surface structures or protruding surface structures to provide this feedback. For example, small dimples can be provided in one or more of the upper slot or the lower slot to provide the user with tactile feedback. The protrusions and/or recesses provided along the inner surfaces of the needle driver slot are generally symmetrically arranged along either side of the needle driver slot to provide the user with a sense of depth within the slot as the needle is advanced. While the size of the structures that are used can be varied in many ways, in many embodiments the structures generally extend inwardly toward the needle driver slot at least about a quarter of a millimeter, for example at least a millimeter and generally within a range for about a $\frac{1}{10}$ of a millimeter to about a millimeter on either side of the needle driver slot.

FIG. 327B shows varied apertures 3273 along the needle driver slot 3272. The varied apertures generally comprise a concave surface and a tip oriented toward the needle driver slot. As the needle driver is guided by the needle driver slot, the needle driver will generally engage one or both surfaces. As the needle driver is advanced toward the stop on the end, the needle driver provides tactile feedback to the user as the needle driver moves along the concave portions and the tip portion of the needle driver slot. The surface structures provided along the inner surface of the needle driver slot can be provided on the upper needle driver slot or the lower needle driver slot or both. When the structures are provided on both the upper needle driver slot and the lower needle driver slot, structures are generally aligned in order to provide the user feedback as the needle driver is advanced.

FIGS. 328 to 333 show a chiral barrier in accordance with embodiments.

FIG. 328 shows a chiral barrier 3280 for placement on the left forearm of the surgeon. While the barrier can be formed in many ways, work in relationship to embodiment suggests that the chiral barrier customized for a left forearm can be preferred. It is contemplated that barriers for the left forearm for right-handed surgeons can be provided and barriers for the right forearm for left-handed surgeons can be provided. The chiral barrier has the advantage of providing better fit to a plurality of left-handed users and a plurality of right-handed users. Although reference is made to a chiral barrier, it is contemplated that the barrier can be symmetric and used on either arm. For example, the barrier may comprise a conic section with conic ends having a pre-form conic shape, or can be chiral as described herein. The barrier comprises a volar edge on a volar side 3281 and a dorsal edge on a dorsal side 3282. The volar edge can separate from the dorsal edge when advanced over the forearm for placement.

Referring again to FIG. 328, the chiral barrier comprises a dorsal side 3282 and a ventral or volar side 3281, a proximal end 3283 and a distal end 3284. The proximal end is located toward the elbow of the user, and the distal end is oriented toward the wrist of the user. The chiral barrier comprises a plurality of tabs such as proximal tab 3285a and a distal tab 3285*b*. The plurality of tabs may be located on either the dorsal edge or the volar edge. The barrier may comprise a pre-formed material such as a thermally formed material. The preformed material may comprise a sheet of material having substantially uniform thickness pre-formed thermoforming to desired shape to accommodate anatomical structures of the user. For example, the barrier may comprise shaping to accommodate musculature near the elbow of the user and wrist movement and wrist anatomy in the wrist of the user. The chiral shape can be customized with respect to a left arm for a right-handed user in order to better accommodate the musculature of the proximal forearm and the wrist movement of the distal forearm. The barrier may comprise a barrier material as described herein in order to inhibit penetration or sticks with sharp objects such as needles.

The chiral barrier can be located along a coordinate reference system, in which the origin corresponds to a central point 3321 of the proximal forearm. The +X direction extends toward the volar side of the forearm; the +Y direction extends in a direction toward the radius of the forearm; and the −Z axis extends toward the distal end of the forearm near the wrist.

FIG. 329 shows a top plan view of the barrier 3280 of FIG. 328 prior to thermal forming. The barrier comprises a proximal ergonomic end profile 3286 on the proximal end 3283. The proximal end generally comprises convexly curved surfaces near the corners of the barrier on opposite sides and in generally tapered decreased length toward the center of the barrier for example to accommodate musculature and flexing of the forearm toward the biceps of the user. The distal end 3284 of the barrier may comprise may comprise an ergonomic distal end profile 3287. The distal end profile may comprise curved corners near the ends of the barrier. The ergonomic distal end profile may be shaped to provide a decreased length of the barrier toward the wrist of the user. The decreased length of the barrier toward the distal end near the wrist of the user can allow the user to flex and extend the wrist with decreased contact on the distal end profile. In use the barrier may tend to move toward the wrist of the user and the distal end profile having the shape shown in FIG. 329 can provide improved comfort by appropriately contouring to the forearm near the wrist. The barrier may comprise a length extending between the proximal end and the distal end and the length of the barrier can vary with location around the forearm of the user. The ergonomic proximal end profile and the ergonomic distal end profile can be arranged such that the length of the barrier is decreased between the ergonomic distal end profile and the ergonomic proximal end profile in relation to the corner sections or ends of the barrier displaced laterally away from the ergonomic inner portion of the barrier. For example, the radial ridge length 3299 along the radial ridge aspect 3289 of the barrier may be shorter than the volar length 3291 along the volar aspect 3281 and the dorsal length 3292 along the dorsal aspect 3282 of the barrier. The ergonomic proximal end profile 3286 and/or the distal end profile 8287 may comprise radial ridge indicia 3293 and 3294 along the radial ridge aspect 3289.

The barrier comprises proximal tabs 3285*a* and distal tabs 3285*b* configured to allow the user an ergonomic fit. The proximal tab comprises the proximal tab length 3288*a* and the distal tab comprises the distal tab length 3288*b*. The distal tab length is generally shorter than the proximal tab length to provide improved comfort. The distal tab length generally comprises a length that is within a range from about 20% to about 80% of the proximal tab length. The proximal tab may comprise a length within a range of about ½ inch to about 2 inches for example. The barrier may comprise one or more tab couplings 3295 for securing the barrier about the arm of the user. For example, the proximal tab and/or the distal tab, extending from the dorsal aspect 3282 of the barrier, may comprise one or more tab couplings configured to engage corresponding tab couplings disposed at the volar aspect 3281 of the barrier.

FIG. 330 shows axes of the pre-formed barrier 3280. The barrier is generally pre-formed with a self-supporting sheath as shown in FIG. 328. The pre-formed barrier with the self-supporting sheath will generally assume the shape shown in FIG. 328. The memory of the barrier allows the barrier to fit well on many users. It allows the barrier to be stretched slightly in order to fit a user. The barrier can be provided with straps as described herein.

The barrier generally comprises a generally elliptical cross-section in the preformed shape on the proximal end 3283 and it also comprises a generally elliptical shape on the distal end 3284. Although reference is made to an elliptical shape, the shape may comprise non-elliptical shapes having the first dimension across longer than the second dimension across perpendicular to the first dimension across. For example, the shape may correspond to an oblong shape along one dimension or an egg shaped profile for example.

FIG. 330 shows primary axes for the proximal and distal portions in the self-supporting shape of the barrier. The primary axis refers to the axis having the longest length of the cross-section of the barrier. A secondary proximal axis 3303*b* extends generally perpendicular to the primary proximal axis 3303*a*. On the distal end the primary axis 3304*a* extends along the longest dimension of the cross-section of the pre-formed self-supporting barrier. A secondary axis 3304*b* extends perpendicular to the primary axis and may correspond to the shortest dimension of the cross-section through a center of the cross-section.

The self-supporting barrier may comprise a primary axis 3303*a* having a substantially vertical orientation on the proximal end and a primary axis 3304*a* on the distal end rotated relative to the primary axis within an angle α as shown in FIG. 330. This rotation of the distal primary axis relative to the proximal primary axis provides improved comfort to the user.

A person of ordinary skill and art will recognize that various adaptations can be made of the self-supporting thermal-formed barrier as shown in FIGS. 330 and 328. For example, the barrier may comprise a generally conic shape such that the primary end has a substantially circular cross-section and the distal end has a substantially circular cross-section in which the distal end has a substantially circular cross-section in which the distal end has a diameter less than the proximal end.

The inventors have conducted experiments with many shapes of pre-formed barriers and determined that the chiral barrier as shown with reference to FIGS. 330, 328 and 329 provides improved comfort. Although the barrier can be provided with foam and foam can provide improved comfort, the inventors have determined that the chiral barrier as described herein provides improved comfort when used with foam or without foam. The foam lining provided on the inner surface can provide improved comfort and can allow sizing to many shapes of users.

FIG. 331 shows a view from the proximal end 3283 of the barrier 3280 toward the distal end 3284 of the barrier. As can be seen with reference to FIG. 331, the proximal end comprises a generally oval shape having a longest dimension across and a shortest dimension across in which both dimensions extend through the center of the proximal end. The distal end similarly comprises an oval shape having a maximum dimension across along the primary axis and a shorter dimension across along a secondary axis orthogonal to the primary axis. The primary axis of the distal end is shown rotated to the primary axis of the proximal end. This rotation of the primary axis of the distal end in relation to the primary axis of the proximal end can help the user orient the wrist in an ergonomic position during surgery which can last for several hours.

FIG. 332 schematically illustrates structures of chiral barrier 3280. The proximal end 3283 of the barrier comprises a primary (long) axis 3303a and a secondary (short axis) 3303b having a length that is shorter than the primary axis. The distal end 3284 of the barrier comprises a primary (long) axis 3304a and a secondary (short) axis 3304b. The long axis 3304a on the distal end is rotated relative to the long axis 3303a of the proximal end. The rotation angle can be within a range from about 5 to 45 degrees, for example within a range from about 10 degrees to about 30 degrees, and can be 20 degrees, for example.

The distal end can also be offset relative to an axis of the proximal end. A path can extend from the center 3321 of the proximal end 3283 to the center 3322 of the distal end 3284. The path can be defined with the center of the barrier at locations between the proximal end and the distal end. As the forearm comprises musculature and other chiral structures, the shape profile of the forearm may comprise chirality. The chiral barrier is shaped to generally correspond to the chirality of the forearm. The center points of the forearm define a curved chiral path 3323 extending between the elbow and the wrist. At the proximal end, the barrier is shaped to correspond to the shape of the forearm and the curved central path of the forearm. The proximal end of the forearm can be defined with a plane extending perpendicular to the path corresponding to the center of the forearm. The plane defines a z-axis 3324 orthogonal to the cross-section through the forearm at the proximal end. The barrier is shaped similarly to the forearm. The proximal cross-section of the barrier comprises a central point 3322 and a plane 3325 that extends substantially perpendicular to the barrier surface on the proximal end. The z-axis 33224 from the center point of the barrier on the proximal end can be projected to the distal end. The inventors have learned that the distal end is offset from this projection of the z-axis by an extending between the proximal end and the distal end. The center of the forearm can be placed between the proximal end and the distal end. The offset can be within a range from about 0.25 inches to about 0.75 inches, for example.

FIG. 333 shows outer surface profiles 3326 of the barrier 3280 and the curved path 3323 of the center of the barrier. The profile of the barrier along the dorsal and volar aspects are shown. As the volar aspect of the forearm may comprise greater amounts of muscle mass than the dorsal aspect of the forearm, the barrier may comprise greater amounts of taper on the volar aspect of the forearm than the dorsal aspect. The curved path comprising the center of the barrier can extend in relation to changing muscle mass of the forearm.

The barrier comprises a shape memory material as described herein, which may comprise a thermoformed material. The thermoformed barrier material comprises a free standing self-supporting configuration with the geometrical features as shown in FIGS. 328, 330-333, for example.

As noted above with reference to FIG. 328, the coordinate reference can be defined as:

+X=volar aspect
+Y=radial aspect
Distal offset can be (8 mm, 20 mm)=(x,y)
Range from (0.2, 0.4) to about (2 cm, 4 cm) for example.

X offset (volar) can be within a range from about 0.2 cm to about 2 cm, for example within a range from about 0.5 cm to about 1.5 cm. They offset (radial) can be within a range from about 0.4 to 4 cm, for example within a range from about 0.8 cm to about 3 cm. Although offsets are described, these are optional and in some embodiments the preformed barrier may comprise no offset, while still being chiral, for example with rotations of the long axes on the ends of the barrier as described herein.

The barrier as described herein can be configured with or without chirality.

The barrier can be configured with a shape memory material as described herein, and configured with force characteristics suitable for placement on the forearm of the user. The barrier comprises a volar edge on a volar side and a dorsal edge on a dorsal side. The volar edge can separate from the dorsal edge when advanced over the forearm for placement. An amount of force to separate the volar edge from the dorsal by about one inch from a free standing configuration can be within a range from about 25 grams to about 400 grams, for example. The range can be from about 50 grams to about 150 grams, for example. The masses provide correspond to the amount of force to separate based on the force of gravity, which will be readily understood by a person of ordinary skill in the art.

The barrier may comprise a mass within a range from 10 grams to about 250 grams, for example within a range from about 20 grams to about 75 grams. The barrier may comprise a preformed thermoplastic shell having a weight within a range from about 20 grams to about 60 grams, for example.

The barrier may comprise foam on an underlying surface beneath the shell. The weight of the barrier with foam can be within a range from about 35 grams to about 500 grams. The weight of the barrier with foam can be a range from 20 grams to about 260 grams, for example within a range from about 20 grams to about 85 grams. The barrier may comprise a preformed thermoplastic shell and foam beneath having a weight within a range from about 30 grams to about 70 grams, for example.

The barrier may comprise a weight as described herein and the weight of the barrier can be less than the amount of force required to separate the volar and distal ends for placement on the forearm of the user.

The barrier may comprise a longitudinal length within a range from about 6 inches to about 11 inches. The barrier may comprise a ratio of the distance across the proximal end to the distance across the distal end within a range from about 1.1 to about 1.5.

The barrier may comprise a shell wherein an underlying foam extends distally beyond the distal border of a shell of the barrier and wherein the foam curves over a leading distal edge of the shell to pad the interface of the shell when the barrier impinges on the wrist to provide comfort.

The barrier may comprise a shell having a radial curvature at a distal edge of shell with displacement within a range from about 3 mm to 1.5 cm to distribute a load of the barrier on a wrist of a user.

The barrier may comprise a shell, and inner foam padding may extend beyond distal edge of the shell. The foam layer can extend beyond a distal end of the shell by a distance within a range from about 1 mm to about 15 mm. The inner foam layer may comprise a thickness within a range from about 1 mm to about 15 mm.

The barrier may comprise a thickened distal edge.

The barrier can be configured to distribute a load when device abuts the dorsal or radial or volar aspect of the wrist with motion of the wrist.

The barrier can be configured to allow movement of proximal or distal ends of the barrier so as to allow greater amounts of movement of the wrist of the user relative to the barrier. For example, the barrier may comprise extensions on the proximal end that allow the barrier to be substantially fixed in relation to the proximal forearm of the user. Alternatively the barrier can be tighter on the proximal strap than the distal strap in order to allow the user's distal forearm to move more than the proximal forearm in relation to the barrier.

The barrier can be configured to couple to the proximal forearm in order to move with the proximal forearm more than the distal forearm. For example, the barrier may comprise a distal strap that can be tightened more than the proximal strap, in order to allow the barrier to move with rotation of the wrist of the user, for example.

The barrier can comprise a layer of padding on the bottom and a layer of mechanical barrier on the top, with magnets placed on the undersurface of the mechanical barrier between layer of padding and the layer of mechanical barrier. The mechanical barrier can comprise a polymer material, and can have a thickness in the range of about 0.5 mm to about 5 mm.

FIGS. 334A-334C illustrate the use of a needle handling system as described herein. FIG. 334A shows a user U, such as a surgeon, securing a needle 3341 within a needle receptacle 3342 mounted on a barrier 3343 coupled to the forearm VF of the user's non-dominant arm, as described herein. As shown, the needle receptacle is disposed on the plane of the volar forearm VF. To secure the needle in the needle receptacle, the user sweeps the needle, grasped with a needle driver 3344, from a distal position to a proximal position along the plane of the volar arm. Therefore, the needle is not directed towards the arm, and the risk of needle stick injury is minimized. FIG. 334B is a schematic illustration of the top view of the user U as the user secures the needle 3341 in the barrier-mounted needle receptacle 3342. The anatomical neutral plane NP of the user's arm is shown with respect to the coronal plane CP, wherein the anatomical neutral plane is substantially orthogonal to the coronal plane. Securing a needle in the forearm-mounted needle receptacle does not require external rotation 3345a of the arm or shoulders with respect to the anatomical neutral plane, therefore allowing the user to engage only fine motor control, rather than gross motor control, to perform movements related to the dispensing and securing of needles. To secure the needle in the needle receptacle, the user can internally rotate 3345b the forearm F from the elbow E while holding the needle in the needle driver 3344, therefore sweeping the needle along an arc 3346 directed from the anatomical neutral plane NP towards the needle receptacle plane 3347. The needle receptacle plane can be substantially parallel to the plane of the volar forearm carrying the barrier-mounted needle receptacle. FIG. 334C schematically illustrates the path of the needle during securement in the needle receptacle 3342. The needle moves proximally along the needle arc 3346 towards the needle receptacle plane 3347. The needle arc can comprise a substantially flat portion 3348 defined as a portion of the arc that coincides with the needle receptacle plane or is within a small angle α with respect to the needle receptacle plane, for example within about 10°. The needle receptacle may be positioned such that its length 33421 substantially corresponds to the length 33481 of the substantially flat portion. Thus, when the needle reaches the substantially flat portion of the arc as the user sweeps the needle along the arc towards the needle receptacle, the needle can reach the entry zone of the needle receptacle and be secured within the secure zone of the needle receptacle.

FIG. 335 illustrates an exemplary embodiment of a needle receptacle 3350 comprising a cover 3351 for the needle driver slot 3352. A needle driver slot cover may provide an additional safety feature by more securely enclosing the ends of the needle 3353 within the needle receptacle, and preventing the accidental dislodging of a needle placed within the secure zone 3354. The needle receptacle may be any needle receptacle as described herein that comprises a slot or a groove 3352 within which a needle driver may be moved while the needle grasped by the needle driver is secured in the needle receptacle. The needle driver slot cover 3351 can comprise a flexible strip with a slit 3355 going through a portion of the flexible strip covering the needle driver slot. Alternatively, the needle driver slot cover can comprise opposed overlapping flexible strips covering the needle driver slot, such that the needle driver can move through the slot between the overlapping strips. The flexible strip can elastically deform 3356 to accommodate translation of the needle from the entry zone 3358 to the secure zone 3354 via translation of the needle driver tip 3357 within the needle driver slot. FIG. 336 illustrates another exemplary embodiment of a needle receptacle 3360 comprising a cover 3361 for the needle driver slot 3362. The needle driver slot cover may comprise flexible strips as described with reference to FIG. 335. In addition to a longitudinal slit 3363 to allow translation of the needle driver therein, the cover may further comprise a plurality of vertical or transverse slits 3364. The vertical slits can create a plurality of vertical segments 3365, wherein the needle driver moves through the vertical segments as it is translated along the needle driver slot. The vertical segments may be coupled to the needle receptacle at the bases 3366 substantially parallel to the longitudinal sides of the needle driver slot. For any embodiment of a needle driver slot cover comprising flexible strips, the strips may be transparent and comprise silicone or polyethylene, for example.

FIGS. 337A-337D illustrate another exemplary embodiment of a needle receptacle 3370 comprising a cover 3371 for the needle driver slot 3372. FIG. 337A shows the top view, FIG. 337B shows the end view, FIG. 337C shows the side view, and FIG. 337D shows the bottom view of the needle receptacle. As shown in FIG. 337A, the needle driver slot cover 3371 is positioned over the needle driver slot or groove 3372. In the default or "closed" configuration, the cover substantially covers the needle driver slot. When a needle driver is translated along the needle driver slot, the cover may be configured to slide along the longitudinal needle driver slot axis 3373 (in the direction shown by the arrow 3374) to expose the needle driver slot, thereby allowing the needle driver to secure a needle within the secure zone 3375. When the needle driver exits the needle driver slot, the cover may be configured to slide back to resume the default closed configuration. The needle driver slot cover may be configured to slide by translating within one or more rails 3376 parallel to the needle driver slot axis. As shown in FIGS. 337B and 337D, the one or more rails 3376 may comprise grooves in the bottom shell 3377 or housing of the needle receptacle, wherein the needle driver slot cover can fit into the grooves to couple to the bottom shell. The grooves may extend through the end of the bottom shell, to allow the cover to translate towards the secure zone 3375 to the full extent possible. As shown in FIGS. 337C and 337D, a spring 3378 may be mounted under the bottom shell and coupled to the needle driver slot cover. The spring 3378 can constrain the translation of the cover away from the entry zone 3379 as the needle driver translates along the needle driver slot towards the secure zone 3375, and pull the cover back towards the entry zone to the closed position after the needle driver exits the needle driver slot.

FIG. 338 illustrates an exemplary embodiment of a needle receptacle 3380 comprising a compressive cover 3381 for the needle driver slot 3382. The needle receptacle, which may be any receptacle as described herein comprising a needle driver slot, may comprise a needle driver slot cover configured to slide along a vertical axis 3383 that is substantially orthogonal to the longitudinal axis 3384 of the needle driver slot. In the default or "closed" configuration, the cover may be covering the needle driver slot, such that the needles disposed within the secure zone are substantially covered. The cover may be configured to slide up when a needle driver translates along the needle driver slot to secure a needle, and return to the default "closed" configuration when the needle driver exits the needle driver slot. For example, the cover may comprise a mechanism similar to the spring mechanism described with reference to the embodiment of FIGS. 337A-337D. In this configuration, the needle driver slot cover can compressively push the ends of the needles disposed within the secure zone 3385 downwards into the opposite longitudinal edge of the needle receptacle housing, thereby further securing the needles inside the receptacle. Such a configuration may be particularly useful for the securing of small needles, since small needles may have some freedom of movement even when secured within the secure zone. Compressively pushing the needles downwards against the needle receptacle housing can help ensure that the ends of the needles are contained within the receptacle housing.

FIG. 339 illustrates another exemplary embodiment of a needle receptacle 3390 comprising a compressive cover 3391 for the needle driver slot 3392. The needle driver slot cover can comprise a foam strip 3393 mounted laterally above the needle driver slot. The foam strip may function as a spring member, providing downward compression in the vertical axis 3394 substantially orthogonal to the longitudinal axis 3395 of the needle driver slot. In the default or "closed" configuration, the foam strip covers the needle driver slot. When a needle driver enters the needle driver slot and begins to translate along the slot, the foam strip may be compressed upwards along the vertical axis to allow the needle driver to translate along the slot. When the needle driver exits the slot, the cover can spring back to the default configuration, compressively pushing the needles 3397 disposed in the receptacle downwards into the opposite longitudinal edge of the receptacle housing. The lower edge of the foam strip may further be lined with a rigid material 3396, such as a plastic strip, in order to facilitate the application of the downwards compressive force to the needles, particularly when the cover is in contact with and compressively pushing against the tips of the needles.

FIGS. 340A-340C illustrate another exemplary embodiment of a needle receptacle 3400 comprising a compressive cover 3401 for the needle driver slot 3402. FIG. 340A shows an exploded view, FIG. 340B shows an oblique view, and FIG. 340C shows a top view of the needle receptacle. As shown in FIG. 340A, the needle receptacle 3400 may comprise a bottom shell or housing 3403 having a planar needle slot 3404 to receive one or more needles N, and an upper cover 3405 coupled to the bottom shell and configured to contain the needles within the planar needle slot. The upper cover may comprise a transparent material to allow a user to view the needles secured within the needle receptacle. The bottom shell may comprise a needle driver slot 3402 to allow translation of the needle driver therein. The bottom shell may further comprise a filleted recess 3406 to receive a first compressive member 3407 such as a foam strip, configured to compress the needle disposed in the planar needle slot against the upper cover to secure the needle within the needle receptacle, as described herein. The bottom shell may further comprise a lead-in chamfer 3408 to guide the needle, grasped by the needle driver, into the plane of the needle slot. Additionally, the bottom shell may comprise a mounting surface 3409 for the compressive needle driver slot cover, the mounting surface comprising an upper longitudinal edge of the needle driver slot. The compressive needle driver slot cover 3401 may comprise a compressive member such as a foam strip 3401f mounted to the mounting surface, laterally above the needle driver slot. The foam strip may be lined with a rigid material (e.g., plastic strip 3401p) at the bottom edge to further facilitate the application of the downward compressive force to the needle tip. As shown in FIG. 340C, the compressive needle driver slot cover can provide downward compressive force CF along a vertical axis substantially orthogonal to the longitudinal axis 34021 of the needle driver slot, so as to push the needles disposed in the planar needle slot downwards against the opposite longitudinal edge 3403e of the bottom shell. In use, the compressive member may be displaced by translation of the needle driver along the needle driver slot, and upon removal of the needle driver compressively push the needles downward against the longitudinal edge of the bottom shell opposite the mounting surface. The configuration as shown in FIGS. 340A-340C can further improve safety of the needle receptacle by ensuring that the sharp ends of the needles disposed within the needle receptacle do not protrude through the needle driver slot, and by increasing the needle surface area that is in contact with the first compressive member configured to secure the needle within the needle receptacle.

FIGS. 341A-341C illustrate exemplary embodiments of a backlit needle receptacle. FIG. 341A shows a needle receptacle 3410a that is lit from one longitudinal end of the needle receptacle. The body of the needle receptacle, such as the top and/or bottom shell of the needle receptacle as described herein, may be optically coupled to a light source, such as one or more optical fibers 3411 or light-emitting diodes (LEDs). The needle receptacle body 3412 may comprise a light guide, configured to transmit light 3413 from the light source throughout the body of the needle receptacle via total internal reflection. For example, the needle receptacle body may comprise one or more optical grade materials such as acrylic resin, polycarbonate, or epoxy. FIG. 341B shows a top view and FIG. 341C shows a side view of a needle receptacle 3410b that is lit from the bottom side 3414 of the needle receptacle. The bottom side of the bottom shell of the needle receptacle may be optically coupled to a light source, such as one or more LEDs 3415 or optical fibers. The body 3412 of the needle receptacle, such as the top and/or bottom shell, may comprise a light guide configured to transmit light 3416 from the LEDs throughout the needle receptacle body. A backlit needle receptacle as shown in FIGS. 341A-341C may help the user visualize the needle receptacle or parts thereof (e.g., needle driver slot), thereby facilitating the securing of needles N within the needle receptacle. In addition, a backlit needle receptacle can facilitate user counting of needles N secured within the receptacle.

Figure 342A:
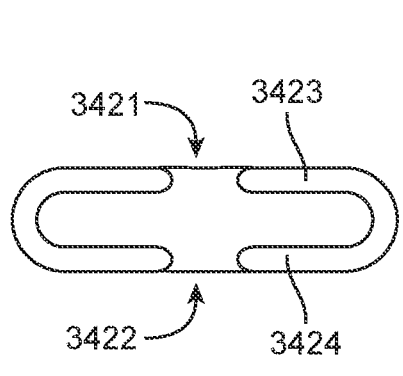
Figure 342B:
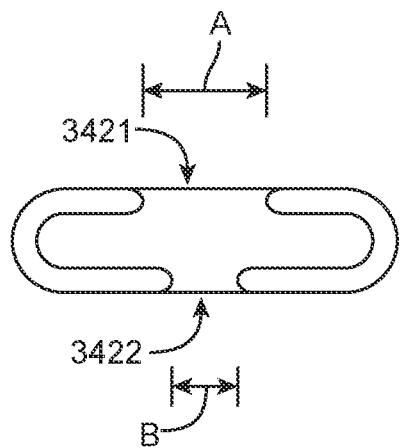
Figure 342C:
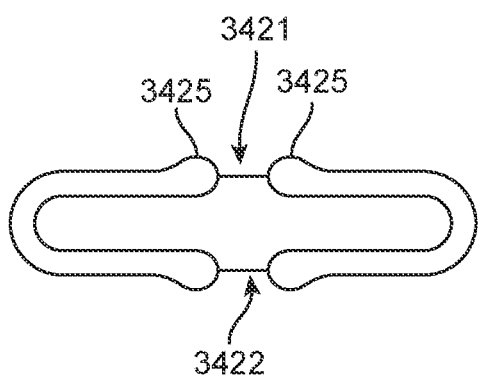
Figure 342D:
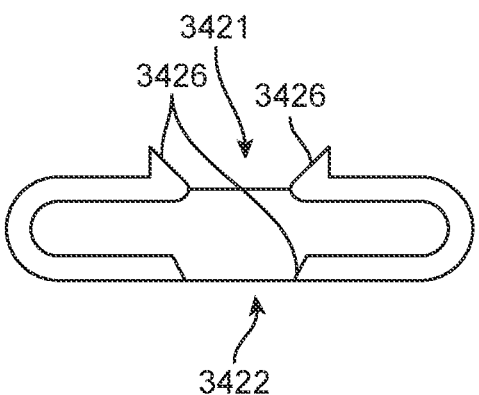
Figure 342E:
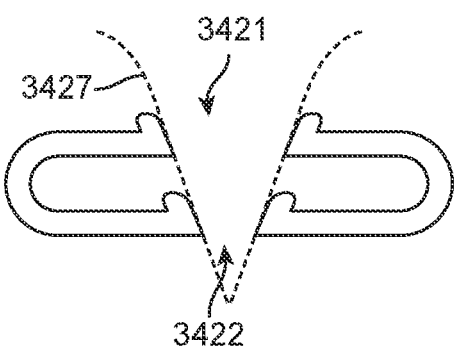
Figure 342F:
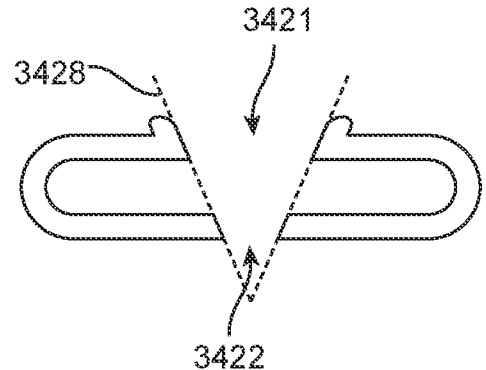

FIGS. 342A-342E schematically illustrate various configurations of a needle driver slot of a needle receptacle. As described herein, a needle receptacle may comprise a needle driver slot or groove to allow the translation of a needle driver within the slot while the needle is secured in the needle receptacle. The needle driver slot often comprises an upper groove in a top shell of the needle receptacle and a corresponding lower groove in a bottom shell of the needle receptacle. FIG. 342A shows a needle driver slot configuration wherein the upper groove 3421 and the lower groove 3422 are uniform. The plane of the top shell 3423 may be parallel to the plane of the bottom shell 3424, and the upper groove and the lower groove may be aligned in position. FIG. 342B shows a needle driver slot configuration wherein the upper groove 3421 has a larger width A than the width B of the lower groove 3422. Such a configuration can help conform to the shape of the needle driver tip, which often narrows in width at the tip. FIG. 342C shows a needle driver slot configuration wherein the walls of the upper 3421 and lower grooves 3422 are rounded or radiused. The rounded walls 3425 of the upper and lower grooves may help improve the receipt of the needle driver tip within the needle driver slot. FIG. 342D shows a needle driver slot wherein the walls of the upper 3421 and lower grooves 3422 are beveled 3426 to better conform with the dimensions of the needle driver tip. FIG. 342E shows a needle driver slot wherein the walls of the upper 3421 and lower grooves 3422 are curved to form a subsection of a prolonged curving plane, such that the cross-sectional profile of the needle driver slot comprises a curved v-shape 3427. FIG. 342F shows a needle driver slot wherein the walls of the upper 3421 and lower grooves 3422 are angular and collinear, such that the cross sectional profile of the needle driver slot comprises a v-shape 3428. The various configurations of the needle driver slot can help improve the conformation of the needle driver slot to the shape of the needle driver tip, thereby facilitating the insertion of the needle driver tip into the needle drive slot and improving the stability of translation of the needle driver tip within the needle driver slot during securement of the needle.

Figure 343A:
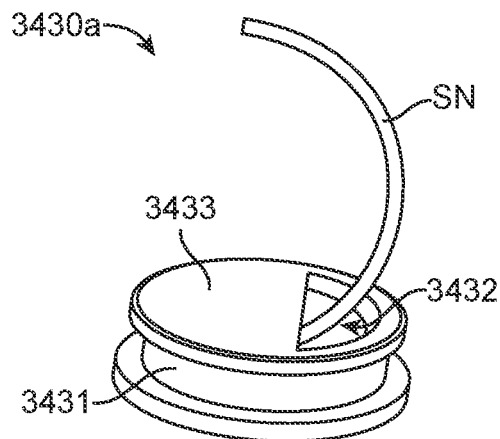
Figure 343B:
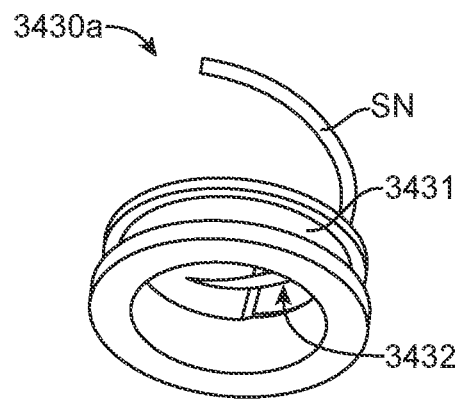
Figure 343C:
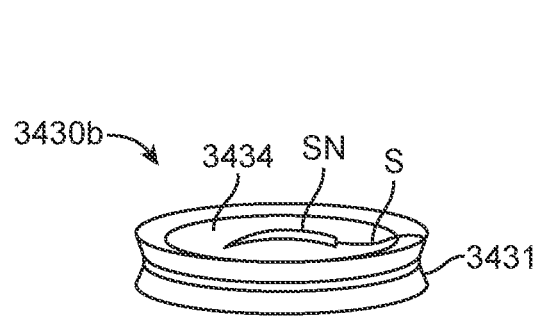
Figure 343D:
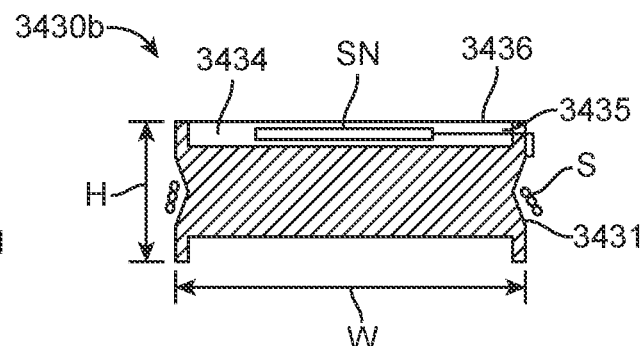

FIGS. 343A-343G illustrate exemplary embodiments of a swaged needle device for dispensing and securing a swaged needle. Swaged needles SN with a running suture S can be used for repeated passage of a needle with the same suture thread in closing an incision. The swaged needle device can be provided in a similar manner as described herein for a suture package and a needle receptacle, for example mounted to a barrier coupled to a forearm of a surgeon. A swaged needle device comprises one or more swaged on needles with an attached running suture, coupled to the device such that the tip or leading end of the needle is rendered innocuous. As shown in FIGS. 343A and 343B, a swaged needle device 3430*a* can comprise a spindle 3431 for the suture to be wrapped around, and an opening 3432 on a top surface 3433 of the device for securing the needle. The spindle may comprise a side wall with a lateral groove and/or lateral borders or protruding edges at the top and bottom edges of the spindle, to securely hold the suture wrapped around the side wall. The swaged needle may be securely coupled to the opening via one of various means such as a magnetic coupling between the needle and the top surface of the device, or a foam member disposed below the top surface and configured to receive the tip of the needle inserted through the opening. FIGS. 343C and 343D show an oblique view and a side cross-sectional view of a swaged needle device 3430*b* comprising a spindle 3431 and a top container 3434 for the swaged needle SN. The suture S attached to the swaged needle can be wrapped around the spindle, wherein the spindle can be fixed or configured to rotate to dispense the suture. The top container can comprise a recessed region 3435 at the top surface of the device within which the swaged needle may be placed, and a cover 3436 configured to cover the recessed region so as to secure the needle within the recessed region. Preferably, a swaged needle device has a low profile of about 0.3 mm to about 1.5 cm in height H, and a width W or diameter of about 1.5 cm to about 8 cm.

Figure 343E:
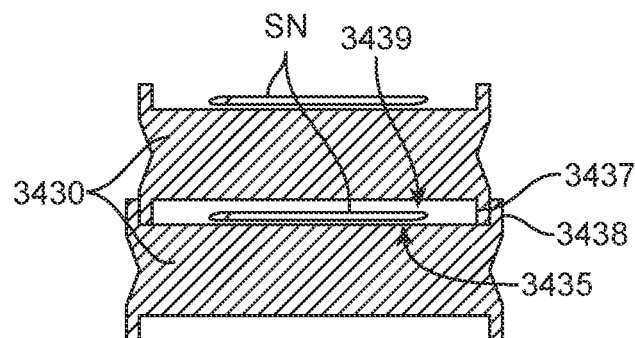
Figure 343F:
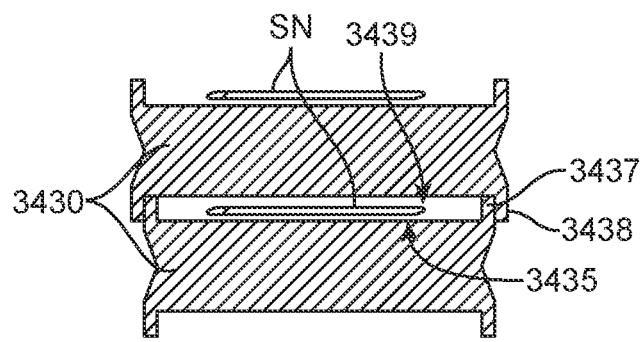
Figure 343G:
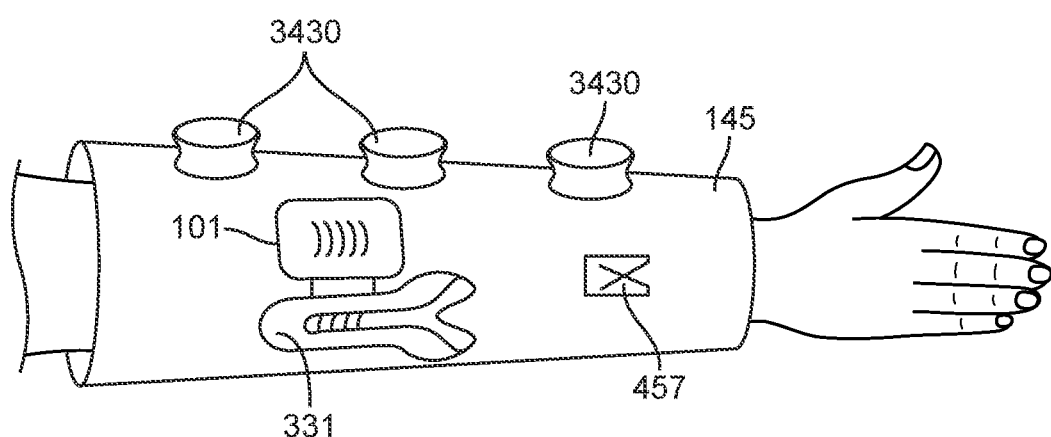

A swaged needle device as described herein may be stackable with another swaged needle device. For example, as shown in FIG. 343E, the bottom portion 3437 of each swaged needle device 3430 may be configured to nest within the top portion 3438 of another swaged needle device 3430, such as a recessed region 3435 in the top surface of the device for containing the swaged needle. Alternatively, as shown in FIG. 343F, the top portion 3438 of each swaged needle device 3430 may be configured to nest within the bottom portion 3437 of another swaged needle device 3430, such as a recessed region in the bottom surface of the device. In the stacked configuration, the needle SN may be disposed within a nesting region 3439 between two stacked swaged needle devices. In embodiments of the swaged needle device comprising a top container for the needle with a cover 3436, the cover may also be configured to nest within the nesting region. Two stacked swaged needle devices may be coupled to one another via one or more of a clip, magnetic coupling, velcro, or removable adhesives. Alternatively, a plurality of swaged needle devices may also couple to one another as a side-by-side array, or as overlapping series of spindle devices. In use, a swaged needle device 3430 may be coupled to a forearm barrier 145 as described herein, as shown in FIG. 343G. The swaged needle device may be coupled to the barrier via a velcro attachment, magnetic coupling, or a removable adhesive, for example. A surgeon may remove a sterile swaged needle from a swaged needle device, use the needle with the running suture to close an incision, and secure the used needle within the swaged needle device. As shown, a plurality of swaged needle devices may be provided on the barrier, wherein the plurality of swaged needle devices may comprise devices providing swaged needles of different sizes. A swaged needle device may comprise a stack of a plurality of swaged needle devices as described herein. As shown, the barrier may additionally support one or more suture packages 101 containing needles coupled to pop-off sutures, and one or more needle receptacles 331 for securing dispensed/used needles. The barrier may therefore provide a surgeon with an array of suture needle options including swaged and pop-off suture needles, wherein the array can be readily customized to fit a particular surgeon's needs. To facilitate cutting of running sutures by the surgeon, the barrier may be additionally provided with a suture cutter 457 as described herein.

As described herein, a needle receptacle may be coupled to a distal end of a surgical tool, such as forceps, for the securing of needles by a surgeon within the near surgical field without requiring the passing of needles out of the near surgical field. A tool-mounted needle receptacle may be particularly well-suited for the securing of small needles. The tool-mounted needle receptacle can be configured to removably couple to various surgical tools without requiring the use of coupling tools (e.g., screwdrivers). A tool-mounted needle receptacle may be configured to couple to a range of surgical tool sizes, for example via an elastic cap that fits onto the distal ends of tools of various sizes. In use, one or more suture packs containing suture needles with pop-off sutures may be supported by the surgeon on a non-dominant hand, wrist, or arm, as described herein. The tool-mounted needle receptacle may be coupled to the distal end of a tool held by the surgeon with the surgeon's non-dominant hand. The surgeon may dispense a suture needle from the suture pack, install the suture, and secure the used needle in the tool-mounted needle receptacle, using the surgeon's dominant hand. Preferably, a tool-mounted needle receptacle is configured to support at least 5 suture needles, in order to accommodate the minimum number of needles provided in a single suture pack. Ideally, a tool-mounted needle receptacle is symmetric for left and right hand use.

FIGS. 344A-344C illustrate an exemplary embodiment of a tool-mounted needle receptacle 3440. FIG. 344A shows a front view, FIG. 344B shows a rear view, and FIG. 344C shows an exploded view of the tool-mounted needle receptacle 3440. The tool-mounted needle receptacle comprises a housing 3441 configured to secure one or more needles N therein, a tool-mounting interface 3442 to couple the housing to a surgical tool, and a coupling mechanism 3443 to couple the housing to the tool-mounting interface. As shown in the exploded view of FIG. 344C, the housing can comprise a front shell 3441a and a rear shell 3441b configured to couple together to form an enclosure for the needles. The front shell may comprise a needle driver slot 3444 configured to allow translation of a needle driver tip therein, as described herein with respect to various embodiments of a needle receptacle comprising a planar needle slot and configured to be supported on a barrier. The housing can further comprise an elastomeric member 3445 also comprising a needle driver slot, coupled to an interior surface of the front shell such that the needle driver slots of the front shell and the elastomeric member are aligned. The elastomeric member may comprise a material such as a silicone, configured to partially cover the needle driver slot of the front shell to reduce the risk of having needle ends exposed through the needle driver slot. The housing can further comprise a rigid backing 3446 and a compressive member 3447 (e.g., a piece of foam) configured to exert a compressive force into the rigid backing when the housing is fully assembled. In use, the needle receptacle may be coupled to a tool held in the non-dominant hand of a user, with the needle driver slot facing the opposite (dominant) hand of the user. A needle driver holding a needle in the mid-body portion of the needle can be placed at the entry zone 3448 of the receptacle and inserted along the needle driver slot, placing the needle in the planar needle slot formed between the compressive member and the backing. The compressive member can compress during translation of the needle driver in the needle driver slot, and when the needle driver exits the needle driver slot, can compressively push the backing into the elastomeric member, thereby securing the needle in the secure zone 3449 within the planar needle slot between the rigid backing and the elastomeric member. The tool-mounted needle receptacle may be mounted on a surgical tool via the tool-mounting interface, which may comprise an elastomeric cap configured to fit onto the distal ends of various tools within a range of sizes. The tool-mounting interface may comprise surface features 3442f such as a plurality of protrusions to facilitate gripping and coupling of the tool-mounted needle receptacle to a tool. The rear shell may comprise the coupling mechanism configured to couple the housing the tool-mounting interface, wherein the coupling mechanism may comprise a protrusion configured to engage a corresponding cavity of the tool-mounting interface. One or more components of the housing may comprise a transparent material to allow visualization of needles secured within the receptacle.

Figure 345A:
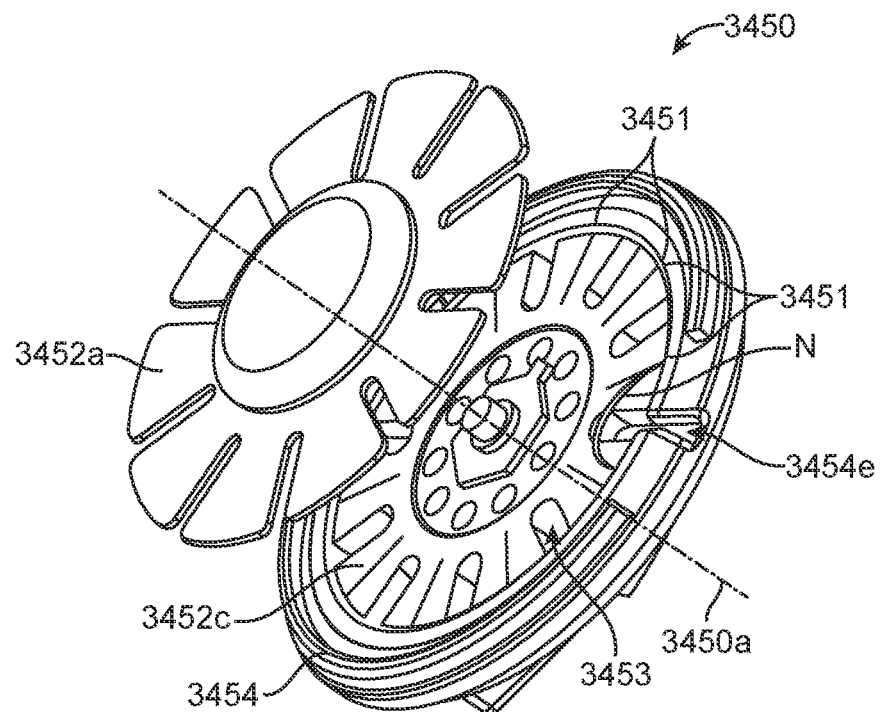

FIGS. 345A-345D illustrate another exemplary embodiment of a tool-mounted needle receptacle 3450. As shown in FIG. 345A, the tool-mounted needle receptacle 3450 comprises a circular array of cells 3451 each configured to contain a needle N. A needle may be captured between a cover 3452a and a compressive member 3452c to secure the needle within the cell. Each cell may comprise a needle driver slot 3453 extending radially inwards from the outer edge of the cell, the needle driver slot configured to allow a needle driver holding a needle to be inserted into and translated radially inwards along the needle driver slot to secure the needle in the needle receptacle. As best shown in the exploded view of FIG. 345B, the needle receptacle may comprise a cover 3452a, a compressive member 3452c, and a backing 3452d, wherein a needle can be configured to be placed between the compressive member and the cover, such that the compressive member pushes the needle against the cover to secure the needle within the cell. The cover, compressive member, and backing may be coupled together in a fixed alignment to form a rotatable assembly 3452, wherein the needle driver slots of each component is aligned with the needle driver slots of the other components. For example, the compressive member may be adhesively coupled to the backing, and the compressive member/backing assembly may be coupled to the cover via a central hinge 3452b configured to space the cover from the compressive member/backing assembly at a sufficient clearance to accommodate a thickness of a needle. The needle receptacle may further comprise a housing 3454, wherein the rotatable assembly can be coupled to the housing via the central hinge 3452b so as to allow rotation of the rotatable assembly about the central axis 3450a of the needle receptacle. The needle receptacle may further comprise a tool-mounting interface 3455 similar to the tool-mounting interface described in reference to the embodiment of FIGS. 344A-344C. The tool mounting interface may be coupled to the housing via a coupling mechanism 3456, such as a protrusion 3456a of the housing configured to engage a cavity of the tool-mounting interface, with an optional coupling member 3456b configured to secure the coupling between the protrusion and the cavity. The cover may comprise a transparent material to allow visualization of needles secured within the needle receptacle. The cover and/or the backing may comprise an elastomeric material to allow for translation of the needle driver along the needle driver slot while keeping the width of the needle driver slot minimal, to decrease the risk that needle ends may be exposed through the needle driver slot.

Figure 345B:
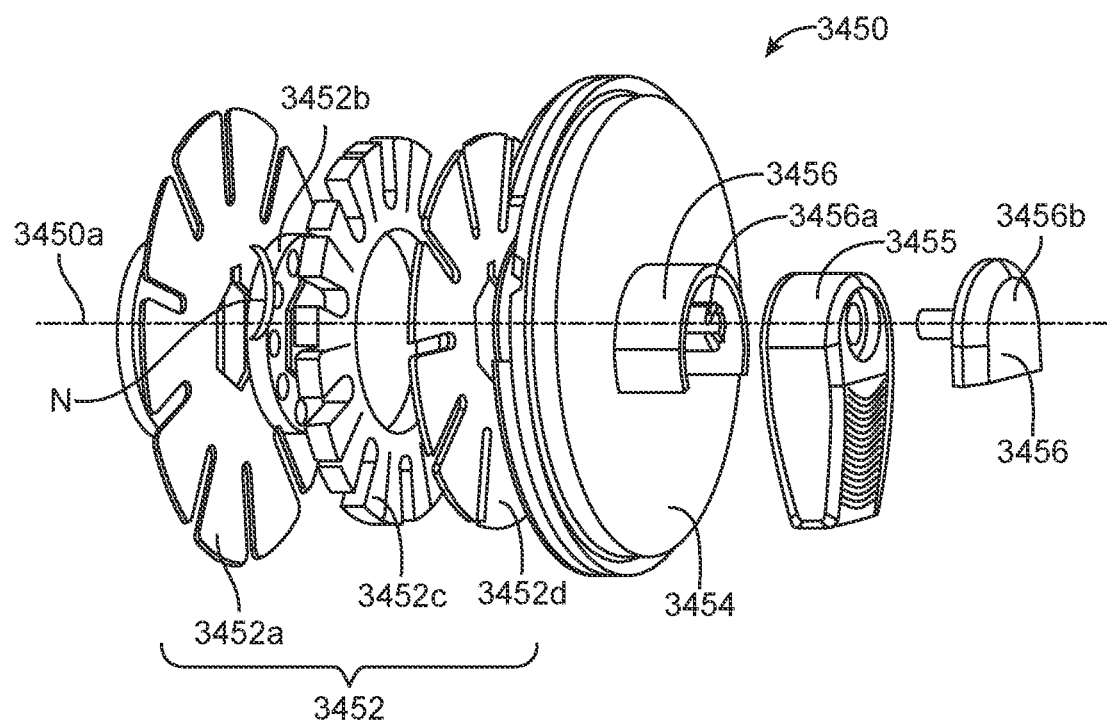
Figure 345C:
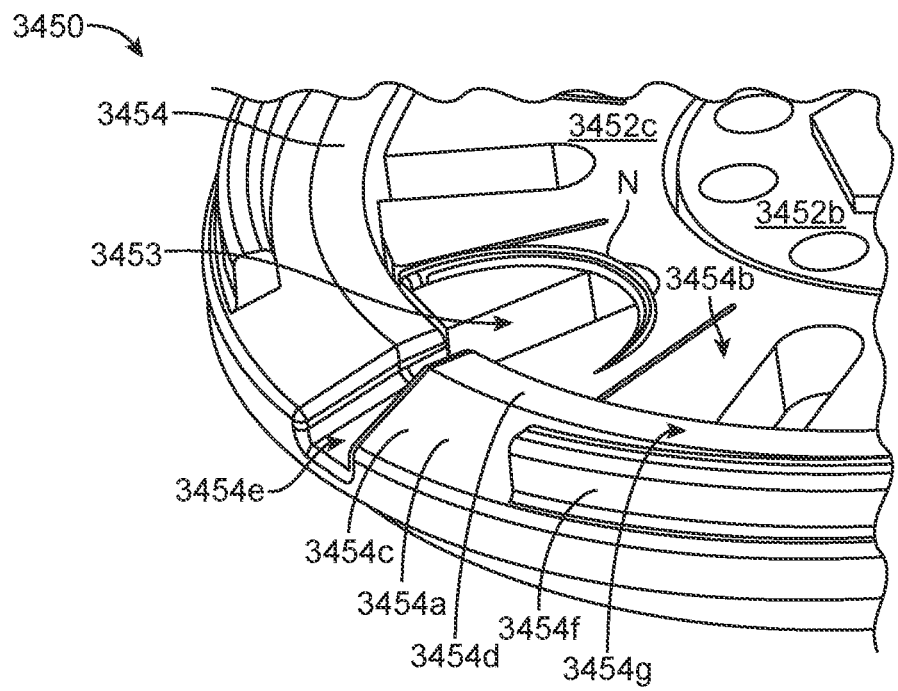
Figure 345D:
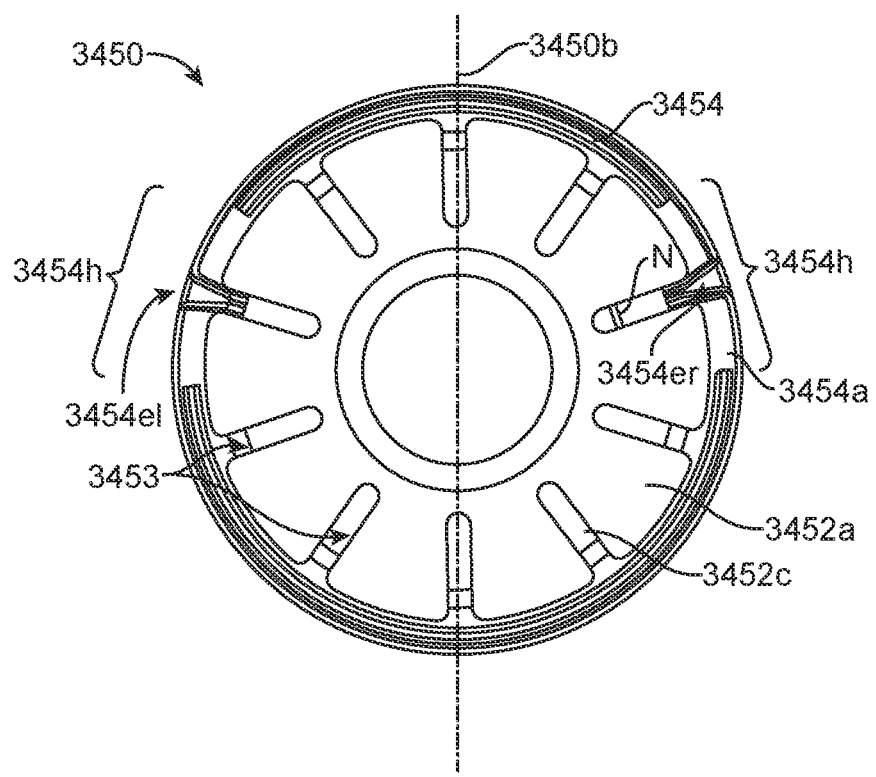

As best seen in the close-up view of FIG. 345C, the housing 3454 may comprise a first raised edge 3454a extending along its circumference, the first raised edge forming a first circular recess 3454b of the housing within which the backing and the compressive member may be nested. The first raised edge may comprise a bevel 3454c and a substantially flat portion 3454d, wherein the substantially flat portion can be configured to be flush with the top surface of the compressive member, and the bevel can be configured to facilitate the insertion of the needle driver in the needle driver slot. The housing may further comprise at least one notch 3454e extending radially through the first raised edge, configured to allow insertion of a needle driver tip therethrough. Preferably, the housing comprises two notches disposed opposite from one another across the vertical axis 3450b as shown in FIG. 345D, wherein one is a left hand notch 3454e1 configured to accommodate a left-handed user and the other a right hand notch 3454er configured to accommodate a right-handed user. The housing may further comprise a second raised edge 3454f protruding from the first raised edge about the periphery of the housing, wherein the cover may be configured to nest within the second circular recess 3454g formed by the second raised edge. As best shown in FIG. 345D, the second raised edge may have a clearing or break 3454h extending on either side of a notch 3454e, the length of the clearing corresponding to the length of the outer edge of an individual cell. The clearing can help a user identify the cell currently available for access, and facilitate location of the needle driver slot. As shown in FIG. 345B, the cover may have a larger diameter than the compressive member and the backing, and accordingly, the second circular recess accommodating the cover may have a larger diameter than the first circular recess accommodating the compressive member/backing assembly. The slightly larger diameter of the cover can help improve safety by preventing a secured needle from potentially escaping the cell through the gap between the compressive member and the first raised edge of the housing.

In use, the tool-mounted needle receptacle may be coupled to a tool held in the non-dominant hand of a user with the rotatable assembly facing the opposite (dominant) hand of the user. The notch of the housing may be aligned with a needle driver slot of an unoccupied cell of the rotatable assembly. To secure a needle, the user may align the tip of a needle driver holding the needle with the notch of the housing, and translate the needle driver radially inwards along the needle driver slot to place the needle within the cell, between the compressive member and the cover. The user may then release the needle from the needle driver, and rotate the rotatable assembly to align the notch of the housing with the needle driver slot of the next unoccupied cell in the rotatable assembly. For example, the user may push the needle driver upwards or downwards against the needle driver slot to rotate the rotatable assembly about the central axis via the central hinge.

In many embodiments, the present disclosure provides systems and devices for securing one or more needles. The systems devices for securing one or more needles described herein can be used to secure used needles (e.g., serve as a needle receptacle), used to dispense unused needles (e.g., serve as a suture package), or combinations thereof.

In many embodiments, the systems and devices provided herein utilize one or more clips to physically secure a needle or other sharp surgical instrument. A clip can include any device used to hold an object at a certain position and/or orientation relative to the clip and/or another object. For example, a clip can be used to hold one or more needles in place within a needle receptacle or suture package so as to prevent the needle(s) from falling out or becoming dislodged. A clip can constrain the movement of the object, e.g., with respect to up to six degrees of freedom of movement such that the object cannot move relative to the clip and/or another object. Optionally, a clip can constrain movement of the object along certain directions while permitting movement along other directions. In many embodiments, a clip is configured to compress an inserted object or portion(s) thereof in order to secure the physically object. The compressive forces can be applied using a spring or other flexible element that is sufficiently compliant to permit insertion of the object into the clip and sufficiently stiff to secure the object in place.

FIG. 346 illustrates an exemplary embodiment of a device 3460 for securing a plurality of needles, in accordance with many embodiments. The device 3460 can be used to secure used needles, unused needles, or combinations thereof. In many embodiments, the device 3460 includes a plurality of clips 3461 each used to secure a respective needle 3462. Each clip 3461 includes a first arm portion 3463a and a second arm portion 3463b joined to each other via a base portion 3464. The first arm portion 3463a and second arm portion 3463b can each include a respective slot 3465a, 3465b shaped to receive a respective portion of an inserted needle 3462. The first and second arm portions 3463a, 3463b can be arranged such that when the needle 3462 is inserted into the clip 343a, the ends of the needle 3462 are securely enclosed within the slots 3465a, 3465b of the first and second portions 3463a, 3463b. Accordingly, when the needle 3462 is placed within the clip 3461, there are no exposed ends that could potentially injure a user. The clip 3461 can be formed from and/or include spring materials that apply compressive force against the ends of the needle 3462 within the slots 3465a, 3465b in order to secure the needle 3462 in place.

Optionally, the first arm portion 3463a and second arm portion 3463b can be spaced apart from each other so as to form a gap 3466 between the first and second arm portions 3463a, 3463b, such that a middle portion of the needle 3462 is exposed. In such embodiments, the received needle 3462 is secured only at its ends and not at its middle portion. The size of the gap 3466 can be selected based on geometry (e.g., length and/or curvature) of the needle 3462 in order to ensure that the ends of the needle 3462 will not protrude from the first and second arm portions 3463a, 3463b. The gap 3466 can be used to accommodate the tip of a needle driver or other instrument for inserting the needle 3462 into the clip 3461 and/or removing the needle 3462 from the clip 3461.

The device 3460 can include any suitable number of clips, such as one, two, three, four, five, six, seven, eight, nine, ten, or more clips. The clips can be arranged in a linear array along a longitudinal axis of the device 3460 so as to form a rack of clips. The plurality of clips can be integrally formed with each other so as to form a single continuous device. Alternatively, the clips can be removably coupled so as to permit adjustments to the size of the device 3460.

FIGS. 347A-347D illustrate an exemplary embodiment of a device 3470 for securing a plurality of needles, in accordance with many embodiments. FIG. 347A illustrates a top view, FIG. 347B illustrates a side view, FIG. 347C illustrates a front view, and FIG. 347D illustrates a back view. The device 3470 includes a plurality of clips 3471 arranged in a linear array and each used to secure a respective needle 3472. The clips 3471 of the device 3470 can be similar to the clips 3432 of the device 3430.

In many embodiments, the device 3470 is used to dispense unused needles as well as secure used needles, without requiring distinctly separate sections for each needle type. Used and unused needles can be differentiated from each other based their orientation within the device 3470. For example, an unused needle 3473 can be positioned within the device 3470 in a "concave down" configuration with the ends of the needle 3473 pointing downwards, as shown in FIG. 347D. This configuration can facilitate grasping of the exposed arched middle portion of the needle 3473 by a needle driver. A used needle 3474 can be positioned in the device 3470 in a "concave up" configuration with the ends of the needle 3474 pointing upwards, as shown in FIG. 347C. Unused needles 3473 can be dispensed from clips at the back section 3475 of the device 3470, while used needles 3474 can be secured using clips at the front section 3476 of the device 3470, or vice-versa. Optionally, the back section of the device 3470 can be closed, e.g., by a back wall 3477.

FIGS. 348A-B illustrate an exemplary embodiment of a device 3480 for securing a plurality of needles, in accordance with many embodiments. FIG. 348A illustrates a top view and FIG. 348B illustrates a cross-sectional side view. Each needle 3481 is secured by a respective clip assembly 3482 including a first clip 3483a and a second clip 3483b. The first clip 3483a and second clip 3483b each include a respective slot 3484a, 3484b shaped to receive a respective end of the needle 3481. The clips 3483a, 3483b can be formed from and/or include spring materials that apply compressive force against the ends of the needle 3481 within the slots 3484a, 3484b in order to secure the needle 3432 in place without any exposed ends. The first clip 3483a and second clip 3483b are arranged with the openings of the slots 3484a, 3484b facing each other such that the needle 3481 can be inserted into the clip assembly 3482 along a direction substantially parallel to the plane of the device 3480.

Optionally, the first clip 3483a and second clip 3483b can be spaced apart from each other so as to form a gap 3485 between the first and second clips 3483a, 3483b, such that a middle portion of the needle 3481 is exposed. In such embodiments, the received needle 3481 is secured only at its ends and not at its middle portion. The size of the gap 3485 can be selected based on the geometry (e.g., length and/or curvature) of the needle 3481 in order to ensure that the ends of the needle 3481 will not protrude from the first and second clips 3483a, 3483b.

By providing a plurality of such clip assemblies, the device 3480 can be used to hold a plurality of needles in a planar array. The device 3480 can include any suitable number of clip assemblies, such as one, two, three, four, five, six, seven, eight, nine, ten, or more clip assemblies. The clip assemblies can be arranged in a linear array along a longitudinal axis of the device 3481 so as to form a rack of clip assemblies. The plurality of clip assemblies can be integrally formed with each other so as to form a single continuous device. Alternatively, the clip assemblies can be removably coupled so as to permit adjustments to the size of the device 3480.

FIGS. 349A-B illustrate an exemplary embodiment of a device 3490 for securing a plurality of needles, in accordance with many embodiments. FIG. 349A illustrates an oblique top view and FIG. 349B illustrates a cross-sectional side view. The device 3490 includes a housing 3491 defining an elongate slot 3492 for receiving and securing one or more needles 3493. The slot 3492 includes a first slot portion 3494a and a second slot portion 3494b shaped to receive respective portions (e.g., ends) of the needle 3493. The portions of the housing 3491 surrounding the first and second slot portions 3494a, 3494b can be formed from and/or include spring materials that apply compressive force to the ends of the needle 3493, such that the housing 3491 itself serves as a "clip" for physically securing the needle 3493. Optionally, in embodiments where the needle 3493 is carrying a suture, the trailing portion of the suture 3497 can also be received within the housing 3491, or carried within a flexible multislot tube or ribbon coupled to the housing 3491.

In many embodiments, the slot 3492 extends to the upper surface of the housing 3491 so as to define an elongate opening 3495 is formed along the length of the housing 3491. Optionally, the slot 3492 can extend below the plane of the needle 3493 towards the bottom surface of the housing 3491. As can be seen in FIG. 349B, the positioning of the opening 3495 results in the needle 3493 being secured within the housing 3491 by its ends, while the middle portion of the needle 3493 is exposed. The geometry of the slot 3492 permits insertion of a needle driver tip into the housing 3491 in order to grasp the exposed middle portion of the needle 3493, e.g., to remove an unused needle or to insert a used needle. For example, a used needle can be secured by aligning the needle and needle driver with the slot 3492, sliding the needle into the slot 3492 along the direction indicated by arrow 3496, then releasing the needle from the needle driver when the desired position has been reached. As another example, an unused needle can be removed from the device 3490 by inserting the tip of the needle driver into the opening 3495, grasping the exposed middle portion of the needle with the needle driver, then sliding the needle within the slot 3492 along the direction indicated by the arrow 3496 and out of the housing 3491. Advantageously, this embodiment permits securing and/or dispensing of needles without opening or closing the housing 3491, thus improving ease of use.

FIGS. 350A-B illustrate an exemplary embodiment of a device 3500 for securing a plurality of needles, in accordance with many embodiments. FIG. 350A illustrates a top view and FIG. 350B illustrates a side view. The device 3500 includes a u-shaped housing 3501 including a first arm portion 3502a and a second arm portion 3502b. Each arm portion includes a slot 3503 extending along the length of the arm portion. The first and second arm portions 3502a, 3502b can be arranged such that when a needle 3504 is inserted into the housing 3501, the ends of the needle 3504 are securely enclosed within the slots 3503 of the first and second arm portions 3502a, 3502b. The arm portions 3502a, 3502b of the housing 3501 can be formed from and/or include spring materials that apply compressive force against the ends of the needle 3504 within the slots 3503 in order to secure the needle 3503 in place. Alternatively or in combination, each arm portion can include a lining 3505 formed from a deformable material (e.g., foam, silicone rubber, composites) to facilitate retention of the needle 3503 within the slot. The lining 3505 can be located on the upper interior surface 3506a of the arm portion, the lower interior surface 3506b of the arm portion, or on both surfaces.

In many embodiments, the first arm portion 3502a and second arm portion 3502b can be spaced apart from each other so as to form a gap 3507 between the first and second arm portions 3502a, 3502b, such that a middle portion of the needle 3504 is exposed. In such embodiments, the received needle 3504 is secured only at its ends and not at its middle portion. The size of the gap 3507 can be selected based on the geometry (e.g., length and/or curvature) of the needle 3504 in order to ensure that the ends of the needle 3504 will not protrude from the first and second arm portions 3502a, 3502b. The gap 3507 can be shaped to accommodate insertion of a needle driver tip into the gap 3507, e.g., in order to grasp the exposed middle portion of the needle 3504. For example, the needle driver can be used to deposit a used needle into the device 3500, e.g., by aligning and sliding the needle along the slot 3503 from, the back portion 3508a of the housing 3501 towards the front portion 3508b of the device 3501. Optionally, the housing 3501 can be closed at the front portion 3508b so as to "trap" the received needles within the housing 3501.

FIGS. 351A-C illustrate an exemplary embodiment of a device 3510 for securing a plurality of needles, in accordance with many embodiments. FIG. 351A illustrates a top view, FIG. 351B illustrates a side view, and FIG. 351C illustrates a front view. The device 3510 includes a housing 3511 including an upper wall 3512 and a lower wall 3513 movably coupled to each other by a hinge member 3514. The upper and lower walls 3512, 3513 may be movable relative to each other, e.g., along the direction indicated by arrow 3518. The space between the upper wall 3512 and lower wall 3513 forms an elongate slot 3515 for receiving one or more needles 3516. The hinge member 3514 can be spring-loaded to bias the upper wall 3512 and lower wall 3513 towards each other such that the inserted needle 3516 is secured within the slot 3515 by the compressive forces exerted by the upper wall 3512 and lower wall 3513.

In many embodiments, the housing 3511 includes lateral walls 3517 arranged to capture and enclose the ends of the needle 3516 when the needle 3516 is received within the slot 3515. In the depicted embodiment, the lateral walls 3517 are joined to the upper wall 3512 such that the lower wall 3513 is positioned between the lateral walls 3517. In alternative embodiments, the lateral walls 3517 can joined to the lower wall 3513, and the upper wall can be positioned between the lateral walls 3517.

In many embodiments, the upper wall 3512 includes an opening 3519 connected to the slot 3515 such that a middle portion of the inserted needle 3516 is exposed. In such embodiments, the received needle 3516 is secured only at its ends and not at its middle portion. The gap 3519 can be shaped to accommodate insertion of a needle driver tip into the gap 3519, e.g., while grasping the exposed middle portion of the needle 3516 in order to insert and/or remove the needle 3516 from the device 3510.

FIGS. 352A-C illustrate an exemplary embodiment of a device 3520 for securing a plurality of needles, in accordance with many embodiments. FIG. 352A illustrates a top view and FIG. 352B illustrates a side view. The device 3520 includes a plurality of clips 3521 each used to secure a respective needle. Each clip 3521 can be u-shaped with a first arm portion 3522a and a second arm portion 3522b, and the arm portions can each include a slot 3523 shaped to receive a respective end of an inserted needle 3524. The first and second arm portions 3522a, 3522b can be arranged such that when the needle 3524 is inserted into the clip 3521, the ends of the needle 3524 are securely enclosed within the slots 3523 of the first and second arm portions 3522a, 3522b. The clip 3521 can be formed from and/or include spring materials that apply compressive force against the ends of the needle 3524 within the slot 3523 in order to secure the needle 3524 in place without any exposed ends. Similar to other embodiments herein, the arm portions 3522a, 3522b can be spaced apart to form a gap 3525, such that the middle portion of the needle 3524 is exposed. In such embodiments, the received needle 3524 is secured only at its ends and not at its middle portion. The size of the gap 3525 can be selected based on the geometry (e.g., length and/or curvature) of the needle 3524 in order to ensure that the ends of the needle 3525 will not protrude from the clip 3521. The gap 3525 can be used to facilitate insertion of the needle 3524 into the clip 3521 and/or dispensing of the needle 3524 from the clip 3521 using a needle driver or other instrument.

Each clip 3521 permits insertion of a needle 3524 along a horizontal orientation. Horizontal may be used herein to refer to an orientation in which the plane of the slot of the clip is aligned with and/or substantially parallel to the ground, such that the needle is inserted along a direction aligned with and/or substantially parallel to the ground (e.g., as indicated by arrow 3526). A device configured for horizontal needle insertion may in some instances be safer than devices configured for insertion along other directions (e.g., vertical direction), and may also provide a lower profile for securing a plurality of needles.

In many embodiments, the plurality of clips 3521 of the device 3520 are configured to be stacked with each other. FIG. 352C illustrates exemplary configurations of the device 3520 in which a plurality of clips are stacked together. Any suitable number of clips may be stacked together, such as two, three, four, five, six, seven, eight, nine, ten, or more clips. The clips may be vertically stacked such that each clip is located at a different height along the device 3520. The planes of the slots of each clip can be substantially parallel to each other such that each needle is inserted along a horizontal orientation. The heights of the clips can be offset along the vertical direction to enable a clear path to insertion of the needle and to accommodate the needle driver tip. In many embodiments, when stacked, the gaps 3525 of the clips 3521 are aligned with each other so that the needle driver tip has an unobstructed path to each clip.

The stackable clips 3521 of the device 3520 can be removably coupled to each other, e.g., using snap fits, interference fits, interlocking structures, and the like. In embodiments where removably coupled clips are used, the number of clips in the device 3520 can be varied as desired by removing or adding clips in order to accommodate a corresponding number of needles. Alternatively, the clips 3521 of the device 3520 can be permanently affixed to each other in a stacked configuration, e.g., using adhesives, fasteners, and the like, or by being integrally formed with each other.

FIG. 353 illustrates an exemplary embodiment of a clip assembly 3530 for securing a needle 3531, in accordance with many embodiments. The clip assembly 3530 can include a first clip 3532 and a second clip 3533. Each clip can include a front outer side 3534a, a back outer side 3534b, a front inner side 3535a, and a back inner side 3535b. As used herein, "front" and "back" may be defined relative to the insertion direction 3536 for the needle 3531, while "inner" and "outer" may be used to refer to portions closer to and away from the needle 3531, respectively. In many embodiments, the inner sides 3535a, 3535b of each clip 3532, 3533 are open so as to define a slot in the interior of the respective clip for receiving a respective end of the needle 3531. The outer sides 3534a, 3534b of each clip 3532, 3533 can be closed so as to enclose the ends of the needle 3531 within the respective clip. The clips 3532, 3533 can be spaced apart from each other by a certain amount so as to accommodate the tip of a needle driver 3537 between the clips 3532, 3533. Similar to other embodiments herein, the needle driver 3537 can be used to grasp the middle portion of the needle 3531 in order to insert it into the clip assembly 3530 along the insertion direction 3536. When inserted, the ends of the needle 3531 are enclosed within the clips 3532, 3533, while the middle portion of the needle 3531 is exposed.

In many embodiments, the clips 3532, 3533 are each oriented at an oblique angle relative to the insertion direction 3536 for the needle 3531, such that the sides 3534a, 3534b, 3535a, 3535b of each clip 3532, 3533 are not parallel or orthogonal to the insertion direction 3536. The oblique angle can be selected based on the geometry (e.g., length and/or curvature) of the needle 3531 such that when the needle 3531 is inserted along the insertion direction 3536 convex side first, as illustrated in FIG. 353, the front outer sides 3534a of the clips 3532, 3533 act as a stop to catch and constrain the ends of the needle 3531. Accordingly, it can be seen that the orientation of the clips 3532, 3533 determine the extent to which the needle 3531 can be moved along the insertion direction 3536.

FIGS. 354A-G illustrate an exemplary embodiment of a device 3540 for securing a plurality of needles, in accordance with many embodiments. FIG. 354A illustrates a top view of the device 3540. The device 3540 includes a housing 3541 including a upper wall 3542 and a lower wall 3543. The upper wall 3542 and lower wall 3543 can be integrally formed with each other. Alternatively, the upper wall 3542 and lower wall 3543 can be provided as discrete components that are removably or non-removably coupled to each other. A slot 3544 is formed between the upper wall 3542 and lower wall 3543 such that one or more needles can be received between the upper wall 3542 and lower wall 3543. The slot 3544 can extend through the upper wall 3542 of the housing 3541 such that an elongate opening 3545a is formed in the upper wall 3542. Alternatively or in combination, the slot 3544 can extend through the lower wall 3543 of the housing 3543 so as to form an elongate opening 3545b in the lower wall 3543. Similar to the other embodiments presented herein, the elongate opening 3545a and/or elongate opening 3545b can be shaped to accommodate a needle driver such that a needle can be inserted into the device 3540 by grasping the middle portion of the needle with the needle driver, then sliding the needle through the slot 3544 along the direction indicated by arrow 3546. The ends of the inserted needle are secured between the upper wall 3542 and lower wall 3543, while the middle portion of the needle is exposed via the opening 3545 and/or opening 3546. The front end of the device 3540 can be closed so as to constrain the extent of movement of the needle along the insertion direction 3546.

In many embodiments, the upper wall 3542 includes a plurality of slits or fenestrations 3547. Alternatively or in combination, the plurality of fenestrations can be formed in the lower wall 3543. The fenestrations 3547 can be arranged substantially parallel to each other along the longitudinal axis of the device 3540. The spacing between fenestrations 3547 can be used to modulate the overall stiffness of the upper wall 3542 and/or lower wall 3543. For example, widely spaced fenestrations may result in a higher stiffness, while closely spaced fenestrations may result in a lower stiffness. The portions of the upper wall 3542 and/or lower wall 3543 between each adjacent pair of fenestrations can be considered to act as an individual "clip" for securing a respective needle. Accordingly, the plurality of fenestrations 3547 can be used to define a linear array of "clips" for securing a plurality of needles within the device 3540.

The upper wall 3542 and lower wall 3543 can be formed from and/or include spring materials that apply compressive force against the ends of the needle within the slot 3544 in order to secure the needle in place. Accordingly, the lateral portions 3548 of the housing 3541 joining the upper wall 3542 and lower wall 3543 can act as a spring-loaded hinge that biases the upper wall 3542 and lower wall 3543 towards each other. The design of the lateral hinge portion 3548 can be used to tune compressive forces applied to the received needle. For example, as illustrated in FIG. 354C, the upper wall 3542 and lower wall 3543 can be biased toward each other such that the height A of the slot 3544 at portions away from the opening 3545 and/or opening 3546 can be greater than the height B of the slot 3544 at portions near the opening 3546 and/or opening 3546. Optionally, as illustrated in FIG. 354D, the inner surface of the upper wall 3542 and/or the inner surface of the lower wall 3543 can include a lining 3549 formed from a deformable material (e.g., foam, silicone rubber, composites) to further facilitate retention of the needle within the slot.

In many embodiments, the interior surfaces of the upper wall 3542 and lower wall 3543 are arranged substantially parallel to each other, as illustrated in FIG. 354E. This arrangement can produce a substantially constant resistance as the needle is advanced along the insertion direction. In alternative embodiments, the interior surfaces can be arranged at an angle relative to each other, as illustrated in FIGS. 354F and 354G, so as to form a linear array of "clips" with beveled edges. This arrangement can produce a linear increase in resistance as the needle is advanced along the insertion direction within a single "clip," followed by a drop in resistance as the needle exits one "clip" and enters the next "clip." This variable resistance can provide tactile feedback that allows the user to determine when the next "clip" has been reached, e.g., for more accurate positioning of the needle within the device 3540.

FIGS. 355A-B illustrate an exemplary embodiment of a device 3550 for securing a plurality of needles, in accordance with many embodiments. The device 3550 includes a housing 3551 including a upper wall 3552 and a lower wall 3553. The upper wall 3552 and lower wall 3513 can be integrally formed with each other. Alternatively, the upper wall 3552 and lower wall 3553 can be provided as discrete components that are removably or non-removably coupled to each other. A slot 3554 is formed between the upper wall 3552 and lower wall 3553 such that one or more needles can be received between the upper wall 3552 and lower wall 3553. The slot 3554 can extend through the upper wall 3552 of the housing 3551 such that an elongate opening 3555 is formed in the upper wall 3512. Similar to the other embodiments presented herein, the elongate opening 3555 can be shaped to accommodate a needle driver such that a needle can be inserted into the device 3550 by grasping the middle portion of the needle with the needle driver, then sliding the needle through the slot 3554 along the direction indicated by arrow 3556. The ends of the inserted needle are secured between the upper wall 3552 and lower wall 3553, while the middle portion of the needle is exposed via the opening 3555. The front end of the device 3550 can be closed so as to constrain the extent of movement of the needle along the insertion direction 3556.

The upper wall 3552 and lower wall 3553 can be formed from and/or include spring materials that apply compressive force against the ends of the needle within the slot 3554 in order to secure the needle in place. In many embodiments, one or more fenestrations or slits 3557 are formed in the upper wall 3552 so as to define a corresponding one or more tabs 3558 in the upper wall 3552. For example, as shown in FIG. 355A, a pair of u-shaped slits 3557 are formed in the upper wall 3552 on either side of the elongate opening 3555 so as to define a pair of elongate tabs 3558 in the upper wall 3552 on either side of the elongate opening 3555. The longitudinal axis of the elongate tabs 3558 can be aligned with the longitudinal axis of the device 3550. The hinge portion 3559 of each tab 3558 can be located near the front end of the device 3550. Optionally, as illustrated in FIG. 355B (middle), the tab 3558 can be biased inwards relative to the surrounding portions of the upper wall 3552 so as to apply compressive forces to the received needle(s). Additionally, as illustrated in FIG. 355B (bottom), the inner surface of the tab 3558 and/or the lower wall 3553 can include a lining 3559 formed from a deformable material (e.g., foam, silicone rubber, composites) to further facilitate retention of the needle within the slot 3554.

Alternatively or in addition to the use of clips, the systems and devices described herein can use other mechanisms to physically secure one or more needles. For example, deformable materials such as foam can be used to entangle the end(s) of a needle in order to render it innocuous. Entanglement can occur when the needle is pierced or tacked into the deformable material. The deformable material can encapsulate the needle end so as to protect the user from injury due to needle sticks, etc. Additionally, once entangled by the deformable material, the movement of the needle may be constrained so as to reduce the risk of the needle becoming loosened or dislodged. As another example, adhesive materials can be used to physically secure one or more needles within a device. The adhesive materials can be used to cover and/or encase the needle so as to constrain its movement, as well as to encase the ends of the needle to render them innocuous.

FIG. 356 illustrates an exemplary embodiment of a device 3560 for securing a plurality of needles, in accordance with many embodiments. The device 3560 may be similar to the devices 3470 and 3480 previously discussed herein. The device 3560 includes a housing 3561 including an upper wall 3562 and a lower wall 3563. The space between the upper wall 3562 and lower wall 3563 forms an elongate slot 3564 for receiving and securing the ends of one or more needles 3565. The upper wall 3562 includes an opening 3566 connected to the slot 3565 such that a middle portion of the inserted needle 3565 is exposed. In such embodiments, the received needle 3565 is secured only at its ends and not at its middle portion. The opening 3566 can be shaped to accommodate insertion of a needle driver tip into the opening 3566, e.g., while grasping the exposed middle portion of the needle 3565 in order to insert and/or remove the needle 3565 from the device 3560.

In many embodiments, the housing 3561 includes lateral walls 3566 arranged to capture and enclose the ends of the needle 3566 when the needle 3566 is received within the slot 3565. In the depicted embodiment, the lateral walls 3567 are joined to the upper wall 3562 such that the lower wall 3563 is positioned between the lateral walls 3567. In alternative embodiments, the lateral walls 3567 can joined to the lower wall 3563, and the upper wall can be positioned between the lateral walls 3567.

In many embodiments, the upper wall 3562 and lower wall 3562 can be formed from and/or include spring materials that apply compressive force against the ends of the needle 3565 within the slot 3564 in order to secure the needle 3565 in place. Alternatively or in combination, the device 3560 can include a pair of elongate blocks 3566a, 3566b formed from foam or any other deformable material suitable for entangling the ends of the needle 3565 as it is inserted into the slot 3564. The blocks 3566a, 3566b can be formed from the same material or from different materials. The blocks 3566a, 3566b can be positioned between the upper wall 3562 and lower wall 3563 and be aligned with the longitudinal axis of the device 3560. The distance between the blocks 3566a, 3566b can be determined based on the geometry (e.g., length and/or curvature) of the needle 3565 so as to be sufficiently far apart to allow the needle 3565 to be advanced within the slot 3564 in a convex-first orientation, while also being sufficiently close together to cause deformation of the foam by the ends of the needle 3565 as the ends are positioned within the outer limits of the blocks 3566a, 3566b. In many embodiments, the foam can be used to retain the needle 3565 within the device 3560 through one or more of the following mechanisms: deformation of the foam by the needle ends, piercing of the foam by the needle ends, entanglement and/or entrapment of the needle ends within the foam, or indirect tacking of the needle ends within the foam (e.g., tacking that occurs when the needle ends are drawn across the foam substantially in an orthogonal relationship relative to the surfaces of the foam blocks). For example, advancing the needle 3565 within the slot 3564 in an convex-first orientation may result first in deformation of the foam, followed by a passive piercing of the foam as a secondary effect. In many embodiments, the amount of force to remove an inserted needle 3565 from within the device 3560 is greater than the amount of force to introduce the needle into the device 3560.

FIGS. 357A-C illustrate an exemplary embodiment of a device 3570 for securing a plurality of needles, in accordance with many embodiments. The device 3570 includes an upper u-shaped compression element 3571 and a lower u-shaped compression element 3572. Each compression element includes a respective first arm portion 3573a and second arm portion 3573b. A slot 3574 is formed in each arm portion between the upper compression element 3571 and lower compression element 3572 and shaped to receive a corresponding portion of an inserted needle 3575. In many embodiments, the first arm portion 3573a and second arm portion 3573b are spaced apart by a gap 3576, such that a middle portion of the inserted needle 3575 is exposed. The gap 3576 can be shaped to accommodate insertion of a needle driver tip into the gap 3576, e.g., while grasping the exposed middle portion of the needle 3575 in order to insert and/or remove the needle 3575 from the device 3570. In many embodiments, the upper and lower compression elements 3571, 3572 form a clip that exerts compressive forces on the received needle 3575 in order to secure it in place. In alternative embodiments, the upper and lower compression elements 3571, 3572 are passive elements that do not exert compressive forces on the needle 3575.

In many embodiments, the upper and lower compression elements 3571, 3572 are shaped based on the geometry (e.g., length and/or curvature) of the needle 3574 such that when the needle 3574 is inserted into the device 3570, the ends of the needle 3574 protrude outward from the outer edges of the compression elements 3571, 3572. The exposed ends of the needle 3574 can be rendered innocuous through the use of adhesive casings 3577. The adhesive casings 3577 can be attached to the outer edges of the first and second arm portions 3573a, 3573b spanning the "boundary zone" where the exposed needle ends are located. In many embodiments, the adhesive casing 3577 can be connected to both the upper compression element 3571 and lower compression elements 3572 so as to enclose the exposed needle ends, as illustrated in FIG. 357B. Once the needle 3574 is advanced into the device 3570, the upper portion 3578a and lower portion 3578b of the adhesive casing 3577 can be pressed together so as to physically secure the needle ends and thereby render the needle 3574 innocuous, as illustrated in FIG. 357C. The adhesive bonds can be sufficiently strong such that the upper and lower portions 3578a, 3578b of the adhesive casing 3577 and needle 3574 cannot be easily separated from each other once adhesively secured.

FIG. 358 illustrates an exemplary embodiment of a device 3580 for securing a plurality of needles, in accordance with many embodiments. The device 3580 includes a an lower surface 3581 having a plurality of lower adhesive panels 3582 and an upper surface 3583 having a plurality of upper adhesive panels 3584. The size and shape of each adhesive panel can be configured to span the entirety of a needle 3585 placed on the panel such that the ends of the needle 3585 do not extend past the boundary of the panel. In many embodiments, the adhesive panel includes and/or is formed from an adhesive material capable of physically securing the needle 3585 when the needle 3585 is placed on the panel. Optionally, light pressure may be applied to the needle 3585 in order to ensure tight adhesion to the panel. In many embodiments, the needle 3585 is first placed on the lower adhesive panel 3582. The corresponding upper adhesive panel 3584 is then folded along crease 3586 in order to enclose the needle 3585 and render it innocuous. The upper adhesive panels 3584 can be separated from each other by cuts 3587 so as to permit each upper adhesive panel 3584 to be folded down independently. The adhesive bonds can be sufficiently strong such that the lower adhesive panel 3582, upper adhesive panel 3584, and needle 3585 cannot be easily separated from each other once adhesively secured. Additionally, the adhesive panels can be formed from a material with sufficient strength and/or thickness such that the sharp end of the enclosed needle 3585 cannot pierce through the panels.

FIG. 359 illustrates an exemplary embodiment of a device 3590 for securing a needle 3591, in accordance with many embodiments. The device 3590 includes a foam block or capsule 3592 and a clip 3593. In order to secure the needle 3591, the sharp leading end of the needle 3591 is pierced or tacked into the foam block 3592. Optionally, the foam block 3592 can include a protective outer shell to prevent the sharp end from piercing through the surface of the foam block 3592 and becoming exposed. The clip 3593 is then used to secure the blunt trailing end of the needle 3591. Accordingly, both ends of the needle 3591 are rendered innocuous.

FIGS. 360A-C illustrate an exemplary embodiment of a device 3600 for securing a plurality of needles, in accordance with many embodiments. The device 3600 includes a rack 3601 with a plurality of receptacles for holding a corresponding plurality of foam blocks or capsules 3602. A needle 3603 can be rendered innocuous by piercing or tacking the sharp leading end into the foam block 3602. Each block 3602 can optionally include a protective outer shell configured to prevent the sharp end from piercing through the surface of the foam block 3562 and becoming exposed. The user (e.g., a surgeon) can then hand the entire rack 3601 with the secured needle(s) to a second user (e.g., a scrub tech), such that the second user does not need to handle each needle individually, thus reducing the risk of needle sticks or other injuries during the handover.

In many embodiments, each foam block 3602 also includes a tail 3604 at the end of the block 3602 away from the end where the needle 3603 is inserted. Alternatively, the user can tack each needle 3603 into the foam block 3602 using a needle driver 3604. The tail 3604 can enable handling of the secured needle without requiring the user to directly touch the needle itself, thereby improving safety. For example, a user (e.g., a surgeon) can tack the needle 3603 into the foam block 3602 using a needle driver 3605, and a second user (e.g., a scrub tech) can handle the secured needle 3603 using the tail 3604. Optionally, the tail 3604 can be used to hang the secured needle 3603 onto a wall or other surface 3606, as shown in FIG. 360C, e.g., to facilitate counting of the needles during or after the surgical procedure in order to ensure that all needles are accounted for.

The device 3600 can be used to secure only the sharp leading end of the needle 3603 via the foam block 3602 without also securing the blunt trailing end of the needle 3603. While an unsecured trailing end may be hazardous within the surgical field due to the potential for ripping gloves, catching on surgical garments, etc., it may not be necessary to secure the trailing end in the embodiments where the needle 3603 is immediately transferred to a scrub tech outside of the near surgical field. In alternative embodiments, the embodiment of FIGS. 360A-C may further involve securing the trailing end of the needle 3603 with a clip, similar to the device 3560, such that both ends of the needle 3603 are rendered innocuous.

FIG. 361A illustrates an exemplary embodiment of a device 3610a for securing a plurality of needles, in accordance with many embodiments. The device 3610a includes a housing 3611 enclosing a foam core 3612. The foam core 3612 can be affixed to the housing 3611 in a fixed position and orientation via a tab or other fastener 3613 passing through the foam core 3612. The housing 3611 includes a curved slot 3614 defining an insertion path for one or more needles 3615. The geometry (e.g., length and/or curvature) of the curved slot 3614 can be determined based on the geometry (e.g., length and/or curvature) of the needle 3615 so as to permit insertion of the needle 3615 into the interior space within the housing 3611. In many embodiments, a needle 3615 is rendered innocuous using the device 3610a according to the following procedure. First, the sharp leading end of the needle 3615 is inserted into the housing 3611 via the slot 3614 along an insertion trajectory such that the sharp end of the needle is away from the foam core 3612. The needle 3615 is then rotated to tack or pierce the needle into the foam core 3612, thus physically securing the needle within the device 3610a. Optionally, one or more tabs 3616 can be positioned in the interior of the housing 3611 in order to constrain and guide the movement of the needle 3615 within the housing 3611. This procedure can be repeated with a plurality of needles in order to secure multiple needles within the device 3610a.

FIG. 361B illustrates an exemplary embodiment of a device 3610b for securing a plurality of needles, in accordance with many embodiments. The components of the device 3610b are similar to those of the device 3610a, with the exception that the device 3610b includes a foam core 3617 coupled to the housing 3611 via a rotational tab or other rotational fastener 3618 permitting rotation of the foam core 3617 relative to the housing 3611. In many embodiments, a needle 3615 is rendered innocuous using the device 3610b according to the following procedure. First, the sharp leading end of the needle 3615 is inserted into the housing 3611 via the slot 3614 along an insertion trajectory such that the sharp end of the needle 3615 is tacked or pierced into the foam core 3617. The foam core 3617 is then rotated by pushing the needle 3615 (e.g., using a needle driver or other instrument) along the direction indicated by arrow 3619 so as to move the needle 3615 to the rear of the housing 3611, thus making room for additional needles to be inserted.

Figure 362A:
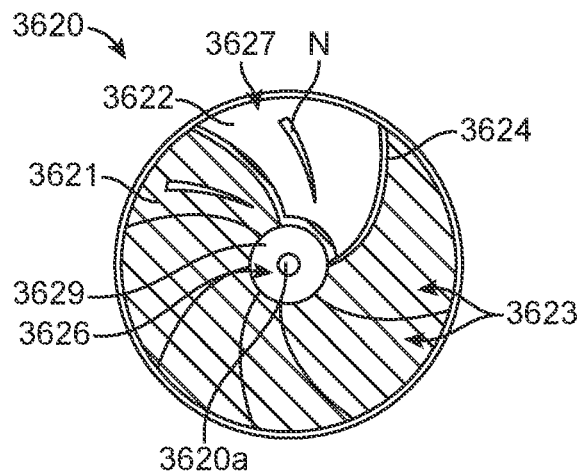
Figure 362B:
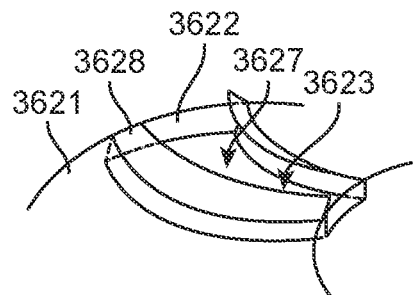
Figure 362C:
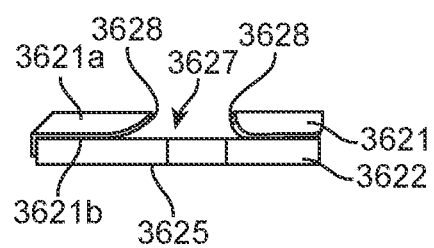
Figure 362D:
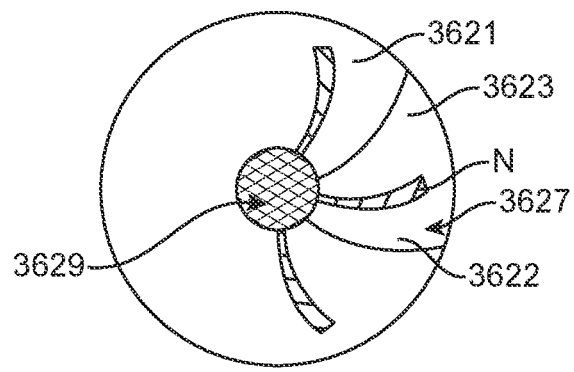

FIGS. 362A-362D illustrate an embodiment of a needle receptacle 3620 with a rotatable cover 3621. The needle receptacle may comprise a circular housing 3622 with a plurality of cells or compartments 3623 for storing individual needles N. Each compartment may comprise curvilinear walls 3624 separating the compartment from adjacent compartments, wherein a needle may be placed within each compartment with the curvature of the needle substantially aligned with the curvature of the curvilinear walls, thus maximizing the number of compartments available on the needle receptacle. Each compartment may optionally further comprise a magnetic or adhesive base 3625 to securely couple the needle to the base of the compartment. The needle receptacle may further comprise a circular cover 3621 configured to couple to the housing via rotatable central hinge 3626. The cover may comprise a window 3627 that can be aligned with a single compartment to allow access to the compartment. The window may be formed by curvilinear walls configured to substantially align with the curvilinear walls of the housing compartments. The cover may be rotated about the central axis 3620a of the needle receptacle to enclose a needle within a compartment, and to expose an adjacent unoccupied compartment for the securing of the next needle. As shown in FIGS. 362B and 362C, the window may be formed with beveled edges 3628 of the cover to cause a needle to lay flat when cover is rotated to align the window with the next compartment. For example, the edges of the curvilinear walls of the cover defining the window may be beveled such that the top or exterior surface 3621*a* of the cover extends over the bottom or interior surface 3621*b* of the cover. The cover and the housing may be configured to provide a clearance between the bottom surface of the cover and the base of the compartment that is close to the thickness of the needle. Optionally, as shown in FIG. 362D, the housing may further comprise a core 3629 at the center comprising a foam material, such that a needle placed inside a compartment may be further secured by tacking an end thereof into the foam core. In use, a user may place a needle inside an empty compartment with the window aligned over the compartment, then rotate the cover to align the window over another empty compartment. A user may rotate the cover by grabbing the edges of the cover with the fingers, or by pushing a needle driver tip against an edge of the window.

FIG. 363 illustrates another embodiment of a needle receptacle 3630 with a rotatable cover 3631. The needle receptacle of FIG. 363 may be similar in many aspects to the embodiment shown in FIGS. 362A-362D. For example, the needle receptacle may comprise a circular housing 3632 with a plurality of compartments 3633, and a circular cover 3631 coupled to the housing having a window 3634 with similar dimensions as a single compartment, optionally having beveled edges 3637. The rotating cover may comprise a plurality of tabs 3635 coupled to the outer edge of the cover, to facilitate rotation of the cover by a user. The housing may further comprise an outer border 3636 comprising a foam material, coupled to the internal surface of the outer wall of each compartment. A needle N placed inside a compartment may be further secured by tacking an end thereof into the foam border.

FIG. 364 illustrates another embodiment of a needle receptacle 3640 with a rotatable cover 3641. The needle receptacle of FIG. 364 may be similar in many aspects to the embodiments shown in FIGS. 362A-362D and FIG. 363. For example, the needle receptacle may comprise a circular housing 3642 coupled to a rotatable cover 3641 having a window 3643 to allow access to the housing. The housing may comprise a landing zone 3644 configured to receive and securely couple to a needle. For example, the landing zone may comprise a magnetic surface or an adhesive surface. The walls of the window may be oriented for placement of a needle in any orientation with respect to the compartment of the housing. The cover may be configured to rotate in either direction about the central axis 3640*a* of the needle receptacle. The window may comprise beveled edges 3645 as described in reference to FIGS. 362A-362D, wherein the beveled edges can cause a needle placed in a non-planar orientation to lay flat when the cover is rotated.

FIGS. 365A-365D illustrate an exemplary embodiment of a swaged needle device 3650 for dispensing and securing a swaged needle SN, comprising a rotatable cover 3651. The swaged needle device comprises a circular housing 3652 coupled to a rotatable cover 3651, wherein the housing comprises a plurality of compartments 3653 and the cover comprises a window 3654 configured to provide access to a single compartment. The housing and the rotatable cover may be similar in many aspects to the housing and rotatable cover as described in reference to FIGS. 362A-362D. For example, each compartment may comprise spiral or curvilinear walls separating the compartment from adjacent compartments, and the window may be sized and shaped to be similarly to a compartment. The window may comprise beveled edges 3655 to cause a needle SN placed within a compartment to lay flat when the rotatable cover is rotated to align the window with an adjacent compartment. The swaged needle device may be preloaded with sterile swaged needles SN having running sutures S attached thereto. A needle may be securely coupled to a compartment in one of many ways described herein with respect to various embodiments. For example, the base surface 3658 of the compartment may comprise a magnetic surface configured to magnetically couple to a needle, or an adhesive surface configured to adhere to the needle. The compartment may comprise a foam member 3659 coupled to the base, into which an end of the needle may be inserted to secure the needle. The compartment may comprise a clip coupled to the base, configured to compressively hold the needle therein. The compartment may further comprise a needle driver slot or recess 3656 formed in the base surface 3658 of the compartment, below the middle portion of the needle body. The needle driver recess can facilitate the grasping of a needle with a needle driver, or the securing of a needle in the compartment with a needle driver. The running sutures S attached the needles may be wrapped around a spindle 3657 provided by the rounded outer surface of the housing, best shown in FIG. 365B. The housing may be configured to rotate about a central axis 3650*a* of the needle receptacle to facilitate the dispensing of the running suture. One of the compartments may be provided without a sterile swaged needle, such that the window may be aligned with the empty compartment when the swaged needle device is not in use. In use, a sterile swaged needle may be removed from a compartment by first aligning the window with the compartment containing the sterile needle, then grasping the needle with a needle driver and removing the needle from the compartment. The swaged needle may be used to close an incision, and then the suture may be detached from the needle. The used needle may be placed back in the compartment, and then the cover may be rotated to expose the next sterile swaged needle to be used. A user may rotate the cover by grabbing the edges of the cover with the fingers, or by pushing a needle driver tip against an edge of the window. As described in reference to the swaged needle device shown in FIGS. 343A-343G, the device may be mounted on a barrier coupled to the forearm of a surgeon. A plurality of swaged needle devices providing swaged needles of different sizes may be provided on the barrier. Further, two or more swaged needle devices may be provided stacked on top of one another.

FIGS. 366A-366C illustrate an exemplary embodiment of an integrated suture needle dispensing and securing apparatus 3660. The apparatus may comprise a needle dispensing portion 3661 on a first end, and a needle securing portion 3662 on a second end opposite the first end. Both portions may be encased within a single housing 3663 configured to provide physically separated interior portions for sterile needles NS to be dispensed and used needles NU to be secured. Both portions may be configured to hold needles securely in a planar slot between a top shell or cover and a bottom shell of the housing, for example via compressive members disposed between the top and bottom shells and configured to compress the needles against the top shell. Both portions may further comprise a needle driver slot 3664 extending along a longitudinal axis of the apparatus, configured to allow translation of a needle driver tip along the slot to secure the needle within the housing. The dispensing portion may be preloaded with sterile suture needles NS, wherein the sutures S may be wrapped around the planar needle slot and encased in the housing. The sterile needles may be loaded into the dispensing portion in the orientation shown in FIG. 366A, such that needles are removed from the dispensing portion with the curved body leading and the ends trailing, to minimize risk of needle stick injury to the user during removal of the needles. In use, a user may grasp a sterile suture needle with a needle driver and remove the needle from the dispensing portion by translating the needle driver tip along the needle driver slot towards the open end of the slot. After using the sutured needle, the suture may be detached from the needle, and the dispensed or used needle may be secured in the securing portion. To secure the used needle, the needle driver holding the used needle may be inserted into the needle driver slot of the securing portion and translated towards the closed end of the slot.

Optionally, the integrated needle dispensing and securing apparatus may be provided with a hinge 3665 (e.g., a living hinge) between the dispensing portion and the securing portion, to allow the apparatus to be folded or collapsed along the hinge axis 3665*a* as shown in FIGS. 366B and 366C. For example, the hinge may be configured to allow folding of the apparatus with the flat bottom shells of each portion facing each other. The hinge can allow the apparatus to be packaged or stored in a reduced length configuration.

FIG. 367 illustrates an exemplary embodiment of a suture needle dispensing device 3670. The dispensing device may be similar in many aspects to the needle dispensing portion of the integrated dispensing and securing apparatus described in reference to FIGS. 366A-366C. For example, the dispensing device may comprise a top shell coupled to a bottom shell, wherein a plurality of sterile suture needles NS are configured to be secured in the planar slot between the top shell and the bottom shell (e.g., secured via compression of needles into top shell by compression members coupled to bottom shell). The device can comprise a needle driver slot 3671 configured to allow translation of a needle driver tip therein to facilitate grasping and removal of a needle from the dispensing device. The sutures S attached to the needles may be enclosed in a flexible tail 3672 having a plurality of individual channels for each of the sutures. Such a configuration for the storage of the sutures can help avoid kinking and/or knotting of the sutures within the dispensing device.

FIGS. 368A and 368B illustrate an exemplary configuration for coupling a needle receptacle 3681 to a suture package 3682. The needle receptacle 3681 may be coupled to a suture package 3682, such as any commercially available suture package pre-packaged with a plurality of sterile suture needles NS, and the suture package may be mounted on a barrier as described herein, in order to reduce the footprint of the suture package and needle receptacle on the barrier. For example, in many commercially available suture packages, a significant portion of the surface area of the package is unused, and the needle receptacle may be coupled to the unused portion of the suture package. The needle receptacle may be directly adhered onto the top surface of the suture package, or the needle receptacle may be indirectly coupled to the suture package via a mounting interface 3683 as shown in FIG. 368B, such as adhesive strips.

FIGS. 369A-369C illustrate another exemplary configuration for coupling a needle receptacle 3691 to a needle dispensing unit 3692. The needle receptacle 3691, such as any needle receptacle described herein, may be coupled to the needle dispensing unit 3692, such as any commercially available suture package or any needle dispensing device or apparatus as described herein, by way of a barrier mounting base 3693. The barrier mounting base may comprise any material capable of providing sufficient rigidity to stably support the needle dispensing device or receptacle while mounted on the barrier. The barrier mounting base may comprise a first portion 3693*a* and a second portion 3693*b*, wherein the first portion is configured to couple to the needle dispensing unit (such as suture package as shown in FIG. 369A), and wherein the second portion is configured to couple to the needle receptacle. The needle dispensing unit and the needle receptacle may each be coupled to the barrier mounting base by way of one or more adhesive members, magnetic coupling, velcro attachment, or mechanical coupling mechanisms such as a snap-fit. As shown in FIG. 369B of the top side of the barrier mounting base, the first portion may comprise one or more adhesive members 3694 configured to adhesively couple to a rear surface of the needle dispensing device. The needle receptacle may be coupled to the second portion by way of an adhesive backing coupled to the rear surface of the needle receptacle. As shown in FIG. 369C of the bottom side of the barrier mounting base, the bottom surface of each of the first and second portions may comprise one or more adhesive members 3695 configured to couple to the barrier. Alternatively, the barrier mounting base may be coupled to the barrier by way of a velcro attachment or a mechanical coupling mechanism.

Optionally, the barrier mounting base may be provided with a hinge 3696 between the first portion and the second portion, such as a living hinge. The hinge may allow at least partial folding of the base along the hinge, such that the plane of the first portion may be positioned at an angle with respect to the plane of the second portion.

FIG. 370A schematically illustrates an exemplary configuration of a needle dispensing unit 3702 and a needle receptacle 3701 mounted on a barrier 3703. The needle receptacle may comprise any needle receptacle as described herein, and the needle dispensing unit may comprise any commercially available suture package or any needle dispensing device or apparatus as described herein. The barrier is shown coupled to a forearm F, wherein the needle dispensing unit and the needle receptacle are generally disposed on the volar forearm side. As shown, the plane 3704 of the needle dispensing unit is disposed at an angle α with respect to the plane 3705 of the needle receptacle, such that the needle dispensing unit and needle receptacle are not coplanar. Such a configuration may be achieved by way of a hinged mounting interface, such as the barrier mounting base described in reference to FIGS. 369A-369C. Such a configuration may improve the conformation of the needle handling system to the shape of the forearm, reducing the profile of the system when mounted on the barrier.

FIG. 370B schematically illustrates another exemplary configuration of a needle dispensing unit 3702 and a needle receptacle 3701 mounted on a barrier 3703. The needle receptacle may comprise any needle receptacle as described herein, and the needle dispensing unit may comprise any commercially available suture package or any needle dispensing device or apparatus as described herein. The barrier is shown coupled to a forearm F, wherein the needle dispensing unit and the needle receptacle are disposed on a plane of the volar forearm. As shown, the needle dispensing unit and the needle receptacle are substantially co-planar, with the two units partially overlapping. Such a configuration may be achieved by coupling the needle receptacle to a portion of the needle dispensing unit as described in reference to FIGS. 368A-368B. Such a configuration may maintain both the needle dispensing unit and the needle receptacle in the plane of the volar forearm, while reducing the profile of the needle handling system in comparison to a configuration wherein the needle dispensing unit and the needle receptacle are non-overlapping and co-planar.

FIGS. 371A and 371B illustrate an exemplary configuration of a needle receptacle 3711 mounted on a barrier 3712. The barrier may be a forearm-coupled barrier as described herein, and the needle receptacle may be any needle receptacle as described herein. The barrier may comprise a recess 3713 to receive a portion of the needle receptacle therein, such as a protrusion of the rear surface of the needle trap housing. The protrusion may be configured to fit into the recess of the barrier such the surface 3714 of the needle receptacle entry zone 3715 is substantially flush with the plane 3716 of the barrier. Such a configuration can reduce the profile of the needle receptacle mounted on the barrier.

FIGS. 372A and 372B illustrate exemplary labels that may be provided for commercially available suture packages to be used with a needle handing system described herein. Many commercially available suture packages, while labeled clearly on the outside packaging, comprise sterile inner packaging with poorly visible labels or no labels indicating the size and/or type of the suture needle contained therein. When suture packages are placed within the surgical field (e.g., on a Mayo stand), they are typically stripped of their outer packaging such that only the sterile inner packaging is displayed. Due to the poor visibility of labeling or lack of adequate labeling on the inner packaging, it can often be difficult for a surgeon to visually identify the size or type of suture needles contained in each package. To facilitate surgeon identification and selection of a suture package containing the desired size and/or type of needles, sterile adhesive labels may be applied to the inner packaging of suture packs that clearly display the size and/or type of the contained needles. The sterile adhesive labels may comprise, for example, large text and/or color coding sufficient for allowing identification of the suture pack contents from at least 3 feet away. Such sterile adhesive labels may be provided with a needle receptacle and barrier assembly as described herein, such that a user may easily label the sterile inner packaging of a commercially available suture package to be used in conjunction with the needle receptacle and the barrier. As shown in FIG. 372A, a large-size needle receptacle may be provided with a set of adhesive labels 3720a for larger-sized suture needles. As shown in FIG. 372B, a small-size needle receptacle may be provided with a set of adhesive labels 3720b for smaller-sized suture needles.

FIGS. 373A and 373B illustrate an exemplary embodiment of a forearm barrier 3730 comprising sliding longitudinal panels 3731. The barrier may comprise a plurality of longitudinal panels 3731 that are coupled to one another, wherein each panel is configured to slide out from underneath another panel. Each panel may be longitudinally aligned along the length of the forearm. During storage, the barrier may lay flat in the storage configuration 3732 as shown in FIG. 373A, thereby reducing storage profile and facilitating packaging and shipping of the barrier. For use, the barrier may be wrapped around the forearm to cause the panels to slide out appropriately to conform to the size and shape of the user's forearm, as shown in FIG. 373B. The barrier may be secured to the forearm in the wrapped configuration 3733 via one of many closure mechanisms, such as a tab, a velcro strap, one or more adhesive members, or one or more mechanical fasteners.

FIGS. 374A and 374B illustrate an exemplary embodiment of a forearm barrier 3740 comprising sliding c-shaped sections or "bracelets" 3741. The barrier may comprise a plurality of c-shaped sections 3471 that are coupled to one another, wherein each section is configured to slide out from underneath another section. Each c-shaped section may be configured to wrap around a portion of a user's forearm. During storage, the plurality of c-shaped sections may be in a nested configuration 3742 as shown in FIG. 374A, thereby reducing the storage volume of the barrier. For use, the inner sections of the nested bracelets may be pulled out relative to the outer sections to achieve the extended configuration 3743 as shown in FIG. 374B. In the extended configuration, the combined lengths of the c-shaped sections can extend along the length of the forearm. The plurality of c-shaped sections may be coupled to one another such that, when the inner sections are pulled out to achieve the desired combined length, the barrier remains at said combined length without the c-shaped sections recoiling or resuming the nested configuration. The barrier may be stretched out to its full length and subsequently coupled to the forearm, or the barrier may be coupled to the forearm in the nested configuration and subsequently pulled out to its desired length. The barrier may be coupled to the forearm such that the innermost nested c-shaped section is disposed near a distal portion of the forearm, and the outermost c-shaped section is disposed near a proximal portion of the forearm.

FIG. 375 illustrates a barrier 3750 comprising one or more plug-ins 3751 for electrically powered surgical tools. A forearm barrier as described herein may be further provided with one or more plug-ins for one or more electrically powered surgical tools 3753, such as electrocautery pens or suction tubes. In many instances, during a surgical operation, electrically-powered surgical tools are connected to a power source 3752 disposed outside the near surgical field. The power cord connecting the tool to the power source is often clamped into a fixed position above the incision site, in order to prevent the tool from being accidentally displaced during use via pulling of the power cord or movement of the power source. Rather than clamping the power cords near the incision site, a surgical tool may be connected to its power source via a plug-in disposed on the forearm-mounted barrier. The barrier plug-in can provide a more secure coupling to the tool's power cord than a clamp disposed above the incision site, thereby further reducing the risk of the tool being accidentally displaced during use. The one or more plug-ins may be provided on the dorsal side of the forearm F, so that the cords do not obstruct the needle dispensing unit and/or needle receptacle provided on the volar side of the forearm.

Figure 376A:
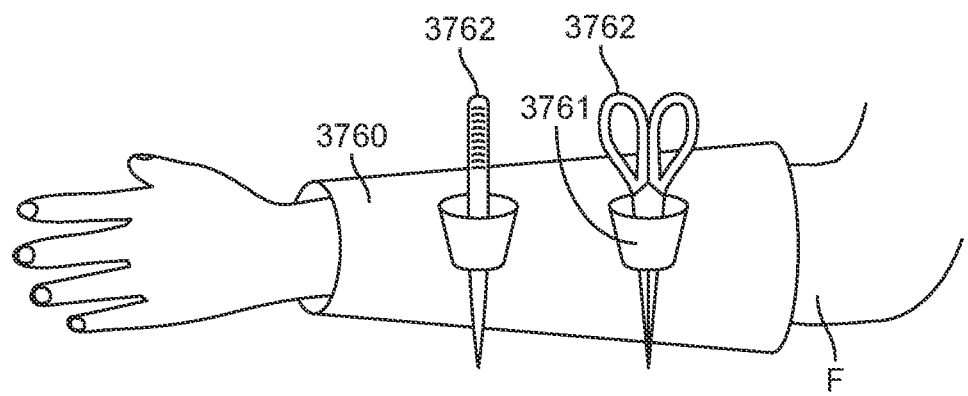
Figure 376B:
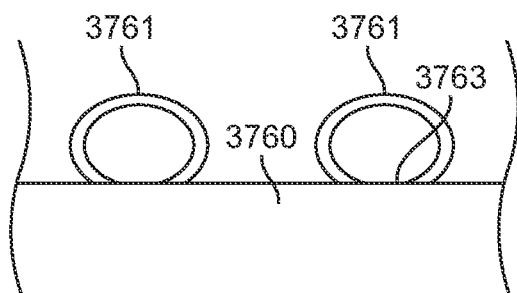
Figures 376C, 376D:
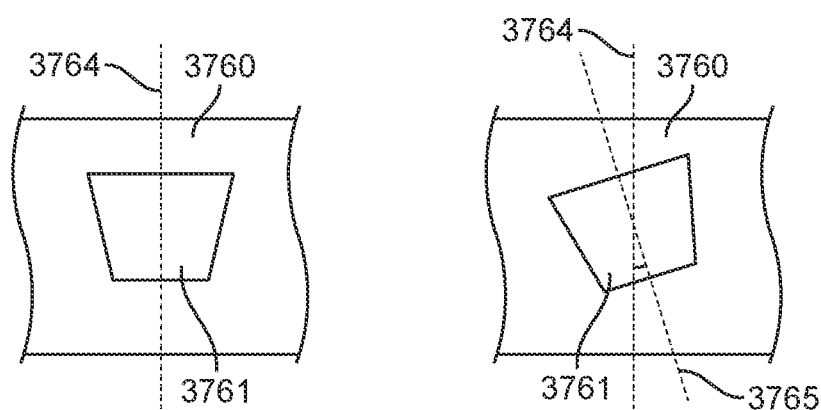

FIGS. 376A-376D illustrate a barrier 3760 comprising one or more tool loops 3761 for supporting one or more surgical tools 3672. As shown in FIG. 376A, the tool loops 3761 are preferably provided on the dorsal side of the forearm F, such that the tools 3762 coupled thereto do not obstruct the needle dispensing unit and/or needle receptacle provided on the volar side of the forearm. A tool loop may comprise a tapering loop with the larger end facing up and the smaller end facing down. The tapering shape of the loop can facilitation insertion of a tool into the loop by a user, and stably support the tool therein. As shown in FIG. 376B, which is a top view of the barrier comprising the tool loops, the tool loops are preferably mounted such that they are flush against the outer surface 3763 of the barrier. For example, a tool loop may comprise a partial loop, the two ends of which are attached to two different positions on the barrier, such that a portion of the complete loop comprises an outer surface of the barrier. Alternatively, a tool loop comprising a complete loop may be coupled to a recess in the outer surface of the barrier, such that the interior surface of the portion of the loop disposed within the recess is flush with the outer surface of the barrier. Such a configuration may facilitate the insertion of a tool into a tool loop, by allowing a user to use the outer surface of the barrier as a guiding surface in the insertion of the tool without interference from a bump or a lip formed by the interior surface of the tool loop protruding over the outer surface of the barrier. A tool loop may be aligned along a vertical axis 3764 as shown in FIG. 376C, or may be aligned along an axis 3765 offset from the vertical axis by a non-zero angle α as shown in FIG. 376D. In particular, the tool loop may be slanted with respect to the vertical axis such that the smaller end of the tool loop is pointed towards the elbow, away from the wrist. Such a slanted tool loop can provide better ergonomics for the insertion of a tool into the tool loop, by aligning the orientation of the tool loop generally with the direction of movement of the user's hand in inserting the tool into the tool loop (an internal rotation of the elbow to sweep the tool-holding hand from the incision site towards the barrier, as shown in FIG. 334B). The tool loops may be coupled to the barrier using one of many methods described herein for coupling a device to the barrier, such as adhesive coupling, magnetic coupling, or mechanical coupling. Preferably, the tool loops can be removably coupled to the barrier (for example via velcro straps), such that a barrier may be customized with any number or sizes of tools loops coupled to any appropriate location of the barrier.

FIGS. 377A and 377B illustrate exemplary embodiments of surgical gowns 3770 comprising integrated forearm barriers. As shown in FIG. 377A, the forearm portion of a sleeve of a surgical gown 3770 may be provided with an integrated forearm barrier 3771. The forearm barrier may comprise a tab that may be used to couple barrier to a user's forearm in a fixed position. The tab may be an exposed tab 3772 extending from the sides of the barrier and over the gown sleeve, or partially enclosed tab 3773, partially enclosed within the sleeve. As shown in FIG. 377B, the forearm portion of a sleeve of a surgical gown may comprise one or more pockets 3774 configured to receive one or more barriers 3771 or one or more portions of a barrier therein. Alternatively, the barrier may be coupled to a tie 3775 sewed onto an edge of the gown and configured the wrap around the gown.

FIGS. 378A and 378B illustrate exemplary staging devices suitable for incorporation with the needle handling systems as described herein. A staging device may be configured to store one or more needle dispensing units (e.g., unused suture packs) or empty needle receptacles, for easy access to additional units during an operation. As shown in FIG. 378A, a staging device may comprise an upper arm staging device 3780*a*, configured to couple to an upper arm of the user U, and/or a chest staging device 3780*b*, configured to couple to the chest of the user. As shown in FIG. 378B, an upper arm staging device may comprise an enclosure 3783 providing an interior space 3784 for storing the additional suture packs 3781 and/or needle receptacles 3782. The upper arm staging device may further comprise a fastening mechanism 3785 to securely couple the device to the upper arm of a user, wherein the fastening mechanism may comprise a strap, a velcro strap, or any other fastening mechanism for wearable devices.

FIGS. 379A-379C illustrate exemplary kits for suture handling systems. FIG. 379A shows an exemplary spinal/regional anesthesia kit 3790, comprising a barrier 3795, one or more spinal needles 3790*a*, one or more syringes 3790*b* (#1-3), a sponge mount 3790*c* and one or more sponges 3790*d*, a bandage mount 3790*e* and one or more bandages 3790*f*, one or more instrument or tool loops 3793, one or more safety needles 3790*g* (#1-3), and a pouch 3790*h*. FIG. 379B shows an emergency room suture kit 3791, comprising a barrier 3795, one or more instrument or tool loops 3793 (2-3) and a pair of scissors 3791*a*, one or more swaged needle devices 3791*b* (1-4), a needle receptacle 3791*c* for large needles, a needle receptacle 3791*d* for small needles, a needle driver 3791*e* and forceps 3791*f*, and one or more sponges 3791*g*. FIG. 379C shows a IV line placement kit 3792 comprising a barrier 3795, one or more catheters 3792*a*, suture 3792*b* for closing (e.g., 3-0 Nylon), syringe 3792*c* and needles 3792*d*, a needle receptacle 3792*e*, needle driver 3792*f*, forceps 3792*g*, and scissors 3792*h*, and prep materials 3792*i*. The kits shown in FIGS. 379A-379C are provided by way of example only, and many different kits may be assembled to accommodate specific uses or procedures.

FIGS. 380A and 380B illustrate exemplary needle receptacles suitable for incorporation with the needle handling systems as described herein. FIG. 380A shows a needle receptacle 3800*a* comprising a housing 3801*a* forming an interior space that defines a needle storage chamber or needle slot 3802. The housing also forms a lateral opening 3803 comprising the needle entry aperture, through which a needle may be inserted into the needle slot 3802. The housing further defines a needle driver slot or channel 3804 extending longitudinally along an upper portion of the housing, wherein the needle driver slot is configured to accommodate translation of the tip of a needle driver along the needle driver slot, as described herein. In use, a needle grasped by a needle driver may be inserted through the lateral opening with the tip of the needle driver aligned with the needle driver slot, and then the needle driver tip may be translated in a direction away from the lateral opening and towards the closed end 3805 of the housing to secure the needle within the needle slot.

The lateral opening 3803 may have a width 3803*a* that is greater than the height 3803*b*, in order to constrain the orientation of the needles being inserted through the opening into a substantially lateral orientation. The lateral opening 3803 may be oversized with respect to a needle to be placed into the needle receptacle, in order to facilitate the insertion of the needle through the lateral opening. For example, the width 3803*a* of the lateral opening may be greater than the length of the needle (or, in the case of a curved needle, the straight-line distance between the two ends of the needle), and the height 3803*b* of the lateral opening may be greater than the thickness or wire diameter of the needle. For example, the height may be greater than 10 times the thickness of the needle, such that a user could easily insert the needle through the lateral opening without having to carefully align the needle with the opening.

The needle slot 3802 may have a width 3802*a*, height 3802*b*, and length 3802*c*, wherein the width 3802*a* and height 3802*b* may be similar or equal to the width 3803*a* and height 3803*b* of the lateral opening. Alternatively, the dimensions of the needle slot may be different from the dimensions of the lateral opening, as described herein in reference to FIGS. 382A-D. The height 3802*b* of the needle slot is preferably less than the length of a needle (or, in the case of a curved needle, the straight-line distance between the two ends of the needle), in order to constrain the needles stored within the needle slot into a substantially lateral orientation.

The housing may be substantially box-shaped as shown in FIG. 380A, having a top wall, a bottom wall, and three lateral walls, wherein the needle driver slot extends lengthwise along the top wall. Alternatively, the housing may comprise a single, continuous body or any number of portions coupled together to collectively define the needle slot, the lateral opening into the needle slot, and the needle driver slot. The housing may comprise a rigid material, a flexible material, or a combination thereof. For embodiments of the housing comprising a flexible or deformable material, the width 3804a of the needle driver slot 3804 is preferably less than the thickness or wire diameter of a needle to be placed in the needle receptacle, to reduce the risk of accidental protrusion of a needle tip through the needle driver slot when the flexible material is flexed or deformed. For example, the housing may comprise a flexible upper portion wherein the needle driver slot comprises a slit cut through the flexible upper portion, wherein the flexible material can deform to allow translation of the needle driver tip through the slit.

FIG. 380B shows a needle receptacle 3800b that may be similar in many aspects to needle receptacle 3800a of FIG. 380A. The needle receptacle 3800b comprises a housing 3801b defining a needle slot 3802 therein, a lateral opening 3803 into the needle slot, and a needle driver slot 3804 extending along an upper portion of the housing. The housing 3801b further comprises an extended portion 3806 that extends beyond the lateral opening 3803 of the housing. The extended portion may extend from the bottom portion of the housing as shown, wherein the upper surface of the extended portion may be flush with the bottom surface of the needle slot 3802. The extended portion may function as a landing zone for the needles to be placed into the needle receptacle, wherein a user may place the tip of the needle driver holding the needle against the upper surface of the extended portion, then translate the needle driver along the needle driver slot to place the needle into the needle slot. The extended portion may be configured to fold up to cover and seal off the lateral opening 3803 once the needle receptacle is full. For example, the extended portion may comprise an adhesive or a fastening mechanism to attach the extended portion to the upper portion of the housing when the extended portion is folded up, to cover the lateral opening.

Optionally, the needle receptacle 3800a or 3800b may be provided with one or more internal retaining mechanisms to securely hold the needles in place within the needle slot 3802. For example, the needle receptacle 3800a or 3800b may comprise a spring member 3806 as shown in FIG. 380A, configured to compress the needles within the needle slot against the upper portion of the housing. The spring member may be coupled to the bottom portion of the housing near the lateral opening 3803, such that in use, as a needle is translated along the needle slot away from the lateral opening and towards the closed end 3805, increasing load may be applied to the needle against the upper portion of the housing. The needles placed within the needle slot can thus be held securely between the spring member and the upper portion of the housing. Alternatively, the needle receptacle 3800a or 3800b may comprise one or more clips 3807 as shown in FIG. 380B, extending along the length of the housing and facing the lateral opening 3803. Each clip 3807 may comprise an upper portion 3807a, a lower portion 3807b, and a hinge portion 3807c connecting the upper and lower portions, wherein the clip is configured to apply a compressive force against a needle placed between the upper and lower portions. One or more clips may be coupled to the housing at the lateral opening, such that a needle placed into the needle slot is directed into the one or more clips, and held securely between the upper and lower portions of the clips as the needle is translated away from the lateral opening and towards the closed end 3805. Other suitable internal retaining mechanisms may include brushes or other inwardly projecting members, adhesives, magnets, mechanical dividers, or combinations thereof. The internal retaining mechanisms can provide a secure zone of the needle receptacle wherein from being unintentionally dislodged or removed.

FIGS. 381A and 381B illustrate exemplary needle receptacles suitable for incorporation with the needle handling systems as described herein. FIG. 381A shows a needle receptacle 3810a comprising a housing 3811a, the housing having an interior space defining a needle storage chamber or needle slot 3812a for storing a plurality of needles therein. The upper portion of the housing forms a needle driver slot or channel 3813a configured to receive a tip of a needle driver holding a needle to be placed in the needle receptacle. The housing 3811a, needle slot 3812a, and needle driver slot 3813a may be similar in many aspects to the correspondingly named elements described with reference to FIGS. 380A and 380B. However, rather than the lateral opening shown in FIGS. 380A and 380B, the housing 3811a forms a top opening 3814a comprising the needle entry aperture through which a needle may be inserted into the needle receptacle. The top opening 3814a may comprise a cut-out in the upper portion of the housing, for example. The top opening may define a landing zone and entry zone of the needle receptacle. The top opening may be oversized with respect to the size of the needle to be inserted through the top opening, to facilitate the insertion of the needle through the top opening. For example, the length 3815a of the top opening may be greater than the length of the needle (or, in the case of a curved needle, the straight-line distance between the two ends of the needle), and the width 3815b of the top opening may be greater than the thickness or wire diameter of the needle (or, in the case of a curved needle, the distance between the midpoint of the needle body and the midpoint of a straight-line drawn between the two ends of the needle). Optionally, the length 3815a of the top opening may be greater than the width 3815b of the top opening in order to encourage the user to orient the needle with the length of the needle (or, in the case of a curved needle, the straight-line distance between the two ends of the needle) substantially aligned with the length of the top opening.

FIG. 381B shows a needle receptacle 3810b that may be substantially similar in many aspects to the needle receptacle 3810a. For example, the housing 3811b forms an interior space defining the needle slot 3812b, and the upper portion of the housing defines a needle driver slot 3813b configured to receive a tip of a needle driver tip therein. The upper portion of the housing further defines a top opening 3814b through which a needle may be inserted. The top opening 3814b may comprise a cut-out in the upper portion of the housing, for example. The top opening 3814b may be oversized with respect to the dimensions of the needle to secured inside the needle receptacle, to facilitate the insertion of the needle through the top opening. While FIG. 381A shows a housing 3811a that is substantially box-shaped, the housing 3811b of FIG. 381B is generally arrow-shaped, wherein the closed end 3816b of the needle receptacle forms the head of the arrow, and the second end 3816a adjacent the top opening forms the tail of the arrow. Accordingly, the top opening 3814b may be shaped to conform to the curvature of a curved needle, so as to encourage placement of the needle through the opening in an orientation with both ends of the needle pointing away from the direction of translation of the needle along the needle slot. Other aspects of the housing 3811b, needle slot 3812b, and needle driver slot 3813b may be similar in many aspects to the correspondingly named elements of needle receptacles 3800a and 3800b shown in FIGS. 380A and 380B.

Optionally, the needle receptacle 3810a or 3810b may further comprise one or more internal retaining mechanisms as described in reference to FIGS. 380A and 380B. The one or more internal retaining mechanisms can secure the needles within the needles slot to provide a secure zone of the needle receptacle.

FIGS. 382A-382D illustrate optional configurations of a needle receptacle as in FIGS. 380A-381B. To prevent the unintentional removal of the needles from the needle receptacle once the needles have been placed inside the needle slot, the height or depth of the needle slot may vary along the length of the needle slot. For example, as shown in the cross-sectional side view of FIG. 382A, a needle slot 3820a may have an entry zone 3821a near the needle entry aperture of the needle receptacle and a secure zone 3822a near the closed end of the needle receptacle. The lower interior surface 3824a of the needle slot, which may be formed by the bottom portion of the housing as described herein, may be positioned at a first elevation (or z-axis position) at the entry zone, and at a second elevation (or z-axis position) at the secure zone, the first elevation higher than the second elevation. Further, the needle slot may have a first depth 3825a at the entry zone and a second depth 3826a at the secure zone, the second depth greater than the first depth. Thus, when a needle is inserted through the needle entry aperture (e.g., lateral opening or top opening as shown in FIGS. 380A-381B) and subsequently translated away from the entry aperture and towards the closed end of the needle receptacle, the needle transitions from the shallow entry zone at a relatively higher elevation into the deeper secure zone at a relatively lower elevation. The needle is thus stored within the secure zone at a lower elevation than the elevation at the entry zone, such that there is decreased risk of the needle being accidentally removed from the needle slot, particularly while the needle receptacle is maintained at a substantially lateral or planar orientation. The shallow, higher-elevation entry zone 3821 may be formed by an elevated bottom portion of the housing near the entry aperture, for example. The needle slot may be shaped to transition gradually from the first thickness into the second thickness, with a transition zone 3823a in which the depth of the needle slot increases proportionally to the position along the length (x-axis) of the needle slot. Alternatively, the needle slot may transition abruptly from the entry zone into the secure zone, for example with a vertical drop-off from the first elevation down to the second elevation.

Figure 382A:
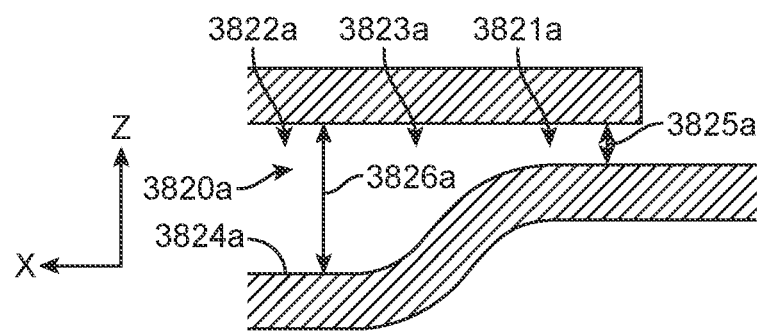
Figure 382B:
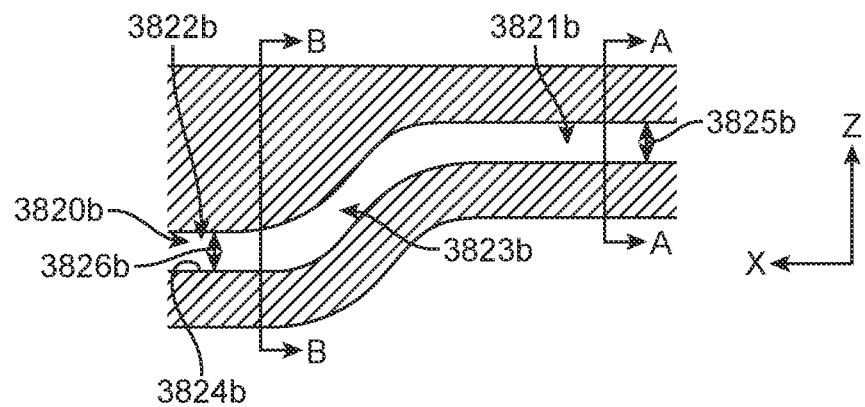
Figure 382C:
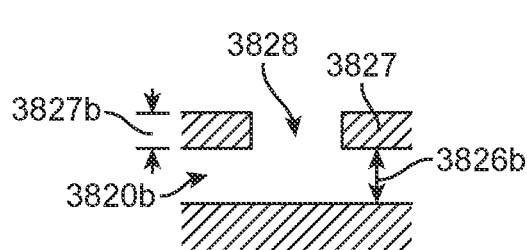
Figure 382D:
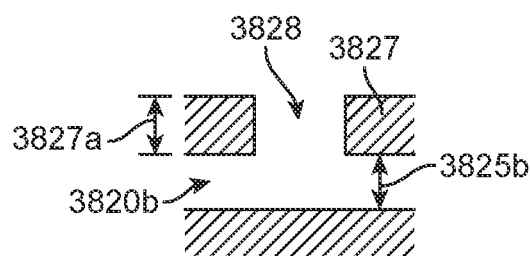

FIG. 382B shows a cross-sectional side view of another exemplary configuration of a needle slot 3820b. Similarly to the needle slot 3820a of FIG. 382A, the needle slot 3820b may comprise an entry zone 3821b near the entry aperture of the housing and a secure zone 3822b near the closed end of the housing, wherein the lower interior surface 3824b of the needle slot may be positioned at a relatively higher elevation (or z-axis position) with respect to the elevation at the secure zone. However, the first depth 3825b of the needle slot at the entry zone and the second depth 3826b of the needle slot at the secure zone may be similar or substantially equal. Such a configuration may be achieved with an upper portion of the housing having varying thickness along the length (x-axis) of the needle receptacle, as shown in FIGS. 382C and 382D. FIG. 382C is a transverse cross-sectional view of the needle slot 3820b along line A-A as shown in FIG. 382B, and FIG. 382D is a transverse cross-sectional view of the needle slot 3820b along line B-B as shown in FIG. 382B. Cross-section A-A of FIG. 382C shows the cross-section of the needle slot at the entry zone, where the upper portion 3827 of the housing, defining the needle driver slot 3828, has a first thickness 3827a. Cross-section B-B of FIG. 382D shows the cross-section of the needle slot at the secure zone, where the upper portion 3827 of the housing has a second thickness 3827b that is greater than the first thickness 3827a. The greater thickness of the upper housing at the secure zone compensates for the relatively lower elevation of the lower interior surface of the needle slot at the secure zone to result in a needle slot depth 3826b at the secure zone that is similar to the needle slot depth 3825b at the entry zone. The first needle slot depth 3826a and the second needle slot depth 3826b may be dimensioned to securely hold a needle between the upper and lower portions of the housing. The needle slot may be shaped to transition gradually from the first thickness into the second thickness, with a transition zone 3823b in which the depth of the needle slot increases proportionally to the position along the length (x-axis) of the needle slot.

FIGS. 383A-C show an exemplary needle receptacle 3830 configured to store a plurality of needles in an ordered array. The needle receptacle 3830 comprises a housing 3831, which forms an interior space that defines a needle storage chamber or needle slot 3832 for storing a plurality of needles. The housing also defines a needle entry aperture comprising a lateral opening 3833, through which a needle may be inserted into the needle slot. The needle slot 3832 may comprise a planar needle slot dimensioned to store the plurality of needles in substantially planar or lateral orientation. The housing further defines a needle driver channel or slot 3834 extending along a length 3836 of an upper portion of the housing. The housing 3831, needle slot 3832, lateral opening 3833, and needle driver slot 3833 may be similar in many aspects to correspondingly named elements of needle receptacles described herein, such as the needle receptacles described with reference to FIGS. 380A-381B. The needle slot may comprise a plurality of segments 3835, each segment extending across the needle driver slot and along the width 3837 of the housing. Each segment may be configured to hold a single needle therein, for example by way of securing elements configured to immobilize each needle within a single segment of the needle slot. For example, as shown, the upper portion of the housing may comprise a plurality of securing elements such as a plurality of tabs 3838, configured to secure each needle within a single segment. FIG. 383B shows a cross-sectional view of the needle receptacle 3830 with the tab 3838 in the default configuration, wherein the needle N, disposed within a single segment of the needle slot 3832, is not yet secured in place by the tab. FIG. 383C shows a cross-sectional view of the needle receptacle 3830 with the tab 3838 in the secured configuration, wherein the tab has been pushed down to secure the needle N between the tab and the lower portion of the housing. Optionally, the plurality of tabs may comprise an adhesive and/or a magnet to further secure the needle between the tab and the lower portion of the housing. The plurality of tabs can thus enable the storage of the plurality of needles within the needle slot in a non-overlapping ordered array, wherein the needles may be stored spaced apart from one another to facilitate visual counting of the needles stored inside the needle receptacle.

FIGS. 384A-384B show another exemplary needle receptacle 3840 configured to store a plurality of needles in an ordered array. The needle receptacle 3840 comprises a housing 3841 defining a needle storage chamber or needle slot 3842 for storing a plurality of needles, and a needle entry aperture comprising a lateral opening 3843, through which a needle may be inserted into the needle slot. The upper portion of the housing further defines a needle driver channel or slot 3844 extending along a length 3846 of the housing. The housing 3841, needle slot 3842, lateral opening 3843, and needle driver slot 3843 may be similar in many aspects to correspondingly named elements of needle receptacles described herein, such as the needle receptacles described with reference to FIGS. 380A-381B and 383A-C. The needle receptacle 3840 may further comprise a plurality of dividers 3848 disposed within the needle slot 3842 and configured to divide the needle slot into a plurality of segments 3845, each segment extending along the width 3847 of the needle receptacle and configured to hold a single needle therein. The plurality of dividers may be coupled to the internal surface of the bottom portion of the housing, for example. In use, a needle may be inserted into the needle receptacle through the lateral opening 3843, translated along the needle slot in a direction away from the lateral opening, then released into an empty segment of the needle slot that is farthest from the lateral opening. The needle may be stored spaced apart from other needles in the needle slot by way of the dividers separating the plurality of segments.

Optionally, as shown in FIG. 384A, to further secure a needle within a single segment, the needle receptacle may be provided with one or more magnets 3849 configured to hold the needle in place within the needle slot. For example, the bottom portion of the housing may have one or more magnets integrated within or attached to the internal surface of the bottom portion, such that a needle placed onto the surface is securely held in place by the one or more magnets. Optionally, as shown in FIG. 384B, the needle receptacle 3840 may be adapted to compress down into a reduced-height configuration, to further stabilize the needles into the ordered array within the needle slot. For example, the upper and lower portions of the housing may be configured to compress together when a user pushes downwards onto the needle receptacle.

FIGS. 385A-385B illustrate an exemplary embodiment of devices 3850 and 3855 for securing a plurality of needles, in accordance with many embodiments. FIG. 385A illustrates a top view, FIG. 385B illustrates a longitudinal cross-sectional view. In the illustrated embodiment, the needle trap 3850 can be a planar device that is comprised of several zones: 1) an entry zone 3850a, 2) an entryway or transition zone 3850b and 3) a secure zone 3850c, in accordance with many embodiments described herein (e.g., needle trap 331). The needle trap 3850 may comprise an upper structure 3851 and a lower structure 3852 that are securely coupled together around an outer portion of the needle trap 3850. The needle trap 3850 may comprise a needle driver slot 3853 extending through both the upper structure 3851 and the lower structure 3852, the needle driver slot configured to provide clearance for a needle driver along the entire length of the needle trap 3850 for translation of a needle 3853 from the entry zone 3850a to the secure zone 3850c. The needle trap can further comprise a needle slot 3854 that constrains the secured needles into a single needle depth array when received by needle receiver 3855, to minimize overall depth profile and facilitate needle counting. The lower structure 3852 may comprise a through opening 3859 that runs transverse to the long axis of the needle trap 3850, and may be located anywhere within the entry zone 3850a and the entryway or transition zone 3850b. The through opening 3859 of needle holder 3850 may be configured to receive the needle receiver 3855 and allow the needle receiver 3855 to slide freely or with a desired resistance therethrough. The needle receiver 3855 may comprise a plurality of needle receiving tabs 3857a and 3857b, which may be located on opposing sides of the longitudinal axis of the needle receiver 3955 as shown in FIG. 385A. The plurality of needle receiving tabs 3857a/b may be shaped so as to receive one or more needles 3858 in an orientation that would locate the sharp ends of the one or more needles 3858 away from the direction of movement when the one or more needles are placed against surface 3856 of the needle receiver 3855 and translated into the needle trap 3850 with the needle driver (i.e., such that the sharp ends of the needles face away from a user when the needle trap 3850 is donned and the needle receiver 3855 is loaded, to minimize accidental needle-stick injury). As shown in FIG. 385A, the needle receiving tabs 3857a/b can be spaced longitudinally such that one needle can be located between adjacent needle receiving tabs 3857a/b.

The needle receiver 3855 may be translated into the needle trap 3850 by conveyance. The needle receiver, initially without needles, may be slide along the underside of the lower structure 3852 of needle trap 3850, through opening 3859 of the needle trap 3850, and then onto the upper side of lower structure 3852 of needle trap 3850. In this configuration, the needle receiver 3855 may present surface 3856 between adjacent needle receiving tabs 3857a/b for receiving a needle 3858 at the entry zone 3850a of needle trap 3850. Through the motion of placing a needle onto surface 3856 of the needle receiver 3855 and against needle receiving tabs 3857a/b, and translating the needle from the entry zone 3850a through to the secure zone 3850c of needle trap 3850, the needle receiver 3855 translates into the needle trap 3850 and presents the next adjacent pair of needle receiving tabs 3857a/b and surface 3856 for subsequent needle placement and disposal (i.e, no separate action is required to advance the needle receiver 3855 into the needle trap 3850). The needle receiver may prevent bunching of subsequently placed needles, may allow for easy segregation of adjacent needles, and thereby may allow for easy needle counting.

In different embodiments, the needle trap 3850 and needle receiver 3855 may have different dimension depending upon the size of the needles 3858 being stored. Thus, a small needle receiver and complementary needle trap used to store small needles may have smaller dimensions than a large needle receiver and complementary needle trap used to store larger needles.

In many embodiments, the tip to tip distance of each of the plurality of needles is within a range selected from the group consisting of 75% to 100% of the width of the needle slot, 80% to 99% of the width of the needle slot, and 85% to 98% of the width of the needle slot and 90 to 97% of the width of the needle slot.

In many embodiments, the tip to tip distance of each of the plurality of needles is within a percentage of the width of the needle slot in the expanded configuration, the percentage within range selected from the group consisting of 75% to 100% of the second width of the needle slot, 80% to 99% of the second width of the needle slot, and 85% to 98% of the second width of the needle slot and 90 to 97% of the second width of the needle slot. The needle slot may comprise a length, a width, and a height, the length being greater than the width and the width being greater than the height.

The needle receiver 3855 may be comprised of a flexible material that allows the needle receiver to bend through the opening 3859 as shown in FIG. 385B. The needle receiver 3855 and plurality of needle receiving tabs 3857a/b may comprise a one-piece design or multi-piece design. In a multi-piece design, the plurality of needle receiving tabs 3857a/b may be comprised of a foam or rubber material, and may be adhered to the surface 3856 of the needle receiver 3855.

The needle receiver 3855 may comprise a series of through openings to receive a needle driver tip, the through openings located along the longitudinal axis of the needle receiver 3855 and located between adjacent needle receiving tabs 3857a/b. This series of through opening may be sized to match the needle driver slot 3853 of the needle trap 3850, such that a needle 3858 can easily be placed into the needle receiver 3855 and translated with the needle driver from the entry zone 3850a through to the secure zone 3850c of the needle trap 3850.

FIGS. 386A-386B illustrate an exemplary embodiment of devices 3860 and 3865 for securing a plurality of needles, in accordance with many embodiments. FIG. 386A illustrates a top view, FIG. 386B illustrates a longitudinal cross-sectional view. In the illustrated embodiment, a needle trap 3860 may be configured according to the many embodiments described herein (e.g., as the needle trap 3850 shown in FIGS. 385A-B, with like identifiers incremented by 10). Further, in this embodiment a needle receiver 3865 may be configured to engage a needle trap 3860 according to embodiments described herein (e.g., as the needle receiver 3855 engages needle trap 3850 shown in FIGS. 385A-B), and operate by conveyance. In this embodiment, needle receiver 3865 may comprise a plurality of needle receiving tabs 3857 located along the longitudinal centerline of the needle receiver 3866 and configured to receive one or more needles 3868.

The needle receiver 3865 may be comprised of a flexible material that allows the needle receiver to bend through the opening 3869 as shown in FIG. 385B. The needle receiver 3855 and plurality of needle receiving tabs 3857a/b may comprise a one-piece design, wherein the needle receiving tabs 3857 are formed by the cutting of a pattern in the needle receiver 3865 and bent upwards so as to receive a needle 3866. As shown in FIG. 386A, this pattern may be in the form of a backwards "C," however any appropriate pattern may be cut so as to allow the tabs to bend upwards and receive a needle. In many embodiments, the needle receiving tabs 3857 may deflect as the needle receiver 3865 is slid through the opening 3869 of needle trap 3860, but return to their bent upwards configuration afterwards so as to receive a needle 3868.

Figure 387A:
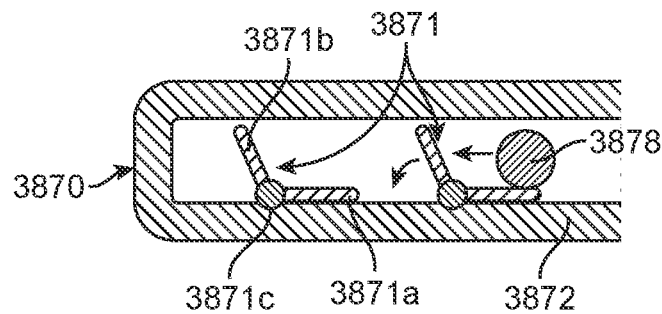
Figure 387B:
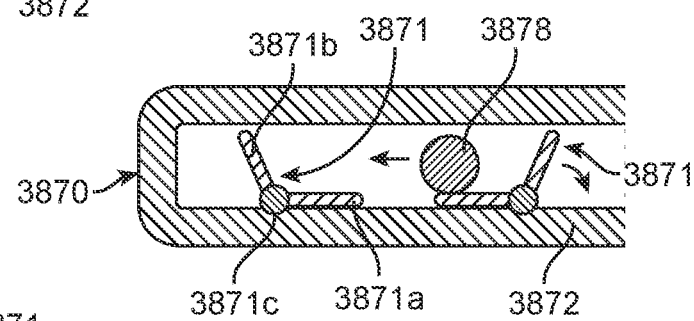
Figure 387C:
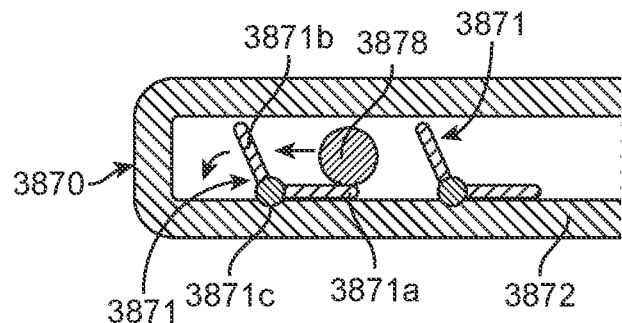
Figure 387D:
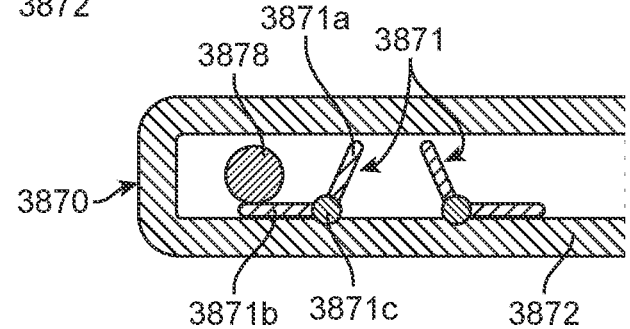

FIGS. 387A-387D illustrate longitudinal cross-sectional views of exemplary internal spring dividers suitable for incorporation with the needle handling systems as described herein. The internal spring dividers 3871 may be configured to prevent bunching of needles 3878 upon sequential placement of needles into needle trap 3870. The internal spring dividers may each comprise a leading structure 3871a and a tailing structure 3871b attached at a pivot structure 3871c. The internal spring dividers 3871 may be rotatably attached to a lower structure 3872 of needle trap 3870 via a helical torsion spring or similar at pivot structure 3871c. At rest, the internal spring dividers 3871 may be configured such that the spring forces the leading structure 3871a against the lower structure 3872 of needle trap 3870, and thereby in position to receive a needle 3878 (as shown in FIG. 387A). As a needle 3878 is translated into the needle trap 3870, the trailing structure 3871b of an internal spring divider 3871 may receive the needle, and with continued translation of the needle into the needle trap the internal spring divider may rotate in the direction of needle translation as the spring force is overcome, forcing the trailing edge 3871b of the internal spring divider against the lower structure 3872 (as shown in FIG. 387B). With continued translation of the needle 3878, the internal spring divider may return to its resting position and a next internal spring divider 3871 may receive the needle (as shown in FIG. 387C), these actions repeated until the needle 3878 is translated to the end of needle trap 3870. Once at the end of the needle trap 3870, the trailing structure 3871b of the internal spring divider 3871 nearest the end of the needle trap may be held against the lower structure 3872, as the spring of the internal spring divider may be configured so as not to overcome the weight of the needle (and thus not return the internal spring divider to its resting position). Thus, as subsequent needles 3878 are deposited into the needle trap 3870, the leading structure 3871a of the internal spring divider 3871 nearest the end of the needle trap 3870 may block any further translation of subsequent needles towards the end of the needle trap. In this way, each deposited needle may be kept from bunching, and facilitate the easy counting of deposited needles.

FIG. 388 illustrates a longitudinal cross-sectional view of an exemplary embodiment of a device for securing a plurality of needles, suitable for incorporation with the needle handling systems as described herein. In this embodiment, a needle receiver 3886 may be rolled or coiled around a rotatable element and comprise a series of slits 3887 on a side of the needle receiver opposite that of the rotatable element center. Each slit 3887 may be sized so as to receive a needle 3888. Adjacent slits 3887 in the needle receiver 3886 may be spaced apart longitudinally as necessary according to the size of the needles being received. As shown in FIG. 388, the needle receiver 3886 has been partially unrolled and laid against a structure 3880 of a needle trap of any of the embodiments described herein (structure 3880 may comprise, for example, a lower structure 341 of needle trap 331), such that the slits 3887 are facing towards the structure 3880. A needle 3888 may be placed in a vacant slit 3887, thereby allowing the safe disposal of the needle. Upon further unrolling and advancement of the needle receiver 3886 translationally along the surface of structure 3880, two things may occur: 1) the needle placed in the previously vacant (but now occupied) slit 3887 may be trapped between the needle receiver 3886 and the structure 3880, and 2) the next vacant slit 3887 may be made available to receive another needle. This cycle of needle disposal can be repeated as necessary to dispose of needles 3888. In some embodiments, the unrolling and translation of the needle receiver may be performed in a single motion via the action of depositing a needle 3888 into a slit 3887 and moving it translationally along the structure 3880. In some embodiments, the unrolling and translation of the needle receiver may be performed in two motions: the first action being the depositing of a needle 3888 into a slit 3887; the second action being a user manually translating the needle receiver 3886 so as to trap the deposited needle, unroll the needle receiver, and present the next vacant slit 3887. The needle receiver 3886 may comprise a flexible material. In some embodiments, the needle receiver 3886 may comprise a transparent or semi-transparent material. In some embodiments, the needle receiver slits 3887 may rely on the physical trapping of a needle 3888 against the structure 3880 to keep the needle in place. In some embodiments, the needle receiver slits 3887 may rely on the addition of an adhesive or other surface treatment to aid in the physical trapping of a needle 3888. In many embodiments, the needle receiver may prevent bunching of deposited needles, and facilitate the easy counting of deposited needles.

FIGS. 389A-389B illustrate an exemplary embodiment of a device for securing a plurality of needles comprising internal filaments, in accordance with many embodiments. FIG. 389A illustrates a top view, FIG. 389B illustrates a longitudinal cross-sectional view. In the illustrated embodiment, a needle trap 3890 may be configured according to the many embodiments described herein (e.g., as the needle trap 3850 shown in FIGS. 385A-B, with like identifiers incremented by 40). A plurality of internal filaments 3897 may be configured to prevent bunching of one or more needles 3898 upon sequential placement of needles into needle trap 3890. The internal filaments 3897 may each be comprised of internal filaments 3897a and internal filaments 3897b, which may attach to the internal (i.e., within the needle slot 3894) surface of the upper structure 3894 at opposing sides of the longitudinal needle driver slot 3893. As shown in FIG. 389A, the internal filaments 3897a/b may be configured so as to extend from their attachment points towards the center of the needle trap 3890 (and thus the center of the needle driver slot 3893), and form a plurality of needle receiving spaces between adjacent pairs of internal filaments 3897a/b within the needle slot 3894 that can complementarily receive a needle 3898. As shown in FIG. 389B, the internal filaments 3897 may also be configured to extend from their respective attachment points at the internal surface of the upper structure 3894 to the internal surface of the lower structure 3892 of needle trap 3890 (i.e., configured to span the entire height of the needle slot 3894).

In some embodiments, each internal filament 3897a/b may be attached within the needle trap 3893 as described above via a torsion spring, a helical torsion spring, or similar. In these embodiments, the internal filaments may comprise a rigid or semi-rigid material. In some embodiments, each internal filament 3897a/b may be attached within the needle trap 3893 as described above via an adhesive, a weld, or similar permanent attachment. In these embodiments, the internal filaments may comprise a flexible material capable of deforming.

At rest, the internal filaments 3897a/b may be configured such that the ends of the internal filaments opposite their respective attachment points are forced down or touch against the internal surface of lower structure 3892 (e.g., by the force of their respective springs at their attachment points, or by deforming, see FIG. 389B). As a needle 3898 is translated into the needle trap 3890, the needle may abut a pair of internal filaments 3897a/b, and with continued translation of the needle into the needle trap the internal filaments 3897a/b may deflect in the direction of needle translation to allow the needle to advance further into the needle trap and into a receiving space between adjacent pairs of internal filaments. The internal filaments 3987a/b may return to their resting position and a next pair of internal filaments 3897a/b may deflect with continued translation of the needle into the needle trap 3890, these actions repeated until the needle 3898 is translated to the end of needle trap 3890. Once at the end of the needle trap 3890, the needle 3898 may hold the internal filaments 3897a/b nearest the end of the needle trap in their resting position by inhibiting the internal filaments from deflecting further upon subsequent translation of a next needle. Thus, as subsequent needles 3898 are deposited into the needle trap 3890, the needle receiving spaces between adjacent pairs of internal filaments 3897a/b within the needle slot 3894 may successively become occupied by a needle 3898. In this way, each deposited needle may be kept from bunching, and facilitate the easy counting of deposited needles.

Figure 390A:
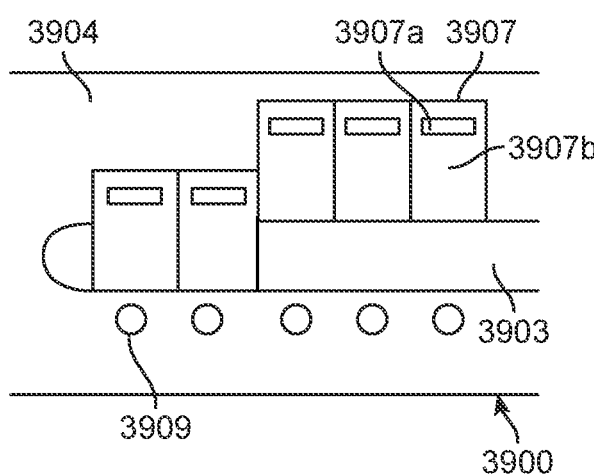
Figure 390B:
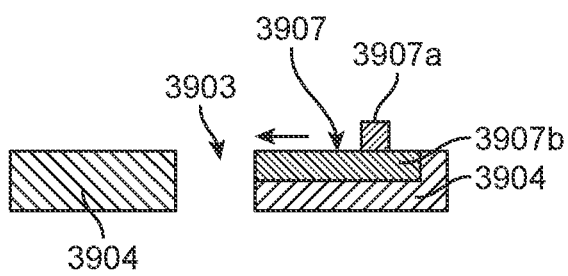
Figure 390C:
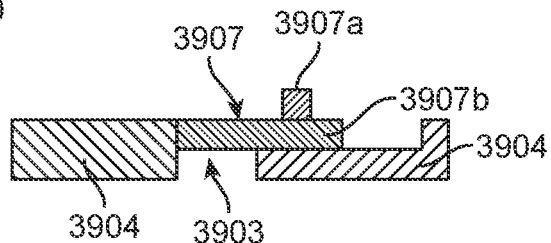
Figure 390D:
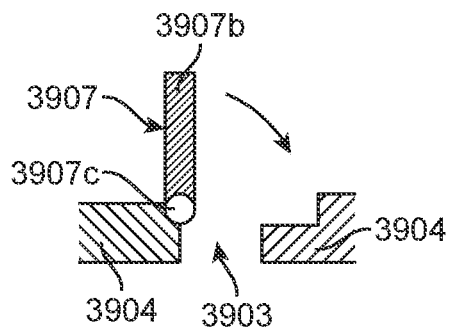
Figure 390E:
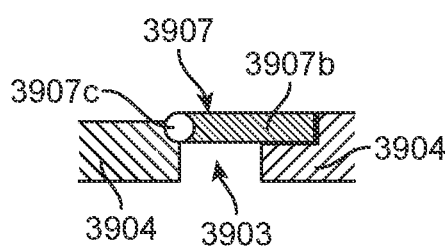

FIGS. 390A-390E illustrate exemplary embodiments of needle driver slot covers suitable for incorporation with the needle handling systems as described herein. FIGS. 390A-390C illustrate a top view (FIG. 390A), and lateral cross-sectional views (FIGS. 390B-390C) of one exemplary embodiment, and FIGS. 390D-390E illustrate lateral cross-sectional views of another exemplary embodiment. In the illustrated embodiments, a needle trap 3900 may be configured according to the many embodiments described herein (e.g., as the needle trap 3850 shown in FIGS. 385A-385B, with like identifiers incremented by 50). In the illustrated embodiments, the needle driver slot covers 3907 may be configured to slidably or rotatably attach to upper structure 3904 of needle trap 3900 at one side of the needle driver slot 3903. In the illustrated embodiments, the needle trap 3900 may comprise a plurality of indicators 3909 that correspond to a needle driver slot cover 3907, which may indicate when a corresponding needle driver slot is actuated in order to facilitate easy needle counting (e.g., by a change of indicator color).

In some embodiments (as shown in FIGS. 390A-390C), the needle slot covers 3907 may comprise a rectangular body 3907b slidably attached to a recess in the upper structure 3904 of needle trap 3900. Further, in this embodiment needle slot covers 3907 may comprise a tab 3907a attached to each rectangular body 3907b, which may be configured to facilitate the actuation of the needle slot cover by a surgeon (i.e., sliding of the tab from its open position, where the needle driver slot cover 3907 does not cover the needle driver slot 3903, to its closed position, where the needle driver slot cover 3907 does cover the needle driver slot 3903). After a needle is deposited fully into the needle trap 3900 by the surgeon, the surgeon may actuate the needle slot cover 3907 directly above the deposited needle so as prevent further deposition of a subsequent needle into the underlying space within the needle trap. In this way, the needle trap covers may prevent bunching of needles and facilitate the counting thereof.

In some embodiments (as shown in FIGS. 390D-390E), the needle slot covers 3907 may comprise a rectangular body 3907b rotatably attached to the upper structure 3904 of needle trap 3900 at rotating element 3907c. Further, in this embodiment needle slot covers 3907 may be initially configured to be in an open state (i.e., the needle driver slot covers 3907 do not cover the needle driver slot 3903). After a needle is deposited fully into the needle trap 3900 by the surgeon, the surgeon may actuate the needle slot cover 3907 directly above the deposited needle by rotating the needle slot cover down over the needle driver slot 3903, allowing the end of the needle slot cover opposite the rotating element to be seated into a recess in the upper structure 3904 (as shown in FIG. 390E). By this action, further deposition of a subsequent needle into the underlying space within the needle trap is prevented. In this way, the needle trap covers may prevent bunching of needles and facilitate the counting thereof.

FIGS. 391A-391B illustrate exemplary embodiments of devices for securing a plurality of needles with a ratcheting cover, in accordance with many embodiments. FIG. 391A illustrates a top view of an embodiment of a needle trap with a ratcheting cover being displaced longitudinally with the placement of a needle 3918 by a needle driver 3919, FIG. 391B illustrates a top view of the embodiment after the needle 3918 has been placed and the ratcheting cover has ratcheted longitudinally over the last placed needle. In the illustrated embodiment, a needle trap 3910 may be configured according to the many embodiments described herein (e.g., as the needle trap 3850 shown in FIGS. 385A-385B, with like identifiers incremented by 60). In the illustrated embodiment, the ratcheting cover 3915 may be configured to engage the needle trap 3910 at the end of the needle trap opposite the entry zone 3910a, and cover the upper structure 3911. In this embodiment, when needle 3918 is translated into the far end of the needle trap 3910 with needle driver 3919 through the needle driver slot 3913, the needle driver 3919 may laterally shift the ratcheting cover 3915 in the direction of needle driver motion; upon subsequent release of the needle and removal of the needle driver from the needle trap, the ratcheting cover may translate longitudinally towards the entry zone 3910a so as to cover the needle just deposited. In many embodiments, the ratcheting cover may be a spring-loaded device, configured to translate/ratchet longitudinally in increments according to the size of the needle 3918 being placed in the needle trap 3910.

Figure 4:
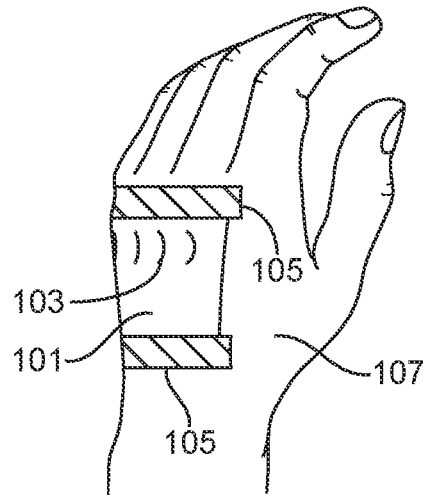
FIG. 4 illustrates a side view of a suture package attached to a glove with adhesive strips.
Figure 392C:
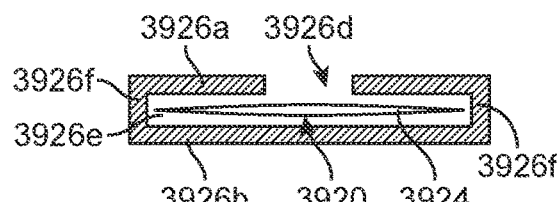
Figure 392D:
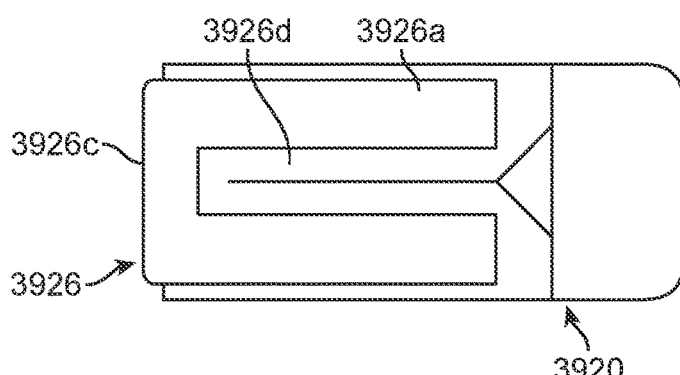
Figure 392E:
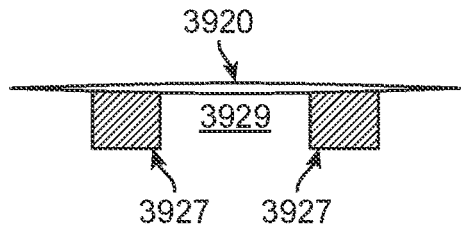
Figure 392F:
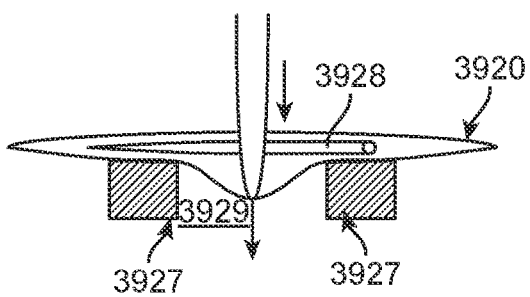

FIGS. 392A-392F, FIGS. 392A1-392A12, and FIGS. 392B1-392B5 illustrate exemplary embodiments of devices for securing a plurality of needles, in accordance with many embodiments. FIG. 392A illustrates a perspective view of an embodiment of a needle trap, FIG. 392B illustrates a perspective view of the embodiment of a needle trap of FIG. 392A placed inside an embodiment of a second structure, FIG. 392C illustrates a lateral cross-sectional view of the embodiments shown in FIG. 392B, FIG. 392D illustrates a top view of the embodiment of a needle trap of FIG. 392A placed inside an embodiment of a second structure, and FIGS. 392E-392F illustrate lateral cross-sectional views of an embodiment of a needle trap. FIGS. 392A1 illustrates a top view of an embodiment of how a needle trap as described herein may be constructed out of one sheet of material, and 392A2 illustrates a perspective view of an embodiment of how a needle trap as described herein may be constructed out of two separate sheets of material. FIGS. 392A3-392A4 illustrate top views of embodiments of a needle trap. FIG. 392A5 illustrates a top view of an embodiment of a needle trap, and FIG. 392A6 shows a longitudinal cross-sectional view of the needle trap shown in FIG. 392A5. FIG. 392A7 illustrates a top view of an embodiment of a needle trap, and FIG. 392A8 shows a longitudinal cross-sectional view of the needle trap shown in FIG. 392A5. FIGS. 329A9-392A11 show lateral cross-sectional views of a needle trap as described herein before, during, and after placement of a needle into the trap. FIG. 392A12 illustrates a perspective view of an embodiment of a needle trap as described herein with internals configured to aid in securing needles after being placed into the trap.

In the illustrated embodiments of FIG. 392A, FIG. 392A3, and FIG. 392B, a needle trap 3920 may be a planar device comprised of several zones: 1) an entry zone 3920a, 2) an entryway or transition zone 3920b and 3) a secure zone 3920c. The needle trap 3920 may comprise an upper structure 3921 and a lower structure 3922 that are securely coupled together around an outer portion of the needle trap 3920. The needle trap 3920 may comprise a needle driver slot 3923 extending through the upper structure 3921, the needle driver slot configured to provide clearance for a needle driver along the entire length of needle translation from entry zone 3920a to secure zone 3920c. The needle trap 3920 may further comprise a needle slot 3924 that constrains the secured needles into a single needle depth array, to minimize overall depth profile and facilitate needle counting. The configuration of the needle trap 3920 can be described with reference to an X-axis, Y-axis, and Z-axis as shown in FIG. 392A.

In an embodiment, the entry zone 3920a of the needle trap 3920 may comprise a partially rectangular flat zone or area in the X-Y plane that is an exposed part of the lower structure 3922. A surgeon can hold used needles 3928 with a needle driver and place the used needles 3928 on an upper surface of the entry zone 3922 (i.e., surface in the positive Z-axis). The contact and/or force of the needle 3928 against the entry zone 3928 may cause the curvature of the used needle 3928 to be moved into a planar orientation flat against the entry zone upper surface in the X-Y plane with the convex mid-portion of the curved needle 3928 facing or pointing towards the transition zone 3920b.

The entry zone 3920a may be the same width (Y-axis) relative to needle slot 3924 and the perimeter around the entry zone 3920a may have a contrasting color to aid visual recognition. The upper surface of the entry zone 3920a may comprise a low friction material. The upper surface of the entry zone 3920a may include graphic guides to indicate proper needle orientation to the surgeon. The entry zone 3920a may be folded over upper structure 3921 to secure needles deposited within the needle trap 3920.

The transition zone 3920b may be disposed between the entry zone 3920a and the secure zone 3920c. In some embodiments, in the transition zone, edges 3925 of the upper structure 3921 where the upper structure intersects with the needle driver slot 3923 at the entry zone/transition zone may be folded inward into the needle slot 3924 as shown in FIG. 392A5-392A6. In a folded inward configuration, edges 3925 may increase the depth (Z-axis) of the needle slot at the entry zone/transition zone intersection and facilitate loading of needles into the needle trap, as exemplified in the longitudinal cross-sectional view of FIG. 392A6. Additionally, the inward-folded edges 3925 may prevent needles 3928 from exiting back out of the needle trap 3920 by blocking any egress (e.g, the inward folded edges may catch the needles). In the transition zone, the compressive side load on the needles ends may be increased and the height (Z-axis) of the needle slot may be decreased as the secured needles are translated through the transition zone, thus constraining the needles to a single needle deep array extending longitudinally along the secure zone 3920c. In some embodiments, in the transition zone, edges 3925 of the upper structure 3921 where the upper structure intersects with the needle driver slot 3923 at the entry zone/transition zone may be folded outward as shown in FIG. 392A7-392A8. In a folded outward configuration, edges 3925 may help guide a needle driver into the needle driver slot 3923. In some embodiments, edges 3925 may not be folded, and the height (Z-axis) of the needle slot 3924 may remain constant from the transition zone 3920b through the secure zone 3920c. In some embodiments, the width (Y-axis) of the entry zone 3920a, transition zone 3920b, and secure zone 3920c may be the same.

The secure zone 3920c may be disposed adjacent the transition zone 3920b, and comprise the region in which full compressive side loading is applied to the needle ends to prevent unintentional removal or dislodging of the needles 3928.

The needle trap 3920 may be configured to promote needles, upon entry, to assume an orientation where the convex side of the needle 3928 faces the secure zone 3920c, and the concave side, sharp point, and tail of the needle 3928 face the entry zone 3920a. Thus, the needle trap 3920 may be configured to have the sharp point and tail end of the needle 3928 pointing away from the direction of motion, thereby reducing the risk of needle-stick injury. The needle driver slot 3923 may intersect a portion of the needle slot 3924, such as a middle portion of the needle slot, and may be disposed in the midline of the needle trap 3920 in the X-axis such that the distal tip of the needle driver can translate the needle 3928 along the X-axis of the needle trap 3920. Alternatively, the needle driver slot 3923 may intersect the needle slot 3924 off the midline or asymmetrically, such that the needle driver slot extends along an axis substantially parallel to, but not overlapping, the X-axis of the needle trap 3920. The needles 3928 may slide/translate within the needle slot 3928 deeper into the secure zone 3920c (i.e., away from the entry zone 3920a) without excessive resistance or sensitivity as to how the needles 3928 are grasped by the needle holder. In an embodiment, the secure zone 3920c can prevent used needles 3928 from being removed from the needle trap 3920.

In a preferred embodiment, the needle 3928 is moved into contact with the entry zone 3920a of the lower structure 3922 by the surgeon manipulating the tip of the needle driver holding the needle. The needle 3928 can be pushed against the entry zone 3920a and become aligned with the X-Y plane of the needle trap 3920. The needle 3928 can then be moved in translation along the longitudinal X-axis of the needle trap 3928 from the entry zone 3920a into the transition zone 3920b where the needle 3928 slides into the needle slot 3924 with the convex side facing the secure zone 3920c and the sharp point and tail of the needle 3928 facing the entry zone 3920a. The needle driver can be translated to move the needle 3928 into the needle slot 3924 in the secure zone 3920c until the needle driver runs into the end of the needle slot 3924 or the last inserted used needle 3928.

In some embodiments, the needle driver slot 3928 may comprise a linear cut through the upper and lower surfaces of the upper structure 3921 as exemplified in FIG. 392A3. In these embodiments, inherent flexibility of the needle trap material may allow the linear edges of the needle driver slot to deform and allow translation of the needle driver. In some embodiments, the needle driver slot 3928 may comprise a width in the Y-axis configured to receive the distal tip of the needle driver holding a needle 3928. In these embodiments, this width may narrow in the secure zone 3920c so that the distal tip of a needle driver with an elongated cross section must orient with the needle driver slot 3923 such that the held needle 3928 is properly aligned across the width of the secure zone 3920c within the needle trap 3920. In some embodiments, the needle driver slot 3928 may comprise a width in the Y-axis that is constant throughout its length in the X-axis, as exemplified in FIG. 392A4.

In many embodiments, the needle trap 3920 comprises a deformable, flexible, and/or compliant material. In many embodiments, the needle trap 3920 comprises a deformable, flexible, and/or compliant material that can provide compressive force to secure the one or more needles 3928 within the needle slot 3924. Alternatively or in combination, and as exemplified in FIG. 392A12, the needle trap 3920 may comprise magnetic strips, foam, surface coatings, gel, and the like identified as 3924a within the needle slot 3924 as described herein to prevent needles from exiting the envelope.

In many embodiments, and as shown in FIG. 329A9, needle trap 3920 may assume a planar configuration wherein the lower surface of upper structure 3921 and the upper surface of the lower structure 3922 rest against one another without the presence of any needles in the needle slot 3924 (i.e., without needles in the needle trap, the needle trap lays flat against its mounting surface). As shown in FIG. 329A10, as a needle 3928 is loaded into the needle trap 3920 through needle slot 3924 by the needle driver 327, the inherent flexibility of the needle trap material may allow the edges 3925 of the upper structure 3921, the linear edges of the needle driver slot 3923 of the upper structure 3921, and the upper structure 3921 to deform and conform to the needle 3928 and needle driver 327 as the needle driver 327 holding needle 3928 is translated into the needle trap 3920 for placement of needle 3928. As shown in FIG. 392A11, after the needle 3928 has been placed into the needle slot 3924 of the needle trap 3920, the inherent flexibility of the needle trap material may allow the edges 3925 of the upper structure 3921, the linear edges of the needle driver slot 3923 of the upper structure 3921, and the upper structure 3921 to conform to the needle 3928. In some embodiments, the conforming of the edges 3925 of the upper structure 3921, the linear edges of the needle driver slot 3923 of the upper structure 3921, and the upper structure 3921 may apply a compressive force to the needle 3928 within the needle trap 3920, thereby securing needle 3928 in place. In some embodiments, the conforming of the edges 3925 of the upper structure 3921, the linear edges of the needle driver slot 3923 of the upper structure 3921, and the upper structure 3921 may be limited to the location of the needle 3928 (i.e., remote from needle 3928, the lower surface of upper structure 3921 and the upper surface of the lower structure 3922 rest against one another). In some embodiments, the lower structure 3922 may additionally deform and conform to the needle 3928. In some embodiments, the lower structure 3922 may additionally deform and conform to the needle 3928 and needle driver 327.

In many embodiments, the needle trap 3920 may comprise a deformable, flexible, and/or compliant material that can prevent the one or more needles 3928 from puncturing through the lateral and longitudinal walls of the needle trap (i.e., puncture resistant material). The thickness of the material used to construct the needle trap 3920 may be in the range of 0.008 inches to 0.030 inches. The material used to construct the needle trap 3920 may comprise PTFE, Tyvek, polycarbonate, polyamide, Kevlar, PVC, and PETG; preferably PETG. The material used to construct the needle trap 3920 may have a puncture resistance of with strength to resist puncture with a sharp tip of a needle with at least 0.3 pound force applied to the tip of the needle, wherein the needle is a United States Surgical Corporation GS-21 needle or to resist puncture with a sharp tip of a needle with at least 0.3 pound force applied to the tip of the needle, wherein the needle is a United States Surgical Corporation CV-23 needle, or to resist puncture with a sharp tip of a needle with at least 0.3 pound force applied to the tip of the needle, wherein the needle is a United States Surgical Corporation thin bodied half-circle needle, or to resist puncture with a sharp tip of a needle with at least 0.3 pound force applied to the tip of the needle, wherein the needle is a United States Surgical Corporation medium bodied half-circle needle, or to resist puncture with a sharp tip of a needle with at least 0.5 pound force applied to the tip of the needle, wherein the needle is a United States Surgical Corporation GS-21 needle, or to resist puncture with a sharp tip of a needle with at least 0.5 pound force applied to the tip of the needle, wherein the needle is a United States Surgical Corporation CV-23 needle, or to resist puncture with a sharp tip of a needle with at least 0.5 pound force applied to the tip of the needle, wherein the needle is a United States Surgical Corporation thin bodied half-circle needle, or to resist puncture with a sharp tip of a needle with at least 1 pound force applied to the tip of the needle, wherein the needle is a United States Surgical Corporation medium bodied half-circle needle, to resist puncture with a sharp tip of a needle with at least 1 pound force applied to the tip of the needle, wherein the needle is a United States Surgical Corporation GS-21 needle, or to resist puncture with a sharp tip of a needle with at least 1 pound force applied to the tip of the needle, wherein the needle is a United States Surgical Corporation CV-23 needle, or to resist puncture with a sharp tip of a needle with at least 1 pound force applied to the tip of the needle, wherein the needle is a United States Surgical Corporation thin bodied half-circle needle, or to resist puncture with a sharp tip of a needle with at least 1 pound force applied to the tip of the needle, wherein the needle is a United States Surgical Corporation medium bodied half-circle needle, or to resist puncture with a sharp tip of a needle with at least 3 pound force applied to the tip of the needle, wherein the needle is a United States Surgical Corporation GS-21 needle, or to resist puncture with a sharp tip of a needle with at least 3 pound force applied to the tip of the needle, wherein the needle is a United States Surgical Corporation CV-23 needle, or to resist puncture with a sharp tip of a needle with at least 3 pound force applied to the tip of the needle, wherein the needle is a United States Surgical Corporation thin bodied half-circle needle, or to resist puncture with a sharp tip of a needle with at least 3 pound force applied to the tip of the needle, wherein the needle is a United States Surgical Corporation medium bodied half-circle needle.

In different embodiments, the needle trap 3920 may have different dimensions depending upon the size of the needles 3928 being stored. Thus, a small needle trap used to store small needles may have smaller dimensions than a large needle trap used to store larger needles. Needles may include the needles sizes listed above or other available needles, such as surgical needles available from United States Surgical Corporation.

In some embodiments, the needle trap 3920 may be constructed out of one sheet of material as shown in FIG. 392A1. In these embodiments, the needle driver slot 3923 may be cut through the needle trap 3920 and dimensioned as described herein (e.g., the needle driver slot may comprise a single cut, forming a linear cut through the material, or may comprise a through cut with a width 3923b as shown herein). Further, the single sheet of material may be folded over on itself and the outer perimeter along the longitudinal axis of the needle trap may be sealed so as to create the needle trap 3920 with a needle slot 3924 bounded by closed-in walls as described herein. In some embodiments the needle trap 3920 may be constructed out of two separate sheets of material as shown in FIG. 392A2. In these embodiments, the needle driver slot 3923 may be cut through one sheet of material that will form the upper structure 3921 of the needle trap 3920 (i.e., the top sheet shown in FIG. 392A2) and dimensioned as described herein (e.g., the needle driver slot may comprise a single cut, forming a linear cut through the material, or may comprise a through cut with a width 3923b as shown herein). Further, this one sheet of material that will form the upper structure 3921 may then be adhered to another sheet of material that will form the lower structure 3922 of the needle trap 3920 (i.e., the bottom sheet shown in FIG. 329A2) so as to seal the outer perimeter along the longitudinal axis of the needle trap and the lateral perimeter of the needle trap opposite the entry zone. In many embodiments, sealing the outer perimeter may comprise the use of an adhesive, a glue, a weld, a stitch, or any other joining means.

In some embodiments, the lower surface of lower structure 3922 of needle trap 3920 may comprise adhesive, velcro, or other bonding means to releasably attach the needle trap 3920 to a mounting surface, such as the barrier mounting base, barrier, or base as described herein. In some embodiments, the lower surface of lower structure 3922 of needle trap 3920 may comprise adhesive, or other bonding means to permanently attach the needle trap 3920 to a surface.

In some embodiments, the needle trap 3920 as described herein may be placed/inserted into a re-usable secondary structure 3926 (as shown in FIGS. 392B-392D and FIGS. 392B1-392B5) configured to receive the needle trap 3920. The secondary structure 3926 may comprise an upper structure 3926a, a lower structure 3926b, a needle driver slot 3926d, a needle trap receiving slot 3926e, and a lateral wall 3926c (which may join upper structure 3926a to lower structure 3926b at the lateral perimeter of secondary structure 3926 at the end opposite the needle trap receiving slot 3926e). The secondary structure may also comprise one or more longitudinal walls 3926f (which may join upper structure 3926a to lower structure 3926b at the longitudinal perimeters of the secondary structure 3926). Alternatively or in combination, the secondary structure may also comprise inner grooves 3926g configured to receive the needle trap 3920.

The needle trap receiving slot 3926e of the secondary structure 3926 may be configured so as to receive the needle trap 3920. Thus, in different embodiments, the secondary structure may have different dimensions depending upon the size of the needle trap 3920. The fit of the needle trap 3920 within the needle trap receiving slot 3926e may be loose or tight, and rely on friction or surface treatments to accomplish the desired fit. In some embodiments, the secondary structure provides a compressive force to the needle trap within.

The needle driver slot 3926d of the secondary structure 3926 may be configured to match the dimensions of the needle driver slot 3923 of the needle trap 3920. Alternatively, the needle driver slot 3926d may be oversized (i.e., has greater width in the Y-axis) than the needle driver slot 3923.

The lateral wall 3926c of the secondary structure 3926 may serve as a stop for the needle trap 3920 (i.e., the needle trap is fully seated/inserted into the secondary structure when the needle trap abuts the lateral wall). Optional longitudinal walls 3926f may additionally serve to constrain the needle trap 3920 from lateral movement during use.

In some embodiments, the needle driver slot 3926d of the secondary structure 3926 may extend through both the upper structure 3926a (as shown in FIGS. 392B-392D) and the lower structure 3926b (as shown in FIG. 392B1). Configured as such, the distal end of the needle driver is allowed to traverse the entire height (Z-axis) of the secondary structure, which may facilitate depositing of needles 3928 into needle trap 3920.

In further detail the secondary structure 3926 of FIG. 392B1 may include a first stiff member 3926j having first and second ends and a second stiff member 3926h extending from the first end of the first stiff member and third stiff member 3926i extending from the second end of the first stiff and in a same plane as the second stiff member 3926h. The stiff structure 3926 may be configured to receive a needle receptacle 3920 of any of the preceding claims between the second and third stiff members 3926h, 3926i.

In some embodiments, the distance 3926d between the second and third members 3926h, 3926i at an end proximate the first member 3926j is less than a distance 3926k between the second and third member 3926h, 3926i at a distal end such that when the needle receptacle is received within the stiff structure, the second and third members impart a force, such as a lateral compressive force on the needle receptacle 3920, deforming the needle receptacle and enlarging an entry to the needle slot of the needle receptacle.

As shown in FIGS. 392E-392F, in some embodiments the needle trap 3920 may comprise one or more longitudinal runners 3927 adhered to the bottom of lower structure 3922. In some embodiments, the longitudinal runners may be configured to provide a needle driver space 3929 defined by the space between the bottom of the needle trap 3920, the adjacent vertical surfaces of the longitudinal runners 3927, and the barrier surface of which the needle trap is attached. In some embodiments, the longitudinal runners 3920 may be sized so as to span the length of the needle trap comprised of the secure zone 3920*c* and the transition zone 3920*b*. In some embodiments, the longitudinal runners 3920 may be comprised of a foam, rubber, or rigid material.

In many embodiments, the longitudinal runners 3927, by providing needle driver space 3929, allow for the distal tip of the needle driver to deflect the lower structure 3922 of needle trap 3920 downward (as shown in FIG. 392F) so as to facilitate translation of needle 3928 into the needle trap. In some embodiments, only one longitudinal runner 3927 may be adhered to the underside of the needle trap 3920, and a needle 3928 is loaded into the needle with compliance of the needle trap material.

In some embodiments, the needle trap 3290 and the secondary structure 3926 may be configured to provide a compressive lateral force on the needle trap 3290 so as to promote spreading open of the needle slot 3924 (i.e., to facilitate easy placing of needles into the needle trap). FIGS. 392B2-392B3 and FIGS. 392B4-392B5 illustrate exemplary embodiments of such configurations. In these exemplary embodiments, the needle trap 3290 may have a lateral width 3920*d* at the end of the needle trap opposite the needle slot 3924, and a lateral width 3920*k* at the needle slot 3924. Further, in these exemplary embodiments, the inner grooves 3926*g* of the secondary structure 3926 may have an inner lateral width 3926*d* within the secondary structure opposite the needle trap receiving slot 3926*e* entrance, and an inner lateral width 3926*k* at the entrance of the needle trap receiving slot 3926*e*. In the embodiments shown in FIGS. 392B2-392B3, the inner lateral widths 3926*d* and 3926*e* of the secondary structure 3926 may be the same, while the lateral width 3920*d* of the needle trap may be less than the lateral width 3920*k* of the needle trap 3290. Further, the lateral widths 3926*d* and 3926*e* of the secondary structure may be sized complementarily to the lateral width 3920*d* of the needle trap 3290. Thus, the lateral width 3920*k* of the needle trap 3920 is greater than the lateral widths 3926*d* and 3926*e* of the secondary structure. Dimensioned as such, when the needle trap 3290 is placed into the secondary structure 3926, the secondary structure 3926 may provide a compressive lateral force on the needle trap 3290 so as to promote spreading open of the needle slot 3924, as shown in FIG. 392B3. Alternatively, in the embodiments shown in FIGS. 392B4-392B5, the lateral widths 3920*d* and 3920*k* of the needle trap 3290 may be the same, while the inner lateral width 3926*k* of the secondary structure may be less than the inner lateral width 3926*d* of the secondary structure 3296. Further, the inner lateral width 3926*d* of the secondary structure 3926 may be sized complementarily to the lateral width 3920*d* of the needle trap 3290. Thus, the inner lateral width 3296*k* of the secondary structure is less than the lateral widths 3920*d* and 3920*k* of the needle trap 3290. Dimensioned as such, when the needle trap 3290 is placed into the secondary structure 3926, the secondary structure 3926 may provide a compressive lateral force on the needle trap 3290 so as to promote spreading open of the needle slot 3924, as shown in FIG. 392B5. In some embodiments, the lateral dimensions 3920*d* and 3920*k* of the needle trap, and inner lateral dimensions 3926*d* and 3926*k* of the secondary structure, may be configured as necessary to provide a compressive lateral force on the needle trap 3290 so as to promote spreading open of the needle slot 3924.

FIGS. 393A-393B illustrate an exemplary embodiment of a device 3930 for securing a plurality of needles, in accordance with many embodiments. The device 3930 comprises a u-shaped housing 3931 having an upper portion 3932 and a lower portion 3933 coupled together by a hinge portion 3934 at the back end of the housing. The space, or cavity, between the upper portion and the lower portion forms a planar needle slot 3935 for storing a plurality of needles N. The hinge portion 3934 may be spring-loaded to bias the upper and lower portions of the housing towards one another, such that the needles can be secured within the needle slot by the compressive forces exerted by the upper and lower portions. Each of the upper portion and the lower portion comprises a first arm and a second arm, wherein the space between the first arm and the second arm defines a needle driver channel or slot 3936 extending down the center of the "U". In use, the tip of a needle driver holding a needle may be aligned with the needle driver slot 3936, and the needle aligned with the planar needle slot 3935, and then the needle driver tip may be translated along the needle driver slot towards the hinge portion of the housing to secure the needle within the needle slot.

Optionally, the lower portion of the housing may comprise an extended portion 3937 that extends beyond the front end of the upper portion of the housing. In use, the extended portion 3937 can provide a landing zone for a needle to be secured in the device, wherein the needle may be placed in contact with the upper surface of the extended portion with the needle driver tip aligned with the needle driver slot. The landing zone can facilitate the insertion of the needle into the needle slot by eliminating the need for a user to carefully align the needle with the plane of the needle slot. Optionally, the housing may further comprise blocking tabs 3938*a*, 3938*b* located at the front end of the housing, extending from the front outer edge of the lower housing portion to the front outer edge of the upper housing portion. The blocking tabs can prevent a needle from entering the needle slot with one or both ends of the needle exposed beyond the arms of the u-shaped housing, thus reducing the risk of needle stick injury by ensuring that both ends of the needle are secured between the upper and lower portions of the housing.

Optionally, to further reduce the risk of an exposed needle end extending beyond the arms of the u-shaped housing 3931, the device 3930 may be provided with lateral walls 3939 disposed over the outer lateral edges of the u-shaped housing, as shown in FIG. 393B. The lateral walls 3939 may be integrated portions of the housing 3931, or they may be provided a separate accessory that can be removably coupled to the device 3930. For example, the device 3930 may be provided with a u-shaped accessory comprising the lateral walls 3939 and dimensioned to fit closely over the outer edges of the housing 3931.

FIG. 394 illustrates an exemplary embodiment of a device 3940 for securing a plurality of needles, in accordance with many embodiments. The device 3940 comprises a housing 3941 having an upper portion 3942 and a lower portion 3943 coupled together by a hinge portion 3944 at the back end of the housing. The space between the upper and lower portions forms a planar needle slot 3945 for storing a plurality of needles N. The hinge portion 3944 may be spring-loaded to bias the upper and lower portions towards each other, such that the needles can be secured within the needle slot by the compressive forces exerted by the upper and lower portions of the housing. The upper portion may define an upper needle driver slot 3947a extending along the length of the housing and configured to allow translation of a needle driver tip therein. The lower portion may define a lower needle driver slot 3947b substantially aligned with the upper needle driver slot. Further, the lower portion comprises an extended portion 3948 that extends beyond the front end of the upper housing portion, to provide a landing zone for the needle to be placed into the device. The lower needle driver slot 3947b can extend into the extended portion, as shown. In use, a needle driver holding a needle may be placed over the extended portion with the tip of the needle driver aligned with the front end of the lower needle driver slot 3947b and the needle contacting the upper surface of the extended portion. Subsequently, the needle driver tip may be translated along the upper needle driver slot towards the back end of the device, to secure the needle within the needle slot. The landing zone can facilitate the insertion of the needle into the needle slot by eliminating the need for a user to carefully align the needle with the plane of the needle slot.

FIG. 395 illustrates an exemplary embodiment of a device 3950 for securing a plurality of needles, in accordance with many embodiments. The device 3950 may be similar in many aspects to the device 3510 shown and described in reference to FIGS. 351A-351C, and the device 3940 shown and described in reference to FIG. 394. The device 3950 comprises a housing 3951 having an upper portion 3952 and a lower portion 3953 movably coupled to one another by a hinge portion 3954 at the back end of the housing. The space between the upper portion and the lower portion forms a planar needle slot (best seen in FIG. 351C, slot 3515) for storing a plurality of needles N. The upper portion 3952, lower portion 3953, and hinge portion 3954 may be similar in many aspects to the correspondingly named elements of the device 3940 described in reference to FIG. 394. The upper portion may further include lateral walls 3955 configured to capture and enclose the ends of the needles disposed within the needle slot, thereby reducing the risk of needle stick injury from an exposed needle end extending beyond the lateral sides of the housing.

FIG. 396 illustrates an exemplary embodiment of a device 3960 for securing a plurality of needles, in accordance with many embodiments. The device 3960 comprises a first clip 3961a and a second clip 3961b, also referred to as elongated members. Each clip having a respective slot 3962a and 3962b shaped to receive ends of a plurality of needles N. The clips may be formed from and/or include spring materials configured to apply compressive force against the ends of the needles disposed within the slots in order to secure the needles in place with the tips of needles covered. The two clips are aligned and arranged with the openings of the slots facing each other, such that a needle N may be inserted into the device with one end of the needle entering the slot of the first clip, and the other end entering the slot of the second clip, with the needle in a substantially planar orientation with respect to the plan of the device 3960. The first clip and the second clip may be spaced apart to define a needle driver slot 3963 between the two clips, wherein the tip of a needle driver holding a needle may be translated along the needle driver slot to secure the needle within the device. The device may further comprise a back wall 3964 disposed across the back end of the device to block the back end of the first and second clips, to prevent a user from accidentally translating the needle driver holding the needle beyond the back end of the device. The back wall 3964 may be provided as an integral portion of the device, or it may be provided as a separate component that may be coupled to the two clips before use, for example via adhesives or mechanical fasters.

FIGS. 397A-397B illustrate exemplary embodiments of a device for dispensing and securing a plurality of needles, in accordance with many embodiments. FIGS. 397A and 397B both illustrates top views of exemplary embodiments of a needle trap 3970 wherein a lateral side 3972 of the needle trap is not enclosed. Needle trap 3970 can be as per any of the needle trap embodiments as described herein. In the exemplary embodiments shown, a plurality of unused needles 103 may be provided within the needle trap 3970 in a new needle secure zone near the lateral end 3972 that is not enclosed, allowing unused needles 103 to be grabbed and translated out of the open lateral end 3972, also referred to as an exit, for use. Further, one or more needles 104 may be placed into the needle trap 3970 with a needle driver through needle driver slot 3973 and a needle slot as described in the many embodiments of needle traps herein. As shown in FIG. 397A the needle driver slot 3973 may be formed through the upper structure and extending from the perimeter of the upper structure at a first end to the perimeter of the upper structure at a second end. In this way, the needle trap 3970 may be both a needle dispenser and a needle trap. As shown in FIG. 397A, in some embodiments, new needles may be separated from used needles by one or more stops 3971 located within the needle driver slot 3973 or needle slot. The one or more stops may comprise one or more raised surfaces that can inhibit translation of a needle driver holding a used needle 104 from translating past the one or more stops, thereby separating a used needle secure zone having used needles 104 from new needle secure zone having unused needles 103. Alternatively or in combination, the one or more stops may comprise surface treatments than increase friction between a used needle 104 and the complementary needle slot so as to prevent translation of used needles 104 into unused needles 103. In some embodiments, the needle driver slot 3973 may comprise a lateral bridge (i.e., the needle driver slot is not continuous) so as to block translation of a needle driver holding used needles 104, and thus prevent translation of used needles 104 into unused needles 103. As shown in FIG. 397B, in some embodiments, no needle stops may be provided. In some embodiments, needle trap 3970 may be configured with a decrease in the height of the needle slot to prevent translation of used needles 104 into unused needles 103.

Figure 398A:
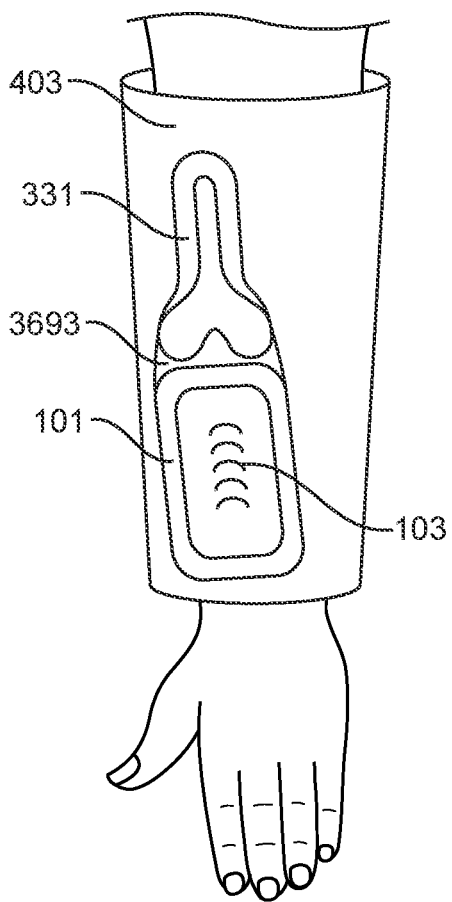
Figure 398B:
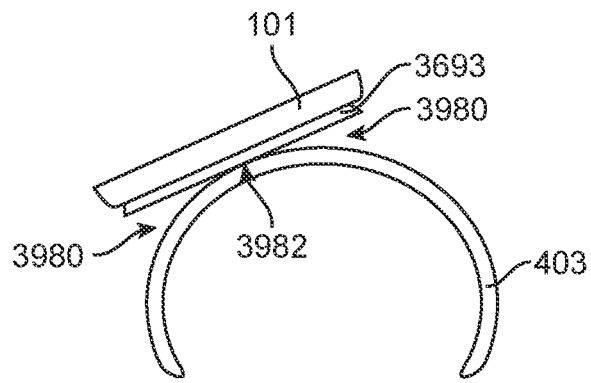
Figure 398C:
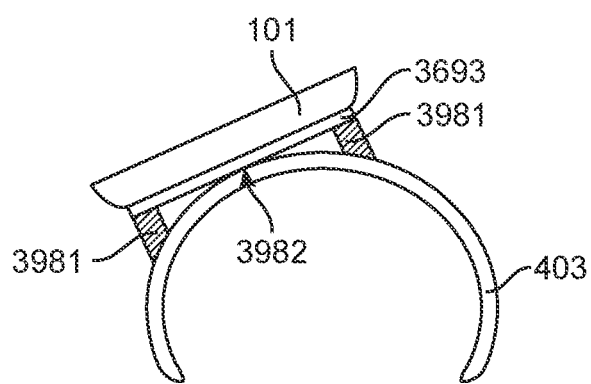
Figure 398D:
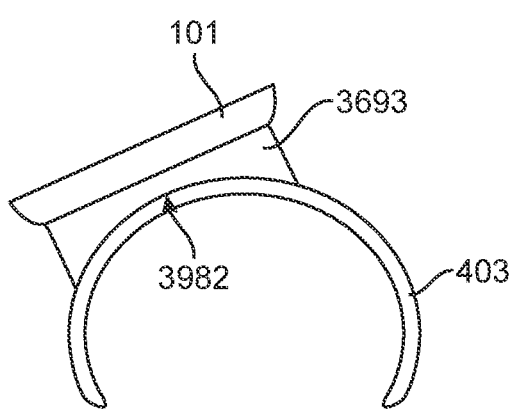

FIGS. 398A-398D illustrate exemplary embodiments of a barrier mounting base with a needle dispenser and needle trap mounted to a barrier for dispensing and securing a plurality of needles, in accordance with many embodiments. FIG. 398A illustrates a top view of a barrier mounting base 3693 with a needle dispenser 101 containing needles 103 and with a needle trap 331 mounted thereto, and this assembly mounted to a barrier 403 donned by a surgeon, as described herein. FIGS. 398B-398D illustrate end views of exemplary embodiments of barrier mounting base 3693 and how it may interact with the barrier 403 when coupled thereto.

As shown in FIGS. 398B-398D, and in accordance with many embodiments described herein, the barrier mounting base 3693 may serve as the substrate for mounting devices such as needle dispenser 101. As described herein, the barrier mounting base 3693 may comprise any material capable of providing sufficient rigidity to stably support devices such as the needle dispenser 101 while coupled to the barrier 403 at a mating surface 3982, the mating surface 3982 defined as the area where the underside of the barrier mounting base 3693 couples to the external/exposed surface of the barrier 403. Also as described herein, adhesive members, magnetic couplings, velcro attachments, mechanical coupling mechanisms such as a snap-fit, or other coupling mechanisms may be used to couple the barrier mounting base 3693 to the barrier 403 at mating surface 3982. In many embodiments, and as shown in FIG. 398B, the barrier mounting base 3693 may be configured to resist torsion and/or bending, such that when coupled to the barrier 403 at mating surface 3982, gaps 3980 between the barrier mounting base 3693 and barrier 403 may be present. In some embodiments, and as shown in FIG. 398C, the underside of the barrier mounting base 3693 may comprise one or more extensions 3981 that may span all or part of the gaps between the underside of the barrier mounting base 3693 and the external/exposed surface of the barrier 403, thus acting to add torsional stability to the barrier mounting base 3693 when coupled to the barrier 403. The extensions 3981 may comprise foam, rubber, or any other material capable of conforming to the external/exposed surface of the barrier 403. The extensions 3981 may be configured as necessary to add torsional stability to the barrier mounting base 3693 when coupled to the barrier 403 and thereby be torsional stiffeners. In some embodiments, and as shown in FIG. 398D, the barrier mounting base 3693 may be configured with a concave underside dimensioned to complement the convex external/exposed surface of the barrier 403 and receive a barrier therein. In these embodiments, the mating surface 3982 may be maximized, thus acting to maximize torsional stability to the barrier mounting base 3693 when coupled to the barrier 403. In some embodiments, a lower surface of the barrier mounting base contacts a curved surface of the barrier at a first location and the first and second extensions contact the curved surface of the batter at respective second and third locations.

FIGS. 399A-399D illustrate exemplary embodiments of a device for dispensing one or more swaged needles, in accordance with many embodiments. FIG. 399A illustrates a perspective view of an embodiment of a swaged needle dispenser 3990 for dispensing a swaged needle 103, and FIGS. 399B-399D illustrate cross-sectional views of exemplary embodiments of posts 3992, also referred to as couplings or extensions, and post receivers 3995, also referred to as couplings, of swaged needle dispenser 3990.

In the illustrated embodiments of FIGS. 399A-399D, a swaged needle dispenser 3990 may be a substantially planar device for dispensing one or more swaged needles 103, comprising a planar base 3991, two or more posts 3992 disposed on the upper surface of the planar base 3991, two or more post receivers 3995 disposed on the lower surface of the planar base 3991, and one or more swaged needle receivers 3993 disposed on the upper surface of the planar base 3991. In some embodiments, the posts 3992 and post receivers are part of a spindle. The swaged needle dispenser 3990 may be configured as shown in FIG. 399A, wherein posts 3992 are disposed along the outer perimeter of the planar base 3991, and the needle receiver 3993 is disposed at the center of the planar base 3991, post receivers 3995 may be disposed on the underside of the planar base 3991 at locations matching the posts 3992). Also as shown in FIG. 399A, a swaged needle 103 may be held by the needle receiver 3993, and suture 3994 coupled to the swaged needle 103 wrapped around posts 3992. Posts 3992 may comprise a head 3992b attached to a neck 3992a, wherein the neck 3992a attaches to the planar base 3991. Post heads 3992b may comprise one or more slots 3992c recessed into the heads, which may serve to receive the terminal end of suture 3994.

In many embodiments, and as exemplified in FIGS. 399B-399D, posts 3992 may comprise a neck 3992a with a height 3992i, and a head with height 3992h and width 3992w. Further, post receivers 3995 (couplings) may comprise a height 3992y and width 3992x that are complementarily dimensioned so as to receive post heads 3992c upon stacking of two or more swaged needle dispensers 3990. The heights 3992i and 3992h of post 3992 neck 3992a and head 3992b may be configured as necessary to accept suture 3994 when wrapped therearound. In preferred embodiments, height 3992h may be less than or equal to 1 centimeter. The heads of posts 3992 may be configured in many different ways and comprise a circular, square, oval, rectangular, multi-faceted, or other cross-sectional shape. As shown in FIG. 399B, the head of post 3992 may be configured with a step in. As shown in FIG. 399C, the head of post 3992 may be configured with a shoulder or step out so as to aid in retention of suture 3994 when wrapped. As shown in FIG. 399D, the head of post 3992 may be configured to flare out so as to aid in retention of suture 3994 when wrapped.

The planar base 3991, two or more posts 3992, and two or more post receivers 3995 may comprise any material suitable to provide a rigid or semi-rigid swaged needle dispenser 3990, for example plastic, metal, or similar. In many embodiments, the swaged needle dispenser 3990 comprises materials capable of being sterilized.

The planar base 3991 of swaged needle dispenser 3990 may comprise any shape desired, and with any number of posts 3992, post receivers 3995, and needle receivers 3993 as necessary to hold any number of swaged needles 103 with attached sutures 3994. For example, the planar base 3991 may assume a circular, square, oval, rectangular, multi-faceted, or any other shape. In many embodiments, two or more swaged needle dispensers may be stacked upon one another.

FIGS. 400A-400D illustrate exemplary embodiments of a device for dispensing one or more swaged needles, in accordance with many embodiments. FIG. 400A illustrates a perspective view of an embodiment of a swaged needle dispenser 4000 for dispensing one or more swaged needles 103, and FIGS. 400B-400D illustrate cross-sectional views of exemplary embodiments of posts 4002 of swaged needle dispenser 4000.

In the illustrated embodiments of FIGS. 400A-400D, a swaged needle dispenser 4000, also referred to as a housing, may be a substantially planar device for dispensing one or more swaged needles 103, comprising a planar base 4001, two or more posts 4002, also referred to as spindles, disposed on the upper surface of the planar base 4001, also referred to as a bottom portion, and one or more swaged needle receivers 3993 disposed on the upper surface of the planar base 4001 and coupling the swaged needle to the swaged needle dispenser. The swaged needle dispenser 4000 may be configured as shown in FIG. 400A, wherein posts 4002 are disposed in pairs along the opposite sides of the planar base 4001, and the needle receiver 3993 is disposed at the center of the planar base 3991 between opposing posts 4002. Configured in this way, swaged needles 103 may be stored by the swaged needle dispenser 4000 in an array. Also as shown in FIG. 400A, a swaged needle 103 may be held by the needle receiver 3993, and suture 3994 coupled to the swaged needle 103 wrapped around opposing pairs of posts 4002. Posts 4002 may comprise a head 4002b attached to a neck 4002a, wherein the neck 4002a attaches to the planar base 4001. Post heads 4002b may comprise one or more slots 4002c recessed into the heads, which may serve to receive the terminal end of suture 3994.

In many embodiments, and as exemplified in FIGS. 400B-400D, posts 4002 may comprise a neck 4002a with a height 4002i, and a head with height 4002h and width 4002w. The heights 4002i and 4002h of post 4002 neck 4002a and head 4002b may be configured as necessary to accept suture 3994 when wrapped therearound. In preferred embodiments, height 4002h may be less than or equal to 1 centimeter. The heads of posts 4002 may be configured in many different ways and comprise a circular, square, oval, rectangular, multi-faceted, or other cross-sectional shape. As shown in FIG. 400B, the head of post 4002 may be configured with a rounded top and flat bottom (e.g., like a mushroom) so as to aid in retention of suture 3994 when wrapped. As shown in FIG. 400C, the head of post 4002 may be configured with a rounded top and bottom so as to aid in retention of suture 3994 when wrapped. As shown in FIG. 400D, the head of post 4002 may be configured with a flat top and bottom so as to aid in retention of suture 3994 when wrapped.

The planar base 4001 and two or more posts 4002 may comprise any material suitable to provide a rigid or semi-rigid swaged needle dispenser 4000, for example plastic, metal, or similar. In many embodiments, the swaged needle dispenser 4000 comprises materials capable of being sterilized.

The planar base 4001 of swaged needle dispenser 4000 may comprise any shape desired, and with any number of posts 4002 and needle receivers 3993 as necessary to hold any number of swaged needles 103 with attached sutures 3994. For example, the planar base 4001 may assume a circular, square, oval, rectangular, multi-faceted, or any other shape.

In some embodiments, the top and bottom of the spindles include a coupling the top coupling having a first shape and the bottom coupling being shaped to receive the top coupling. In some embodiments, the top and bottom of the spindles include a coupling. The top coupling having a first shape and the bottom coupling being shaped to engage with the first shape of the top coupling. In some embodiments, the top of the spindle includes an extension and the top of the spindle includes a recess shaped to receive the extension.

FIGS. 401A-401C, FIGS. 402A-402C, FIGS. 403A-403C, and FIGS. 404A-404C illustrate exemplary embodiments of a base for mounting one or more devices for dispensing and/or securing a plurality of needles, in accordance with many embodiments. FIG. 401A, FIG. 402A, FIG. 403A, and FIG. 404A illustrate perspective views of exemplary embodiments of a base 4011. FIG. 401B, FIG. 402B, FIG. 403B, and FIG. 404B illustrate top views of the exemplary embodiments of base 4011 shown in FIG. 401A, FIG. 402A, FIG. 403A, and FIG. 404A, respectively. FIG. 401C, FIG. 402C, FIG. 403C, and FIG. 404C illustrate end views of the exemplary embodiments of base 4011 shown in FIG. 401A, FIG. 402A, FIG. 403A, and FIG. 404A, respectively.

Base 4011 may comprise a planar structure 4010c, a planar structure 4010a, in some instances a planar structure 4010b, and in some instances a planar structure 4010d. Planar structure 4010c may be considered the base planar structure of base 4010 (i.e., in use it primarily lays in the horizontal), and may be placed on or coupled to surgical drapes, tables, stands, and the like via coupling means at its underside (e.g., Velcro, adhesive, magnets, mechanical joining means, and the like). Planar structure 4010c may comprise a rectangular configuration with a length and width as appropriate to provide stability to base 4010. Planar structure 4010a, including a mounting surface, may be coupled to planar structure 4010c at a living hinge 4011a, with an interior angle 4012 defining the angle between the planar structure 4010c and planar structure 4010a. Planar structure 4010a may be considered the planar surface or may include a planar surface that is a mounting surface whereon the needle dispensers, needle receptacles, and various tools as described herein may be coupled for use during surgical procedures. Thus, planar structure 4010a may comprise a surface configured to couple to the needle dispensers, needle receptacles, and various tools as described herein (e.g., may comprise Velcro, adhesive, magnets, mechanical joining means, and the like). Further, planar structure 4010c may comprise a rectangular configuration with a length and width as appropriate for coupling the needle dispensers, needle receptacles, and various tools as described herein thereto. In some embodiments (as shown in FIGS. 401A-401C, FIGS. 402A-402C, and FIGS. 404A-404C), planar structure 4010b may be coupled to planar structure 4010b at a living hinge 4011b. Planar structure 4010b may be considered a supporting structure in that it may rest against planar structure 4010c and provide further structural stability to base 4010. In some embodiments, planar structure 4010b may rest against planar structure 4010c (as shown in FIGS. 401A-401C). In some embodiments, planar structure 4010c may rest against or engage with the planar structure 4010c at stops 4013, or adjustment structures, of planar structure 4010c, wherein the stops 4013 may be configured with an inter-stop spacing 4013a to present the surface of planar structure 4010a via its connection to planar surface 4010b as desired as described further herein (i.e., to provide for adjustability of interior angle 4012 as shown in FIGS. 404A-404C). In some embodiments (as shown in FIGS. 402A-402C), planar structure 4010d may be coupled to planar structure 4010b at a living hinge 4011c. Planar structure 4010d may be oriented co-planar with planar structure 4010c and rest against planar structure 4010c. In some embodiments, the surface of planar structure 4010d that rests against planar structure 4010c may be coupled to the surface of planar structure 4010c that it rests against (e.g., by Velcro, adhesive, magnets, mechanical joining means, and the like). In this way, in these embodiments the coupling of planar structure 4010d to planar structure 4010c may provide for adjustability of interior angle 4012.

In some embodiments, the living hinge 4011a, the living hinge 4011b (if present), and living hinge 4011c (if present) may comprise passive hinges. In some embodiments, the living hinge 4011a, the living hinge 4011b (if present), and living hinge 4011c (if present) may comprise active hinges. In some embodiments, the living hinge 4011a, the living hinge 4011b (if present), and living hinge 4011c (if present) may comprise a passive or active hinge.

In some embodiments, the base 4010 may be configured for infinite adjustability of interior angle 4012. In some embodiments, the base 4010 may be configured for finite adjustability of interior angle 4012. In many embodiments, the base 4010 may be configured to present the surface of planar structure 4010a configured to couple to the needle dispensers, needle receptacles, and various tools as described herein (e.g., via Velcro, adhesive, magnets, mechanical joining means, and the like) at an angle desired by the surgeon by adjustability of interior angle 4012. In preferred embodiments, the interior angle 4012 may be adjustable between 30 degrees and 90 degrees, between 60 degrees and 75 degrees, between 45 degrees and 75 degrees, or between 60 degrees and 90 degrees.

In many embodiments, the coupling of base 4010 to surgical drapes, tables, stands, and the like via coupling means located at the underside of planar structure 4010c may be releasable. In many embodiments, the coupling of base 4010 to surgical drapes, tables, stands, and the like via coupling means located at the underside of planar structure 4010c may be releasable and may not pull, tear, or otherwise damage the surgical drapes, tables, stands, or the like it is coupled thereto. In many embodiments, the strength of the coupling of base 4010 to surgical drapes, tables, stands, and the like via coupling means located at the underside of planar structure 4010c may be stronger than the coupling of needle dispensers, needle receptacles, and various tools as described herein to the surface of planar structure 4010a.

FIGS. 405A-405B illustrate exemplary mounting positions of a base for coupling one or more devices for dispensing and/or securing a plurality of needles or for coupling one or more tools as described herein, in accordance with many embodiments. FIG. 405A illustrates a top view of an exemplary embodiment wherein one or more bases 4010 as described in FIGS. 401A-401C, FIGS. 402A-402C, FIGS. 403A-403C, and FIGS. 404A-404C are mounted to a surgical drape 4052 covering a patient 4050 resting on an operating room table 4051. FIG. 405B illustrates a top view of an exemplary embodiment wherein one or more bases 4010 as described in FIGS. 401A-401C, FIGS. 402A-402C, FIGS. 403A-403C, and FIGS. 404A-404C are mounted to one or more surgical trays, tables, and/or stands 4056 in the operating room As shown in FIG. 405A, surgical drape 4052 may comprise a window 4054 exposing an incision 4055 in patient 4050. One or more bases 4010 may be coupled to surgical drape 4052 to allow coupling of one or more of the needle dispensers, needle receptacles, and various tools as described herein. With reference to the X-Y axes, one or more bases 410 may be coupled to surgical drape 4052 in any X-Y position, and at any angle relative to the X-axis or Y-axis as desired by a surgeon 4053 performing the operation. In some embodiments, one or more bases 4010 may be coupled to surgical drape 4052 parallel to the X-axis. In some embodiments, one or more bases 4010 may be coupled to surgical drape 4052 parallel to the Y-axis. In some embodiments, one or more bases 4010 may be coupled to surgical drape 4052 at any angle relative to the X-axis or Y-axis. In some embodiments one or more bases 4010 may be coupled to surgical drape 4052 near the dominant-arm side of surgeon. In some embodiments one or more bases 4010 may be coupled to surgical drape 4052 near the non-dominant-arm side of surgeon. In some embodiments one or more bases 4010 may be coupled to surgical drape 4052 in front of the of surgeon. In some embodiments, one or more bases 4010 may be coupled to surgical drape 4052 in the near surgical field. In some embodiments, one or more bases 4010 may be coupled to surgical drape 4052 outside the near surgical field. In some embodiments, one or more bases 4010 may be coupled to surgical drape 4052 in any combination of positions as described herein.

In various embodiments, the support, also called a base 4010, may be mounted to a drape over the over a patient, within the near surgical field, to a table within the near surgical field, to a stand within the near surgical field, at a location opposite the surgeon from an incision, proximal the incision of the patient, distal the incision of the patient, superior to the incision of the patient, or inferior the incision of the patient.

As shown in FIG. 405B, surgical drape 4052 may comprise a window 4054 exposing an incision 4055 in patient 4050. One or more bases 4010 may be coupled to one or more surgical trays, tables, and/or stands 4056 to allow coupling of one or more of the needle dispensers, needle receptacles, and various tools as described herein. With reference to the X-Y axes, one or more bases 410 may be coupled to one or more surgical trays, tables, and/or stands 4056 in any X-Y position, and at any angle relative to the X-axis or Y-axis as desired by a surgeon 4053 performing the operation. In some embodiments, one or more bases 4010 may be coupled to one or more surgical trays, tables, and/or stands 4056 parallel to the X-axis. In some embodiments, one or more bases 4010 may be coupled to one or more surgical trays, tables, and/or stands 4056 parallel to the Y-axis. In some embodiments, one or more bases 4010 may be coupled to one or more surgical trays, tables, and/or stands 4056 at any angle relative to the X-axis or Y-axis. In some embodiments one or more bases 4010 may be coupled to one or more surgical trays, tables, and/or stands 4056 near the dominant-arm side of surgeon. In some embodiments one or more bases 4010 may be coupled to one or more surgical trays, tables, and/or stands 4056 near the non-dominant-arm side of surgeon. In some embodiments one or more bases 4010 may be coupled to one or more surgical trays, tables, and/or stands 4056 in front of the of surgeon. In some embodiments, one or more bases 4010 may be coupled to one or more surgical trays, tables, and/or stands 4056 in the near surgical field. In some embodiments, one or more bases 4010 may be coupled to one or more surgical trays, tables, and/or stands 4056 outside the near surgical field. In some embodiments, one or more bases 4010 may be coupled to one or more surgical trays, tables, and/or stands 4056 in any combination of positions as described herein. In some embodiments, further adjustability in the location of one or more bases 4010 may be attained through movement and/or rotation of the one or more surgical trays, tables, and/or stands.

FIGS. 406A-406C illustrate exemplary kits including one or more devices for dispensing and/or securing a plurality of needles, in accordance with many embodiments. As shown in the top views of FIGS. 406A-406C (with a top packaging of the kit removed for clarity), kits 4060 may comprise sheet structure 4061 having a length 4061h and width 4061w configured to contain internal contents. Internal contents of kits 4060 may comprise one or more of a needle dispenser 101 with needles 103, one or more of a needle receptacle 331 or 3920 or the like, and/or one or more barrier mounting base 3693 as described herein. Furthermore, in many embodiments, the internal contents of kits 4060 may comprise one or more of a needle dispenser 101 with needles 103, one or more of a needle receptacle 331 or 3920 or the like, and/or one or more barrier mounting base 3693 complementarily sized to each other as described herein.

As shown in FIG. 406A, kit 4060 may comprise one or more of a needle dispenser 101 with needles 103, which may be combined to form a suture pack with needles 103, one or more of a needle receptacle 331, and/or one or more barrier mounting base 3693, all packaged coplanar. In many embodiments, the needle dispenser 101, needle receptacle 331, and barrier mounting base 3693 may be any of the needle dispensers, needle receptacles, and/or barrier mounting bases as described herein (i.e., needle receptacle 3920 may be contained within kit 4060).

As shown in FIG. 406B, kit 4060 may comprise one or more of a needle dispenser 101 with needles 103, one or more of a needle receptacle 331, and/or one or more barrier mounting base 3693, with the needle dispenser 101 and needle receptacle 331 coupled to barrier mounting base 3693. In many embodiments, the needle dispenser 101, needle receptacle 331, and barrier mounting base 3693 may be any of the needle dispensers, needle receptacles, and/or barrier mounting bases as described herein (i.e., needle receptacle 3920 may be contained within kit 4060).

As shown in FIG. 406C, kit 4060 may comprise one or more of a needle dispenser 101 with needles 103 coupled to a needle receptacle 3920. In some embodiments, kit 4060 may comprise one or more of a needle dispenser 101 with needles 103 coupled to a needle receptacle 3920 without a barrier mounting base (i.e., the lower structure 3922 of needle receptacle 3920 may be directly coupled to the needle dispenser 101). In some embodiments, and as shown in FIG. 406C, the needle dispenser 101 with needles 103 coupled to a needle receptacle 3920 may be coplanar. In some embodiments, the needle receptacle 3920 coupled to the needle dispenser 101 with needles 103 may be folded under the needle dispenser 101 in the kit packaging, which may be sterile packaging including a sterile barrier, such as the sterile enclosure 505 of FIG. 308. In these embodiments, the kit height may be increased, however the overall length 4061h and width 4061w may be substantially decreased.

In many embodiments, the kit 4060 may be planar or substantially planar (e.g., to facilitate easy shipping and/or storing). In many embodiments, the top and bottom surfaces of kit 4060 contents may touch the internal walls of kit 4060 packaging. In many embodiments, the contents of kit 4060 may be sterilized. In many embodiments, the length 4061h and width 4061w of kit 4060 may be minimized so as to minimize the overall size of the kit 4060.

Each of the components of the kits 4060, including for example, the needle dispenser 101 with needles 103, the needle receptacle 3920 and the barrier mounting base may be contained together within an sterile package for distribution.

Figure 407:
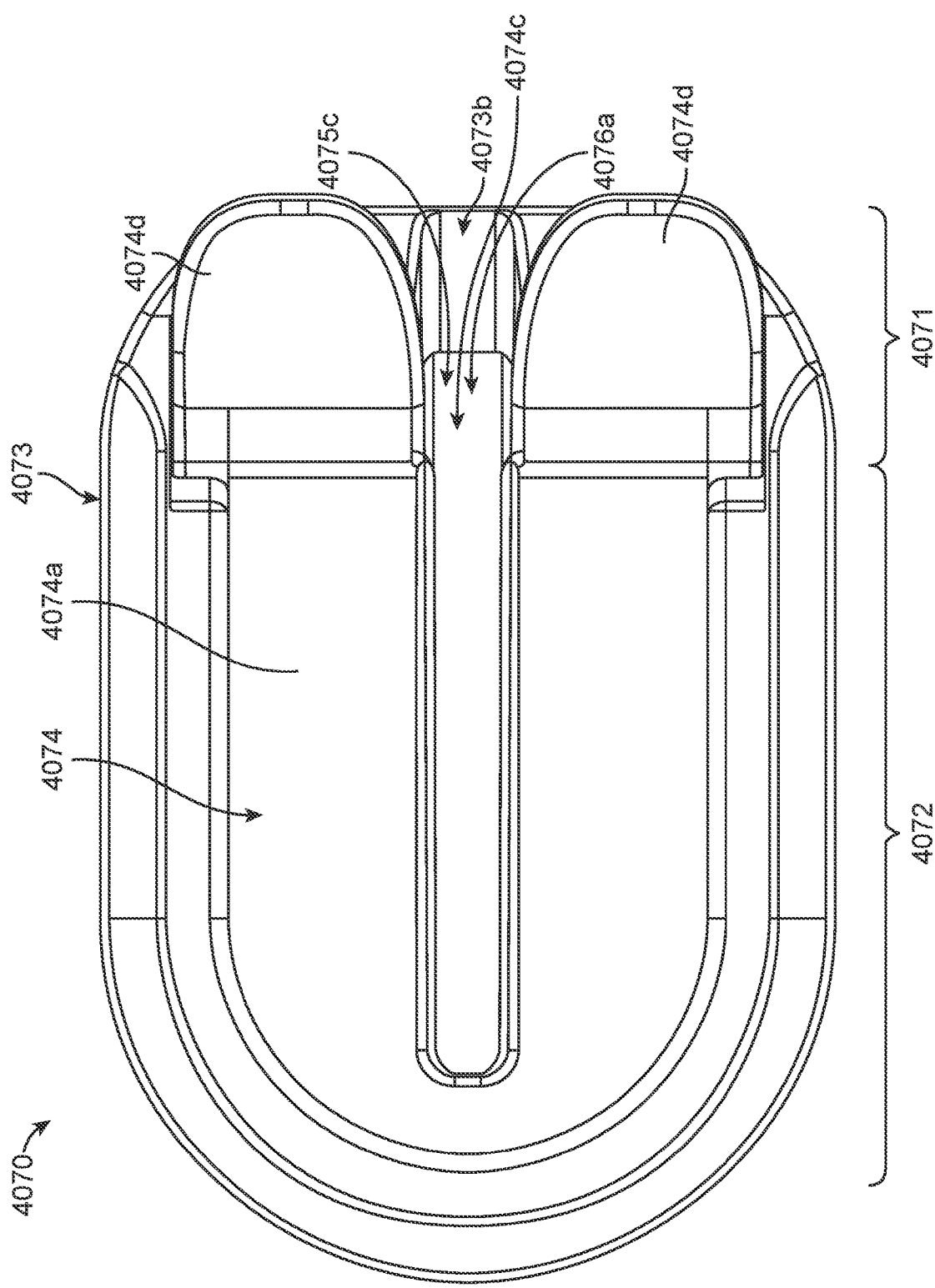
Figure 408:
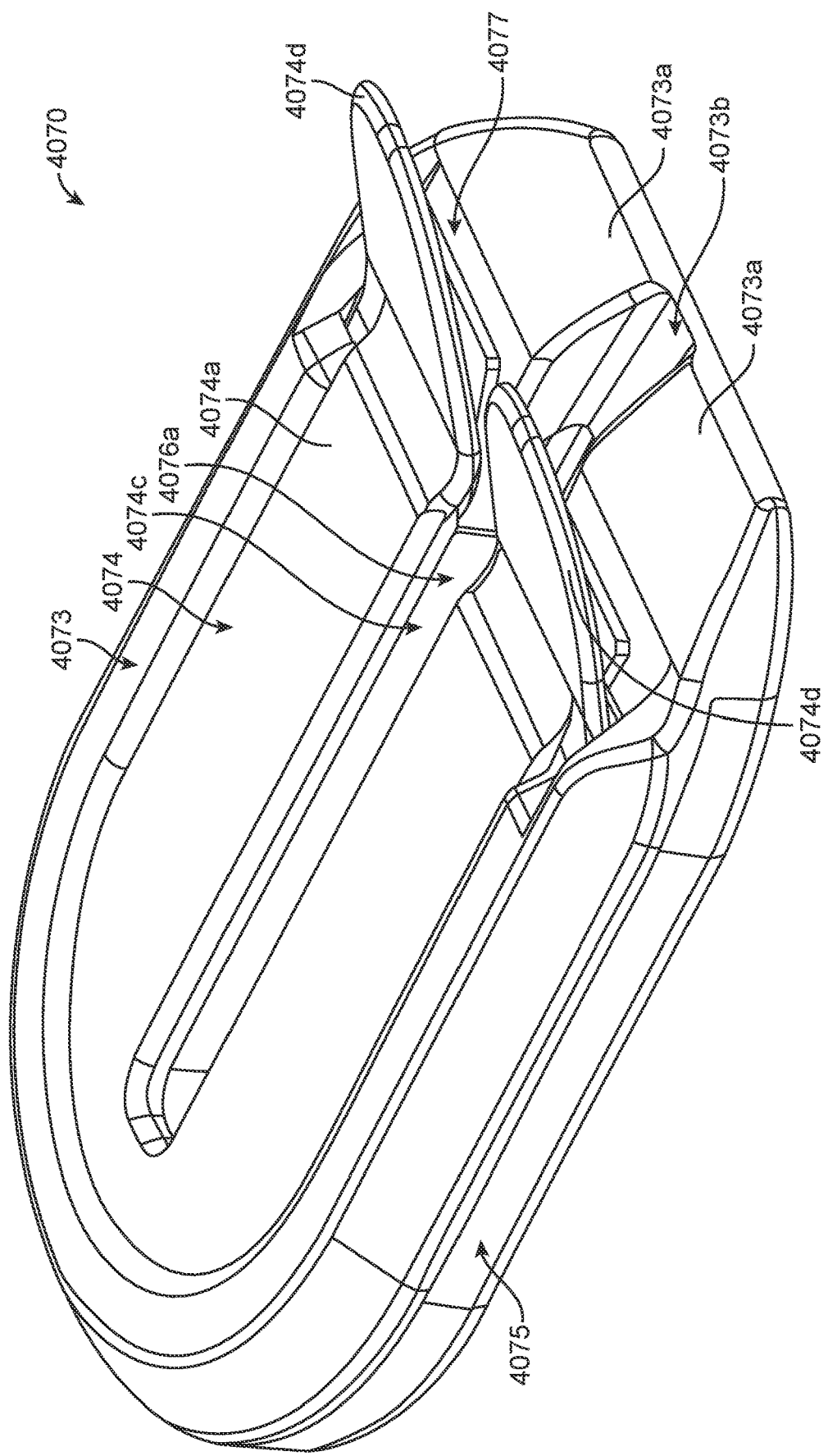
Figure 409:
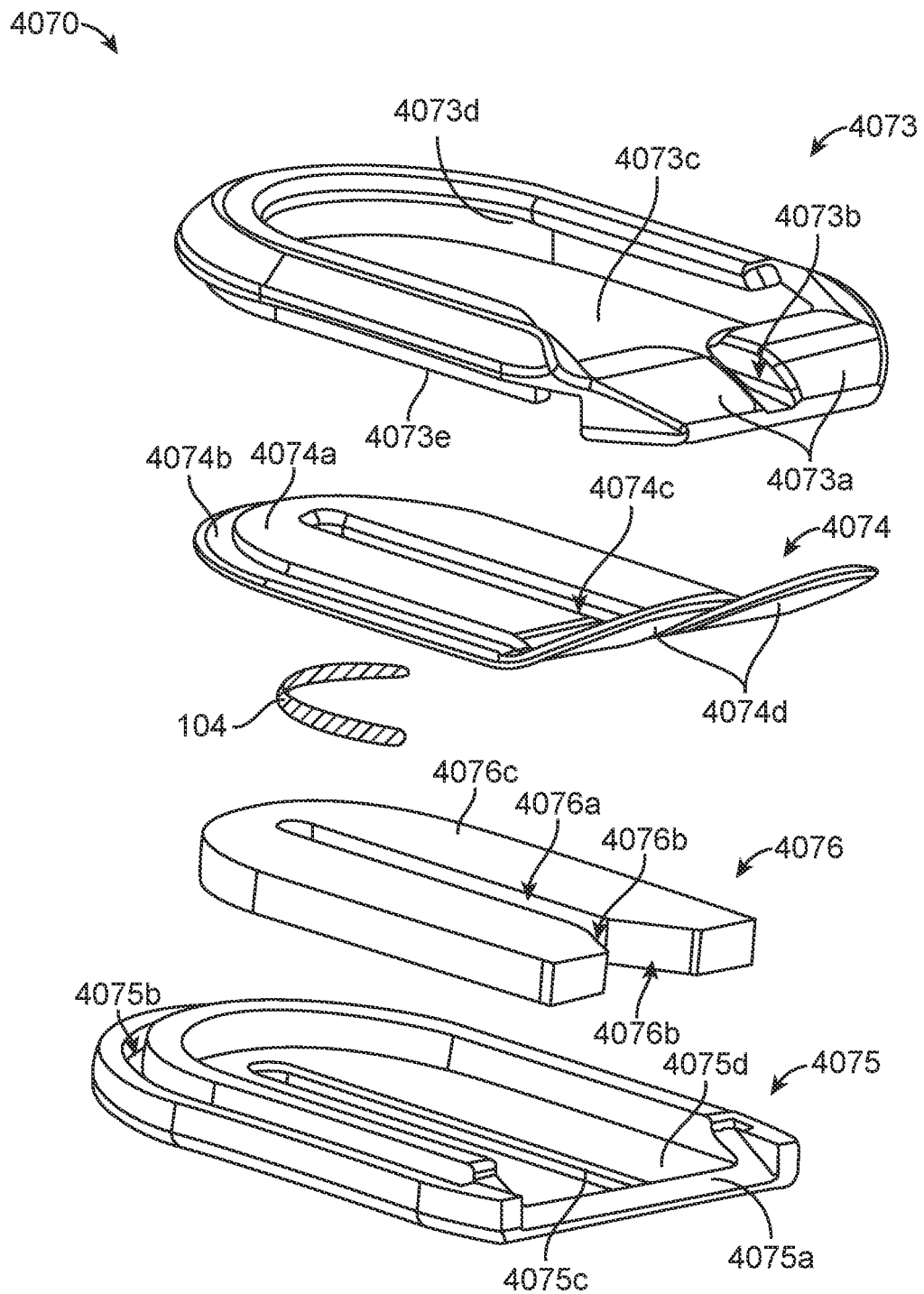
Figure 410:
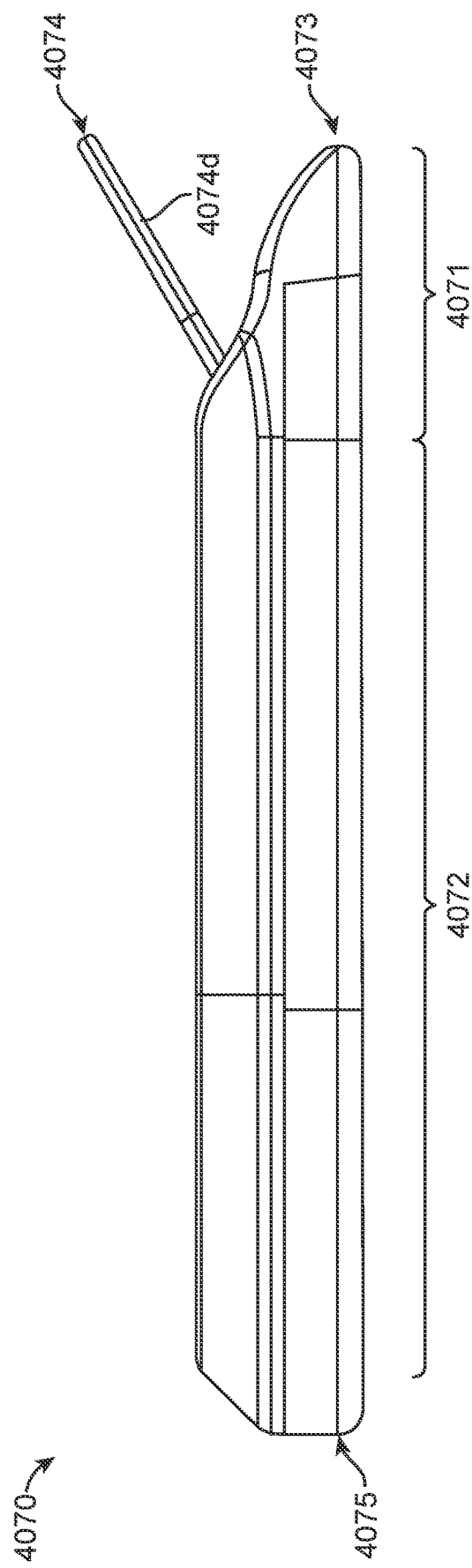
Figure 411:
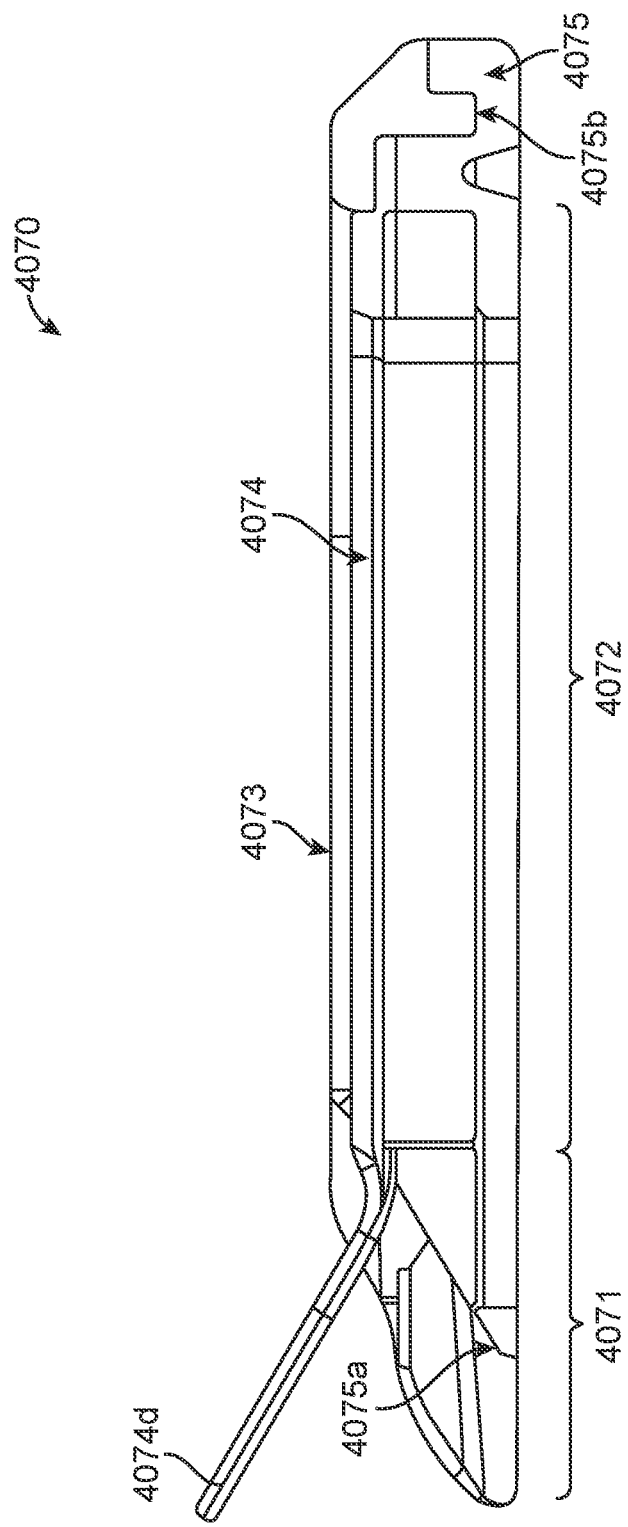
Figure 412:
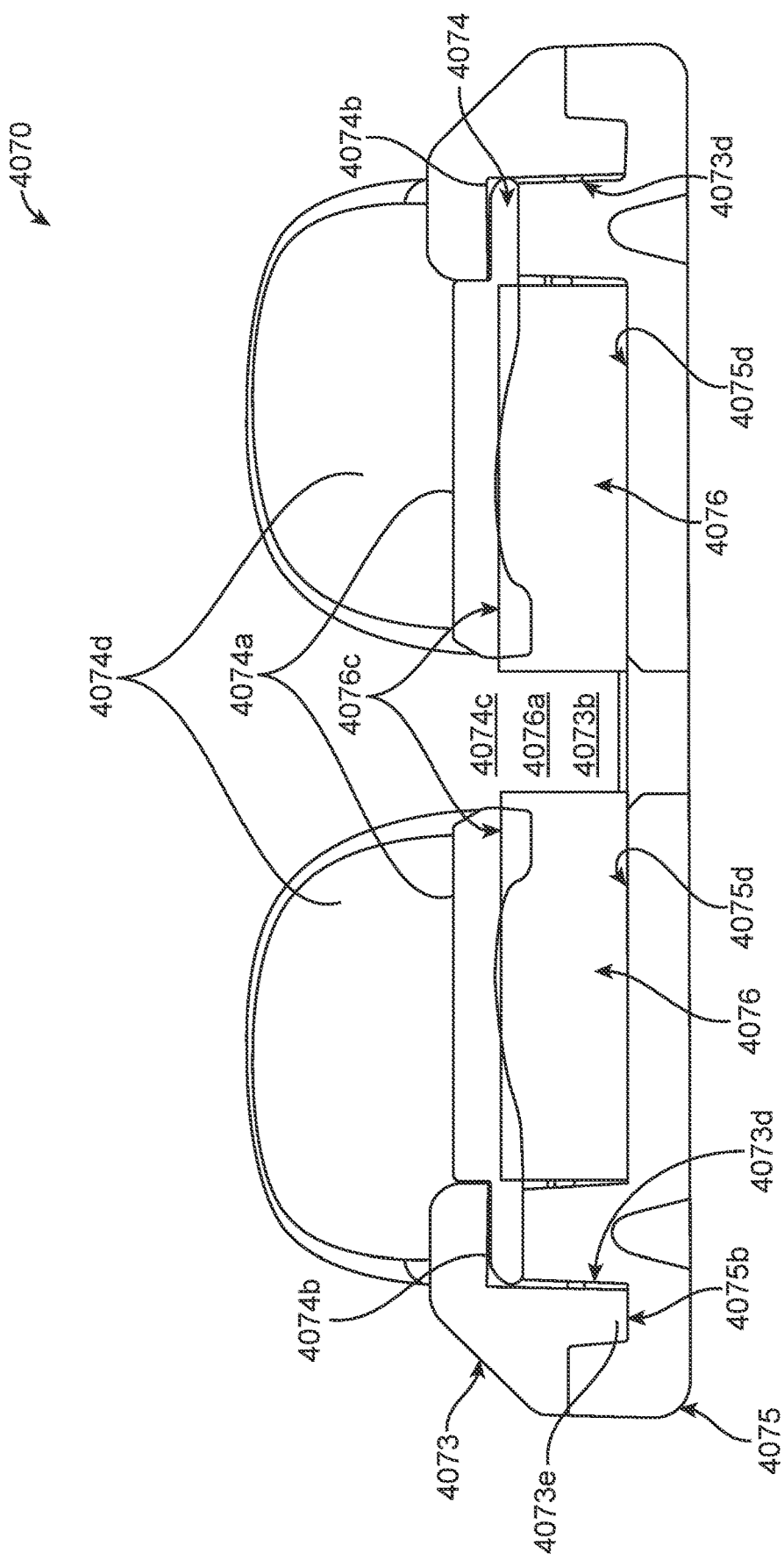
Figure 413:
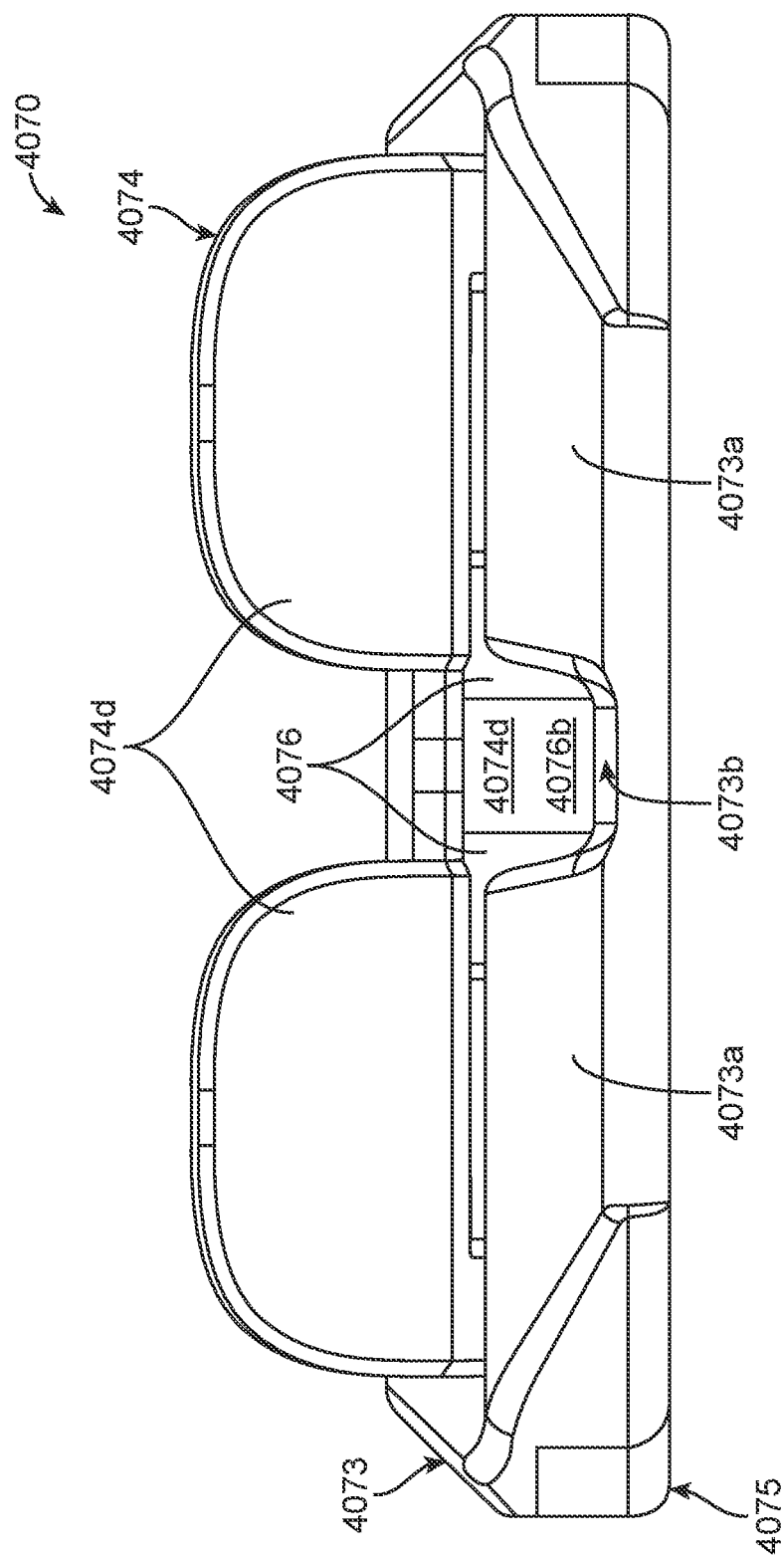

FIGS. 407-413 illustrate an exemplary embodiment of needle receptacle 4070, in accordance with many embodiments. The needle receptacle 4070 may comprise many of the structures shown with reference to FIGS. 167-179 and FIGS. 309-320, and a person of ordinary skill in the art will recognize that many of these embodiments are well suited for combination with each other, as well as other embodiments as shown and described herein. FIG. 407 illustrates a top view of needle receptacle 4070, FIG. 408 illustrates a perspective view of needle receptacle 4070, FIG. 409 illustrates an exploded view of needle receptacle 4070, FIG. 410 illustrates a left side view of needle receptacle 4070, FIG. 411 illustrates a cross-sectional right side view of needle receptacle 4070, FIG. 412 illustrates a cross-sectional end view of needle receptacle 4070, and FIG. 413 illustrates a front view of needle receptacle 4070.

In the illustrated embodiment, the needle receptacle 4070 may be a substantially planar device comprised of an entry zone 4071 and a secure zone 4072, as described herein. The needle receptacle 4070 may include an upper structure 4073, an upper structure 4074, a lower structure 4075, and a compliant structure 4076. The upper structure 4073 may comprise a ramp structure 4073a that couples to and forms a part of the lower structure 4075 and forms an entry way located below a needle slot 4077, a needle driver slot 4073b that intersects the ramp structure 4073a and extends at least partially through the upper structure 4073, and a window 4073c defined by an opening through the upper structure 4073 bound by the continuous upper structure inner wall 4073d and the ramp structure 4073a. The window 4073c may be configured to complementarily receive a raised planar surface 4074a of upper structure 4074, such that when the upper structure 4073 receives the upper structure 4074 from below the raised planar surface 4074a fits into window 4073c, and a recessed planar surface 4074b of upper structure 4074 stops against the underside of upper structure 4073. The upper structure 4074 may comprise a needle driver slot 4074c that extends partially therethrough and in line with the needle driver slot 4073b of upper structure 4073. The upper side of lower structure 4075 may comprise a ramp structure 4075a and a recess 4075b partially along its perimeter to complementary receive and couple to the underside of the ramp structure 4073a and a lower protrusion 4073e of upper structure 4073. The lower structure 4075 may also comprise a needle driver slot 4075c that extends partially therethrough and in line with the needle driver slot 4073b of upper structure 4073 and needle driver slot 4074c of upper structure 4074. The compliant structure 4076 may be configured to be received by the lower structure 4075 from above, wherein a lower surface of the compliant structure stops against a planar surface 4075d of the lower structure 4075. The compliant structure 4076 may also comprise a needle driver slot 4076a that extends partially therethrough and in line with the needle driver slot 4073b of upper structure 4073, the needle driver slot 4074c of upper structure 4074, and the needle driver slot 4075c of lower structure 4075. The compliant structure 4076 may also comprise bevels 4076b at the entrance of needle driver slot 4076a to aid in guiding of a needle driver therethrough. When assembled, the needle receptacle 4070 may comprise the planar needle slot 4077 formed by the empty vertical space between an upper planar surface 4076c of compliant structure 4076 and the lower surface of upper structure 4074, and closed in at the sides by the inner wall 4073d of upper structure 4073, thus the needle slot 4077 may be configured for receiving one or more needles 104. To aid in placement of one or more needles into the needle slot 4077 of needle receiver 4070, upper structure 4074 may comprise tabs 4074d within the entry zone 4071 that may angle vertically away from the opposing and angled down ramp structure 4073a.

The needle driver slots 4073b, 4074c, 4075c, and 4076a of needle receiver 4070 may align and be configured to provide clearance for a needle driver along the entire length of the needle translation from entry zone 4071 to secure zone 4072. The needle slot 4077 of needle receiver 4070 may constrain needles 104 placed therein into a single needle depth array, to minimize overall depth profile and facilitate needle counting. In many embodiments, the compliant structure 4067 may apply a holding force against one or more needles 104 within the needle slot 4077 and the secure zone 4072 to resist translation of the needle out of the needle slot 4077 and the secure zone 4072. In many embodiments, the compliant structure 4067 may comprise foam. In many embodiments, the compliant structure 4067 may comprise a compliant element. In many embodiments, the upper structure 4074 may apply a holding force against one or more needles 104 within the needle slot 4077 and the secure zone 4072 to resist translation of the needle out of the needle slot 4077 and the secure zone 4072.

In a preferred embodiment, the needle 104 is moved into contact between the ramp structure 4073a and the tabs 4074d of upper structure 4074 at entry zone 4071 of needle receptacle 4070 by the surgeon manipulating the tip of the needle driver in the needle driver slots of needle receptacle 4070 as described herein. The needles 104 can be pushed into the entry zone 4071 towards the needle slot 4077 and become aligned with the needle slot 4077 of needle receptacle 4070. The needles 104 can then be moved in translation along the longitudinal axis of the needle receptacle 4070 (i.e., the axis of orientation of the needle driver slots) from the entry zone 4071 into the secure zone 4072 where the needles 104 slide into the needle slot 4077 with the convex side facing the secure zone 4072 and the sharp tip and tail of the needle 104 facing the entry zone 4071. The needle driver can move the used needles 104 into the needle slot 4077 in the secure zone 4072 until the needle driver runs into the end of the needle slots of needle receptacle 4070 or the last inserted used needle 104.

In different embodiments, the needle receptacle 4070 can have different dimension depending upon the size of the needles 104 being received. Thus, a small needle receptacle 4070 used to receive smaller needles 104 can have smaller dimensions than a large needle receptacle 4070 used to store larger needles.

Structural components of needle receptacle 4070 may be joined as described herein (e.g., adhesive, mechanical fits, welds). The underside of needle receptacle 4070 may be configured to attach and/or couple (e.g., by hook and look couplings, adhesive) to many of the structures described herein, including barriers, barrier mounting bases, bases, and the like. In many embodiments, needle receptacle 4070 may be configured to releasably attach to many of the structures described herein.

Figure 414:
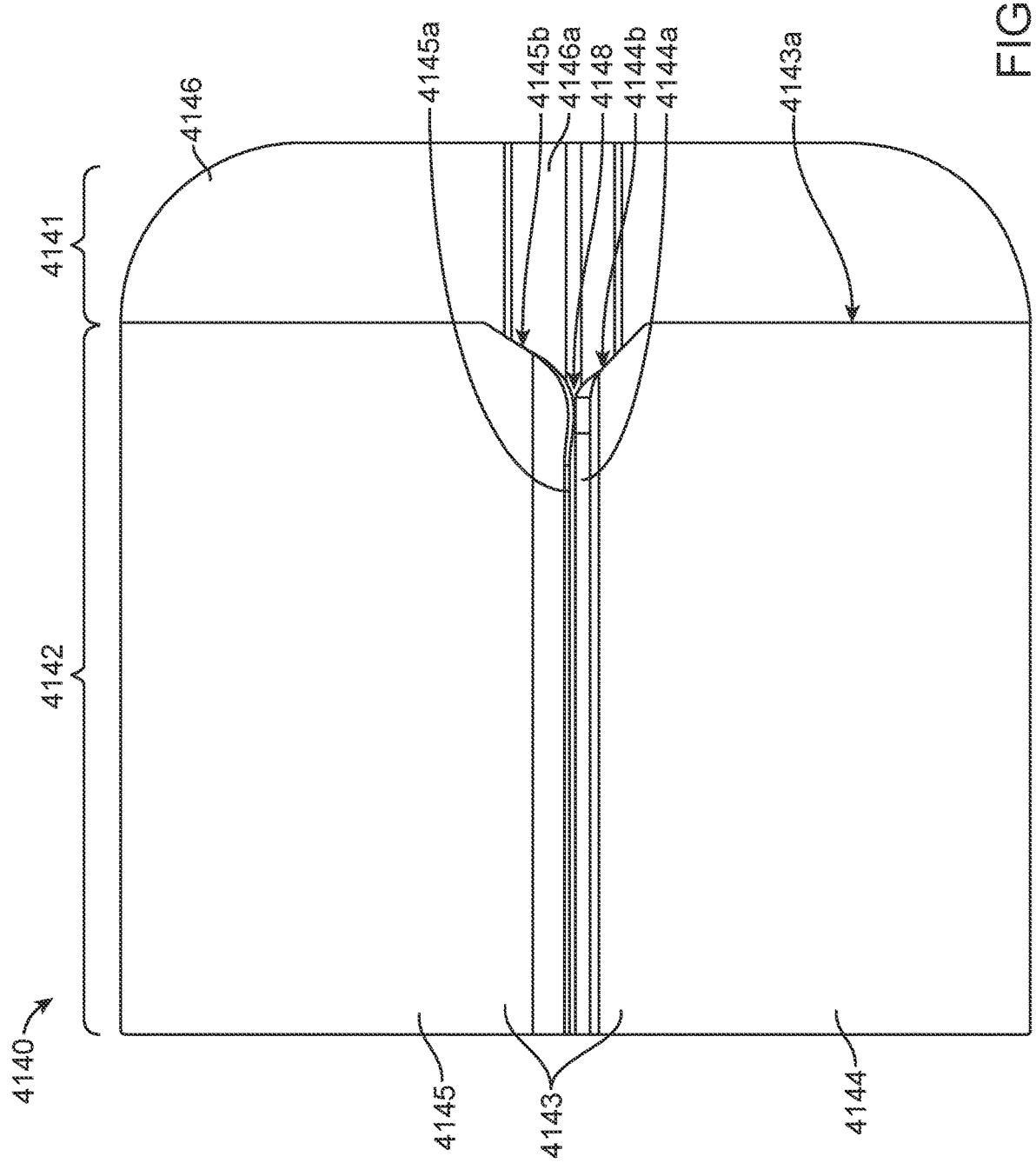
Figure 415:
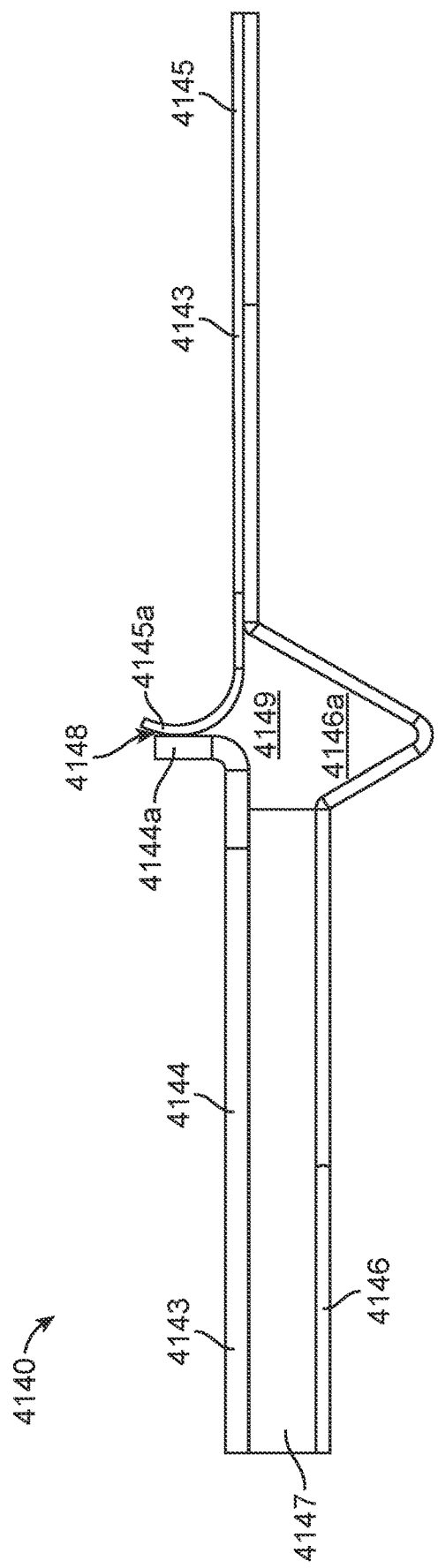
Figure 416:
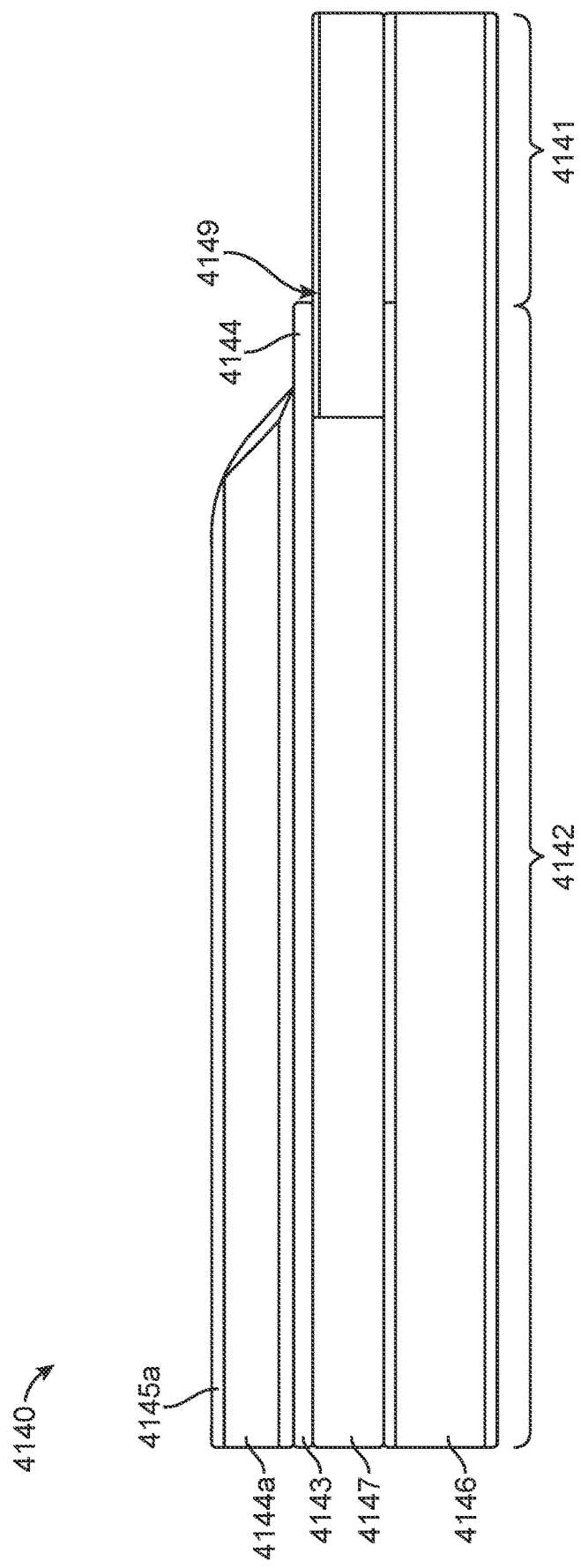
Figure 417:
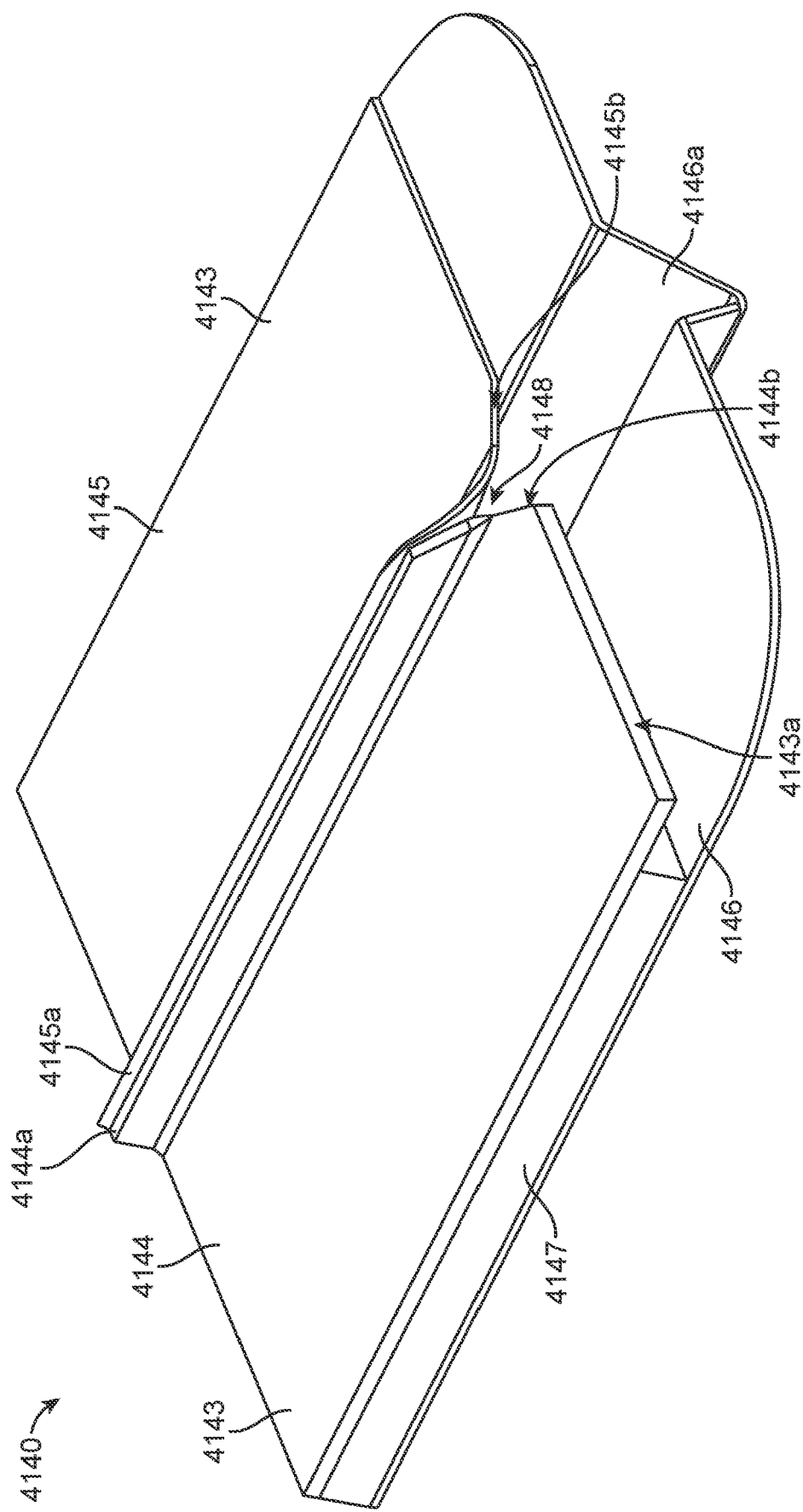
Figure 418:
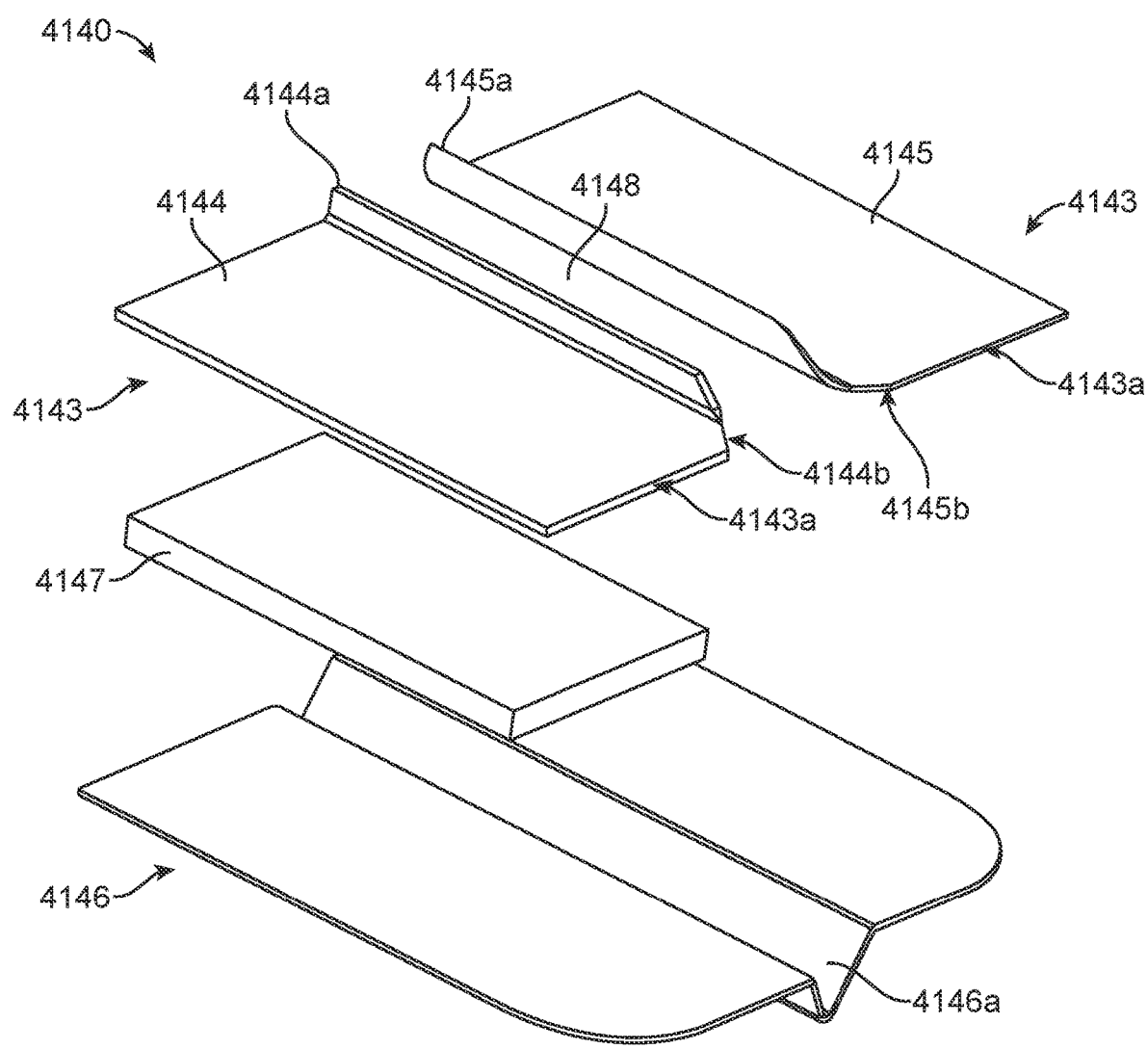

FIGS. 414-418 illustrate an exemplary embodiment of needle receptacle 4140, in accordance with many embodiments. The needle receptacle 4140 may comprise many of the structures shown with reference to FIGS. 167-179, FIGS. 309-320, FIGS. 392A-392F, and FIGS. 392A1-392A12, and a person of ordinary skill in the art will recognize that many of these embodiments are well suited for combination with each other, as well as other embodiments as shown and described herein. FIG. 414 illustrates a top view of needle receptacle 4140, FIG. 415 illustrates a front view of needle receptacle 4140, FIG. 416 illustrates a left side view of needle receptacle, FIG. 417 illustrates a perspective view of needle receptacle 4140, and FIG. 418 illustrates an exploded view of needle receptacle 4140.

In the illustrated embodiment, the needle receptacle 4140 may be a substantially planar device comprised of a secure zone 4142, as described herein. The needle receptacle 4140 may also comprise a landing zone 4141, as described herein. The needle receptacle 4140 may include an upper structure 4143, a lower structure 4146, and a needle slot 4149 disposed between the upper structure 4143 and the lower structure 4146. The needle slot 4149 may be configured for securing one or more needles, as described herein. The needle slot 4149 of needle receiver 4140 may constrain needles placed therein into a single needle depth array, to minimize overall depth profile and facilitate needle counting as described herein. The needle slot 4149 may be enclosed at all sides except at end 4143a of the upper structure 4143, in accordance with many embodiments described herein. The lower structure 4146 may comprise a channel 4146a formed in the upper surface thereof. The channel 4146a may be sized to receive a needle driver tip. The upper structure 4143 may comprise a stiff structure 4144, a flexible structure 4145, and a needle driver slot 4148 formed between the stiff structure 4144 and the flexible structure 4145.

The needle driver slot 4148 may be formed between an edge 4145a of the flexible structure 4145 and an edge 4144a of the upper structure. In many embodiments, edge 4145a of the flexible structure may separate from edge 4144a of the stiff structure to receive a needle driver, as described herein.

In many embodiments, edges 4145a and 4144a may contact each other in a non-deformed free standing state without a needle driver extending therebetween. In some embodiments, edges 4145a and 4144a may be spaced apart from each other in a non-deformed state, a gap being defined therebetween.

The needle receptacle 4140 may comprise a compliant structure 4147 disposed between the upper surface of the lower structure 4146 and the lower surface of the stiff structure 4144. In many embodiments, the compliant structure 4147 may apply a holding force against one or more needles within the needle slot 4149 and the secure zone 4142 to resist translation of the needle out of the needle slot 4149 and the secure zone 4142. In many embodiments, the upper structure 4143 may apply a holding force against one or more needles within the needle slot 4149 and the secure zone 4142 to resist translation of the needle out of the needle slot 4149 and the secure zone 4142. In many embodiments, the compliant structure 4147 may comprise foam. In many embodiments, the compliant structure 4147 may comprise a compliant element.

In many embodiments, the needle driver slot 4148 may be disposed parallel to channel 4146 of the lower structure 4146. In many embodiments, the needle driver slot 4148 may be disposed parallel to and above channel 4146 of the lower structure 4146.

In many embodiments, a portion of the lower structure 4146 may extend beyond end 4143a of the upper structure 4143, forming a landing zone 4141. In some embodiments, the needle may be placed in contact with the upper surface of the extended portion of the lower structure 4146 with the needle driver tip holding the needle aligned with the needle driver slot 4148 of needle receptacle 4140. In some embodiments, channel 4146 may extend into the landing zone 4141. In some embodiments, the needle may be placed in contact and within channel 4146 of the upper surface of the extended portion of the lower structure 4146 with the needle driver tip holding the needle aligned with channel 4146 of the lower structure 4146 and needle driver slot 4148 of needle receptacle 4140.

In some embodiments, stiff upper structure 4143 and flexible upper structure 4145 may comprise beveled edges 4144b and 4145b, respectively, at opposing sides of needle driver slot 4148. The beveled edges 4144b and 4145b may facilitate easy locating of the needle driver into the needle driver slot 4148 when placing needles in needle receptacle 4140.

In different embodiments, the needle receptacle 4140 can have different dimension depending upon the size of the needles being received. Thus, a small needle receptacle 4140 used to receive smaller needles can have smaller dimensions than a large needle receptacle 4140 used to store larger needles.

Structural components of needle receptacle 4140 may be joined as described herein (e.g., adhesive, mechanical fits, welds). The underside of needle receptacle 4140 may be configured to attach and/or couple (e.g., by Velcro, adhesive) to many of the structures described herein, including barriers, barrier mounting bases, bases, and the like. In many embodiments, needle receptacle 4140 may be configured to releasably attach to many of the structures described herein. In some embodiments, needle receptacle 4140 may be configured to be received by a receiving element or other structure as described herein.

Forceps Mounted Receptacle: The dispenser, trap and forceps may comprise an all in one sterile configuration.

These can be manufactured together, with each being disposable. The forceps could contain the suture material, for example.

The needles can be packaged with the barrier as a unit. The needles can be arrayed for deployment from the barrier wall with the barrier having an area available for suture coiling.

Alternatively, suture coiling may not be provided. The packaging can be configured to be dispensed from the barrier or the forceps.

It can be easier to load a trap onto a forceps along with the suture pack and have five or so such "set ups" ready on the Mayo stand. When one has been used up, it can be placed the Mayo and the next one grabbed.

The combination of both dispensing unit (suture package) and used needle repository can be associated together on the forceps.

More than one setup of a suture package and needle receptacle can be combined and ready for use.

The sterile packaging may comprise disposable single use forceps, needle and suture dispenser in combination with a used needle receptacle. These can be co-manufactured.

The forceps mounted receptacles may comprise one or more of many different shapes and sizes. The weight can be sufficiently low in order to provide balance to the forceps mounted instrument. The needle receptacles configured for mounting on the forceps can be configured to provide a balanced surgical instrument with the attachment of needle retention device onto the forceps.

Any design weighing less than 250 grams.

The needle receptacle can be located on one side of forceps, dispensing unit (suture pack) on the other side to save space and volume. The forceps can be easily be rotated to gain access to one or other side when the suture package and needle receptacle are mounted on opposing sides of the forceps.

The needle receptacle may comprise adhesive and can be placed on the back of suture pack or vice versa.

The needle receptacle and suture package can be configured to use a back to back on opposing sides relationship of needle dispensing device and needle receptacle.

The suture packs and needle receptacles as described herein can be configured to coupled to, for example attach, to the forceps that allows for containment, coverage, securement, of both tip and end (tail) of one or more needles.

The needle arrangement in the receptacle may not need to be planar, and can be stacked into trough, side by side, for example.

The forceps mounted needle receptacle as described herein can promote an organized deposition or array of used needles to facilitate counting and reconciliation of needle count.

Needle Count Reconciliation: The scrub assistant and circulator often to maintain an ongoing count of needles (needles in use, needles in the field, needles on the mayo stand, needles on the back table). The receptacle can be specifically designed to hold five needles for easy counting by the surgeon and staff. This can facilitate reconciliation and communication with the rest of the team. The trap or securement, containment device can be specifically designed for five needles, and sized and shaped accordingly. The needle receptacle as described herein may comprise five zones, one for each needle. For example five tactile protrusions as described herein can be used to facilitate localization into each of the five individual zones.

One or more of the needle receptacle, the barrier or the suture package may comprise light sources to indicate needle status. Five light sources, one for each needle entry into the trap, can be provided, for example. Five light sources on could mean five needles in in the receptacle. This configuration could be easier to see from a distance. These sources could be in the trap (receptacle) or there could be a means of communication between trap and barrier with light sources on the barrier. Lighting could be anywhere on the barrier, but be preferred if lighting is dorsal for ease of visualization by the assistant such as a scrub nurse, for example when the trap is on the volar surface and perhaps less visible for the assistant to see. Both volar lighting and dorsal lighting could be provided, for example. There could be five zone specific light sources with one light on per needle into the trap, for example with light sources on the trap. Five light sources on the trap could be in communication with the barrier, and the five lights on the barrier light up according to number of needles in the trap.

This longitudinal receptacle that receives needles with sliding could have five stops with each stop representing an additional needle added to the slot. The longitudinal sliding cover can be spring loaded. Each time the needle driver is abutted against the leading edge of the cover, it triggers a unit translational movement. This movement can be repeated with each needle entry until the slot is fully covered. Each translational unit movement can be numbered 1 through five.

The needle receptacle (for example having a slot to receive needles and the driver) can be configured with ratcheted counting mechanism. There can be an active count of needles to be dispensed as well. A user can start with five needles in the dispenser and zero in the trap (0:5). The user would end with (5:0), when needles are reconciled. The apparatus can be configured with five light sources on the dispenser and count down to zero. This reconciliation by lighting can be helpful.

In some embodiments, the needle receptacle comprises means for reconciling needles during or after the procedure.

In some embodiments, a first set of needles from a first suture pack are reconciled before a second suture pack enters the near surgical field.

In some embodiments, a dispensed needle receptacle comprising five or more dispensed surgical needles is received from a surgeon, wherein the dispensed surgical needles are stabilized and innocuous within the needle receptacle, the needle receptacle comprising one or more of an opening, a window or a transparent material for counting the stabilized innocuous dispensed needles, wherein the needles are arranged for counting within the receptacle.

In some embodiments, a dispensed needle receptacle comprising five or more dispensed surgical needles is received from a person who reconciled the surgical needles, wherein the dispensed surgical needles are stabilized and innocuous within the needle receptacle, the needle receptacle comprising one or more of an opening, a window or a transparent material for counting the stabilized innocuous dispensed needles, wherein the needles are arranged for counting within the receptacle.

The kits shown in FIGS. 379A-379C are provided by way of example only, and many different kits may be assembled to accommodate specific uses or procedures, for example, arterial line or central line placement.

In some embodiments of needle receptacles disclosed herein, a housing of a needle receptacle may include a light scattering material or a light scattering surface for non-uniform light transmission therethrough. In some embodiments the upper or lower structure or surface of the upper or lower structure may be the light scattering surface or material. The light scattering surface or material may be a roughened surface or a sandblasted surface.

With respect to FIG. 171 and other embodiments of needle receptacles, the inner surface of the upper structure may have protrusions or nubs 361, also referred to as tactile bumps. The upper structure may include 2-20 tactile bumps, 5-8 tactile bumps, or 3-10 tactile bumps.

With reference to FIGS. 334A-334C and other embodiments herein, the needle receptacle or suture pack may be placed such that dispensing or securing a needle from or to the suture pack or needle receptacle does not require external rotation 3345a of the arm or shoulders beyond a plane perpendicular to the coronal plane of the surgeon at the surgeon's shoulder, therefore allowing the user to engage only fine motor control, rather than gross motor control, to perform movements related to the dispensing and securing of needles.

In some embodiments, the needle receptacle or suture pack may be placed such that dispensing or securing a needle from or to the suture pack or needle receptacle does not require external rotation 3345a of the arm or shoulders with respect to a sagittal plane that bisects the coronal plane at the surgeon's shoulders, therefore allowing the user to engage only fine motor control, rather than gross motor control, to perform movements related to the dispensing and securing of needles.

In some embodiments, the needle receptacle or suture pack may be placed such that dispensing or securing a needle from or to the suture pack or needle receptacle does not require external rotation 3345a of the arm or shoulders with respect to a mid sagittal plane of the surgeon, therefore allowing the user to engage only fine motor control, rather than gross motor control, to perform movements related to the dispensing and securing of needles.

In some embodiments, the needle receptacle may be placed or otherwise configured such that securing a needle into the needle receptacle uses only gross motor movement of the surgeon.

In some embodiments, the needle receptacle may be placed or otherwise configured to facilitate needle insertion into the needle receptacle using only articulation or rotation of the shoulder or elbow joints of a surgeon.

In some embodiments, the resistance of the needle driver along the needle driver slot is less than the resistance of the needle along the needle slot when the needle is advanced along the slot with a needle driver.

The systems and methods as described herein may be used to safely handle sutures during procedures involving non-living subjects, such as during the performance of autopsies on cadavers, wherein the person operating on the subject may still be exposed to blood-borne pathogens. Alternatively or in combination, the systems and methods described herein may be used to safely handle sutures during procedures involving non-human subjects, such as during the performance of an operation of an animal (e.g., in a veterinary practice or in animal studies).

While preferred embodiments of the present invention have been shown and described herein, it will be obvious to those skilled in the art that such embodiments are provided by way of example only. Numerous variations, changes, and substitutions will now be apparent to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A needle receptacle comprising:
an enclosure comprising a cavity extending from an opening that provides access to the cavity and a secure zone within the cavity; and
a slot extending through the enclosure to the cavity; and
a needle receiver sized and shaped to receive one or more needles and configured to move within the cavity with advancement of the one or more needles into the secure zone within the cavity.

2. The needle receptacle of claim 1, wherein the needle receiver comprises an elongate body shaped to be received within the secure zone.

3. The needle receptacle of claim 2, wherein the elongate body of the needle receiver comprises a surface shaped to receive the one or more needles.

4. The needle receptacle of claim 1, wherein the needle receiver comprises:
a surface; and
one or more needle receiving tabs extending from the surface therefrom.

5. The needle receptacle of claim 4, wherein the one or more needle receiving tabs is configured to be engaged with the one or more needles to allow the needle receiver to slide with the one or more needles when the one or more needles moves into the secure zone.

6. The needle receptacle of claim 5, wherein the needle receiver is configured to translate toward the secure zone when the one or needles engages the one or more needle receiving tabs and translates into the secure zone of the cavity.

7. The needle receptacle of claim 1, where in the needle receiver is configured to allow the one or more needles to pull a portion of the needle receiver into the cavity when a needle driver slides along the slot and advances the one or more needles into the secure zone.

8. The needle receptacle of claim 1, further comprising an aperture through a wall of the enclosure and within an entry zone or a transition zone of the wall, wherein the needle receiver is configured to pass from outside the enclosure, through the aperture, and into the cavity.

9. The needle receptacle of claim 1, wherein one or more needle receiving tabs is connected to a surface of the needle receiver.

10. The needle receptacle of claim 9, wherein the one or more needle receiving tabs has been formed by cutting a slit through the needle receiver and deforming the one or more needle receiving tabs formed by the slit in a direction through the surface of the needle receiver.

11. The needle receptacle of claim 9, wherein the one or more needle receiving tabs comprises a slit through the needle receiver and a portion of the needle receiver at the slit deflected in a direction through the surface of the needle receiver.

12. The needle receptacle claim 1, wherein the needle receiver is configured to ratchet into the cavity.

13. The needle receptacle of claim 1, wherein the needle receiver is configured to permit movement of the needle receiver into the cavity and resist movement of the needle receiver out of the cavity.

14. The needle receptacle of claim 1, wherein one or more needle receiving tabs is configured to hold the needles within the cavity in a spaced apart array.

15. The needle receptacle of claim 14, wherein the spaced apart array comprises an ordered array.

16. The needle receptacle of claim 1, wherein the slot extends through an external wall of the enclosure.

17. The needle receptacle of claim 1, wherein the needle receiver comprises a flexible material.

18. The needle receptacle of claim 1, wherein the needle receiver comprises one or more openings to receive a tip of a needle driver.

19. The needle receptacle of claim 1, wherein the needle receiver comprises one or more protrusions sized and shaped to engage the one or more needles to advance the needle receiver toward the secure zone.

20. The needle receptacle of claim 1, wherein the needle receiver comprises one or more channels sized and shaped to engage the one or more needles to advance the needle receiver toward the secure zone.

* * * * *